US012582683B2

(12) United States Patent
Bachman et al.

(10) Patent No.: US 12,582,683 B2
(45) Date of Patent: Mar. 24, 2026

(54) PROSTATE NEOANTIGENS AND THEIR USES

(71) Applicant: Jansen Biotech, Inc., Horsham, PA (US)

(72) Inventors: Kurtis E. Bachman, Chester Springs, PA (US); Vipul Bhargava, Springfield, PA (US); Darryl L. Davis, Collegeville, PA (US); Vinod Krishna, Philadelphia, PA (US); Guido Leoni, Rome (IT); David Pocalyko, Doylestown, PA (US); Pegah Safabakhsh, Philadelphia, PA (US); Manuel Sepulveda, West Windsor, NJ (US); Derick Siegel, Radnor, PA (US); Marco Gottardis, Princeton, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 115 days.

(21) Appl. No.: 18/342,322

(22) Filed: Jun. 27, 2023

(65) Prior Publication Data

US 2024/0139265 A1 May 2, 2024

Related U.S. Application Data

(62) Division of application No. 16/737,950, filed on Jan. 9, 2020, now Pat. No. 11,793,843.

(60) Provisional application No. 62/913,969, filed on Oct. 11, 2019, provisional application No. 62/883,786, filed on Aug. 7, 2019, provisional application No. 62/851,273, filed on May 22, 2019, provisional application No. 62/790,673, filed on Jan. 10, 2019.

(51) Int. Cl.

| | |
|---|---|
| ***A61K 35/761*** | (2015.01) |
| ***A61K 39/00*** | (2006.01) |
| ***A61K 45/06*** | (2006.01) |
| ***C07K 16/30*** | (2006.01) |

(52) U.S. Cl.

CPC ........ *A61K 35/761* (2013.01); *A61K 39/0011* (2013.01); *A61K 39/001193* (2018.08); *A61K 39/001194* (2018.08); *A61K 39/001195* (2018.08); *C07K 16/3069* (2013.01); *A61K 2039/51* (2013.01); *A61K 2039/545* (2013.01); *A61K 2039/572* (2013.01); *A61K 45/06* (2013.01)

(58) Field of Classification Search

None

See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,603,112 | A | 7/1986 | Paoletti et al. |
| 4,769,330 | A | 9/1988 | Paoletti et al. |
| 4,772,848 | A | 9/1988 | Hummel |
| 4,837,028 | A | 6/1989 | Allen |
| 4,897,445 | A | 1/1990 | Coy et al. |
| 5,100,587 | A | 3/1992 | Clough et al. |
| 5,179,993 | A | 1/1993 | Bak et al. |
| 5,185,146 | A | 2/1993 | Altenburger |
| 5,223,409 | A | 6/1993 | Ladner et al. |
| 5,225,539 | A | 7/1993 | Winter |
| 5,403,484 | A | 4/1995 | Ladner et al. |
| 5,427,908 | A | 6/1995 | Dower et al. |
| 5,559,099 | A | 9/1996 | Wickham et al. |
| 5,571,698 | A | 11/1996 | Ladner et al. |
| 5,580,717 | A | 12/1996 | Dower et al. |
| 5,595,897 | A | 1/1997 | Midoux et al. |
| 5,635,363 | A | 6/1997 | Altman et al. |
| 5,635,483 | A | 6/1997 | Pettit et al. |
| 5,734,023 | A | 3/1998 | Nag et al. |
| 5,744,166 | A | 4/1998 | Illum |
| 5,747,323 | A | 5/1998 | Darlix et al. |
| 5,780,588 | A | 7/1998 | Pettit et al. |
| 5,820,866 | A | 10/1998 | Kappler et al. |
| 5,837,511 | A | 11/1998 | Falck-Pedersen et al. |
| 5,846,782 | A | 12/1998 | Wickham et al. |
| 5,851,806 | A | 12/1998 | Kovesdi et al. |
| 5,885,793 | A | 3/1999 | Griffiths et al. |
| 5,891,690 | A | 4/1999 | Massie |
| 5,932,448 | A | 8/1999 | Tso et al. |
| 5,965,541 | A | 10/1999 | Wickham et al. |
| 5,969,108 | A | 10/1999 | Mccafferty et al. |
| 5,972,707 | A | 10/1999 | Roy et al. |
| 5,976,551 | A | 11/1999 | Mottez et al. |

(Continued)

FOREIGN PATENT DOCUMENTS

| | | |
|---|---|---|
| CL | 202101835 | 8/2021 |
| CO | 2017012891 A2 | 3/2018 |

(Continued)

OTHER PUBLICATIONS

Singh et al 2012 (Ipilimumab in prostate cancer. Expert Opinion on Biological Therapy, 13(2), 303-313) (Year: 2012).*

(Continued)

*Primary Examiner* — Zachariah Lucas
*Assistant Examiner* — Sarah A Alsomairy
(74) *Attorney, Agent, or Firm* — BakerHostetler

(57) ABSTRACT

The disclosure relates to prostate neoantigens, polynucleotides encoding them, vectors, host cells, recombinant virus particles, vaccines comprising the neoantigens, proteinaceous molecules binding the prostate neoantigens, and methods of making and using them.

23 Claims, 12 Drawing Sheets

Specification includes a Sequence Listing.

(56) References Cited

U.S. PATENT DOCUMENTS 5,976,567 A 11/1999 Wheeler et al.
5,981,225 A 11/1999 Kochanek et al.
5,981,501 A 11/1999 Wheeler et al.
5,994,106 A 11/1999 Kovesdi et al.
5,994,128 A 11/1999 Fallaux et al.
6,013,240 A 1/2000 Behr et al.
6,020,191 A 2/2000 Scaria et al.
6,025,337 A 2/2000 Truong et al.
6,040,174 A 3/2000 Imler et al.
6,110,735 A 8/2000 Chartier et al.
6,113,913 A 9/2000 Brough et al.
6,150,584 A 11/2000 Kucherlapati et al.
6,172,197 B1 1/2001 Mccafferty et al.
6,197,302 B1 3/2001 Hirsch et al.
6,204,060 B1 3/2001 Mehtali et al.
6,207,195 B1 3/2001 Walsh et al.
6,218,370 B1 4/2001 Bischoff et al.
6,268,411 B1 7/2001 Schneck et al.
6,270,772 B1 8/2001 Burrows et al.
6,312,948 B1 11/2001 Cohen-Haguenauer
6,335,199 B1 1/2002 Bischoff et al.
6,348,584 B1 2/2002 Hodgson et al.
6,440,442 B1 8/2002 Ehrhard et al.
6,521,404 B1 2/2003 Griffiths et al.
6,534,484 B1 3/2003 Wheeler et al.
6,544,731 B1 4/2003 Griffiths et al.
6,555,313 B1 4/2003 Griffiths et al.
6,582,915 B1 6/2003 Griffiths et al.
6,586,410 B1 7/2003 Wheeler et al.
6,593,081 B1 7/2003 Griffiths et al.
6,673,901 B2 1/2004 Koide
6,815,432 B2 11/2004 Wheeler et al.
6,818,749 B1 11/2004 Kashmiri et al.
6,833,441 B2 12/2004 Wang et al.
7,074,904 B2 7/2006 Wong et al.
7,074,905 B2 7/2006 Rhode et al.
7,141,656 B2 11/2006 Rhode et al.
7,264,958 B1 9/2007 Koehl et al.
7,270,811 B2 9/2007 Bout et al.
7,329,731 B2 2/2008 Jakobsen et al.
7,569,664 B2 8/2009 Jakobsen et al.
7,709,226 B2 5/2010 Foote
7,718,369 B2 5/2010 Tomlins et al.
7,871,817 B2 1/2011 Voss et al.
8,133,724 B2 3/2012 Qiu et al.
8,163,293 B2 4/2012 Chaplin
8,211,645 B2 7/2012 Tomlins et al.
8,268,329 B2 9/2012 Chaplin et al.
8,313,740 B2 11/2012 Delcayre et al.
8,377,447 B2 2/2013 Burrows et al.
8,377,688 B2 2/2013 Delcayre et al.
8,394,385 B2 3/2013 Hausmann et al.
8,580,509 B2 11/2013 Tomlins et al.
8,685,660 B2 4/2014 Vogelstein et al.
8,748,356 B2 6/2014 Raghunathan
8,828,379 B2 9/2014 Loset et al.
8,940,290 B2 1/2015 Roy et al.
9,061,059 B2 6/2015 Chakraborty et al.
9,079,941 B2 7/2015 Ovaa et al.
9,133,264 B2 9/2015 Blankenstein et al.
9,146,238 B2 9/2015 Luo et al.
9,284,609 B2 3/2016 Tomlins et al.
9,593,077 B2 3/2017 Payne et al.
9,617,560 B2 4/2017 Brough et al.
9,624,292 B2 4/2017 Voss et al.
9,745,635 B2 8/2017 Tomlins et al.
9,750,801 B2 9/2017 Barouch et al.
9,790,256 B2 10/2017 Bunnik et al.
9,884,075 B2 2/2018 Bethune et al.
10,035,832 B2 7/2018 Schlom et al.
10,111,940 B2 10/2018 Mcneel et al.
10,155,031 B2 12/2018 Sahin et al.
10,190,173 B2 1/2019 Tomlins et al.
10,350,275 B2 7/2019 Aguilar-Cordova
10,441,643 B2 10/2019 Pulido et al.
10,512,662 B2 12/2019 Deng et al.
10,532,067 B2 1/2020 Geall et al.
10,548,930 B2 2/2020 Deng et al.
10,640,786 B2 5/2020 Barry et al.
10,736,962 B2 8/2020 Deng et al.
10,781,169 B2 9/2020 Payne et al.
10,973,892 B2 4/2021 Lauterbach et al.
11,110,159 B2 9/2021 Demoitie et al.
11,179,456 B2 11/2021 Dorrell et al.
2001/0036927 A1 11/2001 Bischoff et al.
2001/0049136 A1 12/2001 Imler et al.
2002/0028497 A1 3/2002 Blanche et al.
2002/0192763 A1 12/2002 Xu et al.
2003/0198953 A1 10/2003 Spytek et al.
2005/0112705 A1 5/2005 Bracco et al.
2005/0244851 A1 11/2005 Blume et al.
2006/0115821 A1 6/2006 Einstein et al.
2007/0148774 A1 6/2007 Mccafferty et al.
2007/0287170 A1 12/2007 Davis et al.
2008/0208783 A1 8/2008 Jaros et al.
2009/0104225 A1 4/2009 Delcayre et al.
2009/0182127 A1 7/2009 Naergaard et al.
2010/0015133 A1 1/2010 Igawa et al.
2010/0143247 A1 6/2010 Fenske et al.
2010/0143302 A1 6/2010 Havenga et al.
2010/0216708 A1 8/2010 Jacobs et al.
2010/0255056 A1 10/2010 Jacobs et al.
2010/0261620 A1 10/2010 Almagro et al.
2010/0286374 A1 11/2010 Kannan et al.
2011/0123532 A1 5/2011 Gurney et al.
2011/0300205 A1 12/2011 Geall et al.
2012/0015839 A1 1/2012 Chinnaiyan
2012/0093934 A1 4/2012 Santamaria
2012/0252742 A1 10/2012 Kranz et al.
2012/0296070 A1 11/2012 Tomlins et al.
2013/0289253 A1 10/2013 Luescher et al.
2013/0330335 A1 12/2013 Bremel et al.
2014/0271829 A1 9/2014 Lilja et al.
2015/0329617 A1 11/2015 Winther et al.
2015/0344965 A1 12/2015 Luo et al.
2016/0078168 A1 3/2016 Zhuo et al.
2016/0130319 A1 5/2016 Li
2016/0271239 A1 9/2016 Foy et al.
2017/0003288 A1 1/2017 Heath et al.
2017/0039314 A1 2/2017 Bremel et al.
2017/0095544 A1 4/2017 Santamaria
2017/0106065 A1 4/2017 Foy et al.
2017/0121409 A1 5/2017 Verona et al.
2017/0182139 A1 6/2017 Mcneel et al.
2017/0266270 A1 9/2017 Foy et al.
2017/0334963 A1 11/2017 Johnston
2018/0000912 A1 1/2018 Meruelo et al.
2018/0002393 A1 1/2018 Bancel et al.
2018/0028626 A1 2/2018 Slos et al.
2018/0064803 A1 3/2018 Tomaka et al.
2018/0104359 A1 4/2018 Kamrud
2018/0118849 A1 5/2018 Klein et al.
2018/0126003 A1 5/2018 Hoerr
2018/0141998 A1 5/2018 Nguyen et al.
2018/0153975 A1 6/2018 Fritsch et al.
2018/0171340 A1 6/2018 Kamrud et al.
2018/0311269 A1 11/2018 Lobb et al.
2019/0030147 A1 1/2019 Artomov et al.
2019/0038732 A1 2/2019 Mcneel et al.
2019/0041771 A1 2/2019 Chang
2019/0093085 A1 3/2019 Tufaro et al.
2019/0192691 A1 6/2019 Gladstone et al.
2019/0350993 A1 11/2019 Cai
2019/0351040 A1 11/2019 Valiante et al.
2020/0054728 A1 2/2020 Artomov et al.
2020/0061174 A1 2/2020 Kalla et al.
2020/0121774 A1 4/2020 Lubaroff et al.
2020/0138923 A1 5/2020 Bendjama et al.
2020/0148742 A1 5/2020 Grandi et al.
2020/0171151 A1 6/2020 Yeung
2020/0197500 A1 6/2020 Blair et al.
2020/0222478 A1 7/2020 Bachman et al.
2020/0222519 A1* 7/2020 Nicosia .................. C12N 15/00
2020/0239906 A1 7/2020 Roeth et al.

(56) References Cited

U.S. PATENT DOCUMENTS

| | | | |
|---|---|---|---|
| 2020/0283497 | A1 | 9/2020 | Oehm et al. |
| 2020/0299725 | A1 | 9/2020 | Beissert et al. |
| 2020/0306352 | A1 | 10/2020 | Hochrein et al. |
| 2020/0330534 | A1 | 10/2020 | Delgoffe et al. |
| 2020/0339959 | A1 | 10/2020 | Deng et al. |
| 2021/0015878 | A1 | 1/2021 | Larson et al. |
| 2021/0023100 | A1 | 1/2021 | Sahin et al. |
| 2021/0046130 | A1 | 2/2021 | Jia et al. |
| 2021/0069322 | A1 | 3/2021 | Ammendola et al. |
| 2021/0130848 | A1 | 5/2021 | Nicosia et al. |
| 2021/0238244 | A1 | 8/2021 | Plasterk |
| 2021/0361760 | A1 | 11/2021 | Philip |

FOREIGN PATENT DOCUMENTS

| | | | | |
|---|---|---|---|---|
| CO | 2018006023 | A2 | 6/2018 | |
| CO | 2018007417 | A2 | 9/2018 | |
| CO | 2019006541 | A2 | 6/2019 | |
| CO | 2019012345 | A2 | 1/2020 | |
| CO | 2019013609 | A2 | 4/2020 | |
| CO | 2021004019 | A2 | 7/2021 | |
| CO | 2021009307 | A2 | 8/2021 | |
| EP | 0901463 | A1 | 3/1999 | |
| EP | 0919627 | A2 | 6/1999 | |
| EP | 1230354 | A2 | 8/2002 | |
| EP | 1670823 | A1 | 6/2006 | |
| EP | 1882700 | A1 | 1/2008 | |
| EP | 2061807 | A2 | 5/2009 | |
| EP | 1934363 | B1 | 3/2013 | |
| EP | 3215164 | A1 | 9/2017 | |
| EP | 3286210 | A1 | 2/2018 | |
| EP | 3721899 | A1 | 10/2020 | |
| WO | 88/01649 | A1 | 3/1988 | |
| WO | 90/04036 | A1 | 4/1990 | |
| WO | 90/07861 | | 7/1990 | |
| WO | 92/01047 | A1 | 1/1992 | |
| WO | 92/22653 | A1 | 12/1992 | |
| WO | 94/13804 | A1 | 6/1994 | |
| WO | 95/01447 | A1 | 1/1995 | |
| WO | 95/24221 | A1 | 9/1995 | |
| WO | 96/02655 | A1 | 2/1996 | |
| WO | 96/17070 | A1 | 6/1996 | |
| WO | 96/19240 | A1 | 6/1996 | |
| WO | 96/27677 | A2 | 9/1996 | |
| WO | 96/40964 | A2 | 12/1996 | |
| WO | 97/04119 | A1 | 2/1997 | |
| WO | 97/35996 | A1 | 10/1997 | |
| WO | 98/00524 | A1 | 1/1998 | |
| WO | 98/26048 | A1 | 6/1998 | |
| WO | 98/34910 | A1 | 8/1998 | |
| WO | 98/37916 | A1 | 9/1998 | |
| WO | 98/39411 | A1 | 9/1998 | |
| WO | 98/44001 | A1 | 10/1998 | |
| WO | 99/45962 | A1 | 9/1999 | |
| WO | 00/50573 | A1 | 8/2000 | |
| WO | 00/70071 | A1 | 11/2000 | |
| WO | 01/30382 | A1 | 5/2001 | |
| WO | 01/30847 | A1 | 5/2001 | |
| WO | 01/36615 | A2 | 5/2001 | |
| WO | 02/43478 | A2 | 6/2002 | |
| WO | 02/66630 | A1 | 8/2002 | |
| WO | 02/88172 | A2 | 11/2002 | |
| WO | 2003/076610 | A2 | 9/2003 | |
| WO | 2004/044176 | A2 | 5/2004 | |
| WO | 2004/113571 | A2 | 12/2004 | |
| WO | 2005/046621 | A2 | 5/2005 | |
| WO | 2005/048957 | A2 | 6/2005 | |
| WO | 2005/051991 | A2 | 6/2005 | |
| WO | 2005/071093 | A2 | 8/2005 | |
| WO | 2006/056766 | A2 | 6/2006 | |
| WO | 2007/104792 | A2 | 9/2007 | |
| WO | 2007/147901 | A1 | 12/2007 | |
| WO | 2008/106615 | A1 | 9/2008 | |
| WO | 2009/006479 | A2 | 1/2009 | |
| WO | 2009/065546 | A1 | 5/2009 | |
| WO | 2009/085462 | A1 | 7/2009 | |
| WO | 2009/127060 | A1 | 10/2009 | |
| WO | 2009/134776 | A2 | 11/2009 | |
| WO | 2010/081001 | A2 | 7/2010 | |
| WO | 2010/086189 | A2 | 8/2010 | |
| WO | 2010/132867 | A1 | 11/2010 | |
| WO | 2011/005799 | A2 | 1/2011 | |
| WO | 2011/068810 | A1 | 6/2011 | |
| WO | 2011/143545 | A1 | 11/2011 | |
| WO | 2012/006369 | A2 | 1/2012 | |
| WO | 2012/006372 | A1 | 1/2012 | |
| WO | 2012/006376 | A2 | 1/2012 | |
| WO | 2012/006378 | A1 | 1/2012 | |
| WO | 2012/022811 | A1 | 2/2012 | |
| WO | 2012/030901 | A1 | 3/2012 | |
| WO | 2012/031043 | A1 | 3/2012 | |
| WO | 2012/089225 | A1 | 7/2012 | |
| WO | 2012/089338 | A1 | 7/2012 | |
| WO | 2012/149522 | A1 | 11/2012 | |
| WO | 2012/172277 | A1 | 12/2012 | |
| WO | 2012/177624 | A2 | 12/2012 | |
| WO | 2013/006825 | A1 | 1/2013 | |
| WO | 2013/006838 | A1 | 1/2013 | |
| WO | 2013/006842 | A2 | 1/2013 | |
| WO | 2013/033563 | A1 | 3/2013 | |
| WO | 2013/096291 | A2 | 6/2013 | |
| WO | 2013/116778 | A2 | 8/2013 | |
| WO | 2013/151672 | A2 | 10/2013 | |
| WO | 2013/157954 | A1 | 10/2013 | |
| WO | 2013/176772 | A1 | 11/2013 | |
| WO | 2014/127917 | A1 | 8/2014 | |
| WO | 2015/069571 | A1 | 5/2015 | |
| WO | 2015/069770 | A1 | 5/2015 | |
| WO | 2015/077624 | A1 | 5/2015 | |
| WO | 2015/078856 | A1 | 6/2015 | |
| WO | 2015/103037 | A2 | 7/2015 | |
| WO | 2015/123496 | A1 | 8/2015 | |
| WO | 2015/164674 | A1 | 10/2015 | |
| WO | 2015/175334 | A2 | 11/2015 | |
| WO | 2015/175340 | A1 | 11/2015 | |
| WO | 2015/176033 | A1 | 11/2015 | |
| WO | 2015/192068 | A1 | 12/2015 | |
| WO | 2016/046357 | A1 | 3/2016 | |
| WO | 2016/128542 | A1 | 8/2016 | |
| WO | 2016/170176 | A1 | 10/2016 | |
| WO | 2016/184822 | A1 | 11/2016 | |
| WO | 2016/187508 | A2 | 11/2016 | |
| WO | 2016/197067 | A1 | 12/2016 | |
| WO | 2016/203025 | A1 | 12/2016 | |
| WO | 2016/207164 | A2 | 12/2016 | |
| WO | 2017/001491 | A2 | 1/2017 | |
| WO | 2017/015064 | A1 | 1/2017 | |
| WO | 2017/020026 | A1 | 2/2017 | |
| WO | 2017/070110 | A1 | 4/2017 | |
| WO | 2017/070618 | A1 | 4/2017 | |
| WO | 2017/091905 | A1 | 6/2017 | |
| WO | 2017/106638 | A1 | 6/2017 | |
| WO | 2017/147554 | A2 | 8/2017 | |
| WO | 2017/173321 | A1 | 10/2017 | |
| WO | 2017/177207 | A1 | 10/2017 | |
| WO | 2017/180587 | A2 | 10/2017 | |
| WO | 2017/180770 | A1 | 10/2017 | |
| WO | 2017/201325 | A1 | 11/2017 | |
| WO | 2017/201350 | A1 | 11/2017 | |
| WO | 2017/201352 | A1 | 11/2017 | |
| WO | 2017/205810 | A1 | 11/2017 | |
| WO | 2017/220499 | A1 | 12/2017 | |
| WO | 2018/033254 | A2 | 2/2018 | |
| WO | 2018/037085 | A1 | 3/2018 | |
| WO | 2018/046803 | A1 | 3/2018 | |
| WO | 2018/075235 | A1 | 4/2018 | |
| WO | 2018/081480 | A1 | 5/2018 | |
| WO | 2018/093907 | A1 | 5/2018 | |
| WO | 2018/098362 | A1 | 5/2018 | |
| WO | 2018/102584 | A1 | 6/2018 | |
| WO | 2018/107011 | A1 | 6/2018 | |
| WO | WO-2018102585 | A1 * | 6/2018 | ............ A61K 35/74 |
| WO | 2018/143949 | A1 | 8/2018 | |
| WO | 2018/144082 | A1 | 8/2018 | |

(56) References Cited

FOREIGN PATENT DOCUMENTS

| | | | |
|---|---|---|---|
| WO | 2018/146205 | A1 | 8/2018 |
| WO | 2018/148381 | A1 | 8/2018 |
| WO | 2018/148501 | A1 | 8/2018 |
| WO | 2018/161092 | A1 | 9/2018 |
| WO | 2018/167320 | A1 | 9/2018 |
| WO | 2018/187356 | A2 | 10/2018 |
| WO | 2018/195357 | A1 | 10/2018 |
| WO | 2018/223093 | A1 | 12/2018 |
| WO | 2019/008111 | A1 | 1/2019 |
| WO | 2019/012082 | A1 | 1/2019 |
| WO | 2019/012091 | A1 | 1/2019 |
| WO | 2019/023566 | A1 | 1/2019 |
| WO | 2019/046377 | A1 | 3/2019 |
| WO | 2019/053056 | A1 | 3/2019 |
| WO | 2019/086615 | A1 | 5/2019 |
| WO | 2019/094396 | A1 | 5/2019 |
| WO | 2019/115816 | A1 | 6/2019 |
| WO | 2019/134048 | A1 | 7/2019 |
| WO | 2019/135086 | A1 | 7/2019 |
| WO | 2019/137999 | A1 | 7/2019 |
| WO | 2019/152922 | A1 | 8/2019 |
| WO | 2019/191780 | A1 | 10/2019 |
| WO | 2019/219851 | A1 | 11/2019 |
| WO | 2019/226939 | A1 | 11/2019 |
| WO | 2019/226941 | A1 | 11/2019 |
| WO | 2019/232103 | A1 | 12/2019 |
| WO | WO-2019238023 | A1 * | 12/2019 |
| WO | 2020/003126 | A1 | 1/2020 |
| WO | 2020/014539 | A1 | 1/2020 |
| WO | 2020/022898 | A2 | 1/2020 |
| WO | 2020/025642 | A1 | 2/2020 |
| WO | 2020/048990 | A1 | 3/2020 |
| WO | 2020/056424 | A1 | 3/2020 |
| WO | 2020/070303 | A1 | 4/2020 |
| WO | 2020/072371 | A1 | 4/2020 |
| WO | 2020/073045 | A1 | 4/2020 |
| WO | 2020/079234 | A1 | 4/2020 |
| WO | 2020/096640 | A2 | 5/2020 |
| WO | 2020/097291 | A1 | 5/2020 |
| WO | 2020/097393 | A1 | 5/2020 |
| WO | 2020/099614 | A1 | 5/2020 |
| WO | 2020/104531 | A1 | 5/2020 |
| WO | 2020/121273 | A1 | 6/2020 |
| WO | 2020/123912 | A1 | 6/2020 |
| WO | 2020/131586 | A2 | 6/2020 |
| WO | 2020/132275 | A1 | 6/2020 |
| WO | 2020/143634 | A1 | 7/2020 |
| WO | 2020/144614 | A1 | 7/2020 |
| WO | 2020/144615 | A1 | 7/2020 |
| WO | 2020/150152 | A1 | 7/2020 |
| WO | 2020/154189 | A1 | 7/2020 |
| WO | 2020/205412 | A1 | 10/2020 |
| WO | 2020/243719 | A1 | 12/2020 |
| WO | 2020/247547 | A1 | 12/2020 |
| WO | 2022/009049 | A1 | 1/2022 |
| WO | 2022/009051 | A1 | 1/2022 |
| WO | 2023/111861 | A1 | 6/2023 |

OTHER PUBLICATIONS

Ahl et al., "Enhancement of the in vivo circulation lifetime of L-a-distearoylphosphatidylcholine liposomes: importance of liposomal aggregation versus complement opsonization", Biochim. Biophys. Acta, 1997, vol. 1329, pp. 370-382.
Akimaru et al., "Formulation and antitumor efficacy of liposomal-caprylated-TNF-SAM2.", Cytokines Mol. Ther., 1995, vol. 1, No. 3, pp. 197-210.
Aldous et al., "Personalized neoantigen vaccines: A new approach to cancer immunotherapy", Bioorganic & Medicinal Chemistry, 2018, vol. 26, pp. 2842-2849.
Altschul et al., "BLAST—(see, for example), in Basic Local Alignment Search Tool", J. Mol. Biol., 1993, vol. 215, pp. 403-410.
Alving et al., "Liposomes as carriers of peptide antigens: induction of antibodies and cytotoxic T lymphocytes to conjugated and unconjugated peptides", Immunol. Rev., 1995, vol. 145, pp. 5-31.
Anassi et al., "Sipuleucel-T (Provenge) Injection, Pharmacy & Therapeutics," Apr. 2011, vol. 36, No. 4, pp. 197-202.
Antonarakis, "Cyclin-Dependent Kinase 12, Immunity, and Prostate Cancer", NEJM, 2018, vol. 379, No. 13, pp. 1087-1089.
Bakker et al., "Conditional MHC class I ligands and peptide exchange technology for the human MHC gene products HLA-A1, -A3, -A11, and -B7.", Proc Natl Acad Sci, USA, Mar. 22, 2008, vol. 105, No. 10, pp. 3825-3830.
Behr et al., "Efficient gene transfer into mammalian primary endocrine cells with lipopolvamine-coated DNA.", Proc. Natl. Acad. Sci., USA, 1999, vol. 86, No. 18, pp. 6982-6986.
Beissert et al., "Improvement of In Vivo Expression of Genes Delivered by Self-Amplifying RNA Using Vaccinia Virus Immune Evasion Proteins", Human Gene Therapy, 2017, vol. 28, No. 12, pp. 1138-1146.
Bruckdorfer et al, "From Production of Peptides in Milligram Amounts for Research to Multi-Tons Quantities for Drugs of the Future," Current Pharmaceutical Biotechnology, 2004, vol. 5, Issue 1, pp. 29-43.
Bruggemann et al., "Human antibody production in transgenic mice: expression from 100 kb of the human IqH locus*. ", Eur J Immunol, 1991, vol. 21, pp. 1323-1326.
Bruggemann et al., "Production of human antibody repertoires in transgenic mice.", Curr Opin Biotechnol, 1997, vol. 8, pp. 455-458.
Cappuccini et al., "5T4 oncofoetal glycoprotein: an old target for a novel prostate cancer immunotherapy", Oncotarget, 2017, vol. 8, No. 29, pp. 47474-47489.
Cappuccini et al., "Immunogenicity and efficacy of the novel cancer vaccine based on simian adenovirus and MVA vectors alone and in combination with PD-1 mAb in a mouse model of prostate cancer", Cancer Immunol Immunotherapy, 2016, vol. 65, pp. 701-713.
Cappuccini et al., "Safety and immunogenicity of novel 5T4 viral vectored vaccination regimens in early stage prostate cancer: a phase I clinical trial", Journal for Immunotherapy of Cancer, 2020, vol. 8, e000928, pp. 1-13.
Chothia et al., "Canonical Structures for the Hypervariable Regions of Immunoglobulins.", Mol Biol, 1987, vol. 196, pp. 901-917.
Coligan et al., Chapter 15 of Current Protocols In Protein Science, Eds., John Wiley and Sons NY 1995-2000.
Correa et al., "The NLR-related protein NWD1 is associated with prostate cancer and modulates androgen receptor signaling", Oncotarget, Mar. 2014, vol. 5, No. 6, pp. 1666-1682.
Danner et al., "Vaccination against pox diseases under immunosuppressive conditions", Dev. Biol. Stand., 1978, vol. 41, pp. 225-234.
Danos et al., "Safe and efficient generation of recombinant retroviruses with amphotropic and ecotropic host ranges.", Proc. Natl. Acad. Sci., USA, 1988, vol. 85, No. 17, pp. 6460-6464.
Feigner et al., "Cationic Lipid-Mediated Delivery of Polynucleotides.", Methods, 1993, vol. 5, pp. 67-75.
Feigner et al., "Lipofection: a highly efficient, lipid-mediated DNA-transfection procedure.", Proc. Natl. Acad. Sci., USA, Nov. 1987, vol. 84, No. 21, pp. 7413-7417.
Fishwild et al., "High-avidity human IgGk monoclonalantibodies from a novel strain of minilocus transgenic mice", Nat Biotechnol, Jul. 1996, vol. 14, pp. 845-851.
Gadi et al., "In vivo sensitization of ovarian tumors to chemotherapy by expression of *E. coli* purine nucleoside phosphorylase in a small fraction of cells", 7 Gene Ther., 2000, vol. 7, No. 20, pp. 1738-1743.
Gao et al, "A novel cationic liposome reagent for efficient transfection of mammalian cells," Biochemical and Biophysical Research Communications, Aug. 1991, vol. 179, Issue 1, pp. 280-285.
Ge et al., "FusionMap: detecting fusion genes from next-generation sequencing data at base-pair resolution.", Bioinformatics., 2011, vol. 27, No. 14, pp. 1922-1928.
Geall et al., "Nonviral delivery of self-amplifying RNA vaccines," PNAS, 2012, vol. 109, pp. 14604-14609.
Gilboa et al., "Retroviral Gene Transfer: Applications To Human Therapy.", Adv. Exp. Med. Biol., 1988, vol. 241, pp. 29-33.
Goding, "Monoclonal Antibodies: Principles and Practice", Chapter 3, Academic Press, 1986, pp. 59-103.

(56) References Cited

OTHER PUBLICATIONS

Gomes et al., "STEAP 1 is overexpressed in prostate cancer and prostatic intraepithelial neoplasia lesions, and it is positively associated with Gleason score", Urologic Oncology, 2014, vol. 32, pp. 53.e26-53.e29.
Gorchakov et al., "Different Types of nsP3-Containing Protein Complexes in Sindbis Virus-Infected Cells," Journal Of Virology, vol. 82, Issue 20, 2008, pp. 10088-10101.
Graff et al., "Sipuleucel-T in the treatment of prostate cancer: an evidence based review of its place in therapy", Core Evidence, 2015, pp. 1-10.
Graham et al., "Characteristics of a Human Cell Line Transformed by DNA from Human Adenovirus Type 5.", J. Gen. Viral., 1977, vol. 36, pp. 59-72.
Green et al., "Antigen-specific human monoclonal antibodies from mice engineered with human Iq heavy and light chain YACs.", Nature Genet., 1994, vol. 7, pp. 13-21.
Green et al., "Regulation of B Cell Development by Variable Gene Complexity in Mice Reconstituted with Human Immunoglobulin Yeast Artificial Chromosomes.", J. Exp. Med., Aug. 1998, vol. 188, No. 3, pp. 483-495.
Green, "Antibody engineering via genetic engineering of the mouse: XenoMouse strains are a vehicle for the facile generation of therapeutic human monoclonal antibodies.", J Immunol Methods, 1999, vol. 231, pp. 11-23.
Gulley et al., "Phase III Trial of PROSTVAC in Asymptomatic or Minimally Symptomatic Metastatic Castration-Resistant Prostate Cancer", Journal of Clinical Oncology, 2019, vol. 37, Issue 13, pp. 1051-1061.
Haensler et al., "Polyamidoamine cascade polymers mediate efficient transfection of cells in culture", Bioconiuaate Chem., Sep. 1993, vol. 4, No. 5, pp. 372-379.
Harrop et al., "Recombinant viral vectors: Cancer vaccines", Advanced Drug Delivery Reviews, 2006, vol. 58, pp. 931-947.
Heninger et al., "Inducible expression of cancer-testis antigens in human prostate cancer", Oncotarget, 2016, vol. 7, No. 51, pp. 84359-84374.
Hoganson et al., "Development of a Stable Adenoviral Vector Formulation," Bioprocessing, Technical Developments and Opportunities; vol. 1, No. 1, Mar. 2002, pp. 43-48.
Honegger et al., "Yet Another Numbering Scheme for Immunoglobulin Variable Domains: An Automatic Modeling and Analysis Tool.", J Mol Biol, 2001, vol. 309, pp. 657-670.
Hoogenboom et al., "By-passing Immunisation. Human Antibodies from Synthetic Repertoires of Germline VH Gene Segments Rearranged in Virto.", J Mol Biol, 1992, vol. 227, pp. 381-388.
Hosse et al., "A New Generation of Protein Display Scaffolds for Molecular Recognition.", Protein Sci., 2006, vol. 15, pp. 14-27.
Joshua et al., "The long tail of oncogenic drivers in prostate cancer", Nature Genetics, Nature Publishing Group, New York, US, vol. 50, No. 5, Apr. 2018, pp. 645-651.
Juliano et al., "The effect of particle size and charge on the clearance rates of liposomes and liposome encapsulated drugs", Biochem. Biophys. Res. Commun, vol. 63, Issue 3, 1975, pp. 651-658.
Kabat et al., Sequences of Proteins of Immunological Interest, 5th Ed. Public Health Service, National Institutes of Health, Bethesda, Md., 1991.
Kim et al., "Enhancement of protein expression by alphavirus replicons by designing self-replicating subgenomic RNAs," PNAS, vol. 111, 2014, pp. 10708-10713.
Knappik et al., "Fully Snythetic Human Combinatorial Antibody Libraries (HuCAL) Based on Modular Consensus Frameworks and CDRs Randomized with Trinucleotides.", J. Mol. Biol, 2000, vol. 296, pp. 57-86.
Cheever et al., "Provenge (Sipuleucel-T) in Prostate Cancer: The First FDA-Approved Therapeutic Cancer Vaccine", Clin Cancer Res; 17(11) Jun. 1, 2011, 3520-3526.
Karan, Formulation of the bivalent prostate cancer vaccine with surgifoam elicits antigen-specific effector T cells in PSA-transgenic mice, Vaccine, vol. 35, Published Sep. 20, 2017, pp. 5794-5798.
Kubler, et al., "Self-adjuvanted mRNA vaccination in advanced protate cancer patients: a first-in-in phase I/IIa study", Journal for Immuno Therapy of Cancer, vol. 3, 26, Jun. 16, 2015.
Rickman et al., SLC45A3-ELK4 is a Novel and Frequent ETS Fusion Transcript in Prostate Cancer, Cancer Res., Published Apr. 1, 2009, pp. 2734-2738.
Westdorp et al., "Immunotherapy for prostate cancer: lessons from responses to tumor-associated antigens", Frontiers in Immunology, vol. 5, Published May 6, 2014, pp. 1-15.
Ying et al., "Cancer Therapy using a self-replicating RNA vaccine", Nat Med., Published Jul. 1999, pp. 823-827.
Kohler et al., "Continuous cultures of fused cells secreting antibody of predefined specificity", Nature, 1975, vol. 256, pp. 495-497.
Krebs et al., "High-Throughput generation and engineering of recombinant human antibodies.", J Immunol Meth, 2001, vol. 254, pp. 67-84.
Kroughak et al., "Development of Cell Lines Capable of Complementing E1, E4, and Protein IX Defective Adenovirus Type 5 Mutants.", Human Gene Ther., 1995, vol. 6, No. 12, pp. 1575-1586.
Le et al., "PD-1 Blockade in Tumors with Mismatch-Repair Deficiency.", N Engl J Med., Jun. 25, 2015, vol. 372, No. 26, pp. 2509-2520.
Lefranc et al., "IMGT unique numbering for immunoglobulin and T cell receptor variable domains and Ig superfamily V-like domains.", Dev Comparat Immunol, 2003, vol. 27, pp. 55-77.
Lonberg and Huszar, "Human Antibodies from Transgenic Mice.", Int Rev Immunol, 1995, vol. 13, pp. 65-93.
Lonberg et al., "Antigen-specific human antibodies from mice comprising four distinct genetic modifications", Nature, 1994, vol. 368, pp. 856-859.
Lopata, et al., "High level trasient expression of a chloramphenicol acetyl transferase gene by DEAE-dextran mediated DNA transfection coupled with a dimethyl sulfoxide or glycerol shock treatment.", 1984, Nucleic Acid Res., 1984, vol. 12, No. 14, pp. 5707-5717.
Lukas. et al., "Solid-phase peptide synthesis under continuous-flow conditions," Proc. Nati. Acad. Sci. USA, vol. 78, Issue 5, 1981, pp. 2791-2795.
Lundblad, Chemical Reagents for Protein Modification, 3rd ed., CRC Press, 2004.
Lusky, et al., "In Vitro and In Vivo Biology of Recombinant Adenovirus Vectors with E1, E1/E2A, or E1/E4 Deleted.", J. Viral., Mar. 1998, vol. 72, No. 3, pp. 2022-2032.
Markowitz et al., "Construction and use of a safe and efficient amphotropic packaging cell line.", Virology, 1988, vol. 167, No. 2, pp. 400-406.
Marks et al., "By-passing Immunization. Human antibodies from V-gene Libraries Displayed on Phage.", J Mol Biol, 1991, vol. 222, pp. 581-587.
Martin and Thornton, "Structural Families in Loops of Homologous Proteins: Automatic Classification, Modelling and Application to Antibodies.", J Bmol Biol, 1996, vol. 263, pp. 800-815.
Mayr et al., "Vaccination against pox diseases under immunosuppressive conditions", Dev. Biol. Stand., 1978, vol. 41, pp. 225-234.
Mclachlan et al., "Evaluation in vitro and in vivo of cationic liposome-expression construct complexes for cystic fibrosis gene therapy", Gene Therapy, 1995, vol. 2, No. 9, pp. 614-622.
Meisinger-Henschel et al., "Genomic sequence of chorioallantois vaccinia virus Ankara, the ancestor of modified vaccinia virus.", J. Gen. Virol., Dec. 2007, vol. 88, Part 12, pp. 3249-3259.
Mendez et al., "Functional transplant of megabase human immunoglobulin loci recapitulates human antibody response in mice.", Nat Genet., Feb. 1997, vol. 15, pp. 146-156.
Meyer, H. et al., "Mapping of deletions in the genome of the highly attenuated vaccinia virus MVA and their influence on virulence", J. Gen. Virol. Vol. 72, 1991, pp. 1031-1038.
Meyers et al., "Optimal alignments in linear space," Comput Appl Biosci, vol. 4, 1988, pp. 11-17.
Miller and Rossman, "Improved Retroviral Vectors for Gene Transfer and Expression", BioTechniques, Oct. 1989, vol. 7, No. 9, pp. 980-990.
Myers. E. W. et al, "Optimal alignments in linear space," Bioinformatics, vol. 4, Issue 1, Mar. 1988, pp. 11-17.

(56) References Cited

OTHER PUBLICATIONS

Needleman et al., "A General Method applicable to the search for similarities in the Amino acid sequence of two proteins" J. Mol. Biol., 1970, vol. 48, pp. 444-453.
Nicaise et al., "Affinity Transfer by CDR Grafting on a Nonimmunoglobulin Scaffold", Protein Sci., 2004, vol. 13, pp. 1882-1891.
Nygren and Uhlen, "Scaffolds for Engineering Novel Binding Sites in Proteins," Curr. Opin. Struc. Biol., 1997, vol. 7, pp. 463-469.
Padlan, E., "A Possible Procedure For Reducing The Immunogenicity of Antibody Variable Domains While Preserving Their Ligand-Binding Properties.", Mol Immunol, 1991, vol. 28, No. 4/5, pp. 489-499.
Parisa M. et al., "Neoantigen screening identifies broad TP53 mutant immunogenicity in patients with epithelial cancers," J Clin Invest, vol. 129, Issue 3, Mar. 2019, pp. 1109-1114.
Piccini et al., "Vaccina Virus as an Expression Vector", Methods of Enzymology, 1987, vol. 153, pp. 545-563.
Quetglas J I et al., "Alphavirus vectors for cancer therapy," Virus Research, Amsterdam, NL, vol. 153, Issue 2, Nov. 2010, pp. 179-196.
Rizvi et al., "Mutational landscape determines sensitivity to PD-1 blockade in non-small cell lung cancer.", Science, Apr. 3, 2015, vol. 348, No. 6230, pp. 124-128.
Robinson et al., "Integrative Clinical Genomics of Advanced Prostate Cancer", Cell, May 21, 2015, vol. 161, No. 5, pp. 1215-1228.
Rodenko et al., "Generation of peptide-MHC class I complexes through UV-mediated ligand exchange", Nature Protocols, 2006, vol. 1, No. 3, pp. 1120-1132.
Romani et al., "Presentation of exogenous protein antigens by dendritic cells to T cell clones. Intact protein is presented best by immature, epidermal Langerhans cells", J. Exp. Med., Mar. 1, 1989, vol. 169, No. 3, pp. 1169-1178.
Sheets et al., "Efficient construction of a large nonimmune phage antibody library: The production of high-affinity human single-chain antibodies to protein antigens.", PTAS (USA), May 1998, vol. 95, pp. 6157-6162.
Shi et al., "De Novo Selection of High-Affinity Antibodies from Synthetic Fab Libraries Displayed on Phage as pIX Fusion Proteins", J Mol Biol, 2010, vol. 397, pp. 385-396.
Skerra, A., "Alternative Non-Antibody Scaffolds for Molecular Recognition", Curr. Opin. Biotechnol., 2005, vol. 18, pp. 295-304.
Snyder et al., "Genetic Basis for Clinical Response to CTLA-4 Blockade in Melanoma.", N Enal J Med., Dec. 4, 2014, vol. 371, No. 23, pp. 2189-2199.
Sun et al., "An enhanced immune response against G250, induced by a heterologous DNA prime-protein boost vaccination, using polyethyleneimine as a DNA vaccine adjuvant", Mol. Med. Rep., 2014, vol. 10, No. 5, pp. 2657-2662.
Szoka et al., "Comparative properties and methods of preparation of lipid vesicles (liposomes).", Ann. Rev. Biophys. Bioena., 1980, vol. 9, pp. 467-508.
The Cancer Genome Atlas Research Network, "The Molecular taxonomy of primary prostate cancer.", Cell, Nov. 5, 2015, vol. 163, No. 4, pp. 1011-1025.
Tim Beissert et al., "Improvement of In Vivo Expression of Genes Delivered by Self-Amplifying RNA Using vaccinia Virus Immune Evasion Proteins," Homan Gene Therapy, vol. 28, Issue 12, Dec. 1, 2017, pp. 1138-1146.
Toebes et al., "Design and use of conditional MHC class I ligands.", Nat Med, Mar. 2006, vol. 12, No. 2, pp. 246-251.
Toribio et al., "New insights into the topology of the scanning ribosome during translation initiation: Lessons from viruses," Nucleic Acids Res, vol. 44, Issue 9, 2016, pp. 4368-4380.
Van Allen et al., "Genomic correlates of response to CTLA-4 blockade in metastatic melanoma.", Science, Oct. 9, 2015, vol. 350, No. 6257, pp. 207-211.
Vaughan et al., "Human Antibodies with Sub-nanomolar Affinities Isolated from a large Non-immunized Phage Display Library.", Nature Biotechnology, 1996, vol. 14, pp. 309-314.
Ventoso "Adaptive Changes in Alphavirus mRNA Translation Allowed Colonization of Vertebrate Hosts", vol. 86, Sep. 2012, pp. 9484-9494.
Wang et al., "A packaging cell line for propagation of recombinant adenovirus vectors containing two lethal gene-region deletions.", Gene Ther., 1995, vol. 2, pp. 775-783.
Woyke et al., "In Vitro Activities and Postantifungal Effects of the Potent Dolastatin 10 Derivative Auristatin PHE", Antimicrob agents and chemother., 2001, vol. 45, No. 12, pp. 3580-3584.
Wu et al., "An Analysis of the Sequences of the Variable Regions of Bence Jones Proteins and Myeloma Light Chains And Their Implications for Anti-body Complementarity", J Exp Med, 1970, vol. 132, pp. 211-250.
Yadav et al., "Predicting immunogenic tumour mutations by combining mass spectrometry and exome sequencing", Nature, 2014, vol. 515, pp. 572-576.
Yamada et al., Next-generation peptide vaccines for advanced cancer, Cancer Science, Dec. 4, 2012, vol. 104, No. 1, pp. 15-21.
Yang et al., "Eradication of Established Tumors by a Fully Human Monoclonal Antibody to the Epidermal Growth Factor Receptor without Concomitant Chemotherapy.", Cancer Res, Mar. 1999, vol. 59, pp. 1236-1243.
Yeh et al., "Efficient Dual Transcomplementation of Adenovirus E1 and E4 Regions from a 293-Derived Cell Line Expressing a Minimal E4 Functional Unit.", J. Viral., Jan. 1996, vol. 70, No. 1, pp. 559-565.
Zhang et al., "Integrate-neo: a pipeline for personalized gene fusion neoantigen discovery," Bioinformatics, vol. 33, Issue 4, Feb. 2017, pp. 555-557.

* cited by examiner

PROSTATE NEOANTIGENS AND THEIR USES

CROSS-REFERENCE TO RELATED APPLICATIONS

This application is a divisional of U.S. application Ser. No. 16/737,950, filed Jan. 9, 2020, which claims the benefit of U.S. Provisional Application Ser. No. 62/913,969, filed 11 Oct. 2019, U.S. Provisional Application Ser. No. 62/883,786, filed 7 Aug. 2019, U.S. Provisional Application Ser. No. 62/851,273, filed 22 May 2019, and U.S. Provisional Application Ser. No. 62/790,673, filed 10 Jan. 2019, the entire content of the aforementioned applications are incorporated herein by reference in its entirety.

SEQUENCE LISTING

The contents of the electronic sequence listing (103693002376_Sequence Listing.xml; Size: 1,025,506 bytes; and Date of Creation: Jun. 26, 2023) is herein incorporated by reference in its entirety.

BACKGROUND

Prostate cancer is the most common non-cutaneous malignancy in men and the second leading cause of death in men from cancer in the western world. Prostate cancer results from the uncontrolled growth of abnormal cells in the prostate gland. Once a prostate cancer tumor develops, androgens such as testosterone promote prostate cancer growth. At its early stages, localized prostate cancer is often curable with local therapy including, for example, surgical removal of the prostate gland and radiotherapy. However, when local therapy fails to cure prostate cancer, as it does in up to a third of men, the disease progresses into incurable metastatic disease.

For many years, the established standard of care for men with malignant castration-resistant prostate cancer (mCRPC) was docetaxel chemotherapy. More recently, abiraterone acetate (ZYTIGA®) in combination with prednisone has been approved for treating metastatic castrate resistant prostate cancer. Androgen receptor (AR)-targeted agents, such as enzalutamide (XTANDJ®) have also entered the market for treating metastatic castrate resistant prostate cancer. Platinum-based chemotherapy has been tested in a number of clinical studies in molecularly unselected prostate cancer patients with limited results and significant toxicities. However, there remains a subset of patients who either do not respond initially or become refractory (or resistant) to these treatments. No approved therapeutic options are available for such patients.

Therefore, a need remains for therapies against a prostate cancer, including hormone sensitive, hormone naive high risk, and castration-resistant prostate cancers.

BRIEF SUMMARY

The disclosure provides an isolated polynucleotide encoding a polypeptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides an isolated polynucleotide comprising a polynucleotide sequence of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 503, 504, 505, 506, 507, 508, 509, 510, 511, 512, 513, 514, 515, 516, 517, 519, 520, 521, 522, 523, 524, 525, 528, 529, 530, 531, 532, 533, 534, 535, 536, 537, 538, 539 or 540, or fragments thereof.

The disclosure also provides an isolated heterologous polynucleotide comprising two or more polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide encoding a heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated polypeptide comprising an amino acid sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides an isolated heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a vector comprising

- a polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof;
- one or more polynucleotides of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 or 458, or fragments thereof;
- a heterologous polynucleotide encoding a heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof; or
- a heterologous polynucleotide comprising two or more polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a recombinant human adenovirus (rAd) comprising the vector of the disclosure.

The disclosure also provides a recombinant modified vaccinia Ankara (rMVA) comprising the vector of the disclosure.

The disclosure also provides a recombinant great ape adenovirus (rGAd) comprising the vector of the disclosure.

The disclosure also provides a cell comprising or transduced with the vector of the disclosure or the recombinant virus of the disclosure.

The disclosure also provides a vaccine comprising the polynucleotide of the disclosure.

The disclosure also provides a vaccine comprising the heterologous polynucleotide of the disclosure.

The disclosure also provides a vaccine comprising the polypeptide of the disclosure.

The disclosure also provides a vaccine comprising the heterologous polypeptide of the disclosure.

The disclosure also provides a vaccine comprising the vector of the disclosure.

The disclosure also provides a vaccine comprising the rAd of the disclosure.

The disclosure also provides a vaccine comprising the rMVA of the disclosure.

The disclosure also provides a vaccine comprising the rGAd of the disclosure.

The disclosure also provides a vaccine comprising the cell of the disclosure.

The disclosure also provides a pharmaceutical composition comprising the vaccine of the disclosure and a pharmaceutically acceptable carrier or adjuvant.

The disclosure also provides a kit comprising one or more vaccines of the disclosure or the pharmaceutical composition of the disclosure.

The disclosure also provides a method of preventing or treating a prostate cancer in a subject, comprising administering to the subject a therapeutically effective amount of one or more vaccines of the disclosure or one or more pharmaceutical composition of the disclosure.

The disclosure also provides a method of inducing an immune response against one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof in a subject, comprising administering to the subject one or more vaccines of the disclosure.

The disclosure also provides an isolated heterologous polynucleotide encoding two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides a vector comprising:

a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;

a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24, 178, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 503, 504, 505, 506, 507, 508, 509, 510, 511, 512, 513, 514, 515, 516, 517, 519, 520, 521, 522, 523, 524, 525, 528, 529, 530, 531, 532, 533, 534, 535, 536, 537, 538, 539 and 540, and fragments thereof;

a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof;

a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof;

- a heterologous polynucleotide encoding the heterologous polypeptide of SEQ ID NOs: 541, 550, 554, 555, 556, 623 or 624;
- a heterologous polynucleotide encoding the heterologous polypeptide of SEQ ID NOs: 543, 552, 557, 558, 559, 625 or 626;
- a heterologous polynucleotide comprising a polynucleotide sequence of SEQ ID NO: 542 or SEQ ID NO: 551; or
- a heterologous polynucleotide comprising the polynucleotide sequence of SEQ ID NO: 544 or SEQ ID NO: 553.

The disclosure also provides a recombinant human adenovirus (rAd), comprising:

- a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;
- a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof;
- a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499 and fragments thereof; or
- a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a recombinant great ape adenovirus (rGAd), comprising:

- a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;

- a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof;
- a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof; or
- a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a recombinant modified vaccinia Ankara (rMVA), comprising:

- a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;
- a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof;
- a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof; or
- a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a vaccine comprising a rAd, comprising a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;

a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof;

a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof; or a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a vaccine comprising rGAd20, comprising a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;

a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof;

a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof; or a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a vaccine comprising rMVA comprising a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;

a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof;

a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof; or a heterologous polynucleotide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a vaccine comprising a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides a method of treating or preventing a prostate cancer in a subject, comprising:

administering to the subject a therapeutically effective amount of a vaccine comprising a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof as a prime; and administering to the subject a therapeutically effective amount of a vaccine comprising a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof as a boost; thereby treating or preventing the prostate cancer in the subject.

The disclosure also provides a vaccine comprising a heterologous polynucleotide encoding a heterologous polypeptide of SEQ ID NOs: 541, 550, 554, 555, 556, 623 or 624.

The disclosure also provides a vaccine comprising a heterologous polynucleotide encoding a heterologous polypeptide of SEQ ID NOs: 543, 552, 557, 558, 559, 625 or 626.

The disclosure also provides a method of treating or preventing a prostate cancer in a subject, comprising administering to the subject a first vaccine comprising a first heterologous polynucleotide encoding a first heterologous polypeptide, wherein the first heterologous polypeptide comprises two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177; and a second vaccine comprising a second heterologous polynucleotide encoding a second heterologous polypeptide, wherein the second heterologous polypeptide comprises two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177; wherein the first heterologous polypeptide and the second heterologous polypeptide have distinct amino acid sequences.

The disclosure also provides a method of inducing an immune response in a subject, comprising administering to the subject a first vaccine comprising a first heterologous polynucleotide encoding a first heterologous polypeptide, wherein the first heterologous polypeptide comprises two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177; and a second vaccine comprising a second heterologous polynucleotide encoding a second heterologous polypeptide, wherein the second heterologous polypeptide comprises two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177; wherein the first heterologous polypeptide and the second heterologous polypeptide have distinct amino acid sequences.

The disclosure also provides an isolated proteinaceous molecule that specifically binds the polypeptide of the disclosure.

The disclosure also provides a method of preventing or treating a prostate cancer in a subject, comprising administering to the subject the proteinaceous molecule of the disclosure. It is to be understood, that the above embodiments of the invention encompass polypeptides comprising, in addition to the specifically recited polypeptides and fragments thereof, also additional polypeptide sequences, including one or more polypeptides different from those specifically recited. Similarly, the above embodiments of the invention also encompass polynucleotides comprising, in addition to the specifically recited polynucleotides and fragments thereof, also additional polynucleotide sequences, including one or more polynucleotides different from those specifically recited.

DETAILED DESCRIPTION

Definitions

Figure 1:
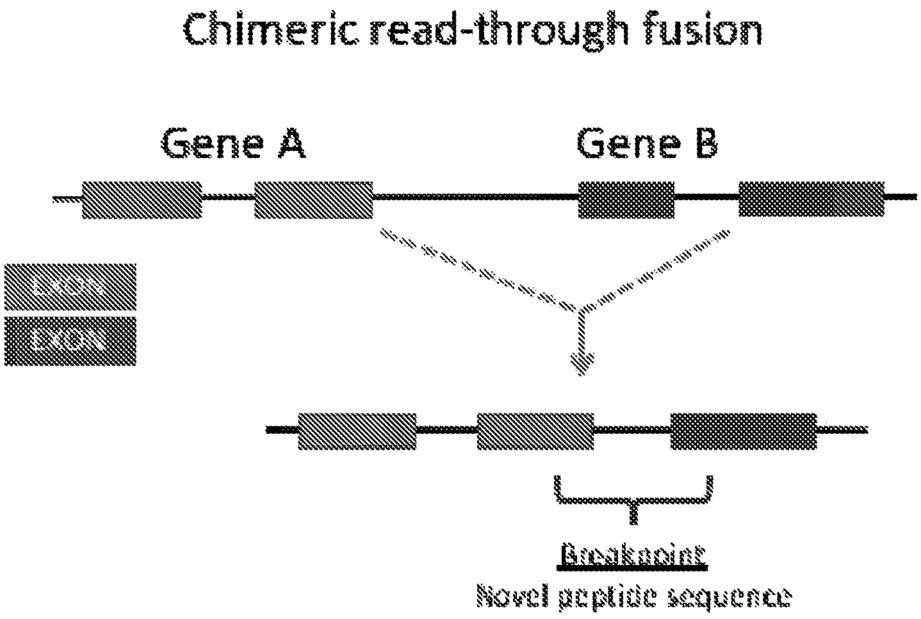
FIG. 1 shows a cartoon of chimeric read-through fusions between Gene A and Gene B. Neoantigenic peptide sequences arise at the breakpoint junction.

All publications, including but not limited to patents and patent applications, cited in this specification are herein incorporated by reference as though fully set forth.

It is to be understood that the terminology used herein is for describing particular embodiments only and is not intended to be limiting. Unless defined otherwise, all technical and scientific terms used herein have the same meaning as commonly understood by one of ordinary skill in the art to which the disclosure pertains.

Although any methods and materials similar or equivalent to those described herein may be used in the practice for testing of the present disclosure, exemplary materials and methods are described herein. In describing and claiming the present disclosure, the following terminology will be used.

As used in this specification and the appended claims, the singular forms "a," "an," and "the" include plural referents unless the content clearly dictates otherwise. Thus, for example, reference to "a cell" includes a combination of two or more cells, and the like.

The transitional terms "comprising," "consisting essentially of," and "consisting of" are intended to connote their generally accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed disclosure. Embodiments described in terms of the phrase "comprising" (or its equivalents) also provide as embodiments those independently described in terms of "consisting of" and "consisting essentially of."

As used in this specification and the appended claims, the phrase "and fragments thereof" when appended to a list includes fragments of one or more members of the associated list. The list may comprise a Markush group so that, as an example, the phrase "the group consisting of peptides A, B, and C, and fragments thereof" specifies or recites a Markush group including A, B, C, fragments of A, fragments of B, and/or fragments of C.

"Isolated" refers to a homogenous population of molecules (such as synthetic polynucleotides or polypeptides) which have been substantially separated and/or purified away from other components of the system the molecules are produced in, such as a recombinant cell, as well as a protein that has been subjected to at least one purification or isolation step. "Isolated" refers to a molecule that is substantially free of other cellular material and/or chemicals and encompasses molecules that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

"Polynucleotide" refers to a synthetic molecule comprising a chain of nucleotides covalently linked by a sugar-phosphate backbone or other equivalent covalent chemistry. cDNA is a typical example of a polynucleotide.

"Polypeptide" or "protein" refers to a molecule that comprises at least two amino acid residues linked by a peptide bond to form a polypeptide. Small polypeptides of less than 50 amino acids may be referred to as "peptides".

"Immunogenic fragment" refers to a polypeptide that is recognized by cytotoxic T lymphocytes, helper T lymphocytes or B cells when the fragment is in complex with MHC class I or MHC class II molecules.

"In-frame" refers to the reading frame of codons in a first polynucleotide being the same as the reading frame of codons in a second polynucleotide which are joined together to form a heterologous polynucleotide. In-frame heterologous polynucleotide encodes a heterologous polypeptide encoded by both the first polynucleotide and the second polynucleotide.

"Immunogenic" refers to a polypeptide that comprises one or more immunogenic fragments.

"Heterologous" refers to two or more polynucleotides or two or more polypeptides that are not found in the same relationship to each other in nature.

"Heterologous polynucleotide" refers to a non-naturally occurring polynucleotide that encodes two or more neoantigens as described herein.

"Heterologous polypeptide" refers to a non-naturally occurring polypeptide comprising two or more neoantigen polypeptides as described herein.

"Non-naturally occurring" refers to a molecule that does not exist in nature.

"Vector" refers to a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

"Expression vector" refers to a vector that can be utilized in a biological system or in a reconstituted biological system to direct the translation of a polypeptide encoded by a polynucleotide sequence present in the expression vector.

"Viral vector" refers to a vector construct that includes at least one polynucleotide element of viral origin and has the capacity to be packaged into a viral vector particle.

"Neoantigen" refers to a polypeptide that is present in prostate tumor tissue that has at least one alteration that makes it distinct from the corresponding wild-type polypeptide present in non-malignant tissue, e.g., via mutation in a tumor cell or post-translational modification specific to a tumor cell. A mutation can include a frameshift or nonframeshift insertion or deletion, missense or nonsense substitution, splice site alteration, aberrant splice variants, genomic rearrangement or gene fusion, or any genomic or expression alteration giving rise to the neoantigen.

"Prevalence" refers to a percentage of a population studied harboring a prostate neoantigen.

"Recombinant" refers to polynucleotides, polypeptides, vectors, viruses and other macromolecules that are prepared, expressed, created or isolated by recombinant means.

"Vaccine" refers to a composition that comprises one or more immunogenic polypeptides, immunogenic polynucleotides or fragments, or any combination thereof intentionally administered to induce acquired immunity in the recipient (e.g. subject).

"Treat", "treating" or "treatment" of a disease or disorder such as cancer refers to accomplishing one or more of the following: reducing the severity and/or duration of the disorder, inhibiting worsening of symptoms characteristic of the disorder being treated, limiting or preventing recurrence of the disorder in subjects that have previously had the disorder, or limiting or preventing recurrence of symptoms in subjects that were previously symptomatic for the disorder.

"Prevent", "preventing", "prevention", or "prophylaxis" of a disease or disorder means preventing that a disorder occurs in subject.

"Therapeutically effective amount" refers to an amount effective, at doses and for periods of time necessary, to achieve a desired therapeutic result. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient.

"Relapsed" refers to the return of a disease or the signs and symptoms of a disease after a period of improvement after prior treatment with a therapeutic.

"Refractory" refers to a disease that does not respond to a treatment. A refractory disease can be resistant to a treatment before or at the beginning of the treatment, or a refractory disease can become resistant during a treatment.

"Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. The terms "subject" and "patient" can be used interchangeably herein.

"In combination with" means that two or more therapeutic agents are be administered to a subject together in a mixture, concurrently as single agents or sequentially as single agents in any order.

"Enhance" or "induce" when in reference to an immune response refers to increasing the scale and/or efficiency of an immune response or extending the duration of the immune response. The terms are used interchangeably with "augment".

"Immune response" refers to any response to an immunogenic polypeptide or polynucleotide or fragment by the immune system of a vertebrate subject. Exemplary immune responses include local and systemic cellular as well as humoral immunity, such as cytotoxic T lymphocyte (CTL) responses, including antigen-specific induction of CD8*CTLs, helper T-cell responses including T-cell proliferative responses and cytokine release, and B-cell responses including antibody response.

"Specifically binds", "specific binding", "specifically binding" or "binds" refer to a proteinaceous molecule binding to an antigen or an epitope within the antigen (e.g. to prostate neoantigen) with greater affinity than for other antigens. Typically, the proteinaceous molecule binds to the antigen or the epitope within the antigen with an equilibrium dissociation constant ($K_D$) of about $1\times10^{-7}$ M or less, for example about $5\times10^{-8}$ M or less, about $1\times10^{-8}$ M or less, about $1\times10^{-9}$ M or less, about $1\times10^{-10}$ M or less, about $1\times10^{-11}$ M or less, or about $1\times10^{-12}$ M or less, typically with the $K_D$ that is at least one hundred fold less than its $K_D$ for binding to a non-specific antigen (e.g., BSA, casein). In the context of the prostate neoantigens described here, "specific binding" refers to binding of the proteinaceous molecule to the prostate neoantigen without detectable binding to a wild-type protein the neoantigen is a variant of.

"Variant", "mutant" or "altered" refers to a polypeptide or a polynucleotide that differs from a reference polypeptide or a reference polynucleotide by one or more modifications, for example one or more substitutions, insertions or deletions.

"Antibody" refers to an immunoglobulin molecule including monoclonal antibodies including murine, human, humanized and chimeric monoclonal antibodies, antigen-binding fragments, bispecific or multispecific antibodies, dimeric, tetrameric or multimeric antibodies, single chain antibodies, domain antibodies and any other modified configuration of the immunoglobulin molecule that comprises an antigen binding site of the required specificity.

"Full length antibody" is comprised of two heavy chains (HC) and two light chains (LC) inter-connected by disulfide bonds as well as multimers thereof (e.g. IgM). Each heavy chain is comprised of a heavy chain variable domain (VH) and a heavy chain constant domain, the heavy chain constant domain comprised of subdomains CH1, hinge, CH2 and CH3. Each light chain is comprised of a light chain variable domain (VL) and a light chain constant domain (CL). The VH and the VL may be further subdivided into regions of hypervariability, termed complementarity determining regions (CDR), interspersed with framework regions (FR). Each VH and VL is composed of three CDRs and four FR segments, arranged from amino-to-carboxy-terminus in the following order: FR1, CDR1, FR2, CDR2, FR3, CDR3 and FR4.

"Complementarity determining regions (CDR)" are antibody regions that bind an antigen. There are three CDRs in the VH (HCDR1, HCDR2, HCDR3) and three CDRs in the VL (LCDR1, LCDR2, LCDR3). CDRs may be defined using various delineations such as Kabat (Wu et al. (1970) J Exp Med 132: 211-50; Kabat et al., Sequences of Proteins of Immunological Interest, 5th Ed. Public Health Service, National Institutes of Health, Bethesda, Md., 1991), Chothia (Chothia et al. (1987) J Mol Biol 196: 901-17), IMGT (Lefranc et al. (2003) Dev Comp Immunol 27: 55-77) and AbM (Martin and Thornton J Bmol Biol 263: 800-15, 1996). The correspondence between the various delineations and variable region numbering are described (see e.g. Lefranc et al. (2003) Dev Comp Immunol 27: 55-77; Honegger and Pluckthun, J Mol Biol (2001) 309:657-70; International ImMunoGeneTics (IMGT) database; Web resources, http://www-imgt-org). Available programs such as abYsis by UCL Business PLC may be used to delineate CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification.

Immunoglobulins may be assigned to five major classes, IgA, IgD, IgE, IgG and IgM, depending on the heavy chain constant region amino acid sequence. IgA and IgG are further sub-classified as isotypes IgA1, IgA2, IgG1, IgG2, IgG3 and IgG4. Antibody light chains of any vertebrate species may be assigned to one of two clearly distinct types, namely kappa (w) and lambda (λ), based on the amino acid sequences of their constant domains.

"Antigen-binding fragment" refers to a portion of an immunoglobulin molecule that retains the antigen binding properties of the parental full length antibody. Exemplary antigen-binding fragments are heavy chain complementarity determining regions (HCDR) 1, 2 and/or 3, light chain complementarity determining regions (LCDR) 1, 2 and/or 3, the VH, the VL, the VH and the VL, Fab, F(ab')2, Fd and Fv fragments as well as domain antibodies (dAb) consisting of either one VH domain or one VL domain. The VH and the VL domains may be linked together via a synthetic linker to form various types of single chain antibody designs in which the VH/VL domains pair intramolecularly, or intermolecularly in those cases when the VH and VL domains are expressed by separate chains, to form a monovalent antigen binding site, such as single chain Fv (scFv) or diabody; described for example in Int. Pat. Publ. No. WO1998/44001, Int. Pat. Publ. No. WO1988/01649, Int. Pat. Publ. No. WO1994/13804 or Int. Pat. Publ. No. WO1992/01047.

"Monoclonal antibody" refers to an antibody obtained from a substantially homogenous population of antibody molecules, i.e., the individual antibodies comprising the population are identical except for possible well-known alterations such as removal of C-terminal lysine from the antibody heavy chain or post-translational modifications such as amino acid isomerization or deamidation, methionine oxidation or asparagine or glutamine deamidation. Monoclonal antibodies typically bind one antigenic epitope. A bispecific monoclonal antibody binds two distinct antigenic epitopes. Monoclonal antibodies may have heterogeneous glycosylation within the antibody population. Monoclonal antibody may be monospecific or multispecific such as bispecific, monovalent, bivalent or multivalent.

"Humanized antibody" refers to an antibody in which at least one CDR is derived from non-human species and at least one framework is derived from human immunoglobulin sequences. Humanized antibody may include substitutions in the frameworks so that the frameworks may not be exact copies of expressed human immunoglobulin or human immunoglobulin germline gene sequences.

"Human antibody" refers to an antibody that is optimized to have minimal immune response when administered to a human subject. Variable regions of human antibody are derived from human immunoglobulin sequences. If human antibody contains a constant region or a portion of the constant region, the constant region is also derived from human immunoglobulin sequences. Human antibody comprises heavy and light chain variable regions that are "derived from" sequences of human origin if the variable regions of the human antibody are obtained from a system that uses human germline immunoglobulin or rearranged immunoglobulin genes. Such exemplary systems are human immunoglobulin gene libraries displayed on phage, and transgenic non-human animals such as mice or rats carrying human immunoglobulin loci. "Human antibody" typically contains amino acid differences when compared to the immunoglobulins expressed in humans due to differences between the systems used to obtain the human antibody and human immunoglobulin loci, introduction of somatic mutations or intentional introduction of substitutions into the frameworks or CDRs, or both. Typically, "human antibody" is at least about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin or rearranged immunoglobulin genes. In some cases, "human antibody" may contain consensus framework sequences derived from human framework sequence analyses, for example as described in Knappik et al., (2000) J Mol Biol 296:57-86, or a synthetic HCDR3 incorporated into human immunoglobulin gene libraries displayed on phage, for example as described in Shi et al., (2010) J Mol Biol 397:385-96, and in Int. Patent Publ. No. WO2009/085462. Antibodies in which at least one CDR is derived from a non-human species are not included in the definition of "human antibody".

"Alternative scaffold" refers to a single chain protein framework that contains a structured core associated with variable domains of high conformational tolerance. The variable domains tolerate variation to be introduced without compromising scaffold integrity, and hence the variable domains can be engineered and selected for binding to a specific antigen.

"Chimeric antigen receptor" or "CAR" refers to engineered T cell receptors which graft a ligand or antigen specificity onto T cells (for example naïve T cells central memory T cells effector memory T cells or combinations thereof). CARs are also known as artificial T-cell receptors, chimeric T-cell receptors or chimeric immunoreceptors. CARs comprise an extracellular domain capable of binding to an antigen, a transmembrane domain and at least one intracellular domain. CAR intracellular domain comprises a polypeptide known to function as a domain that transmits a signal to cause activation or inhibition of a biological process in a cell. The transmembrane domain comprises any peptide or polypeptide known to span the cell membrane and that can function to link the extracellular and signaling domains. A chimeric antigen receptor may optionally comprise a hinge domain which serves as a linker between the extracellular and transmembrane domains.

"T cell receptor" or "TCR" refers to a molecule capable of recognizing a peptide when presented by an MHC molecule. Naturally-occurring TCR heterodimer consists of an alpha (a) and beta (3) chain in around 95% of T-cells, whereas around 5% of T-cells have TCRs consisting of gamma (γ) and delta (6) chains. Each chain of a natural TCR is a member of the immunoglobulin superfamily and possesses one N-terminal immunoglobulin (Ig)-variable (V) domain, one Ig-constant (C) domain, a transmembrane/cell membrane-spanning region, and a short cytoplasmic tail at the C-terminal end. The variable domain of both the TCR a chain and 3 chain have three hypervariable or complementarity determining regions (CDRs), CDR1, CDR2 and CDR3, which are responsible for recognizing processed antigens presented on MHC.

TCR may be a full length α/β or γ/δ heterodimer or a soluble molecule comprising a portion of the extracellular domain of the TCR that retains binding the peptide/MHC complex. TCR may be engineered into a single chain TCR.

"T cell receptor complex" or "TCR complex" refers to a known TCR complex comprising of a TCRα and TCRβ chains, CD3ε, CD3γ, CD3δ and CD3ζ molecules. In some instances, TCRα and TCRβ chains are replaced by TCRγ and TCRδ chains. The amino acid sequences of the various proteins forming the TCR complex are well-known.

"T cell" and "T lymphocyte" are interchangeable and used synonymously herein. T cell includes thymocytes, naïve T lymphocytes, memory T cells, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; $CD4^+$ T cell) $CD4^+$ T cell, a cytotoxic T cell (CTL; $CD8^+$ T cell), a tumor infiltrating cytotoxic T cell (TIL; $CD8^+$ T cell), $CD4^*CD8^+$ T cell, or any other subset of T cells. Also included are "NKT cells", which refer to a specialized population of T cells that express a semi-invariant αβ T-cell receptor, but also express a variety of molecular markers that are typically associated with NK cells, such as NK1.1. NKT cells include $NK1.1^+$ and $NK1.1^-$, as well as $CD4^+$, $CD4^-$, $CD8^+$ and $CD8^-$ cells. The TCR on NKT cells is unique in that it recognizes glycolipid antigens presented by the MHC I-like molecule CD Id. NKT cells can have either protective or deleterious effects due to their abilities to produce cytokines that promote either inflammation or immune tolerance. Also included are "gamma-delta T cells (γδ T cells)," which refer to a specialized population that to a small subset of T cells possessing a distinct TCR on their surface, and unlike the majority of T cells in which the TCR is composed of two glycoprotein chains designated α- and β-TCR chains, the TCR in γδ T cells is made up of a γ-chain and a δ-chain. γδ T cells can play a role in immunosurveillance and immunoregulation, and were found to be an important source of IL-17 and to induce robust $CD8^+$ cytotoxic T cell response. Also included are "regulatory T cells" or "Tregs" which refer to T cells that suppress an abnormal or excessive immune response and play a role in immune tolerance. Tregs are typically transcription factor Foxp3-positive $CD4^+$ T cells and can also include transcription factor Foxp3-negative regulatory T cells that are IL-10-producing $CD4^+$ T cells.

"Natural killer cell" or "NK cell" refers to a differentiated lymphocyte with a CD $16^+$ $CD56^+$ and/or $CD57^+$ $TCR^-$ phenotype. NKs are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

"Antigen presenting cell" (APC) refers to any cell that presents on its surface an antigen in association with a major histocompatibility complex molecule, either MHC class I or MHC class II molecule, or both.

"Prime-boost" or "prime-boost regimen" refers to a method of treating a subject involving priming a T-cell response with a first vaccine followed by boosting the immune response with a second vaccine. The first vaccine and the second vaccine are typically distinct. These prime-boost immunizations elicit immune responses of greater height and breadth than can be achieved by priming and boosting with the same vaccine. The priming step initiates memory cells and the boost step expands the memory response. Boosting can occur once or multiple times.

"Facilitator element" refers to any polynucleotide or polypeptide element that is operably linked to a polynucleotide or a polypeptide, and include promoters, enhancers, polyadenylation signals, stop codons, protein tags, such as histidine tag, and the like. Facilitator elements herein include regulatory elements.

"Distinct" in the context of polypeptide or polynucleotide sequences refers to polypeptide or polynucleotide sequences that are not identical.

Compositions of Matter

The disclosure relates to prostate neoantigens, polynucleotides encoding them, vectors, host cells, vaccines comprising the neoantigens or polynucleotides encoding the neoantigens, proteinaceous molecules binding the prostate neoantigens, and methods of making and using them. The disclosure also provides vaccines comprising the prostate neoantigens of the disclosure that are prevalent in a population of prostate cancer patients, thereby providing a pan-vaccine that may be useful to treating a broad population of patients having diagnosed with various stages of prostate cancer, such as localized or metastasized prostate cancer.

Cancer cells produce neoantigens that result from genomic alterations and aberrant transcriptional programs. Neoantigen burden in patients has been associated with response to immunotherapy (Snyder et al., N Engl J Med. 2014 Dec. 4; 371(23):2189-2199. doi: 10.1056/NEJMoa1406498. Epub 2014 Nov. 19; Le et al., N Engl J Med. 2015 Jun. 25; 372(26):2509-20. doi: 10.1056/NEJMoa1500596. Epub 2015 May 30; Rizvi et al., Science. 2015 Apr. 3; 348(6230):124-8. doi: 10.1126/science.aaa1348. Epub 2015 Mar. 12; Van Allen et al., Science. 2015 Oct. 9; 350(6257):207-211. doi: 10.1126/science.aad0095. Epub 2015 Sep. 10). The disclosure is based, at least in part, on the identification of prostate neoantigens that are common in prostate cancer patients and hence can be utilized to develop a therapy amenable to treatment of a spectrum of prostate cancer patients. One or more neoantigens or polynucleotides encoding the neoantigens of the disclosure may also be used for diagnostic or prognostic purposes.

Polypeptides and Polynucleotides of the Disclosure

The disclosure provides an isolated polynucleotide encoding a polypeptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297,299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides an isolated polynucleotide comprising a polynucleotide sequence of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 or 458, or fragments thereof The disclosure also provides an isolated polynucleotide comprising a polynucleotide sequence of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 or 540, or fragments thereof.

The disclosure also provides an isolated heterologous polynucleotide comprising two or more polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide encoding a heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the fragments comprise at least 18 nucleotides. In some embodiments, the fragments comprise at least 21 nucleotides. In some embodiments, the fragments comprise at least 24 nucleotides. In some embodiments, the fragments comprise at least 27 nucleotides. In some embodiments, the fragments comprise at least 30 nucleotides. In some embodiments, the fragments comprise at least 33 nucleotides. In some embodiments, the fragments comprise at least 36 nucleotides. In some embodiments, the fragments comprise at least 39 nucleotides. In some embodiments, the fragments comprise at least 42 nucleotides. In some embodiments, the fragments comprise at least 45 nucleotides. In some embodiments, the fragments comprise at least 48 nucleotides. In some embodiments, the fragments comprise at least 51 nucleotides. In some embodiments, the fragments comprise at least 54 nucleotides. In some embodiments, the fragments comprise at least 57 nucleotides. In some embodiments, the fragments comprise at least 60 nucleotides. In some embodiments, the fragments comprise at least 63 nucleotides. In some embodiments, the fragments comprise at least 66 nucleotides. In some embodiments, the fragments comprise at least 69 nucleotides. In some embodiments, the fragments comprise at least 72 nucleotides. In some embodiments, the fragments comprise at least 75 nucleotides. In some embodiments, the fragments comprise about 18 nucleotides. In some embodiments, the fragments comprise about 21 nucleotides. In some embodiments, the fragments comprise about 24 nucleotides. In some embodiments, the fragments comprise about 27 nucleotides. In some embodiments, the fragments comprise about 30 nucleotides. In some embodiments, the fragments comprise about 33 nucleotides. In some embodiments, the fragments comprise about 36 nucleotides. In some embodiments, the fragments comprise about 39 nucleotides. In some embodiments, the fragments comprise about 42 nucleotides. In some embodiments, the fragments comprise about 45 nucleotides. In some embodiments, the fragments comprise about 48 nucleotides. In some embodiments, the fragments comprise about 51 nucleotides. In some embodiments, the fragments comprise about 54 nucleotides. In some embodiments, the fragments comprise about 57 nucleotides. In some embodiments, the fragments comprise about 60 nucleotides. In some embodiments, the fragments comprise about 63 nucleotides. In some embodiments, the fragments comprise about 66 nucleotides. In some embodiments, the fragments comprise about 69 nucleotides. In some embodiments, the fragments comprise about 72 nucleotides. In some embodiments, the fragments comprise about 75 nucleotides. In some embodiments, the fragments comprise about 18-75 nucleotides. In some embodiments, the fragments comprise about 21-75 nucleotides. In some embodiments, the fragments comprise about 24-75 nucleotides. In some embodiments, the fragments comprise about 24-72 nucleotides. In some embodiments, the fragments comprise about 24-69 nucleotides. In some embodiments, the fragments comprise about 24-66 nucleotides. In some embodiments, the fragments comprise about 24-63 nucleotides. In some embodiments, the fragments comprise about 24-60 nucleotides. In some embodiments, the fragments comprise about 24-57 nucleotides. In some embodiments, the fragments comprise about 24-54 nucleotides. In some embodiments, the fragments comprise about 24-51 nucleotides. In some embodiments, the fragments comprise about 24-48 nucleotides. In some embodiments, the fragments comprise about 24-45 nucleotides. In some embodiments, the fragments comprise about 24-42 nucleotides. In some embodiments, the fragments comprise about 27-42 nucleotides. In some embodiments, the fragments comprise about 27-39 nucleotides. In some embodiments, the fragments comprise about 27-36 nucleotides. In some embodiments, the fragments comprise about 27-33 nucleotides. In some embodiments, the fragments comprise about 27-30 nucleotides.

The polynucleotides and the heterologous polynucleotides of the disclosure encode the prostate neoantigens and heterologous polypeptides comprising two or more prostate neoantigens described herein. The polynucleotides and the heterologous polynucleotides of the disclosure are useful in generating the polypeptides, the heterologous polypeptides, the vectors, the recombinant viruses, the cells and the vaccines of the disclosure. The polynucleotides and the heterologous polynucleotides of the disclosure may be utilized as therapeutics by delivering them to a subject having a prostate cancer using various technologies, including viral vectors as described herein or other delivery technologies as also described herein.

The disclosure also provides an isolated polynucleotide encoding the polypeptide of SEQ ID NO: 1 or a fragment thereof. In some embodiments, the polypeptide of SEQ ID NO: 1, or a fragment thereof, is encoded by the polynucleotide of SEQ ID NO: 2 or a fragment thereof.

The disclosure also provides an isolated polynucleotide encoding the polypeptide of SEQ ID NO: 3 or a fragment thereof. In some embodiments, the polypeptide of SEQ ID NO: 3, or a fragment thereof, is encoded by the polynucleotide of SEQ ID NO: 4 or a fragment thereof.

The disclosure also provides an isolated polynucleotide encoding the polypeptide of SEQ ID NO: 5 or a fragment thereof. In some embodiments, the polypeptide of SEQ ID NO: 5, or a fragment thereof, is encoded by the polynucleotide of SEQ ID NO: 6 or a fragment thereof.

The disclosure also provides an isolated polynucleotide encoding the polypeptide of SEQ ID NO: 7 or a fragment thereof. In some embodiments, the polypeptide of SEQ ID NO: 7, or a fragment thereof, is encoded by the polynucleotide of SEQ ID NO: 8 or a fragment thereof.

The disclosure also provides an isolated polynucleotide encoding the polypeptide of SEQ ID NO: 9 or a fragment thereof. In some embodiments, the polypeptide of SEQ ID NO: 9, or a fragment thereof, is encoded by the polynucleotide of SEQ ID NO: 10 or a fragment thereof.

The disclosure also provides an isolated polynucleotide encoding the polypeptide of SEQ ID NO: 11 or a fragment thereof. In some embodiments, the polypeptide of SEQ ID NO: 11, or a fragment thereof, is encoded by the polynucleotide of SEQ ID NO: 12 or a fragment thereof.

The disclosure also provides an isolated polynucleotide encoding the polypeptide of SEQ ID NO: 13 or a fragment thereof. In some embodiments, the polypeptide of SEQ ID NO: 13, or a fragment thereof, is encoded by the polynucleotide of SEQ ID NO: 14 or a fragment thereof.

The disclosure also provides an isolated polynucleotide encoding the polypeptide of SEQ ID NO: 15 or a fragment thereof. In some embodiments, the polypeptide of SEQ ID NO: 15, or a fragment thereof, is encoded by the polynucleotide of SEQ ID NO: 16 or a fragment thereof.

The disclosure also provides an isolated polynucleotide encoding the polypeptide of SEQ ID NO: 17 or a fragment thereof. In some embodiments, the polypeptide of SEQ ID NO: 17, or a fragment thereof, is encoded by the polynucleotide of SEQ ID NO: 18 or a fragment thereof.

The disclosure also provides an isolated polynucleotide encoding the polypeptide of SEQ ID NO: 19 or a fragment thereof. In some embodiments, the polypeptide of SEQ ID NO: 19, or a fragment thereof, is encoded by the polynucleotide of SEQ ID NO: 20 or a fragment thereof. In some embodiments, the polypeptide of SEQ ID NO: 19, or a fragment thereof, is encoded by the polynucleotide of SEQ ID NO: 497 or a fragment thereof. In some embodiments, the polypeptide of SEQ ID NO: 19, or a fragment thereof, is encoded by the polynucleotide of SEQ ID NO: 538 or a fragment thereof.

The disclosure also provides an isolated polynucleotide encoding the polypeptide of SEQ ID NO: 21 or a fragment thereof. In some embodiments, the polypeptide of SEQ ID NO: 21, or a fragment thereof, is encoded by the polynucleotide of SEQ ID NO: 22 or a fragment thereof.

The disclosure also provides an isolated polynucleotide encoding the polypeptide of SEQ ID NO: 23 or a fragment thereof. In some embodiments, the polypeptide of SEQ ID NO: 23, or a fragment thereof, is encoded by the polynucleotide of SEQ ID NO: 24 or a fragment thereof. In some embodiments, the polypeptide of SEQ ID NO: 23, or a fragment thereof, is encoded by the polynucleotide of SEQ ID NO: 498 or a fragment thereof. In some embodiments, the polypeptide of SEQ ID NO: 23, or a fragment thereof, is encoded by the polynucleotide of SEQ ID NO: 539 or a fragment thereof.

The disclosure also provides an isolated polynucleotide encoding the polypeptide of SEQ ID NO: 25 or a fragment thereof. In some embodiments, the polypeptide of SEQ ID NO: 25, or a fragment thereof, is encoded by the polynucleotide of SEQ ID NO: 26 or a fragment thereof.

The disclosure also provides an isolated polynucleotide encoding the polypeptide of SEQ ID NO: 27 or a fragment thereof. In some embodiments, the polypeptide of SEQ ID NO: 27, or a fragment thereof, is encoded by the polynucleotide of SEQ ID NO: 28 or a fragment thereof.

The disclosure also provides an isolated polynucleotide encoding the polypeptide of SEQ ID NO: 29 or a fragment thereof. In some embodiments, the polypeptide of SEQ ID NO: 29, or a fragment thereof, is encoded by the polynucleotide of SEQ ID NO: 30 or a fragment thereof.

The disclosure also provides an isolated polynucleotide encoding the polypeptide of SEQ ID NO: 31 or a fragment thereof. In some embodiments, the polypeptide of SEQ ID NO: 31, or a fragment thereof, is encoded by the polynucleotide of SEQ ID NO: 32 or a fragment thereof.

The disclosure also provides an isolated polynucleotide encoding the polypeptide of SEQ ID NO: 33 or a fragment thereof. In some embodiments, the polypeptide of SEQ ID NO: 33, or a fragment thereof, is encoded by the polynucleotide of SEQ ID NO: 34 or a fragment thereof.

The disclosure also provides an isolated polynucleotide encoding the polypeptide of SEQ ID NO: 35 or a fragment thereof. In some embodiments, the polypeptide of SEQ ID NO: 35, or a fragment thereof, is encoded by the polynucleotide of SEQ ID NO: 36 or a fragment thereof.

The disclosure also provides an isolated polynucleotide encoding the polypeptide of SEQ ID NO: 37 or a fragment thereof. In some embodiments, the polypeptide of SEQ ID NO: 37, or a fragment thereof, is encoded by the polynucleotide of SEQ ID NO: 38 or a fragment thereof.

The disclosure also provides an isolated polynucleotide encoding the polypeptide of SEQ ID NO: 39 or a fragment thereof. In some embodiments, the polypeptide of SEQ ID NO: 39, or a fragment thereof, is encoded by the polynucleotide of SEQ ID NO: 40 or a fragment thereof.

The disclosure also provides an isolated polynucleotide encoding the polypeptide of SEQ ID NO: 41 or a fragment thereof. In some embodiments, the polypeptide of SEQ ID NO: 41, or a fragment thereof, is encoded by the polynucleotide of SEQ ID NO: 42 or a fragment thereof.

The disclosure also provides an isolated polynucleotide encoding the polypeptide of SEQ ID NO: 43 or a fragment thereof. In some embodiments, the polypeptide of SEQ ID NO: 43, or a fragment thereof, is encoded by the polynucleotide of SEQ ID NO: 44 or a fragment thereof.

The disclosure also provides an isolated polynucleotide encoding the polypeptide of SEQ ID NO: 45 or a fragment thereof. In some embodiments, the polypeptide of SEQ ID NO: 45, or a fragment thereof, is encoded by the polynucleotide of SEQ ID NO: 46 or a fragment thereof.

The disclosure also provides an isolated polynucleotide encoding the polypeptide of SEQ ID NO: 47 or a fragment thereof. In some embodiments, the polypeptide of SEQ ID NO: 47, or a fragment thereof, is encoded by the polynucleotide of SEQ ID NO: 48 or a fragment thereof.

The disclosure also provides an isolated polynucleotide encoding the polypeptide of SEQ ID NO: 49 or a fragment thereof. In some embodiments, the polypeptide of SEQ ID NO: 49, or a fragment thereof, is encoded by the polynucleotide of SEQ ID NO: 50 or a fragment thereof.

The disclosure also provides an isolated polynucleotide encoding the polypeptide of SEQ ID NO: 51 or a fragment thereof. In some embodiments, the polypeptide of SEQ ID NO: 51, or a fragment thereof, is encoded by the polynucleotide of SEQ ID NO: 52 or a fragment thereof.

The disclosure also provides an isolated polynucleotide encoding the polypeptide of SEQ ID NO: 53 or a fragment thereof. In some embodiments, the polypeptide of SEQ ID NO: 53, or a fragment thereof, is encoded by the polynucleotide of SEQ ID NO: 54 or a fragment thereof.

The disclosure also provides an isolated polynucleotide encoding the polypeptide of SEQ ID NO: 55 or a fragment thereof. In some embodiments, the polypeptide of SEQ ID NO: 55, or a fragment thereof, is encoded by the polynucleotide of SEQ ID NO: 56 or a fragment thereof.

The disclosure also provides an isolated polynucleotide encoding the polypeptide of SEQ ID NO: 57 or a fragment thereof. In some embodiments, the polypeptide of SEQ ID NO: 57, or a fragment thereof, is encoded by the polynucleotide of SEQ ID NO: 58 or a fragment thereof.

The disclosure also provides an isolated polynucleotide encoding the polypeptide of SEQ ID NO: 59 or a fragment thereof. In some embodiments, the polypeptide of SEQ ID NO: 59, or a fragment thereof, is encoded by the polynucleotide of SEQ ID NO: 60 or a fragment thereof.

The disclosure also provides an isolated polynucleotide encoding the polypeptide of SEQ ID NO: 61 or a fragment thereof. In some embodiments, the polypeptide of SEQ ID NO: 61, or a fragment thereof, is encoded by the polynucleotide of SEQ ID NO: 62 or a fragment thereof.

The disclosure also provides an isolated polynucleotide encoding the polypeptide of SEQ ID NO: 63 or a fragment thereof. In some embodiments, the polypeptide of SEQ ID NO: 63, or a fragment thereof, is encoded by the polynucleotide of SEQ ID NO: 64 or a fragment thereof.

The disclosure also provides an isolated polynucleotide encoding the polypeptide of SEQ ID NO: 65 or a fragment thereof. In some embodiments, the polypeptide of SEQ ID NO: 65, or a fragment thereof, is encoded by the polynucleotide of SEQ ID NO: 66 or a fragment thereof.

The disclosure also provides an isolated polynucleotide encoding the polypeptide of SEQ ID NO: 67 or a fragment thereof. In some embodiments, the polypeptide of SEQ ID NO: 67, or a fragment thereof, is encoded by the polynucleotide of SEQ ID NO: 68 or a fragment thereof.

The disclosure also provides an isolated polynucleotide encoding the polypeptide of SEQ ID NO: 69 or a fragment thereof. In some embodiments, the polypeptide of SEQ ID NO: 69, or a fragment thereof, is encoded by the polynucleotide of SEQ ID NO: 70 or a fragment thereof.

The disclosure also provides an isolated polynucleotide encoding the polypeptide of SEQ ID NO: 71 or a fragment thereof. In some embodiments, the polypeptide of SEQ ID NO: 71, or a fragment thereof, is encoded by the polynucleotide of SEQ ID NO: 72 or a fragment thereof.

The disclosure also provides an isolated polynucleotide encoding the polypeptide of SEQ ID NO: 73 or a fragment thereof. In some embodiments, the polypeptide of SEQ ID NO: 73, or a fragment thereof, is encoded by the polynucleotide of SEQ ID NO: 74 or a fragment thereof.

The disclosure also provides an isolated polynucleotide encoding the polypeptide of SEQ ID NO: 75 or a fragment thereof. In some embodiments, the polypeptide of SEQ ID NO: 75, or a fragment thereof, is encoded by the polynucleotide of SEQ ID NO: 76 or a fragment thereof.

The disclosure also provides an isolated polynucleotide encoding the polypeptide of SEQ ID NO: 77 or a fragment thereof. In some embodiments, the polypeptide of SEQ ID NO: 77, or a fragment thereof, is encoded by the polynucleotide of SEQ ID NO: 78 or a fragment thereof.

The disclosure also provides an isolated polynucleotide encoding the polypeptide of SEQ ID NO: 79 or a fragment thereof. In some embodiments, the polypeptide of SEQ ID NO: 79, or a fragment thereof, is encoded by the polynucleotide of SEQ ID NO: 80 or a fragment thereof.

The disclosure also provides an isolated polynucleotide encoding the polypeptide of SEQ ID NO: 81 or a fragment thereof. In some embodiments, the polypeptide of SEQ ID NO: 81, or a fragment thereof, is encoded by the polynucleotide of SEQ ID NO: 82 or a fragment thereof.

The disclosure also provides an isolated polynucleotide encoding the polypeptide of SEQ ID NO: 83 or a fragment thereof. In some embodiments, the polypeptide of SEQ ID NO: 83, or a fragment thereof, is encoded by the polynucleotide of SEQ ID NO: 84 or a fragment thereof.

The disclosure also provides an isolated polynucleotide encoding the polypeptide of SEQ ID NO: 85 or a fragment thereof. In some embodiments, the polypeptide of SEQ ID NO: 85, or a fragment thereof, is encoded by the polynucleotide of SEQ ID NO: 86 or a fragment thereof.

The disclosure also provides an isolated polynucleotide encoding the polypeptide of SEQ ID NO: 87 or a fragment thereof. In some embodiments, the polypeptide of SEQ ID NO: 87, or a fragment thereof, is encoded by the polynucleotide of SEQ ID NO: 88 or a fragment thereof.

The disclosure also provides an isolated polynucleotide encoding the polypeptide of SEQ ID NO: 89 or a fragment thereof. In some embodiments, the polypeptide of SEQ ID NO: 89, or a fragment thereof, is encoded by the polynucleotide of SEQ ID NO: 90 or a fragment thereof.

The disclosure also provides an isolated polynucleotide encoding the polypeptide of SEQ ID NO: 91 or a fragment thereof. In some embodiments, the polypeptide of SEQ ID NO: 91, or a fragment thereof, is encoded by the polynucleotide of SEQ ID NO: 92 or a fragment thereof.

The disclosure also provides an isolated polynucleotide encoding the polypeptide of SEQ ID NO: 93 or a fragment thereof. In some embodiments, the polypeptide of SEQ ID NO: 93, or a fragment thereof, is encoded by the polynucleotide of SEQ ID NO: 94 or a fragment thereof.

The disclosure also provides an isolated polynucleotide encoding the polypeptide of SEQ ID NO: 95 or a fragment thereof. In some embodiments, the polypeptide of SEQ ID NO: 95, or a fragment thereof, is encoded by the polynucleotide of SEQ ID NO: 96 or a fragment thereof.

The disclosure also provides an isolated polynucleotide encoding the polypeptide of SEQ ID NO: 97 or a fragment thereof. In some embodiments, the polypeptide of SEQ ID NO: 97, or a fragment thereof, is encoded by the polynucleotide of SEQ ID NO: 98 or a fragment thereof.

The disclosure also provides an isolated polynucleotide encoding the polypeptide of SEQ ID NO: 99 or a fragment thereof. In some embodiments, the polypeptide of SEQ ID NO: 99, or a fragment thereof, is encoded by the polynucleotide of SEQ ID NO: 100 or a fragment thereof.

The disclosure also provides an isolated polynucleotide encoding the polypeptide of SEQ ID NO: 101 or a fragment thereof. In some embodiments, the polypeptide of SEQ ID NO: 101, or a fragment thereof, is encoded by the polynucleotide of SEQ ID NO: 102 or a fragment thereof.

The disclosure also provides an isolated polynucleotide encoding the polypeptide of SEQ ID NO: 103 or a fragment thereof. In some embodiments, the polypeptide of SEQ ID NO: 103, or a fragment thereof, is encoded by the polynucleotide of SEQ ID NO: 104 or a fragment thereof.

The disclosure also provides an isolated polynucleotide encoding the polypeptide of SEQ ID NO: 105 or a fragment thereof. In some embodiments, the polypeptide of SEQ ID NO: 105, or a fragment thereof, is encoded by the polynucleotide of SEQ ID NO: 106 or a fragment thereof.

The disclosure also provides an isolated polynucleotide encoding the polypeptide of SEQ ID NO: 107 or a fragment thereof. In some embodiments, the polypeptide of SEQ ID NO: 107, or a fragment thereof, is encoded by the polynucleotide of SEQ ID NO: 108 or a fragment thereof.

The disclosure also provides an isolated polynucleotide encoding the polypeptide of SEQ ID NO: 109 or a fragment thereof. In some embodiments, the polypeptide of SEQ ID NO: 109, or a fragment thereof, is encoded by the polynucleotide of SEQ ID NO: 110 or a fragment thereof.

The disclosure also provides an isolated polynucleotide encoding the polypeptide of SEQ ID NO: 111 or a fragment thereof. In some embodiments, the polypeptide of SEQ ID NO: 111, or a fragment thereof, is encoded by the polynucleotide of SEQ ID NO: 112 or a fragment thereof.

The disclosure also provides an isolated polynucleotide encoding the polypeptide of SEQ ID NO: 113 or a fragment thereof. In some embodiments, the polypeptide of SEQ ID NO: 113, or a fragment thereof, is encoded by the polynucleotide of SEQ ID NO: 114 or a fragment thereof.

The disclosure also provides an isolated polynucleotide encoding the polypeptide of SEQ ID NO: 115 or a fragment thereof. In some embodiments, the polypeptide of SEQ ID NO: 115, or a fragment thereof, is encoded by the polynucleotide of SEQ ID NO: 116 or a fragment thereof.

The disclosure also provides an isolated polynucleotide encoding the polypeptide of SEQ ID NO: 117 or a fragment thereof. In some embodiments, the polypeptide of SEQ ID NO: 117, or a fragment thereof, is encoded by the polynucleotide of SEQ ID NO: 118 or a fragment thereof.

The disclosure also provides an isolated polynucleotide encoding the polypeptide of SEQ ID NO: 119 or a fragment thereof. In some embodiments, the polypeptide of SEQ ID NO: 119, or a fragment thereof, is encoded by the polynucleotide of SEQ ID NO: 120 or a fragment thereof.

The disclosure also provides an isolated polynucleotide encoding the polypeptide of SEQ ID NO: 121 or a fragment thereof. In some embodiments, the polypeptide of SEQ ID NO: 121, or a fragment thereof, is encoded by the polynucleotide of SEQ ID NO: 122 or a fragment thereof.

The disclosure also provides an isolated polynucleotide encoding the polypeptide of SEQ ID NO: 123 or a fragment thereof. In some embodiments, the polypeptide of SEQ ID NO: 123, or a fragment thereof, is encoded by the polynucleotide of SEQ ID NO: 124 or a fragment thereof.

The disclosure also provides an isolated polynucleotide encoding the polypeptide of SEQ ID NO: 125 or a fragment thereof. In some embodiments, the polypeptide of SEQ ID NO: 125, or a fragment thereof, is encoded by the polynucleotide of SEQ ID NO: 126 or a fragment thereof.

The disclosure also provides an isolated polynucleotide encoding the polypeptide of SEQ ID NO: 127 or a fragment thereof. In some embodiments, the polypeptide of SEQ ID NO: 127, or a fragment thereof, is encoded by the polynucleotide of SEQ ID NO: 128 or a fragment thereof.

The disclosure also provides an isolated polynucleotide encoding the polypeptide of SEQ ID NO: 129 or a fragment thereof. In some embodiments, the polypeptide of SEQ ID NO: 129, or a fragment thereof, is encoded by the polynucleotide of SEQ ID NO: 130 or a fragment thereof.

The disclosure also provides an isolated polynucleotide encoding the polypeptide of SEQ ID NO: 131 or a fragment thereof. In some embodiments, the polypeptide of SEQ ID NO: 131, or a fragment thereof, is encoded by the polynucleotide of SEQ ID NO: 132 or a fragment thereof.

The disclosure also provides an isolated polynucleotide encoding the polypeptide of SEQ ID NO: 133 or a fragment thereof. In some embodiments, the polypeptide of SEQ ID NO: 133, or a fragment thereof, is encoded by the polynucleotide of SEQ ID NO: 134 or a fragment thereof.

The disclosure also provides an isolated polynucleotide encoding the polypeptide of SEQ ID NO: 135 or a fragment thereof. In some embodiments, the polypeptide of SEQ ID NO: 135, or a fragment thereof, is encoded by the polynucleotide of SEQ ID NO: 136 or a fragment thereof.

The disclosure also provides an isolated polynucleotide encoding the polypeptide of SEQ ID NO: 137 or a fragment thereof. In some embodiments, the polypeptide of SEQ ID NO: 137, or a fragment thereof, is encoded by the polynucleotide of SEQ ID NO: 138 or a fragment thereof.

The disclosure also provides an isolated polynucleotide encoding the polypeptide of SEQ ID NO: 139 or a fragment thereof. In some embodiments, the polypeptide of SEQ ID NO: 139, or a fragment thereof, is encoded by the polynucleotide of SEQ ID NO: 140 or a fragment thereof.

The disclosure also provides an isolated polynucleotide encoding the polypeptide of SEQ ID NO: 141 or a fragment thereof. In some embodiments, the polypeptide of SEQ ID NO: 141, or a fragment thereof, is encoded by the polynucleotide of SEQ ID NO: 142 or a fragment thereof.

The disclosure also provides an isolated polynucleotide encoding the polypeptide of SEQ ID NO: 143 or a fragment thereof. In some embodiments, the polypeptide of SEQ ID NO: 143, or a fragment thereof, is encoded by the polynucleotide of SEQ ID NO: 144 or a fragment thereof.

The disclosure also provides an isolated polynucleotide encoding the polypeptide of SEQ ID NO: 145 or a fragment thereof. In some embodiments, the polypeptide of SEQ ID NO: 145, or a fragment thereof, is encoded by the polynucleotide of SEQ ID NO: 146 or a fragment thereof.

The disclosure also provides an isolated polynucleotide encoding the polypeptide of SEQ ID NO: 147 or a fragment thereof. In some embodiments, the polypeptide of SEQ ID NO: 147, or a fragment thereof, is encoded by the polynucleotide of SEQ ID NO: 148 or a fragment thereof.

The disclosure also provides an isolated polynucleotide encoding the polypeptide of SEQ ID NO: 149 or a fragment thereof. In some embodiments, the polypeptide of SEQ ID NO: 149, or a fragment thereof, is encoded by the polynucleotide of SEQ ID NO: 150 or a fragment thereof.

The disclosure also provides an isolated polynucleotide encoding the polypeptide of SEQ ID NO: 151 or a fragment thereof. In some embodiments, the polypeptide of SEQ ID NO: 151, or a fragment thereof, is encoded by the polynucleotide of SEQ ID NO: 152 or a fragment thereof.

The disclosure also provides an isolated polynucleotide encoding the polypeptide of SEQ ID NO: 153 or a fragment thereof. In some embodiments, the polypeptide of SEQ ID NO: 153, or a fragment thereof, is encoded by the polynucleotide of SEQ ID NO: 154 or a fragment thereof.

The disclosure also provides an isolated polynucleotide encoding the polypeptide of SEQ ID NO: 155 or a fragment thereof. In some embodiments, the polypeptide of SEQ ID NO: 155, or a fragment thereof, is encoded by the polynucleotide of SEQ ID NO: 156 or a fragment thereof.

The disclosure also provides an isolated polynucleotide encoding the polypeptide of SEQ ID NO: 157 or a fragment thereof. In some embodiments, the polypeptide of SEQ ID NO: 157, or a fragment thereof, is encoded by the polynucleotide of SEQ ID NO: 158 or a fragment thereof.

The disclosure also provides an isolated polynucleotide encoding the polypeptide of SEQ ID NO: 159 or a fragment thereof. In some embodiments, the polypeptide of SEQ ID NO: 159, or a fragment thereof, is encoded by the polynucleotide of SEQ ID NO: 160 or a fragment thereof.

The disclosure also provides an isolated polynucleotide encoding the polypeptide of SEQ ID NO: 161 or a fragment thereof. In some embodiments, the polypeptide of SEQ ID NO: 161, or a fragment thereof, is encoded by the polynucleotide of SEQ ID NO: 162 or a fragment thereof.

The disclosure also provides an isolated polynucleotide encoding the polypeptide of SEQ ID NO: 163 or a fragment thereof. In some embodiments, the polypeptide of SEQ ID NO: 163, or a fragment thereof, is encoded by the polynucleotide of SEQ ID NO: 164 or a fragment thereof.

The disclosure also provides an isolated polynucleotide encoding the polypeptide of SEQ ID NO: 165 or a fragment thereof. In some embodiments, the polypeptide of SEQ ID NO: 165, or a fragment thereof, is encoded by the polynucleotide of SEQ ID NO: 166 or a fragment thereof.

The disclosure also provides an isolated polynucleotide encoding the polypeptide of SEQ ID NO: 167 or a fragment thereof. In some embodiments, the polypeptide of SEQ ID NO: 167, or a fragment thereof, is encoded by the polynucleotide of SEQ ID NO: 168 or a fragment thereof. In some embodiments, the polypeptide of SEQ ID NO: 167, or a fragment thereof, is encoded by the polynucleotide of SEQ ID NO: 495 or a fragment thereof. In some embodiments, the polypeptide of SEQ ID NO: 167, or a fragment thereof, is encoded by the polynucleotide of SEQ ID NO: 536 or a fragment thereof.

The disclosure also provides an isolated polynucleotide encoding the polypeptide of SEQ ID NO: 169 or a fragment thereof. In some embodiments, the polypeptide of SEQ ID NO: 169, or a fragment thereof, is encoded by the polynucleotide of SEQ ID NO: 170 or a fragment thereof.

The disclosure also provides an isolated polynucleotide encoding the polypeptide of SEQ ID NO: 171 or a fragment thereof. In some embodiments, the polypeptide of SEQ ID NO: 171, or a fragment thereof, is encoded by the polynucleotide of SEQ ID NO: 172 or a fragment thereof. In some embodiments, the polypeptide of SEQ ID NO: 171, or a fragment thereof, is encoded by the polynucleotide of SEQ ID NO: 496 or a fragment thereof. In some embodiments, the polypeptide of SEQ ID NO: 171, or a fragment thereof, is encoded by the polynucleotide of SEQ ID NO: 537 or a fragment thereof.

The disclosure also provides an isolated polynucleotide encoding the polypeptide of SEQ ID NO: 173 or a fragment thereof. In some embodiments, the polypeptide of SEQ ID NO: 173, or a fragment thereof, is encoded by the polynucleotide of SEQ ID NO: 174 or a fragment thereof.

The disclosure also provides an isolated polynucleotide encoding the polypeptide of SEQ ID NO: 175 or a fragment thereof. In some embodiments, the polypeptide of SEQ ID NO: 175, or a fragment thereof, is encoded by the polynucleotide of SEQ ID NO: 176 or a fragment thereof.

The disclosure also provides an isolated polynucleotide encoding the polypeptide of SEQ ID NO: 177 or a fragment thereof. In some embodiments, the polypeptide of SEQ ID NO: 177, or a fragment thereof, is encoded by the polynucleotide of SEQ ID NO: 178 or a fragment thereof. In some embodiments, the polypeptide of SEQ ID NO: 177, or a fragment thereof, is encoded by the polynucleotide of SEQ ID NO: 499 or a fragment thereof. In some embodiments, the polypeptide of SEQ ID NO: 177, or a fragment thereof, is encoded by the polynucleotide of SEQ ID NO: 540 or a fragment thereof.

The disclosure also provides an isolated polynucleotide encoding the polypeptide of SEQ ID NO: 179 or a fragment thereof. In some embodiments, the polypeptide of SEQ ID NO: 179, or a fragment thereof, is encoded by the polynucleotide of SEQ ID NO: 180 or a fragment thereof.

The disclosure also provides an isolated polynucleotide encoding the polypeptide of SEQ ID NO: 181 or a fragment thereof. In some embodiments, the polypeptide of SEQ ID NO: 181, or a fragment thereof, is encoded by the polynucleotide of SEQ ID NO: 182 or a fragment thereof.

The disclosure also provides an isolated polynucleotide encoding the polypeptide of SEQ ID NO: 183 or a fragment thereof. In some embodiments, the polypeptide of SEQ ID NO: 183, or a fragment thereof, is encoded by the polynucleotide of SEQ ID NO: 184 or a fragment thereof.

The disclosure also provides an isolated polynucleotide encoding the polypeptide of SEQ ID NO: 185 or a fragment thereof. In some embodiments, the polypeptide of SEQ ID NO: 185, or a fragment thereof, is encoded by the polynucleotide of SEQ ID NO: 186 or a fragment thereof.

The disclosure also provides an isolated polynucleotide encoding the polypeptide of SEQ ID NO: 187 or a fragment thereof. In some embodiments, the polypeptide of SEQ ID NO: 187, or a fragment thereof, is encoded by the polynucleotide of SEQ ID NO: 188 or a fragment thereof.

The disclosure also provides an isolated polynucleotide encoding the polypeptide of SEQ ID NO: 189 or a fragment thereof. In some embodiments, the polypeptide of SEQ ID NO: 189, or a fragment thereof, is encoded by the polynucleotide of SEQ ID NO: 190 or a fragment thereof.

The disclosure also provides an isolated polynucleotide encoding the polypeptide of SEQ ID NO: 191 or a fragment thereof. In some embodiments, the polypeptide of SEQ ID NO: 191, or a fragment thereof, is encoded by the polynucleotide of SEQ ID NO: 192 or a fragment thereof.

The disclosure also provides an isolated polynucleotide encoding the polypeptide of SEQ ID NO: 193 or a fragment thereof. In some embodiments, the polypeptide of SEQ ID NO: 193, or a fragment thereof, is encoded by the polynucleotide of SEQ ID NO: 194 or a fragment thereof.

The disclosure also provides an isolated polynucleotide encoding the polypeptide of SEQ ID NO: 195 or a fragment thereof. In some embodiments, the polypeptide of SEQ ID NO: 195, or a fragment thereof, is encoded by the polynucleotide of SEQ ID NO: 196 or a fragment thereof.

The disclosure also provides an isolated polynucleotide encoding the polypeptide of SEQ ID NO: 197 or a fragment thereof. In some embodiments, the polypeptide of SEQ ID NO: 197, or a fragment thereof, is encoded by the polynucleotide of SEQ ID NO: 198 or a fragment thereof.

The disclosure also provides an isolated polynucleotide encoding the polypeptide of SEQ ID NO: 199 or a fragment thereof. In some embodiments, the polypeptide of SEQ ID NO: 199, or a fragment thereof, is encoded by the polynucleotide of SEQ ID NO: 200 or a fragment thereof.

The disclosure also provides an isolated polynucleotide encoding the polypeptide of SEQ ID NO: 201 or a fragment thereof. In some embodiments, the polypeptide of SEQ ID NO: 201, or a fragment thereof, is encoded by the polynucleotide of SEQ ID NO: 202 or a fragment thereof.

The disclosure also provides an isolated polynucleotide encoding the polypeptide of SEQ ID NO: 203 or a fragment thereof. In some embodiments, the polypeptide of SEQ ID NO: 203, or a fragment thereof, is encoded by the polynucleotide of SEQ ID NO: 204 or a fragment thereof.

The disclosure also provides an isolated polynucleotide encoding the polypeptide of SEQ ID NO: 205 or a fragment thereof. In some embodiments, the polypeptide of SEQ ID NO: 205, or a fragment thereof, is encoded by the polynucleotide of SEQ ID NO: 206 or a fragment thereof.

The disclosure also provides an isolated polynucleotide encoding the polypeptide of SEQ ID NO: 207 or a fragment thereof. In some embodiments, the polypeptide of SEQ ID NO: 207, or a fragment thereof, is encoded by the polynucleotide of SEQ ID NO: 208 or a fragment thereof.

The disclosure also provides an isolated polynucleotide encoding the polypeptide of SEQ ID NO: 209 or a fragment thereof. In some embodiments, the polypeptide of SEQ ID NO: 209, or a fragment thereof, is encoded by the polynucleotide of SEQ ID NO: 210 or a fragment thereof.

The disclosure also provides an isolated polynucleotide encoding the polypeptide of SEQ ID NO: 211 or a fragment thereof. In some embodiments, the polypeptide of SEQ ID NO: 211, or a fragment thereof, is encoded by the polynucleotide of SEQ ID NO: 212 or a fragment thereof. In some embodiments, the polypeptide of SEQ ID NO: 211, or a fragment thereof, is encoded by the polynucleotide of SEQ ID NO: 484 or a fragment thereof. In some embodiments, the polypeptide of SEQ ID NO: 211, or a fragment thereof, is encoded by the polynucleotide of SEQ ID NO: 525 or a fragment thereof.

The disclosure also provides an isolated polynucleotide encoding the polypeptide of SEQ ID NO: 213 or a fragment thereof. In some embodiments, the polypeptide of SEQ ID NO: 213, or a fragment thereof, is encoded by the polynucleotide of SEQ ID NO: 214 or a fragment thereof. In some embodiments, the polypeptide of SEQ ID NO: 213, or a fragment thereof, is encoded by the polynucleotide of SEQ ID NO: 486 or a fragment thereof.

The disclosure also provides an isolated polynucleotide encoding the polypeptide of SEQ ID NO: 215 or a fragment thereof. In some embodiments, the polypeptide of SEQ ID NO: 215, or a fragment thereof, is encoded by the polynucleotide of SEQ ID NO: 216 or a fragment thereof. In some embodiments, the polypeptide of SEQ ID NO: 215, or a fragment thereof, is encoded by the polynucleotide of SEQ ID NO: 487 or a fragment thereof. In some embodiments, the polypeptide of SEQ ID NO: 215, or a fragment thereof, is encoded by the polynucleotide of SEQ ID NO: 528 or a fragment thereof.

The disclosure also provides an isolated polynucleotide encoding the polypeptide of SEQ ID NO: 217 or a fragment thereof. In some embodiments, the polypeptide of SEQ ID NO: 217, or a fragment thereof, is encoded by the polynucleotide of SEQ ID NO: 218 or a fragment thereof.

The disclosure also provides an isolated polynucleotide encoding the polypeptide of SEQ ID NO: 219 or a fragment thereof. In some embodiments, the polypeptide of SEQ ID NO: 219, or a fragment thereof, is encoded by the polynucleotide of SEQ ID NO: 220 or a fragment thereof. In some embodiments, the polypeptide of SEQ ID NO: 219, or a fragment thereof, is encoded by the polynucleotide of SEQ ID NO: 489 or a fragment thereof. In some embodiments, the polypeptide of SEQ ID NO: 219, or a fragment thereof, is encoded by the polynucleotide of SEQ ID NO: 530 or a fragment thereof.

The disclosure also provides an isolated polynucleotide encoding the polypeptide of SEQ ID NO: 221 or a fragment thereof. In some embodiments, the polypeptide of SEQ ID NO: 221, or a fragment thereof, is encoded by the polynucleotide of SEQ ID NO: 222 or a fragment thereof. In some embodiments, the polypeptide of SEQ ID NO: 221, or a fragment thereof, is encoded by the polynucleotide of SEQ ID NO: 488 or a fragment thereof. In some embodiments, the polypeptide of SEQ ID NO: 221, or a fragment thereof, is encoded by the polynucleotide of SEQ ID NO: 529 or a fragment thereof.

The disclosure also provides an isolated polynucleotide encoding the polypeptide of SEQ ID NO: 223 or a fragment thereof. In some embodiments, the polypeptide of SEQ ID NO: 223, or a fragment thereof, is encoded by the polynucleotide of SEQ ID NO: 224 or a fragment thereof. In some embodiments, the polypeptide of SEQ ID NO: 223, or a fragment thereof, is encoded by the polynucleotide of SEQ ID NO: 494 or a fragment thereof. In some embodiments, the polypeptide of SEQ ID NO: 223, or a fragment thereof, is encoded by the polynucleotide of SEQ ID NO: 535 or a fragment thereof.

The disclosure also provides an isolated polynucleotide encoding the polypeptide of SEQ ID NO: 225 or a fragment thereof. In some embodiments, the polypeptide of SEQ ID NO: 225, or a fragment thereof, is encoded by the polynucleotide of SEQ ID NO: 226 or a fragment thereof. In some embodiments, the polypeptide of SEQ ID NO: 225, or a fragment thereof, is encoded by the polynucleotide of SEQ ID NO: 490 or a fragment thereof. In some embodiments, the polypeptide of SEQ ID NO: 225, or a fragment thereof, is encoded by the polynucleotide of SEQ ID NO: 531 or a fragment thereof.

The disclosure also provides an isolated polynucleotide encoding the polypeptide of SEQ ID NO: 227 or a fragment thereof. In some embodiments, the polypeptide of SEQ ID NO: 227, or a fragment thereof, is encoded by the polynucleotide of SEQ ID NO: 228 or a fragment thereof.

The disclosure also provides an isolated polynucleotide encoding the polypeptide of SEQ ID NO: 229 or a fragment thereof. In some embodiments, the polypeptide of SEQ ID NO: 229, or a fragment thereof, is encoded by the polynucleotide of SEQ ID NO: 230 or a fragment thereof.

The disclosure also provides an isolated polynucleotide encoding the polypeptide of SEQ ID NO: 231 or a fragment thereof. In some embodiments, the polypeptide of SEQ ID NO: 231, or a fragment thereof, is encoded by the polynucleotide of SEQ ID NO: 232 or a fragment thereof.

The disclosure also provides an isolated polynucleotide encoding the polypeptide of SEQ ID NO: 233 or a fragment thereof. In some embodiments, the polypeptide of SEQ ID NO: 233, or a fragment thereof, is encoded by the polynucleotide of SEQ ID NO: 234 or a fragment thereof.

The disclosure also provides an isolated polynucleotide encoding the polypeptide of SEQ ID NO: 235 or a fragment thereof. In some embodiments, the polypeptide of SEQ ID NO: 235, or a fragment thereof, is encoded by the polynucleotide of SEQ ID NO: 236 or a fragment thereof. In some embodiments, the polypeptide of SEQ ID NO: 235, or a fragment thereof, is encoded by the polynucleotide of SEQ ID NO: 493 or a fragment thereof. In some embodiments, the polypeptide of SEQ ID NO: 235, or a fragment thereof, is encoded by the polynucleotide of SEQ ID NO: 534 or a fragment thereof.

The disclosure also provides an isolated polynucleotide encoding the polypeptide of SEQ ID NO: 237 or a fragment thereof. In some embodiments, the polypeptide of SEQ ID NO: 237, or a fragment thereof, is encoded by the polynucleotide of SEQ ID NO: 238 or a fragment thereof.

The disclosure also provides an isolated polynucleotide encoding the polypeptide of SEQ ID NO: 239 or a fragment thereof. In some embodiments, the polypeptide of SEQ ID NO: 239, or a fragment thereof, is encoded by the polynucleotide of SEQ ID NO: 240 or a fragment thereof.

The disclosure also provides an isolated polynucleotide encoding the polypeptide of SEQ ID NO: 241 or a fragment thereof. In some embodiments, the polypeptide of SEQ ID NO: 241, or a fragment thereof, is encoded by the polynucleotide of SEQ ID NO: 242 or a fragment thereof.

The disclosure also provides an isolated polynucleotide encoding the polypeptide of SEQ ID NO: 243 or a fragment thereof. In some embodiments, the polypeptide of SEQ ID NO: 243, or a fragment thereof, is encoded by the polynucleotide of SEQ ID NO: 244 or a fragment thereof.

The disclosure also provides an isolated polynucleotide encoding the polypeptide of SEQ ID NO: 245 or a fragment thereof. In some embodiments, the polypeptide of SEQ ID NO: 245, or a fragment thereof, is encoded by the polynucleotide of SEQ ID NO: 246 or a fragment thereof. In some embodiments, the polypeptide of SEQ ID NO: 245, or a fragment thereof, is encoded by the polynucleotide of SEQ ID NO: 470 or a fragment thereof. In some embodiments, the polypeptide of SEQ ID NO: 245, or a fragment thereof, is encoded by the polynucleotide of SEQ ID NO: 511 or a fragment thereof.

The disclosure also provides an isolated polynucleotide encoding the polypeptide of SEQ ID NO: 247 or a fragment thereof. In some embodiments, the polypeptide of SEQ ID NO: 247, or a fragment thereof, is encoded by the polynucleotide of SEQ ID NO: 248 or a fragment thereof.

The disclosure also provides an isolated polynucleotide encoding the polypeptide of SEQ ID NO: 249 or a fragment thereof. In some embodiments, the polypeptide of SEQ ID NO: 249, or a fragment thereof, is encoded by the polynucleotide of SEQ ID NO: 250 or a fragment thereof.

The disclosure also provides an isolated polynucleotide encoding the polypeptide of SEQ ID NO: 251 or a fragment thereof. In some embodiments, the polypeptide of SEQ ID NO: 251, or a fragment thereof, is encoded by the polynucleotide of SEQ ID NO: 252 or a fragment thereof. In some embodiments, the polypeptide of SEQ ID NO: 251, or a fragment thereof, is encoded by the polynucleotide of SEQ ID NO: 469 or a fragment thereof. In some embodiments, the polypeptide of SEQ ID NO: 251, or a fragment thereof, is encoded by the polynucleotide of SEQ ID NO: 510 or a fragment thereof.

The disclosure also provides an isolated polynucleotide encoding the polypeptide of SEQ ID NO: 253 or a fragment thereof. In some embodiments, the polypeptide of SEQ ID NO: 253, or a fragment thereof, is encoded by the polynucleotide of SEQ ID NO: 254 or a fragment thereof. In some embodiments, the polypeptide of SEQ ID NO: 253, or a fragment thereof, is encoded by the polynucleotide of SEQ ID NO: 464 or a fragment thereof. In some embodiments, the polypeptide of SEQ ID NO: 253, or a fragment thereof, is encoded by the polynucleotide of SEQ ID NO: 505 or a fragment thereof.

The disclosure also provides an isolated polynucleotide encoding the polypeptide of SEQ ID NO: 255 or a fragment thereof. In some embodiments, the polypeptide of SEQ ID NO: 255, or a fragment thereof, is encoded by the polynucleotide of SEQ ID NO: 256 or a fragment thereof. In some embodiments, the polypeptide of SEQ ID NO: 255, or a fragment thereof, is encoded by the polynucleotide of SEQ ID NO: 474 or a fragment thereof. In some embodiments, the polypeptide of SEQ ID NO: 255, or a fragment thereof, is encoded by the polynucleotide of SEQ ID NO: 515 or a fragment thereof.

The disclosure also provides an isolated polynucleotide encoding the polypeptide of SEQ ID NO: 257 or a fragment thereof. In some embodiments, the polypeptide of SEQ ID NO: 257, or a fragment thereof, is encoded by the polynucleotide of SEQ ID NO: 258 or a fragment thereof.

The disclosure also provides an isolated polynucleotide encoding the polypeptide of SEQ ID NO: 259 or a fragment thereof. In some embodiments, the polypeptide of SEQ ID NO: 259, or a fragment thereof, is encoded by the polynucleotide of SEQ ID NO: 260 or a fragment thereof.

The disclosure also provides an isolated polynucleotide encoding the polypeptide of SEQ ID NO: 261 or a fragment thereof. In some embodiments, the polypeptide of SEQ ID NO: 261, or a fragment thereof, is encoded by the polynucleotide of SEQ ID NO: 262 or a fragment thereof. In some embodiments, the polypeptide of SEQ ID NO: 261, or a fragment thereof, is encoded by the polynucleotide of SEQ ID NO: 471 or a fragment thereof. In some embodiments, the polypeptide of SEQ ID NO: 261, or a fragment thereof, is encoded by the polynucleotide of SEQ ID NO: 512 or a fragment thereof.

The disclosure also provides an isolated polynucleotide encoding the polypeptide of SEQ ID NO: 263 or a fragment thereof. In some embodiments, the polypeptide of SEQ ID NO: 263, or a fragment thereof, is encoded by the polynucleotide of SEQ ID NO: 264 or a fragment thereof.

The disclosure also provides an isolated polynucleotide encoding the polypeptide of SEQ ID NO: 265 or a fragment thereof. In some embodiments, the polypeptide of SEQ ID NO: 265, or a fragment thereof, is encoded by the polynucleotide of SEQ ID NO: 266 or a fragment thereof. In some embodiments, the polypeptide of SEQ ID NO: 265, or a fragment thereof, is encoded by the polynucleotide of SEQ ID NO: 472 or a fragment thereof. In some embodiments, the polypeptide of SEQ ID NO: 265, or a fragment thereof, is encoded by the polynucleotide of SEQ ID NO: 513 or a fragment thereof.

The disclosure also provides an isolated polynucleotide encoding the polypeptide of SEQ ID NO: 267 or a fragment thereof. In some embodiments, the polypeptide of SEQ ID NO: 267, or a fragment thereof, is encoded by the polynucleotide of SEQ ID NO: 268 or a fragment thereof.

The disclosure also provides an isolated polynucleotide encoding the polypeptide of SEQ ID NO: 269 or a fragment thereof. In some embodiments, the polypeptide of SEQ ID NO: 269, or a fragment thereof, is encoded by the polynucleotide of SEQ ID NO: 270 or a fragment thereof. In some embodiments, the polypeptide of SEQ ID NO: 269, or a fragment thereof, is encoded by the polynucleotide of SEQ ID NO: 463 or a fragment thereof. In some embodiments, the polypeptide of SEQ ID NO: 269, or a fragment thereof, is encoded by the polynucleotide of SEQ ID NO: 504 or a fragment thereof.

The disclosure also provides an isolated polynucleotide encoding the polypeptide of SEQ ID NO: 271 or a fragment thereof. In some embodiments, the polypeptide of SEQ ID NO: 271, or a fragment thereof, is encoded by the polynucleotide of SEQ ID NO: 272 or a fragment thereof. In some embodiments, the polypeptide of SEQ ID NO: 271, or a fragment thereof, is encoded by the polynucleotide of SEQ ID NO: 465 or a fragment thereof. In some embodiments, the polypeptide of SEQ ID NO: 271, or a fragment thereof, is encoded by the polynucleotide of SEQ ID NO: 508 or a fragment thereof.

The disclosure also provides an isolated polynucleotide encoding the polypeptide of SEQ ID NO: 273 or a fragment thereof. In some embodiments, the polypeptide of SEQ ID NO: 273, or a fragment thereof, is encoded by the polynucleotide of SEQ ID NO: 274 or a fragment thereof.

The disclosure also provides an isolated polynucleotide encoding the polypeptide of SEQ ID NO: 275 or a fragment thereof. In some embodiments, the polypeptide of SEQ ID NO: 275, or a fragment thereof, is encoded by the polynucleotide of SEQ ID NO: 276 or a fragment thereof. In some embodiments, the polypeptide of SEQ ID NO: 275, or a fragment thereof, is encoded by the polynucleotide of SEQ ID NO: 459 or a fragment thereof. In some embodiments, the polypeptide of SEQ ID NO: 275, or a fragment thereof, is encoded by the polynucleotide of SEQ ID NO: 500 or a fragment thereof.

The disclosure also provides an isolated polynucleotide encoding the polypeptide of SEQ ID NO: 277 or a fragment thereof. In some embodiments, the polypeptide of SEQ ID NO: 277, or a fragment thereof, is encoded by the polynucleotide of SEQ ID NO: 278 or a fragment thereof. In some embodiments, the polypeptide of SEQ ID NO: 277, or a fragment thereof, is encoded by the polynucleotide of SEQ ID NO: 475 or a fragment thereof. In some embodiments, the polypeptide of SEQ ID NO: 277, or a fragment thereof, is encoded by the polynucleotide of SEQ ID NO: 516 or a fragment thereof.

The disclosure also provides an isolated polynucleotide encoding the polypeptide of SEQ ID NO: 279 or a fragment thereof. In some embodiments, the polypeptide of SEQ ID NO: 279, or a fragment thereof, is encoded by the polynucleotide of SEQ ID NO: 280 or a fragment thereof.

The disclosure also provides an isolated polynucleotide encoding the polypeptide of SEQ ID NO: 281 or a fragment thereof. In some embodiments, the polypeptide of SEQ ID NO: 281, or a fragment thereof, is encoded by the polynucleotide of SEQ ID NO: 282 or a fragment thereof.

The disclosure also provides an isolated polynucleotide encoding the polypeptide of SEQ ID NO: 283 or a fragment thereof. In some embodiments, the polypeptide of SEQ ID NO: 283, or a fragment thereof, is encoded by the polynucleotide of SEQ ID NO: 284 or a fragment thereof.

The disclosure also provides an isolated polynucleotide encoding the polypeptide of SEQ ID NO: 285 or a fragment thereof. In some embodiments, the polypeptide of SEQ ID NO: 285, or a fragment thereof, is encoded by the polynucleotide of SEQ ID NO: 286 or a fragment thereof. In some embodiments, the polypeptide of SEQ ID NO: 285, or a fragment thereof, is encoded by the polynucleotide of SEQ ID NO: 477 or a fragment thereof.

The disclosure also provides an isolated polynucleotide encoding the polypeptide of SEQ ID NO: 287 or a fragment thereof. In some embodiments, the polypeptide of SEQ ID NO: 287, or a fragment thereof, is encoded by the polynucleotide of SEQ ID NO: 288 or a fragment thereof.

The disclosure also provides an isolated polynucleotide encoding the polypeptide of SEQ ID NO: 289 or a fragment thereof. In some embodiments, the polypeptide of SEQ ID NO: 289, or a fragment thereof, is encoded by the polynucleotide of SEQ ID NO: 290 or a fragment thereof.

The disclosure also provides an isolated polynucleotide encoding the polypeptide of SEQ ID NO: 291 or a fragment thereof. In some embodiments, the polypeptide of SEQ ID NO: 291, or a fragment thereof, is encoded by the polynucleotide of SEQ ID NO: 292 or a fragment thereof.

The disclosure also provides an isolated polynucleotide encoding the polypeptide of SEQ ID NO: 293 or a fragment thereof. In some embodiments, the polypeptide of SEQ ID NO: 293, or a fragment thereof, is encoded by the polynucleotide of SEQ ID NO: 294 or a fragment thereof.

The disclosure also provides an isolated polynucleotide encoding the polypeptide of SEQ ID NO: 295 or a fragment thereof. In some embodiments, the polypeptide of SEQ ID NO: 295, or a fragment thereof, is encoded by the polynucleotide of SEQ ID NO: 296 or a fragment thereof.

The disclosure also provides an isolated polynucleotide encoding the polypeptide of SEQ ID NO: 297 or a fragment thereof. In some embodiments, the polypeptide of SEQ ID NO: 297, or a fragment thereof, is encoded by the polynucleotide of SEQ ID NO: 298 or a fragment thereof. In some embodiments, the polypeptide of SEQ ID NO: 297, or a fragment thereof, is encoded by the polynucleotide of SEQ ID NO: 476 or a fragment thereof. In some embodiments, the polypeptide of SEQ ID NO: 297, or a fragment thereof, is encoded by the polynucleotide of SEQ ID NO: 517 or a fragment thereof.

The disclosure also provides an isolated polynucleotide encoding the polypeptide of SEQ ID NO: 299 or a fragment thereof. In some embodiments, the polypeptide of SEQ ID NO: 299, or a fragment thereof, is encoded by the polynucleotide of SEQ ID NO: 300 or a fragment thereof.

The disclosure also provides an isolated polynucleotide encoding the polypeptide of SEQ ID NO: 301 or a fragment thereof. In some embodiments, the polypeptide of SEQ ID NO: 301, or a fragment thereof, is encoded by the polynucleotide of SEQ ID NO: 302 or a fragment thereof.

The disclosure also provides an isolated polynucleotide encoding the polypeptide of SEQ ID NO: 303 or a fragment thereof. In some embodiments, the polypeptide of SEQ ID NO: 303, or a fragment thereof, is encoded by the polynucleotide of SEQ ID NO: 304 or a fragment thereof.

The disclosure also provides an isolated polynucleotide encoding the polypeptide of SEQ ID NO: 305 or a fragment thereof. In some embodiments, the polypeptide of SEQ ID NO: 305, or a fragment thereof, is encoded by the polynucleotide of SEQ ID NO: 306 or a fragment thereof. In some embodiments, the polypeptide of SEQ ID NO: 305, or a fragment thereof, is encoded by the polynucleotide of SEQ ID NO: 468 or a fragment thereof. In some embodiments, the polypeptide of SEQ ID NO: 305, or a fragment thereof, is encoded by the polynucleotide of SEQ ID NO: 509 or a fragment thereof.

The disclosure also provides an isolated polynucleotide encoding the polypeptide of SEQ ID NO: 307 or a fragment thereof. In some embodiments, the polypeptide of SEQ ID NO: 307, or a fragment thereof, is encoded by the polynucleotide of SEQ ID NO: 308 or a fragment thereof.

The disclosure also provides an isolated polynucleotide encoding the polypeptide of SEQ ID NO: 309 or a fragment thereof. In some embodiments, the polypeptide of SEQ ID NO: 309, or a fragment thereof, is encoded by the polynucleotide of SEQ ID NO: 310 or a fragment thereof. In some embodiments, the polypeptide of SEQ ID NO: 309, or a fragment thereof, is encoded by the polynucleotide of SEQ ID NO: 465 or a fragment thereof. In some embodiments, the polypeptide of SEQ ID NO: 309, or a fragment thereof, is encoded by the polynucleotide of SEQ ID NO: 506 or a fragment thereof.

The disclosure also provides an isolated polynucleotide encoding the polypeptide of SEQ ID NO: 311 or a fragment thereof. In some embodiments, the polypeptide of SEQ ID NO: 311, or a fragment thereof, is encoded by the polynucleotide of SEQ ID NO: 312 or a fragment thereof.

The disclosure also provides an isolated polynucleotide encoding the polypeptide of SEQ ID NO: 313 or a fragment thereof. In some embodiments, the polypeptide of SEQ ID NO: 313, or a fragment thereof, is encoded by the polynucleotide of SEQ ID NO: 314 or a fragment thereof.

The disclosure also provides an isolated polynucleotide encoding the polypeptide of SEQ ID NO: 315 or a fragment thereof. In some embodiments, the polypeptide of SEQ ID NO: 315, or a fragment thereof, is encoded by the polynucleotide of SEQ ID NO: 316 or a fragment thereof.

The disclosure also provides an isolated polynucleotide encoding the polypeptide of SEQ ID NO: 317 or a fragment thereof. In some embodiments, the polypeptide of SEQ ID NO: 317, or a fragment thereof, is encoded by the polynucleotide of SEQ ID NO: 318 or a fragment thereof. In some embodiments, the polypeptide of SEQ ID NO: 317, or a fragment thereof, is encoded by the polynucleotide of SEQ ID NO: 473 or a fragment thereof. In some embodiments, the polypeptide of SEQ ID NO: 317, or a fragment thereof, is encoded by the polynucleotide of SEQ ID NO: 514 or a fragment thereof.

The disclosure also provides an isolated polynucleotide encoding the polypeptide of SEQ ID NO: 319 or a fragment thereof. In some embodiments, the polypeptide of SEQ ID NO: 319, or a fragment thereof, is encoded by the polynucleotide of SEQ ID NO: 320 or a fragment thereof.

The disclosure also provides an isolated polynucleotide encoding the polypeptide of SEQ ID NO: 321 or a fragment thereof. In some embodiments, the polypeptide of SEQ ID NO: 321, or a fragment thereof, is encoded by the polynucleotide of SEQ ID NO: 322 or a fragment thereof.

The disclosure also provides an isolated polynucleotide encoding the polypeptide of SEQ ID NO: 323 or a fragment thereof. In some embodiments, the polypeptide of SEQ ID NO: 323, or a fragment thereof, is encoded by the polynucleotide of SEQ ID NO: 324 or a fragment thereof.

The disclosure also provides an isolated polynucleotide encoding the polypeptide of SEQ ID NO: 325 or a fragment thereof. In some embodiments, the polypeptide of SEQ ID NO: 325, or a fragment thereof, is encoded by the polynucleotide of SEQ ID NO: 326 or a fragment thereof. In some embodiments, the polypeptide of SEQ ID NO: 325, or a fragment thereof, is encoded by the polynucleotide of SEQ ID NO: 466 or a fragment thereof. In some embodiments, the polypeptide of SEQ ID NO: 325, or a fragment thereof, is encoded by the polynucleotide of SEQ ID NO: 507 or a fragment thereof.

The disclosure also provides an isolated polynucleotide encoding the polypeptide of SEQ ID NO: 327 or a fragment thereof. In some embodiments, the polypeptide of SEQ ID NO: 327, or a fragment thereof, is encoded by the polynucleotide of SEQ ID NO: 328 or a fragment thereof.

The disclosure also provides an isolated polynucleotide encoding the polypeptide of SEQ ID NO: 329 or a fragment thereof. In some embodiments, the polypeptide of SEQ ID NO: 329, or a fragment thereof, is encoded by the polynucleotide of SEQ ID NO: 330 or a fragment thereof.

The disclosure also provides an isolated polynucleotide encoding the polypeptide of SEQ ID NO: 331 or a fragment thereof. In some embodiments, the polypeptide of SEQ ID NO: 331, or a fragment thereof, is encoded by the polynucleotide of SEQ ID NO: 332 or a fragment thereof.

The disclosure also provides an isolated polynucleotide encoding the polypeptide of SEQ ID NO: 333 or a fragment thereof. In some embodiments, the polypeptide of SEQ ID NO: 333, or a fragment thereof, is encoded by the polynucleotide of SEQ ID NO: 334 or a fragment thereof. In some embodiments, the polypeptide of SEQ ID NO: 333, or a fragment thereof, is encoded by the polynucleotide of SEQ ID NO: 461 or a fragment thereof.

The disclosure also provides an isolated polynucleotide encoding the polypeptide of SEQ ID NO: 335 or a fragment thereof. In some embodiments, the polypeptide of SEQ ID NO: 335, or a fragment thereof, is encoded by the polynucleotide of SEQ ID NO: 336 or a fragment thereof.

The disclosure also provides an isolated polynucleotide encoding the polypeptide of SEQ ID NO: 337 or a fragment thereof. In some embodiments, the polypeptide of SEQ ID NO: 337, or a fragment thereof, is encoded by the polynucleotide of SEQ ID NO: 338 or a fragment thereof. In some embodiments, the polypeptide of SEQ ID NO: 337, or a fragment thereof, is encoded by the polynucleotide of SEQ ID NO: 462 or a fragment thereof. In some embodiments, the polypeptide of SEQ ID NO: 337, or a fragment thereof, is encoded by the polynucleotide of SEQ ID NO: 503 or a fragment thereof.

The disclosure also provides an isolated polynucleotide encoding the polypeptide of SEQ ID NO: 339 or a fragment thereof. In some embodiments, the polypeptide of SEQ ID NO: 339, or a fragment thereof, is encoded by the polynucleotide of SEQ ID NO: 340 or a fragment thereof.

The disclosure also provides an isolated polynucleotide encoding the polypeptide of SEQ ID NO: 341 or a fragment thereof. In some embodiments, the polypeptide of SEQ ID NO: 341, or a fragment thereof, is encoded by the polynucleotide of SEQ ID NO: 342 or a fragment thereof.

The disclosure also provides an isolated polynucleotide encoding the polypeptide of SEQ ID NO: 343 or a fragment thereof. In some embodiments, the polypeptide of SEQ ID NO: 343, or a fragment thereof, is encoded by the polynucleotide of SEQ ID NO: 344 or a fragment thereof. In some embodiments, the polypeptide of SEQ ID NO: 343, or a fragment thereof, is encoded by the polynucleotide of SEQ ID NO: 483 or a fragment thereof. In some embodiments, the polypeptide of SEQ ID NO: 343, or a fragment thereof, is encoded by the polynucleotide of SEQ ID NO: 524 or a fragment thereof.

The disclosure also provides an isolated polynucleotide encoding the polypeptide of SEQ ID NO: 345 or a fragment thereof. In some embodiments, the polypeptide of SEQ ID NO: 345, or a fragment thereof, is encoded by the polynucleotide of SEQ ID NO: 346 or a fragment thereof. In some embodiments, the polypeptide of SEQ ID NO: 345, or a fragment thereof, is encoded by the polynucleotide of SEQ ID NO: 491 or a fragment thereof. In some embodiments, the polypeptide of SEQ ID NO: 345, or a fragment thereof, is encoded by the polynucleotide of SEQ ID NO: 532 or a fragment thereof.

The disclosure also provides an isolated polynucleotide encoding the polypeptide of SEQ ID NO: 347 or a fragment thereof. In some embodiments, the polypeptide of SEQ ID NO: 347, or a fragment thereof, is encoded by the polynucleotide of SEQ ID NO: 348 or a fragment thereof.

The disclosure also provides an isolated polynucleotide encoding the polypeptide of SEQ ID NO: 349 or a fragment thereof. In some embodiments, the polypeptide of SEQ ID NO: 349, or a fragment thereof, is encoded by the polynucleotide of SEQ ID NO: 350 or a fragment thereof. In some embodiments, the polypeptide of SEQ ID NO: 349, or a fragment thereof, is encoded by the polynucleotide of SEQ ID NO: 485 or a fragment thereof.

The disclosure also provides an isolated polynucleotide encoding the polypeptide of SEQ ID NO: 351 or a fragment thereof. In some embodiments, the polypeptide of SEQ ID NO: 351, or a fragment thereof, is encoded by the polynucleotide of SEQ ID NO: 352 or a fragment thereof.

The disclosure also provides an isolated polynucleotide encoding the polypeptide of SEQ ID NO: 353 or a fragment thereof. In some embodiments, the polypeptide of SEQ ID NO: 353, or a fragment thereof, is encoded by the polynucleotide of SEQ ID NO: 354 or a fragment thereof. In some embodiments, the polypeptide of SEQ ID NO: 353, or a fragment thereof, is encoded by the polynucleotide of SEQ ID NO: 492 or a fragment thereof. In some embodiments, the polypeptide of SEQ ID NO: 353, or a fragment thereof, is encoded by the polynucleotide of SEQ ID NO: 533 or a fragment thereof.

The disclosure also provides an isolated polynucleotide encoding the polypeptide of SEQ ID NO: 355 or a fragment thereof. In some embodiments, the polypeptide of SEQ ID NO: 355, or a fragment thereof, is encoded by the polynucleotide of SEQ ID NO: 356 or a fragment thereof.

The disclosure also provides an isolated polynucleotide encoding the polypeptide of SEQ ID NO: 357 or a fragment thereof. In some embodiments, the polypeptide of SEQ ID NO: 357, or a fragment thereof, is encoded by the polynucleotide of SEQ ID NO: 358 or a fragment thereof.

The disclosure also provides an isolated polynucleotide encoding the polypeptide of SEQ ID NO: 359 or a fragment thereof. In some embodiments, the polypeptide of SEQ ID NO: 359, or a fragment thereof, is encoded by the polynucleotide of SEQ ID NO: 360 or a fragment thereof.

The disclosure also provides an isolated polynucleotide encoding the polypeptide of SEQ ID NO: 361 or a fragment thereof. In some embodiments, the polypeptide of SEQ ID NO: 361, or a fragment thereof, is encoded by the polynucleotide of SEQ ID NO: 362 or a fragment thereof.

The disclosure also provides an isolated polynucleotide encoding the polypeptide of SEQ ID NO: 363 or a fragment thereof. In some embodiments, the polypeptide of SEQ ID NO: 363, or a fragment thereof, is encoded by the polynucleotide of SEQ ID NO: 364 or a fragment thereof.

The disclosure also provides an isolated polynucleotide encoding the polypeptide of SEQ ID NO: 365 or a fragment thereof. In some embodiments, the polypeptide of SEQ ID NO: 365, or a fragment thereof, is encoded by the polynucleotide of SEQ ID NO: 366 or a fragment thereof.

The disclosure also provides an isolated polynucleotide encoding the polypeptide of SEQ ID NO: 367 or a fragment thereof. In some embodiments, the polypeptide of SEQ ID NO: 367, or a fragment thereof, is encoded by the polynucleotide of SEQ ID NO: 368 or a fragment thereof.

The disclosure also provides an isolated polynucleotide encoding the polypeptide of SEQ ID NO: 369 or a fragment thereof. In some embodiments, the polypeptide of SEQ ID NO: 369, or a fragment thereof, is encoded by the polynucleotide of SEQ ID NO: 370 or a fragment thereof.

The disclosure also provides an isolated polynucleotide encoding the polypeptide of SEQ ID NO: 371 or a fragment thereof. In some embodiments, the polypeptide of SEQ ID NO: 371, or a fragment thereof, is encoded by the polynucleotide of SEQ ID NO: 372 or a fragment thereof.

The disclosure also provides an isolated polynucleotide encoding the polypeptide of SEQ ID NO: 373 or a fragment thereof. In some embodiments, the polypeptide of SEQ ID NO: 373, or a fragment thereof, is encoded by the polynucleotide of SEQ ID NO: 374 or a fragment thereof.

The disclosure also provides an isolated polynucleotide encoding the polypeptide of SEQ ID NO: 375 or a fragment thereof. In some embodiments, the polypeptide of SEQ ID NO: 375, or a fragment thereof, is encoded by the polynucleotide of SEQ ID NO: 376 or a fragment thereof.

The disclosure also provides an isolated polynucleotide encoding the polypeptide of SEQ ID NO: 379 or a fragment thereof. In some embodiments, the polypeptide of SEQ ID NO: 379, or a fragment thereof, is encoded by the polynucleotide of SEQ ID NO: 380 or a fragment thereof. In some embodiments, the polypeptide of SEQ ID NO: 379, or a fragment thereof, is encoded by the polynucleotide of SEQ ID NO: 482 or a fragment thereof. In some embodiments, the polypeptide of SEQ ID NO: 379, or a fragment thereof, is encoded by the polynucleotide of SEQ ID NO: 523 or a fragment thereof.

The disclosure also provides an isolated polynucleotide encoding the polypeptide of SEQ ID NO: 381 or a fragment thereof. In some embodiments, the polypeptide of SEQ ID NO: 381, or a fragment thereof, is encoded by the polynucleotide of SEQ ID NO: 382 or a fragment thereof. In some embodiments, the polypeptide of SEQ ID NO: 381, or a fragment thereof, is encoded by the polynucleotide of SEQ ID NO: 460 or a fragment thereof. In some embodiments, the polypeptide of SEQ ID NO: 381, or a fragment thereof, is encoded by the polynucleotide of SEQ ID NO: 501 or a fragment thereof.

The disclosure also provides an isolated polynucleotide encoding the polypeptide of SEQ ID NO: 383 or a fragment thereof. In some embodiments, the polypeptide of SEQ ID NO: 383, or a fragment thereof, is encoded by the polynucleotide of SEQ ID NO: 384 or a fragment thereof.

The disclosure also provides an isolated polynucleotide encoding the polypeptide of SEQ ID NO: 385 or a fragment thereof. In some embodiments, the polypeptide of SEQ ID NO: 385, or a fragment thereof, is encoded by the polynucleotide of SEQ ID NO: 386 or a fragment thereof.

The disclosure also provides an isolated polynucleotide encoding the polypeptide of SEQ ID NO: 387 or a fragment thereof.

The disclosure also provides an isolated polynucleotide encoding the polypeptide of SEQ ID NO: 388 or a fragment thereof.

The disclosure also provides an isolated polynucleotide encoding the polypeptide of SEQ ID NO: 389 or a fragment thereof.

The disclosure also provides an isolated polynucleotide encoding the polypeptide of SEQ ID NO: 390 or a fragment thereof.

The disclosure also provides an isolated polynucleotide encoding the polypeptide of SEQ ID NO: 391 or a fragment thereof.

The disclosure also provides an isolated polynucleotide encoding the polypeptide of SEQ ID NO: 392 or a fragment thereof.

The disclosure also provides an isolated polynucleotide encoding the polypeptide of SEQ ID NO: 393 or a fragment thereof.

The disclosure also provides an isolated polynucleotide encoding the polypeptide of SEQ ID NO: 394 or a fragment thereof.

The disclosure also provides an isolated polynucleotide encoding the polypeptide of SEQ ID NO: 395 or a fragment thereof.

The disclosure also provides an isolated polynucleotide encoding the polypeptide of SEQ ID NO: 396 or a fragment thereof.

The disclosure also provides an isolated polynucleotide encoding the polypeptide of SEQ ID NO: 397 or a fragment thereof.

The disclosure also provides an isolated polynucleotide encoding the polypeptide of SEQ ID NO: 398 or a fragment thereof.

The disclosure also provides an isolated polynucleotide encoding the polypeptide of SEQ ID NO: 399 or a fragment thereof.

The disclosure also provides an isolated polynucleotide encoding the polypeptide of SEQ ID NO: 400 or a fragment thereof.

The disclosure also provides an isolated polynucleotide encoding the polypeptide of SEQ ID NO: 401 or a fragment thereof.

The disclosure also provides an isolated polynucleotide encoding the polypeptide of SEQ ID NO: 402 or a fragment thereof.

The disclosure also provides an isolated polynucleotide encoding the polypeptide of SEQ ID NO: 403 or a fragment thereof.

The disclosure also provides an isolated polynucleotide encoding the polypeptide of SEQ ID NO: 404 or a fragment thereof.

The disclosure also provides an isolated polynucleotide encoding the polypeptide of SEQ ID NO: 405 or a fragment thereof.

The disclosure also provides an isolated polynucleotide encoding the polypeptide of SEQ ID NO: 406 or a fragment thereof.

The disclosure also provides an isolated polynucleotide encoding the polypeptide of SEQ ID NO: 407 or a fragment thereof.

The disclosure also provides an isolated polynucleotide encoding the polypeptide of SEQ ID NO: 408 or a fragment thereof.

The disclosure also provides an isolated polynucleotide encoding the polypeptide of SEQ ID NO: 426 or a fragment thereof.

The disclosure also provides an isolated polynucleotide encoding the polypeptide of SEQ ID NO: 427 or a fragment thereof.

The disclosure also provides an isolated polynucleotide encoding the polypeptide of SEQ ID NO: 428 or a fragment thereof.

The disclosure also provides an isolated polynucleotide encoding the polypeptide of SEQ ID NO: 429 or a fragment thereof.

The disclosure also provides an isolated polynucleotide encoding the polypeptide of SEQ ID NO: 430 or a fragment thereof.

The disclosure also provides an isolated polynucleotide encoding the polypeptide of SEQ ID NO: 431 or a fragment thereof.

The disclosure also provides an isolated polynucleotide encoding the polypeptide of SEQ ID NO: 432 or a fragment thereof.

The disclosure also provides an isolated polynucleotide encoding the polypeptide of SEQ ID NO: 433 or a fragment thereof.

The disclosure also provides an isolated polynucleotide encoding the polypeptide of SEQ ID NO: 434 or a fragment thereof.

The disclosure also provides an isolated polynucleotide encoding the polypeptide of SEQ ID NO: 435 or a fragment thereof.

The disclosure also provides an isolated polynucleotide encoding the polypeptide of SEQ ID NO: 436 or a fragment thereof.

The disclosure also provides an isolated polynucleotide encoding the polypeptide of SEQ ID NO: 437 or a fragment thereof. In some embodiments, the polypeptide of SEQ ID NO: 437, or a fragment thereof, is encoded by the polynucleotide of SEQ ID NO: 448 or a fragment thereof. In some embodiments, the polypeptide of SEQ ID NO: 437, or a fragment thereof, is encoded by the polynucleotide of SEQ ID NO: 478 or a fragment thereof. In some embodiments, the polypeptide of SEQ ID NO: 437, or a fragment thereof, is encoded by the polynucleotide of SEQ ID NO: 519 or a fragment thereof.

The disclosure also provides an isolated polynucleotide encoding the polypeptide of SEQ ID NO: 438 or a fragment thereof. In some embodiments, the polypeptide of SEQ ID NO: 438, or a fragment thereof, is encoded by the polynucleotide of SEQ ID NO: 449 or a fragment thereof.

The disclosure also provides an isolated polynucleotide encoding the polypeptide of SEQ ID NO: 439 or a fragment thereof. In some embodiments, the polypeptide of SEQ ID NO: 439, or a fragment thereof, is encoded by the polynucleotide of SEQ ID NO: 450 or a fragment thereof. In some embodiments, the polypeptide of SEQ ID NO: 439, or a fragment thereof, is encoded by the polynucleotide of SEQ ID NO: 479 or a fragment thereof. In some embodiments, the polypeptide of SEQ ID NO: 439, or a fragment thereof, is encoded by the polynucleotide of SEQ ID NO: 520 or a fragment thereof.

The disclosure also provides an isolated polynucleotide encoding the polypeptide of SEQ ID NO: 440 or a fragment thereof. In some embodiments, the polypeptide of SEQ ID NO: 440, or a fragment thereof, is encoded by the polynucleotide of SEQ ID NO: 451 or a fragment thereof.

The disclosure also provides an isolated polynucleotide encoding the polypeptide of SEQ ID NO: 441 or a fragment thereof. In some embodiments, the polypeptide of SEQ ID NO: 441, or a fragment thereof, is encoded by the polynucleotide of SEQ ID NO: 452 or a fragment thereof.

The disclosure also provides an isolated polynucleotide encoding the polypeptide of SEQ ID NO: 442 or a fragment thereof. In some embodiments, the polypeptide of SEQ ID NO: 442, or a fragment thereof, is encoded by the polynucleotide of SEQ ID NO: 453 or a fragment thereof. In some embodiments, the polypeptide of SEQ ID NO: 442, or a fragment thereof, is encoded by the polynucleotide of SEQ ID NO: 480 or a fragment thereof. In some embodiments, the polypeptide of SEQ ID NO: 442, or a fragment thereof, is encoded by the polynucleotide of SEQ ID NO: 521 or a fragment thereof.

The disclosure also provides an isolated polynucleotide encoding the polypeptide of SEQ ID NO: 443 or a fragment thereof. In some embodiments, the polypeptide of SEQ ID NO: 443, or a fragment thereof, is encoded by the polynucleotide of SEQ ID NO: 454 or a fragment thereof.

The disclosure also provides an isolated polynucleotide encoding the polypeptide of SEQ ID NO: 444 or a fragment thereof. In some embodiments, the polypeptide of SEQ ID NO: 444, or a fragment thereof, is encoded by the polynucleotide of SEQ ID NO: 455 or a fragment thereof. In some embodiments, the polypeptide of SEQ ID NO: 444, or a fragment thereof, is encoded by the polynucleotide of SEQ ID NO: 481 or a fragment thereof. In some embodiments, the polypeptide of SEQ ID NO: 444, or a fragment thereof, is encoded by the polynucleotide of SEQ ID NO: 522 or a fragment thereof.

The disclosure also provides an isolated polynucleotide encoding the polypeptide of SEQ ID NO: 445 or a fragment thereof. In some embodiments, the polypeptide of SEQ ID NO: 445, or a fragment thereof, is encoded by the polynucleotide of SEQ ID NO: 456 or a fragment thereof.

The disclosure also provides an isolated polynucleotide encoding the polypeptide of SEQ ID NO: 446 or a fragment thereof. In some embodiments, the polypeptide of SEQ ID NO: 446, or a fragment thereof, is encoded by the polynucleotide of SEQ ID NO: 457 or a fragment thereof.

The disclosure also provides an isolated polynucleotide encoding the polypeptide of SEQ ID NO: 447 or a fragment thereof. In some embodiments, the polypeptide of SEQ ID NO: 447, or a fragment thereof, is encoded by the polynucleotide of SEQ ID NO: 458 or a fragment thereof.

In some embodiments, the heterologous polynucleotide is an in-frame heterologous polynucleotide.

The disclosure also provides an isolated heterologous polynucleotide comprising 3 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 4 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 5 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 6 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 7 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 8 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 9 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 10 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 11 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 12 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 13 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 14 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 15 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 16 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 17 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 18 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 19 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 20 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 21 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 22 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 23 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 24 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 25 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 26 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 27 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 28 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 29 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 30 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 31 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 32 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 33 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 34 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 35 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 36 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 37 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 38 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 39 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 40 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 41 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 42 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 43 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 44 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 45 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 46 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 47 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 48 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 49 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 50 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 51 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 52 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 53 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 54 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 55 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 56 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 57 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 58 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 59 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 60 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 61 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 62 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 63 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 64 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 65 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 66 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 67 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 68 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 69 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 70 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 71 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 72 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 73 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 74 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 75 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 76 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 77 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 78 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 79 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 80 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 81 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 82 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 83 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 84 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 85 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 86 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 87 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 88 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 89 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 90 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 91 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 92 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 93 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 94 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 95 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 96 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 97 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 98 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 99 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 100 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 101 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 102 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 103 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 104 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 105 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 106 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 107 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 108 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 109 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 110 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 111 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 112 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 113 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 114 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 115 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 116 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 117 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 118 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 119 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 120 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 121 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 122 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 123 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 124 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 125 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 126 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 127 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 128 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 129 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 130 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 131 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 132 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 133 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 134 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 135 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 136 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 137 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 138 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 139 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 140 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 141 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 142 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 143 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 144 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 145 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 146 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 147 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 148 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 149 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 150 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 151 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 152 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 153 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 154 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 155 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 156 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 157 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 158 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 159 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 160 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 161 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 162 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 163 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 164 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 165 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 166 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 167 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 168 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 169 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 170 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 171 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 172 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 173 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 174 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 175 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 176 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 177 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 178 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 179 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 180 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 181 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 182 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 183 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 184 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 185 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 186 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 187 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 188 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 189 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 190 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 191 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 192 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 193 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 194 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 195 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 196 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 197 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 198 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 199 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 200 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 201 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 202 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 203 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising 204 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 3 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 4 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 5 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 6 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 7 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 8 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 9 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 10 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 11 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 12 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 13 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 14 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 15 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 16 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 17 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 18 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 19 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 20 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 21 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 22 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 23 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 24 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 25 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 26 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 27 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 28 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 29 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 30 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 31 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 32 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 33 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 34 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 35 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 36 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 37 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 38 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 39 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 40 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides an isolated heterologous polynucleotide comprising 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

For expression in various hosts, the polynucleotides may be codon-optimized utilizing known methods. For example, for adenoviral expression, a heterologous polynucleotide comprising at least one of the polynucleotides of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 or 499 may be used. For expression in a modified vaccinia Ankara (MVA), a heterologous polynucleotide comprising at least one of the polynucleotides of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 or 540 may be used.

The disclosure also provides an isolated heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 3 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 4 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 5 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 6 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 7 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and thereof.

The disclosure also provides an isolated heterologous polynucleotide comprising 8 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 9 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and thereof.

The disclosure also provides an isolated heterologous polynucleotide comprising 10 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 11 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 12 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 13 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 14 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 15 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 16 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 17 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 18 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 19 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 20 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 21 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 22 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 23 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 24 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 25 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 26 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 27 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 28 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 29 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 30 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 31 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 32 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 33 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 34 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 35 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 36 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 37 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 38 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 39 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 40 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides an isolated heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 3 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 4 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 5 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 6 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 7 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 8 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 9 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 10 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 11 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 12 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 13 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 14 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 15 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 16 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 17 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 18 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 19 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 20 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 21 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 22 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 23 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 24 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 25 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 26 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 27 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 28 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 29 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 30 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 31 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 32 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 33 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 34 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 35 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 36 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 37 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 38 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 39 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 40 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polynucleotide comprising 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

In some embodiments, the isolated heterologous polynucleotide is an in-frame heterologous polynucleotide.

The disclosure also provides an isolated heterologous polynucleotide encoding a heterologous polypeptide comprising 3 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 4 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 5 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 6 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 7 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 8 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 9 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 10 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 11 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 12 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 13 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 14 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 15 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 16 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 17 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 18 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 19 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 20 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 21 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 22 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 23 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 24 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 25 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 26 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 27 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 28 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 29 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 30 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 31 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 32 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 33 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 34 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 35 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 36 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 37 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 38 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 39 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 40 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 41 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 42 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 43 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 44 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 45 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 46 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 47 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 48 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 49 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 50 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 51 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 52 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 53 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 54 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 55 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 56 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 57 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 58 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 59 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 60 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 61 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 62 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 63 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 64 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 65 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 66 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 67 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 68 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 69 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 70 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 71 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 72 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 73 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 74 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 75 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 76 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 77 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 78 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 79 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 80 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 81 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 82 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 83 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 84 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 85 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 86 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 87 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 88 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 89 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 90 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 91 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 92 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 93 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 94 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 95 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 96 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 97 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 98 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 99 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 100 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 101 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 102 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 103 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 104 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 105 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 106 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 107 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 108 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 109 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 110 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 111 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 112 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 113 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 114 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 115 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 116 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 117 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 118 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 119 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 120 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 121 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 122 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 123 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 124 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 125 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 126 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 127 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 128 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 129 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 130 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 131 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 132 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 133 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 134 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 135 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 136 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 137 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 138 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 139 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 140 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 141 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 142 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 143 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 144 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 145 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 146 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 147 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 148 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 149 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 150 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 151 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 152 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 153 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 154 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 155 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 156 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 157 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 158 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 159 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 160 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 161 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 162 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 163 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 164 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 165 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 166 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 167 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 168 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 169 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 170 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 171 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 172 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 173 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 174 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 175 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 176 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 177 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 178 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 179 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 180 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 181 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 182 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 183 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 184 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 185 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 186 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 187 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 188 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 189 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 190 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 191 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 192 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 193 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 194 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 195 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 196 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 197 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 198 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 199 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 200 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 201 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 202 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 203 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 204 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 205 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 206 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 207 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 208 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 209 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 210 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 211 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 212 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 213 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 214 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 215 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 216 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 217 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 218 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 219 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 220 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 221 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 222 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 223 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 224 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 225 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 226 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 227 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 228 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 229 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 230 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 231 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 232 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 233 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 234 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 235 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 236 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising 237 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 2 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 3 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 4 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 5 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 6 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 7 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 8 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 9 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 10 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 11 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 12 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 13 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 14 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 15 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 16 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 17 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 18 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 19 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 20 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 21 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 22 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 23 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 24 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 25 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 26 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 27 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 28 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 29 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 30 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 31 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 32 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 33 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 34 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 35 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 36 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 37 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 38 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 39 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 40 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide encoding a heterologous polypeptide comprising 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the fragments comprise about 6-24 amino acids in length.

In some embodiments, the fragments comprise at least 6 amino acids. In some embodiments, the fragments comprise at least 7 amino acids In some embodiments, the fragments comprise at least 8 amino acids. In some embodiments, the fragments comprise at least 9 amino acids. In some embodiments, the fragments comprise at least 10 amino acids. In some embodiments, the fragments comprise at least 11 amino acids. In some embodiments, the fragments comprise at least 12 amino acids. In some embodiments, the fragments comprise at least 13 amino acids. In some embodiments, the fragments comprise at least 14 amino acids. In some embodiments, the fragments comprise at least 15 amino acids. In some embodiments, the fragments comprise at least 16 amino acids. In some embodiments, the fragments comprise at least 17 amino acids. In some embodiments, the fragments comprise at least 18 amino acids. In some embodiments, the fragments comprise at least 19 amino acids. In some embodiments, the fragments comprise at least 20 amino acids. In some embodiments, the fragments comprise at least 21 amino acids. In some embodiments, the fragments comprise at least 22 amino acids. In some embodiments, the fragments comprise at least 23 amino acids. In some embodiments, the fragments comprise at least 24 amino acids. In some embodiments, the fragments comprise at least 25 amino acids. In some embodiments, the fragments comprise about 6 amino acids. In some embodiments, the fragments comprise about 7 amino acids. In some embodiments, the fragments comprise about 8 amino acids. In some embodiments, the fragments comprise about 9 amino acids. In some embodiments, the fragments comprise about 10 amino acids. In some embodiments, the fragments comprise about 11 amino acids. In some embodiments, the fragments comprise about 12 amino acids. In some embodiments, the fragments comprise about 13 amino acids. In some embodiments, the fragments comprise about 14 amino acids. In some embodiments, the fragments comprise about 15 amino acids. In some embodiments, the fragments comprise about 16 amino acids. In some embodiments, the fragments comprise about 17 amino acids. In some embodiments, the fragments comprise about 18 amino acids. In some embodiments, the fragments comprise about 19 amino acids. In some embodiments, the fragments comprise about 20 amino acids. In some embodiments, the fragments comprise about 21 amino acids. In some embodiments, the fragments comprise about 22 amino acids. In some embodiments, the fragments comprise about 23 amino acids. In some embodiments, the fragments comprise about 24 amino acids. In some embodiments, the fragments comprise about 25 amino acids. In some embodiments, the fragments comprise about 6-25 amino acids. In some embodiments, the fragments comprise about 7-25 amino acids. In some embodiments, the fragments comprise about 8-25 amino acids. In some embodiments, the fragments comprise about 8-24 amino acids. In some embodiments, the fragments comprise about 8-23 amino acids. In some embodiments, the fragments comprise about 8-22 amino acids. In some embodiments, the fragments comprise about 8-21 amino acids. In some embodiments, the fragments comprise about 8-20 amino acids. In some embodiments, the fragments comprise about 8-19 amino acids. In some embodiments, the fragments comprise about 8-18 amino acids. In some embodiments, the fragments comprise about 8-17 amino acids. In some embodiments, the fragments comprise about 8-16 amino acids. In some embodiments, the fragments comprise about 8-15 amino acids. In some embodiments, the fragments comprise about 8-14 amino acids. In some embodiments, the fragments comprise about 9-14 amino acids. In some embodiments, the fragments comprise about 9-13 amino acids. In some embodiments, the fragments comprise about 9-12 amino acids. In some embodiments, the fragments comprise about 9-11 amino acids. In some embodiments, the fragments comprise about 9-10 amino acids.

In some embodiments, the fragments comprise SEQ ID NOs: 387, 388, 389, 390, 391, 392, 393, 394, 395, 396, 397, 398, 399, 400, 401, 402, 403, 404, 405, 406, 407, 408, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620 or 621.

In some embodiments, the fragments comprise SEQ ID NOs: 377, 378, 415, 417, 418, 420, 502, 518, 526, 527, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 74, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 487, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980 or 548.

In some embodiments, the fragments are immunogenic fragments.

Immunogenic fragments in general are peptides that activate T cells, for example those that induce cytotoxic T cells when presented on MHC. Methods for assessing activation of T cells and/or induction of cytotoxic T lymphocytes are well known. In an exemplary assay, PBMCs isolated from a prostate cancer patient are cultured in vitro in the presence of a test neoantigen or fragments thereof and IL-25. The cultures may be replenished periodically with IL-15 and IL-2 and cultured for an additional 12 days. On day 12, the cultures are re-stimulated with the test neoantigen or fragments thereof and the following day T cell activation may be assessed by measuring a percentage of $IFN\gamma^+TNA\alpha^+CD8^+$ cells when compared to a control culture.

The disclosure also provides an isolated polypeptide comprising an amino acid sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

In some embodiments, the polypeptide is encoded by a polynucleotide sequence of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 or 458, or fragments thereof.

In some embodiments, the polypeptide is encoded by a polynucleotide sequence of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 or 499, or fragments thereof.

In some embodiments, the polypeptide is encoded by a polynucleotide sequence of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 or 540, or fragments thereof.

The polypeptides and the heterologous polypeptides of the disclosure comprise one or more prostate neoantigens described herein. The polypeptides and the heterologous polypeptides of the disclosure are useful in generating the recombinant viruses, the cells and the vaccines of the disclosure and proteinaceous molecules that specifically bind the one or more prostate neoantigens of the disclosure or may be used directly as therapeutic agents by delivering them to a subject having a prostate cancer using various technologies. The two or more neoantigens (e.g. polypeptides) may be incorporated into the vaccine in any order using standard cloning methods.

The disclosure also provides an isolated polypeptide comprising an amino acid sequence of SEQ ID NO: 1 or fragments thereof.

The disclosure also provides an isolated polypeptide comprising an amino acid sequence of SEQ ID NO: 3 or fragments thereof.

The disclosure also provides an isolated polypeptide comprising an amino acid sequence of SEQ ID NO: 5 or fragments thereof.

The disclosure also provides an isolated polypeptide comprising an amino acid sequence of SEQ ID NO: 7 or fragments thereof.

The disclosure also provides an isolated polypeptide comprising an amino acid sequence of SEQ ID NO: 9 or fragments thereof.

The disclosure also provides an isolated polypeptide comprising an amino acid sequence of SEQ ID NO: 11 or fragments thereof.

The disclosure also provides an isolated polypeptide comprising an amino acid sequence of SEQ ID NO: 13 or fragments thereof.

The disclosure also provides an isolated polypeptide comprising an amino acid sequence of SEQ ID NO: 15 or fragments thereof.

The disclosure also provides an isolated polypeptide comprising an amino acid sequence of SEQ ID NO: 17 or fragments thereof.

The disclosure also provides an isolated polypeptide comprising an amino acid sequence of SEQ ID NO: 19 or fragments thereof.

The disclosure also provides an isolated polypeptide comprising an amino acid sequence of SEQ ID NO: 21 or fragments thereof.

The disclosure also provides an isolated polypeptide comprising an amino acid sequence of SEQ ID NO: 23 or fragments thereof.

The disclosure also provides an isolated polypeptide comprising an amino acid sequence of SEQ ID NO: 25 or fragments thereof.

The disclosure also provides an isolated polypeptide comprising an amino acid sequence of SEQ ID NO: 27 or fragments thereof.

The disclosure also provides an isolated polypeptide comprising an amino acid sequence of SEQ ID NO: 29 or fragments thereof.

The disclosure also provides an isolated polypeptide comprising an amino acid sequence of SEQ ID NO: 31 or fragments thereof.

The disclosure also provides an isolated polypeptide comprising an amino acid sequence of SEQ ID NO: 33 or fragments thereof.

The disclosure also provides an isolated polypeptide comprising an amino acid sequence of SEQ ID NO: 35 or fragments thereof.

The disclosure also provides an isolated polypeptide comprising an amino acid sequence of SEQ ID NO: 37 or fragments thereof.

The disclosure also provides an isolated polypeptide comprising an amino acid sequence of SEQ ID NO: 39 or fragments thereof.

The disclosure also provides an isolated polypeptide comprising an amino acid sequence of SEQ ID NO: 41 or fragments thereof.

The disclosure also provides an isolated polypeptide comprising an amino acid sequence of SEQ ID NO: 43 or fragments thereof.

The disclosure also provides an isolated polypeptide comprising an amino acid sequence of SEQ ID NO: 45 or fragments thereof.

The disclosure also provides an isolated polypeptide comprising an amino acid sequence of SEQ ID NO: 47 or fragments thereof.

The disclosure also provides an isolated polypeptide comprising an amino acid sequence of SEQ ID NO: 49 or fragments thereof.

The disclosure also provides an isolated polypeptide comprising an amino acid sequence of SEQ ID NO: 51 or fragments thereof.

The disclosure also provides an isolated polypeptide comprising an amino acid sequence of SEQ ID NO: 53 or fragments thereof.

The disclosure also provides an isolated polypeptide comprising an amino acid sequence of SEQ ID NO: 55 or fragments thereof.

The disclosure also provides an isolated polypeptide comprising an amino acid sequence of SEQ ID NO: 57 or fragments thereof.

The disclosure also provides an isolated polypeptide comprising an amino acid sequence of SEQ ID NO: 59 or fragments thereof.

The disclosure also provides an isolated polypeptide comprising an amino acid sequence of SEQ ID NO: 61 or fragments thereof.

The disclosure also provides an isolated polypeptide comprising an amino acid sequence of SEQ ID NO: 63 or fragments thereof.

The disclosure also provides an isolated polypeptide comprising an amino acid sequence of SEQ ID NO: 65 or fragments thereof.

The disclosure also provides an isolated polypeptide comprising an amino acid sequence of SEQ ID NO: 67 or fragments thereof.

The disclosure also provides an isolated polypeptide comprising an amino acid sequence of SEQ ID NO: 69 or fragments thereof.

The disclosure also provides an isolated polypeptide comprising an amino acid sequence of SEQ ID NO: 71 or fragments thereof.

The disclosure also provides an isolated polypeptide comprising an amino acid sequence of SEQ ID NO: 73 or fragments thereof.

The disclosure also provides an isolated polypeptide comprising an amino acid sequence of SEQ ID NO: 75 or fragments thereof.

The disclosure also provides an isolated polypeptide comprising an amino acid sequence of SEQ ID NO: 77 or fragments thereof.

The disclosure also provides an isolated polypeptide comprising an amino acid sequence of SEQ ID NO: 79 or fragments thereof.

The disclosure also provides an isolated polypeptide comprising an amino acid sequence of SEQ ID NO: 81 or fragments thereof.

The disclosure also provides an isolated polypeptide comprising an amino acid sequence of SEQ ID NO: 83 or fragments thereof.

The disclosure also provides an isolated polypeptide comprising an amino acid sequence of SEQ ID NO: 85 or fragments thereof.

The disclosure also provides an isolated polypeptide comprising an amino acid sequence of SEQ ID NO: 87 or fragments thereof The disclosure also provides an isolated polypeptide comprising an amino acid sequence of SEQ ID NO: 89 or fragments thereof.

The disclosure also provides an isolated polypeptide comprising an amino acid sequence of SEQ ID NO: 91 or fragments thereof.

The disclosure also provides an isolated polypeptide comprising an amino acid sequence of SEQ ID NO: 93 or fragments thereof.

The disclosure also provides an isolated polypeptide comprising an amino acid sequence of SEQ ID NO: 95 or fragments thereof.

The disclosure also provides an isolated polypeptide comprising an amino acid sequence of SEQ ID NO: 97 or fragments thereof.

The disclosure also provides an isolated polypeptide comprising an amino acid sequence of SEQ ID NO: 99 or fragments thereof.

The disclosure also provides an isolated polypeptide comprising an amino acid sequence of SEQ ID NO: 101 or fragments thereof.

The disclosure also provides an isolated polypeptide comprising an amino acid sequence of SEQ ID NO: 103 or fragments thereof.

The disclosure also provides an isolated polypeptide comprising an amino acid sequence of SEQ ID NO: 105 or fragments thereof.

The disclosure also provides an isolated polypeptide comprising an amino acid sequence of SEQ ID NO: 107 or fragments thereof.

The disclosure also provides an isolated polypeptide comprising an amino acid sequence of SEQ ID NO: 109 or fragments thereof.

The disclosure also provides an isolated polypeptide comprising an amino acid sequence of SEQ ID NO: 111 or fragments thereof.

The disclosure also provides an isolated polypeptide comprising an amino acid sequence of SEQ ID NO: 113 or fragments thereof.

The disclosure also provides an isolated polypeptide comprising an amino acid sequence of SEQ ID NO: 115 or fragments thereof.

The disclosure also provides an isolated polypeptide comprising an amino acid sequence of SEQ ID NO: 117 or fragments thereof.

The disclosure also provides an isolated polypeptide comprising an amino acid sequence of SEQ ID NO: 119 or fragments thereof.

The disclosure also provides an isolated polypeptide comprising an amino acid sequence of SEQ ID NO: 121 or fragments thereof.

The disclosure also provides an isolated polypeptide comprising an amino acid sequence of SEQ ID NO: 123 or fragments thereof.

The disclosure also provides an isolated polypeptide comprising an amino acid sequence of SEQ ID NO: 125 or fragments thereof.

The disclosure also provides an isolated polypeptide comprising an amino acid sequence of SEQ ID NO: 127 or fragments thereof.

The disclosure also provides an isolated polypeptide comprising an amino acid sequence of SEQ ID NO: 129 or fragments thereof.

The disclosure also provides an isolated polypeptide comprising an amino acid sequence of SEQ ID NO: 131 or fragments thereof.

The disclosure also provides an isolated polypeptide comprising an amino acid sequence of SEQ ID NO: 133 or fragments thereof.

The disclosure also provides an isolated polypeptide comprising an amino acid sequence of SEQ ID NO: 135 or fragments thereof.

The disclosure also provides an isolated polypeptide comprising an amino acid sequence of SEQ ID NO: 137 or fragments thereof.

The disclosure also provides an isolated polypeptide comprising an amino acid sequence of SEQ ID NO: 139 or fragments thereof.

The disclosure also provides an isolated polypeptide comprising an amino acid sequence of SEQ ID NO: 141 or fragments thereof.

The disclosure also provides an isolated polypeptide comprising an amino acid sequence of SEQ ID NO: 143 or fragments thereof.

The disclosure also provides an isolated polypeptide comprising an amino acid sequence of SEQ ID NO: 145 or fragments thereof.

The disclosure also provides an isolated polypeptide comprising an amino acid sequence of SEQ ID NO: 147 or fragments thereof.

The disclosure also provides an isolated polypeptide comprising an amino acid sequence of SEQ ID NO: 149 or fragments thereof.

The disclosure also provides an isolated polypeptide comprising an amino acid sequence of SEQ ID NO: 151 or fragments thereof.

The disclosure also provides an isolated polypeptide comprising an amino acid sequence of SEQ ID NO: 153 or fragments thereof.

The disclosure also provides an isolated polypeptide comprising an amino acid sequence of SEQ ID NO: 155 or fragments thereof.

The disclosure also provides an isolated polypeptide comprising an amino acid sequence of SEQ ID NO: 157 or fragments thereof.

The disclosure also provides an isolated polypeptide comprising an amino acid sequence of SEQ ID NO: 159 or fragments thereof.

The disclosure also provides an isolated polypeptide comprising an amino acid sequence of SEQ ID NO: 161 or fragments thereof.

The disclosure also provides an isolated polypeptide comprising an amino acid sequence of SEQ ID NO: 163 or fragments thereof.

The disclosure also provides an isolated polypeptide comprising an amino acid sequence of SEQ ID NO: 165 or fragments thereof.

The disclosure also provides an isolated polypeptide comprising an amino acid sequence of SEQ ID NO: 167 or fragments thereof.

The disclosure also provides an isolated polypeptide comprising an amino acid sequence of SEQ ID NO: 169 or fragments thereof.

The disclosure also provides an isolated polypeptide comprising an amino acid sequence of SEQ ID NO: 171 or fragments thereof.

The disclosure also provides an isolated polypeptide comprising an amino acid sequence of SEQ ID NO: 173 or fragments thereof.

The disclosure also provides an isolated polypeptide comprising an amino acid sequence of SEQ ID NO: 175 or fragments thereof.

The disclosure also provides an isolated polypeptide comprising an amino acid sequence of SEQ ID NO: 177 or fragments thereof.

The disclosure also provides an isolated polypeptide comprising an amino acid sequence of SEQ ID NO: 179 or fragments thereof.

The disclosure also provides an isolated polypeptide comprising an amino acid sequence of SEQ ID NO: 181 or fragments thereof.

The disclosure also provides an isolated polypeptide comprising an amino acid sequence of SEQ ID NO: 183 or fragments thereof.

The disclosure also provides an isolated polypeptide comprising an amino acid sequence of SEQ ID NO: 185 or fragments thereof.

The disclosure also provides an isolated polypeptide comprising an amino acid sequence of SEQ ID NO: 187 or fragments thereof.

The disclosure also provides an isolated polypeptide comprising an amino acid sequence of SEQ ID NO: 189 or fragments thereof.

The disclosure also provides an isolated polypeptide comprising an amino acid sequence of SEQ ID NO: 191 or fragments thereof.

The disclosure also provides an isolated polypeptide comprising an amino acid sequence of SEQ ID NO: 193 or fragments thereof.

The disclosure also provides an isolated polypeptide comprising an amino acid sequence of SEQ ID NO: 195 or fragments thereof.

The disclosure also provides an isolated polypeptide comprising an amino acid sequence of SEQ ID NO: 197 or fragments thereof.

The disclosure also provides an isolated polypeptide comprising an amino acid sequence of SEQ ID NO: 199 or fragments thereof.

The disclosure also provides an isolated polypeptide comprising an amino acid sequence of SEQ ID NO: 201 or fragments thereof.

The disclosure also provides an isolated polypeptide comprising an amino acid sequence of SEQ ID NO: 203 or fragments thereof.

The disclosure also provides an isolated polypeptide comprising an amino acid sequence of SEQ ID NO: 205 or fragments thereof.

The disclosure also provides an isolated polypeptide comprising an amino acid sequence of SEQ ID NO: 207 or fragments thereof.

The disclosure also provides an isolated polypeptide comprising an amino acid sequence of SEQ ID NO: 209 or fragments thereof.

The disclosure also provides an isolated polypeptide comprising an amino acid sequence of SEQ ID NO: 211 or fragments thereof.

The disclosure also provides an isolated polypeptide comprising an amino acid sequence of SEQ ID NO: 213 or fragments thereof.

The disclosure also provides an isolated polypeptide comprising an amino acid sequence of SEQ ID NO: 215 or fragments thereof.

The disclosure also provides an isolated polypeptide comprising an amino acid sequence of SEQ ID NO: 217 or fragments thereof.

The disclosure also provides an isolated polypeptide comprising an amino acid sequence of SEQ ID NO: 219 or fragments thereof.

The disclosure also provides an isolated polypeptide comprising an amino acid sequence of SEQ ID NO: 221 or fragments thereof.

The disclosure also provides an isolated polypeptide comprising an amino acid sequence of SEQ ID NO: 223 or fragments thereof.

The disclosure also provides an isolated polypeptide comprising an amino acid sequence of SEQ ID NO: 225 or fragments thereof.

The disclosure also provides an isolated polypeptide comprising an amino acid sequence of SEQ ID NO: 227 or fragments thereof.

The disclosure also provides an isolated polypeptide comprising an amino acid sequence of SEQ ID NO: 229 or fragments thereof.

The disclosure also provides an isolated polypeptide comprising an amino acid sequence of SEQ ID NO: 231 or fragments thereof.

The disclosure also provides an isolated polypeptide comprising an amino acid sequence of SEQ ID NO: 233 or fragments thereof.

The disclosure also provides an isolated polypeptide comprising an amino acid sequence of SEQ ID NO: 235 or fragments thereof.

The disclosure also provides an isolated polypeptide comprising an amino acid sequence of SEQ ID NO: 237 or fragments thereof.

The disclosure also provides an isolated polypeptide comprising an amino acid sequence of SEQ ID NO: 239 or fragments thereof.

The disclosure also provides an isolated polypeptide comprising an amino acid sequence of SEQ ID NO: 241 or fragments thereof.

The disclosure also provides an isolated polypeptide comprising an amino acid sequence of SEQ ID NO: 243 or fragments thereof.

The disclosure also provides an isolated polypeptide comprising an amino acid sequence of SEQ ID NO: 245 or fragments thereof.

The disclosure also provides an isolated polypeptide comprising an amino acid sequence of SEQ ID NO: 247 or fragments thereof.

The disclosure also provides an isolated polypeptide comprising an amino acid sequence of SEQ ID NO: 249 or fragments thereof.

The disclosure also provides an isolated polypeptide comprising an amino acid sequence of SEQ ID NO: 251 or fragments thereof.

The disclosure also provides an isolated polypeptide comprising an amino acid sequence of SEQ ID NO: 253 or fragments thereof.

The disclosure also provides an isolated polypeptide comprising an amino acid sequence of SEQ ID NO: 255 or fragments thereof.

The disclosure also provides an isolated polypeptide comprising an amino acid sequence of SEQ ID NO: 257 or fragments thereof.

The disclosure also provides an isolated polypeptide comprising an amino acid sequence of SEQ ID NO: 259 or fragments thereof.

The disclosure also provides an isolated polypeptide comprising an amino acid sequence of SEQ ID NO: 261 or fragments thereof.

The disclosure also provides an isolated polypeptide comprising an amino acid sequence of SEQ ID NO: 263 or fragments thereof.

The disclosure also provides an isolated polypeptide comprising an amino acid sequence of SEQ ID NO: 265 or fragments thereof.

The disclosure also provides an isolated polypeptide comprising an amino acid sequence of SEQ ID NO: 267 or fragments thereof.

The disclosure also provides an isolated polypeptide comprising an amino acid sequence of SEQ ID NO: 269 or fragments thereof.

The disclosure also provides an isolated polypeptide comprising an amino acid sequence of SEQ ID NO: 271 or fragments thereof.

The disclosure also provides an isolated polypeptide comprising an amino acid sequence of SEQ ID NO: 273 or fragments thereof.

The disclosure also provides an isolated polypeptide comprising an amino acid sequence of SEQ ID NO: 275 or fragments thereof.

The disclosure also provides an isolated polypeptide comprising an amino acid sequence of SEQ ID NO: 277 or fragments thereof.

The disclosure also provides an isolated polypeptide comprising an amino acid sequence of SEQ ID NO: 279 or fragments thereof.

The disclosure also provides an isolated polypeptide comprising an amino acid sequence of SEQ ID NO: 281 or fragments thereof.

The disclosure also provides an isolated polypeptide comprising an amino acid sequence of SEQ ID NO: 283 or fragments thereof.

The disclosure also provides an isolated polypeptide comprising an amino acid sequence of SEQ ID NO: 285 or fragments thereof.

The disclosure also provides an isolated polypeptide comprising an amino acid sequence of SEQ ID NO: 287 or fragments thereof.

The disclosure also provides an isolated polypeptide comprising an amino acid sequence of SEQ ID NO: 289 or fragments thereof.

The disclosure also provides an isolated polypeptide comprising an amino acid sequence of SEQ ID NO: 291 or fragments thereof.

The disclosure also provides an isolated polypeptide comprising an amino acid sequence of SEQ ID NO: 293 or fragments thereof.

The disclosure also provides an isolated polypeptide comprising an amino acid sequence of SEQ ID NO: 295 or fragments thereof.

The disclosure also provides an isolated polypeptide comprising an amino acid sequence of SEQ ID NO: 297 or fragments thereof.

The disclosure also provides an isolated polypeptide comprising an amino acid sequence of SEQ ID NO: 299 or fragments thereof.

The disclosure also provides an isolated polypeptide comprising an amino acid sequence of SEQ ID NO: 301 or fragments thereof.

The disclosure also provides an isolated polypeptide comprising an amino acid sequence of SEQ ID NO: 303 or fragments thereof.

The disclosure also provides an isolated polypeptide comprising an amino acid sequence of SEQ ID NO: 305 or fragments thereof.

The disclosure also provides an isolated polypeptide comprising an amino acid sequence of SEQ ID NO: 307 or fragments thereof.

The disclosure also provides an isolated polypeptide comprising an amino acid sequence of SEQ ID NO: 309 or fragments thereof.

The disclosure also provides an isolated polypeptide comprising an amino acid sequence of SEQ ID NO: 311 or fragments thereof.

The disclosure also provides an isolated polypeptide comprising an amino acid sequence of SEQ ID NO: 313 or fragments thereof.

The disclosure also provides an isolated polypeptide comprising an amino acid sequence of SEQ ID NO: 315 or fragments thereof.

The disclosure also provides an isolated polypeptide comprising an amino acid sequence of SEQ ID NO: 317 or fragments thereof.

The disclosure also provides an isolated polypeptide comprising an amino acid sequence of SEQ ID NO: 319 or fragments thereof.

The disclosure also provides an isolated polypeptide comprising an amino acid sequence of SEQ ID NO: 321 or fragments thereof.

The disclosure also provides an isolated polypeptide comprising an amino acid sequence of SEQ ID NO: 323 or fragments thereof.

The disclosure also provides an isolated polypeptide comprising an amino acid sequence of SEQ ID NO: 325 or fragments thereof.

The disclosure also provides an isolated polypeptide comprising an amino acid sequence of SEQ ID NO: 327 or fragments thereof.

The disclosure also provides an isolated polypeptide comprising an amino acid sequence of SEQ ID NO: 329 or fragments thereof.

The disclosure also provides an isolated polypeptide comprising an amino acid sequence of SEQ ID NO: 331 or fragments thereof.

The disclosure also provides an isolated polypeptide comprising an amino acid sequence of SEQ ID NO: 333 or fragments thereof.

The disclosure also provides an isolated polypeptide comprising an amino acid sequence of SEQ ID NO: 335 or fragments thereof.

The disclosure also provides an isolated polypeptide comprising an amino acid sequence of SEQ ID NO: 337 or fragments thereof.

The disclosure also provides an isolated polypeptide comprising an amino acid sequence of SEQ ID NO: 339 or fragments thereof.

The disclosure also provides an isolated polypeptide comprising an amino acid sequence of SEQ ID NO: 341 or fragments thereof.

The disclosure also provides an isolated polypeptide comprising an amino acid sequence of SEQ ID NO: 343 or fragments thereof.

The disclosure also provides an isolated polypeptide comprising an amino acid sequence of SEQ ID NO: 345 or fragments thereof.

The disclosure also provides an isolated polypeptide comprising an amino acid sequence of SEQ ID NO: 347 or fragments thereof.

The disclosure also provides an isolated polypeptide comprising an amino acid sequence of SEQ ID NO: 349 or fragments thereof.

The disclosure also provides an isolated polypeptide comprising an amino acid sequence of SEQ ID NO: 351 or fragments thereof.

The disclosure also provides an isolated polypeptide comprising an amino acid sequence of SEQ ID NO: 353 or fragments thereof.

The disclosure also provides an isolated polypeptide comprising an amino acid sequence of SEQ ID NO: 355 or fragments thereof.

The disclosure also provides an isolated polypeptide comprising an amino acid sequence of SEQ ID NO: 357 or fragments thereof.

The disclosure also provides an isolated polypeptide comprising an amino acid sequence of SEQ ID NO: 359 or fragments thereof.

The disclosure also provides an isolated polypeptide comprising an amino acid sequence of SEQ ID NO: 361 or fragments thereof.

The disclosure also provides an isolated polypeptide comprising an amino acid sequence of SEQ ID NO: 363 or fragments thereof.

The disclosure also provides an isolated polypeptide comprising an amino acid sequence of SEQ ID NO: 365 or fragments thereof.

The disclosure also provides an isolated polypeptide comprising an amino acid sequence of SEQ ID NO: 367 or fragments thereof.

The disclosure also provides an isolated polypeptide comprising an amino acid sequence of SEQ ID NO: 369 or fragments thereof.

The disclosure also provides an isolated polypeptide comprising an amino acid sequence of SEQ ID NO: 371 or fragments thereof.

The disclosure also provides an isolated polypeptide comprising an amino acid sequence of SEQ ID NO: 373 or fragments thereof.

The disclosure also provides an isolated polypeptide comprising an amino acid sequence of SEQ ID NO: 375 or fragments thereof.

The disclosure also provides an isolated polypeptide comprising an amino acid sequence of SEQ ID NO: 379 or fragments thereof.

The disclosure also provides an isolated polypeptide comprising an amino acid sequence of SEQ ID NO: 381 or fragments thereof.

The disclosure also provides an isolated polypeptide comprising an amino acid sequence of SEQ ID NO: 383 or fragments thereof.

The disclosure also provides an isolated polypeptide comprising an amino acid sequence of SEQ ID NO: 385 or fragments thereof.

The disclosure also provides an isolated polypeptide comprising an amino acid sequence of SEQ ID NO: 387 or fragments thereof.

The disclosure also provides an isolated polypeptide comprising an amino acid sequence of SEQ ID NO: 388 or fragments thereof.

The disclosure also provides an isolated polypeptide comprising an amino acid sequence of SEQ ID NO: 389 or fragments thereof.

The disclosure also provides an isolated polypeptide comprising an amino acid sequence of SEQ ID NO: 390 or fragments thereof.

The disclosure also provides an isolated polypeptide comprising an amino acid sequence of SEQ ID NO: 391 or fragments thereof.

The disclosure also provides an isolated polypeptide comprising an amino acid sequence of SEQ ID NO: 392 or fragments thereof.

The disclosure also provides an isolated polypeptide comprising an amino acid sequence of SEQ ID NO: 393 or fragments thereof.

The disclosure also provides an isolated polypeptide comprising an amino acid sequence of SEQ ID NO: 394 or fragments thereof.

The disclosure also provides an isolated polypeptide comprising an amino acid sequence of SEQ ID NO: 395 or fragments thereof.

The disclosure also provides an isolated polypeptide comprising an amino acid sequence of SEQ ID NO: 396 or fragments thereof.

The disclosure also provides an isolated polypeptide comprising an amino acid sequence of SEQ ID NO: 397 or fragments thereof.

The disclosure also provides an isolated polypeptide comprising an amino acid sequence of SEQ ID NO: 398 or fragments thereof.

The disclosure also provides an isolated polypeptide comprising an amino acid sequence of SEQ ID NO: 399 or fragments thereof.

The disclosure also provides an isolated polypeptide comprising an amino acid sequence of SEQ ID NO: 400 or fragments thereof.

The disclosure also provides an isolated polypeptide comprising an amino acid sequence of SEQ ID NO: 401 or fragments thereof.

The disclosure also provides an isolated polypeptide comprising an amino acid sequence of SEQ ID NO: 402 or fragments thereof.

The disclosure also provides an isolated polypeptide comprising an amino acid sequence of SEQ ID NO: 403 or fragments thereof.

The disclosure also provides an isolated polypeptide comprising an amino acid sequence of SEQ ID NO: 404 or fragments thereof.

The disclosure also provides an isolated polypeptide comprising an amino acid sequence of SEQ ID NO: 405 or fragments thereof.

The disclosure also provides an isolated polypeptide comprising an amino acid sequence of SEQ ID NO: 406 or fragments thereof.

The disclosure also provides an isolated polypeptide comprising an amino acid sequence of SEQ ID NO: 407 or fragments thereof.

The disclosure also provides an isolated polypeptide comprising an amino acid sequence of SEQ ID NO: 408 or fragments thereof.

The disclosure also provides an isolated polypeptide comprising an amino acid sequence of SEQ ID NO: 426 or fragments thereof.

The disclosure also provides an isolated polypeptide comprising an amino acid sequence of SEQ ID NO: 427 or fragments thereof.

The disclosure also provides an isolated polypeptide comprising an amino acid sequence of SEQ ID NO: 428 or fragments thereof.

The disclosure also provides an isolated polypeptide comprising an amino acid sequence of SEQ ID NO: 429 or fragments thereof.

The disclosure also provides an isolated polypeptide comprising an amino acid sequence of SEQ ID NO: 430 or fragments thereof.

The disclosure also provides an isolated polypeptide comprising an amino acid sequence of SEQ ID NO: 431 or fragments thereof.

The disclosure also provides an isolated polypeptide comprising an amino acid sequence of SEQ ID NO: 432 or fragments thereof.

The disclosure also provides an isolated polypeptide comprising an amino acid sequence of SEQ ID NO: 433 or fragments thereof.

The disclosure also provides an isolated polypeptide comprising an amino acid sequence of SEQ ID NO: 434 or fragments thereof.

The disclosure also provides an isolated polypeptide comprising an amino acid sequence of SEQ ID NO: 435 or fragments thereof.

The disclosure also provides an isolated polypeptide comprising an amino acid sequence of SEQ ID NO: 436 or fragments thereof.

The disclosure also provides an isolated polypeptide comprising an amino acid sequence of SEQ ID NO: 437 or fragments thereof.

The disclosure also provides an isolated polypeptide comprising an amino acid sequence of SEQ ID NO: 438 or fragments thereof.

The disclosure also provides an isolated polypeptide comprising an amino acid sequence of SEQ ID NO: 439 or fragments thereof.

The disclosure also provides an isolated polypeptide comprising an amino acid sequence of SEQ ID NO: 440 or fragments thereof.

The disclosure also provides an isolated polypeptide comprising an amino acid sequence of SEQ ID NO: 441 or fragments thereof.

The disclosure also provides an isolated polypeptide comprising an amino acid sequence of SEQ ID NO: 442 or fragments thereof.

The disclosure also provides an isolated polypeptide comprising an amino acid sequence of SEQ ID NO: 443 or fragments thereof.

The disclosure also provides an isolated polypeptide comprising an amino acid sequence of SEQ ID NO: 444 or fragments thereof.

The disclosure also provides an isolated polypeptide comprising an amino acid sequence of SEQ ID NO: 445 or fragments thereof.

The disclosure also provides an isolated polypeptide comprising an amino acid sequence of SEQ ID NO: 446 or fragments thereof.

The disclosure also provides an isolated polypeptide comprising an amino acid sequence of SEQ ID NO: 447 or fragments thereof.

The disclosure also provides an isolated polypeptide comprising an amino acid sequence of SEQ ID NO: 560 or fragments thereof.

The disclosure also provides an isolated polypeptide comprising an amino acid sequence of SEQ ID NO: 561 or fragments thereof.

The disclosure also provides an isolated polypeptide comprising an amino acid sequence of SEQ ID NO: 562 or fragments thereof.

The disclosure also provides an isolated polypeptide comprising an amino acid sequence of SEQ ID NO: 563 or fragments thereof.

The disclosure also provides an isolated polypeptide comprising an amino acid sequence of SEQ ID NO: 564 or fragments thereof.

The disclosure also provides an isolated polypeptide comprising an amino acid sequence of SEQ ID NO: 565 or fragments thereof.

The disclosure also provides an isolated polypeptide comprising an amino acid sequence of SEQ ID NO: 566 or fragments thereof.

The disclosure also provides an isolated polypeptide comprising an amino acid sequence of SEQ ID NO: 567 or fragments thereof.

The disclosure also provides an isolated polypeptide comprising an amino acid sequence of SEQ ID NO: 568 or fragments thereof.

The disclosure also provides an isolated polypeptide comprising an amino acid sequence of SEQ ID NO: 569 or fragments thereof.

The disclosure also provides an isolated polypeptide comprising an amino acid sequence of SEQ ID NO: 570 or fragments thereof.

The disclosure also provides an isolated polypeptide comprising an amino acid sequence of SEQ ID NO: 571 or fragments thereof.

The disclosure also provides an isolated polypeptide comprising an amino acid sequence of SEQ ID NO: 572 or fragments thereof.

The disclosure also provides an isolated polypeptide comprising an amino acid sequence of SEQ ID NO: 573 or fragments thereof.

The disclosure also provides an isolated polypeptide comprising an amino acid sequence of SEQ ID NO: 574 or fragments thereof.

The disclosure also provides an isolated polypeptide comprising an amino acid sequence of SEQ ID NO: 575 or fragments thereof.

The disclosure also provides an isolated polypeptide comprising an amino acid sequence of SEQ ID NO: 576 or fragments thereof.

The disclosure also provides an isolated polypeptide comprising an amino acid sequence of SEQ ID NO: 577 or fragments thereof.

The disclosure also provides an isolated polypeptide comprising an amino acid sequence of SEQ ID NO: 578 or fragments thereof.

The disclosure also provides an isolated polypeptide comprising an amino acid sequence of SEQ ID NO: 579 or fragments thereof.

The disclosure also provides an isolated polypeptide comprising an amino acid sequence of SEQ ID NO: 580 or fragments thereof.

The disclosure also provides an isolated polypeptide comprising an amino acid sequence of SEQ ID NO: 581 or fragments thereof.

The disclosure also provides an isolated polypeptide comprising an amino acid sequence of SEQ ID NO: 582 or fragments thereof.

The disclosure also provides an isolated polypeptide comprising an amino acid sequence of SEQ ID NO: 583 or fragments thereof.

The disclosure also provides an isolated polypeptide comprising an amino acid sequence of SEQ ID NO: 584 or fragments thereof.

The disclosure also provides an isolated polypeptide comprising an amino acid sequence of SEQ ID NO: 585 or fragments thereof.

The disclosure also provides an isolated polypeptide comprising an amino acid sequence of SEQ ID NO: 586 or fragments thereof.

The disclosure also provides an isolated polypeptide comprising an amino acid sequence of SEQ ID NO: 587 or fragments thereof.

The disclosure also provides an isolated polypeptide comprising an amino acid sequence of SEQ ID NO: 588 or fragments thereof.

The disclosure also provides an isolated polypeptide comprising an amino acid sequence of SEQ ID NO: 589 or fragments thereof.

The disclosure also provides an isolated polypeptide comprising an amino acid sequence of SEQ ID NO: 590 or fragments thereof.

The disclosure also provides an isolated polypeptide comprising an amino acid sequence of SEQ ID NO: 591 or fragments thereof.

The disclosure also provides an isolated polypeptide comprising an amino acid sequence of SEQ ID NO: 592 or fragments thereof.

The disclosure also provides an isolated polypeptide comprising an amino acid sequence of SEQ ID NO: 593 or fragments thereof.

The disclosure also provides an isolated polypeptide comprising an amino acid sequence of SEQ ID NO: 594 or fragments thereof.

The disclosure also provides an isolated polypeptide comprising an amino acid sequence of SEQ ID NO: 595 or fragments thereof.

The disclosure also provides an isolated polypeptide comprising an amino acid sequence of SEQ ID NO: 596 or fragments thereof.

The disclosure also provides an isolated polypeptide comprising an amino acid sequence of SEQ ID NO: 597 or fragments thereof.

The disclosure also provides an isolated polypeptide comprising an amino acid sequence of SEQ ID NO: 598 or fragments thereof.

The disclosure also provides an isolated polypeptide comprising an amino acid sequence of SEQ ID NO: 599 or fragments thereof.

The disclosure also provides an isolated polypeptide comprising an amino acid sequence of SEQ ID NO: 600 or fragments thereof.

The disclosure also provides an isolated polypeptide comprising an amino acid sequence of SEQ ID NO: 601 or fragments thereof.

The disclosure also provides an isolated polypeptide comprising an amino acid sequence of SEQ ID NO:602 or fragments thereof.

The disclosure also provides an isolated polypeptide comprising an amino acid sequence of SEQ ID NO: 603 or fragments thereof.

The disclosure also provides an isolated polypeptide comprising an amino acid sequence of SEQ ID NO: 604 or fragments thereof.

The disclosure also provides an isolated polypeptide comprising an amino acid sequence of SEQ ID NO: 605 or fragments thereof.

The disclosure also provides an isolated polypeptide comprising an amino acid sequence of SEQ ID NO: 606 or fragments thereof.

The disclosure also provides an isolated polypeptide comprising an amino acid sequence of SEQ ID NO: 607 or fragments thereof.

The disclosure also provides an isolated polypeptide comprising an amino acid sequence of SEQ ID NO: 608 or fragments thereof.

The disclosure also provides an isolated polypeptide comprising an amino acid sequence of SEQ ID NO: 609 or fragments thereof.

The disclosure also provides an isolated polypeptide comprising an amino acid sequence of SEQ ID NO: 610 or fragments thereof.

The disclosure also provides an isolated polypeptide comprising an amino acid sequence of SEQ ID NO: 611 or fragments thereof.

The disclosure also provides an isolated polypeptide comprising an amino acid sequence of SEQ ID NO: 612 or fragments thereof.

The disclosure also provides an isolated polypeptide comprising an amino acid sequence of SEQ ID NO: 613 or fragments thereof.

The disclosure also provides an isolated polypeptide comprising an amino acid sequence of SEQ ID NO: 614 or fragments thereof.

The disclosure also provides an isolated polypeptide comprising an amino acid sequence of SEQ ID NO: 615 or fragments thereof.

The disclosure also provides an isolated polypeptide comprising an amino acid sequence of SEQ ID NO: 616 or fragments thereof.

The disclosure also provides an isolated polypeptide comprising an amino acid sequence of SEQ ID NO: 617 or fragments thereof.

The disclosure also provides an isolated polypeptide comprising an amino acid sequence of SEQ ID NO: 618 or fragments thereof.

The disclosure also provides an isolated polypeptide comprising an amino acid sequence of SEQ ID NO: 619 or fragments thereof.

The disclosure also provides an isolated polypeptide comprising an amino acid sequence of SEQ ID NO: 620 or fragments thereof.

The disclosure also provides an isolated polypeptide comprising an amino acid sequence of SEQ ID NO: 621 or fragments thereof.

The disclosure also provides an isolated heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the heterologous polypeptide is encoded by two or more polynucleotides selected from the group consisting of 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

In some embodiments, the fragments are about 6-25 amino acids in length, such as about 8-25 amino acids in length.

In some embodiments, the fragments comprise polypeptides of SEQ ID NOs: 387, 388, 389, 390, 391, 392, 393, 394, 395, 396, 397, 398, 399, 400, 401, 402, 403, 404, 405, 406, 407, 408, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620 or 621.

In some embodiments, the fragments comprise polypeptides of SEQ ID NOs: 377, 378, 415, 417, 418, 420, 502, 518, 526, 527, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 74, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 487, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980 or 548.

The disclosure also provides an isolated heterologous polypeptide comprising 3 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 4 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 5 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 6 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 7 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 8 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 9 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 10 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 11 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 12 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 13 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 14 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 15 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 16 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 17 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 18 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 19 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 20 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 21 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 22 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 23 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 24 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 25 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 26 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 27 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 28 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 29 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 30 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 31 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 32 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 33 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 34 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 35 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 36 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 37 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 38 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 39 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 40 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 41 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 42 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 43 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 44 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 45 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 46 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 47 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 48 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 49 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 50 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 51 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 52 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 53 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 54 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 55 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 56 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 57 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 58 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 59 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 60 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 61 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 62 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 63 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 64 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 65 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 66 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 67 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 68 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 69 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 70 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 71 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 72 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 73 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 74 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 75 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 76 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 77 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 78 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 79 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 80 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 81 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 82 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 83 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 84 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 85 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 86 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 87 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 88 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 89 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 90 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 91 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 92 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 93 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 94 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 95 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 96 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 97 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 98 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 99 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 100 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 101 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 102 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 103 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 104 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 105 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 106 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 107 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 108 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 109 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 110 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 111 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 112 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 113 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 114 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 115 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 116 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 117 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 118 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 119 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 120 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 121 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 122 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 123 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 124 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 125 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 126 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 127 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 128 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 129 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 130 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 131 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 132 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 133 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 134 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 135 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 136 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 137 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 138 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 139 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 140 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 141 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 142 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 143 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 144 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 145 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 146 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 147 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 148 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 149 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 150 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 151 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 152 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 153 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 154 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 155 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 156 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 157 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 158 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 159 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 160 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 161 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 162 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 163 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 164 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 165 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 166 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 167 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 168 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 169 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 170 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 171 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 172 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 173 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 174 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 175 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 176 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 177 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 178 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 179 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 180 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 181 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 182 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 183 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 184 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 185 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 186 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 187 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 188 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 189 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 190 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 191 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 192 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 193 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 194 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 195 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 196 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 197 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 198 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 199 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 200 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 201 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 202 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 203 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 204 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 205 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 206 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 207 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 208 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 209 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 210 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 211 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 212 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 213 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 214 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 215 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 216 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 217 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 218 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 219 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 220 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 221 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 222 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 223 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 224 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 225 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 226 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 227 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 228 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 229 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 230 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 231 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 232 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 233 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 234 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 235 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 236 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising 237 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the isolated heterologous polypeptide is encoded by a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 3 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 3 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 3 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 3 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 4 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 4 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotides comprising 4 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 4 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 5 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 5 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 5 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 5 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 6 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 6 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 6 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 6 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 7 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 7 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 7 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 7 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 8 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 8 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 8 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 8 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 9 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 9 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 9 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 9 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 10 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 10 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 10 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 10 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 11 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 11 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 11 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 11 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 12 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 12 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 12 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 12 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 13 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 13 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 13 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 13 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 14 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 14 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 14 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 14 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 15 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 15 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 15 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 15 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 16 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 16 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 16 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 16 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 17 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 17 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 17 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 17 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 18 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 18 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 18 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 18 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 19 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 19 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 19 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 19 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 20 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 20 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 20 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 20 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 21 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 21 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 21 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 21 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 22 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 22 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 22 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 22 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 23 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 23 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 23 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 23 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 24 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 24 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 24 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 24 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 25 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 25 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 25 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 25 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 26 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 26 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 26 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 26 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 27 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 27 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 27 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 27 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 28 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 28 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 28 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 28 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 29 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 29 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 29 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 29 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 30 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 30 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 30 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 30 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 31 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 31 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 31 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 31 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 32 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 32 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 32 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 32 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 33 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 33 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 33 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 33 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 34 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 34 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 34 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 34 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 35 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 35 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 35 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 35 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 36 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 36 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 36 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 36 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 37 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 37 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 37 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 37 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 38 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 38 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 38 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 38 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 39 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 39 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 39 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 39 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 40 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 40 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 40 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 40 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated heterologous polypeptide comprising 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polypeptide is encoded by a heterologous polynucleotide comprising 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the heterologous polypeptide is encoded by a heterologous polynucleotide comprising 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the heterologous polypeptide is encoded by a heterologous polynucleotide comprising 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

Variants of Engineered Polynucleotides, Polypeptides, Heterologous Polynucleotides and Heterologous Polypeptides of the Disclosure Variants of the polynucleotides, polypeptides, heterologous polynucleotides and heterologous polypeptides or fragments thereof are within the scope of the disclosure. For example, variants may comprise one or more substitutions, deletions or insertions, as long as the variants retain or have improved characteristics (such as immunogenicity or stability) when compared to the parent. In some embodiments, the sequence identity may be about 80%, 81%, 82%, 83%, 84%, 85%, 86%, 87%, 88%, 89%, 90%, 91%, 92%, 93%, 94%, 95%, 96%, 97%, 98% or 99% between the parent and the variant. In some embodiments, variants are generated by conservative substitutions.

In some embodiments, the identity is about 80%. In some embodiments, the identity is about 85%. In some embodiments, the identity is about 90%. In some embodiments, the identity is about 91%. In some embodiments, the identity is about 91%. In some embodiments, the identity is about 92%. In some embodiments, the identity is about 93%. In some embodiments, the identity is about 94%. In some embodiments, the identity is 94%. In some embodiments, the identity is about 95%. In some embodiments, the identity is about 96%. In some embodiments, the identity is about 97%. In some embodiments, the identity is about 98%. In some embodiments, the identity is about 99%.

In some embodiments, variants may comprise 1, 2, 3, 4, 5, 6, 7, 8, 9, 10, 11, 12, 13, 14, 15, 16, 17, 18, 19 or 20 substitutions, deletions or insertions, as long as the variants retain or have improved characteristics (such as immunogenicity or stability) when compared to the parent.

The percent identity between the two sequences is a function of the number of identical positions shared by the sequences (i.e., % identity=number of identical positions/total number of positions×100), taking into account the number of gaps, and the length of each gap, which need to be introduced for optimal alignment of the two sequences. The percent identity between two amino acid sequences may be determined using the algorithm of E. Meyers and W. Miller (*Comput Appl Biosci* 4:11-17 (1988)) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch (*J Mol Biol* 48:444-453 (1970)) algorithm which has been incorporated into the GAP program in the GCG software package (available at http_//_www_gcg_com), using either a Blossum 62 matrix or a PAM250 matrix, and a gap weight of 16, 14, 12, 10, 8, 6, or 4 and a length weight of 1, 2, 3, 4, 5, or 6.

The variants of the polypeptides or the heterologous polypeptides or fragments thereof containing one amino acid alteration generally retain similar tertiary structure and antigenicity relative to the parent. In some instances, the variant may also contain at least one amino acid alteration that causes the variant to have increased antigenicity, increased binding affinity to TCR or to antibody, or both. The variants of the polypeptides or the heterologous polypeptides may also have improved ability to bind to a HLA molecule.

The variants of the disclosure may be engineered to contain conservative substitutions. Conservative substitutions are herein defined as exchanges within one of the following five groups: Group 1-small aliphatic, nonpolar or slightly polar residues (Ala, Ser, Thr, Pro, Gly); Group 2-polar, negatively charged residues and their amides (Asp, Asn, Glu, Gin); Group 3-polar, positively charged residues (His, Arg, Lys); Group 4-large, aliphatic, nonpolar residues (Met, Leu, lie, Val, Cys); and Group 5-large, aromatic residues (Phe, Tyr, Trp).

The variants of the disclosure may be engineered to contain less conservative substitutions, such as the replacement of one amino acid by another that has similar characteristics but is somewhat different in size, such as replacement of an alanine by an isoleucine residue. The variants of the disclosure may also be engineered to contain highly non-conservative substitutions which may involve substituting an acidic amino acid for one that is polar, or even for one that is basic in character.

Additional substitutions that may be made to generate variants of the disclosure include substitutions may involve structures other than the common L-amino acids. Thus, D-amino and non-standard amino acids (i.e., other than the common naturally occurring proteinogenic amino acids) may also be used for substitution purposes to produce variants with enhanced immunogenicity when compared to the parent.

If substitutions at more than one position are found to result in polypeptides or heterologous polypeptides with substantially equivalent or greater immunogenicity, then combinations of those substitutions may be tested to determine if the combined substitutions result in additive or synergistic effects on the immunogenicity of the variant.

The amino acid residues that do not substantially contribute to interactions with the TCR may be modified by replacement with other amino acid whose incorporation does not substantially affect T-cell reactivity and does not eliminate binding to the relevant MHC. The amino acid residues that do not substantially contribute to interactions with the TCR may also be deleted as long as the deletion does not substantially affect T-cell reactivity and does not eliminate binding to the relevant MHC.

In addition, the polypeptides or the heterologous polypeptides or fragments thereof or variants may be further modified to improve stability and/or binding to MHC molecules in order to elicit a stronger immune response. Methods for such an optimization of a peptide sequence are well known in the art and include, for example, the introduction of reverse peptide bonds or non-peptide bonds. In a reverse peptide bond amino acid residues are not joined by peptide (—CO—NH—) linkages but the peptide bond is reversed. Such retro-inverso peptidomimetics may be made using methods known in the art. This approach involves making pseudopeptides containing changes involving the backbone, and not the orientation of side chains. Retro-inverse peptides, which contain NH—CO bonds instead of CO—NH peptide bonds are much more resistant to proteolysis. Additional non-peptide bond that may be used are, for example, $—CH_2—NH$, $—CH_2S—$, $—CH_2CH_2—$, $—CH{=}CH—$, $—COCH_2—$, $—CH(OH)CH_2—$, and $—CH_2SO—$.

The polypeptides or the heterologous polypeptides or fragments thereof, or variants of the disclosure may be synthesized with additional chemical groups present at their amino and/or carboxy termini, to enhance the stability, bioavailability, and/or affinity of the peptides. For example, hydrophobic groups such as carbobenzoxyl, dansyl, or t-butyloxycarbonyl groups may be added to the amino terminus. Likewise, an acetyl group or a 9-fluorenylmethoxy-carbonyl group may be placed at the amino termini. Additionally, the hydrophobic group, t-butyloxycarbonyl, or an amido group may be added to the carboxy termini.

Further, the polypeptides or the heterologous polypeptides or fragments thereof, or variants of the disclosure may be synthesized to alter their steric configuration. For example, the D-isomer of one or more of the amino acid residues of the peptide may be used, rather than the usual L-isomer.

Similarly, the polypeptides or the heterologous polypeptides or fragments thereof, or variants of the disclosure may be modified chemically by reacting specific amino acids either before or after synthesis of the polypeptides or the heterologous polypeptides or fragments thereof, or variants of the disclosure. Examples for such modifications are well known in the art and are summarized e.g. in R. Lundblad, Chemical Reagents for Protein Modification, 3rd ed. CRC Press, 2004 (Lundblad, 2004). Chemical modifications of amino acids include modification by acylation, amidation, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto. In this regard, the skilled person is referred to Chapter 15 of Current Protocols In Protein Science, Eds. Coligan et al. (John Wiley and Sons NY 1995-2000) (Coligan et al., 1995) for more extensive methodology relating to chemical modification of proteins.

Briefly, modification of e.g. arginyl residues in proteins is often based on the reaction of vicinal dicarbonyl compounds such as phenylglyoxal, 2,3-butanedione, and 1,2-cyclohexanedione to form an adduct. Another example is the reaction of methylglyoxal with arginine residues. Cysteine can be modified without concomitant modification of other nucleophilic sites such as lysine and histidine. As a result, a large number of reagents are available for the modification of cysteine. The websites of companies such as Sigma-Aldrich (http_://www_sigma-aldrich.com) provide information on specific reagents. Selective reduction of disulfide bonds in proteins is also common. Disulfide bonds can be formed and oxidized during the heat treatment of biopharmaceuticals. Woodward's Reagent K may be used to modify specific glutamic acid residues. N-(3-(dimethylamino)propyl)-N'-ethylcarbodiimide can be used to form intra-molecular crosslinks between a lysine residue and a glutamic acid residue. For example, diethylpyrocarbonate is a reagent for the modification of histidyl residues in proteins. Histidine can also be modified using 4-hydroxy-2-nonenal. The reaction of lysine residues and other α-amino groups is, for example, useful in binding of peptides to surfaces or the cross-linking of proteins/peptides. Lysine is the site of attachment of poly(ethylene)glycol and the major site of modification in the glycosylation of proteins. Methionine residues in proteins can be modified with e.g. iodoacetamide, bromoethylamine, and chloramine T. Tetranitromethane and N-acetylimidazole can be used for the modification of tyrosyl residues. Cross-linking via the formation of dityrosine can be accomplished with hydrogen peroxide/copper ions. Recent studies on the modification of tryptophan have used N-bromosuccinimide, 2-hydroxy-5-nitrobenzyl bromide or 3-bromo-3-methyl-2-(2-nitrophenylmercapto)-3H-indole (BPNS-skatole). Successful modification of therapeutic proteins and peptides with PEG is often associated with an extension of circulatory half-life while cross-linking of proteins with glutaraldehyde, polyethylene glycol diacrylate and formaldehyde is used for the preparation of hydrogels. Chemical modification of allergens for immunotherapy is often achieved by carbamylation with potassium cyanate.

The disclosure provides an isolated polypeptide that is about 80%, 81%, 82%, 83%, 84%, 85%, 86%, 87%, 88%, 89%, 90%, 91%, 92%, 93%, 94%, 95%, 96%, 97%, 98% or 99% identical to the polypeptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447.

The disclosure also provides an isolated polypeptide comprising a polypeptide sequence having 1, 2, 3, 4, 5, 6, 7, 8, 9, 10, 11, 12, 13, 14, 15, 16, 17, 18, 19 or 20 substitutions, deletions or insertions when compared to the polypeptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447.

The disclosure also provides an isolated polynucleotide that is about 80%, 81%, 82%, 83%, 84%, 85%, 86%, 87%, 88%, 89%, 90%, 91%, 92%, 93%, 94%, 95%, 96%, 97%, 98% or 99% identical to the polynucleotide of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 or 458.

The disclosure also provides an isolated polypeptide that is about 80%, 81%, 82%, 83%, 84%, 85%, 86%, 87%, 88%, 89%, 90%, 91%, 92%, 93%, 94%, 95%, 96%, 97%, 98% or 99% identical to the polypeptide of SEQ ID NOs: 387, 388, 389, 390, 391, 392, 393, 394, 395, 396, 397, 398, 399, 400, 401, 402, 403, 404, 405, 406, 407, 408, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620 or 621.

The disclosure also provides an isolated polypeptide that is about 80%, 81%, 82%, 83%, 84%, 85%, 86%, 87%, 88%, 89%, 90%, 91%, 92%, 93%, 94%, 95%, 96%, 97%, 98% or 99% identical to the polypeptide of SEQ ID NOs: 377, 378, 415, 417, 418, 420, 502, 518, 526, 527, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 74, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 487, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980 or 548.

The disclosure also provides an isolated polypeptide that is about 80%, 81%, 82%, 83%, 84%, 85%, 86%, 87%, 88%, 89%, 90%, 91%, 92%, 93%, 94%, 95%, 96%, 97%, 98% or 99% identical to the polypeptide of SEQ ID NOs: 541, 550, 554, 555, 556, 623 or 624.

The disclosure also provides an isolated polynucleotide that is about 80%, 81%, 82%, 83%, 84%, 85%, 86%, 87%, 88%, 89%, 90%, 91%, 92%, 93%, 94%, 95%, 96%, 97%, 98% or 99% identical to the polypeptide of SEQ ID NOs: 542 or SEQ ID NO: 551.

The disclosure also provides an isolated polypeptide that is about 80%, 81%, 82%, 83%, 84%, 85%, 86%, 87%, 88%, 89%, 90%, 91%, 92%, 93%, 94%, 95%, 96%, 97%, 98% or 99% identical to the polypeptide of SEQ ID NOs: 543, 552, 557, 558, 559, 625 or 626.

The disclosure also provides an isolated polynucleotide that is about 80%, 81%, 82%, 83%, 84%, 85%, 86%, 87%, 88%, 89%, 90%, 91%, 92%, 93%, 94%, 95%, 96%, 97%, 98% or 99% identical to the polypeptide of SEQ ID NOs: 544 or SEQ ID NO: 553.

The disclosure also provides an isolated polypeptide comprising an amino acid sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof, wherein the polypeptide comprises one or more reverse peptide bonds.

The disclosure also provides an isolated polypeptide comprising an amino acid sequence of SEQ ID NOs: 387, 388, 389, 390, 391, 392, 393, 394, 395, 396, 397, 398, 399, 400, 401, 402, 403, 404, 405, 406, 407, 408, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620 or 621, wherein the polypeptide comprises one or more reverse peptide bonds.

The disclosure also provides an isolated polypeptide comprising an amino acid sequence of SEQ ID NOs: 377, 378, 415, 417, 418, 420, 502, 518, 526, 527, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 74, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 487, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980 or 548, wherein the polypeptide comprises one or more reverse peptide bonds.

The disclosure also provides an isolated heterologous polypeptide comprising an amino acid sequence of SEQ ID NOs: 541, 550, 554, 555, 556, 623 or 624, wherein the heterologous polypeptide comprises one or more reverse peptide bonds.

The disclosure also provides an isolated heterologous polypeptide comprising an amino acid sequence of SEQ ID NOs: EQ ID NOs: 543, 552, 557, 558, 559, 625 or 626, wherein the heterologous polypeptide comprises one or more reverse peptide bonds.

In some embodiments, the reverse peptide bond comprises NH—CO bond.

In some embodiments, the reverse peptide bond comprises $CH_2$—NH, —$CH_2$S—, —$CH_2CH_2$—, —CH═CH—, —$COCH_2$—, —CH(OH)$CH_2$—, or —$CH_2$SO— bond.

The disclosure also provides an isolated polypeptide comprising an amino acid sequence of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof, wherein the polypeptide comprises one or more chemical modifications.

The disclosure also provides an isolated polypeptide comprising an amino acid sequence of SEQ ID NOs: 387, 388, 389, 390, 391, 392, 393, 394, 395, 396, 397, 398, 399, 400, 401, 402, 403, 404, 405, 406, 407, 408, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620 or 621, wherein the polypeptide comprises one or more chemical modifications.

The disclosure also provides an isolated polypeptide comprising an amino acid sequence of SEQ ID NOs: 377, 378, 415, 417, 418, 420, 502, 518, 526, 527, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 74, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 487, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980 or 548, wherein the polypeptide comprises one or more chemical modifications.

The disclosure also provides an isolated heterologous polypeptide comprising an amino acid sequence of SEQ ID NOs: 541, 550, 554, 555, 556, 623 or 624, wherein the heterologous polypeptide comprises one or more chemical modifications.

The disclosure also provides an isolated heterologous polypeptide comprising an amino acid sequence of SEQ ID NOs: EQ ID NOs: 543, 552, 557, 558, 559, 625 or 626, wherein the heterologous polypeptide comprises one or more chemical modifications.

In some embodiments, the one or more chemical modification comprises modification with carbobenzoxyl, dansyl, t-butyloxycarbonyl, 9-fluorenylmethoxy-carbonyl or D-isomer of an amino acid.

Methods of Making Polynucleotides and Polypeptides of the Disclosure

The polynucleotides of the disclosure or variants may be in the form of RNA or in the form of DNA obtained by cloning or produced synthetically. The DNA may be double-stranded or single-stranded.

Methods of generating polynucleotides and heterologous polynucleotides of the disclosure or variants are known in the art and include chemical synthesis, enzymatic synthesis (e.g. in vitro transcription), enzymatic or chemical cleavage of a longer precursor, chemical synthesis of smaller fragments of the polynucleotides followed by ligation of the fragments or known PCR methods. The polynucleotide sequence to be synthesized may be designed with the appropriate codons for the desired amino acid sequence. In general, preferred codons may be selected for the intended host in which the sequence will be used for expression.

Methods of making polypeptides and heterologous polypeptides of the disclosure are known in the art and include standard molecular biology techniques for cloning and expression of the polypeptides and chemical synthesis of the polypeptides.

Peptides may be synthesized by the Fmoc-polyamide mode of solid-phase peptide synthesis as disclosed by Lukas et al. (Lukas et al., 1981) and by references as cited therein. Temporary N-amino group protection is afforded by the 9-fluorenylmethyloxycarbonyl (Fmoc) group. Repetitive cleavage of this highly base-labile protecting group is done using 20% piperidine in N, N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalizing agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N, N-dicyclohexyl-carbodiimide/1 hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used include ethanedithiol, phenol, anisole and water, the exact choice depending on the constituent amino acids of the peptide being synthesized. Also a combination of solid phase and solution phase methodologies for the synthesis of peptides is possible (see, for example, (Bruckdorfer et al., 2004), and the references as cited therein).

U.S. Pat. No. 4,897,445 provides a method for the solid phase synthesis of non-peptide bonds (—$CH_2$—NH) in polypeptide chains which involves polypeptides synthesized by standard procedures and the non-peptide bond synthesized by reacting an amino aldehyde and an amino acid in the presence of $NaCNBH_3$.

Vectors and Recombinant Viruses of the Disclosure

The disclosure also provides a vector comprising a polynucleotide or a heterologous polynucleotide of the disclosure, or fragments or variants thereof.

In some embodiments, the vector is an expression vector. In some embodiments, the vector is a viral vector. The vectors of the disclosure may be utilized to generate recombinant viruses comprising the vectors of the disclosure or to express the polypeptides of the disclosure.

The disclosure also provides a vector comprising a polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides a vector comprising a polynucleotide encoding a 25 polypeptide that is about 80%, 81%, 82%, 83%, 84%, 85%, 86%, 87%, 88%, 89%, 90%, 91%, 92%, 93%, 94%, 95%, 96%, 97%, 98% or 99% identical to the polypeptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides a vector comprising one or more polynucleotides of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 or 458, or fragments thereof.

The disclosure also provides a vector comprising a polynucleotide that is about 80%, 81%, 82%, 83%, 84%, 85%, 86%, 87%, 88%, 89%, 90%, 91%, 92%, 93%, 94%, 95%, 96%, 97%, 98% or 99% identical to the polynucleotide of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 or 458, or fragments thereof.

The disclosure also provides a vector comprising a heterologous polynucleotide encoding a heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a vector comprising a heterologous polynucleotide comprising two or more polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a vector comprising a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides a vector comprising a heterologous polynucleotide encoding a heterologous polypeptide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides a vector comprising a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides a vector comprising a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

The disclosure also provides a vector comprising a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a vector comprising a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a recombinant virus comprising the vector of the disclosure.

The disclosure also provides a recombinant adenovirus comprising the vector of the disclosure.

The disclosure also provides a recombinant human adenovirus (rAd) comprising the vector of the disclosure.

The disclosure also provides a recombinant human adenovirus derived from serotype 26 (rAd26) comprising the vector of the disclosure.

The disclosure also provides a recombinant great ape adenovirus (rGAd) comprising the vector of the disclosure.

In some embodiments, the rGAd is derived from GAd20. In some embodiments, the rGAd is derived from GAd19. In some embodiments, the rGAd is derived from GAd21. In some embodiments, the rGAd is derived from GAd25. In some embodiments, the rGAd is derived from GAd26. In some embodiments, the rGAd is derived from GAd27, In some embodiments, the rGAd is derived from GAd28. In some embodiments, the rGAd is derived from GAd29. In some embodiments, the rGAd is derived from GAd30. In some embodiments, the rGAd is derived from GAd31. GAd19-21 and GAd25-31 are described in Int. Pat. Publ. No. WO2019/008111 and represent strains with high immunogenicity and no pre-existing immunity in the general human population. The polynucleotide sequence of GAd20 genome is shown in SEQ ID NO: 622 as disclosed in WO2019/008111.

```
                                         SEQ ID NO: 622
CATCATCAATAATATACCTTATTTTGGATTGAGGCCAATATGATAATGAGGTGGGCG

GGGCGAGGCGGGGCGGGTGACGTAGGACGCGCGAGTAGGGTTGGGAGGTGTGGCG

GAAGTGTGGCATTTGCAAGTGGGAGGAGCTGACATGCAATCTTCCGTCGCGGAAAA

TGTGACGTTTTTGATGAGCGCCGCCTACCTCCGGAAGTGCCAATTTTCGCGCGCTTTT

CACCGGATATCGTAGTAATTTTGGGCGGGACCATGTAAGATTTGGCCATTTTCGCGC

GAAAAGTGAAACGGGGAAGTGAAAACTGAATAATAGGGCGTTAGTCATAGCGCGTA

ATATTTACCGAGGGCCGAGGGACTTTGACCGATTACGTGGAGGACTCGCCCAGGTGT

TTTTTACGTGAATTTCCGCGTTCCGGGTCAAAGTCTCCGTTTTTATTGTCGCCGTCAT

CTGACGCGGAGGGTATTTAAACCCGCTGCGCTCCTAAAGAGGCCACTCTTGAGTGCC

AGCGAGAAGAGTTTTCTCCTCCGCTCCGTTTCGGCGATCGAAAAATGAGACATTTAG

CCTGCACTCCGGGTCTTTTGTCCGGCCGGGCGGCGTCCGAGCTTTTGGACGCTTTGCT

CAATGAGGTTCTGAGCGATGATTTTCCGTCTACTACCCACTTTAGCCCACCTACTCTT

CACGAACTGTACGATCTGGATGTACTGGTGGATGTGAACGATCCCAACGAGGAGGC

GGTTTCTACGTTTTTTCCCGAGTCTGCGCTTTTGGCTGCCCAGGAGGGATTTGACCTA

CACACTCCGCCGCTGCCTATTTTAGAGTCTCCGCTGCCGGAGCCCAGTGGTATACCTT

ATATGCCTGAACTGCTTCCCGAAGTGGTAGACCTGACCTGCCACGAGCCGGGCTTTC

CGCCCAGCGACGATGAGGGTGAGCCTTTTGCTTTAGACTATGCTGAGATACCTGGGC

TCGGTTGCAGGTCTTGTGCATATCATCAGAGGGTTACCGGAGACCCCGAGGTTAAGT

GTTCGCTGTGCTATATGAGGCTGACCTCTTCCTTTATCTACAGTAAGTTTTTTTGTGT

AGGTGGGCTTTTTGGGTAGGTGGGTTTTGTGGCAGGACAGGTGTAAATGTTGCTTGT

GTTTTTTGTACCTGCAGGTCCGGTGTCCGAGCCAGACCCGGAGCCCGACCGCGATCC

CGAGCCGGATCCCGAGCCTCCTCGCAGGCCAAGGAAATTACCTTCCATTTTGTGCAA

GCCTAAGACACCTGTGAGGACCAGCGAGGCGGACAGCACTGACTCTGGCACTTCTA

CCTCTCCTCCTGAAATTCACCCAGTGGTTCCTCTGGGTATACATAGACCTGTTGCTGT

TAGAGTTTGCGGGCGACGCCCTGCAGTAGAGTGCATTGAGGACTTGCTTAACGATCC

CGAGGGACCTTTGGACTTGAGCATTAAACGCCCTAGGCAATAAACCCCACCTAAGTA

ATAAACCCCACCTAAGTAATAAACTTTACCGCCCTTGGTTATTGAGATGACGCCCAA

TGTTTGCTTTTGAATGACTTCATGTGTATAATAAAAGTGAGTGTGGTCATAGGTCTCT

TGTTTGTCTGGGCGGGGTTTAAGGGTATATAAGTTTCTCGGGGCTAAACTTGGTTAC

ACTTGACCCCAATGGAGGCGTGGGGGTGCTTGGAGGAGTTTGCGGACGTGCGCCGTT

TGCTGGACGAGAGCTCTAGCAATACCTATAGTATTTGGAGGTATCTGTGGGGCTCTA

CTCAGGCCAAGTTGGTCTTCAGAATTAAGCAGGATTACAAGTGCGATTTTGAAGAGC

TTTTTAGTTCCTGTGGTGAGCTTTTGCAATCCTTGAATCTGGGCCACCAGGCTATCTT

CCAGGAAAAGGTTCTCTCGACTTTGGATTTTTCCACTCCCGGGCGCACCGCCGCTTGT

GTGGCTTTTGTGTCTTTTGTGCAAGATAAATGGAGCGGGGAGACCCACCTGAGTCAC

GGCTACGTGCTGGATTTCATGGCGATGGCTCTTTGGAGGGCTTACAACAAATGGAAG

ATTCAGAAGGAACTGTACGGTTCCGCCCTACGTCGTCCACTTCTGCAGCGGCAGGGG

CTGATGTTTCCCGACCATCGCCAGCATCAGAATCTGGAAGACGAGCGAGCGGAGAA

GATCAGCTTGAGAGCCGGCCTGGACCCTCCTCAGGAGGAATGAATCTCCCGCAGGT

GGTTGAGCTGTTTCCCGAACTGAGACGGGTCCTGACTATCAGGGAGGATGGTCAGTT
```

-continued

TGTGAAGAAGCTGAAGAGGGATCGGGGTGAGGGAGATGATGAGGCGGCTAGCAATT

TAGCTTTTAGTCTGATAACTCGCCACCGACCGGAATGTATTACCTATCAGCAGATTA

AGGAGAGTTGTGCCAACGAGCTGGATCTTTTGGGTCAGAAGTATAGCATAGAACAG

CTTACCACTTACTGGCTTCAGCCCGGGGATGATTGGGAAGAGGCGATTAGGGTGTAT

GCAAAGGTGGCCCTGCGGCCCGATTGCAAGTATAAGATTACTAAGTTGGTTAATATT

AGAAACTGCTGCTATATTTCTGGAAACGGGGCCGAAGTGGAGATAGATACTGAGGA

CAGGGTGGCTATTAGGTGTTGCATGATAAACATGTGGCCCGGGATACTGGGGATGG

ATGGGGTGATATTTATGAATGTGAGGTTCACGGGCCCCAACTTTAATGGTACGGTGT

TCATGGGCAACACCAACTTGCTCCTGCATGGTGCGAGTTTCTATGGGTTTAACAACA

CCTGTATAGAGGCCTGGACCGATGTAAAGGTTCGAGGTTGTTCCTTTTATAGCTGTT

GGAAGGCGGTGGTGTGTCGCCCTAAAAGCAGGGGTTCTGTGAAGAAATGCTTGTTTG

AAAGGTGCACCCTAGGTATCCTTTCTGAGGGCAACTCCAGGGTGCGCCATAATGTGG

CTTCGAACTGCGGTTGCTTCATGCAAGTGAAGGGGGTGAGCGTTATCAAGCATAACT

CGGTCTGTGGAAACTGCGAGGATCGCGCCTCTCAGATGCTGACCTGCTTTGATGGCA

ACTGTCACCTGTTGAAGACCATTCATATAAGCAGTCACCCCAGAAAGGCCTGGCCCG

TGTTTGAGCATAACATTCTGACCCGCTGTTCCTTGCATCTGGGGGTCAGGAGGGGTA

TGTTCCTGCCTTACCAGTGTAACTTTAGCCACACTAAAATCCTGCTGGAACCCGAGT

GCATGACTAAGGTCAGCCTGAATGGTGTGTTTGATGTGAGTCTGAAGATTTGGAAGG

TGCTGAGGTATGATGAGACCAGGACCAGGTGCCGACCCTGCGAGTGCGGCGGCAAG

CACATGAGAAATCAGCCTGTGATGTTGGATGTGACCGAGGAGCTTAGGCCTGACCAT

CTGGTGCTGGCCTGCACCAGGGCCGAGTTTGGGTCTAGCGATGAGGATACCGATTGA

GGTGGGTAAGGTGGGCGTGGCTAGCAGGGTGGGCGTGTATAAATTGGGGGTCTAAG

GGGTCTCTCTGTTTGTCTTGCAACAGCCGCCGCCATGAGCGACACCGGCAACAGCTT

TGATGGAAGCATCTTTAGTCCCTATCTGACAGTGCGCATGCCTCACTGGGCCGGAGT

GCGTCAGAATGTGATGGGTTCCAACGTGGATGGACGTCCCGTTCTGCCTTCAAATTC

GTCTACTATGGCCTACGCGACCGTGGGAGGAACTCCGCTGGACGCCGCGACCTCCGC

CGCCGCCTCCGCCGCCGCCGCGACCGCGCGCAGCATGGCTACGGACCTTTACAGCTC

TTTGGTGGCGAGCAGCGCGGCCTCTCGCGCGTCTGCTCGGGATGAGAAACTGACTGC

TCTGCTGCTTAAACTGGAAGACTTGACCCGGGAGCTGGGTCAACTGACCCAGCAGGT

TTCCAGCTTGCGTGAGAGCAGCCTTGCCTCCCCCTAATGGCCCATAATATAAATAAA

AGCCAGTCTGTTTGGATTAAGCAAGTGTATGTTCTTTATTTAACTCTCCGCGCGCGGT

AAGCCCGGGACCAGCGGTCTCGGTCGTTTAGGGTGCGGTGGATTTTTTCCAACACGT

GGTACAGGTGGCTCTGGATGTTTAGATACATGGGCATGAGTCCATCCCTGGGGTGGA

GGTAGCACCACTGCAGAGCTTCGTGCTCGGGGGTGGTGTTGTATATGATCCAGTCGT

AGCAGGAGCGCTGGGCGTGGTGCTGAAAAATGTCCTTAAGCAAGAGGCTTATAGCT

AGGGGGAGGCCCTTGGTGTAAGTGTTTACAAATCTGCTTAGCTGGGAGGGGTGCATC

CGGGGGGATATGATGTGCATCTTGGACTGGATTTTTAGGTTGGCTATGTTCCCGCCC

AGATCCCTTCTGGGATTCATGTTGTGCAGGACCACCAGCACGGTATATCCAGTGCAC

TTGGGAAATTTATCGTGGAGCTTAGACGGGAATGCATGGAAGAACTTGGAGACGCC

CTTGTGGCCTCCCAGATTTTCCATACATTCGTCCATGATGATGGCAATGGGCCCGTG

GGAAGCTGCCTGAGCAAAAACGTTTCTGGCATCGCTCACATCGTAGTTATGTTCCAG

-continued

GGTGAGGTCATCATAGGACATCTTTACGAATCGGGGGCGAAGGGTCCCGGACTGGG

GGATGATGGTACCCTCGGGCCCCGGGGCGTAGTTCCCCTCACAGATCTGCATCTCCC

AGGCTTTCATTTCAGAGGGAGGGATCATATCCACCTGCGGGGCGATGAAAAAGACA

GTTTCTGGCGCAGGGGAGATTAACTGGGATGAGAGCAGGTTTCTGAGCAGCTGTGA

CTTTCCACAGCCGGTGGGCCCATATATCACGCCTATCACCGGCTGCAGCTGGTAGTT

AAGAGAGCTGCAGCTGCCGTCCTCCCGGAGCAGGGGGGCCACCTCGTTGAGCATAT

CCCTGACGTGGATGTTCTCCCTGACCAGTTCCGCCAGAAGGCGCTCGCCGCCCAGCG

AAAGCAGCTCTTGCAAGGAAGCAAAATTTTTCAGCGGTTTCAGGCCATCGGCCGTGG

GCATGTTTTTCAGCGTCTGGGTCAGCAGCTCCAGCCTGTCCCAGAGCTCGGTGATGT

GCTCTACGGCATCTCGATCCAGCAGATCTCCTCGTTTCGCGGGTTGGGGCGGCTTTC

GCTGTAGGGCACCAGCCGATGGGCGTCCAGCGGGGCCAGAGTCATGTCCTTCCATG

GGCGCAGGGTCCTCGTCAGGGTGGTCTGGGTCACGGTGAAGGGGTGCGCTCCGGGT

TGGGCACTGGCCAGGGTGCGCTTGAGGCTGGTTCTGCTGGTGCTGAATCGCTGCCGC

TCTTCGCCCTGCGCGTCGGCCAGGTAGCATTTGACCATGGTCTCGTAGTCGAGACCC

TCGGCGGCGTGCCCCTTGGCGCGGAGCTTTCCCTTGGAGGTGGCGCCGCACGAGGGG

CACTGCAGGCTCTTCAGGGCGTAGAGCTTGGGAGCGAGAAACACGGACTCTGGGGA

GTAGGCGTCCGCGCCGCAGGCCGAGCAGACCGTCTCGCATTCCACCAGCCAAGTGA

GTTCCGGGCGGTCAGGGTCAAAAACCAGGTTGCCCCCATGCTTTTTGATGCGTTTCTT

ACCTTGGCTCTCCATGAGGCGGTGTCCCTTCTCGGTGACGAAGAGGCTGTCCGTGTC

CCCGTAGACCGACTTCAGGGGCCTGTCTTCCAGCGGAGTGCCTCTGTCCTCCTCGTA

GAGAAACTCTGACCACTCTGAGACGAAGGCCCGCGTCCAGGCCAGGACGAAGGAGG

CCACGTGGGAGGGGTAGCGGTCGTTGTCCACTAGCGGGTCCACCTTCTCCAGGGTGT

GCAGGCACATGTCCCCCTCCTCCGCGTCCAGAAAAGTGATTGGCTTGTAGGTGTAGG

ACACGTGACCGGGGGTTCCCAACGGGGGGGTATAAAAGGGGGTGGGTGCCCTTTCA

TCTTCACTCTCTTCCGCATCGCTGTCTGCGAGAGCCAGCTGCTGGGGTAAGTATTCCC

TCTCGAAGGCGGGCATGACCTCAGCGCTCAGGTTGTCAGTTTCTAAAAATGAGGAGG

ATTTGATGTTCACCTGTCCGGAGGTGATACCTTTGAGGGTACCTGGGTCCATCTGGTC

AGAAAACACTATTTTTTTGTTATCAAGCTTGGTGGCGAATGACCCGTAGAGGGCGTT

GGAGAGCAGCTTGGCGATGGAGCGCAGGGTCTGGTTTTTGTCGCGGTCGGCTCGCTC

CTTGGCCGCGATGTTGAGTTGCACGTACTCGCGGGCCACGCACTTCCACTCGGGGAA

CACGGTGGTGCGCTCGTCTGGGATCAGGCGCACCCTCCAGCCGCGGTTGTGCAGGGT

GACCATGTCGACGCTGGTGGCGACCTCACCGCGCAGACGCTCGTTGGTCCAGCAGA

GGCGGCCGCCCTTGCGCGAGCAGAAGGGGGGTAGGGGGTCCAGCTGGTCCTCGTTT

GGGGGGTCCGCGTCGATGGTAAAGACCCCGGGGAGCAGGCGCGGGTCAAAGTAGTC

GATCTTGCAAGCTTGCATGTCCAGAGCCCGCTGCCATTCGCGGGCGGCGAGCGCGCG

CTCGTAGGGGTTGAGGGGCGGGCCCCAGGGCATGGGGTGGGTGAGCGCGGAGGCGT

ACATGCCGCAGATGTCATACACGTACAGGGGTTCCCTGAGGATACCGAGGTAGGTG

GGGTAGCAGCGCCCCCCGCGGATGCTGGCGCGCACGTAGTCATAGAGCTCGTGGGA

GGGGGCCAGCATGTTGGGCCCGAGGTTGGTGCGCTGGGGGCGCTCGGCGCGGAAGA

CGATCTGCCTGAAGATGGCGTGGGAGTTGGAGGAGATGGTGGGCCGCTGGAAGACG

-continued
TTGAAGCTTGCTTCTTGCAAGCCCACGGAGTCCCTGACGAAGGAGGCGTAGGACTCG

CGCAGCTTGTGCACCAGCTCGGCGGTGACCTGGACGTCGAGCGCACAGTAGTCGAG

GGTCTCGCGGATGATGTCATACCTATCCTCCCCCTTCTTTTTCCACAGCTCGCGGTTG

AGGACGAACTCTTCGCGGTCTTTCCAGTACTCTTGGAGGGGAAACCCGTCCGTGTCC

GAACGGTAAGAGCCTAGCATGTAGAACTGGTTGACGGCCTGGTAGGGGCAGCAGCC

CTTCTCCACGGGCAGCGCGTAGGCCTGCGCCGCCTTGCGGAGGGAGGTGTGGGTGA

GGGCGAAAGTGTCCCTGACCATGACTTTGAGGTATTGATGTCTGAAGTCTGTGTCAT

CGCAGCCGCCCTGTTCCCACAGGGTGTAGTCCGTGCGCTTTTTGGAGCGCGGGTTGG

GCAGGGAGAAGGTGAGGTCATTGAAGAGGATCTTCCCCGCTCGAGGCATGAAGTTT

CTGGTGATGCGAAAGGGCCCTGGGACCGAGGAGCGGTTGTTGATGACCTGGGCGGC

CAGGACGATCTCGTCAAAGCCGTTTATGTTGTGTCCCACGATGTAGAGCTCCAGGAA

GCGGGGCTGGCCCTTGATGGAGGGGAGCTTTTTAAGTTCCTCGTAGGTAAGCTCCTC

GGGCGATTCCAGGCCGTGCTCCTCCAGGGCCCAGTCTTGCAAGTGAGGGTTGGCCGC

CAGGAAGGATCGCCAGAGGTCGCGGGCCATGAGGGTCTGCAGGCGGTCGCGGAAGG

TTCTGAACTGCCGCCCCACGGCCATTTTTTCGGGGGTGATGCAGTAGAAGGTGAGGG

GGTCTTTCTCCCAGGGGTCCCATCTGAGCTCTCGGGCGAGGTCGCGCGCGGCAGCGA

CCAGAGCCTCGTCGCCCCCCAGTTTCATGACCAGCATGAAGGGCACGAGTTGCTTGC

CAAAGGCTCCCATCCAAGTGTAGGTTTCTACATCGTAGGTGACAAAGAGGCGCTCCG

TGCGAGGATGAGAGCCGATTGGGAAGAACTGGATCTCCCGCCACCAGTTGGAGGAT

TGGCTGTTGATGTGGTGAAAGTAGAAGTCCCGTCTGCGGGCCGAGCACTCGTGCTGG

CTTTTGTAAAAGCGACCGCAGTACTGGCAGCGCTGCACGGGTTGTATATCTTGCACG

AGGTGAACCTGGCGACCTCTGACGAGGAAGCGCAGCGGGAATCTAAGTCCCCCGCC

TGGGGTCCCGTGTGGCTGGTGGTCTTTTACTTTGGTTGTCTGGCCGCCAGCATCTGTC

TCCTGGAGGGCGATGGTGGAACAGACCACCACGCCGCGAGAGCCGCAGGTCCAGAT

CTCGGCGCTCGGCGGGCGGAGTTTGATGACGACATCGCGCACATTGGAGCTGTCCAT

GGTCTCCAGCTCCCGCGGCGGCAGGTCAGCCGGGAGTTCCTGGAGGTTCACCTCGCA

GAGACGGGTCAAGGCGCGGACAGTGTTGAGATGGTATCTGATTTCAAGGGGCATGT

TGGAGGCGGAGTCGATGGCTTGCAGGAGGCCGCAGCCCCGGGGGGCCACGATGGTT

CCCCGCGGGGCGCGAGGGGAGGCGGAAGCTGGGGGTGTGTTCAGAAGCGGTGACGC

GGGCGGGCCCCCGGAGGTAGGGGGGGTTCCGGCCCCACAGGCATGGGCGGCAGGG

GCACGTCTTCGCCGCGCGCGGGCAGGGGCTGGTGCTGGCTCCGAAGAGCGCTTGCGT

GCGCGACGACGCGACGGTTGGTGTCCTGTATCTGGCGCCTCTGAGTGAAGACCACGG

GTCCCGTGACCTTGAACCTGAAAGAGAGTTCGACAGAATCAATCTCGGCATCGTTGA

CAGCGGCCTGGCGCAGGATCTCCTGCACGTCGCCCGAGTTGTCCTGGTAGGCGATTT

CTGCCATGAACTGCTCGATCTCTTCCTCCTGGAGATCTCCTCGTCCGGCGCGCTCCAC

GGTGGCCGCCAGGTCGTTGGAGATGCGACCCATGAGCTGCGAGAAGGCGTTGAGTC

CGCCCTCGTTCCAGACCCGGCTGTAGACCACGCCCCCCTCGGCGTCGCGGGCGCGCA

TGACCACCTGGGCCAGGTTGAGCTCCACGTGTCGCGTGAAGACGGCGTAGTTGCGCA

GGCGCTGGAAAAGGTAGTTCAGGGTGGTGGCGGTGTGCTCGGCGACGAAGAAGTAC

ATGACCCAGCGCCGCAACGTGGATTCATTGATGTCCCCCAAGGCCTCCAGGCGCTCC

ATGGCCTCGTAGAAGTCCACGGCGAAGTTGAAAAACTGGGAGTTGCGAGCGGACAC

-continued

GGTCAACTCCTCCTCCAGAAGACGGATGAGCTCGGCGACAGTGTCGCGCACCTCGCG

CTCGAAGGCCACGGGGGGCGCTTCTTCCTCTTCCACCTCTTCTTCCATGATTGCTTCT

TCTTCTTCCTCAGCCGGGACGGGAGGGGGCGGCGGCGGGGGAGGGGCGCGGCGGCG

GCGGCGGCGCACCGGGAGGCGGTCGATGAAGCGCTCGATCATCTCCCCCCGCATGC

GGCGCATGGTCTCGGTGACGGCGCGGCCGTTCTCCCGGGGGCGCAGCTCGAAGACG

CCGCCTCTCATTTCGCCGCGGGGCGGGCGGCCGTGAGGTAGCGAGACGGCGCTGAC

TATGCATCTTAACAATTGCTGTGTAGGTACGCCGCCAAGGGACCTGATTGAGTCCAG

ATCCACCGGATCCGAAAACCTTTGGAGGAAAGCGTCTATCCAGTCGCAGTCGCAAG

GTAGGCTGAGCACCGTGGCGGGCGGGGGCGGGTCGGGAGAGTTCCTGGCGGAGATG

CTGCTGATGATGTAATTAAAGTAGGCGGTCTTGAGAAGGCGGATGGTGGACAGGAG

CACCATGTCTTTGGGTCCGGCCTGTTGGATGCGGAGGCGGTCGGCCATGCCCCAGGC

CTCGTTCTGACACCGGCGCAGGTCTTTGTAGTAATCTTGCATGAGTCTTTCCACCGGC

ACTTCTTCTCCTTCCTCTTCTTCATCTCGCCGGTGGTTTCTCGCGCCGCCCATGCGCGT

GACCCCAAAGCCCCTGAGCGGCTGCAGCAGGGCCAGGTCGGCGACCACGCGCTCGG

CCAAGATGGCCTGCTGTACCTGAGTGAGGGTCCTCTCGAAGTCATCCATGTCCACGA

AGCGGTGGTAGGCACCCGTGTTGATGGTGTAGGTGCAGTTGGCCATGACGGACCAG

TTGACGGTCTGGTGTCCCGGCTGCGAGAGCTCCGTGTACCGCAGGCGCGAGAAGGC

GCGGGAATCGAACACGTAGTCGTTGCAAGTCCGCACCAGATACTGGTAGCCCACCA

GGAAGTGCGGCGGAGGTTGGCGATAGAGGGGCCAGCGCTGGGTGGCGGGGGCGCC

GGGCGCCAGGTCTTCCAGCATGAGGCGGTGGTATCCGTAGATGTACCTGGACATCCA

GGTGATGCCTGCGGCGGTGGTGGTGGCGCGCGCGTAGTCGCGGACCCGGTTCCAGA

TGTTTCGCAGGGGCGAGAAGTGTTCCATGGTCGGCACGCTCTGGCCGGTGAGGCGCG

CGCAGTCGTTGACGCTCTATACACACACAAAAACGAAAGCGTTTACAGGGCTTTCGT

TCTGTAGCCTGGAGGAAAGTAAATGGGTTGGGTTGCGGTGTGCCCCGGTTCGAGACC

AAGCTGAGCTCAGCCGGCTGAAGCCGCAGCTAACGTGGTATTGGCAGTCCCGTCTCG

ACCCAGGCCCTGTATCCTCCAGGATACGGTCGAGAGCCCTTTTGCTTTCTTGGCCAA

GCGCCCGTGGCGCGATCTGGGATAGATGGTCGCGATGAGAGGACAAAAGCGGCTCG

CTTCCGTAGTCTGGAGAAACAATCGCCAGGGTTGCGTTGCGGCGTACCCCGGTTCGA

GCCCCTATGGCGGCTTGGATCGGCCGGAACCGCGGCTAACGTGGGCTGTGGCAGCC

CCGTCCTCAGGACCCCGCCAGCCGACTTCTCCAGTTACGGGAGCGAGCCCCTTTTGT

TTTTTTATTTTTTAGATGCATCCCGTGCTGCGGCAGATGCGCCCCTCGCCCCGGCCCG

ATCAGCAGCAGCAACAGCAGGCATGCAGACCCCCCTCTCCTCTCCCCGCCCCGGTCA

CCACGGCCGCGGCGGCCGTGTCCGGTGCGGGGGCGCGCTGGAGTCAGATGAGCCA

CCGCGGCGGCGACCTAGGCAGTATCTGGACTTGGAAGAGGGCGAGGGACTGGCGCG

GCTGGGGGCGAGCTCTCCAGAGCGCCACCCGCGGGTGCAGTTGAAAAGGGACGCGC

GTGAGGCGTACCTGCCGCGGCAAAACCTGTTTCGCGACCGCGGGGGCGAGGAGCCC

GAGGAGATGCGGGACTGCAGGTTCCAAGCGGGGCGCGAGCTGCGCCGCGGCTTGGA

CAGACAGCGCCTGCTGCGCGAGGAGGACTTTGAGCCCGACACGCAGACGGGCATCA

GCCCCGCGCGCGCGCACGTGGCCGCGGCCGACCTGGTGACCGCCTACGAGCAGACG

GTGAACCAGGAGCGCAACTTCCAAAAAAGCTTCAACAACCACGTGCGCACGCTGGT

-continued

GGCGCGCGAGGAGGTGACCCTGGGTCTCATGCATCTGTGGGACCTGGTGGAGGCGA

TCGTGCAGAACCCCAGCAGCAAGCCCCTGACCGCGCAGCTGTTCCTGGTGGTGCAGC

ACAGCAGGGACAACGAGGCCTTCAGGGAGGCGCTGCTGAACATCACCGAGCCGGAG

GGGCGCTGGCTCCTGGACCTGATAAACATCCTGCAGAGCATAGTGGTGCAGGAGCG

CAGCCTGAGCCTGGCCGAGAAGGTGGCGGCCATTAACTATTCTATGCTGAGCCTGGG

CAAGTTCTACGCTCGCAAGATCTACAAGACCCCCTACGTGCCCATAGACAAGGAGGT

GAAGATAGACAGCTTCTACATGCGCATGGCGCTGAAGGTGCTAACCCTGAGCGACG

ACCTGGGAGTGTACCGCAACGAGCGCATCCACAAGGCCGTGAGCGCCAGCCGGCGG

CGCGAGCTGAGCGACCGCGAACTGATGCACAGTCTGCAGCGCGCGCTGACCGGCGC

GGGCGAGGGCGACAGGGAGGTCGAGTCCTACTTTGACATGGGGGCCGACCTGCACT

GGCAGCCGAGCCGCCGCGCCCTGGAAGCGGCGGGGGCGTACGGCGGCCCCCTGGCG

GCCGATGACGAGGAAGAGGAGGACTATGAGCTAGAGGAGGGCGAGTACCTGGAGG

ACTGACCTGGCTGGTGGTGTTTTGGTATAGATGCAAGATCCGAACGTGGCGGACCCG

GCGGTCCGGGCGGCGCTGCAGAGCCAGCCGTCCGGCATTAACTCCTCTGACGACTGG

GCCGCGGCCATGGGTCGCATCATGGCCCTGACCGCGCGCAACCCCGAGGCCTTCAG

GCAGCAGCCTCAGGCTAACCGGCTGGCGGCCATCTTGGAAGCGGTAGTGCCCGCGC

GCTCCAACCCCACCCACGAGAAGGTGCTGGCCATAGTCAACGCGCTGGCGGAGAGC

AGGGCCATCCGGGCAGACGAGGCCGGACTGGTGTACGATGCGCTGCTGCAGCGGGT

GGCGCGGTACAACAGCGGCAACGTGCAGACCAACCTGGACCGCCTGGTGACGGACG

TGCGCGAGGCCGTGGCGCAGCGCGAGCGCTTGCATCAGGACGGCAACCTGGGCTCG

CTGGTGGCGCTAAACGCCTTCCTTAGCACCCAGCCGGCCAACGTACCGCGGGGGCA

GGAGGACTACACCAACTTCTTGAGCGCGCTGCGGCTGATGGTGACCGAGGTCCCTCA

GAGCGAGGTGTACCAGTCGGGGCCCGACTACTTCTTCCAGACCAGCAGACAGGGCT

TGCAAACCGTGAACCTGAGCCAGGCTTTCAAGAACCTGCGGGGGCTGTGGGGAGTG

AAGGCGCCCACCGGCGACCGGGCTACGGTGTCCAGCCTGCTAACCCCCAACTCGCG

CCTGCTGCTGCTGCTGATCGCGCCCTTCACGGACAGCGGGAGCGTCTCGCGGGAGAC

CTATCTGGGCCACCTGCTGACGCTGTACCGCGAGGCCATCGGGCAGGCGCAGGTGG

ACGAGCACACCTTCCAGGAGATCACCAGCGTGAGCCACGCGCTGGGGCAGGAGGAC

ACGGGCAGCCTGCAGGCGACCCTGAACTACCTGCTGACCAACAGGCGGCAGAAGAT

TCCCACGCTGCACAGCCTGACCCAGGAGGAGGAGCGCATCTTGCGCTACGTGCAGC

AGAGCGTGAGCCTGAACCTGATGCGCGACGGCGTGACGCCCAGCGTGGCGCTGGAC

ATGACCGCGCGCAACATGGAACCGGGCATGTACGCTTCCCAGCGGCCGTTCATCAAC

CGCCTGATGGACTACTTGCATCGGGCGGCGGCCGTGAACCCCGAGTACTTCACCAAT

GCCATTCTGAATCCCCACTGGATGCCCCCTCCGGGTTTCTACAACGGGGACTTCGAG

GTGCCTGAGGTCAACGATGGGTTCCTCTGGGATGACATGGATGACAGTGTGTTCTCC

CCCAACCCGCTGCGCGCCGCGTCTCTGCGATTGAAGGAGGGCTCTGACAGGGAAGG

ACCAAGGAGTCTGGCCTCCTCCCTGGCTCTGGGGGCGGTGGGCGCCACGGGCGCGG

CGGCGCGGGGCAGCAGCCCCTTCCCCAGCCTGGCGGACTCTCTGAATAGCGGGCGG

GTGAGCAGGCCCCGCTTGCTAGGCGAGGAGGAGTATCTGAACAACTCCCTGCTGCA

GCCCGTGAGGGACAAAAACGCTCAGCGGCAGCAGTTTCCCAACAATGGGATAGAGA

GCCTGGTGGACAAGATGTCCAGATGGAAGACGTATGCGCAGGAGTACAAGGAGTGG

-continued

GAGGACCGCCAGCCGCGGCCCCTGCCGCCCCCTAGACAGCGCTGGCAGCGGCGCGC

GTCCAACCGCCGCTGGAGGCAGGGGCCCGAGGACGATGATGACTCTGCAGATGACA

GCAGCGTGTTGGACCTGGGCGGGAGCGGGAACCCCTTTTCGCACCTGCGCCCACGCC

TGGGCAAGATGTTTTAAAAGAGAAAAATAAAAACTCACCAAGGCCATGGCGACGAG

CGTTGGTTTTTTGTTCCCTTCCTTAGTATGCGGCGCGCGGCGATGTTCGAGGAGGGGC

CTCCCCCCTCTTACGAGAGCGCGATGGGAATTTCTCCTGCGGCGCCCCTGCAGCCTC

CCTACGTGCCTCCTCGGTACCTGCAACCTACAGGGGGGAGAAATAGCATCTGTTACT

CTGAGCTGCAGCCCCTGTACGATACCACCAGACTGTACCTGGTGGACAACAAGTCCG

CGGACGTGGCCTCCCTGAACTACCAGAACGACCACAGCGATTTTTTGACCACGGTGA

TCCAAAACAACGACTTCACCCCAACCGAGGCCAGTACCCAGACCATAAACCTGGAC

AACAGGTCGAACTGGGGCGGCGACCTGAAGACTATCCTGCACACCAATATGCCCAA

CGTGAACGAGTTCATGTTCACCAACTCTTTTAAGGCGCGGGTGATGGTGGCGCGCGA

GCAGGGGGAGGCGAAGTACGAGTGGGTGGACTTCACGCTGCCCGAGGGCAACTACT

CAGAGACCATGACTCTCGACCTGATGAACAATGCGATCGTGGAACACTATCTGAAA

GTGGGCAGGCAGAACGGGGTGAAGGAGAGCGATATCGGGGTCAAGTTTGACACCAG

AAACTTCCGTCTGGGCTGGGACCCTGTGACCGGGCTGGTCATGCCGGGGGTCTACAC

CAACGAGGCCTTTCATCCCGATATAGTGCTCCTGCCCGGCTGTGGGGTGGACTTCAC

CCAGAGCCGGCTGAGCAACCTGCTGGGCGTTCGCAAGCGGCAACCTTTCCAGGAGG

GTTTCAAGATCACCTATGAGGATCTGGAGGGGGGCAACATTCCCGCGCTCCTTGATC

TGGACGCCTACGAGGAGAGCTTGAAACCCGAGGAGAGCGCTGGCGACAGCGGCGA

GAGTGGCGAGGAGCAAGCCGGCGGCGGCGGCAGCGCGTCGGTAGAAAACGAAAGT

ACTCCCGCAGTGGCGGCGGACGCTGCGGAGGTCGAGCCGGAGGCCATGCAGCAGGA

CGCAGAGGAGGGCGCGCAGGAGGACATGAACAATGGGGAGATCAGGGGCGACACT

TTCGCCACCCGGGGCGAAGAAAAAGAGGCAGAGGCGGCGGCGGCGACGGCGGAAG

CCGAAACCGAGGCAGAGGCAGAGCCCGAGACCGAAGTTATGGAAGACATGAATGA

TGGAGAACGTAGGGGTGACACGTTTGCCACCCGGGGCGAAGAGAAGGCGGCGGAG

GCAGAAGCCGCGGCTGAGGAGGCGGCTGCGGCTGCGGCCAAGGCTGAGGCTGCGGC

TGAGGCTAAGGTCGAAGCCGATGTTGCGGTTGAGGCTCAGGCTGAGGAGGAGGCGG

CGGCTGAAGCAGTTAAGGAAAAGGCCCAGGCAGAGCAGGAAGAGAAAAAACCTGT

CATTCAACCTCTAAAAGAAGATAGCAAAAAGCGCAGTTACAACGTCATTGAGGGCA

GCACCTTTACCCAATACCGCAGCTGGTACCTGGCTTACAACTACGGCGACCCGGTCA

AGGGGGTGCGCTCGTGGACCCTGCTCTGCACGCCGGACGTCACCTGCGGCTCCGAGC

AGATGTACTGGTCGCTGCCAAACATGATGCAAGACCCGGTGACCTTCCGTTCCACGC

GGCAGGTTAGCAACTTTCCGGTGGTGGGCGCCGAACTGCTGCCAGTACACTCCAAGA

GTTTTTACAACGAGCAGGCCGTCTACTCCCAGCTGATCCGCCAGGCCACCTCTCTGA

CCCACGTGTTCAATCGCTTTCCCGAGAACCAGATTTTGGCGCGCCCGCCGGCCCCCA

CCATCACCACCGTCAGTGAAAACGTTCCTGCCCTCACAGATCACGGGACGCTACCGC

TGCGCAACAGCATCTCAGGAGTCCAGCGAGTGACCATTACTGACGCCAGACGCCGG

ACCTGCCCCTACGTTTACAAGGCCTTGGGCATAGTCTCGCCGCGCGTCCTCTCCAGTC

GCACTTTTTAAAACACATCCACCCACACGCTCCAAAATCATGTCCGTACTCATCTCG

-continued

CCCAGCAACAACACCGGCTGGGGGCTGCGCGCACCCAGCAAGATGTTTGGAGGGGC

AAGGAAGCGCTCCGACCAGCACCCCGTGCGCGTGCGCGGCCACTACCGCGCGCCCT

GGGGTGCGCACAAGCGCGGGCGCACAGGGCGCACCACTGTGGATGATGTCATTGAC

TCCGTAGTGGAGCAGGCGCGCCACTACACACCCGGCGCGCCGACCGCCTCCGCCGT

GTCCACCGTGGACCAGGCGATCGAAAGCGTGGTACAGGGGGCGCGGCACTATGCCA

ACCTTAAAAGTCGCCGCCGCCGCGTGGCGCGCCGCCATCGCCGGAGACCCCGGGCT

ACTGCCGCCGCGCGCCTTACCAAGGCTCTGCTCAAGCGCGCCAGGCGAACTGGCCAC

CGGGCCGCCATGAGGGCCGCACGGCGGGCTGCCGCTGCCGCGAGCGCCGTGGCCCC

GCGGGCACGAAGGCGCGCGGCCGCTGCCGCCGCCGCCGCCATTTCCAGCTTGGCCTC

GACGCGGCGCGGTAACATATACTGGGTGCGCGACTCGGTGAGCGGCACACGTGTGC

CCGTGCGCTTTCGCCCCCCACGGAATTAGCACAAGACAACATACACACTGAGTCTCC

TGCTGTTGTGTATCCCAGCGGCGACCGTCAGCAGCGGCGACATGTCCAAGCGCAAA

ATTAAAGAAGAGATGCTCCAGGTCATCGCGCCGGAGATCTATGGGCCCCCGAAGAA

GGAGGAGGAGGATTACAAGCCCCGCAAGCTAAAGCGGGTCAAAAAGAAAAAGAAA

GATGATGACGTTGACGAGGCGGTGGAGTTTGTCCGCCGCATGGCGCCCAGGCGCCCT

GTGCAGTGGAAGGGTCGGCGCGTGCAGCGAGTCCTGCGCCCCGGCACCGCGGTGGT

CTTTACGCCCGGCGAGCGTTCCACGCGCACTTTCAAGCGGGTGTACGATGAGGTGTA

CGGCGACGAGGATCTGTTGGAGCAGGCCAACCATCGATTTGGGGAGTTTGCATATG

GGAAACGGCCTCGCGAGAGTCTAAAAGAGGACCTGCTGGCGCTACCGCTGGACGAG

GGCAATCCCACCCCGAGTCTGAAGCCGGTGACCCTGCAACAGGTGCTGCCTTTGAGC

GCGCCCAGCGAGCAGAAGCGAGGGTTAAAGCGCGAGGGCGGGGACCTGGCACCCA

CCGTGCAGTTGATGGTGCCCAAGCGGCAGAAGCTGGAGGACGTGCTGGAGAAAATG

AAAGTAGAGCCCGGGATCCAGCCCGAGATCAAGGTCCGCCCTATCAAGCAGGTGGC

GCCCGGCGTGGGAGTCCAGACCGTGGACGTTAGGATTCCCACGGAGGAGATGGAAA

CCCAAACCGCCACTCCCTCTTCGGCAGCAAGCGCCACCACCGGCGCCGCTTCGGTAG

AGGTGCAGACGGACCCCTGGCTACCCGCCGCCACTATCGCCGTCGCCGCCGCCCCCC

GTTCGCGCGGACGCAAGAGAAATTATCCAGCGGCCAGCGCGCTTATGCCCCAGTAT

GCGCTGCATCCATCCATCGCGCCCACCCCCGGCTACCGCGGGTACTCGTACCGCCCG

CGCAGATCAGCCGGCACTCGCGGCCGCCGCCGCCGTGCGACCACAACCAGCCGCCG

CCGTCGCCGCCGCCGCCAGCCAGTGCTGACCCCCGTGTCTGTAAGGAAGGTGGCTCG

CTCGGGGAGCACGCTGGTGGTGCCCAGAGCGCGCTACCACCCCAGCATCGTTTAAA

GCCGGTCTCTGTATGGTTCTTGCAGATATGGCCCTCACTTGTCGCCTTCGCTTCCCGG

TGCCGGGATACCGAGGAAGAACTCACCGCCGCAGGGGCATGGCGGGCAGCGGTCTC

CGCGGCGGCCGTCGCCATCGCCGGCGCGCAAAGAGCAGGCGCATGCGCGGCGGTGT

GTTGCCCCTGCTGGTCCCGCTACTCGCCGCGGCGATCGGCGCCGTGCCCGGGATCGC

CTCCGTGGCCCTGCAGGCGTCCCAGAAACATTGACTCTTGCAACCTTGCAAGCTTGC

ATTTTTGGAGGAAAAAATAAAAAAGTCTAGACTCTCACGCTCGCTTGGTCCTGTGAC

TATTTTGTAGAAAAAAGATGGAAGACATCAACTTTGCGTCGCTGGCCCCGCGTCACG

GCTCGCGCCCGTTCATGGGAGACTGGACAGATATCGGCACCAGCAATATGAGCGGT

GGCGCCTTCAGCTGGGGCAGTCTGTGGAGCGGCCTTAAAAATTTTGGTTCCACCATT

AAGAACTATGGCAACAAAGCGTGGAACAGCAGCACGGGTCAGATGCTGAGAGACA

-continued

AGTTGAAAGAGCAGAACTTCCAGGAGAAGGTGGCGCAGGGCCTGGCCTCTGGCATC

AGCGGGGTGGTGGACATAGCTAACCAGGCCGTGCAGAAAAAGATAAACAGTCATCT

GGACCCCCGCCCTCAGGTGGAGGAAACGCCTCCAGCCATGGAGACGGTGTCTCCCG

AGGGCAAAGGCGAAAAGCGCCCGCGGCCCGACAGGGAAGAGACCCTGGTGTCACA

CACCGAGGAGCCGCCCTCTTACGAGGAGGCAGTCAAGGCCGGCCTGCCCACCACTC

GCCCCATAGCTCCCATGGCCACCGGTGTGGTGGGTCACAGGCAACACACCCCCGCA

ACACTAGATCTGCCCCCGCCGTCCGAGCCGACTCGCCAGCCAAAGGCGGTGACGGT

GTCCGCTCCCTCCACTTCCGCCGCCAACAGAGTGCCTCTGCGCCGCGCTGCGAGCGG

CCCCCGGGCCTCGCGAGTCAGCGGCAACTGGCAGAGCACACTGAACAGCATCGTGG

GCCTGGGAGTGAGGAGTGTGAAGCGCCGCCGTTGCTACTGAATGAGCAAGCTAGCT

AACGTGTTGTATGTGTGTATGCGTCCTATGTCGCCGCCAGAGGAGCTGTTGAGCCGC

CGGCGCCGTCTGCACTCCAGCGAATTTCAAGATGGCGACCCCATCGATGATGCCTCA

GTGGTCGTACATGCACATCTCGGGCCAGGACGCTTCGGAGTACCTGAGCCCCGGGCT

GGTGCAGTTCGCCCGCGCCACAGACACCTACTTCAACATGAGTAACAAGTTCAGGA

ACCCCACTGTGGCGCCCACCCACGATGTGACCACGGACCGGTCGCAGCGCCTGACG

CTGCGGTTCATCCCCGTGGATCGGGAGGACACCGCTTACTCTTACAAGGCGCGGTTC

ACGCTGGCCGTGGGCGACAACCGCGTGCTGGACATGGCCTCCACTTACTTTGACATC

CGGGGGGTGCTGGACAGGGGCCCCACTTTTAAGCCCTACTCGGGCACTGCCTACAAC

CCCCTGGCCCCCAAGGGCGCCCCCAATTCTTGTGAGTGGGAACAAGAGGAAAATCA

GGTGGTCGCTGCAGATGATGAACTTGAAGATGAAGAAGCGCAAGCACAAGAGGAA

GCCCCTGTGAAAAAAATTCATGTATATGCTCAGGCGCCTCTTTCTGGCGAAAAGATT

TCCAAGGATGGTATCCAAATAGGTACTGAAGTCGTAGGAGATACATCTAAGGACAC

TTTTGCAGATAAAACATTCCAACCCGAACCTCAGATAGGCGAGTCTCAGTGGAACGA

GGCTGATGCCACAGCAGCAGGAGGTAGAGTTTTGAAAAAGACTACCCCTATGAGAC

CTTGCTATGGATCCTATGCCAGGCCTACCAATGCCAACGGGGGTCAAGGAATTATGG

TTGCCAATGAACAAGGAGTGTTGGAGTCTAAAGTAGAAATGCAATTTTTCTCTAACA

CCACAACCCTTAATGCGCGGGATGGAACCGGCAATCCCGAACCAAAGGTGGTGTTG

TACAGCGAAGATGTCCACTTGGAATCTCCCGATACTCATCTGTCTTACAAGCCCAAA

AAGGATGATGTTAATGCCAAAATCATGTTGGGTCAGCAAGCCATGCCCAACAGACC

CAACCTCATTGGATTTAGAGATAATTTCATTGGGCTTATGTTTTACAACAGCACCGGT

AACATGGGAGTGCTGGCGGGTCAGGCCTCTCAGTTGAATGCTGTGGTGGACTTGCAG

GATAGAAACACAGAACTGTCATATCAGCTTCTGCTTGATTCAATTGGGGATAGAACC

AGATACTTCTCCATGTGGAACCAGGCAGTGGATAGCTATGATCCAGATGTCAGAATT

ATTGAAAACCATGGGACTGAGGATGAACTGCCCAACTACTGCTTCCCTTTGGGCGGC

ATAGGAGTTACTGATACTTATCAAGGGATAAAAAATACCAATGGCAATGGTCAGTG

GACCAAAGATGATCAGTTCGCGGACCGCAACGAAATAGGGGTGGGAAACAACTTCG

CCATGGAGATCAACATCCAGGCCAACCTTTGGAGAAACTTCCTCTATGCAAACGTGG

GGCTCTACCTGCCAGACAAGCTCAAGTACAACCCCACCAACGTGGACATCTCTGACA

ACCCCAACACCTATGACTACATGAACAAGCGGGTGGTGGCCCCTGGCCTGGTGGACT

GCTTTGTCAATGTGGGAGCCAGGTGGTCCCTGGACTACATGGACAACGTCAACCCCT

-continued

TCAACCACCACCGCAATGCGGGTCTGCGCTACCGCTCCATGATCCTGGGCAACGGGC

GCTATGTGCCCTTTCACATCCAGGTACCCCAGAAGTTCTTTGCCATCAAGAACCTCCT

GCTCCTGCCCGGCTCCTACACCTACGAGTGGAACTTCAGGAAGGATGTGAACATGGT

CCTACAGAGCTCTCTGGGCAATGACCTTAGGGTGGATGGGGCCAGCATCAAGTTTGA

CAGCATCACCCTCTATGCTACATTTTTCCCCATGGCCCACAACACCGCCTCCACGCTT

GAGGCCATGCTGAGAAACGACACCAACGACCAGTCCTTTAATGACTACCTCTCTGGG

GCCAACATGCTCTACCCAATCCCAGCCAAGGCCACCAACGTGCCCATCTCCATCCCC

TCTCGCAACTGGGCCGCCTTTAGAGGCTGGGCCTTTACCCGCCTTAAGACCAAGGAG

ACCCCCTCCCTGGGCTCGGGTTTTGATCCCTACTTTGTTTACTCGGGATCCATCCCCT

ACCTGGATGGCACCTTCTACCTCAACCACACTTTCAAGAAGATATCCATCATGTATG

ACTCCTCCGTCAGCTGGCCGGGCAACGACCGCTTGCTCACCCCCAATGAGTTCGAGG

TCAAGCGCGCCGTGGACGGCGAGGGCTACAACGTGGCCCAGTGCAACATGACCAAG

GACTGGTTCCTGGTGCAGATGCTGGCCAACTACAACATAGGCTACCAGGGCTTTTAC

ATCCCAGAGAGCTACAAGGACAGGATGTACTCCTTCTTCAGAAATTTCCAACCCATG

AGCCGACAGGTGGTGGACGAGACCAATTACAAGGACTATCAAGCCATTGGCATCAC

CCACCAGCACAACAACTCGGGTTTCGTGGGCTACCTGGCGCCCACCATGCGCGAGG

GTCAGGCCTACCCCGCCAACTTCCCCTACCCCTTGATAGGCAAGACCGCGGTCGACA

GCGTCACCCAGAAAAAGTTCCTCTGCGACCGCACCCTCTGGCGCATCCCCTTCTCTA

GCAACTTCATGTCCATGGGTGCGCTCACGGACCTGGGCCAAAACCTGCTTTATGCCA

ACTCTGCCCATGCGCTGGACATGACTTTTGAGGTGGACCCCATGGACGAGCCCACCC

TTCTCTATATTGTGTTTGAAGTGTTCGACGTGGTCAGAGTGCACCAGCCGCACCGCG

GTGTCATCGAGACCGTGTACCTGCGTACGCCCTTCTCAGCCGGCAACGCCACCACCT

AAGGAGACAGCGCCGCCGCCGCCTGCATGACGGGTTCCACCGAGCAAGAGCTCAGG

GCCATTGCCAGAGACCTGGGATGCGGACCCTATTTTTTGGGCACCTATGACAAACGC

TTCCCGGGCTTTATCTCCCGAGACAAGCTCGCCTGCGCCATTGTCAACACGGCCGCG

CGCGAGACCGGGGGCGTGCACTGGCTGGCCTTTGGCTGGGACCCGCGCTCCAAAAC

TTGCTACCTCTTTGACCCCTTTGGCTTCTCCGATCAGCGCCTCAGGCAGATTTATGAG

TTTGAGTACGAGGGGCTGCTGCGCCGCAGCGCGCTCGCCTCCTCGCCCGACCGCTGC

ATCACCCTTGAGAAGTCCACCGAAACCGTGCAGGGGCCCCACTCGGCCGCCTGCGGT

CTCTTCTGTTGCATGTTTTTGCACGCCTTTGTGCACTGGCCTCAGAGTCCCATGGATT

GCAACCCCACCATGAACTTGCTAAAGGGAGTGCCCAACGCCATGCTCCAGAGCCCC

CAGGTCCAGCCCACCCTGCGCCGCAACCAGGAACAGCTTTACCGCTTCCTGGAGCGC

CACTCCCCCTACTTCCGCAGCCACAGCGCGCGCATCCGGGGGGCCACCTCTTTTTGC

CACTTGCAAGAAAACATGCAAGACGGAAAATGATGTACAGCATGCTTTTAATAAAT

GTAAAGACTGTGCACTTTAATTATACACGGGCTCTTTCTGGTTATTTATTCAACACCG

CCGTCGCCATTTAGAAATCGAAAGGGTTCTGCCGTGCGTCGCCGTGCGCCACGGGCA

GAGACACGTTGCGATACTGGAAGCGGCTCGCCCACTTGAACTCGGGCACCACCATG

CGGGGCAGTGGTTCCTCGGGGAAGTTCTCGCTCCACAGGGTGCGGGTCAGCTGCAGC

GCGCTCAGGAGGTCGGGAGCCGAGATCTTGAAGTCGCAGTTGGGGCCGGAACCCTG

CGCGCGCGAGTTGCGGTACACGGGGTTGCAGCACTGGAACACCAGCAGGGCCGGAT

TATTCACGCTGGCCAGCAGGCTCTCGTCGCTGATCATGTCGCTGTCCAGATCCTCCGC

-continued

GTTGCTCAGGGCGAATGGGGTCATCTTGCAGACCTGCCTGCCCAGGAAAGGCGGGA

GCCCAGGCTTGCCGTTGCAGTCGCAGCGCAGGGGCATTAGCAGGTGCCCACGGCCC

GACTGCGCCTGCGGGTACAACGCGCGCATGAAGGCTTCGATCTGCCTAAAAGCCAC

CTGGGTCTTGGCTCCCTCCGAAAAGAACATCCCACAGGACTTGCTGGAGAACTGGTT

CGCGGGACAGCTGGCATCGTGCAGGCAGCAGCGCGCGTCAGTGTTGGCAATCTGCA

CCACGTTGCGACCCCACCGGTTTTTCACTATCTTGGCCTTGGAAGCCTGCTCCTTTAG

CGCGCGCTGGCCGTTCTCGCTGGTCACATCCATCTCTATCACCTGTTCCTTGTTGATC

ATGTTTGTCCCGTGCAGACACTTTAGGTCGCCCTCCGTCTGGGTGCAGCGGTGCTCCC

ACAGCGCGCAACCGGTGGGCTCCCAATTCTTGTGGGTCACCCCCGCGTAGGCCTGCA

GGTAGGCCTGCAGGAAGCGCCCCATCATGGTCATAAAGGTCTTCTGGCTCGTAAAGG

TCAGCTGCAGGCCGCGATGCTCTTCGTTCAGCCAGGTCTTGCAGATGGCGGCCAGCG

CCTCGGTCTGCTCGGGCAGCATCTTAAAATTTGTCTTCAGGTCGTTATCCACGTGGTA

CTTGTCCATCATGGCACGCGCCGCCTCCATGCCCTTCTCCCAGGCGGACACCATGGG

CAGGCTTAGGGGGTTTATCACTTCCAGCGGCGAGGACACCGTACTTTCGATTTCTTCT

TCCTCCCCCTCTTCCCGGCGCGCGCCCCCGCTGTTGCGCGCTCTTACCGCCTGCACCA

AGGGGTCGTCTTCAGGCAAGCGCCGCACCGAGCGCTTGCCGCCCTTGACCTGCTTGA

TCAGTACCGGCGGGTTGCTGAAGCCCACCATGGTCAGCGCCGCCTGCTCTTCTTCGT

CTTCGCTGTCTACCACTATTTCTGGGGAGGGGCTTCTCCGCTCTGCGGCAAAGGCGG

CGGATCGCTTCTTTTTTTTCTTGGGAGCCGCCGCGATGGAGTCCGCCACGGCGACCG

AGGTCGAGGGCGTGGGGCTGGGGGTGCGCGGTACCAGGGCCTCGTCGCCCTCGGAC

TCTTCCTCTGACTCCAGGCGGCGGCGGAGTCGCTTCTTTGGGGGCGCGCGCGTCAGC

GGCGGCGGAGACGGGGACGGGGACGGGGACGGGACGCCCTCCACAGGGGGTGGTC

TTCGCGCAGACCCGCGGCCGCGCTCGGGGGTCTTCTCGCGCTGGTCTTGGTCCCGAC

TGGCCATTGTATCCTCCTCCTCCTAGGCAGAGAGACATAAGGAGTCTATCATGCAAG

TCGAGAAGGAGGAGAGCTTAACCACCCCCTCAGAGACCGCCGATGCGCCCGCCGTC

GCCGTCGCCCCCGCTACCGCCGACGCGCCCGCCACACCGAGCGACACCCCCACGGA

CCCCCCCGCCGACGCACCCCTGTTCGAGGAAGCGGCCGTGGAGCAGGACCCGGGCT

TTGTCTCGGCAGAGGAGGATTTGCAAGAGGAGGAGAATAAGGAGGAGAAGCCCTCA

GTGCCAAAAGATCATAAAGAGCAAGACGAGCACGACGCAGACGCACACCAGGGTG

AAGTCGGGCGGGGGGACGGAGGGCATGGCGGCGCCGACTACCTAGACGAAGGAAA

CGACGTGCTCTTGAAGCACCTGCATCGTCAGTGCGCCATCGTCTGCGACGCTCTGCA

GGAGCGCAGCGAGGTGCCCCTCAGCGTGGCGGAGGTCAGCCGCGCCTACGAGCTCA

GCCTCTTTTCCCCCCGGGTGCCCCCCCGCCGCCGCGAAAACGGCACATGCGAGCCCA

ACCCGCGCCTCAACTTCTACCCCGCCTTTGTGGTGCCCGAGGTCCTGGCCACCTATCA

CATCTTCTTTCAAAATTGCAAGATCCCCATCTCGTGCCGCGCCAACCGTAGCCGCGC

CGATAAGATGCTGGCCCTGCGCCAGGGCGACCACATACCTGATATCGCCGCTTTGGA

AGATGTGCCAAAGATCTTCGAGGGTCTGGGGCGCAACGAGAAGCGGGCAGCAAACT

CTCTGCAACAGGAAAACAGCGAAAATGAGAGTCACACTGGAGCGCTGGTGGAGCTG

GAGGGCGACAACGCCCGCCTGGCGGTGCTCAAGCGCAGCATCGAGGTCACCCACTT

TGCCTACCCCGCGCTCAACCTGCCCCCCAAAGTCATGAACGCGGTCATGGACGGGCT

-continued

GATCATGCGCCGCGGCCGGCCCCTCGCTCCAGATGCAAACTTGCATGAGGAGACCG

AGGACGGTCAGCCCGTGGTCAGCGACGAGCAGCTGACGCGCTGGCTGGAGAGCGCG

GACCCCGCCGAACTGGAGGAGCGGCGCAAGATGATGATGGCCGCGGTGCTGGTCAC

CGTAGAGCTGGAGTGTCTGCAGCGCTTCTTCGGTGACCCCGAGATGCAGAGAAAGG

TCGAGGAGACCCTACACTACACCTTCCGCCAGGGCTACGTGCGCCAGGCTTGCAAGA

TCTCCAACGTGGAGCTCAGCAACCTGGTGTCCTACCTGGGCATCTTGCATGAAAACC

GCCTTGGGCAGAGCGTGCTACACTCCACCCTGCGCGGGGAGGCGCGCCGCGACTAC

GTGCGCGACTGCGTTTACCTCTTCCTCTGCTACACCTGGCAGACGGCCATGGGGGTC

TGGCAGCAGTGCCTGGAGGAGCGCAACCTCAAGGAGCTGGAGAAGCTTCTGCAGCG

CGCGCTCAAAGACCTCTGGACGGGCTTCAACGAGCGCTCGGTGGCCGCCGCGCTAG

CCGACCTCATCTTCCCCGAGCGCCTGCTCAAAACCCTCCAGCAGGGGCTGCCCGACT

TCACCAGCCAAAGCATGTTGCAAAATTTTAGGAACTTTATCCTGGAGCGTTCTGGCA

TCCTACCCGCCACCTGCTGCGCCCTGCCCAGCGACTTTGTCCCCCTCGTGTACCGCGA

GTGCCCCCCGCCGCTGTGGGGCCACTGCTACCTGTTCCAACTGGCCAACTACCTGTC

CTACCACGCGGACCTCATGGAGGACTCCAGCGGCGAGGGGCTCATGGAGTGCCACT

GCCGCTGCAACCTCTGCACGCCCCACCGCTCCCTGGTCTGCAACACCCAACTGCTCA

GCGAGAGTCAGATTATCGGTACCTTCGAGCTACAGGGTCCGTCCTCCTCAGACGAGA

AGTCCGCGGCTCCGGGGCTAAAACTCACTCCGGGGCTGTGGACTTCCGCCTACCTGC

GCAAATTTGTACCTGAAGACTACCACGCCCACGAAATCAGGTTTTACGAGGACCAAT

CCCGCCCGCCCAAGGCGGAGCTGACCGCCTGCGTCATCACCCAGGGCGAGATCCTA

GGCCAATTGCAAGCCATCCAAAAAGCCCGCCAAGAGTTTTTGCTGAAGAGGGGTCG

GGGGGTGTATCTGGACCCCCAGTCGGGTGAGGAGCTCAACCCGGTTCCCCCGCTGCC

ACCGCCGCGGGACCTTGCTTCCCAGGATAAGCATCGCCATGGCTCCCAGAAAGAAG

CAGCAGCGGCCGCCGCTGCCGCCGCCCCACATGCTGGAGGAAGAGGAGGAATACTG

GGACAGTCAGGCAGAGGAGGTTTCGGACGAGGAGGAGCCGGAGACGGAGATGGAA

GAGTGGGAGGAGGACAGCTTAGACGAGGAGGCTTCCGAAGCCGAAGAGGCAGGCG

CAACACCGTCACCCTCGGCCGCAGCCCCCTCGCAGGCGCCCCCGAAGTCCGCTCCCA

GCATCAGCAGCAACAGCAGCGCTATAACCTCCGCTCCTCCACCGCCGCGACCCACGG

CCGACCGCAGACCCAACCGTAGATGGGACACCACCGGAACCGGGGCCGGTAAGTCC

TCCGGGAGAGGCAAGCAAGCGCAGCGCCAAGGCTACCGCTCGTGGCGCGCTCACAA

GAACGCCATAGTCGCTTGCTTGCAAGACTGCGGGGGGAACATCTCCTTCGCCCGCCG

CTTCCTGCTCTTCCACCACGGTGTGGCCTTCCCCCGTAACGTCCTGCATTACTACCGT

CATCTCTACAGCCCCTACTGCGGCGGCAGTGAGCCAGAGGCGGCCAGCGGCGGCGG

CGCCCGTTTCGGTGCCTAGGAAGACCCAGGGCAAGACTTCAGCCAAGAAACTCGCG

GCGACCGCGGCGAACGCGGTCGCGGGGGCCCTGCGCCTGACGGTGAACGAACCCCT

GTCGACCCGCGAACTGAGGAACCGAATCTTCCCCACTCTCTATGCCATCTTCCAGCA

GAGCAGAGGGCAGGATCAGGAACTGAAAGTAAAAAACAGGTCTCTGCGCTCCCTCA

CCCGCAGCTGTCTGTATCACAAGAGCGAAGACCAGCTTCGGCGCACGCTGGAGGAC

GCTGAGGCACTCTTCAGCAAATACTGCGCGCTCACTCTTAAGGACTAGCTCCGCGCC

CTTCTCGAATTTAGGCGGGAACGCCTACGTCATCGCAGCGCCGCCGTCATGAGCAAG

GACATTCCCACGCCATACATGTGGAGCTATCAGCCGCAGATGGGACTCGCGGCGGG

-continued

CGCCTCCCAAGACTACTCCACCCGCATGAACTGGCTCAGTGCCGGCCCACACATGAT

CTCACAGGTTAATGACATCCGCACCCATCGAAACCAAATATTGGTGAAGCAGGCGG

CAATTACCACCACGCCCCGCAATAATCCCAACCCCAGGGAGTGGCCCGCGTCCCTGG

TGTATCAGGAAATTCCCGGCCCCACCACCGTACTACTTCCGCGTGATTCCCAGGCCG

AAGTCCAAATGACTAACTCAGGGGCACAGCTCGCGGGCGGCTGTCGTCACAGGGTG

CGGCCTCCTCGCCAGGGTATAACTCACCTGGAGATCCGAGGCAGAGGTATTCAGCTC

AACGACGAGTCGGTGAGCTCCTCGCTCGGTCTCAGACCTGACGGGACCTTCCAGATA

GCCGGAGCCGGCCGATCTTCCTTCACGCCCCGCCAGGCGTACCTGACTCTGCAGAGC

TCGTCCTCGGCGCCGCGCTCGGGCGGCATCGGGACTCTCCAGTTCGTGCAGGAGTTT

GTGCCCTCGGTCTACTTCAACCCCTTCTCGGGCTCTCCCGGTCGCTACCCGGACCAGT

TTATCCCGAACTTTGACGCCGCGAGGGACTCGGTGGACGGCTACGACTGAATGTCGG

GTGGACCCGGTGCAGAGCAACTTCGCCTGAAGCACCTTGACCACTGCCGCCGCCCTC

AGTGCTTTGCCCGCTGTCAGACCGGTGAGTTCCAGTACTTTTCCCTGCCCGACTCGCA

CCCGGACGGCCCGGCGCACGGGGTGCGCTTTTTCATCCCGAGTCAGGTCCGCTCTAC

CCTAATCAGGGAGTTCACCGCCCGTCCCCTACTGGCGGAGTTGGAAAAGGGGCCTTC

TATCCTAACCATTGCCTGCATTTGCTCTAACCCTGGATTACACCAAGATCTTTGCTGT

CATTTGTGTGCTGAGTATAATAAAGGCTGAGATCAGAATCTACTCGGGCTCCTGTCG

CCATCCTGTCAACGCCACCGTCCAAGCCCGGCCCGATCAGCCCGAGGTGAACCTCAC

CTGTGGTCTGCACCGGCGCCTGAGGAAATACCTAGCTTGGTACTACAACAGCACTCC

CTTTGTGGTTTACAACAGCTTTGACCAGGACGGGGTCTCACTGAGGGATAACCTCTC

GAACCTGAGCTACTCCATCAGGAAGAACAACACCCTCGAGCTACTTCCTCCTTACCT

GCCCGGGACTTACCAGTGTGTCACCGGCCCCTGCACCCACACCCACCTGTTGATCGT

AAACGACTCTCTTCCGAGAACAGACCTCAATAACTCCTCTCCGCAGTTCCCCAGAAC

AGGAGGTGAGCTCAGGAAACCCCGGGTAAAGAAGGGTGGACAAGAGTTAACACTTG

TGGGGTTTCTGGTATATGTGACGCTGGTGGTGGCTCTTTTGATTAAGGCTTTTCCTTC

CATGTCTGAACTATCCCTCTTCTTTTATGAACAACTCGACTAGTGCTAACGGGACCCT

ACCCAACGAATCGGGATTGAATATCGGTAACCAGGTTGCAGTTTCACTTTTGATTAC

CTTCATAGTCCTCTTCCTGCTAGTGCTGTCGCTTCTGTGCCTGCGGATCGGGGGCTGC

TGCATCCACGTTTATATCTGGTGCTGGCTGTTTAGAAGGTTCGGAGACCACCGCAGG

TAGAATAATGCTGCTTACCCTCTTTGTCCTGGCGCTGGCTGCCAGCTGCCAAGCCTTT

TCCGAGGCTGACTTCATAGAGCCCCAGTGCAATATCACTTATAAATCTGAACGTGCC

ATCTGTACTATTCTAATCAAATGTGTTACTCAACACGATAAGGTGACTGTTAAATAC

AAAGATCAATTAAAAAAAGACGCACTTTACAGCAGCTGGCAACCAGGAGATGATCA

AAAATACAATGTAACCGTCTTCCAGGGCAAACTCTCCAAAACTTACAATTACAATTT

CCCATTTGAGCAGATGTGTGACTTTGTCATGTACATGGAAAAGCAGTACAAGCTGTG

GCCTCCAACTCCCCAGGGCTGTGTGGAAAATCCAGGCTCTTTCTGTATGATCTCTCTC

TGTGTAACTGTGCTGGCACTAATACTCACGCTTCTGTATCTCAGATTTAAATCAAGGC

AAAGCTTCATTGATGAAAAGAAAATGCCATAATCGCTCAACGCTTGATTGCTAACAC

CGGGTTTTTATCCGCAGAATGATTGGAATCACCCTACTAATCACCTCCCTCCTTGCGA

TTGCCCATGGGTTGGAACGAATCGAAGTCCCTGTGGGGGCCAATGTTACCCTGGTGG

-continued

```
GGCCTGTCGGCAATGCTACATTAATGTGGGAAAAATATACTAAAAATCAATGGGTTT

CTTACTGCACTAACAAAAACAGCCACAAGCCCAGAGCCATCTGCGATGGGCAAAAT

CTAACCTTGATTGATGTTCAATTGCTGGATGCGGGCTACTATTATGGGCAGCTGGGT

ACAATGATTAATTACTGGAGACCCCACAGAGATTACATGCTTCACGTAGTAAAGGGT

CCCATTAGCAGCCCAACCACCACCTCTACCACACCCACTACCACCACTACTCCCACC

ACCAGCACTGCCGCCCAGCCTCCTCATAGCAGAACAACCACTTTTATCAATTCCAAG

TCCCACTCCCCCCACATTGCCGGCGGGCCCTCCGCCTCAGACTCCGAGACCACCGAG

ATCTGCTTCTGCAAATGCTCTGACGCCATTGCCCAGGATTTGGAAGATCACGAGGAA

GATGAGCATGACTACGCAGATGCATGCCAGGCATCAGAGGCAGAAGCGCTACCGGT

GGCCCTAAAACAGTATGCAGACTCCCACACCACCCCCAACCTTCCTCCACCTTCCCA

GAAGCCAAGTTTCCTGGGGGAAAATGAAACTCTGCCTCTTTCCATACTAGCTCTGAC

ATCTGTTGCTATTTTGGCCGCTCTGCTGGTGCTTCTATGCTCTATATGCTACCTGATCT

GCTGCAGAAAGAAAAAATCTCACGGCCATGCTCACCAGCCCCTCATGCACTTCCCTT

ACCCTCCAGAGCTGGGCGACCACAAACTTTAAGTCTGCAGTAGCTATCTGCCCATCC

CTTGTCAGTCGACAGCGATGAGCCCCACTAATCTAACAGCCTCTGGACTTACAACAT

TGTCTCTTAATGAGACCACCGCTCCTCAAGACCTGTACGATGGTGTCTCCGCGCTGG

TTAACCAGTGGGATCACCTGGGCATATGGTGGCTCCTCATAGGAGCAGTGACCCTGT

GCCTAATCCTGGTCTGGATCATCTGCTGCATCAAAAGCAGAAGACCCAGGCGGCGG

CCCATCTACAGGCCCTTCGTCATCACACCTGAAGATAATGATGATGATGACACCACC

TCCAGGCTGCAGAGCCTAAAGCAGCTACTCTTCTCTTTTACAGCATGGTAAATTGAA

TCATGCCCCGCATTTTCATCTACTTGCTTCTCCTTCCACTTTTTCTGGGCTCCTCTACA

TTGGCCACTGTGTCCCACATCGAGGTAGACTGCCTCACGCCCTTCACAGTCTACCTG

CTTTTCGGCTTTGTCATCTGCACCTTTGTCTGCAGCGTTATCACTGTAGTGATCTGCTT

CATACAGTGCATCGACTACATCTGTGTGCGGGTGGCCTACTTTAGACACCACCCCCA

GTATCGCAACAGGGACATAGCGGCTCTCCTAAGACTTGTTTAAATCATGGCCAAATT

ACCTGTGATTGGTCTTCTGATTATCTGCTGCGTCCTAGCCGCGATTGGGACTCAACCT

AATACCACCACCAGCGCTCCCAGAAAGAGACATGTATCCTGCAGCTTCAAGCGTCCC

TGGAATATACCCCAATGCTTTACTGATGAACCTGAAATCTCTTTGGCTTGGTACTTCA

GCGTCACCGCCCTTCTCATCTTCTGCAGTACGGTTATTGCTCTTGCCATCTACCCTTC

CCTTAACCTGGGCTGGAATGCTGTCAACTCTATGGAATATCCCACCTTCCCAGAACC

AGACCTGCCAGACCTGGTTGTTCTAAACGCGTTTCCTCCTCCTCCAGTTCAAAATCAG

TTTCGCCCTCCGTCCCCTACGCCCACTGAGGTCAGCTACTTTAATCTAACAGGCGGA

GATGACTGAAAACCTAGACCTAGAAATGGACGGTCTCTGCAGCGAGCAACGCACAC

TAGAGAGGCGCCGGCAAAAAGCAGAGCTCGAGCGTCTTAAACAAGAGCTCCAAGAC

GCCGTGGCCATACACCAGTGCAAAAAAGGGCTCTTCTGTCTGGTAAAACAGGCCAC

GCTCACCTATGAAAAAACAGGTGACACCCACCGCCTAGGATACAAGCTGCCCACAC

AGCGCCAAAAGTTTGCCCTTATGATAGGTGAACAACCCATCACCGTCACCCAGCACT

CCGTGGAGACAGAAGGCTGCATTCATGCTCCCTGCAGGGGCGCTGACTGCCTCTACA

CCTTGATCAAAACCCTCTGCGGTCTCAGAGACCTTATCCCTTTCAATTGATCATAACT

GTAATCAATAAAAAATCACTTACTTGAAATCTGATAGCAAGACTCTGTCCAATTTTT

TCAGCAACACTTCCTTCCCCTCCTCCCAACTCTGGTACTCTAGGCGCCTCCTAGCTGC
```

-continued

AAACTTCCTCCACAGTCTGAAGGGAATGTCAGATTCCTCCTCCTGTCCCTCCGCACCC
ACGATCTTCATGTTGTTACAGATGAAACGCGCGAGATCGTCTGACGAGACCTTCAAC
CCCGTGTACCCCTACGATACCGAGATCGCTCCGACTTCTGTCCCTTTCCTTACCCCTC
CCTTTGTATCATCCGCAGGAATGCAAGAAAATCCAGCTGGGGTGCTGTCCCTGCACC
TGTCAGAGCCCCTTACCACCCACAATGGGGCCCTGACTCTAAAAATGGGGGGCGGC
CTGACCCTGGACAAGGAAGGGAATCTCACTTCCCAAAACATCACCAGTGTCGATCCC
CCTCTCAAAAAAAGCAAGAACAACATCAGCCTTCAGACCGCCGCACCCCTCGCCGTC
AGCTCCGGGGCCCTAACCCTTTTTGCCACTCCCCCCCTAGCGGTCAGTGGCGACAAC
CTTACTGTGCAGTCTCAGGCCCCTCTTACTTTGGAAGACTCAAAACTAACTCTGGCC
ACCAAAGGACCCCTAACTGTGTCCGAAGGCAAACTTGTCCTAGAAACAGAGCCTCC
CCTGCATGCAAGTGACAGCAGTAGCCTGGGCCTTAGCGTCACGGCCCCACTTAGCAT
TAACAATGACAGCCTAGGACTAGACATGCAAGCGCCCATCAGCTCTCGAGATGGAA
AACTGGCTCTAACAGTGGCGGCCCCCCTAACTGTGGCCGAGGGTATCAATGCTTTGG
CAGTAGCCACAGGTAATGGTATTGGACTAAATGAAACCAACACACACCTGCAGGCA
AAACTGGTCGCGCCCCTAGGCTTTGATACCAACGGCAACATTAAGCTAAGCGTCGCA
GGAGGCATGAGGCTAAACAATAACACACTGATACTAGATGTAAACTACCCATTTGA
GGCTCAAGGCCAACTGAGCCTAAGAGTGGGCTCGGGCCCACTATATGTAGATTCTAG
TAGTCATAACCTAACCATTAGATGCCTTAGGGGATTGTATGTAACATCTTCTAACAA
CCAAAACGGTCTAGAGGCCAACATTAAACTAACAAAAGGCCTTGTGTATGACGGAA
ATGCCATAGCAGTTAATGTTGGCAAAGGGCTGGAATACAGCCCTACTGGCACAACA
GAAAAACCTATACAGACTAAAATAGGTCTAGGCATGGAGTATGACACTGAGGGAGC
CATGATGACAAAACTAGGCTCTGGACTAAGCTTTGACAATTCAGGAGCCATTGTGGT
GGGAAACAAAAATGATGACAGGCTTACTTTGTGGACCACACCGGACCCATCGCCCA
ACTGTCAGATTTACTCTGAAAAAGATGCTAAACTAACCTTGGTACTGACTAAATGTG
GCAGTCAGGTTGTAGGCACAGTATCTATTGCCGCTCTTAAAGGTAGCCTTGTGCCAA
TCACTAGTGCAATCAGTGTGGTTCAGATATACCTAAGGTTTGATGAAAATGGGGTGC
TGATGAGTAACTCTTCACTTAATGGCGAATACTGGAATTTTAGAAACGGAGACTCAA
CTAATGGCACACCATATACAAACGCAGTGGGTTTTATGCCTAATCTACTGGCCTATC
CTAAAGGTCAAACTACAACTGCAAAAAGTAACATTGTCAGCCAGGTCTACATGAAC
GGGGACGATACTAAACCCATGACATTTACAATCAACTTCAATGGCCTTAGTGAAACA
GGGGATACCCCTGTCAGTAAATATTCCATGACATTCTCATGGAGGTGGCCAAATGGA
AGCTACATAGGGCACAATTTTGTAACAAACTCCTTTACTTTCTCCTACATCGCCCAAG
AATAAAGAAAGCACAGAGATGCTTGTTTTTGATTTCAAAATTGTGTGCTTTTATTTAT
TTTCAAGCTTACAGTATTTCCAGTAGTCATTAGAATAGAGCTTAATTAAACTGCATG
AGAACCCTTCCACATAGCTTAAATTATCACCAGTGCAAATGGAAAAAAATCAACAT
ACCTTTTTATCCAGATATCAAAGAACTCTAGTGGTCAGTTTTCCCCCACCCTCCCAGC
TCACAGAATACACAGTCCTTTCCCCCCGGCTGGCTTTAAACAACACTATCTCATTGGT
AACAGACATATTTTTAGGTGTAATAATCCACACGGTCTCTTGGCGGGCCAAACGCTG
GTCTGTGATGTTAATAAACTCCCCAGGCAGCTCTTTCAAGTTCACGTCGCTGTCCAAC
TGCTGAAGCGCTCGCGGCTCCGACTGCGCCTCTAGCGGAGGCAACGGCAGCACCCG

-continued

ATCCTTGATCTATAAAGGAGTAGAGTCATAATCCCCCATAAGAATAGGGCGGTGATG

CAGCAACAAGGCGCGCAGCAACTCCTGCCGCCGCCTCTCCGTACGACAGGAATGCA

ACGGGGTGGTGGTCTCCTCCGCGATAATCCGCACCGCTCGCAGCATCAGCATCCTCG

TCCTCCGGGCACAGCAGCGCATCCTGATCTCACTGAGATCGGCGCAGTAAGTGCAGC

ACAACACCAAGATGTTATTTAAGATCCCACAGTGCAAAGCACTGTACCCAAAGCTCA

TGGCGGGAAGGACAGCCCCCACGTGACCATCGTACCAGATCCTCAGGTAAATCAAA

TGACGACCTCTCATAAACACGCTGGACATATACATCACCTCCTTGGGCATGAGCTGA

TTCACCACCTCTCGATACCACAGGCATCGCTGATTAATTAAAGACCCCTCGAGCACC

ATCCTGAACCAGGAAGCCAGCACCTGACCCCCCGCCAGGCACTGCAGGGACCCCGG

TGAATCGCAGTGGCAGTGAAGACTCCAGCGCTCGTAGCCGTGAACCATAGAGCTGG

TCATTATATCCACATTGGCACAACACAGACACACTTTCATACACTTTTTCATGATTAG

CAGCTCCTCTCTAGTCAAGACCATATCCCAAGGAATCACCCACTCTTGAATCAAGGT

AAATCCCACACAGCAGGGCAGGCCTCTCACATAACTCACGTTATGCATAGTGAGCGT

GTCGCAATCTGGAAATACCGGATGATCTTCCATCACCGAAGCCCGGGTCTCCGTCTC

AAAGGGAGGTAAACGGTCCCTCGTGTAGGGACAGTGGCGGGATAATCGAGATCGTG

TTGAACGTAGAGTCATGCCAAAGGGAACAGCGGACGTACTCATATTTCCTCCAGCAG

AACCAAGTGCGCGCGTGGCAGCTATCCCTGCGTCTTCTGTCTCGCCGCCTGCCCCGC

TCGGTGTAGTAGTTGTAATACAGCCACTCCCTCAGACCGTCAAGGCGCTCCCTGGCG

TCCGGATCTATAACAACACCGTCCTGCAGCGCCGCCCTGATGACATCCACCACCGTA

GAGTATGCCAAGCCCAGCCACGAAATGCACTCACTTTGACAGCGAGAGATAGGAGG

AGCGGGAAGAGATGGAAGAACCATGATAGTAAAAGAACTTTTATTCCAATCGATCC

TCTACAATGTCAAAGTGTAGATCTATCAGATGGCACTGGTCTCCTCCGCTGAGTCGA

TCAAAAATAACAGCTAAACCACAAACAACACGATTGGTCAAATGCTGCACAAGGGC

TTGCAGCATAAAATCGCCTCGAAAGTCCACCGCAAGCATAACATCAAAGCCACCGC

CCCTATCATGATCTATGATAAAAACCCCACAGCTATCCACCAGACCCATATAGTTTT

CATCTCTCCATCGTGAAAAAATATTTACAAGCTCCTCCTTTAAATCACCTCCAACCAA

TTCAAAAAGTTGAGCCAGACCGCCCTCCACCTTCATTTTCAGCATGCGCATCATGAT

TGCAAAAATTCAGGCTCCTCAGACACCTGTATAAGATTGAGAAGCGGAACGTTAAC

ATCAATGTTTCGCTCGCGAAGATCGCGCCTCAGTGCAAGCATGATATAATCCCACAG

GTCGGAGCGGATCAGCGAGGACATCTCCCCGCCAGGAACCAACTCAACGGAGCCTA

TGCTGATTATAATACGCATATTCGGGGCTATGCTAACCAGCACGGCCCCCAAATAGG

CGTACTGCATAGGCGGCGACAAAAAGTGAACAGTTTGGGTTAAAAAATCAGGCAAA

CACTCGCGCAAAAAAGCAAGAACATCATAACCATGCTCATGCAAATAGATGCAAGT

AAGCTCAGGAACGACCACAGAAAAATGCACAATTTTTCTCTCAAACATGACTGCGA

GCCCTGCAAAAAATAAAAAAGAAACATTACACAAGAGTAGCCTGTCTTACAATGGG

ATAGACTACTCTAACCAACATAAGACGGGCCACGACATCGCCCGCGTGGCCATAAA

AAAAATTATCCGTGTGATTAAAAAGAAGCACAGATAGCTGGCCAGTCATATCCGGA

GTCATCACGTGCGAACCCGTGTAGACCCCCGGGTTGGACACATCGGCCAAACAAAG

AAAGCGGCCAATGTATCCCGGAGGAATGATAACACTAAGACGAAGATACAACAGAA

TAACCCCATGGGGGGGAATAACAAAGTTAGTAGGTGAATAAAAACGATAAACACCC

GAAACTCCCTCCTGCGTAGGCAAAATAGCGCCCTCCCCTTCCAAAACAACATACAGC

-continued

```
GCTTCCACAGCAGCCATGACAAAAGACTCAAAACACTCAAAAGACTCAGTCTTACC

AGGAAAATAAAAGCACTCTCACAGCACCAGCACTAATCAGAGTGTGAAGAGGGCCA

AGTGCCGAACGAGTATATATAGGAATTAAAAATGACGTAAATGTGTAAAGGTCAAA

AAACGCCCAGAAAAATACACAGACCAACGCCCGAAACGAAAACCCGCGAAAAAAT

ACCCAGAAGTTCCTCAACAACCGCCACTTCCGCTTTCCCACGATACGTCACTTCCTCA

AAAATAGCAAACTACATTTCCCACATGTACAAAACCAAAACCCCTCCCCTTGTCACC

GCCCACAACTTACATAATCACAAACGTCAAAGCCTACGTCACCCGCCCCGCCTCGCC

CCGCCCACCTCATTATCATATTGGCCTCAATCCAAAATAAGGTATATTATTGATGATG
```

The disclosure also provides a recombinant chimpanzee adenovirus derived from serotype 20 (rChAd20) comprising the vector of the disclosure.

The disclosure also provides a recombinant modified vaccinia Ankara (rMVA) comprising the vector of the disclosure.

The vector may be a vector intended for expression of the polynucleotide or the heterologous polynucleotide of the disclosure in any host, such as bacteria, yeast or a mammal. Suitable expression vectors are typically replicable in the host organisms either as episomes or as an integral part of the host chromosomal DNA. Commonly, expression vectors contain selection markers such as ampicillin-resistance, hygromycin-resistance, tetracycline resistance, kanamycin resistance or neomycin resistance to permit detection of those cells transformed or transduced with the desired DNA sequences. Exemplary vectors are plasmids, cosmids, phages, viral vectors, transposons or artificial chromosomes.

Vectors of the disclosure may be circular or linear. They may be prepared to contain a replication system functional in a prokaryotic or eukaryotic host cell. Replication systems can be derived, e.g., from ColE1, SV40, 2μ plasmid, λ, bovine papilloma virus, and the like.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. "Suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine deaminase, purine nucleoside phosphorylase, and nitroreductase.

The vectors may also comprise selection markers, which are well known in the art. Selection markers include positive and negative selection marker. Marker genes include biocide resistance, e.g., resistance to antibiotics, heavy metals, etc., complementation in an auxotrophic host to provide prototrophy, and the like. Exemplary marker genes include antibiotic resistance genes (e.g., neomycin resistance gene, a hygromycin resistance gene, a kanamycin resistance gene, a tetracycline resistance gene, a penicillin resistance gene, histidinol resistance gene, histidinol x resistance gene), glutamine synthase genes, HSV-TK, HSV-TK derivatives for ganciclovir selection, or bacterial purine nucleoside phosphorylase gene for 6-methylpurine selection (Gadi et al., 7 *Gene Ther.* 1738-1743 (2000)). A nucleic acid sequence encoding a selection marker or the cloning site may be upstream or downstream of a nucleic acid sequence encoding a polypeptide of interest or cloning site.

Suitable vectors are known; many are commercially available for generating recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene), pSVK3, pBPV, pMSG and pSVL (Pharmacia). Transposon vectors: Sleeping Beauty transposon and PiggyBac transposon.

In some embodiments, the vector is a viral vector. Viral vectors are derived from naturally occurring virus genomes, which typically are modified to be replication incompetent, e.g. non-replicating. Non-replicating viruses require the provision of proteins in trans for replication. Typically, those proteins are stably or transiently expressed in a viral producer cell line, thereby allowing replication of the virus. The viral vectors are, thus, typically infectious and non-replicating. Viral vectors may be adenovirus vectors, adeno-associated virus (AAV) vectors (e.g., AAV type 5 and type 2), alphavirus vectors (e.g., Venezuelan equine encephalitis virus (VEE), Sindbis virus (SIN), Semliki forest virus (SFV), and VEE-SIN chimeras), herpes virus vectors (e.g. vectors derived from cytomegaloviruses, like rhesus cytomegalovirus (RhCMV)), arena virus vectors (e.g. lymphocytic choriomeningitis virus (LCMV) vectors), measles virus vectors, pox virus vectors (e.g., vaccinia virus, modified vaccinia virus Ankara (MVA), NYVAC (derived from the Copenhagen strain of vaccinia), and avipox vectors: canarypox (ALVAC) and fowlpox (FPV) vectors), vesicular stomatitis virus vectors, retrovirus vectors, lentivirus vectors, viral like particles, baculoviral vectors and bacterial spores.

Adenovirus Vectors

Adenovirus vectors may be derived from human adenovirus (Ad) but also from adenoviruses that infect other species, such as bovine adenovirus (e.g. bovine adenovirus 3, BAdV3), a canine adenovirus (e.g. CAdV2), a porcine adenovirus (e.g. PAdV3 or 5), or great apes, such as Chimpanzee (*Pan*), Gorilla (*Gorilla*), Orangutan (*Pongo*), Bonobo (*Pan paniscus*) and common chimpanzee (*Pan troglodytes*). Typically, naturally occurring great ape adenoviruses are isolated from stool samples of the respective great ape.

Human adenovirus vectors may be derived from various adenovirus serotypes, for example from human adenovirus serotypes hAd5, hAd7, hAd11, hAd26, hAd34, hAd35, hAd48, hAd49 or hAd50 (the serotypes are also referred to as Ad5, Ad7, Ad11, Ad26, Ad34, Ad35, Ad48, Ad49 or Ad50).

Great ape adenovirus vectors may be derived from various adenovirus serotypes, for example from great ape adenovirus serotypes GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAdI7, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, or PanAd3.

Adenovirus vectors are known in the art. The sequences of most of the human and non-human adenoviruses are known, and for others can be obtained using routine procedures. An exemplary genome sequence of Ad26 is found in GenBank Accession number EF153474 and in SEQ ID NO: 1 of Int. Pat. Publ. No. WO2007/104792. An exemplary genome sequence of Ad35 is found in FIG. 6 of Int. Pat. Publ. No. WO2000/70071. Vectors based on Ad26 are described for example, in Int. Pat. Publ. No. WO2007/104792. Vectors based on Ad35 are described for example in U.S. Pat. No. 7,270,811 and Int. Pat. Publ. No. WO2000/70071. Vectors based on ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd63 and ChAd82 are described in WO2005/071093. Vectors based on PanAd1, PanAd2, PanAd3, ChAd55, ChAd73, ChAd83, ChAd146, and ChAd147 are described in Int. Pat. Publ. No. WO2010/086189.

Adenovirus vectors are engineered to comprise at least one functional deletion or a complete removal of a gene product that is essential for viral replication, such as one or more of the adenoviral regions E1, E2 and E4, therefore rendering the adenovirus to be incapable of replication. The deletion of the E1 region may comprise deletion of EIA, EIB 55K or EIB 21K, or any combination thereof. Replication deficient adenoviruses are propagated by providing the proteins encoded by the deleted region(s) in trans by the producer cell by utilizing helper plasmids or engineering the produce cell to express the required proteins. Adenovirus vectors may also have a deletion in the E3 region, which is dispensable for replication, and hence such a deletion does not have to be complemented. The adenovirus vector of the disclosure may comprise a functional deletion or a complete removal of the E1 region and at least part of the E3 region. The adenovirus vector of the disclosure may further comprise a functional deletion or a complete removal of the E4 region and/or the E2 region. Suitable producer cells that can be utilized are human retina cells immortalized by E1, e.g. 911 or PER.C6 cells (see, e.g., U.S. Pat. No. 5,994,128), E1-transformed amniocytes (See, e.g., EP 1230354), E 1-transformed A549 cells (see e.g. Int. Pat. Publ. No. WO1998/39411, U.S. Pat. No. 5,891,690). Exemplary vectors that may be used are Ad26 comprising a functional E1 coding region that is sufficient for viral replication, a deletion in the E3 coding region and a deletion in the E4 coding region, provided that E4 open reading frame 6/7 is not deleted (see e.g. U.S. Pat. No. 9,750,801)

In some embodiments, the adenovirus vector is a human adenovirus (Ad) vector. In some embodiments, the Ad vector is derived from Ad5. In some embodiments, the Ad vector is derived from Ad11. In some embodiments, the Ad vector is derived from Ad26. In some embodiments, the Ad vector is derived from Ad34. In some embodiments, the Ad vector is derived from Ad35. In some embodiments, the Ad vector is derived from Ad48. In some embodiments, the Ad vector is derived from Ad49. In some embodiments, the Ad vector is derived from Ad50.

In some embodiments, the adenovirus vector is a great ape adenovirus (GAd) vector. In some embodiments, the GAd vector is derived from GAd20. In some embodiments, the GAd vector is derived from GAd19. In some embodiments, the GAd vector is derived from GAd21. In some embodiments, the GAd vector is derived from GAd25. In some embodiments, the GAd vector is derived from GAd26. In some embodiments, the GAd vector is derived from GAd27. In some embodiments, the GAd vector is derived from GAd28. In some embodiments, the GAd vector is derived from GAd29. In some embodiments, the GAd vector is derived from GAd30. In some embodiments, the GAd vector is derived from GAd31. In some embodiments, the GAd vector is derived from ChAd4. In some embodiments, the GAd vector is derived from ChAd5. In some embodiments, the GAd vector is derived from ChAd6. In some embodiments, the GAd vector is derived from ChAd7. In some embodiments, the GAd vector is derived from ChAd8. In some embodiments, the GAd vector is derived from ChAd9. In some embodiments, the GAd vector is derived from ChAd20. In some embodiments, the GAd vector is derived from ChAd22. In some embodiments, the GAd vector is derived from ChAd24. In some embodiments, the GAd vector is derived from ChAd26. In some embodiments, the GAd vector is derived from ChAd30. In some embodiments, the GAd vector is derived from ChAd31. In some embodiments, the GAd vector is derived from ChAd32. In some embodiments, the GAd vector is derived from ChAd33. In some embodiments, the GAd vector is derived from ChAd37. In some embodiments, the GAd vector is derived from ChAd38. In some embodiments, the GAd vector is derived from ChAd44. In some embodiments, the GAd vector is derived from ChAd55. In some embodiments, the GAd vector is derived from ChAd63. In some embodiments, the GAd vector is derived from ChAd68. In some embodiments, the GAd vector is derived from ChAd73. In some embodiments, the GAd vector is derived from ChAd82. In some embodiments, the GAd vector is derived from ChAd83.

The polypeptide or the heterologous polypeptide of the disclosure may be inserted into a site or region (insertion region) in the vector that does not affect virus viability of the resultant recombinant virus. The polypeptide or the heterologous polypeptide of the disclosure may be inserted into the deleted E1 region in parallel (transcribed 5' to 3') or anti-parallel (transcribed in a 3' to 5' direction relative to the vector backbone) orientation. In addition, appropriate transcriptional regulatory elements that are capable of directing expression of the polypeptide or the heterologous polypeptide of the disclosure in the mammalian host cells that the vector is being prepared for use may be operatively linked to the polypeptide or the heterologous polypeptide of the disclosure. "Operatively linked" sequences include both expression control sequences that are contiguous with the nucleic acid sequences that they regulate and regulatory sequences that act in trans, or at a distance to control the regulated nucleic acid sequence.

Recombinant adenoviral particles may be prepared and propagated according to any conventional technique in the field of the art (e.g., Int. Pat. Publ. No. WO1996/17070) using a complementation cell line or a helper virus, which supplies in trans the missing viral genes necessary for viral replication. The cell lines 293 (Graham et al., 1977, J. Gen. Virol. 36: 59-72), PER.C6 (see e.g. U.S. Pat. No. 5,994,128), E1 A549 and 911 are commonly used to complement E1 deletions. Other cell lines have been engineered to complement defective vectors (Yeh, et al., 1996, J. Virol. 70: 559-565; Kroughak and Graham, 1995, Human Gene Ther. 6: 1575-1586; Wang, et al., 1995, Gene Ther. 2: 775-783; Lusky, et al., 1998, J. Virol. 72: 2022-203; EP 919627 and Int. Pat. Publ. No. WO1997/04119). The adenoviral particles may be recovered from the culture supernatant but also from the cells after lysis and optionally further purified according to standard techniques (e.g., chromatography, ultracentrifugation, as described in Int. Pat. Publ. No. WO1996/27677, Int. Pat. Publ. No. WO1998/00524, Int. Pat. Publ. No. WO1998/26048 and Int. Pat. Publ. No. WO2000/50573). The construction and methods for propagating adenoviral vectors are also described in for example, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913.

Poxvirus Vectors

Poxvirus (Poxviridae) vectors may be derived from smallpox virus (variola), vaccinia virus, cowpox virus or monkeypox virus. Exemplary vaccinia viruses are the Copenhagen vaccinia virus (W), New York Attenuated Vaccinia Virus (NYVAC), ALVAC, TROVAC and Modified Vaccinia Ankara (MVA).

MVA originates from the dermal vaccinia strain Ankara (Chorioallantois vaccinia Ankara (CVA) virus) that was maintained in the Vaccination Institute, Ankara, Turkey for many years and used as the basis for vaccination of humans. However, due to the often severe post-vaccinal complications associated with vaccinia viruses (VACV), there were several attempts to generate a more attenuated, safer smallpox vaccine.

MVA has been generated by 516 serial passages on chicken embryo fibroblasts of the CVA virus (see Meyer et al., *J. Gen. Virol.,* 72: 1031-1038 (1991) and U.S. Pat. No. 10,035,832). As a consequence of these long-term passages the resulting MVA virus deleted about 31 kilobases of its genomic sequence and, therefore, was described as highly host cell restricted to avian cells (Meyer, H. et al., Mapping of deletions in the genome of the highly attenuated vaccinia virus MVA and their influence on virulence, J. Gen. Virol. 72, 1031-1038, 1991; Meisinger-Henschel et al., Genomic sequence of chorioallantois vaccinia virus Ankara, the ancestor of modified vaccinia virus Ankara, J. Gen. Virol. 88, 3249-3259, 2007). Comparison of the MVA genome to its parent, CVA, revealed 6 major deletions of genomic DNA (deletion I, II, III, IV, V, and VI), totaling 31,000 basepairs. (Meyer et al., J. Gen. Virol. 72:1031-8 (1991)). It was shown in a variety of animal models that the resulting MVA was significantly avirulent (Mayr, A. & Danner, K. Vaccination against pox diseases under immunosuppressive conditions, Dev. Biol. Stand. 41: 225-34, 1978). Being that many passages were used to attenuate MVA, there are a number of different strains or isolates, depending on the passage number in CEF cells, such as MVA 476 MG/14/78, MVA-571, MVA-572, MVA-574, MVA-575 and MVA-BN. MVA 476 MG/14/78 is described for example in Int. Pat. Publ. No. WO2019/115816A1. MVA-572 strain was deposited at the European Collection of Animal Cell Cultures ("ECACC"), Health Protection Agency, Microbiology Services, Porton Down, Salisbury SP4 OJG, United Kingdom ("UK"), under the deposit number ECACC 94012707 on Jan. 27, 1994. MVA-575 strain was deposited at the ECACC under deposit number ECACC 00120707 on Dec. 7, 2000; MVA-Bavarian Nordic ("MVA-BN") strain was deposited at the ECACC under deposit number V00080038 on Aug. 30, 2000. The genome sequences of MVA-BN and MVA-572 are available at GenBank (Accession numbers DQ983238 and DQ983237, respectively). The genome sequences of other MVA strains can be obtained using standard sequencing methods.

Vectors and viruses of the disclosure may be derived from any MVA strain or further derivatives of the MVA strain. A further exemplary MVA strain is deposit VR-1508, deposited at the American Type Culture collection (ATCC), Manassas, Va. 20108, USA.

"Derivatives" of MVA refer to viruses exhibiting essentially the same characteristics as the parent MVA, but exhibiting differences in one or more parts of their genomes.

In some embodiments, the MVA vector is derived from MVA 476 MG/14/78. In some embodiments, the MVA vector is derived from MVA-571. In some embodiments, the MVA vector is derived from MVA-572. In some embodiments, the MVA vector is derived from MVA-574. In some embodiments, the MVA vector is derived from MVA-575. In some embodiments, the MVA vector is derived from MVA-BN.

The polynucleotide or the heterologous polynucleotide of the disclosure may be inserted into a site or region (insertion region) in the MVA vector that does not affect virus viability of the resultant recombinant virus. Such regions can be readily identified by testing segments of virus DNA for regions that allow recombinant formation without seriously affecting virus viability of the recombinant virus. The thymidine kinase (TK) gene is an insertion region that may be used and is present in many viruses, such as in all examined poxvirus genomes. Additionally, MVA contains 6 natural deletion sites, each of which may be used as insertion sites (e.g. deletion I, II, III, IV, V, and VI; see e.g. U.S. Pat. Nos. 5,185,146 and 6,440,442). One or more intergenic regions (IGR) of the MVA may also be used as an insertion site, such as IGRs IGR07/08, IGR 44/45, IGR 64/65, IGR 88/89, IGR 136/137, and IGR 148/149 (see e.g. U.S. Pat. Publ. No. 2018/0064803). Additional suitable insertion sites are described in Int. Pat. Publ. No. WO2005/048957.

Recombinant poxviral particles such as rMVA are prepared as described in the art (Piccini, et al., 1987, Methods of Enzymology 153: 545-563; U.S. Pat. Nos. 4,769,330; 4,772,848; 4,603,112; 5,100,587 and 5,179,993). In an exemplary method, the DNA sequence to be inserted into the virus can be placed into an *E. coli* plasmid construct into which DNA homologous to a section of DNA of the MVA has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of MVA DNA containing a non-essential locus. The resulting plasmid construct can be amplified by propagation within *E. coli* bacteria and isolated. The isolated plasmid containing the DNA gene sequence to be inserted can be transfected into a cell culture, e.g., of chicken embryo fibroblasts (CEFs), at the same time the culture is infected with MVA. Recombination between homologous MVA DNA in the plasmid and the viral genome, respectively, can generate an MVA modified by the presence of foreign DNA sequences. rMVA particles may be recovered from the culture supernatant or from the cultured cells after a lysis step (e.g., chemical lysis, freezing/thawing, osmotic shock, sonication and the like). Consecutive rounds of plaque purification can be used to remove contaminating wild type virus. Viral particles can then be purified using the techniques known in the art (e.g., chromatographic methods or ultracentrifugation on cesium chloride or sucrose gradients).

Other Viral Vectors and Recombinant Viruses

Other viral vectors include vectors derived from human adeno-associated viruses, such as AAV-2 (adeno-associated virus type 2). An attractive feature of AAV vectors is that they do not express any viral genes. The only viral DNA sequences included in the AAV vectors are the 145 bp inverted terminal repeats (ITR). Thus, as in immunization with naked DNA, the only gene expressed is that of the antigen, or antigen chimera. Additionally, AAV vectors are known to transduce both dividing and non-dividing cells, such as human peripheral blood monocyte-derived dendritic cells, with persistent transgene expression, and with the possibility of oral and intranasal delivery for generation of mucosal immunity. Moreover, the amount of DNA required appears to be much less by several orders of magnitude, with maximum responses at doses of $10^{10}$ to $10^{11}$ particles or copies of DNA in contrast to naked DNA doses of 50 μg or about $10^{11}$ copies. AAV vectors are packaged by co-transfection of a suitable cell line (e.g., human 293 cells) with the DNA contained in the AAV ITR chimeric protein encoding constructs and an AAV helper plasmid ACG2 containing the AAV coding region (AAV rep and cap genes) without the ITRs. The cells are subsequently infected with the adenovirus Ad5. Vectors can be purified from cell lysates using methods known in the art (e.g., such as cesium chloride density gradient ultracentrifugation) and are validated to ensure that they are free of detectable replication-competent AAV or adenovirus (e.g., by a cytopathic effect bioassay).

Retroviral vectors may also be used. Retroviruses are a class of integrative viruses which replicate using a virus-encoded reverse transcriptase, to replicate the viral RNA genome into double stranded DNA which is integrated into chromosomal DNA of the infected cells (e.g., target cells). Such vectors include those derived from murine leukemia viruses, especially Moloney (Gilboa, et al., 1988, Adv. Exp. Med. Biol. 241: 29) or Friend's FB29 strains (Int. Pat. Publ. No. WO1995/01447). Generally, a retroviral vector is deleted of all or part of the viral genes gag, pol and env and retains 5' and 3' LTRs and an encapsidation sequence. These elements may be modified to increase expression level or stability of the retroviral vector. Such modifications include the replacement of the retroviral encapsidation sequence by one of a retrotransposon such as VL30 (see, e.g., U.S. Pat. No. 5,747,323). The polynucleotides of the disclosure may be inserted downstream of the encapsidation sequence, such as in opposite direction relative to the retroviral genome. Retroviral particles are prepared in the presence of a helper virus or in an appropriate complementation (packaging) cell line which contains integrated into its genome the retroviral genes for which the retroviral vector is defective (e.g. gag/pol and env). Such cell lines are described in the prior art (Miller and Rosman, 1989, BioTechniques 7: 980; Danos and Mulligan, 1988, Proc. Natl. Acad. Sci. USA 85: 6460; Markowitz, et al., 1988, Virol. 167: 400). The product of the env gene is responsible for the binding of the viral particle to the viral receptors present on the surface of the target cell and, therefore determines the host range of the retroviral particle. Packaging cell line, such as the PA317 cells (ATCC CRL 9078) or 293EI6 (WO97/35996) containing an amphotropic envelope protein may therefore be used to allow infection of human and other species' target cells. The retroviral particles are recovered from the culture supernatant and may optionally be further purified according to standard techniques (e.g. chromatography, ultracentrifugation).

Regulatory Elements

The polynucleotide or the heterologous polynucleotide of the disclosure may be operably linked to one or more regulatory elements in the vector. The regulatory elements may comprise promoters, enhancers, polyadenylation signals, repressors and the like.

Some of the commonly used enhancer and promoter sequences in expression vectors and viral vectors are, for example, human cytomegalovirus (hCMV), vaccinia P7.5 early/late promoter, CAG, SV40, mouse CMV (mCMV), EF-1 and hPGK promoters. Due to its high potency and moderate size of ca. 0.8 kB, the hCMV promoter is one of the most commonly used of these promoters. The hPGK promoter is characterized by a small size (ca. 0.4 kB), but it is less potent than the hCMV promoter. On the other hand, the CAG promoter consisting of a cytomegalovirus early enhancer element, promoter, first exon and intron of chicken beta-actin gene, and splice acceptor of the rabbit beta-globin gene, can direct very potent gene expression that is comparable to the hCMV promoter, but its large size makes it less suitable in viral vectors where space constraints can be a significant concern, e.g., in adenoviral vectors (AdV), adeno-associated viral vectors (AAV) or lentiviral vectors (LVs).

Additional promoters that may be used are Aotine Herpesvirus 1 major immediate early promoter (AoHV-1 promoter) described in Int. Pat. Publ. No. WO2018/146205. The promoter may be operably coupled to a repressor operator sequence, to which a repressor protein can bind in order to repress expression of the promoter in the presence of the repressor protein. In certain embodiments, the repressor operator sequence is a TetO sequence or a CuO sequence (see e.g. U.S. Pat. No. 9,790,256).

In certain cases, it may be desirable to express at least two separate polypeptides from the same vector. In this case each polynucleotide may be operably linked to the same or different promoter and/or enhancer sequences, or well-known bicistronic expression systems for example by utilizing internal ribosome entry site (IRES) from encephalomyocarditis virus may be used. Alternatively, bidirectional synthetic promoters may be used, such as a hCMV-rhCMV promoter and other promoters described in Int. Pat. Publ. No. WO2017/220499.

Polyadenylation signals may be derived from SV40 or bovine growth hormone (BGH).

The vectors of the disclosure may be generated using known techniques.

Exemplary regulatory elements that may be included into the vector comprise vaccinia P7.5 early/late promoter (SEQ ID NO: 630), TetOCMV promoter (SEQ ID NO: 628), BGH poly A site (SEQ ID NO: 629), T cell enhancer (SEQ ID NO: 546).

The disclosure also provides an isolated viral vector comprising a heterologous polynucleotide encoding a heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising two or more polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

In some embodiments, the viral vector is an adenovirus vector.

In some embodiments, the viral vector is derived from a human adenovirus.

In some embodiments, the viral vector is derived from Ad26.

In some embodiments, the viral vector is derived from a great ape adenovirus.

In some embodiments, the vial vector is derived from GAd20.

In some embodiments, the viral vector is derived from ChAd20.

In some embodiments, the viral vector is a poxvirus vector.

In some embodiments, the viral vector is derived from modified virus Ankara (MVA).

The disclosure also provides an isolated viral vector comprising a heterologous polynucleotide encoding a heterologous polypeptide comprising 3 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 3 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 4 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 4 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 5 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 5 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 6 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 6 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 7 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 7 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 8 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 8 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 9 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 9 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 10 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 10 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 11 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 11 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 12 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 12 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 13 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 13 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 14 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 14 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 15 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 15 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 16 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 16 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 17 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 17 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 18 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 18 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 19 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 19 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 20 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 20 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 21 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 21 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 22 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 22 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 23 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 23 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 24 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 24 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 25 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 25 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 26 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 26 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 27 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 27 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 28 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 28 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 29 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 29 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 30 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 30 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 31 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 31 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 32 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 32 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 33 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 33 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 34 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 34 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 35 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 35 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 36 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 36 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 37 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 37 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 38 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 38 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 39 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 39 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 40 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 40 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 41 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 41 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 42 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 42 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 43 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 43 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 44 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 44 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 45 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 45 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 46 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 46 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 47 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 47 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 48 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 48 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 49 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 49 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 50 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 50 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 51 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 51 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 52 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 52 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 53 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 53 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 54 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 54 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 55 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 55 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 56 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 56 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 57 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 57 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 58 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 58 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 59 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 59 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 60 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 60 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 61 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 61 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 62 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 62 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 63 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 63 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 64 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 64 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 65 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 65 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 66 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 66 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 67 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 67 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 68 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 68 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 69 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 69 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 70 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 70 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 71 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 71 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 72 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 72 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 73 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 73 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 74 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 74 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 75 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 75 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 76 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 76 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 77 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 77 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 78 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 78 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 79 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 79 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 80 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 80 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 81 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 81 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 82 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 82 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 83 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 83 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 84 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 84 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 85 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 85 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 86 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 86 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 87 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 87 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 88 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 88 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 89 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 89 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 90 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 90 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 91 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 91 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 92 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 92 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 93 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 93 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 94 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 94 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 95 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 95 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 96 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 96 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 97 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 97 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 98 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 98 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 99 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 99 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 100 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 100 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 101 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 101 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 102 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 102 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 103 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 103 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 104 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 104 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 105 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 105 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 106 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 106 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 107 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 107 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 108 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 108 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 109 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 109 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 110 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 110 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 111 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 111 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 112 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 112 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 113 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 113 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 114 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 114 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 115 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 115 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 116 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 116 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 117 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 117 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 118 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 118 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 119 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 119 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 120 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 120 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 121 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 121 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 122 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 122 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 123 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 123 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 124 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 124 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 125 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 125 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 126 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 126 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 127 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 127 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 128 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 128 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 129 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 129 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 130 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 130 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 131 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 131 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 132 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 132 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 133 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 133 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 134 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 134 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 135 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 135 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 136 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 136 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 137 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 137 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 138 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 138 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 139 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 139 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 140 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 140 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 141 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 141 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 142 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 142 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 143 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 143 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 144 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 144 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 145 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 145 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 146 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 146 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 147 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 147 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 148 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 148 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 149 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 149 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 150 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 150 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 151 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 151 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 152 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 152 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 153 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 153 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 154 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 154 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 155 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 155 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 156 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 156 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 157 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 157 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 158 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 158 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 159 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 159 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 160 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 160 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 161 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 161 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 162 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 162 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 163 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 163 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 164 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 164 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 165 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 165 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 166 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 166 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 167 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 167 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 168 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 168 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 169 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 169 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 170 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 170 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 171 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 171 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 172 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 172 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 173 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 173 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 174 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 174 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 175 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 175 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 176 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 176 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 177 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 177 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 178 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 178 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 179 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 179 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 180 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 180 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 181 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 181 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 182 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 182 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 183 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 183 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 184 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 184 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 185 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 185 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 186 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 186 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 187 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 187 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 188 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 188 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 189 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 189 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 190 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 190 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 191 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 191 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 192 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 192 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 193 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 193 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 194 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 194 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 195 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 195 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 196 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 196 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 197 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 197 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 198 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 198 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 199 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 199 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 200 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 200 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 201 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 201 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 202 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 202 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 203 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 203 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 204 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the viral vector comprises a heterologous polynucleotide comprising 204 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides an isolated viral vector comprising a heterologous polynucleotide encoding a heterologous polypeptide comprising 205 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 206 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 207 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 208 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 209 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 210 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 211 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 212 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 213 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 214 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 215 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 216 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 217 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 218 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 219 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 220 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 221 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 222 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 223 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 224 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 225 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 226 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 227 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 228 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 229 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 230 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 231 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 232 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 233 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 234 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 235 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 236 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising 237 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides an isolated viral vector comprising a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499.

In some embodiments, the viral vector comprises a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540.

The disclosure also provides an isolated viral vector comprising a heterologous polynucleotide encoding a heterologous polypeptide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499.

In some embodiments, the viral vector comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540.

The disclosure also provides an isolated viral vector comprising a heterologous polynucleotide encoding a heterologous polypeptide comprising 2 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 2 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 2 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 2 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 3 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 3 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 3 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 3 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 4 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 4 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 4 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 4 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 5 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 5 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 5 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 5 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 6 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 6 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 6 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 6 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 7 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 7 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 7 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 7 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 8 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 8 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 8 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 8 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 9 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 9 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 9 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 9 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 10 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 10 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 10 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 10 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 11 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 11 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 11 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 11 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 12 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 12 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 12 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 12 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 13 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 13 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 13 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 13 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 14 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 14 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 14 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 14 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 15 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 15 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 15 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 15 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 16 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 16 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 16 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 16 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 17 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 17 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 17 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 17 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 18 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 18 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 18 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 18 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 19 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 19 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 19 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 19 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 20 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 20 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 20 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 20 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 21 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 21 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 21 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 21 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 22 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 22 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 22 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 22 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 23 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 23 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 23 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 23 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 24 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 24 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 24 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 24 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 25 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 25 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 25 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 25 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 26 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 26 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 26 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 26 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 27 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 27 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 27 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 27 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 28 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 28 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 28 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 28 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 29 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 29 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 29 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 29 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 30 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 30 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 30 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 30 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 31 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 31 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 31 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 31 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 32 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 32 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 32 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 32 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 33 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 33 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 33 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 33 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 34 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 34 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 34 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 34 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 35 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 35 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 35 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 35 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 36 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 36 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 36 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 36 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 37 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 37 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 37 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 37 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 38 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 38 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 38 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 38 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 39 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 39 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 39 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 39 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 40 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 40 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 40 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 40 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides an isolated viral vector comprising a heterologous polynucleotide encoding a heterologous polypeptide comprising 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the viral vector comprises a heterologous polynucleotide comprising 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the viral vector comprises a heterologous polynucleotide comprising 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the viral vector comprises a heterologous polynucleotide comprising 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540.

In some embodiments, the viral vector comprises a heterologous polynucleotide comprising 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

In some embodiments, the viral vector is an adenovirus vector.

In some embodiments, the viral vector is derived from a human adenovirus.

In some embodiments, the viral vector is derived from Ad26.

In some embodiments, the viral vector is derived from a great ape adenovirus.

In some embodiments, the viral vector is derived from GAd20.

In some embodiments, the viral vector is derived from GAd19.

In some embodiments, the viral vector is derived from GAd21.

In some embodiments, the viral vector is derived from GAd25.

In some embodiments, the viral vector is derived from GAd26.

In some embodiments, the viral vector is derived from GAd27.

In some embodiments, the viral vector is derived from GAd28.

In some embodiments, the viral vector is derived from GAd29.

In some embodiments, the viral vector is derived from GAd30.

In some embodiments, the viral vector is derived from GAd31.

In some embodiments, the viral vector is derived from ChAd20.

In some embodiments, the viral vector is a poxvirus vector.

In some embodiments, the viral vector is derived from Modified Vaccinia Ankara (MVA).

The disclosure also provides a recombinant human adenovirus serotype 26 (rAd26) comprising a viral vector comprising a heterologous polynucleotide encoding a heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a viral vector comprising two or more polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 3 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 3 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 4 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 4 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 5 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 5 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 6 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 6 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 7 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 7 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 8 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 8 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 9 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 9 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 10 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 10 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 11 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 11 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 12 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 12 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 13 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 13 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 14 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 14 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 15 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 15 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 16 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 16 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 17 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 17 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 18 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 18 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 19 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 19 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 20 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 20 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 21 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 21 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 22 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 22 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 23 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 23 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 24 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 24 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 25 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 25 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 26 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 26 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 27 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 27 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 28 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317,319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 28 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 29 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 29 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 30 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 30 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 31 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 31 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 32 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 32 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 33 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 33 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 34 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 34 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 35 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 35 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 36 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 36 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 37 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 37 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 38 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 38 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 39 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 39 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 40 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 40 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 41 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 41 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 42 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 42 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 43 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 43 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 44 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 44 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 45 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 45 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 46 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 46 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 47 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 47 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 48 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 48 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 49 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 49 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 50 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 50 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 51 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 51 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 52 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 52 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 53 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 53 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 54 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 54 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 55 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 55 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 56 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 56 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 57 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 57 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 58 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 58 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 59 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 59 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 60 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 60 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 61 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 61 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 62 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 62 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 63 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 63 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 64 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 64 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 65 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 65 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 66 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 66 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 67 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 67 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 68 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 68 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 69 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 69 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 70 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 70 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 71 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 71 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 72 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 72 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 73 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 73 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 74 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 74 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 75 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 75 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 76 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 76 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 77 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 77 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 78 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 78 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 79 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 79 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 80 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 80 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

In some embodiments, the rAd26 comprises a heterologous polynucleotide comprising 81 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 81 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 82 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 82 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 83 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 83 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 84 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 84 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 85 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 85 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 86 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 86 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 87 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 87 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 88 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 88 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 89 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 89 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 90 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 90 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 91 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 91 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 92 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 92 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 93 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 93 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 94 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 94 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 95 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 95 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 96 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 96 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 97 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 97 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 98 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 98 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 99 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 99 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 100 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 100 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 101 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 101 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 102 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 102 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 103 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 103 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 104 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 104 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 105 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 105 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 106 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 106 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 107 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 107 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 108 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 108 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 109 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 109 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 110 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 110 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 111 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 111 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 112 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 112 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 113 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 113 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 114 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 114 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 115 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 115 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 116 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 116 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 117 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 117 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 118 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 118 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 119 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 119 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 120 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 120 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 121 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 121 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 122 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 122 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 123 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 123 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 124 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 124 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 125 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 125 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 126 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 126 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 127 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 127 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 128 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 128 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 129 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 129 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 130 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 130 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 131 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 131 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 132 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 132 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 133 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 133 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 134 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 134 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 135 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 135 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 136 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 136 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 137 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 137 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 138 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 138 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 139 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 139 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 140 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 140 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 141 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 141 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 142 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 142 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 143 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 143 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 144 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 144 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 145 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 145 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 146 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 146 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 147 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 147 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 148 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 148 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 149 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 149 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 150 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 150 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 151 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 151 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 152 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 152 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 153 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 153 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 154 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 154 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 155 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 155 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 156 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 156 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 157 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 157 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 158 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 158 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 159 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 159 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 160 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 160 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 161 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 161 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 162 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 162 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 163 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 163 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 164 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 164 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 165 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 165 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 166 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 166 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 167 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 167 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 168 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 168 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 169 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 169 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 170 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 170 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 171 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 171 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 172 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 172 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 173 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 173 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 174 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 174 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 175 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 175 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 176 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 176 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 177 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 177 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 178 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 178 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 179 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 179 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 180 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 180 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 181 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 181 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 182 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 182 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 183 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 183 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 184 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 184 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 185 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 185 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 186 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 186 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 187 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 187 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 188 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 188 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 189 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 189 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 190 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 190 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 191 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 191 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 192 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 192 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 193 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 193 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 194 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 194 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 195 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 195 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 196 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 196 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 197 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 197 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 198 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 198 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 199 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 199 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 200 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 200 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 201 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 201 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 202 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 202 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 203 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 203 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 204 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rAd26 comprises a heterologous polynucleotide comprising 204 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rAd26 comprising a heterologous polynucleotide encoding a heterologous polypeptide comprising 205 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 206 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 207 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 208 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 209 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 210 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 211 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 212 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 213 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 214 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 215 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 216 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 217 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 218 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 219 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 220 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 221 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 222 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 223 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 224 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 225 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 226 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 227 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 228 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 229 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 230 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 231 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 232 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 233 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 234 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 235 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 236 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising 237 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rAd26 comprising a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 2 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 2 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 2 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 2 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 3 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 3 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 3 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 3 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 4 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 4 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 4 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 4 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 5 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 5 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 5 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 5 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 6 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 6 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 6 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 6 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 7 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 7 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 7 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 7 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 8 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 8 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 8 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 8 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 9 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 9 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 9 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 9 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 10 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 10 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 10 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 10 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 11 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 11 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 11 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 11 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 12 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 12 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 12 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 12 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 13 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 13 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 13 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 13 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 14 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 14 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 14 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 14 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 15 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 15 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 15 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 15 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 16 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 16 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 16 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 16 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 17 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 17 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 17 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 17 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 18 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 18 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 18 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 18 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 19 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 19 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 19 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 19 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 20 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 20 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 20 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 20 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 21 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 21 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 21 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 21 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 22 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 22 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 22 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 22 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 23 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 23 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 23 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 23 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 24 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 24 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 24 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 24 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 25 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 25 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 25 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 25 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 26 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 26 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 26 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 26 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 27 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 27 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 27 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 27 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 28 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 28 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 28 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 28 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 29 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 29 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 29 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 29 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 30 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 30 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 30 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 30 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 31 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 31 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 31 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 31 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 32 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 32 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 32 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 32 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 33 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 33 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 33 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 33 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 34 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 34 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 34 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 34 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 35 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 35 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 35 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 35 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 36 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 36 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 36 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 36 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 37 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 37 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 37 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 37 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 38 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 38 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 38 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 38 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 39 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 39 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 39 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 39 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 40 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 40 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 40 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 40 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rAd26 comprising a heterologous polynucleotide encoding a heterologous polypeptide comprising 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rAd26 comprises a heterologous polynucleotide comprising 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rAd26 comprises a heterologous polynucleotide comprising 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rAd26 comprises a heterologous polynucleotide comprising 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a recombinant great ape adenovirus (rGAd) comprising a viral vector comprising a heterologous polynucleotide encoding a heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the rGAd comprises a viral vector comprising a heterologous polynucleotide comprising two or more polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 3 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 3 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 4 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 4 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 5 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 5 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 6 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 6 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 7 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 7 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 8 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 8 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 9 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 9 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 10 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 10 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 11 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 11 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 12 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 12 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 13 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 13 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 14 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 14 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 15 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 15 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 16 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 16 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 17 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245,247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 17 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 18 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 18 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 19 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 19 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 20 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 20 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 21 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 21 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 22 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 22 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 23 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 23 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 24 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 24 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 25 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245,247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 25 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 26 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 26 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 27 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 27 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 28 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 28 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 29 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 29 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 30 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 30 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 31 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 31 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 32 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 32 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 33 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 33 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 34 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 34 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 35 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 35 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 36 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 36 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 37 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 37 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 38 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 38 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 39 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 39 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 40 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 40 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 41 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 41 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 42 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 42 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 43 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 43 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 44 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 44 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 45 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245,247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 45 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 46 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 46 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 47 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 47 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 48 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 48 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 49 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 49 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 50 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 50 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 51 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 51 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 52 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 52 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 53 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245,247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 53 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 54 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 54 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 55 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 55 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 56 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 56 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 57 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 57 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 58 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 58 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 59 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 59 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 60 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 60 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 61 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 61 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 62 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 62 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 63 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 63 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 64 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 64 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 65 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 65 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 66 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 66 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 67 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 67 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 68 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 68 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 69 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 69 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 70 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 70 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 71 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 71 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 72 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 72 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 73 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245,247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 73 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 74 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 74 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 75 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 75 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 76 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 76 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 77 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245,247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 77 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 78 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 78 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 79 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 79 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 80 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 80 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 81 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245,247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 81 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 82 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 82 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 83 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 83 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 84 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 84 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 85 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 85 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 86 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 86 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 87 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 87 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 88 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 88 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 89 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 89 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 90 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 90 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 91 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 91 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 92 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 92 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 93 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 93 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 94 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 94 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 95 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 95 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 96 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 96 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 97 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 97 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 98 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 98 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 99 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311,313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 99 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 100 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 100 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 101 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 101 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 102 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 102 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 103 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 103 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 104 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 104 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 105 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245,247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 105 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 106 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 106 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 107 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 107 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 108 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 108 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 109 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245,247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 109 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 110 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 110 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 111 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 111 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 112 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 112 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 113 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 113 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 114 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 114 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 115 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 115 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 116 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 116 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 117 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 117 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 118 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 118 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 119 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 119 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 120 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 120 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 121 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 121 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 122 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 122 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 123 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 123 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 124 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 124 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 125 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 125 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 126 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 126 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 127 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 127 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 128 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 128 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 129 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 129 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 130 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 130 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 131 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 131 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 132 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 132 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 133 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 133 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 134 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 134 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 135 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 135 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 136 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 136 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 137 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245,247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 137 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 138 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 138 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 139 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 139 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 140 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 140 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 141 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 141 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 142 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 142 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 143 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 143 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 144 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 144 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 145 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 145 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 146 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 146 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 147 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 147 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 148 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 148 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 149 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 149 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 150 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 150 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 151 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 151 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 152 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 152 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 153 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 153 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 154 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 154 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 155 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 155 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 156 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 156 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 157 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 157 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 158 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 158 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 159 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 159 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 160 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 160 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 161 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 161 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 162 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 162 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 163 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 163 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 164 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 164 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 165 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 165 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 166 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 166 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 167 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 167 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 168 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 168 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 169 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 169 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 170 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 170 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 171 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 171 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 172 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 172 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 173 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 173 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 174 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 174 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 175 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 175 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 176 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 176 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 177 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 177 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 178 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 178 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 179 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 179 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 180 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 180 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 181 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 181 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 182 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 182 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 183 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 183 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 184 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 184 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 185 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 185 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 186 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 186 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 187 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 187 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 188 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 188 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 189 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 189 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 190 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 190 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 191 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 191 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 192 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 192 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 193 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245,247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 193 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 194 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 194 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 195 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 195 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 196 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 196 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 197 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 197 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 198 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 198 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 199 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 199 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 200 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 200 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 201 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 201 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 202 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 202 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 203 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 203 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 204 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rGAd comprises a heterologous polynucleotide comprising 204 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rGAd comprising a heterologous polynucleotide encoding a heterologous polypeptide comprising 205 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 206 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 207 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 208 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 209 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 210 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 211 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 212 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 213 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 214 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 215 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 216 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 217 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245,247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 218 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 219 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 220 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 221 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 222 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 223 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 224 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 225 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 226 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 227 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 228 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 229 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245,247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 230 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 231 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 232 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 233 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 234 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 235 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 236 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising 237 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rGAd comprising a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 2 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 2 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 2 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 2 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 3 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 3 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 3 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 3 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 4 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 4 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 4 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 4 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 5 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 5 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 5 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 5 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 6 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 6 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 6 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 6 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 7 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 7 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 7 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 7 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 8 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 8 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 8 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 8 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 9 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 9 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 9 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 9 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 10 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 10 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 10 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 10 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 11 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 11 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 11 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 11 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 12 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 12 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 12 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 12 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 13 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 13 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 13 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 13 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 14 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 14 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 14 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 14 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 15 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 15 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 15 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 15 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 16 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 16 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 16 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 16 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 17 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 17 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 17 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 17 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 18 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 18 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 18 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 18 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 19 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 19 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 19 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 19 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 20 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 20 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 20 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 20 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 21 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 21 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 21 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 21 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 22 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 22 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 22 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 22 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 23 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 23 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 23 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 23 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 24 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 24 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 24 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 24 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 25 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 25 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 25 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 25 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 26 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 26 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 26 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 26 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 27 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 27 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 27 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 27 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 28 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 28 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 28 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 28 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 29 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 29 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 29 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 29 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 30 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 30 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 30 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 30 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 31 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 31 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 31 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 31 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 32 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 32 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 32 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 32 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 33 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 33 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 33 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 33 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 34 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 34 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 34 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 34 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 35 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 35 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 35 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 35 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 36 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 36 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 36 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 36 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 37 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 37 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 37 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 37 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 38 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 38 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 38 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 38 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 39 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 39 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 39 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 39 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 40 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 40 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 40 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 40 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd comprising a heterologous polynucleotide encoding a heterologous polypeptide comprising 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd comprises a heterologous polynucleotide comprising 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd comprises a heterologous polynucleotide comprising 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd comprises a heterologous polynucleotide comprising 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 2 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 2 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 2 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 2 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 3 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 3 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 3 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 3 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 4 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 4 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 4 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 4 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 5 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 5 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 5 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 5 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 6 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 6 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 6 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 6 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 7 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 7 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 7 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 7 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 8 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 8 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 8 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 8 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 9 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 9 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 9 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 9 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 10 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 10 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 10 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 10 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 11 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 11 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 11 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 11 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 12 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 12 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 12 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 12 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 13 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 13 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 13 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 13 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 14 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 14 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 14 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 14 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 15 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 15 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 15 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 15 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 16 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 16 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 16 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 16 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 17 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 17 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 17 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 17 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 18 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 18 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 18 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 18 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 19 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 19 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 19 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 19 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 20 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 20 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 20 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 20 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 21 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 21 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 21 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 21 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 22 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 22 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 22 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 22 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 23 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 23 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 23 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 23 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 24 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 24 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 24 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 24 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 25 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 25 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 25 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 25 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 26 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 26 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 26 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 26 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 27 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 27 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 27 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 27 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 28 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 28 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 28 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 28 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 29 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 29 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 29 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 29 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 30 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 30 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 30 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 30 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 31 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 31 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 31 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 31 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 32 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 32 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 32 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 32 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 33 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 33 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 33 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 33 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 34 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 34 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 34 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 34 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 35 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 35 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 35 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 35 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 36 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 36 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 36 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 36 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 37 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 37 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 37 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 37 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 38 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 38 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 38 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 38 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 39 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 39 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 39 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 39 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 40 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 40 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 40 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 40 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rGAd20 comprising a heterologous polynucleotide encoding a heterologous polypeptide comprising 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rGAd20 comprises a heterologous polynucleotide comprising 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rGAd20 comprises a heterologous polynucleotide comprising 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rGAd20 comprises a heterologous polynucleotide comprising 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a recombinant modified vaccinia Ankara (rMVA) comprising a viral vector comprising a heterologous polynucleotide encoding a heterologous polypeptide comprising two or more polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 and 447, and fragments thereof.

In some embodiments, the rMVA comprises a viral vector comprising a heterologous polypeptide comprising two or more polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 3 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 3 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 4 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 4 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 5 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 5 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 6 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 6 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 7 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 7 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 8 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 8 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 9 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 9 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 10 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 10 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 11 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 11 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 12 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 12 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 13 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 13 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 14 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 14 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 15 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 15 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 16 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 16 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 17 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 17 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 18 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 18 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 19 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 19 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 20 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 20 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 21 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 21 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 22 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 22 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 23 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 23 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 24 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 24 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 25 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 25 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 26 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 26 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 27 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 27 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 28 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 28 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 29 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 29 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 30 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 30 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 31 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 31 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 32 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 32 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 33 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 33 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 34 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 34 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 35 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 35 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 36 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 36 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 37 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 37 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 38 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 38 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 39 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 39 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 40 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 40 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 41 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 41 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 42 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 42 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 43 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 43 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 44 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 44 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 45 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 45 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 46 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 46 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 47 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 47 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 48 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 48 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 49 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 49 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 50 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 50 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 51 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 51 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 52 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 52 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 53 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 53 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 54 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 54 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 55 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 55 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 56 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 56 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 57 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 57 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 58 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 58 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 59 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 59 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 60 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 60 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 61 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 61 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 62 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 62 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 63 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 63 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 64 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 64 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 65 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 65 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 66 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 66 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 67 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 67 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 68 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 68 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 69 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 69 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 70 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 70 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 71 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 71 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 72 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 72 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 73 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 73 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 74 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 74 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 75 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 75 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 76 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 76 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 77 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 77 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 78 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 78 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 79 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 79 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 80 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 80 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 81 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 81 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 82 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 82 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 83 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 83 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 84 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 84 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 85 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 85 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 86 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 86 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 87 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 87 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 88 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 88 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 89 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 89 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 90 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 90 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 91 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 91 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 92 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 92 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 93 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 93 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 94 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 94 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 95 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 95 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 96 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 96 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 97 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 97 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 98 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 98 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 99 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 99 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 100 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 100 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 101 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 101 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 102 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 102 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 103 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 103 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 104 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 104 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 105 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 105 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 106 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 106 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 107 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 107 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 108 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 108 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 109 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 109 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 110 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 110 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 111 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 111 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 112 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 112 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 113 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 113 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 114 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 114 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 115 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 115 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 116 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315,317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 116 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 117 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 117 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 118 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 118 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 119 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 119 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 120 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 120 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 121 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 121 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 122 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 122 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 123 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 123 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 124 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 124 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 125 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 125 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 126 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 126 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 127 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 127 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 128 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 128 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 129 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 129 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 130 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 130 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 131 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 131 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 132 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 132 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 133 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 133 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 134 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 134 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 135 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 135 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 136 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 136 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 137 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 137 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 138 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 138 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 139 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 139 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 140 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 140 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 141 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 141 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 142 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 142 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 143 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 143 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 144 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 144 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 145 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 145 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 146 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 146 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 147 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 147 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 148 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 148 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 149 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 149 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 150 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 150 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 151 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 151 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 152 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 152 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 153 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 153 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 154 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 154 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 155 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 155 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 156 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 156 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 157 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 157 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 158 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 158 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 159 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 159 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 160 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 160 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 161 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 161 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 162 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 162 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 163 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 163 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 164 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315,317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 164 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 165 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 165 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 166 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 166 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 167 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 167 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 168 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 168 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 169 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 169 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 170 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 170 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 171 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 171 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 172 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 172 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 173 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 173 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 174 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 174 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 175 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 175 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 176 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 176 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 177 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 177 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 178 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 178 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 179 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 179 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 180 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 180 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 181 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 181 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 182 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 182 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 183 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 183 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 184 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 184 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 185 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 185 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 186 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 186 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 187 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 187 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 188 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 188 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 189 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 189 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 190 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 190 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 191 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 191 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 192 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315,317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 192 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 193 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 193 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 194 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 194 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 195 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 195 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 196 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 196 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 197 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 197 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 198 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 198 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 199 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 199 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 200 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 200 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 201 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 201 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 202 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 202 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 203 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 203 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 204 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

In some embodiments, the rMVA comprises a heterologous polynucleotide comprising 204 polynucleotides selected from the group consisting of SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 380, 382, 384, 386, 448, 449, 450, 451, 452, 453, 454, 455, 456, 457 and 458, and fragments thereof.

The disclosure also provides a rMVA comprising a heterologous polynucleotide encoding a heterologous polypeptide comprising 205 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 206 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 207 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 208 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 209 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 210 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 211 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 212 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 213 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 214 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 215 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 216 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 217 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 218 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 219 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 220 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 221 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 222 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 223 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 224 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 225 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 226 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 227 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 228 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 229 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 230 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 231 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 232 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 233 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 234 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 235 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 236 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising 237 polypeptides selected from the group consisting of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 and 447, and fragments thereof.

The disclosure also provides a rMVA comprising a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 2 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 2 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 3 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 3 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 3 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 3 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 4 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 4 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 4 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 4 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 5 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 5 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 5 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 5 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 6 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 6 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 6 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 6 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 7 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 7 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 7 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 7 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 8 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 8 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 8 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 8 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 9 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 9 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 9 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 9 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 10 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 10 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 10 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 10 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 11 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 11 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 11 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 11 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 12 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 12 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 12 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 12 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 13 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 13 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 13 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 13 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 14 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 14 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 14 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 14 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 15 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 15 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 15 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 15 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 16 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 16 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 16 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 16 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 17 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 17 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 17 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 17 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 18 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 18 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 18 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 18 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 19 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 19 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 19 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 19 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 20 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 20 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 20 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 20 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 21 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 21 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 21 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 21 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 22 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 22 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 22 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 22 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 23 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 23 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 23 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 23 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 24 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 24 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 24 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 24 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 25 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 25 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 25 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 25 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 26 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 26 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 26 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 26 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 27 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 27 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 27 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 27 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 28 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 28 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 28 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 28 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 29 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 29 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 29 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 29 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 30 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 30 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 30 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 30 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 31 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 31 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 31 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 31 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 32 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 32 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 32 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 32 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 33 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 33 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 33 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 33 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 34 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 34 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 34 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 34 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 35 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 35 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 35 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 35 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 36 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 36 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 36 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 36 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 37 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 37 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 37 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 37 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 38 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 38 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 38 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 38 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 39 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 39 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 39 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 39 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 40 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 40 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 40 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 40 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

The disclosure also provides a rMVA comprising a heterologous polynucleotide encoding a heterologous polypeptide comprising 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the rMVA comprises a heterologous polynucleotide comprising 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the rMVA comprises a heterologous polynucleotide comprising 41 polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof.

In some embodiments, the rMVA comprises a heterologous polynucleotide comprising 41 polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof.

Cells of the Disclosure

The disclosure also provides a cell comprising or transduced with one or more vectors of the disclosure or one or more recombinant viruses of the disclosure. In some embodiments, the cell is a host cell.

Suitable cells include prokaryotic and eukaryotic cells, e.g., mammalian cells, yeast, fungi and bacteria (such as *E. coli*), such as Hek 293, CHO, PER.C6, PER.C6 TetO or chicken embryonic fibroblast (CEF) cells. The cell can be used in vitro, such as for research or for production of the polypeptides or viruses, or the cell can be used in vivo. In some embodiments, the cell is a muscle cell. In some embodiments, the cell is an antigen presenting cell (APC). Suitable antigen presenting cells include dendritic cells, B lymphocytes, monocytes and macrophages.

"Transduced", "transformed", or "transfected" refers to introduction of polynucleotides, heterologous polynucleotides or vectors of the disclosure inside a cell. The introduced polynucleotide may or may not be integrated into chromosomal DNA making up the genome of the cell. "Cell" refers to the original cell and any progeny or clonal cell line established from the original cell.

The cells that are transfected with the polynucleotides or vectors of the disclosure may typically be obtained through cell culture repositories such as ATCC. APCs may be obtained from the peripheral blood using leukopheresis and "FICOLL/HYPAQUE" density gradient centrifugation (stepwise centrifugation through Ficoll and discontinuous Percoll density gradients). APCs may be isolated, cultured and engineered using known methods. For example, immature and mature dendritic cells may be generated from peripheral blood mononuclear cells (PBMCs) using known methods. In an exemplary method, isolated PBMCs are pre-treated to deplete T- and B-cells by means of an immunomagnetic technique. Lymphocyte-depleted PBMC are then cultured for in RPMI medium 9 e.g., about 7 days), supplemented with human plasma (preferably autologous plasma) and GM-CSF/IL-4, to generate dendritic cells. Dendritic cells are nonadherent when compared to their monocyte progenitors. Thus, on approximately day 7, non-adherent cells are harvested for further processing. The dendritic cells derived from PBMC in the presence of GM-CSF and IL-4 are immature, in that they can lose the nonadherence property and revert back to macrophage cell fate if the cytokine stimuli are removed from the culture. The dendritic cells in an immature state are effective in processing native protein antigens for the MHC class II restricted pathway (Romani, et al., J. Exp. Med. 169: 1169, 1989). Further maturation of cultured dendritic cells is accomplished by culturing for 3 days in a macrophage-conditioned medium (CM), which contains the necessary maturation factors. Mature dendritic cells are less able to capture new proteins for presentation but are much better at stimulating resting T cells (both CD4 and CD8) to grow and differentiate. Mature dendritic cells can be identified by their change in morphology, such as the formation of more motile cytoplasmic processes; by their nonadherence; by the presence of at least one of the following markers: CD83, CD68, HLA-DR or CD86; or by the loss of Fc receptors such as CD115 (reviewed in Steinman, Annu. Rev. Immunol. 9: 271, 1991). Mature dendritic cells can be collected and analyzed using typical cytofluorography and cell sorting techniques and devices, such as FACScan and FACStar. Primary antibodies used for flow cytometry are those specific to cell surface antigens of mature dendritic cells and are commercially available. Secondary antibodies can be biotinylated Igs followed by FITC- or PE-conjugated streptavidin. The vectors and recombinant viruses of the disclosure can be introduced into cells including APCs using the methods known in the art, including, but not limited to, transfection, electroporation, fusion, microinjection, viral-based delivery, or cell-based delivery.

Vaccines and Pharmaceutical Compositions of the Disclosure

The polypeptides or the heterologous polypeptides or fragments thereof, or the polynucleotides encoding them may be delivered into the subject utilizing any known delivery vehicle suitable for administering to the subject. It is expected that the polypeptides, the heterologous polypeptides or fragments thereof will be immunogenic in the subject regardless of the delivery vehicle used. It is expected that the various viral strains will be equally effective in mediating delivery of the polypeptides or the heterologous polypeptides in human subjects and therefore can be interchangeable. For example, it is expected that the various MVA strains disclosed herein would be equally efficient in potentiating immune responses against antigens encoded by the same transgene cassette. Similarly, it is expected that the various adenovirus strains would be interchangeable with no or minimal changes in their ability to potentiate immune responses against antigens encoded by the same transgene cassette. The polynucleotide may be DNA or RNA, or derivatives thereof. RNA may be in the form of oligonucleotide RNA, tRNA (transfer RNA), snRNA (small nuclear RNA), rRNA (ribosomal RNA), mRNA (messenger RNA), antisense RNA, siRNA (small interfering RNA), self-replicating RNA, ribozymes, chimeric sequences, or derivatives of these groups.

The disclosure also provides a vaccine comprising the polynucleotide of the disclosure.

In some embodiments, the polynucleotide is DNA.

In some embodiments, the polynucleotides is RNA.

In some embodiments, RNA is mRNA, or self-replicating RNA.

In some embodiments, RNA is self-replicating RNA.

The disclosure also provides a vaccine comprising the heterologous polynucleotide of the disclosure.

In some embodiments, the heterologous polynucleotide is DNA.

In some embodiments, the heterologous polynucleotides is RNA.

In some embodiments, RNA is mRNA, or self-replicating RNA.

In some embodiments, RNA is self-replicating RNA.

The disclosure also provides a vaccine comprising the polypeptide of the disclosure.

The disclosure also provides a vaccine comprising the heterologous polypeptide of the disclosure.

The disclosure also provides a vaccine comprising the vector of the disclosure.

The disclosure also provides a vaccine comprising the rAd26 of the disclosure.

The disclosure also provides a vaccine comprising the rMVA of the disclosure.

The disclosure also provides a vaccine comprising the rGAd of the disclosure.

The disclosure also provides a vaccine comprising the rGAd20 of the disclosure.

The disclosure also provides a vaccine comprising the ChAd20 of the disclosure.

The disclosure also provides a vaccine comprising the cell of the disclosure.

The preparation of vaccine compositions is well known. Vaccines may comprise or may be formulated into a pharmaceutical composition comprising the vaccine and a pharmaceutically acceptable excipient. "Pharmaceutically acceptable" refers to the excipient that at the dosages and concentrations employed, will not cause unwanted or harmful effects in the subjects to which they are administered and include carrier, buffers, stabilizers or other materials well known to those skilled in the art. The precise nature of the carrier or other material may depend on the route of administration, e.g., intramuscular, subcutaneous, oral, intravenous, cutaneous, intramucosal (e.g., gut), intranasal or intraperitoneal routes. Liquid carriers such as water, petroleum, animal or vegetable oils, mineral oil or synthetic oil may be included. Physiological saline solution, dextrose or other saccharide solution or glycols such as ethylene glycol, propylene glycol or polyethylene glycol may be included. Exemplary viral formulation are the Adenovirus World Standard (Hoganson et al, 2002): 20 mM Tris pH 8, 25 mM NaCl, 2.5% glycerol; or 20 mM Tris, 2 mM MgCl2, 25 mM NaCl, sucrose 10% w/v, polysorbate-80 0.02% w/v; or 10-25 mM citrate buffer pH 5.9-6.2, 4-6% (w/w) hydroxypropyl-beta-cyclodextrin (HBCD), 70-100 mM NaCl, 0.018-0.035% (w/w) polysorbate-80, and optionally 0.3-0.45% (w/w) ethanol. Many other buffers can be used, and examples of suitable formulations for the storage and for pharmaceutical administration of purified pharmaceutical preparations are known.

The vaccine may comprise one or more adjuvants. Suitable adjuvants include QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59. Other adjuvants that may be used include lectins, growth factors, cytokines and lymphokines such as alpha-interferon, gamma interferon, platelet derived growth factor (PDGF), granulocyte-colony stimulating factor (gCSF), granulocyte macrophage colony stimulating factor (gMCSF), tumor necrosis factor (TNF), epidermal growth factor (EGF), IL-1, IL-2, IL-4, IL-6, IL-8, IL-10, IL-12 or TLR agonists.

"Adjuvant" and "immune stimulant" are used interchangeably herein and are defined as one or more substances that cause stimulation of the immune system. In this context, an adjuvant is used to enhance an immune response to the vaccines or viral vectors described herein.

A pharmaceutical composition according to the disclosure may in certain embodiments be the vaccine of the disclosure.

Similarly, the polynucleotides, the heterologous polynucleotides, the polypeptides and the heterologous polypeptides of the disclosure may be formulated into pharmaceutical compositions comprising the polynucleotides, the heterologous polynucleotides, the polypeptides and the heterologous polypeptides and the pharmaceutically acceptable excipients.

Kits

The disclosure also provides a kit comprising one or more vaccines of the disclosure. The disclosure also provides a kit comprising one or more recombinant viruses of the disclosure. The kits may be used to facilitate performing the methods described herein. In some embodiments, the kit further comprises reagents to facilitate entry of the vaccines of the disclosure into a cell, such as lipid-based formulations or viral packaging materials.

In some embodiments, the kit comprises the rAd26 of the disclosure. In some embodiments, the kit comprises the rMVA of the disclosure. In some embodiments, the kit comprises the rGAd of the disclosure. In some embodiments, the kit comprises the rAd26 of the disclosure and the rMVA of the disclosure. In some embodiments, the kit comprises the rGAd of the disclosure and the rMVA of the disclosure. In some embodiments, the kit comprises the rAd26 of the disclosure and the rGAd of the disclosure. In some embodiments, the kit comprises one or more polynucleotides of the disclosure. In some embodiments, the kit comprises one or more heterologous polynucleotides of the disclosure. In some embodiments, the kit comprises one or more polypeptides of the disclosure. In some embodiments, the kit comprises one or more heterologous polypeptides of the disclosure. In some embodiments, the kit comprises one or more vectors of the disclosure. In some embodiment, the kit comprises one or more cells of the disclosure.

Non-Viral Delivery Vehicles

Nanoparticles

The polypeptides or the heterologous polypeptides or fragments thereof, the polynucleotides encoding them or vectors comprising the polynucleotides of the disclosure may be attached to nanoparticles for delivery to a subject. Delivery of the polypeptides or the heterologous polypeptides or fragments thereof, the polynucleotides encoding them or the vectors comprising the polynucleotides using nanoparticles may eliminate the need to include a virus or an adjuvant in the vaccine composition. The polynucleotide may be DNA or RNA. The nanoparticles may contain immune danger signals that help to effectively induce an immune response to the peptides. The nanoparticles may induce dendritic cell (DC) activation and maturation, required for a robust immune response. The nanoparticles may contain non-self components that improve uptake of the nanoparticles and thus the peptides by cells, such as antigen presenting cells.

The nanoparticles are typically from about 1 nm to about 100 nm in diameter, such as about 20 nm to about 40 nm. Nanoparticles with a mean diameter of 20 to 40 nm may facilitate uptake of the nanoparticle to the cytosol (see. e.g. WO2019/135086). Exemplary nanoparticles are polymeric nanoparticles, inorganic nanoparticles, liposomes, lipid nanoparticles (LNP), an immune stimulating complex (ISCOM), a virus-like particle (VLP), or a self-assembling protein. The nanoparticles may be calcium phosphate nanoparticles, silicon nanoparticles or gold nanoparticles. The polymeric nanoparticles may comprise one or more synthetic polymers, such as poly(d,l-lactide-co-glycolide) (PLG), poly(d,l-lactic-coglycolic acid) (PLGA), poly(g-glutamic acid) (g-PGA)m poly(ethylene glycol) (PEG), or polystyrene or one or more natural polymers such as a polysaccharide, for example pullulan, alginate, inulin, and chitosan. The use of a polymeric nanoparticles may be advantageous due to the properties of the polymers that may be include in the nanoparticle. For instance, the natural and synthetic polymers recited above may have good biocompatibility and biodegradability, a non-toxic nature and/or the ability to be manipulated into desired shapes and sizes. The polymeric nanoparticle may also form hydrogel nanoparticles, hydrophilic three-dimensional polymer networks with favorable properties including flexible mesh size, large surface area for multivalent conjugation, high water content, and high loading capacity for antigens. Polymers such as Poly(L-lactic acid) (PLA), PLGA, PEG, and polysaccharides are suitable for forming hydrogel nanoparticles. Inorganic nanoparticles typically have a rigid structure and comprise a shell in which an antigen is encapsulated or a core to which the antigen may be covalently attached. The core may comprise one or more atoms such as gold (Au), silver (Ag), copper (Cu) atoms, Au/Ag, Au/Cu, Au/Ag/Cu, Au/Pt, Au/Pd or Au/Ag/Cu/Pd or calcium phosphate (CaP).

The nanoparticles may be liposomes. Liposomes are typically formed from biodegradable, non-toxic phospholipids and comprise a self-assembling phospholipid bilayer shell with an aqueous core. Liposomes may be an unilamellar vesicle comprising a single phospholipid bilayer, or a multilamellar vesicle that comprises several concentric phospholipid shells separated by layers of water. As a consequence, liposomes may be tailored to incorporate either hydrophilic molecules into the aqueous core or hydrophobic molecules within the phospholipid bilayers. Liposomes may encapsulate antigens such as the polypeptides or the heterologous polypeptides or fragments thereof of the disclosure within the core for delivery. Liposomes and liposomal formulations can be prepared according to standard methods and are well known in the art, see, e.g., Remington's; Akimaru, 1995, Cytokines Mol. Ther. 1: 197-210; Alving, 1995, Immunol. Rev. 145: 5-31; Szoka, 1980, Ann. Rev. Biophys. Bioeng. 9: 467; U.S. Pat. Nos. 4,235,871; 4,501,728; and 4,837,028. The liposomes may comprise a targeting molecule for targeting liposome complexes to a particular cell type. Targeting molecule may comprise a binding partner (e.g., a ligand or receptor) for a biomolecule (e.g., a receptor or ligand) on the surface of a blood vessel or a cell found in a target tissue. Liposome charge is an important determinant in liposome clearance from the blood, with negatively charged liposomes being taken up more rapidly by the reticuloendothelial system (Juliano, 1975, Biochem. Biophys. Res. Commun. 63: 651) and thus having shorter half-lives in the bloodstream. Incorporating phosphatidylethanolamine derivatives enhances the circulation time by preventing liposomal aggregation. For example, incorporation of N-(omega-carboxy)acylamidophosphatidylethanolamines into large unilamellar vesicles of L-alpha-distearoylphosphatidylcholine dramatically increases the in vivo liposomal circulation lifetime (see, e.g., Ahl, 1997, Biochim. Biophys. Acta 1329: 370-382). Typically, liposomes are prepared with about 5 to 15 mole percent negatively charged phospholipids, such as phosphatidylglycerol, phosphatidylserine or phosphatidyl-inositol. Added negatively charged phospholipids, such as phosphatidylglycerol, also serve to prevent spontaneous liposome aggregation, and thus minimize the risk of undersized liposomal aggregate formation. Membrane-rigidifying agents, such as sphingomyelin or a saturated neutral phospholipid, at a concentration of at least about 50 mole percent, and 5 to 15 mole percent of monosialylganglioside can also impart desirably liposome properties, such as rigidity (see, e.g., U.S. Pat. No. 4,837,028). Additionally, the liposome suspension can include lipid-protective agents which protect lipids against free-radical and lipid-peroxidative damages on storage. Lipophilic free-radical quenchers, such as alpha-tocopherol and water-soluble iron-specific chelators, such as ferrioxianine, are preferred.

The nanoparticles may be lipid nanoparticles (LNP). LNPs are similar to liposomes but have slightly different function and composition. LNPs are designed toward encapsulating polynucleotides, such as DNA, mRNA, siRNA and sRNA. Traditional liposomes contain an aqueous core surrounded by one or more lipid bilayers. LNPs may assume a micelle-like structure, encapsulating drug molecules in a non-aqueous core. LNPs typically contain a cationic lipid, a non-cationic lipid, and a lipid that prevents aggregation of the particle (e.g., a PEG-lipid conjugate). LNPs are useful for systemic applications, as they exhibit extended circulation lifetimes following intravenous (i.e.) injection and accumulate at distal sites (e.g., sites physically separated from the administration site). The LNPs may have a mean diameter of about 50 nm to about 150 nm, such as about 60 nm to about 130 nm, or about 70 nm to about 110 n, or about 70 nm to about 90 nm, and are substantially nontoxic. Preparation of polynucleotide loaded LNPs are disclosed in, e.g., U.S. Pat. Nos. 5,976,567; 5,981,501; 6,534,484; 6,586,410; 6,815,432; and PCT Publication No. WO 96/40964. Polynucleotide containing LNPs are described for example in WO2019/191780.

The polynucleotides, the heterologous polynucleotides, the polypeptides and the heterologous polypeptides of the disclosure can include multilamellar vesicles of heterogeneous sizes. For example, vesicle-forming lipids can be dissolved in a suitable organic solvent or solvent system and dried under vacuum or an inert gas to form a thin lipid film. If desired, the film can be redissolved in a suitable solvent, such as tertiary butanol, and then lyophilized to form a more homogeneous lipid mixture which is in a more easily hydrated powder like form. This film is covered with an aqueous solution of the polypeptide complex and allowed to hydrate, typically over a 15 to 60 minute period with agitation. The size distribution of the resulting multilamellar vesicles can be shifted toward smaller sizes by hydrating the lipids under more vigorous agitation conditions or by adding solubilizing detergents such as deoxycholate. The hydration medium may comprise the nucleic acid at a concentration which is desired in the interior volume of the liposomes in the final liposome suspension. Suitable lipids that may be used to form multilamellar vesicles include DOTMA (Feigner, et al., 1987, Proc. Natl. Acad. Sci. USA 84: 7413-7417), DOGS or Transfectain™ (Behr, et al., 1989, Proc. Natl. Acad. Sci. USA 86: 6982-6986), DNERIE or DORIE (Feigner, et al., Methods 5: 67-75), DC-CHOL (Gao and Huang, 1991, BBRC 179: 280-285), DOTAP™ (McLachlan, et al., 1995, Gene Therapy 2: 674-622), Lipofectamine™. and glycerolipid compounds (see, e.g., EP901463 and WO98/37916).

The nanoparticle may be an immune-stimulating complex (ISCOM). ISCOMs are cage-like particles which are typically formed from colloidal saponin-containing micelles. ISCOMs may comprise cholesterol, phospholipid (such as phosphatidylethanolamine or phosphatidylcholine) and saponin (such as Quil A from the tree *Quillaia saponaria*).

The nanoparticle may be a virus-like particle (VLP). VLPs are self-assembling nanoparticles that lack infectious nucleic acid, which are formed by self-assembly of biocompatible capsid protein. VLPs are typically about 20 to about 150 nm, such as about 20 to about 40 nm, about 30 to about 140 nm, about 40 to about 130 nm, about 50 to about 120 nm, about 60 to about 110 nm, about 70 to about 100 nm, or about 80 to about 90 nm in diameter. VLPs advantageously harness the power of evolved viral structure, which is naturally optimized for interaction with the immune system. The naturally-optimized nanoparticle size and repetitive structural order means that VLPs induce potent immune responses, even in the absence of adjuvant.

The nanoparticles may contain replicons that encode the polypeptides or the heterologous polypeptides of the disclosure. The replicons may be DNA or RNA.

"Replicon" refers to a viral nucleic acid that is capable of directing the generation of copies of itself and includes RNA as well as DNA. For example, double-stranded DNA versions of arterivirus genomes can be used to generate a single-stranded RNA transcript that constitutes an arterivirus replicon. Generally, a viral replicon contains the complete genome of the virus. "Sub-genomic replicon" refers to a viral nucleic acid that contains something less than the full complement of genes and other features of the viral genome, yet is still capable of directing the generation of copies of itself. For example, the sub-genomic replicons of arterivirus may contain most of the genes for the non-structural proteins of the virus, but are missing most of the genes coding for the structural proteins. Sub-genomic replicons are capable of directing the expression of all of the viral genes necessary for the replication of the viral sub-genome (replication of the sub-genomic replicon), without the production of viral particles.

"RNA replicon" (or "self-replication RNA") refer to RNA which contains all of the genetic information required for directing its own amplification or self-replication within a permissive cell. To direct its own replication, the RNA molecule 1) encodes polymerase, replicase, or other proteins which may interact with viral or host cell-derived proteins, nucleic acids or ribonucleoproteins to catalyze the RNA amplification process; and 2) contain cis-acting RNA sequences required for replication and transcription of the replicon-encoded RNA. Self-replicating RNA is typically derived from the genomes of positive strand RNA viruses and can be used as basis of introducing foreign sequences to host cells by replacing viral sequences encoding structural or non-structural genes or inserting the foreign sequences 5' or 3' of the sequences encoding the structural or non-structural genes. Foreign sequences may also be introduced into the subgenomic regions of alphaviruses. Self-replicating RNA may be packaged into recombinant virus particles, such as recombinant alphavirus particles or alternatively delivered to the host using lipid nanoparticles (LNP). Self-replicating RNA may be at least 1 kb or at least 2 kb or at least 3 kb or at least 4 kb or at least 5 kb or at least 6 kb or at least 7 kb or at least 8 kb or at least 10 kb or at least 12 kb or at least 15 kb or at least 17 kb or at least 19 kb or at least 20 kb in size, or can be 100 bp-8 kb or 500 bp-8 kb or 500 bp-7 kb or 1-7 kb or 1-8 kb or 2-15 kb or 2-20 kb or 5-15 kb or 5-20 kb or 7-15 kb or 7-18 kb or 7-20 kb in size. Self-replicating RNAs are described, for example, in WO2017/180770, WO2018/075235, WO2019143949A2, Other molecules suitable for complexing with the polynucleotides, the heterologous polynucleotides, the polypeptides and the heterologous polypeptides of the disclosure include cationic molecules, such as, polyamidoamine (Haensler and Szoka, 1993, Bioconjugate Chem. 4: 372-379), dendritic polylysine (Int. Pat. Publ. No. WO1995/24221), polyethylene irinine or polypropylene h-nine (Int. Pat. Publ. No. WO1996/02655), polylysine (U.S. Pat. No. 5,595,897), chitosan (U.S. Pat. No. 5,744,166), DNA-gelatin coarcervates (see, e.g., U.S. Pat. Nos. 6,207,195; 6,025,337; 5,972, 707) or DEAE dextran (Lopata, et al., 1984, Nucleic Acid Res. 12: 5707-5717), dendrimers (see, e.g., WO1996/19240), or polyethylenimine (PEI) (see, e.g., Sun et al., 2014, Mol Med Rep. 10(5):2657-2662).

Prostate Neoantigen/HLA Complexes

The disclosure also provides a protein complex comprising a prostate neoantigen and HLA. The disclosure also provides a protein complex comprising a fragment of the prostate neoantigen and HLA. The disclosure also provides a protein complex comprising a variant of the prostate neoantigen and HLA. The disclosure also provides a protein complex comprising a variant of a fragment of the prostate neoantigen and HLA.

In some embodiments, the prostate neoantigen comprises the polypeptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 or 447.

In some embodiments, the fragment of the prostate neoantigen comprises an amino acid sequences of SEQ ID NOs: 387, 388, 389, 390, 391, 392, 393, 394, 395, 396, 397, 398, 399, 400, 401, 402, 403, 404, 405, 406, 407, 408, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620 and 621.

In some embodiments, the fragment of the prostate neoantigen comprises an amino acid sequence of SEQ ID NOs: 377, 378, 415,417, 418, 420, 502, 518, 526, 527, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 74, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 487, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980 or 548.

In some embodiments, HLA is class I HLA. In some embodiments, HLA is class II HLA. In some embodiments, HLA is HLA-A. In some embodiments, HLA is HLA-B. In some embodiments, HLA is HLA-C. In some embodiments, HLA is HLA-DP. In some embodiments, HLA is HLA-DQ. In some embodiments, HLA is HLA-DR. In some embodiments, HLA is HLA-A*01:01, A*02:01, A*03:01, A*24:02, B*07:02 or B*08:01.

The complex of the prostate neoantigen and HLA may be used to for example isolate cognate T cells in vitro or in vivo. The complex of the prostate neoantigen and HLA may also be conjugated to a detectable label and used as a detection agent to detect, visualize or isolate cognate TCR or T cells expressing the cognate TCR. The complex of the prostate neoantigen and HLA may also be conjugated to a cytotoxic agent and used to deplete or reduce the number of cells expressing the cognate TCR. The complex may be in its native configuration or alternatively the prostate neoantigen and/or the HLA may be engineered.

Engineering concepts include covalent coupling of the peptide to the HLA, for example by using covalent linkers that may be cleavable. The prostate neoantigen and HLA complex may be a monomer or a multimer. The prostate neoantigen and HLA complex may be coupled to a toxin or a detection agent. Various engineering concepts include expressing the complex as a covalent prostate neoantigen-β2-α2-α1-β1 chain or prostate neoantigen-β chain, e.g. as a soluble complex. Linkers which are at least 15 amino acids long may be used between the prostate neoantigen and the HLA. Alternatively, the complex may be expressed as covalently coupled prostate neoantigen-single chain β1-α1. The prostate neoantigen/HLA complex may also be expressed as a full length HLAaxp chains to which the prostate neoantigen is covalently coupled to the N-terminus of the α chain or alternatively the prostate neoantigen is associated with the αβ chain via non-covalent interactions. Various expression formats are disclosed in U.S. Pat. Nos. 5,976,551, 5,734,023, 5,820,866, 7,141,656B2, U.S. Pat. No. 6,270,772B1 and U.S. Pat. No. 7,074,905B2. Additionally the HLA may be expressed as a single chain construct which is mutated at al chain or stabilized via disulfide bonds via a2 and P2 domains as described in U.S. Pat. No. 8,377,447B2 and U.S. Pat. No. 8,828,379B2. The prostate neoantigen or fragment thereof may be coupled to the HLA via light sensitive or periodate sensitive cleavable linkers as described in U.S. Pat. No. 9,079,941B2. The prostate neoantigen/HLA complexes may be engineered into multimeric format. Multimeric formats may be generated by incorporating a reactive side chain to the C-terminus of the HLA α or β chain to facilitate cross-linking of two or more prostate neoantigen/HLA complexes, as described in U.S. Pat. No. 7,074,904B2. Alternatively, a biotinylation recognition sequence BirA may be incorporated to the C-terminus of the HLA α or 3 chain which is subsequently biotinylated and the multimer is formed by binding to avidin/streptavidin as described in US563536. Multimeric prostate neoantigen/HLA complexes may further be generated utilizing Fc fusions, coupling the prostate neoantigen/HLA complexes in dextran carriers, oligomerizing the via coiled-coil domains, utilizing additional biotinylation peptides or conjugating the prostate neoantigen/HLA complexes onto nanoparticles or chelate carrier as is described in U.S. Pat. No. 6,197,302B1, US6268411B1, US20150329617A1, EP1670823B1, EP1882700B1, EP2061807B1, US20120093934A1, US20130289253A1, US20170095544A1, US20170003288A1 and WO2017015064A1.

Proteinaceous Molecules that Bind the Prostate Neoantigens or Prostate Neoantigen/HLA Complexes The disclosure also provides a proteinaceous molecule comprising an antigen binding domain that specifically binds the polypeptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 or 447, or fragment thereof. The proteinaceous molecule has insubstantial binding to a wild-type protein the neoantigen is derived from.

The disclosure also provides a proteinaceous molecule comprising an antigen binding domain that specifically binds a prostate neoantigen/HLA complex, wherein the prostate neoantigen comprises a polypeptide of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 or 447, or fragments thereof.

Exemplary fragments comprise amino acid sequences of SEQ ID NOs: 387, 388, 389, 390, 391, 392, 393, 394, 395, 396, 397, 398, 399, 400, 401, 402, 403, 404, 405, 406, 407, 408, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620 or 621.

Other exemplary fragments comprise amino acid sequences of SEQ ID NOs: 377, 378, 415,417, 418, 420, 502, 518, 526, 527, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 74, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 487, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980 or 548.

HLA may comprise class I or class II.

HLA may comprise HLA-A, HLA-B or HLA-C.

HLA may comprise HLA-DP, HLA-DQ or HLA-DR.

HLA may comprise class I alleles HLA-A*01:01, A*02:01, A*03:01, A*24:02, B*07:02 or B*08:01.

In some embodiments, the proteinaceous molecule is an antigen binding fragment of an antibody.

In some embodiments, the proteinaceous molecule is a multispecific molecule. In some embodiments, the proteinaceous molecule is a bispecific molecule. In some embodiments, the proteinaceous molecule is a trispecific molecule. In some embodiments, the multispecific molecule binds two or more distinct prostate neoantigens. In some embodiments, the multispecific molecule binds a prostate neoantigen and a T cell receptor (TCR) complex. In some embodiments, the multispecific molecule binds two or more distinct prostate neoantigens and a T cell receptor (TCR) complex.

In some embodiments, the proteinaceous molecule is an antibody.

In some embodiments, the proteinaceous molecule is a multispecific antibody. In some embodiments, the proteinaceous molecule is a bispecific antibody. In some embodiments, the proteinaceous molecule is a trispecific antibody. In some embodiments, the proteinaceous molecule is a T cell redirecting molecule.

In instances where the prostate neoantigen of the disclosure is part of an extracellular domain of a protein, the prostate neoantigen may be used as a tumor associated antigen for recruiting T cells to tumors or targeting CAR-T and other cellular therapies to tumor utilizing antigen binding domains that selectively bind the prostate neoantigen on tumor cells.

In instances in which the prostate neoantigen is part of an intracellular domain, antigen binding domains having the ability to be delivered into intracellular compartments conjugated to cytotoxic agent or a therapeutic agent may be used as therapeutics. Alternatively, cells engineered to express cognate TCR which bind the prostate neoantigen/HLA complex may be used as therapeutics.

In some embodiments, the proteinaceous molecule is an alternative scaffold.

In some embodiments, the proteinaceous molecule is a chimeric antigen receptor (CAR).

In some embodiments, the proteinaceous molecule is a T cell receptor (TCR).

Binding of the proteinaceous molecule to the prostate neoantigen or the prostate neoantigen/HLA complex of the disclosure may be determined experimentally using any suitable method. Such methods may utilize ProteOn XPR36, Biacore 3000 or KinExA instrumentation, ELISA or competitive binding assays known to those skilled in the art. The measured binding may vary if measured under different conditions (e.g., osmolarity, pH). Thus, measurements of affinity and other binding parameters (e.g., $K_D$, $K_{on}$, $K_{off}$) are typically made with standardized conditions and a standardized buffer, such as the buffer described herein. Skilled in the art will appreciate that the internal error for affinity measurements for example using Biacore 3000 or ProteOn (measured as standard deviation, SD) may typically be within 5-33% for measurements within the typical limits of detection. "Insubstantial" refers to binding that is 100-fold less when compared to the measured binding of the proteinaceous molecule to the prostate neoantigen of the disclosure. The proteinaceous molecule of the disclosure may further be characterized for their activity and function using know methods and those described herein, such as ability of the proteinaceous molecules to kill cells expressing the prostate neoantigens or prostate neoantigen/HLA complexes.

Antibodies and Antigen Binding Domains

Antibodies and antigen binding domains that specifically bind the prostate neoantigens or the prostate neoantigen/HLA complexes may be generated using known methods. Such antibodies may include immunoglobulin molecules of any type (e.g., IgG, IgE, IgM, IgD, IgA and IgY), class (e.g., IgG1, IgG2, IgG3, IgG4, IgA1, and IgA2) or subclass.

For example, the hybridoma method of Kohler and Milstein, Nature 256:495, 1975 may be used to generate monoclonal antibodies. In the hybridoma method, a mouse or other host animal, such as a hamster, rat or monkey, is immunized with one or more prostate neoantigens, or prostate neoantigen/HLA complexes followed by fusion of spleen cells from immunized animals with myeloma cells using standard methods to form hybridoma cells (Goding, Monoclonal Antibodies: Principles and Practice, pp. 59-103 (Academic Press, 1986)). Colonies arising from single immortalized hybridoma cells are screened for production of antibodies with desired properties, such as specificity of binding and affinity for the prostate neoantigen of the disclosure.

Various host animals may be used to produce the antibodies. For example, Balb/c mice, rats or chickens may be used to generate antibodies containing the VH/VL pair, and llama and alpaca may be used to generated heavy chain only (VHH) antibodies using standard immunization protocols. The antibodies made in non-human animals may be humanized using various technologies to generate more human-like sequences.

Exemplary humanization techniques including selection of human acceptor frameworks are known and include CDR grafting (U.S. Pat. No. 5,225,539), SDR grafting (U.S. Pat. No. 6,818,749), resurfacing (Padlan, (1991) *Mol Immunol* 28:489-499), Specificity Determining Residues Resurfacing (U.S. Patent Publ. No. 2010/0261620), human framework adaptation (U.S. Pat. No. 8,748,356) and superhumanization (U.S. Pat. No. 7,709,226). In these methods, CDRs of parental antibodies are transferred onto human frameworks that may be selected based on their overall homology to the parental frameworks, based on similarity in CDR length, or canonical structure identity, or any combination thereof.

Humanized antibodies may be further optimized to improve their selectivity or affinity to a desired antigen by incorporating altered framework support residues to preserve binding affinity (backmutations) by techniques such as those described in Int. Patent Publ. Nos. WO1090/007861 and WO1992/22653, or by introducing variation at any of the CDRs for example to improve affinity of the antibody.

Transgenic animals, such as mice or rats carrying human immunoglobulin (Ig) loci in their genome may be used to generate human antibodies against the prostate neoantigens or the prostate neoantigen/HLA complexes, and are described in for example U.S. Pat. No. 6,150,584, Int. Patent Publ. No. WO99/45962, Int. Patent Publ. Nos. WO2002/066630, WO2002/43478, WO2002/043478 and WO1990/04036, Lonberg et al (1994) *Nature* 368:856-9; Green et al (1994) *Nature Genet.* 7:13-21; Green & Jakobovits (1998) *Exp. Med.* 188:483-95; Lonberg and Huszar (1995) *Int Rev Immunol* 13:65-93; Bruggemann et al., (1991) *Eur J Immunol* 21:1323-1326; Fishwild et al., (1996) *Nat Biotechnol* 14:845-851; Mendez et al., (1997) *Nat Genet* 15:146-156; Green (1999) *J Immunol Methods* 231:11-23; Yang et al., (1999) *Cancer Res* 59:1236-1243; Bruggemann and Taussig (1997) *Curr Opin Biotechnol* 8:455-458. The endogenous immunoglobulin loci in such animal may be disrupted or deleted, and at least one complete or partial human immunoglobulin locus may be inserted into the genome of the animal using homologous or non-homologous recombination, using transchromosomes, or using minigenes. Companies such as Regeneron (http://_www_regeneron_com), Harbour Antibodies (http://_www_harbourantibodies_com), Open Monoclonal Technology, Inc. (OMT) (http://_www_omtinc_net), KyMab (http://_www_kymab_com), Trianni (http://_www.trianni_com) and Ablexis (http://_www-_ablexis_com) may be engaged to provide human antibodies directed against a selected antigen using technologies as described above.

Human antibodies may be selected from a phage display library, where the phage is engineered to express human immunoglobulins or portions thereof such as Fabs, single chain antibodies (scFv), domain antibodies or unpaired or paired antibody variable regions (Knappik et al., (2000) *J Mol Biol* 296:57-86; Krebs et al., (2001) *J Immunol Meth* 254:67-84; Vaughan et al., (1996) *Nature Biotechnology* 14:309-314; Sheets et al., (1998) *PITAS* (USA) 95:6157-6162; Hoogenboom and Winter (1991) *J Mol Biol* 227:381; Marks et al., (1991) *J Mol Biol* 222:581). The antibodies of the disclosure may be isolated for example from phage display library expressing antibody heavy and light chain variable regions as heterologous polypeptides with bacteriophage pIX coat protein as described in Shi et al., (2010) *J Mol Biol* 397:385-96, and Int. Patent Publ. No. WO09/085462). The libraries may be screened for phage binding to the prostate neoantigen or the prostate neoantigen/HLA complex and the obtained positive clones may be further characterized, the Fabs isolated from the clone lysates, and expressed as full length IgGs. Such phage display methods for isolating human antibodies are described in for example: U.S. Pat. Nos. 5,223,409, 5,403,484, 5,571,698, 5,427,908, 5,580,717, 5,969,108, 6,172,197, 5,885,793; 6,521,404; 6,544,731; 6,555,313; 6,582,915 and 6,593,081. The antibodies may further be tested for their binding to the HLA/neoantigen complex or to the neoantigen alone.

Preparation of immunogenic antigens and monoclonal antibody production may be performed using any suitable technique, such as recombinant protein production or by chemical synthesis of peptides. The immunogenic antigens may be administered to an animal in the form of purified protein, or protein mixtures including whole cells or cell or tissue extracts, or the antigen may be formed de novo in the animal's body from nucleic acids encoding said antigen or a portion thereof.

Antigen binding domains that specifically bind the prostate neoantigen or prostate neoantigen/HLA complexes may also be derived from the antibodies described herein. Antigen binding domains include single chain antibodies, Fab fragments, Fv fragments, single-chain Fv fragments (scFv), VHH domains, VH, VL, alternative scaffolds (e.g. non-antibody antigen binding domains), a divalent antibody fragment such as an (Fab)2'-fragment, F(ab') fragments, disulfide-linked Fvs (sdFv), intrabodies, minibodies, diabodies, triabodies and decabodies.

Bispecific and multispecific antibodies that specifically bind the prostate neoantigen or prostate neoantigen/HLA complexes and a second antigen may be generated using known methods. The second antigen may be a T cell receptor complex (TCR complex). The second antigen may be CD3 within the TCR complex. The bispecific and multispecific antibodies that specifically bind the prostate neoantigen or prostate neoantigen/HLA complexes of the disclosure and the second antigen may be engineered into any multivalent format using any known antigen binding domains format that specifically bind the prostate neoantigens or prostate neoantigen/HLA complexes and the second antigen. The antigen binding domain that specifically bind the prostate neoantigen or prostate neoantigen/HLA complex may be conjugated to one or more Fe domains or fragment thereof, or optionally to other scaffolds such as half-life extending moieties including albumin, PEG or transferrin.

Multispecific antibodies that specifically bind two or more prostate neoantigens may provide a benefit in terms of improved specificity in targeting tumor cells expressing the prostate neoantigens.

The antigen binding domains that specifically bind the prostate neoantigen or prostate neoantigen/HLA complexes may be engineered into full length multispecific antibodies which are generated using Fab arm exchange, in which substitutions are introduced into two monospecific bivalent antibodies within the Ig constant region CH3 domain which promote Fab arm exchange in vitro. In the methods, two monospecific bivalent antibodies are engineered to have certain substitutions at the CH3 domain that promote heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl)phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

CH3 mutations that may be used include technologies such as Knob-in-Hole mutations (Genentech), electrostatically-matched mutations (Chugai, Amgen, NovoNordisk, Oncomed), the Strand Exchange Engineered Domain body (SEEDbody) (EMD Serono), Duobody® mutations (Genmab), and other asymmetric mutations (e.g. Zymeworks).

Knob-in-hole mutations are disclosed for example in WO1996/027011 and include mutations on the interface of CH3 region in which an amino acid with a small side chain (hole) is introduced into the first CH3 region and an amino acid with a large side chain (knob) is introduced into the second CH3 region, resulting in preferential interaction between the first CH3 region and the second CH3 region. Exemplary CH3 region mutations forming a knob and a hole are T366Y/F405A, T366W/F405W, F405W/Y407A, T394W/Y407T, T394S/Y407A, T366W/T394S, F405W/T394S and T366W/T366S_L368A_Y407V.

Heavy chain heterodimer formation may be promoted by using electrostatic interactions by substituting positively charged residues on the first CH3 region and negatively charged residues on the second CH3 region as described in US2010/0015133, US2009/0182127, US2010/028637 or US2011/0123532.

Other asymmetric mutations that can be used to promote heavy chain heterodimerization are L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in US2012/0149876 or US2013/0195849 (Zymeworks).

SEEDbody mutations involve substituting select IgG residues with IgA residues to promote heavy chai heterodimerization as described in US20070287170.

Other exemplary mutations that may be used are R409D_K370E/D399K_E357K, S354C_T366W/Y349C_T366S_L368A_Y407V, Y349C_T366W/S354C_T366S_L368A_Y407V, T366K/L351D, L351K/Y349E, L351K/Y349D, L351K/L368E, L351Y_Y407A/T366A_K409F, L351Y_Y407A/T366V_K409F, K392D/D399K, K392D/E356K, K253E_D282K_K322D/D239K_E240K_K292D, K392D_K409D/D356K_D399K as described in WO2007/147901, WO 2011/143545, WO2013157954, WO2013096291 and US2018/0118849.

Duobody® mutations (Genmab) are disclosed for example in U.S. Pat. No. 9,150,663 and US2014/0303356 and include mutations F405L/K409R, wild-type/F405L_R409K, T350I_K370T_F405L/K409R, K370W/K409R, D399AFGHILMNRSTVWY/K409R, T366ADEFGHILMQVY/K409R, L368ADEGHNRSTVQ/K409AGRH, D399FHKRQ/K409AGRH, F405IKLSTVW/K409AGRH and Y407LWQ/K409AGRH.

Additional bispecific or multispecific structures into which the antigen binding domains that specifically bind the prostate neoantigen or prostate neoantigen/HLA complexes can be incorporated include Dual Variable Domain Immunoglobulins (DVD) (Int. Pat. Publ. No. WO2009/134776; DVDs are full length antibodies comprising the heavy chain having a structure VH1-linker-VH2-CH and the light chain having the structure VL1-linker-VL2-CL; linker being optional), structures that include various dimerization domains to connect the two antibody arms with different specificity, such as leucine zipper or collagen dimerization domains (Int. Pat. Publ. No. WO2012/022811, U.S. Pat. Nos. 5,932,448; 6,833,441), two or more domain antibodies (dAbs) conjugated together, diabodies, heavy chain only antibodies such as camelid antibodies and engineered camelid antibodies, Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer), IgG-like Bispecific (InnClone/Eli Lilly), Ts2Ab (Medlmmune/AZ) and BsAb (Zymogenetics), HERCULES (Biogen Idec) and TvAb (Roche), ScFv/Fc Fusions (Academic Institution), SCORPION (Emergent BioSolutions/Trubion, Zymogenetics/BMS), Dual Affinity Retargeting Technology (Fc-DART) (MacroGenics) and Dual $(ScFv)_2$ -Fab (National Research Center for Antibody Medicine—China), Dual-Action or Bis-Fab (Genentech), Dock-and-Lock (DNL) (ImmunoMedics), Bivalent Bispecific (Biotecnol) and Fab-Fv (UCB-Celltech). ScFv-, diabody-based, and domain antibodies, include but are not limited to, Bispecific T Cell Engager (BiTE) (Micromet), Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY (Epigen Biotech), dual targeting nanobodies (Ablynx), dual targeting heavy chain only domain antibodies.

Alternative Scaffolds

Alternative scaffolds (also referred to as antibody mimetics) that specifically bind the prostate neoantigen or prostate neoantigen/HLA complexes may be generated using various scaffolds known in the art and described herein. Alternative scaffolds may be monobodies, designed to incorporate the fibronectin type III domain (Fn3) of fibronectin or tenascin as a protein scaffold (U.S. Pat. No. 6,673,901; 6,348,584) or synthetic FN3 domains such as tencon as described in U.S. Pat. Publ. No. 2010/0216708 and U.S. Pat. Pub. No. 2010/0255056. Additional alternative scaffolds comprise Adnectin™, an iMab, an Anticalin®, an EETI-II/AGRP, a Kunitz domain, a thioredoxin peptide aptamer, an Affibody®, a DARPin, an Affilin, a Tetranectin, a Fynomer, and an Avimer. Alternative scaffolds are single chain polypeptidic frameworks that contains a highly structured core associated with variable domains of high conformational tolerance allowing insertions, deletions, or other substitutions within the variable domains. Libraries introducing diversity to one or more variable domains, and in some instances to the structured core, may be generated using known protocols and the resulting libraries may be screened for binding to the neoantigen of the disclosure, and the identified binders may be further characterized for their specificity using known methods. Alternative scaffold may be derived from Protein A, in particular, the Z-domain thereof (affibodies), ImmE7 (immunity proteins), BPTI/APPI (Kunitz domains), Ras-binding protein AF-6 (PDZ-domains), charybdotoxin (Scorpion toxin), CTLA-4, Min-23 (knottins), lipocalins (anticalins), neokarzinostatin, a fibronectin domain, an ankyrin consensus repeat domain, or thioredoxin (Skerra, A., "Alternative Non-Antibody Scaffolds for Molecular Recognition," *Curr. Opin. Biotechnol.* 18:295-304 (2005); Hosse et al., "A New Generation of Protein Display Scaffolds for Molecular Recognition," *Protein Sci.* 15:14-27 (2006); Nicaise et al., "Affinity Transfer by CDR Grafting on a Nonimmunoglobulin Scaffold," *Protein Sci.* 13:1882-1891 (2004); Nygren and Uhlen, "Scaffolds for Engineering Novel Binding Sites in Proteins," *Curr. Opin. Struc. Biol.* 7:463-469 (1997).

Chimeric Antigen Receptors (CAR)

CARs may be generated that bind the prostate neoantigens or the prostate neoantigen/HLA complex by incorporating an antigen binding domain that specifically binds the prostate neoantigens or the prostate neoantigen/HLA complex to the extracellular domain of the CAR. CARs are genetically engineered receptors. These engineered receptors can be readily inserted into and expressed by immune cells, including T cells in accordance with techniques known in the art. With a CAR, a single receptor can be programmed to both recognize a specific antigen and, when bound to that antigen, activate the immune cell to attack and destroy the cell bearing that antigen. When these antigens exist on tumor cells, an immune cell that expresses the CAR can target and kill the tumor cell.

The CAR typically comprises an extracellular domain that binds the antigen (e.g. the prostate neoantigen or the prostate neoantigen/HLA complex), an optional linker, a transmembrane domain, and a cytosolic domain comprising a costimulatory domain and/or a signaling domain.

The extracellular domain of the CAR may contain any polypeptide that specifically binds the desired antigen (e.g. prostate neoantigen). The extracellular domain may comprise a scFv, a portion of an antibody or an alternative scaffold. The CARs may also be engineered to bind two or more desired antigens that may be arranged in tandem and separated by linker sequences. For example, one or more domain antibodies, scFvs, llama VHH antibodies or other VH only antibody fragments may be organized in tandem via a linker to provide bispecificity or multispecificity to the CAR.

The transmembrane domain of the CAR may be derived from the transmembrane domain of CD8, an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CDI la, CD18), ICOS (CD278), 4-1 BB (CD137), 4-1 BBL, GITR, CD40, BAFFR, HVEM (LIGHTR), SLAMF7, NKp80 (KLRFI), CD160, CD1 9, IL2R beta, IL2R gamma, IL7R a, ITGA1, VLA1, CD49a, ITGA4, IA4, CD49D, ITGA6, VLA-6, CD49f, ITGAD, CDI Id, ITGAE, CD103, ITGAL, CDI la, LFA-1, ITGAM, CDI lb, ITGAX, CDI lc, ITGB1, CD29, ITGB2, CD1 8, LFA-1, ITGB7, TNFR2, DNAM1 (CD226), SLAMF4 (CD244, 2B4), CD84, CD96 (Tactile), CEACAMI, CRT AM, Ly9 (CD229), CD160 (BY55), PSGL1, CD100 (SEMA4D), SLAMF6 (NTB-A, Ly108), SLAM (SLAMFI, CD150, IPO-3), BLAME (SLAMF8), SELPLG (CD162), LTBR, PAG/Cbp, NKp44, NKp30, NKp46, NKG2D, and/or NKG2C.

The intracellular costimulatory domain of CAR may be derived from the intracellular domains of one or more co-stimulatory molecules. Co-stimulatory molecules are well-known cell surface molecules other than antigen receptors or Fc receptors that provide a second signal required for efficient activation and function of T lymphocytes upon binding to antigen. Exemplary co-stimulatory domains that can be used in CARs are intracellular domains of 4-1BB, CD2, CD7, CD27, CD28, CD30, CD40, CD54 (ICAM), CD83, CD134 (OX40), CD150 (SLAMFI), CD152 (CTLA4), CD223 (LAG3), CD270 (HVEM), CD278 (ICOS), DAP10, LAT, NKD2C SLP76, TRIM, BTLA, GITR, CD226, HVEM, and ZAP70.

The intracellular signaling domain of the CAR may be derived from the signaling domains of for example CD3ζ, CD3ε, CD22, CD79a, CD66d, CD39 DAP10, DAP12, Fe epsilon receptor I gamma chain (FCER1G), FcR $β CD36, CD3γ, CD5, CD226, or CD79B. "Intracellular signaling domain" refers to the part of the CAR polypeptide that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited following antigen binding to the extracellular CAR domain.

The optional linker of the CAR positioned between the extracellular domain and the transmembrane domain may be a polypeptide of about 2 to 100 amino acids in length. The linker may include or be composed of flexible residues such as glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. The linker may also be derived from a hinge region or portion of the hinge region of any immunoglobulin. Non-limiting examples of linkers include a part of human CD8α chain, partial extracellular domain of CD28, FcγRllla receptor, IgG, IgM, IgA, IgD, IgE, an Ig hinge, or functional fragment thereof.

Exemplary CARs that may be used are for example CAR that contains an extracellular domain that binds the prostate neoantigen of the disclosure, CD8 transmembrane domain and CD3Q signaling domain. Other exemplary CARs contain an extracellular domain that binds the prostate neoantigen of the disclosure, CD8 or CD28 transmembrane domain, CD28, 41BB or OX40 costimulatory domain and CD3Q signaling domain.

The CARs are generated by standard molecular biology techniques. The extracellular domain that binds the desired antigen may be derived from antibodies or their antigen binding fragments generated using the technologies described herein.

T Cell Receptor (TCR)

TCRs may be generated that bind the prostate neoantigen/HLA complexes. The TCRs may be identified based on T cell binding to the prostate neoantigen/HLA complex, isolating the T cell and sequencing the TCR expressed in the T cells. The identified TCRs may be identified from αβ T cells or γδ T cells. The identified TCRs may be further engineered to improve their affinity, stability, solubility or the like. TCRs may be affinity matured utilizing the same technologies utilized to affinity mature immunoglobulins. TCRs may be expressed as soluble TCRs which have been cysteine stabilized, they can be stabilized by engineering mutations onto a/P interaction surface, for example G192R on a chain and R208G on β chain. TCRs may also be stabilized by engineering cysteine residues which form disulfide bonds into TCR constant domain, by introducing mutations into the hydrophobic core, such as at positions 11, 13, 19, 21, 53, 76, 89, 91 or 94 of α chain, utilizing domain swaps including swaps between a and 3 chain V domains, transmembrane domains or constant domains as described in U.S. Pat. No. 7,329,731, U.S. Pat. No. 7,871,817B2, U.S. Pat. Nos. 7,569,664, 9,133,264, 9,624,292, US20120252742A1, US2016/0130319, EP3215164A1, EP3286210A1, WO2017091905A1 or U.S. Pat. No. 9,884,075.

Cells Expressing the CARs or the TCRs of the Disclosure

Cells expressing the CARs or the TCRs that specifically bind the prostate neoantigens of the disclosure of the prostate neoantigen/HLA complexes of the disclosure are within the scope of the disclosure. The disclosure also provides isolated cells comprising the CAR of the disclosure or the TCR of the disclosure. In some embodiments, the isolated cells are transduced with the CAR or the TCR of the disclosure, resulting in constitutive expression of the CAR or the TCR of the disclosure on the surface of the cell. The cells expressing the CAR or the TCR of the disclosure may further be engineered to express one or more co-stimulatory molecules. Exemplary co-stimulatory molecules are CD28, ICOS, LIGHT, GITR, 4-1BB and OX40. The cells expressing the CAR or the TCR of the disclosure may further be engineered to produce one or more cytokines or chemokines or proinflammatory mediators, such as TNFα, IFNγ, IL-2, IL-3, IL-6, IL-7, IL-11, IL-12, IL-15, IL-17 or IL-21. The cells may have their endogenous TCR locus and/or HLA locus inactivated using known gene editing technologies. In some embodiment, the cell comprising the CAR or the TCR of the disclosure is a T cell, a natural killer (NK) cell, a cytotoxic T lymphocyte (CTL), a regulatory T cell (Treg), a human embryonic stem cell, a lymphoid progenitor cell, a T cell-precursor cell, a pluripotent stem cell or induced pluripotent stem cell (iPSC) from which lymphoid cells may be differentiated.

In some embodiments, the isolated cell comprising the CAR or the TCR of the disclosure is a T cell. The T cell may be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from any source, including to bone marrow, blood, lymph node, thymus, or other tissues or fluids. T cells may also be enriched for or purified. The T cell may be a human T cell. The T cell may be a T cell isolated from a human. The T cell can be any type of T cell and may be of any developmental stage, including, CD4+CD8$^{+}$ double positive T cells, CD8$^{+}$ T cells (e.g., cytotoxic T cells), CD4$^{+}$ helper T cells, e.g., Th1 and Th2 cells, peripheral blood mononuclear cells (PBMCs), peripheral blood leukocytes (PBLs), tumor infiltrating cells, memory T cells, naïve T cells, and the like. The T cell may be a $CD8^+$ T cell or a $CD4^+$ T cell. The T cell may be an $\alpha\beta$ T cell or a $\gamma\delta$ T cell.

In some embodiments, the isolated cell comprising the CAR of the disclosure or the TCR of the disclosure is a NK cell.

In some embodiments, the isolated cell comprising the CAR of the disclosure or the TCR of the disclosure is a $\alpha\beta$ T cell.

In some embodiments, the isolated cell comprising the CAR of the disclosure or the TCR of the disclosure is a $\gamma\delta$ T cell.

In some embodiments, the isolated cell comprising the CAR of the disclosure or the TCR of the disclosure is a $CD8^+$ cytotoxic T lymphocyte In some embodiments, the isolated cell comprising the CAR of the disclosure or the TCR of the disclosure is a human embryonic stem cell.

In some embodiments, the isolated cell comprising the CAR of the disclosure or the TCR of the disclosure is a lymphoid progenitor cell.

In some embodiments, the isolated cell comprising the CAR of the disclosure or the TCR of the disclosure is a pluripotent stem cell.

In some embodiments, the isolated cell comprising the CAR of the disclosure or the TCR of the disclosure is an induced pluripotent stem cell (iPSC).

The cells of the disclosure may be generated by introducing a lentiviral vector comprising a desired CAR or TCR into the cells using known methods. The cells of the disclosure are able to replicate in vivo resulting in long-term persistence that can lead to sustained tumor control.

Conjugates with Cytotoxic Agents, Drugs, Detectable Labels, and the Like

The polypeptides, the heterologous polypeptide and the proteinaceous molecules binding them may be conjugated to a cytotoxic agent, therapeutics, detectable labels and the like. These molecules are referred herein to immunoconjugates. The immunoconjugates comprising the prostate neoantigens may be used to detect, deliver payload or kill cells expressing a HLA molecule that binds the prostate neoantigen. The immunoconjugates comprising the antibodies, antigen binding fragments or alternative scaffolds which specifically bind the prostate neoantigen or the prostate neoantigen/HLA complex may be used to detect, deliver payload or kill cells that express the prostate neoantigen on their surface in the context or a larger protein or in complex with HLA, or detect intracellular prostate neoantigens after lysis of the cells.

In some embodiments, the immunoconjugate comprises a detectable label.

In some embodiments, the immunoconjugate comprises a cytotoxic agent.

In some embodiments, the immunoconjugate comprises a therapeutic.

Detectable labels include compositions that can be visualized via spectroscopic, photochemical, biochemical, immunochemical, or chemical means. Detectable labels may also include cytotoxic agents, an cytotoxic agents may include detectable labels.

Exemplary detectable labels include radioactive isotopes, magnetic beads, metallic beads, colloidal particles, fluorescent dyes, electron-dense reagents, enzymes (for example, as commonly used in an ELISA), biotin, digoxigenin, haptens, luminescent molecules, chemiluminescent molecules, fluorochromes, fluorophores, fluorescent quenching agents, colored molecules, radioactive isotopes, scintillates, avidin, streptavidin, protein A, protein G, antibodies or fragments thereof, polyhistidine, $Ni^{2+}$, Flag tags, myc tags, heavy metals, enzymes, alkaline phosphatase, peroxidase, luciferase, electron donors/acceptors, acridinium esters, and colorimetric substrates.

A detectable label may emit a signal spontaneously, such as when the detectable label is a radioactive isotope. In other cases, the detectable label emits a signal as a result of being stimulated by an external field.

Exemplary radioactive isotopes may be $\gamma$-emitting, Auger-emitting, $\beta$-emitting, an alpha-emitting or positron-emitting radioactive isotope. Exemplary radioactive isotopes include $^{3}H$, $^{11}C$, $^{13}C$, $^{15}N$, $^{18}F$, $^{19}F$, $^{5}Co$, $^{57}Co$, $^{60}Co$, $^{61}Cu$, $^{62}Cu$, $^{64}Cu$, $^{67}Cu$, $^{68}G$, $^{72}As$ $^{75}Br$, $^{86}Y$, $^{89}Zr$, $^{90}Sr$, $^{94m}Tc$, $^{99m}Tc$, $^{115}In$, $^{123}I$, $^{124}I$, $^{125}I$, $^{131}I$, $^{211}At$, $^{212}Bi$, $^{213}Bi$, $^{223}Ra$, $^{226}Ra$, $^{225}Ac$ and $^{227}Ac$.

Exemplary metal atoms are metals with an atomic number greater than 20, such as calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, neptunium atoms, plutonium atoms, americium atoms, curium atoms, berkelium atoms, californium atoms, einsteinium atoms, fermium atoms, mendelevium atoms, nobelium atoms, or lawrencium atoms.

In some embodiments, the metal atoms may be alkaline earth metals with an atomic number greater than twenty.

In some embodiments, the metal atoms may be lanthanides.

In some embodiments, the metal atoms may be actinides.

In some embodiments, the metal atoms may be transition metals.

In some embodiments, the metal atoms may be poor metals.

In some embodiments, the metal atoms may be gold atoms, bismuth atoms, tantalum atoms, and gadolinium atoms.

In some embodiments, the metal atoms may be metals with an atomic number of 53 (i.e. iodine) to 83 (i.e. bismuth).

In some embodiments, the metal atoms may be atoms suitable for magnetic resonance imaging.

The metal atoms may be metal ions in the form of +1, +2, or +3 oxidation states, such as $Ba^{2+}$, $Bi^{3+}$, $Cs^{+}$, $Ca^{2+}$, $Cr^{2+}$, $Cr^{3+}$, $Cr^{6+}$, $Co^{2+}$, $Co^{3+}$, $Cu^{+}$, $Cu^{2+}$, $Cu^{3+}$, $Ga^{3+}$, $Gd^{3+}$, $Au^{+}$, $Au^{3+}$, $Fe^{2+}$, $Fe^{3+}$, $F^{3+}$, $Pb^{2+}$, $Mn^{2+}$, $Mn^{3+}$, $Mn^{4+}$, $Mn^{7+}$, $Hg^{2+}$, $Ni^{2+}$, $Ni^{3+}$, $Ag^{+}$, $Sr^{2+}$, $Sn^{2+}$, $Sn^{4+}$, and $Zn^{2+}$. The metal atoms may comprise a metal oxide, such as iron oxide, manganese oxide, or gadolinium oxide.

Suitable dyes include any commercially available dyes such as, for example, 5(6)-carboxyfluorescein, IRDye 680RD maleimide or IRDye 800CW, ruthenium polypyridyl dyes, and the like.

Suitable fluorophores are fluorescein isothiocyanate (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes.

The immunoconjugates comprising a detectable label may be used as an imaging agent.

In some embodiments, the cytotoxic agent is a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

In some embodiments, the cytotoxic agent is daunomycin, doxorubicin, methotrexate, vindesine, bacterial toxins such as diphtheria toxin, ricin, geldanamycin, maytansinoids or calicheamicin. The cytotoxic agent may elicit their cytotoxic and cytostatic effects by mechanisms including tubulin binding, DNA binding, or topoisomerase inhibition.

In some embodiments, the cytotoxic agent is an enzymatically active toxin such as diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments, the cytotoxic agent is a radionuclide, such as $^{212}$Bi, $^{131}$I, $^{131}$In, $^{90}$Y and $^{186}$Re.

In some embodiments, the cytotoxic agent is dolastatins or dolostatin peptidic analogs and derivatives, auristatin or monomethyl auristatin phenylalanine. Exemplary molecules are disclosed in U.S. Pat. Nos. 5,635,483 and 5,780,588. Dolastatins and auristatins have been shown to interfere with microtubule dynamics, GTP hydrolysis, and nuclear and cellular division (Woyke et al (2001) Antimicrob Agents and Chemother. 45(12):3580-3584) and have anticancer and antifungal activity. The dolastatin or auristatin drug moiety may be attached to the antibody of the invention through the N (amino) terminus or the C (carboxyl) terminus of the peptidic drug moiety (WO02/088172), or via any cysteine engineered into the antibody.

The immunoconjugates may be made using known methods.

In some embodiments, the detectable label is complexed with a chelating agent.

The detectable label, cytotoxic agent or therapeutic may be linked directly, or indirectly via a linker, to the polypeptides, the heterologous polypeptides or the proteinaceous molecules that bind the polypeptides or the heterologous polypeptides. Suitable linkers are known in the art and include, for example, prosthetic groups, non-phenolic linkers (derivatives of N-succimidyl-benzoates; dodecaborate), chelating moieties of both macrocyclics and acyclic chelators, such as derivatives of 1,4,7,10-tetraazacyclododecane-1,4,7,10,tetraacetic acid (DOTA), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA), N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene) and other chelating moieties. Suitable peptide linkers are well known.

Methods of Treatment, Uses and Administration

The various molecules of the disclosure that can be used to introduce the prostate neoantigens of the disclosure into a subject, e.g. the polynucleotides, the heterologous polynucleotides, the polypeptides, the heterologous polypeptides, the vectors, the recombinant viruses and vaccines of the disclosure may be used to treat prostate cancer in a subject. The various molecules of the disclosure that may be used to introduce the prostate neoantigens of the disclosure into a subject, e.g. the polynucleotides, the heterologous polynucleotides, the polypeptides, the heterologous polypeptides, the vectors, the recombinant viruses and vaccines of the disclosure may also be used to prevent prostate cancer in a subject. The proteinaceous molecules that specifically bind the prostate neoantigens of the disclosure or the prostate neoantigen/HLA complexes of the disclosure can be used to treat or prevent prostate cancer in the subject.

The prostate cancer neoantigens identified herein are present at a frequency of at least about 1% or more, about 2% or more, about 3% or more, about 4% or more, about 5% or more, about 6% or more, about 7% or more, about 8% or more, about 9% or more, about 10% or more, about 11% or more, about 12% or more, about 13% or more, about 14% or more, about 15% or more, about 16% or more about 17% or more, about 18% or more, about 19% or more, about 20% or more, about 21% or more, about 22% or more, about 23% or more, about 24% or more, about 25% or more, about 26% or more, about 27% or more, about 28% or more, about 29% or more, about 30% or more, about 35% or more, about 40% or more, about 45% or more, about 50% or more, about 55% or more, about 60% or more, about 65% or more or about 70% or more in a population of subjects having the prostate cancer.

The disclosure provides a method of treating or preventing a prostate cancer in a subject, comprising administering to the subject a therapeutically effective amount of one or more vaccines of the disclosure.

The disclosure also provides a method of treating or preventing a prostate cancer in a subject, comprising administering to the subject a therapeutically effective amount of one or more pharmaceutical compositions of the disclosure.

In some embodiments, the vaccine comprises the rAd26 of the disclosure.

In some embodiments, the vaccine comprises the rMVA of the disclosure.

In some embodiments, the vaccine comprises the rGAd of the disclosure.

In some embodiments, the vaccine comprises the rGAd20 of the disclosure.

In some embodiments, the vaccine comprises the rCh20 of the disclosure.

In some embodiments, the vaccine comprises the rAd26 of the disclosure and rMVA of the disclosure.

In some embodiments, the vaccine comprises the rGAd20 of the disclosure and rMVA of the disclosure.

In some embodiments, the vaccine comprises the heterologous polypeptide of the disclosure.

In some embodiments, the vaccine comprises the heterologous polynucleotide of the disclosure.

In some embodiments, the vaccine comprises the polynucleotide of the disclosure.

In some embodiments, the vaccine comprises the polypeptide of the disclosure.

"Prostate cancer" is meant to include all types of cancerous growths within prostate or oncogenic processes, metastatic tissues or malignantly transformed cells, tissues, or organs, irrespective of histopathology type or stage of invasiveness.

In some embodiments, the prostate cancer is an adenocarcinoma.

In some embodiments, the prostate cancer is a metastatic prostate cancer. In some embodiments, the prostate cancer has metastasized to rectum, lymph node or bone, or any combination thereof.

In some embodiments, the prostate cancer is a relapsed or a refractory prostate cancer.

In some embodiments, the prostate cancer is a castration resistant prostate cancer.

In some embodiments, the prostate cancer is sensitive to an androgen deprivation therapy.

In some embodiments, the prostate cancer is insensitive to the androgen deprivation therapy.

In some embodiments, the subject is treatment naïve.

In some embodiments, the subject has received androgen deprivation therapy.

In some embodiments, the subject has an elevated level of prostate specific antigen (PSA). PSA is elevated in a subject when the level is typically about ≥4.0 ng/mL. In some instances, elevated PSA may refer to level off ≥3.0 ng/mL. PSA levels may also be compared to post-androgen deprivation therapy levels.

Androgen deprivation therapies include abiraterone, ketoconazole, enzalutamide, galeterone, ARN-509 and orteronel (TAK-700), or prostatectomy.

The disclosure also provides a method of treating prostate cancer in a subject, comprising administering to the subject a therapeutically effective amount of a first vaccine comprising the rAd26 of the disclosure for priming the immune response; and administering to the subject a therapeutically effective amount of a second vaccine comprising the rMVA of the disclosure for boosting the immune response; thereby treating the prostate cancer in the subject.

The disclosure also provides a method of treating prostate cancer in a subject, comprising administering to the subject a therapeutically effective amount of a first vaccine comprising the rGAd of the disclosure for priming the immune response; and administering to the subject a therapeutically effective amount of a second vaccine comprising the rMVA of the disclosure for boosting the immune response; thereby treating the prostate cancer in the subject.

The disclosure also provides a method of treating prostate cancer in a subject, comprising administering to the subject a therapeutically effective amount of a first vaccine comprising the rGAd20 of the disclosure for priming the immune response; and administering to the subject a therapeutically effective amount of a second vaccine comprising the rMVA of the disclosure for boosting the immune response; thereby treating the prostate cancer in the subject.

The disclosure also provides a method of preventing prostate cancer in a subject, comprising administering to the subject a therapeutically effective amount of a first vaccine comprising the rAd26 of the disclosure for priming the immune response; and administering to the subject a therapeutically effective amount of a second vaccine comprising the rMVA of the disclosure for boosting the immune response; thereby preventing the prostate cancer in the subject.

The disclosure also provides a method of preventing prostate cancer in a subject, comprising administering to the subject a therapeutically effective amount of a first vaccine comprising the rGAd of the disclosure for priming the immune response; and administering to the subject a therapeutically effective amount of a second vaccine comprising the rMVA of the disclosure for boosting the immune response; thereby preventing the prostate cancer in the subject.

The disclosure also provides a method of preventing prostate cancer in a subject, comprising administering to the subject a therapeutically effective amount of a first vaccine comprising the rGAd20 of the disclosure for priming the immune response; and administering to the subject a therapeutically effective amount of a second vaccine comprising the rMVA of the disclosure for boosting the immune response; thereby preventing the prostate cancer in the subject.

The disclosure also provides a method of enhancing an immune response in a subject, comprising administering to the subject an immunologically effective amount of a first vaccine comprising the rAd26 of the disclosure for priming the immune response; and administering to the subject an immunologically effective amount of a second vaccine comprising the rMVA of the disclosure for boosting the immune response; thereby enhancing the immune response in the subject.

The disclosure also provides a method of enhancing an immune response in a subject, comprising administering to the subject an immunologically effective amount of a first vaccine comprising the rGAd of the disclosure for priming the immune response; and administering to the subject an immunologically effective amount of a second vaccine comprising the rMVA of the disclosure for boosting the immune response; thereby enhancing the immune response in the subject.

The disclosure also provides a method of enhancing an immune response in a subject, comprising administering to the subject an immunologically effective amount of a first vaccine comprising the rGAd20 of the disclosure for priming the immune response; and administering to the subject an immunologically effective amount of a second vaccine comprising the rMVA of the disclosure for boosting the immune response; thereby enhancing the immune response in the subject.

The disclosure also provides a method of treating prostate cancer in a subject, comprising administering to the subject a therapeutically effective amount of a first vaccine comprising the rAd26 of the disclosure for priming the immune response; and administering to the subject a therapeutically effective amount of a second vaccine comprising the rMVA of the disclosure for boosting the immune response; thereby treating the prostate cancer in the subject, wherein the rAd26 and the rMVA comprise a heterologous polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides a method of treating prostate cancer in a subject, comprising administering to the subject a therapeutically effective amount of a first vaccine comprising the rGAd of the disclosure for priming the immune response; and administering to the subject a therapeutically effective amount of a second vaccine comprising the rMVA of the disclosure for boosting the immune response; thereby treating the prostate cancer in the subject, wherein the rGAd and the rMVA comprise a heterologous polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides a method of treating prostate cancer in a subject, comprising administering to the subject a therapeutically effective amount of a first vaccine comprising the rGAd20 of the disclosure for priming the immune response; and administering to the subject a therapeutically effective amount of a second vaccine comprising the rMVA of the disclosure for boosting the immune response; thereby treating the prostate cancer in the subject, wherein the rGAd20 and the rMVA comprise a heterologous polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides a method of preventing prostate cancer in a subject, comprising administering to the subject a therapeutically effective amount of a first vaccine comprising the rAd26 of the disclosure for priming the immune response; and administering to the subject a therapeutically effective amount of a second vaccine comprising the rMVA of the disclosure for boosting the immune response; thereby preventing the prostate cancer in the subject, wherein the rAd26 and the rMVA comprise a heterologous polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides a method of preventing prostate cancer in a subject, comprising administering to the subject a therapeutically effective amount of a first vaccine comprising the rGAd of the disclosure for priming the immune response; and administering to the subject a therapeutically effective amount of a second vaccine comprising the rMVA of the disclosure for boosting the immune response; thereby preventing the prostate cancer in the subject, wherein the rGAd and the rMVA comprise a heterologous polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides a method of preventing prostate cancer in a subject, comprising administering to the subject a therapeutically effective amount of a first vaccine comprising the rGAd20 of the disclosure for priming the immune response; and administering to the subject a therapeutically effective amount of a second vaccine comprising the rMVA of the disclosure for boosting the immune response; thereby preventing the prostate cancer in the subject, wherein the rGAd20 and the rMVA comprise a heterologous polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 or 447, or fragments thereof.

The disclosure also provides a method of enhancing an immune response in a subject, comprising administering to the subject an immunologically effective amount of a first vaccine comprising the rAd26 of the disclosure for priming the immune response; and administering to the subject an immunologically effective amount of a second vaccine comprising the rMVA of the disclosure for boosting the immune response; thereby enhancing the immune response in the subject, wherein the rAd26 and the rMVA comprise a heterologous polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides a method of enhancing an immune response in a subject, comprising administering to the subject an immunologically effective amount of a first vaccine comprising the rGAd of the disclosure for priming the immune response; and administering to the subject an immunologically effective amount of a second vaccine comprising the rMVA of the disclosure for boosting the immune response; thereby enhancing the immune response in the subject, wherein the rGAd and the rMVA comprise a heterologous polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435, 436, 437, 438, 439, 440, 441, 442, 443, 444, 445, 446 or 447, or fragments thereof.

The disclosure also provides a method of enhancing an immune response in a subject, comprising administering to the subject an immunologically effective amount of a first vaccine comprising the rGAd20 of the disclosure for priming the immune response; and administering to the subject an immunologically effective amount of a second vaccine comprising the rMVA of the disclosure for boosting the immune response; thereby enhancing the immune response in the subject, wherein the rGAd20 and the rMVA comprise a heterologous polynucleotide encoding one or more polypeptides of SEQ ID NOs: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, 175, 177, 179, 181, 183, 185, 187, 189, 191, 193, 195, 197, 199, 201, 203, 205, 207, 209, 211, 213, 215, 217, 219, 221, 223, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 311, 313, 315, 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 379, 381, 383, 385, 387, 388, 389, 390, 391, 392, 393, 394, 395, 396, 397, 398, 399, 400, 401, 402, 403, 404, 405, 406, 407, 408, 426, 427, 428, 429, 430, 431, 432, 433, 434, 435,436, 437, 438, 439, 440, 441, 442, 443, 444, 445, 446 or 447, or fragments thereof.

In some embodiments, the subject is suspected to have or is suspected to develop prostate cancer.

The vaccines of the disclosure may be typically administered by intramuscular or subcutaneous injection. However other modes of administration such as intravenous, cutaneous, intradermal or nasal can be envisaged as well. Intramuscular administration of the vaccines can be achieved by using a needle. An alternative is the use of a needleless injection device to administer the composition (using, e.g., Biojector™) or a freeze-dried powder containing the vaccine.

For intravenous, cutaneous or subcutaneous injection, or injection at the site of affliction, the vector may be the form of a parenterally acceptable aqueous solution which is pyrogen-free and has suitable pH, isotonicity and stability. Those of skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required. A slow-release formulation may also be employed.

Typically, administration will have a prophylactic aim to generate an immune response against the prostate neoantigens before development of symptoms of prostate cancer.

The vaccines of the disclosure are administered to a subject, giving rise to an immune response in the subject. An amount of the vaccine to in induce a detectable immune response is defined to be an "immunologically effective dose." The vaccines of the disclosure may induce a humoral as well as a cell-mediated immune response. In a typical embodiment the immune response is a protective immune response.

The actual amount administered, and rate and time-course of administration, will depend on the nature and severity of what is being treated. Prescription of treatment, e.g., decisions on dosage etc., is within the responsibility of general practitioners and other medical doctors, and typically takes account of the disorder to be treated, the condition of the individual patient, the site of delivery, the method of administration and other factors known to practitioners.

In one exemplary regimen, the adenovirus vector is administered (e.g., intramuscularly) in a volume ranging between about 100 μL to about 10 ml containing concentrations of about $10^4$ to $10^{12}$ virus particles/ml. The adenovirus vector may be administered in a volume ranging between 0.25 and 1.0 ml, such as in a volume of 0.5 ml.

The adenovirus may be administered in an amount of about $10^9$ to about $10^{12}$ viral particles (vp) to a human subject during one administration, more typically in an amount of about $10^{10}$ to about $10^{12}$ vp.

In one exemplary regimen, the rMVA of the disclosure is administered (e.g., intramuscularly) in a volume ranging between about 100 μl to about 10 ml of saline solution containing a dose of about $1\times10^7$ $TCID_{50}$ to $1\times10^9$ $TCID_{50}$ (50% Tissue Culture Infective Dose) or InfU. (Infectious Unit). The rMVA may be administered in a volume ranging between 0.25 and 1.0 ml.

Boosting compositions may be administered two or more times, weeks or months after administration of the priming composition, for example, about 1 or 2 weeks or 3 weeks, or 4 weeks, or 6 weeks, or 8 weeks, or 12 weeks, or 16 weeks, or 20 weeks, or 24 weeks, or 28 weeks, or 32 weeks or one to two years after administration of the priming composition. Additional boosting compositions may be administered 6 weeks to 5 years after the boosting step (b), such as 6, 7, 8, 9, 10, 11, 12, 13, 14, 15, 16, 17, 18, 19, 20, 21, 22, 23, 24 or 25 weeks, or 7, 8, 9, 10, 11 or 12 months, or 2, 3, 4 or 5 years, after the initial boosting inoculation. Optionally, the further boosting step (c) can be repeated one or more times as needed.

Prostate Neoantigen Combinations for Vaccine Therapy

The identified neoantigens described herein can be further validated and prioritized for their inclusion into a universal prostate cancer vaccine. The considerations for inclusion are, for example, higher expression in prostate cancer tissues vs. normal prostate tissue and other normal tissues (such as liver, kidney, pancreas, ovary, prostate, mammary gland, colon, stomach, skeletal muscle and lung), or undetectable expression in normal tissues, ability of the neoantigens or their fragments to mediate activation of $CD8^+$ T cells in known assays, binding to HLA, demonstrated in vivo processing and presentation to HLA of peptide fragments derived from the neoantigens and sufficient prevalence in prostate cancer subjects.

Through the validation process, 41 neoantigens (SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177) were identified as particularly useful to be included into a prostate cancer vaccine based on their expression profile, prevalence and in vitro immunogenicity. It is expected that any combination of the 41 neoantigens can be utilized to generate a prostate cancer vaccine that can be delivered to a subject utilizing any available delivery vehicles and any form available, such as peptides, DNA, RNA, replicons, or using viral delivery. The 41 neoantigens may be assembled into heterologous polynucleotides encoding heterologous polypeptides in any neoantigen order, and the neoantigen order may differ between the various delivery options. In general, assembly of the neoantigens into a particular order may be based on generating a minimum number of junctional epitopes utilizing known algorithms. Exemplary orders of the neoantigens are orders providing heterologous polypeptides of SEQ ID NOs: 541, 550, 554, 555, 556, 623, 624, 543, 552, 557, 558, 559, 625 or 626 as described herein and throughout the examples.

The disclosure provides a vaccine comprising a heterologous polynucleotide encoding a heterologous polypeptide, wherein the heterologous polypeptide comprises two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides a vaccine comprising a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the fragments comprise polypeptides of SEQ ID NOs: 387, 388, 390, 392, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710 or 711.

In some embodiments, the vaccine is capable of eliciting a cellular immune response in a subject administered the vaccine.

In some embodiments, the cellular immune response is specific against a fragment of one or more polypeptides of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 or 177.

In some embodiments, the cellular immune response is activation of vaccine-specific $CD8^+$ T cells, $CD4^+$ T cells, or $CD8^+$ T cells and $CD4^+$ T cells, wherein activation is assessed by increased production of TNFα, IFNγ, or TNFα and IFNγ by $CD8^+$ T cells, $CD4^+$ T cells, or $CD8^+$ T cells and $CD4^+$ T cells.

In some embodiments, the heterologous polynucleotide comprises a promoter, an enhancer, a polyadenylation site, a Kozak sequence, a stop codon, a T cell enhancer (TCE), or any combination thereof.

In some embodiments, the promoter comprises a CMV promoter or a vaccinia P7.5 promoter.

In some embodiments, the TCE is encoded by a polynucleotide of SEQ ID NO: 546, the CMV promoter comprises a polynucleotide of SEQ ID NO: 628, the vaccinia P7.5 promoter comprises a polynucleotide of SEQ ID NO: 630 and the polyadenylation site comprises a bovine growth hormone polyadenylation site of SEQ ID NO: 629.

In some embodiments, the heterologous polypeptide comprises an amino acid sequence of SEQ ID NOs: 541, 550, 554, 555, 556, 623 or 624.

In some embodiments, the heterologous polynucleotide comprises a polynucleotide sequence of SEQ ID NO: 542 or SEQ ID NO: 551.

In some embodiments, the heterologous polypeptide comprises the amino acid sequence of SEQ ID NOs: 543, 552, 557, 558, 559, 625 or 626.

In some embodiments, the heterologous polynucleotide comprises the polynucleotide sequence of SEQ ID NO: 544 or SEQ ID NO: 553.

In some embodiments, the heterologous polynucleotide is DNA or RNA.

In some embodiments, RNA is mRNA or self-replicating RNA.

The disclosure also provides a vaccine comprising a heterologous polynucleotide encoding a heterologous polypeptide of SEQ ID NO: 541.

The disclosure also provides a vaccine comprising a heterologous polynucleotide encoding a heterologous polypeptide of SEQ ID NO: 550.

The disclosure also provides a vaccine comprising a heterologous polynucleotide encoding a heterologous polypeptide of SEQ ID NO: 554.

The disclosure also provides a vaccine comprising a heterologous polynucleotide encoding a heterologous polypeptide of SEQ ID NO: 555.

The disclosure also provides a vaccine comprising a heterologous polynucleotide encoding a heterologous polypeptide of SEQ ID NO: 556.

The disclosure also provides a vaccine comprising a heterologous polynucleotide encoding a heterologous polypeptide of SEQ ID NO: 623.

The disclosure also provides a vaccine comprising a heterologous polynucleotide encoding a heterologous polypeptide of SEQ ID NO: 624.

The disclosure also provides a vaccine comprising a heterologous polynucleotide of SEQ ID NO: 542.

The disclosure also provides a vaccine comprising a heterologous polynucleotide of SEQ ID NO: 551.

The disclosure also provides a vaccine comprising a heterologous polynucleotide encoding a heterologous polypeptide of SEQ ID NO: 543.

The disclosure also provides a vaccine comprising a heterologous polynucleotide encoding a heterologous polypeptide of SEQ ID NO: 552.

The disclosure also provides a vaccine comprising a heterologous polynucleotide encoding a heterologous polypeptide of SEQ ID NO: 557.

The disclosure also provides a vaccine comprising a heterologous polynucleotide encoding a heterologous polypeptide of SEQ ID NO: 558.

The disclosure also provides a vaccine comprising a heterologous polynucleotide encoding a heterologous polypeptide of SEQ ID NO: 559.

The disclosure also provides a vaccine comprising a heterologous polynucleotide encoding a heterologous polypeptide of SEQ ID NO: 625.

The disclosure also provides a vaccine comprising a heterologous polynucleotide encoding a heterologous polypeptide of SEQ ID NO: 626.

The disclosure also provides a vaccine comprising a heterologous polynucleotide of SEQ ID NOs: 544.

The disclosure also provides a vaccine comprising a heterologous polynucleotide of SEQ ID NOs: 553.

In some embodiments, the vaccine is a recombinant virus.

In some embodiments, the recombinant virus is derived from adenovirus (Ad), poxvirus, adeno-associated virus (AAV) or retrovirus.

In some embodiments, the recombinant virus is derived from hAd5, hAd7, hAd11, hAd26, hAd34, hAd35, hAd48, hAd49, hAd50, GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, PanAd3, Copenhagen vaccinia virus (W), New York Attenuated Vaccinia Virus (NYVAC), ALVAC, TROVAC, or modified vaccinia Ankara (MVA).

In some embodiments, the recombinant virus is derived from GAd20.

In some embodiments, the recombinant virus derived from GAd20 comprises a polynucleotide sequence of SEQ ID NO: 713.

In some embodiments, the recombinant virus is derived from MVA.

In some embodiments, the recombinant virus is derived from hAd26.

The disclosure also provides a vaccine comprising a heterologous polynucleotide encoding a heterologous polypeptide of SEQ ID NO: 541, wherein the vaccine is a recombinant virus derived from GAd20.

The disclosure also provides a vaccine comprising a heterologous polynucleotide encoding a heterologous polypeptide of SEQ ID NO: 550, wherein the vaccine is a recombinant virus derived from GAd20.

The disclosure also provides a vaccine comprising a heterologous polynucleotide encoding a heterologous polypeptide of SEQ ID NO: 554, wherein the vaccine is a recombinant virus derived from GAd20.

The disclosure also provides a vaccine comprising a heterologous polynucleotide encoding a heterologous polypeptide of SEQ ID NO: 555, wherein the vaccine is a recombinant virus derived from GAd20.

The disclosure also provides a vaccine comprising a heterologous polynucleotide encoding a heterologous polypeptide of SEQ ID NO: 556, wherein the vaccine is a recombinant virus derived from GAd20.

The disclosure also provides a vaccine comprising a heterologous polynucleotide encoding a heterologous polypeptide of SEQ ID NO: 623, wherein the vaccine is a recombinant virus derived from GAd20.

The disclosure also provides a vaccine comprising a heterologous polynucleotide encoding a heterologous polypeptide of SEQ ID NO: 624, wherein the vaccine is a recombinant virus derived from GAd20.

The disclosure also provides a vaccine comprising a polynucleotide sequence of SEQ ID NO: 713, wherein the vaccine is a recombinant virus derived from GAd20.

The disclosure also provides a vaccine comprising a heterologous polynucleotide of SEQ ID NOs: 542, wherein the vaccine is a recombinant virus derived from GAd20.

The disclosure also provides a vaccine comprising a heterologous polynucleotide of SEQ ID NOs: 551, wherein the vaccine is a recombinant virus derived from GAd20.

The disclosure also provides a vaccine comprising a heterologous polynucleotide encoding a heterologous polypeptide of SEQ ID NO: 543, wherein the vaccine is a recombinant virus derived from MVA.

The disclosure also provides a vaccine comprising a heterologous polynucleotide encoding a heterologous polypeptide of SEQ ID NO: 552, wherein the vaccine is a recombinant virus derived from MVA.

The disclosure also provides a vaccine comprising a heterologous polynucleotide encoding a heterologous polypeptide of SEQ ID NO: 557, wherein the vaccine is a recombinant virus derived from MVA.

The disclosure also provides a vaccine comprising a heterologous polynucleotide encoding a heterologous polypeptide of SEQ ID NO: 558, wherein the vaccine is a recombinant virus derived from MVA.

The disclosure also provides a vaccine comprising a heterologous polynucleotide encoding a heterologous polypeptide of SEQ ID NO: 559, wherein the vaccine is a recombinant virus derived from MVA.

The disclosure also provides a vaccine comprising a heterologous polynucleotide encoding a heterologous polypeptide of SEQ ID NO: 625, wherein the vaccine is a recombinant virus derived from MVA.

The disclosure also provides a vaccine comprising a heterologous polynucleotide encoding a heterologous polypeptide of SEQ ID NO: 626, wherein the vaccine is a recombinant virus derived from MVA.

The disclosure also provides a vaccine comprising a heterologous polynucleotide of SEQ ID NOs: 544, wherein the vaccine is a recombinant virus derived from MVA.

The disclosure also provides a vaccine comprising a heterologous polynucleotide of SEQ ID NOs: 553, wherein the vaccine is a recombinant virus derived from MVA.

The disclosure also provides a method of treating or preventing a prostate cancer in a subject, comprising administering to the subject a therapeutically effective amount of a vaccine comprising a recombinant virus derived from GAd20 comprising a heterologous polynucleotide encoding a heterologous polypeptide of SEQ ID NOs: 541, 550, 554, 555, 556, 623 or 624.

The disclosure also provides a method of treating or preventing a prostate cancer in a subject, comprising administering to the subject a therapeutically effective amount of a vaccine comprising a recombinant virus derived from GAd20 comprising a heterologous polynucleotide encoding a heterologous polypeptide of SEQ ID NO: 541.

The disclosure also provides a method of treating or preventing a prostate cancer in a subject, comprising administering to the subject a therapeutically effective amount of a vaccine comprising a recombinant virus derived from GAd20 comprising a heterologous polynucleotide encoding a heterologous polypeptide of SEQ ID NO: 550.

The disclosure also provides a method of treating or preventing a prostate cancer in a subject, comprising administering to the subject a therapeutically effective amount of a vaccine comprising a recombinant virus derived from GAd20 comprising a heterologous polynucleotide encoding a heterologous polypeptide of SEQ ID NO: 554.

The disclosure also provides a method of treating or preventing a prostate cancer in a subject, comprising administering to the subject a therapeutically effective amount of a vaccine comprising a recombinant virus derived from GAd20 comprising a heterologous polynucleotide encoding a heterologous polypeptide of SEQ ID NO: 555.

The disclosure also provides a method of treating or preventing a prostate cancer in a subject, comprising administering to the subject a therapeutically effective amount of a vaccine comprising a recombinant virus derived from GAd20 comprising a heterologous polynucleotide encoding a heterologous polypeptide of SEQ ID NO: 556.

The disclosure also provides a method of treating or preventing a prostate cancer in a subject, comprising administering to the subject a therapeutically effective amount of a vaccine comprising a recombinant virus derived from GAd20 comprising a heterologous polynucleotide encoding a heterologous polypeptide of SEQ ID NO: 623.

The disclosure also provides a method of treating or preventing a prostate cancer in a subject, comprising administering to the subject a therapeutically effective amount of a vaccine comprising a recombinant virus derived from GAd20 comprising a heterologous polynucleotide encoding a heterologous polypeptide of SEQ ID NO: 624.

The disclosure also provides a method of treating or preventing a prostate cancer in a subject, comprising administering to the subject a therapeutically effective amount of a vaccine comprising a recombinant virus derived from MVA comprising a heterologous polynucleotide encoding a heterologous polypeptide of SEQ ID NOs: 543, 552, 557, 558, 559, 625 or 626.

The disclosure also provides a method of treating or preventing a prostate cancer in a subject, comprising administering to the subject a therapeutically effective amount of a vaccine comprising a recombinant virus derived from MVA comprising a heterologous polynucleotide encoding a heterologous polypeptide of SEQ ID NO: 543.

The disclosure also provides a method of treating or preventing a prostate cancer in a subject, comprising administering to the subject a therapeutically effective amount of a vaccine comprising a recombinant virus derived from MVA comprising a heterologous polynucleotide encoding a heterologous polypeptide of SEQ ID NO: 552.

The disclosure also provides a method of treating or preventing a prostate cancer in a subject, comprising administering to the subject a therapeutically effective amount of a vaccine comprising a recombinant virus derived from MVA comprising a heterologous polynucleotide encoding a heterologous polypeptide of SEQ ID NO: 557.

The disclosure also provides a method of treating or preventing a prostate cancer in a subject, comprising administering to the subject a therapeutically effective amount of a vaccine comprising a recombinant virus derived from MVA comprising a heterologous polynucleotide encoding a heterologous polypeptide of SEQ ID NO: 558.

The disclosure also provides a method of treating or preventing a prostate cancer in a subject, comprising administering to the subject a therapeutically effective amount of a vaccine comprising a recombinant virus derived from MVA comprising a heterologous polynucleotide encoding a heterologous polypeptide of SEQ ID NO: 559.

The disclosure also provides a method of treating or preventing a prostate cancer in a subject, comprising administering to the subject a therapeutically effective amount of a vaccine comprising a recombinant virus derived from MVA comprising a heterologous polynucleotide encoding a heterologous polypeptide of SEQ ID NO: 625.

The disclosure also provides a method of treating or preventing a prostate cancer in a subject, comprising administering to the subject a therapeutically effective amount of a vaccine comprising a recombinant virus derived from MVA comprising a heterologous polynucleotide encoding a heterologous polypeptide of SEQ ID NO: 626.

In some embodiments, the vaccine comprising a recombinant virus derived from GAd20 is administered as a prime.

In some embodiments, the vaccine comprising a recombinant virus derived from MVA is administered as a boost.

In some embodiments, the vaccine comprising the heterologous polynucleotide sequence encoding a heterologous polypeptide of SEQ ID NOs: 541 or 550 is administered as a prime.

In some embodiments, the vaccine comprising the heterologous polynucleotide sequence encoding a heterologous polypeptide of SEQ ID NOs 543 or 552 is administered as a boost.

The disclosure also provides a method of treating or preventing a prostate cancer in a subject, comprising administering to the subject a therapeutically effective amount of a vaccine comprising a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof as a prime; and administering to the subject a therapeutically effective amount of a vaccine comprising a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof as a boost; thereby treating or preventing the prostate cancer in the subject.

The disclosure also provides a method of treating or preventing a prostate cancer in a subject, comprising administering to the subject a first vaccine comprising a first heterologous polynucleotide encoding a first heterologous polypeptide, wherein the first heterologous polypeptide comprises two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177; and a second vaccine comprising a second heterologous polynucleotide encoding a second heterologous polypeptide, wherein the second heterologous polypeptide comprises two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177.

The disclosure also provides a method of treating or preventing a prostate cancer in a subject, comprising administering to the subject a first vaccine comprising a first heterologous polynucleotide encoding a first heterologous polypeptide, wherein the first heterologous polypeptide comprises two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177; and a second vaccine comprising a second heterologous polynucleotide encoding a second heterologous polypeptide, wherein the second heterologous polypeptide comprises two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177; wherein the first heterologous polypeptide and the second heterologous polypeptide have distinct amino acid sequences.

In some embodiments, the polypeptides are organized in a first order and in a second order.

In some embodiments, the polypeptides organized in the first order comprises a heterologous polypeptide of SEQ ID NO: 541 or SEQ ID NO: 550.

In some embodiments, the polypeptides organized in the second order comprises a heterologous polypeptide of SEQ ID NO: 543 or SEQ ID NO: 552.

In some embodiments, the heterologous polynucleotide is DNA or RNA.

In some embodiments, RNA is mRNA or self-replicating RNA.

In some embodiments, the vaccine is a recombinant virus.

In some embodiments, the recombinant virus is derived from adenovirus, poxvirus, adeno-associated virus or retrovirus.

In some embodiments, the polypeptides organized in the first order are encoded by a polynucleotide of SEQ ID NO: 542 or SEQ ID NO: 551.

In some embodiments, the polypeptides organized in the second order are encoded by a polynucleotide of SEQ ID NO: 544 or SEQ ID NO: 553.

In some embodiments, the prime comprises the recombinant virus derived from GAd20 comprising a heterologous polypeptide of SEQ ID NO: 541 or SEQ ID NO: 550.

In some embodiments, the boost comprises the recombinant virus derived from MVA comprising the heterologous polypeptide of SEQ ID NO: 543 or SEQ ID NO: 552.

The disclosure also provides a method of treating or preventing a prostate cancer in a subject, comprising administering to the subject a first vaccine comprising a first heterologous polynucleotide encoding a first heterologous polypeptide, wherein the first heterologous polypeptide comprises an amino acid sequence of SEQ ID NOs: 541, 550, 554, 555, 556, 623 or 624; and a second vaccine comprising a second heterologous polynucleotide encoding a second heterologous polypeptide, wherein the second heterologous polypeptide comprises the amino acid sequence of SEQ ID NOs: 543, 552, 557, 558, 559, 625 or 626.

The disclosure also provides a method of treating or preventing a prostate cancer in a subject, comprising administering to the subject a first vaccine comprising a first heterologous polynucleotide encoding a first heterologous polypeptide, wherein the first heterologous polypeptide comprises an amino acid sequence of SEQ ID NO: 541; and a second vaccine comprising a second heterologous polynucleotide encoding a second heterologous polypeptide, wherein the second heterologous polypeptide comprises the amino acid sequence of SEQ ID NO: 543.

The disclosure also provides a method of treating or preventing a prostate cancer in a subject, comprising administering to the subject a first vaccine comprising a first heterologous polynucleotide encoding a first heterologous polypeptide, wherein the first heterologous polypeptide comprises an amino acid sequence of SEQ ID NO: 550; and a second vaccine comprising a second heterologous polynucleotide encoding a second heterologous polypeptide, wherein the second heterologous polypeptide comprises the amino acid sequence of SEQ ID NO: 552.

The disclosure also provides a method of treating or preventing a prostate cancer in a subject, comprising administering to the subject a first vaccine comprising a first heterologous polynucleotide encoding a first heterologous polypeptide, wherein the first heterologous polypeptide comprises an amino acid sequence of SEQ ID NO: 541, wherein the first vaccine is a recombinant Gad20; and a second vaccine comprising a second heterologous polynucleotide encoding a second heterologous polypeptide, wherein the second heterologous polypeptide comprises the amino acid sequence of SEQ ID NO: 543, wherein the second vaccine is a recombinant MVA.

The disclosure also provides a method of treating or preventing a prostate cancer in a subject, comprising administering to the subject a first vaccine comprising a first heterologous polynucleotide encoding a first heterologous polypeptide, wherein the first heterologous polypeptide comprises an amino acid sequence of SEQ ID NO: 550, wherein the first vaccine is a recombinant GAd20; and a second vaccine comprising a second heterologous polynucleotide encoding a second heterologous polypeptide, wherein the second heterologous polypeptide comprises the amino acid sequence of SEQ ID NO: 552, wherein the second vaccine is a recombinant MVA.

The disclosure also provides a method of inducing an immune response in a subject, comprising administering to the subject a vaccine comprising a recombinant virus derived from GAd20 comprising a heterologous polynucleotide encoding a heterologous polypeptide of SEQ ID NOs: 541, 550, 554, 555, 556, 623 or 624.

The disclosure also provides a method of inducing an immune response in a subject, comprising administering to the subject a vaccine comprising a recombinant virus derived from GAd20 comprising a heterologous polynucleotide encoding a heterologous polypeptide of SEQ ID NO: 541.

The disclosure also provides a method of inducing an immune response in a subject, comprising administering to the subject a vaccine comprising a recombinant virus derived from GAd20 comprising a heterologous polynucleotide encoding a heterologous polypeptide of SEQ ID NO: 550.

The disclosure also provides a method of inducing an immune response in a subject, comprising administering to the subject a vaccine comprising a recombinant virus derived from GAd20 comprising a heterologous polynucleotide encoding a heterologous polypeptide of SEQ ID NO: 554.

The disclosure also provides a method of inducing an immune response in a subject, comprising administering to the subject a vaccine comprising a recombinant virus derived from GAd20 comprising a heterologous polynucleotide encoding a heterologous polypeptide of SEQ ID NO: 555.

The disclosure also provides a method of inducing an immune response in a subject, comprising administering to the subject a vaccine comprising a recombinant virus derived from GAd20 comprising a heterologous polynucleotide encoding a heterologous polypeptide of SEQ ID NO: 556.

The disclosure also provides a method of inducing an immune response in a subject, comprising administering to the subject a vaccine comprising a recombinant virus derived from GAd20 comprising a heterologous polynucleotide encoding a heterologous polypeptide of SEQ ID NO: 623.

The disclosure also provides a method of inducing an immune response in a subject, comprising administering to the subject a vaccine comprising a recombinant virus derived from GAd20 comprising a heterologous polynucleotide encoding a heterologous polypeptide of SEQ ID NO: 624.

The disclosure also provides a method of inducing an immune response in a subject, comprising administering to the subject a vaccine comprising a recombinant virus derived from MVA comprising a heterologous polynucleotide encoding a heterologous polypeptide of SEQ ID NOs: 543, 552, 557, 558, 559, 625 or 626.

The disclosure also provides a method of inducing an immune response in a subject, comprising administering to the subject a vaccine comprising a recombinant virus derived from MVA comprising a heterologous polynucleotide encoding a heterologous polypeptide of SEQ ID NO: 543.

The disclosure also provides a method of inducing an immune response in a subject, comprising administering to the subject a vaccine comprising a recombinant virus derived from MVA comprising a heterologous polynucleotide encoding a heterologous polypeptide of SEQ ID NO: 552.

The disclosure also provides a method of inducing an immune response in a subject, comprising administering to the subject a vaccine comprising a recombinant virus derived from MVA comprising a heterologous polynucleotide encoding a heterologous polypeptide of SEQ ID NO: 557.

The disclosure also provides a method of inducing an immune response in a subject, comprising administering to the subject a vaccine comprising a recombinant virus derived from MVA comprising a heterologous polynucleotide encoding a heterologous polypeptide of SEQ ID NO: 558.

The disclosure also provides a method of inducing an immune response in a subject, comprising administering to the subject a vaccine comprising a recombinant virus derived from MVA comprising a heterologous polynucleotide encoding a heterologous polypeptide of SEQ ID NO: 559.

The disclosure also provides a method of inducing an immune response in a subject, comprising administering to the subject a vaccine comprising a recombinant virus derived from MVA comprising a heterologous polynucleotide encoding a heterologous polypeptide of SEQ ID NO: 625.

The disclosure also provides a method of inducing an immune response in a subject, comprising administering to the subject a vaccine comprising a recombinant virus derived from MVA comprising a heterologous polynucleotide encoding a heterologous polypeptide of SEQ ID NO: 626.

The disclosure also provides a method of inducing an immune response in a subject, comprising administering to the subject

- a first vaccine comprising a first heterologous polynucleotide encoding a first heterologous polypeptide, wherein the first heterologous polypeptide comprises an amino acid sequence of SEQ ID NOs: 541, 550, 554, 555, 556, 623 or 624; and
- a second vaccine comprising a second heterologous polynucleotide encoding a second heterologous polypeptide, wherein the second heterologous polypeptide comprises the amino acid sequence of SEQ ID NOs: 543, 552, 557, 558, 559, 625 or 626.

The disclosure also provides a method of inducing an immune response in a subject, comprising administering to the subject

- a first vaccine comprising a first heterologous polynucleotide encoding a first heterologous polypeptide, wherein the first heterologous polypeptide comprises an amino acid sequence of SEQ ID NO: 541; and
- a second vaccine comprising a second heterologous polynucleotide encoding a second heterologous polypeptide, wherein the second heterologous polypeptide comprises the amino acid sequence of SEQ ID NO: 543.

The disclosure also provides a method of inducing an immune response in a subject, comprising administering to the subject

- a first vaccine comprising a first heterologous polynucleotide encoding a first heterologous polypeptide, wherein the first heterologous polypeptide comprises an amino acid sequence of SEQ ID NO: 550; and
- a second vaccine comprising a second heterologous polynucleotide encoding a second heterologous polypeptide, wherein the second heterologous polypeptide comprises the amino acid sequence of SEQ ID NO: 552.

The disclosure also provides a method of inducing an immune response in a subject, comprising administering to the subject

- a first vaccine comprising a first heterologous polynucleotide encoding a first heterologous polypeptide, wherein the first heterologous polypeptide comprises an amino acid sequence of SEQ ID NO: 541, wherein the first vaccine is a recombinant Gad20; and
- a second vaccine comprising a second heterologous polynucleotide encoding a second heterologous polypeptide, wherein the second heterologous polypeptide comprises the amino acid sequence of SEQ ID NO: 543, wherein the second vaccine is a recombinant MVA.

The disclosure also provides a method of inducing an immune response in a subject, comprising administering to the subject

- a first vaccine comprising a first heterologous polynucleotide encoding a first heterologous polypeptide, wherein the first heterologous polypeptide comprises an amino acid sequence of SEQ ID NO: 550, wherein the first vaccine is a recombinant GAd20; and
- a second vaccine comprising a second heterologous polynucleotide encoding a second heterologous polypeptide, wherein the second heterologous polypeptide comprises the amino acid sequence of SEQ ID NO: 552, wherein the second vaccine is a recombinant MVA.

In some embodiments, the subject has, is suspected to have or is suspected to develop prostate cancer. Prostate cancer diagnosis performed by a licensed physician.

In some embodiments, prostate cancer is a relapsed prostate cancer, a refractory prostate cancer, a metastatic prostate cancer or a castration resistant prostate cancer, or any combination thereof.

In some embodiments, the subject is treatment naïve.

In some embodiments, the subject has received androgen deprivation therapy.

In some embodiments, the first vaccine is administered one or more times to the subject.

In some embodiments, the second vaccine is administered one or more times to the subject.

In some embodiments, the first vaccine is administered between about 1-16 weeks prior to administering the second vaccine. In some embodiments, the first vaccine is administered about 1 week prior to administering the second vaccine. In some embodiments, the first vaccine is administered about 2 weeks prior to administering the second vaccine. In some embodiments, the first vaccine is administered about 3 weeks prior to administering the second vaccine. In some embodiments, the first vaccine is administered about 4 weeks prior to administering the second vaccine. In some embodiments, the first vaccine is administered about 5 weeks prior to administering the second vaccine. In some embodiments, the first vaccine is administered about 6 weeks prior to administering the second vaccine. In some embodiments, the first vaccine is administered about 7 weeks prior to administering the second vaccine. In some embodiments, the first vaccine is administered about 8 weeks prior to administering the second vaccine. In some embodiments, the first vaccine is administered about 9 weeks prior to administering the second vaccine. In some embodiments, the first vaccine is administered about 10 weeks prior to administering the second vaccine. In some embodiments, the first vaccine is administered about 11 weeks prior to administering the second vaccine. In some embodiments, the first vaccine is administered about 12 weeks prior to administering the second vaccine. In some embodiments, the first vaccine is administered about 13 weeks prior to administering the second vaccine. In some embodiments, the first vaccine is administered about 14 weeks prior to administering the second vaccine. In some embodiments, the first vaccine is administered about 16 weeks prior to administering the second vaccine.

In some embodiments, the prostate cancer is a relapsed prostate cancer, a refractory prostate cancer, a metastatic prostate cancer, or a castration resistant prostate cancer, or any combination thereof.

In some embodiments, the method comprises further administering an additional cancer therapeutic agent to the subject.

Combination Therapies

The vaccines of the disclosure may be used in combination with at least one additional cancer therapeutic agent for treating prostate cancer.

The additional cancer therapeutic agent may be a surgery, a chemotherapy, an androgen deprivation therapy, radiation therapy, targeted therapy or a checkpoint inhibitor, or any combination thereof.

Exemplary chemotherapeutic agents are alkylating agents; nitrosoureas; antimetabolites; antitumor antibiotics; plant alkyloids; taxanes; hormonal agents; and miscellaneous agents, such as busulfan, carboplatin, chlorambucil, cisplatin, cyclophosphamide, dacarbazine, ifosfamide, mechlorethamine hydrochloride, melphalan, procarbazine, thiotepa, uracil mustard, 5-fluorouracil, 6-mercaptopurine, capecitabine, cytosine arabinoside, floxuridine, fludarabine, gemcitabine, methotrexate, thioguanine, dactinomycin, daunorubicin, doxorubicin, idarubicin, mitomycin-C, and mitoxantrone, vinblastine, vincristine, vindesine, vinorelbine, paclitaxel, docetaxel.

Exemplary androgen deprivation therapies include abiraterone acetate, ketoconazole, enzalutamide, galeterone, ARN-509 and orteronel (TAK-700) and surgical removal of the testicles.

Radiation therapy may be administered using various methods, including external-beam therapy, internal radiation therapy, implant radiation, stereotactic radiosurgery, systemic radiation therapy, radiotherapy and permanent or temporary interstitial brachytherapy. External-beam therapy involves three-dimensional, conformal radiation therapy where the field of radiation is designed, local radiation (e.g., radiation directed to a preselected target or organ), or focused radiation. Focused radiation may be selected from stereotactic radiosurgery, fractionated stereotactic radiosurgery or intensity-modulated radiation therapy. Focused radiation may have particle beam (proton), cobalt-60 (photon) linear accelerator (x-ray) as a radiation source (see e.g. WO 2012/177624). "Brachytherapy," refers to radiation therapy delivered by a spatially confined radioactive material inserted into the body at or near a tumor or other proliferative tissue disease site, and includes exposure to radioactive isotopes (e.g., At-211, 1-131, 1-125, Y-90, Re-186, Re-188, Sm-153, Bi-212, P-32, and radioactive isotopes of Lu). Suitable radiation sources for use as a cell conditioner include both solids and liquids. The radiation source can be a radionuclide, such as 1-125, 1-131, Yb-169, Ir-192 as a solid source, 1-125 as a solid source, or other radionuclides that emit photons, beta particles, gamma radiation, or other therapeutic rays. The radioactive material may also be a fluid made from any solution of radionuclide(s), e.g., a solution of I-125 or I-131, or a radioactive fluid can be produced using a slurry of a suitable fluid containing small particles of solid radionuclides, such as Au-198, Y-90. The radionuclide(s) may be embodied in a gel or radioactive micro spheres.

Targeted therapies include anti-androgen therapies, inhibitors of angiogenesis such as bevacizumab, anti-PSA or anti-PSMA antibodies or vaccines enhancing immune responses to PSA or PSMA.

Exemplary checkpoint inhibitors are antagonists of PD-1, PD-L1, PD-L2, VISTA, BTNL2, B7-H3, B7-H4, HVEM, HHLA2, CTLA-4, LAG-3, TIM-3, BTLA, CD160, CEACAM-1, LAIR1, TGFβ, IL-10, Siglec family protein, KIR, CD96, TIGIT, NKG2A, CD112, CD47, SIRPA or CD244. "Antagonist" refers to a molecule that, when bound to a cellular protein, suppresses at least one reaction or activity that is induced by a natural ligand of the protein. A molecule is an antagonist when the at least one reaction or activity is suppressed by at least about 30%, 40%, 45%, 50%, 55%, 60%, 65%, 70%, 75%, 80%, 85%, 90%, 95%, or 100% more than the at least one reaction or activity suppressed in the absence of the antagonist (e.g., negative control), or when the suppression is statistically significant when compared to the suppression in the absence of the antagonist. Antagonist may be an antibody, a soluble ligand, a small molecule, a DNA or RNA such as siRNA. Exemplary antagonists of checkpoint inhibitors are described in U.S. Pat. Publ. No. 2017/0121409.

In some embodiments, one or more vaccines or the disclosure is administered in combination with a CTLA-4 antibody, a CTLA4 ligand, a PD-1 axis inhibitor, a PD-L1 axis inhibitor, a TLR agonist, a CD40 agonist, an OX40 agonist, hydroxyurea, ruxolitinib, fedratinib, a 41BB agonist, aa CD28 agonist, a STING antagonist, a RIG-1 antagonist, TCR-T therapy, CAR-T therapy, FLT3 ligand, aluminum sulfate, BTK inhibitor, CD38 antibody, CDK inhibitor, CD33 antibody, CD37 antibody, CD25 antibody, GM-CSF inhibitor, IL-2, IL-15, IL-7, CD3 redirection molecules, pomalimib, IFNγ, IFNα, TNFα, VEGF antibody, CD70 antibody, CD27 antibody, BCMA antibody or GPRC5D antibody, any combination thereof.

In some embodiments, the checkpoint inhibitor is ipilimumab, cetrelimab, pembrolizumab, nivolumab, sintilimab. cemiplimab, toripalimab, camrelizumab, tislelizumab, dostralimab, spartalizumab, prolgolimab, AK-105, HLX-10, balstilimab, MEDI-0680, HX-008, GLS-010, BI-754091, genolimzumab, AK-104, MGA-012, F-520, 609A, LY-3434172, AMG-404, SL-279252, SCT-IIOA, RO-7121661, ICTCAR-014, MEDI-5752, CS-1003, XmAb-23104, Sym-021, LZM-009, hAB21, BAT-1306, MGD-019, JTX-4014, budigalimab, XmAb-20717, AK-103, MGD-013, IBI-318, sasanlimab, CC-90006, avelumab, atezolizumab, durvalumab, CS-1001, bintrafusp alpha, envafolimab, CX-072, GEN-1046, GS-4224, KL-A167, BGB-A333, SHR-1316, CBT-502, IL-103, KN-046, ZKAB-001, CA-170, TG 1501, LP-002, INCB-86550, ADG-104, SHR-1701, BCD-135, IMC-001, MSB-2311, FPT-155, FAZ-053, HLX-20, iodapolimab, FS-118, BMS-986189, AK-106, MCLA-145, IBI-318 or CK-301, or any combination thereof.

In some embodiments, one or more vaccines of the disclosure are administered in combination with ipilimumab, cetrelimab, pembrolizumab, nivolumab, sintilimab. cemiplimab, toripalimab, camrelizumab, tislelizumab, dostralimab, spartalizumab, prolgolimab, balstilimab, budigalimab, sasanlimab, avelumab, atezolizumab, durvalumab, envafolimab or iodapolimab, or any combination thereof.

Kits

The disclosure also provides a kit comprising: a first vaccine comprising a recombinant virus derived from GAd20 comprising a heterologous polynucleotide encoding a heterologous polypeptide of SEQ ID NOs: 541, 550, 554, 555, 556, 623 or 624; and a second vaccine comprising a recombinant virus derived from MVA comprising a heterologous polynucleotide encoding a heterologous polypeptide of SEQ ID NOs: 543, 552, 557, 558, 559, 625 or 626.

The disclosure also provides a kit comprising:

a first vaccine comprising a recombinant virus derived from GAd20 comprising a heterologous polynucleotide encoding a heterologous polypeptide of SEQ ID NO:

541; and a second vaccine comprising a recombinant virus derived from MVA comprising a heterologous polynucleotide encoding a heterologous polypeptide of SEQ ID NO: 543.

The disclosure also provides a kit comprising:

a first vaccine comprising a recombinant virus derived from GAd20 comprising a heterologous polynucleotide encoding a heterologous polypeptide of SEQ ID NO: 550; and a second vaccine comprising a recombinant virus derived from MVA comprising a heterologous polynucleotide encoding a heterologous polypeptide of SEQ ID NO: 552.

Heterologous Polypeptides Encoding or Heterologous Polypeptides Comprising a Combination of Select Prostate Neoantigens The disclosure also provides an isolated heterologous polypeptide comprising two or more polypeptides selected from the group consisting of AS18 comprising the amino acid sequence (SEQ ID NO: 275)
WKFEMSYTVGGPPPHVHARPRHWKTDR;

P87 comprising the amino acid sequence (SEQ ID NO: 381)
YEAGMTLGGKILFFLFLLLPLSPFSLIF;

AS55 comprising the amino acid sequence (SEQ ID NO: 333)
DGHSYTSKVNCLLLQDGFHGCVSITGAAGRRNLSIFLFLMLC
KLEFHAC;

AS57 comprising the amino acid sequence (SEQ ID NO: 337)
TGGKSTCSAPGPQSLPSTPFSTYPQWVILITEL;

AS15 comprising the amino acid sequence (SEQ ID NO: 269)
VLRFLDLKVRYLHS;

AS7 comprising the amino acid sequence (SEQ ID NO: 253)
DYWAQKEKGSSSFLRPSC;

AS43 comprising the amino acid sequence (SEQ ID NO: 309)
VPFRELKNVSVLEGLRQGRLGGPCSCHCPRPSQARLTPVDVAGP
FLCLGDPGLFPPVKSSI;

AS51 comprising the amino acid sequence (SEQ ID NO: 325)
GMECTLGQVGAPSPRREEDGWRGGHSRFKADVPAPQGPCWGGQP
GSAPSSAPPEQSLLD;

AS16 comprising the amino acid sequence (SEQ ID NO: 271)
GNTTLQQLGEASQAPSGSLIPLRLPLLWEVRG;

AS41 comprising the amino acid sequence (SEQ ID NO: 305)
EAFQRAAGEGGPGRGGARRGARVLQSPFCRAGAGEWLGHQSLR;

AS6 comprising the amino acid sequence (SEQ ID NO: 251)
DYWAQKEKISIPRTHLC;

AS3 comprising the amino acid sequence (SEQ ID NO: 245)
VAMMVPDRQVHYDFGL;

AS11 comprising the amino acid sequence (SEQ ID NO: 261)
VPFRELKNQRTAQGAPGIHHAASPVAANLCDPARHAQHTRI
PCGAGQVRAGRGPEAGGGVLQPQRPAPEKPGCPCRRGQPRL
HTVKMWRA;

AS13 comprising the amino acid sequence (SEQ ID NO: 265)
KRSFAVTERII;

AS47 comprising the amino acid sequence (SEQ ID NO: 317)
FKKFDGPCGERGGGRTARALWARGDSVLTPALDPQTPVRAP
SLTRAAAAV;

AS8 comprising the amino acid sequence (SEQ ID NO: 255)
LVLGVLSGHSGSRL;

AS19 comprising the amino acid sequence (SEQ ID NO: 277)
QWQHYHRSGEAAGTPLWRPTRN;

AS37 comprising the amino acid sequence (SEQ ID NO: 297)
CHLFLQPQVGTPPPHTASARAPSGPPHPHESCPAGRRPA
RAAQTCARRQHGLPGCEEAGTARVPSLHLHLHQAALGAG
RGRGWGEACAQVPPSRG;

AS23 comprising the amino acid sequence (SEQ ID NO: 285)
KIQNKNCPD;

MS1 comprising the amino acid sequence (SEQ ID NO: 437)
HYKLIQQPISLFSITDRLHKTFSQLPSVHLCSITFQWGHP

PIFCSTNDICVTANFCISVTFLKPCFLLHEASASQ;

MS3 comprising the amino acid sequence (SEQ ID NO: 439)
RTALTHNQDFSIYRLCCKRGSLCHASQARSPAFPKPVRP

LPAPITRITPQLGGQSDSSQPLLTTGRPQGWQDQALRHT

QQASPASCATITIPIHSAALGDHSGDPGPAWDTCPPLPL

TTLIPRAPPPYGDSTARSWPSRCGPLG;

MS6 comprising the amino acid sequence (SEQ ID NO: 442)
YAYKDFLWCFPFSLVFLQEIQICCHVSCLCCICCSTRICLG

CLLELFLSRALRALHVLWNGFQLHCQ;

MS8 comprising the amino acid sequence (SEQ ID NO: 444)
TMPAILKLQKNCLLSL;

and

P82 comprising the amino acid sequence (SEQ ID NO: 379)
YEAGMTLGEKFRVGNCKHLKMTRP, and fragments thereof.

In some embodiments, the isolated heterologous polypeptide further comprises one or more polypeptides selected from the group consisting of P16 comprising the amino acid sequence (SEQ ID NO: 343)
GVPGDSTRRAVRRMNTF;

FUS1 comprising the amino acid sequence (SEQ ID NO: 211)
CGASACDVSLIAMDSA;

P22 comprising the amino acid sequence SLYHREKQLIAMDSAI (SEQ ID NO: 349)
SLYHREKQLIAMDSAI;

FUS2 comprising the amino acid sequence (SEQ ID NO: 213)
TEYNQKLQVNQFSESK;

FUS3 comprising the amino acid sequence (SEQ ID NO: 215)
TEISCCTLSSEENEYLPRPEWQLQ;

FUS6 comprising the amino acid sequence (SEQ ID NO: 221)
CEERGAAGSLISCE;

FUS5 comprising the amino acid sequence (SEQ ID NO: 219)
NSKMALNSEALSVVSE;

FUS8 comprising the amino acid sequence (SEQ ID NO: 225)
WGMELAASRRFSWDHHSAGGPPRVPSVRSGAAQVQPKDPL

PLRTLAGCLARTAHLRPGAESLPQPQLHCT;

FUS15 comprising the amino acid sequence (SEQ ID NO: 345)
HVVGYGHLDTSGSSSSSSWP;

P35 comprising the amino acid sequence (SEQ ID NO: 353)
NSKMALNSLNSIDDAQLTRIAPPRSHCCFWEVNAP;

FUS19 comprising the amino acid sequence (SEQ ID NO: 235)
KMHFSLKEHPPPPCPP;

and

FUS7 comprising the amino acid sequence (SEQ ID NO: 223)
LWFQSSELSPTGAPWPSRRPTWRGTTVSPRTATSSA

RTCCGTKWPSSQEAALGLGSGLLRFSCGTAAIR, and fragments thereof.

The disclosure also provides an isolated heterologous polypeptide comprising one or more polypeptides selected from the group consisting of P16 comprising the amino acid sequence (SEQ ID NO: 343)
GVPGDSTRRAVRRMNTF;

FUS1 comprising the amino acid sequence (SEQ ID NO: 211)
CGASACDVSLIAMDSA;

P22 comprising the amino acid sequence (SEQ ID NO: 349)
SLYHREKQLIAMDSAI;

FUS2 comprising the amino acid sequence (SEQ ID NO: 213)
TEYNQKLQVNQFSESK;

FUS3 comprising the amino acid sequence (SEQ ID NO: 215)
TEISCCTLSSEENEYLPRPEWQLQ;

FUS6 comprising the amino acid sequence (SEQ ID NO: 221)
CEERGAAGSLISCE;

FUS5 comprising the amino acid sequence (SEQ ID NO: 219)
NSKMALNSEALSVVSE;

FUS8 comprising the amino acid sequence (SEQ ID NO: 225)
WGMELAASRRFSWDHHSAGGPPRVPSVRSGAAQVQPK
DPLPLRTLAGCLARTAHLRPGAESLPQPQLHCT;

FUS15 comprising the amino acid sequence (SEQ ID NO: 345)
HVVGYGHLDTSGSSSSSSWP;

P35 comprising the amino acid sequence (SEQ ID NO: 353)
NSKMALNSLNSIDDAQLTRIAPPRSHCCFWEVNAP;

FUS19 comprising the amino acid sequence (SEQ ID NO: 235)
KMHFSLKEHPPPPCPP;

and

FUS7 comprising the amino acid sequence (SEQ ID NO: 223)
LWFQSSELSPTGAPWPSRRPTWRGTTVSPRTATSSARTCCGTKWPSSQE
AALGLGSGLLRFSCGTAAIR, and fragments thereof.

In some embodiments, the isolated heterologous polypeptide further comprises one or more polypeptides selected from the group consisting of AS18 comprising the amino acid sequence (SEQ ID NO: 275)
WKFEMSYTVGGPPPHVHARPRHWKTDR;

P87 comprising the amino acid sequence (SEQ ID NO: 381)
YEAGMTLGGKILFFLFLLLPLSPFSLIF;

AS55 comprising the amino acid sequence (SEQ ID NO: 333)
DGHSYTSKVNCLLLQDGFHGCVSITGAAGRR
NLSIFLFLMLCKLEFHAC;

AS57 comprising the amino acid sequence (SEQ ID NO: 337)
TGGKSTCSAPGPQSLPSTPFSTYPQWVILITEL;

AS15 comprising the amino acid sequence (SEQ ID NO: 269)
VLRFLDLKVRYLHS;

AS7 comprising the amino acid sequence (SEQ ID NO: 253)
DYWAQKEKGSSSFLRPSC;

AS43 comprising the amino acid sequence (SEQ ID NO: 309)
VPFRELKNVSVLEGLRQGRLGGPCSCHCPRP
SQARLTPVDVAGPFLCLGDPGLFPPVKSSI;

AS51 comprising the amino acid sequence (SEQ ID NO: 325)
GMECTLGQVGAPSPRREEDGWRGGHSRFKAD
VPAPQGPCWGGQPGSAPSSAPPEQSLLD;

AS16 comprising the amino acid sequence (SEQ ID NO: 271)
GNTTLQQLGEASQAPSGSLIPLRLPLLWEVRG;

AS41 comprising the amino acid sequence (SEQ ID NO: 305)
EAFQRAAGEGGPGRGGARRGARVLQSPFCRAGAGEWLGHQSLR;

AS6 comprising the amino acid sequence (SEQ ID NO: 251)
DYWAQKEKISIPRTHLC;

AS3 comprising the amino acid sequence (SEQ ID NO: 245)
VAMMVPDRQVHYDFGL;

AS 11 comprising the amino acid sequence (SEQ ID NO: 261)
VPFRELKNQRTAQGAPGIHHAASPVAANLCDPARHAQ
HTRIPCGAGQVRAGRGPEAGGGVLQPQRPAPEKPGCP
CRRGQPRLHTVKMWRA;

AS13 comprising the amino acid sequence (SEQ ID NO: 265)
KRSFAVTERII;

AS47 comprising the amino acid sequence (SEQ ID NO: 317)
FKKFDGPCGERGGGRTARALWARGDSVLTPALDPQT
PVRAPSLTRAAAAV;

AS8 comprising the amino acid sequence (SEQ ID NO: 255)
LVLGVLSGHSGSRL;

AS19 comprising the amino acid sequence (SEQ ID NO: 277)
QWQHYHRSGEAAGTPLWRPTRN;

AS37 comprising the amino acid sequence (SEQ ID NO: 297)
CHLFLQPQVGTPPPHTASARAPSGPPHPHESCPAGRR
PARAAQTCARRQHGLPGCEEAGTARVPSLHLHLHQAA
LGAGRGRGWGEACAQVPPSRG;

AS23 comprising the amino acid sequence KIQNKNCPD (SEQ ID NO: 285);

MS1 comprising the amino acid sequence (SEQ ID NO: 437)
HYKLIQQPISLFSITDRLHKTFSQLPSVHLCSITFQW
GHPPIFCSTNDICVTANFCISVTFLKPCFLLHEASAS
Q;

MS3 comprising the amino acid sequence (SEQ ID NO: 439)
RTALTHNQDFSIYRLCCKRGSLCHASQARSPAFPKPV
RPLPAPITRITPQLGGQSDSSQPLLTTGRPQGWQDQA
LRHTQQASPASCATITIPIHSAALGDHSGDPGPAWDT
CPPLPLTTLIPRAPPPYGDSTARSWPSRCGPLG;

MS6 comprising the amino acid sequence (SEQ ID NO: 442)
YAYKDFLWCFPFSLVFLQEIQICCHVSCLCCICCSTRI
CLGCLLELFLSRALRALHVLWNGFQLHCQ;

MS8 comprising the amino acid sequence (SEQ ID NO: 444)
TMPAILKLQKNCLLSL;

and

P82 comprising the amino acid sequence (SEQ ID NO: 379)
YEAGMTLGEKFRVGNCKHLKMTRP, and fragments thereof.

In some embodiments, the isolated heterologous polypeptide further comprises one or more polypeptides selected from the group consisting of M84 comprising the amino acid sequence (SEQ ID NO: 167)
IARELHQFAFDLLIKSH;

M86 comprising the amino acid sequence (SEQ ID NO: 171)
QPDSFAALHSSLNELGE;

M10 comprising the amino acid sequence (SEQ ID NO: 19)
FVQGKDWGLKKFIRRDF;

M12 comprising the amino acid sequence (SEQ ID NO: 23)
FVQGKDWGVKKFIRRDF;

and

FR1 comprising the amino acid sequence (SEQ ID NO: 177)
QNLQNGGGSRSSATLPGRRRRRWLRRRRQPISVAPAGPPRRPNQKPNPPG
GARCVIMRPTWPGTSAFT, and fragments thereof.

The disclosure also provides a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides an isolated heterologous polynucleotide comprising two or more polynucleotides selected from the group consisting of the polynucleotide sequence of (SEQ ID NO: 276)
TGGAAATTCGAGATGAGCTACACGGTGGGTGGCCCGCCT
CCCCATGTTCATGCTAGACCCAGGCATTGGAAAACTGAT
AGA
(encoding AS18);

the polynucleotide sequence of (SEQ ID NO: 382)
TATGAAGCAGGGATGACTCTGGGAGGTAAGATACTTTT CTTTCTCTTCCTCCTCCTTCCTCTCTCCCCCTTCTCCC TCATTTTC (encoding P87);

the polynucleotide sequence of (SEQ ID NO: 334)
GATGGCCACTCCTACACATCCAAGGTGAATTGTTTACT CCTTCAAGATGGGTTCCATGGCTGTGTGAGCATCACCG GGGCAGCTGGAAGAAGAAACCTGAGCATCTTCCTGTTC TTGATGCTGTGCAAATTGGAGTTCCATGCTTGT (encoding AS55);

the polynucleotide sequence of (SEQ ID NO: 338)
ACAGGGGGCAAAAGCACCTGCTCGGCTCCTGGCCCTC AGTCTCTCCCCTCCACTCCATTCTCCACCTACCCACA GTGGGTCATTCTGATCACCGAACTG (encoding AS57);

the polynucleotide sequence of (SEQ ID NO: 270)
GTGCTGCGCTTTCTGGACTTAAAGGTGAGATACCTGCACTCT (encoding AS15);

the polynucleotide sequence of (SEQ ID NO: 254)
GACTACTGGGCTCAAAAGGAGAAGGGATCATCTTCATTCCTGCGACCAT CCTGT (encoding AS7);

the polynucleotide sequence of (SEQ ID NO: 310)
GTGCCCTTCCGGGAGCTCAAGAACGTGAGTGTCCTGGAGGGGCTCCGTC AAGGCCGGCTTGGGGGTCCCTGTTCATGTCACTGCCCAAGACCTTCCCA GGCCAGGCTCACGCCAGTGGATGTGGCAGGTCCCTTCTTGTGTCTGGGG GATCCTGGGCTGTTCCCCCCAGTCAAGAGCAGTATC (encoding AS43);

the polynucleotide sequence of (SEQ ID NO: 326)
GGCATGGAGTGCACCCTGGGGCAGGTGGGTGCCCCGTCCCCTCGGAGGG AGGAGGACGGTTGGCGTGGGGGCCACAGCCGATTCAAGGCTGATGTACC AGCACCGCAGGGACCCTGCTGGGGTGGCCAACCTGGCTCTGCCCCCTCC TCAGCTCCTCCTGAACAGTCATTATTAGAT (encoding AS51);

the polynucleotide sequence of ((SEQ ID NO: 272)
GGCAACACCACCCTCCAGCAGCTGGGTGAGGCCTCCCAGGCGCCCTCAG GCTCCCTCATCCCTCTGAGGCTGCCTCTGCTCTGGGAAGTGAGGGGC (encoding AS16);

the polynucleotide sequence of (SEQ ID NO: 306)
GAGGCCTTCCAGAGGGCCGCTGGTGAGGGCGGCCCGGGCCGCGGTGGGG CACGGCGCGGTGCCAGGGTGTTGCAGAGCCCCTTTTGCAGGGCAGGAGC TGGGGAGTGGTTAGGACATCAGTCCCTCAGG (encoding AS41);

the polynucleotide sequence of (SEQ ID NO: 252)
GACTACTGGGCTCAAAAGGAGAAGATCAGCATCCCCAGAACACACCTGT GT (encoding AS6);

the polynucleotide sequence of (SEQ ID NO: 246)
GTTGCTATGATGGTTCCTGATAGACAGGTTCATTATGACTTTGGATTG (encoding AS3);

the polynucleotide sequence of (SEQ ID NO: 262)
GTGCCCTTCCGGGAGCTCAAGAACCAGAGAACAGCACAAGGGGCTCCTG GGATCCACCACGCGGCTTCCCCCGTTGCTGCCAACCTCTGCGACCCGGC GAGACACGCACAGCACACACGCATCCCCTGCGGCGCTGGCCAAGTGCGT GCTGGCCGAGGTCCCGAAGCAGGTGGTGGAGTACTACAGCCACAGAGGC CTGCCCCCGAGAAGCCTGGGTGTCCCTGCCGGAGAGGCCAGCCCAGGCT GCACACCGTGAAGATGTGGAGGGCG (encoding AS11);

the polynucleotide sequence of (SEQ ID NO: 266)
AAGAGAAGTTTTGCTGTCACGGAGAGGATCATC (encoding AS13);

the polynucleotide sequence of (SEQ ID NO: 318)
TTCAAGAAGTTCGACGGCCCTTGTGGTGAGCGCGGCGGCGGGCGCACGG CTCGAGCTCTGTGGGCGCGCGGCGACAGCGTCCTGACTCCTGCCCTCGA CCCCCAGACCCCTGTCAGGGCGCCCTCCCTGACCCGAGCCGCAGCTGCC GTG (encoding AS47);

the polynucleotide sequence of (SEQ ID NO: 256)
CTTGTACTTGGTGTATTGAGCGGGCACAGTGGCTCACGCCTA (encoding AS8);

the polynucleotide sequence of (SEQ ID NO: 278)
CAGTGGCAGCACTACCACCGGTCAGGTGAGGCCGCAGGGACTCCCCTCT
GGAGACCCACAAGAAAC (encoding AS19);

the polynucleotide sequence of (SEQ ID NO: 298)
TGCCACCTCTTCCTGCAGCCCCAGGTTGGCACCCCCCCCCCCCACACTG
CCAGTGCTCGAGCCCCCAGTGGTCCACCCCACCCTCATGAAAGTTGCCC
TGCAGGGCGAAGACCTGCGAGAGCTGCGCAGACATGTGCACGCCGACAG
CACGGACTTCCTGGCTGTGAAGAGGCTGGTACAGCGCGTGTTCCCAGCC
TGCACCTGCACCTGCACCAGGCCGCCCTCGGAGCAGGAAGGGGCCGTGG
GTGGGGAGAGGCCTGTGCCCAAGTACCCCCCTCAAGAGGC
(encoding AS37);

the polynucleotide sequence of (SEQ ID NO: 286)
AAAATTCAGAATAAAAATTGTCCAGAC
(encoding AS23);

the polynucleotide sequence of (SEQ ID NO: 448)
CACTACAAATTAATTCAACAACCCATATCCCTCTTCTCCATCACTGATA
GGCTCCATAAGACGTTCAGTCAGCTGCCCTCGGTCCATCTCTGCTCAAT
CACCTTCCAGTGGGGACACCCGCCCATTTTCTGCTCAACAAATGATATC
TGTGTCACGGCCAACTTCTGCATCTCGGTCACATTCCTTAAACCGTGCT
TCCTCCTACATGAGGCATCTGCCTCACAG (encoding MS1);

the polynucleotide sequence of (SEQ ID NO: 450)
AGGACCGCCCTGACACACAATCAGGACTTCTCTATCTACAGGCTCTGTT
GCAAGAGGGGGTCCCTCTGCCACGCTTCCCAGGCCAGATCCCCGGCTTT
CCCGAAGCCGGTCAGACCTCTTCCTGCCCCCATCACCAGAATCACCCCC
CAACTGGGGGGACAATCTGACTCGAGTCAACCCCTTCTCACTACGGGAA
GACCTCAGGGGTGGCAAGATCAAGCTCTTAGACACACCCAGCAAGCCAG
TCCTGCCTCTTGTGCCACCATCACCATTCCCATCCACTCAGCTGCCCTT
GGTGACCACTCCGGAGACCCTGGTCCAGCCTGGGACACCTGCCCGCCGC
TGCCGCTCACTACCCTCATCCCCCGAGCTCCCCCGCCGTATGGAGACAG
CACTGCCAGGTCCTGGCCCTCCCGCTGTGGGCCCCTCGGC
(encoding MS3);

the polynucleotide sequence of (SEQ ID NO: 453)
TATGCTTACAAGGACTTTCTCTGGTGTTTTCCTTTTTCTTTAGTTTTTC
TCCAAGAGATTCAAATCTGCTGCCATGTTAGCTGTCTTTGCTGTATCTG -continued
CTGTAGTACACGAATATGCCTTGGCTGTTTGCTTGAGCTTTTTCTATCC
CGTGCTCTTCGTGCTCTTCATGTTCTTTGGAATGGCTTTCAACTTCATT
GTCAA (encoding MS6);

the polynucleotide sequence of (SEQ ID NO: 455)
ACCATGCCTGCTATTTTAAAGTTACAGAAGAATT
GTCTTCTCTCCTTA
(encoding MS8);

and the polynucleotide sequence of (SEQ ID NO: 380)
TATGAAGCAGGGATGACTCTGGGAGAAAAATTCCGGGTTGGCAATTGCAA
GCATCTCAAAATGACCAGACCC (encoding P82);

and fragments thereof.

In some embodiments, the isolated heterologous polynucleotide further comprises one or more polynucleotides selected from the group consisting of the polynucleotide sequence of (SEQ ID NO: 344)
GGAGTTCCAGGAGATTCAACCAGGAGAGCAGTGAGGAGAATGAAT
ACCTTC
(encoding P16);

the polynucleotide sequence of (SEQ ID NO: 212)
TGCGGGGCCTCTGCCTGTGATGTCTCCCTCATTGCTATGGACAGTGCT
(encoding FUS1);

the polynucleotide sequence of (SEQ ID NO: 350)
TCCCTCTACCACCGGGAGAAGCAGCTCATTGCTATGGACAGTGCTATC
(encoding P22);

the polynucleotide sequence of (SEQ ID NO: 214)
ACCGAATACAACCAGAAATTACAAGTGAATCAATTTAGTGAATCCAAA
(encoding FUS2);

the polynucleotide sequence of (SEQ ID NO: 216)
ACAGAAATTTCATGTTGCACCCTGAGCAGTGAGGAGAATGAATAC
CTTCCAAGACCAGAGTGGCAGCTCCAG
(encoding FUS3);

the polynucleotide sequence of (SEQ ID NO: 222)
TGTGAGGAGCGCGGCGCGGCAGGAAGCCTTATCAGTTGTGAG
(encoding FUS6);

the polynucleotide sequence of (SEQ ID NO: 220)
AACAGCAAGATGGCTTTGAACTCAGAAGCCTTATCAGTTGTGAGTGAG
(encoding FUS5);

the polynucleotide sequence of (SEQ ID NO: 226)
TGGGGGATGGAGTTGGCAGCGTCTCGGAGGTTCTCCTGGGACCACC
ACTCCGCCGGGGGGCCGCCCAGAGTGCCAAGCGTCCGATCCGGCGC
CGCCCAAGTGCAGCCCAAGGACCCGCTCCCGCTCCGCACCCTGGCA
GGCTGCCTAGCCAGGACTGCGCACCTGCGCCCTGGGGCGGAGTCCT
TACCCCAACCCCAGCTTCACTGCACA
(encoding FUS8);

the polynucleotide sequence of (SEQ ID NO: 346)
CACGTGGTGGGCTATGGCCACCTTGATACTTCCGGGTCATCCTCCT
CCTCCTCCTGGCCC
(encoding FUS15);

the polynucleotide sequence of (SEQ ID NO: 354)
AACAGCAAGATGGCTTTGAACTCATTAAACTCCATTGATGATGCA
CAGTTGACAAGAATTGCCCCTCCAAGATCTCATTGCTGTTTCTGG
GAAGTAAACGCTCCT
(encoding P35);

the polynucleotide sequence of (SEQ ID NO: 236)
AAAATGCACTTCTCCCTCAAGGAGCACCCACCGCCCCCTTGCCCGCCT
(encoding FUS19);

and
the polynucleotide sequence of (SEQ ID NO: 224)
CTGTGGTTCCAGAGCAGTGAGCTGTCCCCGACGGGAGCGCCATGGCCCAG
CCGCCGCCCGACGTGGAGGGGGACGACTGTCTCCCCGCGTACCGCCACCT
CTTCTGCCCGGACCTGCTGCGGGACAAAGTGGCCTTCATCACAGGAGGCG
GCTCTGGGATTGGGTTCCGGATTGCTGAGATTTTCATGCGGCACGGCTGC
CATACGG (encoding FUS7), and fragments thereof.

The disclosure also provides an isolated heterologous polynucleotide comprising two or more polynucleotides selected from the group consisting of the polynucleotide sequence of (SEQ ID NO: 344)
GGAGTTCCAGGAGATTCAACCAGGAGAGCAGTGAGGAGAATGAAT
ACCTTC
(encoding P16);

the polynucleotide sequence of (SEQ ID NO: 212)
TGCGGGGCCTCTGCCTGTGATGTCTCCCTCATTGCTATGGACAGT
GCT
(encoding FUS1);

the polynucleotide sequence of (SEQ ID NO: 350)
TCCCTCTACCACCGGGAGAAGCAGCTCATTGCTATGGACAGTGCT
ATC
(encoding P22);

the polynucleotide sequence of (SEQ ID NO: 214)
ACCGAATACAACCAGAAATTACAAGTGAATCAATTTAGTGAATCC
AAA
(encoding FUS2);

the polynucleotide sequence of (SEQ ID NO: 216)
ACAGAAATTTCATGTTGCACCCTGAGCAGTGAGGAGAATGAATAC
CTTCCAAGACCAGAGTGGCAGCTCCAG
(encoding FUS3);

the polynucleotide sequence of (SEQ ID NO: 222)
TGTGAGGAGCGCGGCGCGGCAGGAAGCCTTATCAGTTGTGAG
(encoding FUS6);

the polynucleotide sequence of (SEQ ID NO: 220)
AACAGCAAGATGGCTTTGAACTCAGAAGCCTTATCAGTTGTGAGTGAG
(encoding FUS5);

the polynucleotide sequence of (SEQ ID NO: 226)
TGGGGGATGGAGTTGGCAGCGTCTCGGAGGTTCTCCTGGGACCACCACT
CCGCCGGGGGGCCGCCCAGAGTGCCAAGCGTCCGATCCGGCGCCGCCCA
AGTGCAGCCCAAGGACCCGCTCCCGCTCCGCACCCTGGCAGGCTGCCTA
GCCAGGACTGCGCACCTGCGCCCTGGGGCGGAGTCCTTACCCCAACCCC
AGCTTCACTGCACA (encoding FUS8);

the polynucleotide sequence of (SEQ ID NO: 346)
CACGTGGTGGGCTATGGCCACCTTGATACTTCCGGGTCATCCTCCTCCT
CCTCCTGGCCC (encoding FUS15);

the polynucleotide sequence of

```
                                       (SEQ ID NO: 354)
AACAGCAAGATGGCTTTGAACTCATTAAACTCCATTGATGATGCACAGT

TGACAAGAATTGCCCCTCCAAGATCTCATTGCTGTTTCTGGGAAGTAAA

CGCTCCT (encoding P35);
```

the polynucleotide sequence of

```
                                       (SEQ ID NO: 236)
AAAATGCACTTCTCCCTCAAGGAGCACCCACCGCCCCCTTGCCCGCCT

(encoding FUS19);
```

and the polynucleotide sequence of

```
                                       (SEQ ID NO: 224)
CTGTGGTTCCAGAGCAGTGAGCTGTCCCCGACGGGAGCGCCATGGCCCA

GCCGCCGCCCGACGTGGAGGGGGACGACTGTCTCCCCGCGTACCGCCAC

CTCTTCTGCCCGGACCTGCTGCGGGACAAAGTGGCCTTCATCACAGGAG

GCGGCTCTGGGATTGGGTTCCGGATTGCTGAGATTTTCATGCGGCACGG

CTGCCATACGG (encoding FUS7).
```

In some embodiments, the isolated heterologous poly-nucleotide further comprises one or more polynucleotides or one or more at least 24 nucleotide long contiguous frag-ments of the one or more polynucleotides, wherein the polynucleotides comprise
the polynucleotide sequence of

```
                                       (SEQ ID NO: 276)
TGGAAATTCGAGATGAGCTACACGGTGGGTGGCCCGCCTCCCCATGTTC

ATGCTAGACCCAGGCATTGGAAAACTGATAGA (encoding AS18);
```

the polynucleotide sequence of

```
                                       (SEQ ID NO: 382)
TATGAAGCAGGGATGACTCTGGGAGGTAAGATACTTTTCTTTCTCTTCC

TCCTCCTTCCTCTCTCCCCCTTCTCCCTCATTTTC

(encoding P87);
```

the polynucleotide sequence of

```
                                       (SEQ ID NO: 334)
GATGGCCACTCCTACACATCCAAGGTGAATTGTTTACTCCTTCAAGATG

GGTTCCATGGCTGTGTGAGCATCACCGGGGCAGCTGGAAGAAGAAACCT

GAGCATCTTCCTGTTCTTGATGCTGTGCAAATTGGAGTTCCATGCTTGT

(encoding AS55);
```

the polynucleotide sequence of

```
                                       (SEQ ID NO: 338)
ACAGGGGGCAAAAGCACCTGCTCGGCTCCTGGCCCTCAGTCTCTCCCCT

CCACTCCATTCTCCACCTACCCACAGTGGGTCATTCTGATCACCGAACT

G (encoding AS57);
```

the polynucleotide sequence of

```
                                       (SEQ ID NO: 270)
GTGCTGCGCTTTCTGGACTTAAAGGTGAGATACCTGCACTCT

(encoding AS15);
```

the polynucleotide sequence of

```
                                       (SEQ ID NO: 254)
GACTACTGGGCTCAAAAGGAGAAGGGATCATCTTCATTCCTGCGACCAT

CCTGT (encoding AS7);
```

the polynucleotide sequence of

```
                                       (SEQ ID NO: 310)
GTGCCCTTCCGGGAGCTCAAGAACGTGAGTGTCCTGGAGGGGCTCCGTC

AAGGCCGGCTTGGGGGTCCCTGTTCATGTCACTGCCCAAGACCTTCCCA

GGCCAGGCTCACGCCAGTGGATGTGGCAGGTCCCTTCTTGTGTCTGGGG

GATCCTGGGCTGTTCCCCCCAGTCAAGAGCAGTATC

(encoding AS43);
```

the polynucleotide sequence of

```
                                       (SEQ ID NO: 326)
GGCATGGAGTGCACCCTGGGGCAGGTGGGTGCCCCGTCCCCTCGGAGGG

AGGAGGACGGTTGGCGTGGGGGCCACAGCCGATTCAAGGCTGATGTACC

AGCACCGCAGGGACCCTGCTGGGGTGGCCAACCTGGCTCTGCCCCCTCC

TCAGCTCCTCCTGAACAGTCATTATTAGAT(encoding AS51);
```

the polynucleotide sequence of

```
                                       ((SEQ ID NO: 272)
GGCAACACCACCCTCCAGCAGCTGGGTGAGGCCTCCCAGGCGCCCTCAG

GCTCCCTCATCCCTCTGAGGCTGCCTCTGCTCTGGGAAGTGAGGGGC

(encoding AS16);
```

the polynucleotide sequence of

```
                                       (SEQ ID NO: 306)
GAGGCCTTCCAGAGGGCCGCTGGTGAGGGCGGCCCGGGCCGCGGTGGGGC

ACGGCGCGGTGCCAGGGTGTTGCAGAGCCCCTTTTGCAGGGCAGGAGCTG

GGGAGTGGTTAGGACATCAGTCCCTCAGG (encoding AS41);
```

the polynucleotide sequence of

```
                                       (SEQ ID NO: 252)
GACTACTGGGCTCAAAAGGAGAAGATCAGCATCCCCAGAACACACCTGTG

T (encoding AS6);
```

the polynucleotide sequence of

```
                                       (SEQ ID NO: 246)
GTTGCTATGATGGTTCCTGATAGACAGGTTCATTATGACTTTGGATTG
(encoding AS3);
```

the polynucleotide sequence of (SEQ ID NO: 262)
GTGCCCTTCCGGGAGCTCAAGAACCAGAGAACAGCACAAGGGGCTCCTGG GATCCACCACGCGGCTTCCCCCGTTGCTGCCAACCTCTGCGACCCGGCGA GACACGCACAGCACACACGCATCCCCTGCGGCGCTGGCCAAGTGCGTGCT GGCCGAGGTCCCGAAGCAGGTGGTGGAGTACTACAGCCACAGAGGCCTGC CCCCGAGAAGCCTGGGTGTCCCTGCCGGAGAGGCCAGCCCAGGCTGCACA CCGTGAAGATGTGGAGGGCG (encoding AS11);

the polynucleotide sequence of (SEQ ID NO: 266)
AAGAGAAGTTTTGCTGTCACGGAGAGGATCATC(encoding AS13);

the polynucleotide sequence of (SEQ ID NO: 318)
TTCAAGAAGTTCGACGGCCCTTGTGGTGAGCGCGGCGGCGGGCGCACGGC TCGAGCTCTGTGGGCGCGCGGCGACAGCGTCCTGACTCCTGCCCTCGACC CCCAGACCCCTGTCAGGGCGCCCTCCCTGACCCGAGCCGCAGCTGCCGTG (encoding AS47);

the polynucleotide sequence of (SEQ ID NO: 256)
CTTGTACTTGGTGTATTGAGCGGGCACAGTGGCTCACGCCTA (encoding AS8);

the polynucleotide sequence of (SEQ ID NO: 278)
CAGTGGCAGCACTACCACCGGTCAGGTGAGGCCGCAGGGACTCCCCTCTG GAGACCCACAAGAAAC (encoding AS19);

the polynucleotide sequence of (SEQ ID NO: 298)
TGCCACCTCTTCCTGCAGCCCCAGGTTGGCACCCCCCCCCCCCACACTGC CAGTGCTCGAGCCCCCAGTGGTCCACCCCACCCTCATGAAAGTTGCCCTG CAGGGCGAAGACCTGCGAGAGCTGCGCAGACATGTGCACGCCGACAGCAC GGACTTCCTGGCTGTGAAGAGGCTGGTACAGCGCGTGTTCCCAGCCTGCA CCTGCACCTGCACCAGGCCGCCCTCGGAGCAGGAAGGGGCCGTGGGTGGG GAGAGGCCTGTGCCCAAGTACCCCCCTCAAGAGGC (encoding AS37);

the polynucleotide sequence of (SEQ ID NO: 286)
AAAATTCAGAATAAAAATTGTCCAGAC (encoding AS23);

the polynucleotide sequence of (SEQ ID NO: 448)
CACTACAAATTAATTCAACAACCCATATCCCTCTTCTCCATCACTGATAG GCTCCATAAGACGTTCAGTCAGCTGCCCTCGGTCCATCTCTGCTCAATCA -continued GCCTTCCAGTGGGACACCCGCCCATTTTCTGCTCAACAAATGATATCTGT GTCACGGCCAACTTCTGCATCTCGGTCACATTCCTTAAACCGTGCTTCCT CCTACATGAGGCATCTGCCTCACAG (encoding MS1);

the polynucleotide sequence of (SEQ ID NO: 450)
AGGACCGCCCTGACACACAATCAGGACTTCTCTATCTACAGGCTCTGTTG CAAGAGGGGGTCCCTCTGCCACGCTTCCCAGGCCAGATCCCCGGCTTTCC CGAAGCCGGTCAGACCTCTTCCTGCCCCCATCACCAGAATCACCCCCCAA CTGGGGGGACAATCTGACTCGAGTCAACCCCTTCTCACTACGGGAAGACC TCAGGGGTGGCAAGATCAAGCTCTTAGACACACCCAGCAAGCCAGTCCTG CCTCTTGTGCCACCATCACCATTCCCATCCACTCAGCTGCCCTTGGTGAC CACTCCGGAGACCCTGGTCCAGCCTGGGACACCTGCCCGCCGCTGCCGCT CACTACCCTCATCCCCCGAGCTCCCCCGCCGTATGGAGACAGCACTGCCA GGTCCTGGCCCTCCCGCTGTGGGCCCCTCGGC (encoding MS3);

the polynucleotide sequence of (SEQ ID NO: 453)
TATGCTTACAAGGACTTTCTCTGGTGTTTTCCTTTTTCTTTAGTTTTTCT CCAAGAGATTCAAATCTGCTGCCATGTTAGCTGTCTTTGCTGTATCTGCT GTAGTACACGAATATGCCTTGGCTGTTTGCTTGAGCTTTTTCTATCCCGT GCTCTTCGTGCTCTTCATGTTCTTTGGAATGGCTTTCAACTTCATTGTCA A (encoding MS6);

the polynucleotide sequence of (SEQ ID NO: 455)
ACCATGCCTGCTATTTTAAAGTTACAGAAGAATTGTCTTCTCTCCTTA (encoding MS8);

and the polynucleotide sequence of (SEQ ID NO: 380)
TATGAAGCAGGGATGACTCTGGGAGAAAAATTCCGGGTTGGCAATTGCAA GCATCTCAAAATGACCAGACCC (encoding P82), and fragments thereof.

In some embodiments, the isolated heterologous polynucleotide further comprises one or more polynucleotides selected from the group consisting of the polynucleotide sequence of (SEQ ID NO: 168)
ATTGCGAGAGAGCTGCATCAGTTCGCTTTTGACCTGCTAATCAAGTCACA C (encoding M84);

the polynucleotide sequence of (SEQ ID NO: 172)
CAGCCCGACTCCTTTGCAGCCTTGCACTCTAGCCTCAATGAACTGGGAGA
G (encoding M86);

the polynucleotide sequence of (SEQ ID NO: 20)
TTTGTGCAAGGCAAAGACTGGGGATTAAAGAAATTCATCCGTAGAGATTT
T (encoding M10);

the polynucleotide sequence of:

(SEQ ID NO: 24)
TTTGTGCAAGGCAAAGACTGGGGAGTCAAGAAATTCATCCGTAGAGATT
TT (encoding M12);

and the polynucleotide sequence of (SEQ ID NO: 178)
CAGAACCTGCAGAATGGAGGGGGGAGCAGGTCTTCAGCCACACTGCCGG
GGCGGCGGCGGCGGCGGTGGCTGCGGCGGCGGCGGCAGCCAATATCAGT
AGCTCCTGCGGGGCCCCCTCGCCGACCAAACCAAAAACCAAACCCACCT
GGCGGTGCGAGGTGTGTGATTATGAGACCAACGTGGCCAGGAACCTCCG
CATTCACA (encoding FR1);

and fragments thereof.

The disclosure also provides a heterologous polynucleotide encoding two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof. The polynucleotides are useful in expression in adenovirus.

The disclosure also provides a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof. The polynucleotides are useful in expression in MVA.

For example, a heterologous polynucleotide of SEQ ID NO: 542 encoding a heterologous polypeptide of SEQ ID NO: 541 by may be used to generate adenovirus-based prostate cancer vaccines, such as those based on rGAd20. Alternatively, heterologous polynucleotides encoding heterologous polypeptides of SEQ ID NOs: 550, 554, 555, 556, 623 or 624 may also be used in adenovirus-based vaccines. In addition to the heterologous polynucleotide encoding the combination of the 41 neoantigens, additional facilitator elements may be included to the 5' or 3' of the heterologous polynucleotide, such as regulatory sequences, tags, and the like. Exemplary facilitator elements include CMV promoter, vaccinia P7.5 promoter, TetO repressor, Kozak sequence, a polynucleotide encoding a T cell enhancer (TCE), a polynucleotide encoding a histidine tag, one or more stop codons, a polyadenylation signal or a promoter sequence. Exemplary polynucleotide sequences of the facilitator elements comprise CMVTetO promoter comprising SEQ ID NO: 628, Kozak sequence comprising SEQ ID NO: 545, the polynucleotide encoding the TCE comprising SEQ ID NO: 546, the polynucleotide encoding the histidine tag comprising SEQ ID NO: 547, a BGH polyadenylation site comprising SEQ ID NO: 629, the one or more stop codons comprising the polynucleotide sequence of TAGTAA, the CMV promoter comprising a polynucleotide of SEQ ID NO: 628 or the vaccinia P7.5 promoter comprising a polynucleotide of SEQ ID NO: 630. Thus the heterologous polynucleotide comprising one or more additional facilitator sequences comprises the polynucleotide sequence of SEQ ID NO: 551, encoding the polypeptide of SEQ ID NO: 550.

In some embodiments, the isolated heterologous polypeptide comprises the amino acid sequence of SEQ ID NO: 541.

In some embodiments, the heterologous polypeptide is encoded by the heterologous polynucleotide of SEQ ID NO: 542.

In some embodiments, the heterologous polynucleotide further comprises one or more facilitator elements.

In some embodiments, the facilitator elements comprises a promoter, an enhancer, a polyadenylation site, a Kozak sequence, a stop codon, a T cell enhancer (TCE), or any combination thereof.

In some embodiments, the Kozak sequence comprises SEQ ID NO: 545, the polynucleotide encoding the TCE comprises SEQ ID NO: 546, the polynucleotide encoding the histidine tag comprises SEQ ID NO: 547 and the one or more stop codons comprises the polynucleotide sequence of TAGTAA.

In some embodiments, the TCE is encoded by a polynucleotide of SEQ ID NO: 546, the CMV promoter comprises a polynucleotide of SEQ ID NO: 628, the vaccinia P7.5 promoter comprises a polynucleotide of SEQ ID NO: 630 and the polyadenylation site comprises a bovine growth hormone polyadenylation site of SEQ ID NO: 629.

The disclosure also provides an isolated heterologous polypeptide comprising the amino acid sequence of SEQ ID NO: 550.

In some embodiments, the heterologous polypeptide is encoded by the heterologous polynucleotide of SEQ ID NO: 551.

The disclosure also provides an isolated heterologous polypeptide comprising the amino acid sequence of SEQ ID NO: 554.

In some embodiments, the isolated heterologous polypeptide comprises the amino acid sequence of SEQ ID NO: 555.

The disclosure also provides an isolated heterologous polypeptide comprising the amino acid sequence of SEQ ID NO: 556.

In some embodiments, the isolated heterologous polypeptide comprises the amino acid sequence of SEQ ID NO: 623.

The disclosure also provides an isolated heterologous polypeptide comprising the amino acid sequence of SEQ ID NO: 624.

In some embodiments, the heterologous polynucleotide is DNA. In some embodiments, the heterologous polynucleotide is RNA. In some embodiments, the heterologous polynucleotide is mRNA. In some embodiments, the heterologous polynucleotide is self-replicating RNA.

The heterologous polynucleotide of SEQ ID NO: 544 encoding the heterologous polypeptide of SEQ ID NO: 543 may be used to engineer MVA-based prostate cancer vaccines. Alternatively, the heterologous polypeptides of SEQ ID NOs: 557, 558, 559, 625 or 626 may also be used. In addition to the heterologous polynucleotide encoding the combination of the 41 neoantigens, additional facilitator elements may be included to the 5' or 3' of the heterologous polynucleotide, such as regulatory sequences, tags, and the like. Exemplary facilitator sequences include Kozak sequence, a polynucleotide encoding a T cell enhancer (TCE), a polynucleotide encoding a histidine tag, one or more stop codons, a polyadenylation signal or a promoter sequence. Exemplary polynucleotide sequences of the facilitator elements comprise Kozak sequence comprising SEQ ID NO: 545, the polynucleotide encoding the TCE comprising SEQ ID NO: 546, the polynucleotide encoding the histidine tag comprising SEQ ID NO: 547 and the one or more stop codons comprising the polynucleotide sequence of TAGTAA. Thus a heterologous polynucleotide comprising one or more additional facilitator elements comprises the polynucleotide sequence of SEQ ID NO: 553, encoding the polypeptide of SEQ ID NO: 552.

The disclosure also provides an isolated heterologous polypeptide comprising the amino acid sequence of SEQ ID NO: 543.

In some embodiments, the heterologous polypeptide is encoded by the heterologous polynucleotide of SEQ ID NO: 544.

In some embodiments, the heterologous polynucleotide further comprises one or more facilitator elements.

In some embodiments, the facilitator elements comprises a promoter, an enhancer, a polyadenylation site, a Kozak sequence, a stop codon, a T cell enhancer (TCE), or any combination thereof.

In some embodiments, the Kozak sequence comprises SEQ ID NO: 545, the polynucleotide encoding the TCE comprises SEQ ID NO: 546, the polynucleotide encoding the histidine tag comprises SEQ ID NO: 547 and the one or more stop codons comprises the polynucleotide sequence of TAGTAA.

In some embodiments, the TCE is encoded by a polynucleotide of SEQ ID NO: 546, the CMV promoter comprises a polynucleotide of SEQ ID NO: 628, the vaccinia P7.5 promoter comprises a polynucleotide of SEQ ID NO: 630 and the polyadenylation site comprises a bovine growth hormone polyadenylation site of SEQ ID NO: 629. In some embodiments, the isolated heterologous polypeptide comprises the amino acid sequence of SEQ ID NO: 552.

In some embodiments, the heterologous polypeptide is encoded by the heterologous polynucleotide of SEQ ID NO: 553.

The disclosure also provides an isolated heterologous polypeptide comprising the amino acid sequence of SEQ ID NO: 557.

The disclosure also provides an isolated heterologous polypeptide comprising the amino acid sequence of SEQ ID NO: 558.

The disclosure also provides an isolated heterologous polypeptide comprising the amino acid sequence of SEQ ID NO: 559.

The disclosure also provides an isolated heterologous polypeptide comprising the amino acid sequence of SEQ ID NO: 625.

The disclosure also provides an isolated heterologous polypeptide comprising the amino acid sequence of SEQ ID NO: 626.

In some embodiments, the heterologous polynucleotide is DNA. In some embodiments, the heterologous polynucleotide is RNA. In some embodiments, the heterologous polynucleotide is mRNA. In some embodiments, the heterologous polynucleotide is self-replicating RNA.

One or more fragments of the 41 prostate neoantigens (SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177) may also be used to generate a prostate cancer vaccine, as long as the one or more fragments are immunogenic. Exemplary such fragments that may be used are polypeptides of SEQ ID NOs: 387, 388, 390, 392, 405, 406, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709. Immunogenicity of the fragments can be tested using assays described herein.

In some embodiments, the first N-terminal amino acid residue of the fragment is absent.

The disclosure also provides an isolated heterologous polynucleotide encoding the heterologous polypeptide of the disclosure.

In some embodiments, the first 5' codon of the fragment is absent.

The disclosure also provides a vector comprising a heterologous polynucleotide encoding two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides a vector comprising a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides a vector comprising a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof. The polynucleotides are useful in expression in adenovirus.

The disclosure also provides a vector comprising a heterologous polynucleotide encoding the heterologous polypeptide of SEQ ID NO: 541. In some embodiments, the heterologous polynucleotide comprises the polynucleotide of SEQ ID NO: 542.

The disclosure also provides a vector comprising the heterologous polynucleotide of SEQ ID NO: 542.

The disclosure also provides a vector comprising a heterologous polynucleotide encoding the heterologous polypeptide of SEQ ID NO: 550. In some embodiments, the heterologous polynucleotide comprises the polynucleotide of SEQ ID NO: 551.

The disclosure also provides a vector comprising the heterologous polynucleotide of SEQ ID NO: 551.

The disclosure also provides a vector comprising a heterologous polynucleotide encoding the heterologous polypeptide of SEQ ID NO: 554.

The disclosure also provides a vector comprising a heterologous polynucleotide encoding the heterologous polypeptide of SEQ ID NO: 555.

The disclosure also provides a vector comprising a heterologous polynucleotide encoding the heterologous polypeptide of SEQ ID NO: 556.

The disclosure also provides a vector comprising a heterologous polynucleotide encoding the heterologous polypeptide of SEQ ID NO: 623.

The disclosure also provides a vector comprising a heterologous polynucleotide encoding the heterologous polypeptide of SEQ ID NO: 624.

In some embodiments, the vector is a viral vector.

In some embodiments, the viral vector is an adenovirus vector.

In some embodiments, the adenovirus vector is derived from a human adenovirus, optionally from Ad5, Ad7, Ad 11, Ad26, Ad34, Ad35, Ad48, Ad49 or Ad50.

In some embodiments, the adenovirus vector is derived from Ad26.

In some embodiments, the adenovirus vector is derived from a great ape adenovirus, optionally from GAd20, GAd19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd1, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2 or PanAd3.

In some embodiments, the adenovirus vector is derived from GAd20.

The disclosure also provides a rGAd20 comprising a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

The disclosure also provides a rGAd20 comprising a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides a rGAd20 comprising a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof. The polynucleotides are useful in expression in adenovirus.

The disclosure also provides a rGAd20 comprising a heterologous polynucleotide encoding the heterologous polypeptide of SEQ ID NO: 541. In some embodiments, the heterologous polynucleotide comprises SEQ ID NO: 542.

The disclosure also provides a rGAd20 comprising the heterologous polynucleotide of SEQ ID NO: 542.

The disclosure also provides a rGAd20 comprising a heterologous polynucleotide encoding the heterologous polypeptide of SEQ ID NO: 550. In some embodiments, the heterologous polynucleotide comprises SEQ ID NO: 551.

The disclosure also provides a rGAd20 comprising the heterologous polynucleotide of SEQ ID NO: 551.

The disclosure also provides a rGAd20 comprising a heterologous polynucleotide encoding the heterologous polypeptide of SEQ ID NO: 554.

The disclosure also provides a rGAd20 comprising a heterologous polynucleotide encoding the heterologous polypeptide of SEQ ID NO: 555.

The disclosure also provides a rGAd20 comprising a heterologous polynucleotide encoding the heterologous polypeptide of SEQ ID NO: 556.

The disclosure also provides a rGAd20 comprising a heterologous polynucleotide encoding the heterologous polypeptide of SEQ ID NO: 623.

The disclosure also provides a rGAd20 comprising a heterologous polynucleotide encoding the heterologous polypeptide of SEQ ID NO: 624.

The disclosure also provides a cell comprising or transduced with the rGAd20, wherein the rGAd20 comprises:

- a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;
- a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof;
- a heterologous polynucleotide encoding the heterologous polypeptide of SEQ ID NO: 541; heterologous polynucleotide of SEQ ID NO: 542;
- a heterologous polynucleotide encoding the heterologous polypeptide of SEQ ID NO: 550;
- a heterologous polynucleotide of SEQ ID NO: 551;
- a heterologous polynucleotide encoding the heterologous polypeptide of SEQ ID NO: 554;
- a heterologous polynucleotide encoding the heterologous polypeptide of SEQ ID NO: 555;
- a heterologous polynucleotide encoding the heterologous polypeptide of SEQ ID NO: 556;
- a heterologous polynucleotide encoding the heterologous polypeptide of SEQ ID NO: 623; or
- a heterologous polynucleotide encoding the heterologous polypeptide of SEQ ID NO: 624.

The disclosure also provides a vaccine comprising the rGAd20, wherein the rGAd20 comprises:

- a heterologous polynucleotide encoding a heterologous polypeptide comprising two or more polypeptides selected from the group consisting of SEQ ID NOs:

275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;

a heterologous polynucleotide comprising two or more polynucleotides selected from the group consisting of SEQ ID NOs: 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498 and 499, and fragments thereof;

a heterologous polynucleotide encoding the heterologous polypeptide of SEQ ID NO: 541;

a heterologous polynucleotide of SEQ ID NO: 542;

a heterologous polynucleotide encoding the heterologous polypeptide of SEQ ID NO: 550;

a heterologous polynucleotide of SEQ ID NO: 551;

a heterologous polynucleotide encoding the heterologous polypeptide of SEQ ID NO: 554;

a heterologous polynucleotide encoding the heterologous polypeptide of SEQ ID NO: 555;

a heterologous polynucleotide encoding the heterologous polypeptide of SEQ ID NO: 556;

a heterologous polynucleotide encoding the heterologous polypeptide of SEQ ID NO: 623; or a heterologous polynucleotide encoding the heterologous polypeptide of SEQ ID NO: 624.

The disclosure also provides a vector comprising a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides a vector comprising a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof. The polynucleotides are useful in expression in MVA.

The disclosure also provides a vector comprising a heterologous polynucleotide encoding the heterologous polypeptide of SEQ ID NO: 543. In some embodiments, the heterologous polynucleotide comprises SEQ ID NO: 544.

The disclosure also provides a vector comprising a heterologous polynucleotide of SEQ ID NO: 544.

The disclosure also provides a vector comprising a heterologous polynucleotide encoding the heterologous polypeptide of SEQ ID NO: 552. In some embodiments, the heterologous polynucleotide comprises SEQ ID NO: 553.

The disclosure also provides a vector comprising a heterologous polynucleotide of SEQ ID NO: 553.

The disclosure also provides a vector comprising a heterologous polynucleotide encoding the heterologous polypeptide of SEQ ID NO: 557.

The disclosure also provides a vector comprising a heterologous polynucleotide encoding the heterologous polypeptide of SEQ ID NO: 558.

The disclosure also provides a vector comprising a heterologous polynucleotide encoding the heterologous polypeptide of SEQ ID NO: 559.

The disclosure also provides a vector comprising a heterologous polynucleotide encoding the heterologous polypeptide of SEQ ID NO: 625.

The disclosure also provides a vector comprising a heterologous polynucleotide encoding the heterologous polypeptide of SEQ ID NO: 626.

In some embodiments, the vector is a viral vector.

In some embodiments, the viral vector is MVA.

In some embodiments, the MVA vector is derived from MVA 476 MG/14/78, MVA-571, MVA-572, MVA-574, MVA-575 or MVA-BN.

The disclosure also provides a rMVA comprising a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;

The disclosure also provides a rMVA comprising a heterologous polynucleotide comprising two or more polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

The disclosure also provides a rMVA comprising a heterologous polynucleotide comprising two or more polynucleotides selected from the group consisting of SEQ ID NOs: 500, 501,461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540, and fragments thereof. The polynucleotides are useful in expression in MVA.

The disclosure also provides a rMVA comprising a heterologous polynucleotide encoding the heterologous polypeptide of SEQ ID NO: 543. In some embodiments, the heterologous polynucleotide comprises SEQ ID NO: 544.

The disclosure also provides a rMVA comprising the heterologous polynucleotide of SEQ ID NO: 544.

The disclosure also provides a rMVA comprising a heterologous polynucleotide encoding the heterologous polypeptide of SEQ ID NO: 552. In some embodiments, the heterologous polynucleotide comprises SEQ ID NO: 553.

The disclosure also provides a rMVA comprising the heterologous polynucleotide of SEQ ID NO: 553.

The disclosure also provides a rMVA comprising a heterologous polynucleotide encoding the heterologous polypeptide of SEQ ID NO: 557.

The disclosure also provides a rMVA comprising a heterologous polynucleotide encoding the heterologous polypeptide of SEQ ID NO: 558.

The disclosure also provides a rMVA comprising a heterologous polynucleotide encoding the heterologous polypeptide of SEQ ID NO: 559.

The disclosure also provides a rMVA comprising a heterologous polynucleotide encoding the heterologous polypeptide of SEQ ID NO: 625.

The disclosure also provides a rMVA comprising a heterologous polynucleotide encoding the heterologous polypeptide of SEQ ID NO: 626.

The disclosure also provides a cell comprising or transduced with the rMVA, wherein the rMVA comprises:

a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;

a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540;

a heterologous polynucleotide encoding the heterologous polypeptide of SEQ ID NO: 543;

a heterologous polynucleotide of SEQ ID NO: 544;

a heterologous polynucleotide encoding the heterologous polypeptide of SEQ ID NO: 552;

a heterologous polynucleotide of SEQ ID NO: 553;

a heterologous polynucleotide encoding the heterologous polypeptide of SEQ ID NO: 557;

a heterologous polynucleotide encoding the heterologous polypeptide of SEQ ID NO: 558;

a heterologous polynucleotide encoding the heterologous polypeptide of SEQ ID NO: 559;

a heterologous polynucleotide encoding the heterologous polypeptide of SEQ ID NO: 625; or a heterologous polynucleotide encoding the heterologous polypeptide of SEQ ID NO: 626.

The disclosure also provides a vaccine comprising the rMVA, wherein the MVA comprises:

a heterologous polynucleotide encoding a heterologous polypeptide comprising two or more polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof;

a heterologous polynucleotide comprising two or more polynucleotides selected from the group consisting of SEQ ID NOs: 500, 501, 461, 503, 504, 505, 506, 507, 508, 509, 510, 511, 512, 513, 514, 515, 516, 517, 477, 519, 520, 521, 522, 523, 524, 525, 485, 486, 528, 529, 530, 531, 532, 533, 534, 535, 536, 537, 538, 539 and 540;

a heterologous polynucleotide encoding the heterologous polypeptide of SEQ ID NO: 543;

a heterologous polynucleotide of SEQ ID NO: 544;

a heterologous polynucleotide encoding the heterologous polypeptide of SEQ ID NO: 552;

a heterologous polynucleotide of SEQ ID NO: 553;

a heterologous polynucleotide encoding the heterologous polypeptide of SEQ ID NO: 557;

a heterologous polynucleotide encoding the heterologous polypeptide of SEQ ID NO: 558;

a heterologous polynucleotide encoding the heterologous polypeptide of SEQ ID NO: 559;

a heterologous polynucleotide encoding the heterologous polypeptide of SEQ ID NO: 625; or a heterologous polynucleotide encoding the heterologous polypeptide of SEQ ID NO: 626.

The disclosure also provides a vaccine comprising a heterologous polynucleotide encoding a heterologous polypeptide comprising two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polypeptides selected from the group consisting of SEQ ID NOs: 275, 381, 333, 337, 269, 253, 309, 325, 271, 305, 251, 245, 261, 265, 317, 255, 277, 297, 285, 437, 439, 442, 444, 379, 343, 211, 349, 213, 215, 221, 219, 225, 345, 353, 235, 223, 167, 171, 19, 23 and 177, and fragments thereof.

In some embodiments, the heterologous polynucleotide comprises two, three, four, five, six, seven, eight, nine, ten, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or 41 polynucleotides selected from the group consisting of SEQ ID NOs: 276, 382, 334, 338, 270, 254, 310, 326, 272, 306, 252, 246, 262, 266, 318, 256, 278, 298, 286, 448, 450, 453, 455, 380, 344, 212, 350, 214, 216, 222, 220, 226, 346, 354, 236, 224, 168, 172, 20, 24 and 178, and fragments thereof.

In some embodiments, the fragments comprise peptides of SEQ ID NOs: 387, 388, 390, 392, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620 or 621.

In some embodiments, the heterologous polypeptide comprises SEQ ID NOs: 541, 550, 554, 555, 556, 623 or 624.

In some embodiments, the heterologous polynucleotide comprises SEQ ID NO: 542 or SEQ ID NO: 551.

In some embodiments, the heterologous polypeptide comprises SEQ ID NOs: 543, 552, 557, 558, 559, 625 or 626.

In some embodiments, the heterologous polynucleotide comprises SEQ ID NO: 544 or SEQ ID NO: 553.

In some embodiments, the heterologous polynucleotide is DNA or RNA.

In some embodiments, RNA is mRNA or self-replicating RNA.

In some embodiments, the vaccine is a recombinant virus.

In some embodiments, the recombinant virus is derived from adenovirus, poxvirus, adeno-associated virus or retrovirus.

In some embodiments, the recombinant virus is derived from hAd5, hAd7, hAd11, hAd26, hAd34, hAd35, hAd48, hAd49, hAd50, GAd20, Gad19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, PanAd3, Copenhagen vaccinia virus (W), New York Attenuated Vaccinia Virus (NYVAC), ALVAC, TROVAC, or modified vaccinia Ankara (MVA).

In some embodiments, the recombinant virus is derived from GAd20.

In some embodiments, the recombinant virus is derived from MVA.

In some embodiments, the recombinant virus is derived from Ad26.

The disclosure also provides a vaccine comprising a heterologous polynucleotide sequence encoding a heterologous polypeptide of SEQ ID NO: 541 or 550.

In some embodiments, the heterologous polynucleotide comprises SEQ ID NO: 542 or 551.

In some embodiments, the vaccine is a recombinant virus derived from GAd20.

The disclosure also provides a vaccine comprising a heterologous polynucleotide sequence encoding a heterologous polypeptide of SEQ ID NO: 543 or 552.

In some embodiments, the heterologous polynucleotide comprises SEQ ID NO: 544 or 553.

In some embodiments, the vaccine is a recombinant virus derived from MVA.

The following examples are provided to further describe some of the embodiments disclosed herein. The examples are intended to illustrate, not to limit, the disclosed embodiments.

Example 1 General Methods

Peptide Synthesis

Peptides were synthesized by New England Peptide with purity >80%. The lyophilized peptides were solubilized in 100% DMSO.

In Vitro Immunogenicity Assessment of Neoantigens ("Patient PBMC Restimulation Assay")

PBMCs from human patients with metastatic castrate-resistant prostate cancer were thawed using media (RPMI 1640 supplemented with Glutamax, 10% HI FBS, and 1× Sodium Pyruvate). Cells were counted and plated in a 96 well round bottom microplate at a concentration of 250,000 viable cells per well. Lyophilized peptides were solubilized in 100% DMSO and diluted in media to 10 μg/mL. Neoantigen peptides were added in equal volume to PBMCs for a final concentration of 5 μg/mL. CEF Peptide Pool "Plus" (Cellular Technologies, Ltd.) was utilized as a positive control and DMSO at the same final concentration as the experimental peptides was utilized as a negative control. Human IL-15 (Peprotech) was added to all wells at final concentration of 10 ng/mL.

Plates were incubated at 37° C. (5% $CO_2$) for a total of 13 days. Media was refreshed every 2 days with IL-15 (10 ng/mL final concentration) and IL-2 (R&D systems, 10 IU/mL final concentration). On day 12, PBMCs were re-stimulated with identical experimental peptides or controls, at same concentration as peptide stimulation on Day 1. After 1-hour incubation, protein Inhibitor Cocktail (eBioscience) was added to every well and plate was incubated overnight.

On day 13, cells were stained for intracellular flow cytometry analysis. The cells were washed with PBS and stained with Live/Dead Fixable Aqua Dead Cell stain (Thermo-Fisher). Following the live/dead stain, cells were blocked using Biotin-Free Fe Receptor Blocker (Accurate Chemical & Scientific Corp). Extracellular cellular flow panel (1 μL/antibody per well in 50 μL) consisted of CD3 PerCP-Cy5.5 (Biolegend), CD4 BV421 (Biolegend), and CD8 APC-Cy7 (Biolegend). After extracellular staining, cells were fixed using Foxp3/Transcription Factor Staining Buffer Set (eBioscience) and stained for intracellular proteins (1:50 dilution) using TNFα FITC (R&D Systems) and IFNγ BV785 (Biolegend). Cells were washed and resuspended in stain buffer and analyzed using a BD Celesta flow cytometer.

Flow cytometry cell staining analysis was completed using FlowJo v10. Cells were gated on live, singlet, CD3+ cells. The CD8+ T cells were analyzed for TNFα/IFNγ expression and the frequency of double positive TNFα/IFNγ CD8+ T cells was recorded. Responses were assessed to be positive when the frequency of double positive TNFα/IFNγ CD8+ T cells due to stimulation with an experimental peptide was increased greater than or equal to 2-fold over the DMSO only negative control for that patient. Peptides were analyzed in 1 to 7 patient samples.

In Vitro Immunogenicity Assessment of Neoantigens ("Exogenous Autologous Normal Donor Restimulation Assay")

CD 1c+Dendritic Cells (DC) isolated from human normal PBMCs were thawed using media (IMDM (Gibco) supplemented with glutamine, HEPES, 5% human serum (Sigma), and 1× Pen-Strep). DC cells were resuspended in media supplemented with IL-4 (Peprotech, 80 ng/mL) and GM-CSF (Gibco, 80 ng/mL), plated in 6 well microplates, and rested overnight at 37° C. (5% $CO_2$). The following day, DC cells were counted and plated in a 96 well round bottom microplate at a concentration of 30,000 viable cells per well. Lyophilized peptides (15-mer overlapping peptides) were solubilized in 100% DMSO and pooled by neoantigen to between 5 mg/mL and 20 mg/mL. Neoantigen peptides pools were added to DCs for a final concentration of 2.5 μg/mL to 10 μg/mL and rested for 2 hours at 37° C. (5% $CO_2$). CEF Peptide Pool "Plus" (Cellular Technologies, Ltd.) was utilized as a positive control and DMSO at the same final concentration as the experimental peptides was utilized as a negative control. After 2 hours, DC cells were irradiated with 50 gray of ionizing radiation. Autologous CD3+ Pan-T cells isolated from human normal PBMCs were thawed using media. Following irradiation, autologous Pan-T cells were added to the irradiated DCs at 300,000 viable cells per well. Human IL-15 (Peprotech) was added to all wells at final concentration of 10 ng/mL.

Plates were incubated at 37° C. (5% $CO_2$) for a total of 12 days. Media was refreshed every 2-3 days with IL-15 (10 ng/mL final concentration) and IL-2 (R&D systems, 10 IU/mL final concentration). On day 11 cells were re-stimulated with identical experimental peptide pools or controls, at same concentration as peptide stimulation on Day 1. Protein Inhibitor Cocktail (eBioscience) was added to every well and plate was incubated overnight at 37° C. (5% $CO_2$).

On day 12, cells were stained for intracellular flow cytometry analysis. The cells were washed with PBS and stained with Live/Dead Fixable Aqua Dead Cell stain (Thermo-Fisher). Following the live/dead stain, cells were blocked using Biotin-Free Fe Receptor Blocker (Accurate Chemical & Scientific Corp). Extracellular cellular flow panel (1 μL/antibody per well in 50 μL) consisted of CD3 PerCP-Cy5.5 (Biolegend), CD4 BV421 (Biolegend), and CD8 APC-Cy7 (Biolegend). After extracellular staining, cells were fixed using Foxp3/Transcription Factor Staining Buffer Set (eBioscience) and stained for intracellular proteins (1:50 dilution) using TNFα FITC (R&D Systems) and IFNγ BV785 (Biolegend). Cells were washed and resuspended in stain buffer and analyzed using a BD Celesta flow cytometer.

Flow cytometry cell staining analysis was completed using FlowJo v10. Cells were gated on live, singlet, CD3+ cells. The CD8+ and CD4+ T cells were analyzed for TNFα/IFNγ expression and the frequency of double positive TNFα/IFNγ CD8+ and the frequency of double positive TNFα/IFNγ CD4+ T cells were recorded. Responses were assessed to be positive when the frequency of double positive TNFα/IFNγ CD8+ or TNFα/IFNγ CD4+ T cells due to stimulation with an experimental peptide pool was increased greater than or equal to 3-fold over the DMSO only negative control for that donor and at least 0.01%.

In Vitro Endogenous Immunogenicity Assessment of Neoantigens ("Endogenous Autologous Normal Donor Restimulation Assay")

CD1c+Dendritic Cells (DC) isolated from human normal PBMCs were thawed using media (IMDM (Gibco) supplemented with glutamine, HEPES, 5% human serum (Sigma), and 1× Pen-Strep). DC cells were resuspended in media supplemented with IL-4 (Peprotech, 80 ng/mL) and GM-CSF (Gibco, 80 ng/mL), plated in 6 well microplates, and rested overnight at 37° C. (5% $CO_2$). The following day, DC cells were counted and plated in a 96 well round bottom microplate at a concentration of 30,000 viable cells per well. Ad5 vectors (Vector Biolabs) were dilute in media to an MOI (Multiplicity Of Infection) of 5000 based on Plaque Forming Units. Ad5 vectors for the CEF pool and a "null" were used as controls. DCs were transduced with Ad5 vectors overnight at 37° C. (5% $CO_2$). The following day, the Ad5 vectors were washed off the plate by three sequential centrifugation/aspiration steps using sterile Phosphate Buffered Saline. After the final wash, transduced DCs were resuspended in 100 μL media. Autologous CD3+ Pan-T cells isolated from human normal PBMCs were thawed using media. Pan-T cells were added to the irradiated DCs at 300,000 viable cells per well (100 μL/well). Human IL-15 (Peprotech) was added to all wells at final concentration of 10 ng/mL.

Plates were incubated at 37° C. (5% $CO_2$) for a total of 12 days. Media was refreshed every 2-3 days with IL-15 (10 ng/mL final concentration) and IL-2 (R&D systems, 10 IU/mL final concentration). On day 11 lyophilized peptides (15-mer overlapping peptides) were solubilized in 100% DMSO and pooled by neoantigen to between 5 mg/mL and 20 mg/mL. Neoantigen peptides pools were added to cells for a final concentration of 2.5 μg/mL to 10 μg/mL. CEF Peptide Pool "Plus" (Cellular Technologies, Ltd.) was utilized as a positive control and DMSO at the same final concentration as the experimental peptides was utilized as a negative control. Protein Inhibitor Cocktail (eBioscience) was added to every well and plate was incubated overnight at 37° C. (5% $CO_2$).

On day 12, cells were stained for intracellular flow cytometry analysis. The cells were washed with PBS and stained with Live/Dead Fixable Aqua Dead Cell stain (Thermo-Fisher). Following the live/dead stain, cells were blocked using Biotin-Free Fe Receptor Blocker (Accurate Chemical & Scientific Corp). Extracellular cellular flow panel (1 μL/antibody per well in 50 μL) consisted of CD3 PerCP-Cy5.5 (Biolegend), CD4 BV421 (Biolegend), and CD8 APC-Cy7 (Biolegend). After extracellular staining, cells were fixed using Foxp3/Transcription Factor Staining Buffer Set (eBioscience) and stained for intracellular proteins (1:50 dilution) using TNFα FITC (R&D Systems) and IFNγ BV785 (Biolegend). Cells were washed and resuspended in stain buffer and analyzed using a BD Celesta flow cytometer.

Flow cytometry cell staining analysis was completed using FlowJo v10. Cells were gated on live, singlet, CD3+ cells. The CD8+ and CD4+ T cells were analyzed for TNFα/IFNγ expression and the frequency of double positive TNFα/IFNγ CD8+ and the frequency of double positive TNFα/IFNγ CD4+ T cells were recorded. Responses were assessed to be positive when the frequency of double positive TNFα/IFNγ CD8+ or TNFα/IFNγ CD4+ T cells due to stimulation with an experimental peptide pool was increased greater than or equal to 3-fold over the DMSO only negative control for that donor and at least 0.01%.

In Vitro Binding of Neoantigens to Class I MHC

The 9 mer peptides identified by bioinformatics analysis were analyzed for their binding propensities to 6 common HLA class I alleles (HLA-A*01:01, A*02:01, A*03:01, A*24:02, B*07:02, B*08:01). The principle of the method is briefly described below and consists of two parts, one involving exchange of peptide with a positive control induced by Ultraviolet (UV) radiation, and the second is an enzyme immunoassay to detect stable HLA-peptide and empty HLA complexes.

HLA-bound peptides are critical for the stability of the HLA complex. A conditional HLA class I complex was stabilized by an UV-labile peptide utilizing a different peptide (Pos) for each HLA (Pos: HLA-A*01:01: CTELKLSDY(SEQ ID NO: 409), HLA-A*02:01: NLVPMVATV (SEQ ID NO: 410), HLA-A*03:01: LIYRRRLMK (SEQ ID NO: 411), HLA-A*24:02: LYSACFWWL (SEQ ID NO: 412), HLA-B*07:02: NPKASLLSL (SEQ ID NO: 413), HLA-B*08:01: ELRSRYWAI (SEQ ID NO: 414), which could be cleaved by UV irradiation when bound to the HLA molecule. Upon cleavage, the resulting peptide fragments dissociated from the HLA class I complex since their length was insufficient to bind stably to HLA. Under the conditions in which peptide cleavage was performed (neutral pH, on melting ice), the peptide-free HLA complex remained stable. Thus, when cleavage was performed in the presence of another HLA class I peptide of choice, this reaction resulted in net exchange of the cleaved UV-labile peptide Pos with the chosen peptide (Rodenko, B et al. (2006) Nature Protocols 1: 1120-32, Toebes, M et al. (2006) Nat Med 12: 246-51, Bakker, A H et al. (2008) Proc Natl Acad Sci USA 105: 3825-30).

The exchange efficiency between the peptide of interest and Pos was analyzed using an HLA class I ELISA. The combined technologies allowed the identification of ligands for an HLA molecule of interest which are potentially immunogenic.

Exchange control peptide Pos was a high affinity binder to the relevant HLA class I allele while exchange control peptide Neg was a non-binder. The UV control represented UV-irradiation of conditional HLA class I complex in the absence of a rescue peptide. The binding of exchange control peptide Neg (HLA-A*01:01: NPKASLLSL (SEQ ID NO: 413), HLA-A*02-01: IVTDFSVIK (SEQ ID NO: 416), HLA-A*03:01: NPKASLLSL (SEQ ID NO: 413), HLA-A*24:02: NLVPMVATV (SEQ ID NO: 410), HLA-B*07:02: LIYRRRLMK (SEQ ID NO: 411), HLA-B*08:01: NLVPMVATV (SEQ ID NO: 410) and all experimental peptides were evaluated relative to that of exchange control peptide Pos. The absorption of the latter peptide was set at 100%. This procedure resulted in a range of different exchange percentages that reflected the affinities of the different experimental peptides for the HLA allele used.

The HLA class I ELISA is an enzyme immunoassay based on the detection of beta2-microglobulin (B2M) of (peptide-stabilized) HLA class I complexes. To this end streptavidin was bound onto polystyrene microtiter wells. After washing and blocking, HLA complex present in exchange reaction mixtures or ELISA controls was captured by the streptavidin on the microtiter plate via its biotinylated heavy chain. Non-bound material was removed by washing. Subsequently, horseradish peroxidase (HRP)-conjugated antibody to human B2M was added. The HRP-conjugated antibody binds only to an intact HLA complex present in the microtiter well because unsuccessful peptide exchange results in disintegration of the original UV-sensitive HLA complex upon UV illumination. In the latter case B2M was removed during the washing step. After removal of non-bound HRP conjugate by washing, a substrate solution was added to the wells. A coloured product formed in proportion to the amount of intact HLA complex present in the samples. After the reaction was terminated by the addition of a stop solution, absorbance was measured in a microtiter plate reader. The absorbance was normalized to the absorbance of an exchange control peptide (represents 100%). Suboptimal HLA binding of peptides with a moderate to low affinity for HLA class I molecules can also be detected by this ELISA technique (Rodenko, B et al. (2006) Nature Protocols 1: 1120-32).

Peptides that had 10% or greater exchange efficiency in one of the 6 HLA alleles were considered for further immunogenicity testing and analysis.

Example 2. Identification of Neoantigens by Bioinformatics

A computational framework was developed to analyze various prostate cancer RNA-seq datasets by bioinformatics means to identify common prostate cancer neoantigens resulting from aberrant transcriptional programs such as gene fusion events, intron retention, alternatively spliced variants and aberrant expression of developmentally silenced genes.

The datasets queried were:

The Genotype-Tissue Expression (GTEx) Consortium. This dataset encompasses 6137 RNA-seq datasets from 49 normal tissues and was used to annotate RNA features in normal tissues and assess frequency of potential prostate neoantigen candidates in normal tissue.

The Cancer Genome Atlas Prostate Adenocarcinoma (TCGA PRAD) (Cancer Genome Atlas Research Network. Cell. 2015 Nov. 5; 163(4):1011-25. doi: 10.1016/j.cell.2015.10.025). This dataset encompasses RNA-seq datasets from 508 prostate cancer subjects and was used to identify neoantigen candidates in localized prostate adenocarcinoma.

Stand Up To Cancer (SU2C) (Robinson D et al., Cell. 2015 May 21; 161(5):1215-1228. doi: 10.1016/j.cell.2015.05.001). This dataset encompasses RNA-seq datasets from 43 mCRPC subjects.

Quality control (QC) of raw data was conducted prior to analysis. Sequencing reads were first trimmed to remove Illumina's adapter sequences and reads mapping to human tRNA and rRNA were removed from downstream analysis. Reads were also trimmed of bases with poor base quality score (<10, PHRED scale; indicating a base with a 1 in 10 probability of being incorrect) at either ends. PHRED quality score measures the quality of the identification of the bases generated by automated DNA sequencing instruments. Trimmed reads with less than 25 bps were removed from the datasets. Additionally, following QC steps were considered to remove poor quality reads: remove reads having maximal base quality PHRED score of <15, remove reads with average base quality PHRED score of <10, remove reads having polyATCG rate >80%, remove RNA sequences in which one of the two reads failed.

Reads that passed the QC criteria were mapped to Human Genome Build 38 using ArrayStudio ((https_//www_omicsoft_com/array-studio/) platform. Refseq gene model (release date Jun. 6, 2017) was used for annotation of novel RNA features.

The results published here are in whole or part based upon data generated by The Cancer Genome Atlas managed by the NCJ and NHGRJ. Information about TCGA can be found at http://_cancergenme_nih_gov.

Identification of Gene Fusion Events

FusionMap algorithm (Ge H et al., Bioinformatics. 2011 Jul. 15; 27(14):1922-8. doi: 10.1093/bioinformatics/btr310. Epub 2011 May 18) was used to identify gene fusion events in the prostate cancer datasets described above. FusionMap detects fusion junctions based on seed reads which contain the fusion breakpoint position in the middle region of the reads. The algorithm dynamically creates a pseudo fusion transcript/sequence library based on the consensus of mapped fusion junctions from the seed reads. FusionMap then aligns unmapped possible fusion reads to the pseudo fusion reference to further identify rescued reads. The program reports a list of detected fusion junctions, statistics of supporting reads, fusion gene pairs, as well as genomic locations of breakpoints and junction sequences, which characterize fusion genes comprehensively at base-pair resolution.

Figure 2:
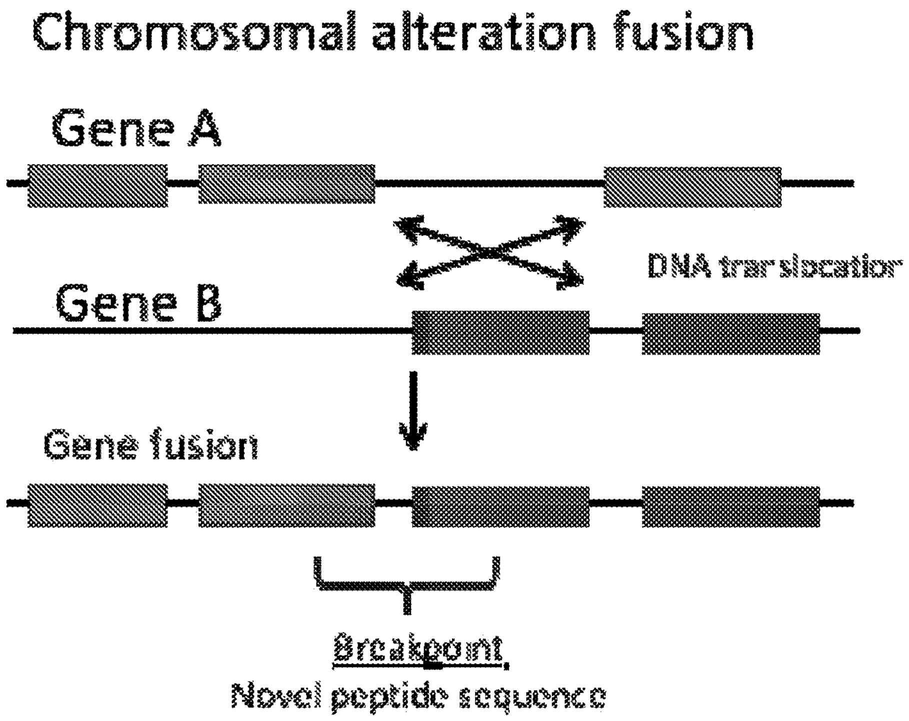
FIG. 2 shows a cartoon of gene fusions resulting from chromosomal alteration, such as DNA translocations.

Neoantigens originating from chimeric read-through fusions as shown in FIG. 1 and fusions resulting from chromosomal alterations as shown in FIG. 2 were identified using FusionMap. Neoantigens were classified as originating from gene fusion events when following criteria were met: fusion junction was supported by at least two seed reads with different mapping positions in the genome, at least 4 sequencing reads (seed and rescued reads) parsing the junction, and at least one junction spanning read. The prevalence of neoantigens were queried in tumor tissue and normal tissue using the datasets mentioned above. Neoantigens were identified as common when the prevalence was identified to be >10% in at least one disease cohort (TCGA and SU2C) and <2% in normal tissue (6137 RNA-seq datasets from 49 normal tissues). Gene fusion events with less than 10% prevalence in disease cohort were included if they generated long stretches of novel peptide sequences or were present in genes of interest.

Identification of Splice Variants

Figure 3:
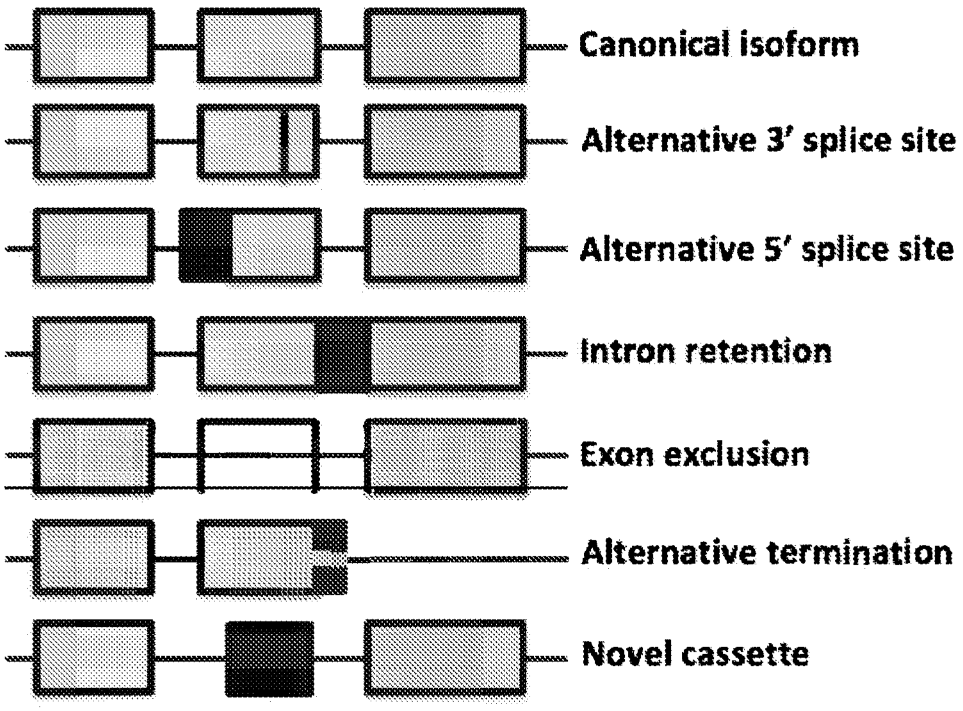
FIG. 3 shows a cartoon of splice variants with alternative 5' or 3' splice sites, retained introns, excluded exons or alternative terminations or insertions.
Figure 4:
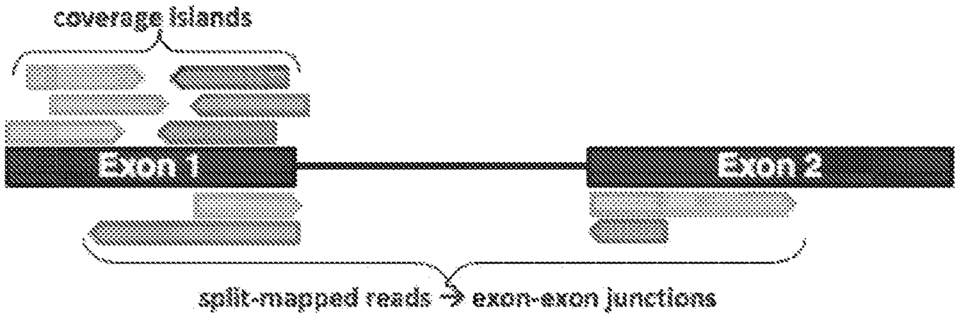
FIG. 4 shows the cartoon for approach of identification of splice variants.

A custom bioinformatic software was developed to analyze paired-end RNA-seq data to identify potential neoantigens arising from alternative splicing events. Utilizing the developed process, splice variants with alternative 5' or 3' splice sites, retained introns, excluded exons, alternative terminations or insertion(s) of novel cassettes as show in in FIG. 3 were identified. The process identified splice variants that were not present in the RefSeq gene model through two main functionalities: 1) Identification of novel junctions based on reads with gaps of 6 or more bp and sequences of at least 15 bp aligned on each side of the gap, henceforth referred to as split-mapped reads. Novel junctions were reported if they were represented by at least 5 split-mapped reads and one mate pair of reads flanking the junction on each end. 2) Identification of islands of aligned reads, henceforth referred to as coverage islands. Further details on parameters used for determining island boundaries are described below. FIG. 4 shows the cartoon of the approach.

In order to differentiate reads mapping to intronic regions due to true splicing variation as opposed to genomic DNA and/or pre-mRNA contamination, two parameters were developed to establish the distribution of contamination across 200 highly expressed housekeeping genes. The tail ends of these distributions were then used as cut-offs for discovery of novel splice variants where relevant.

1. Intron depth of coverage (IDC): $90^{th}$ percentile depth of coverage for all housekeeping intronic bases. If the coverage of a particular region fell below this value, the first base where this occurred was defined as a coverage island boundary.
2. Intron/exon coverage ratio (IECR): $90^{th}$ percentile of the ratio between median intron coverage and median coverage of the nearest upstream exon of all housekeeping gene introns All reported splice variants were required to meet the following criteria:

Alternative 3'15' Splice Site Identification:

Novel splice site was supported by at least 5 split-mapped reads and one mate pair of reads flanking the junction Intronic region resulting from using the splice site (if applicable) exceeded IECR and entire region exceeded IDC Novel Cassette Identification:

Two novel splice sites in an intronic region were supported by at least 5 split-mapped reads and one mate pair of reads flanking the junction Region between the two splice sites exceeded IECR and entire region exceeded IDC Intron Retention Identification:

Intronic region exceeded IECR and entire region exceeded IDC

At least 5 reads span both intron-exon boundaries, with at least 15 bp aligned on each side of the boundaries Alternative Termination Identification:

3' boundary defined as the edge of a coverage island that did not fall within 60 bp of the 3' end of a canonical exon Any intronic regions between 5' end of a canonical exon and the 3' boundary exceeded IECR and entire region exceeded IDC Exon Exclusion Identification:

Novel junction was supported by at least 5 split-mapped reads and one mate pair of reads flanking the junction where one or more canonical exons were skipped Neoantigens derived from aberrant splicing events were identified as common when the incidence was identified to be about >10% in disease cohort (TCGA and SU2C datasets) and about <1% in normal tissue (GTEx Consortium dataset).

Identification of DNA Mutations (Point and Frameshift) Based Neoantigens

The TCGA, SU2C and the integrated DFCI/Sloane Kettering datasets (Integrated DFCI/Sloane Kettering dataset (Armenia et al., Nat Genet. 2018 May; 50(5):645-651. doi: 10.1038/s41588-018-0078-z. Epub 2018 Apr. 2) as described above containing exome sequencing data from patients with prostate cancer were examined. Mutation calls published by the consortia that generated these datasets were downloaded, and gene mutations that were present in >10% of the patient population or in genes known to be drivers of prostate cancer (such as AR) were identified. For each single point mutation chosen, a 17 mer peptide with the mutated amino acid at its center was identified for further validation studies.

Splicing Isoform Prediction

In certain cases, there were multiple reading frames and exons upstream of the identified splicing events that could impact the canonical peptide sequence preceding the neoepitope sequence. In these genes, it was determined which canonical exons neighbored each neoepitope feature based on the split-mapped reads present at the exon boundaries. The most highly expressed isoform with the highest average expression in the disease cohort with the highest prevalence of the event that could contain the predicted neoepitope was chosen for translation into the corresponding protein by choice of the open reading frame associated with the isoform. The neoepitope portion of the protein sequence was extracted, with an additional 8 amino acid residues upstream of the first altered amino acid included and used for subsequent validation studies. A similar procedure was followed to identify putative immunogenic antigens from DNA frameshift alterations. For both frameshift deletions and insertions, the resulting DNA sequence was translated into the corresponding protein by choice of the appropriate open reading frame, and the frameshift altered portion of the protein sequence was extracted, with an additional 8 amino acid residues upstream of the first altered amino acid included.

Table 1 shows the gene origin, the specific mutation, the amino acid sequences of identified neoantigens with single amino acid mutations (M) and frequency in patients. Each mutation is bolded in Table 1. Table 2 shows their corresponding polynucleotide sequences. The mutant sequences are capitalized in Table 2. Patient frequency (%) in Table 1 was obtained from Armenia et al., Nat Genet 50(5): 645-651, 2018.

TABLE 1

| Neo-epitope ID | Gene | Mutation | Patient Frequency (%) | Amino acid sequence | SEQ ID NO: |
|---|---|---|---|---|---|
| M1 | TP53 | R248Q | 1.0859 | SSCMGGMN**Q**RPILTIIT | 1 |
| M2 | TP53 | R248W | 0.0987 | SSCMGGMN**W**RPILTIIT | 3 |
| M3 | TP53 | R273C | 0.6910 | LGRNSFEV**C**VCACPGRD | 5 |
| M4 | TP53 | R273L | 0.3949 | LGRNSFEV**L**VCACPGRD | 7 |
| M5 | TP53 | G245S | 0.6910 | MCNSSCMG**S**MNRRPILT | 9 |
| M6 | TP53 | Y220C | 0.4936 | FRHSVVVP**C**EPPEVGSD | 11 |
| M7 | TP53 | R282W | 0.4936 | VCACPGRD**W**RTEEENLR | 13 |
| M8 | SPOP | F133C | 0.5923 | FVQGKDWG**C**KKFIRRDF | 15 |
| M9 | SPOP | F133I | 0.3949 | FVQGKDWG**I**KKFIRRDF | 17 |
| M10 | SPOP | F133L | 1.1846 | FVQGKDWG**L**KKFIRRDF | 19 |
| M11 | SPOP | F1335 | 0.3949 | FVQGKDWG**S**KKFIRRDF | 21 |
| M12 | SPOP | F133V | 0.9872 | FVQGKDWG**V**KKFIRRDF | 23 |
| M13 | SPOP | W131C | 0.0987 | YRFVQGKD**C**GFKKFIRR | 25 |
| M14 | SPOP | W131G | 1.2833 | YRFVQGKD**G**GFKKFIRR | 27 |
| M15 | SPOP | W131L | 0.1974 | YRFVQGKD**L**GFKKFIRR | 29 |
| M16 | SPOP | W131R | 0.1974 | YRFVQGKD**R**GFKKFIRR | 31 |
| M17 | SPOP | W131S | 0.0987 | YRFVQGKD**S**GFKKFIRR | 33 |
| M18 | KMT2D | R5214H | 0.1974 | YPVGYEAT**H**IYWSLRTN | 35 |
| M19 | FOXA1 | R261C | 0.1974 | MFENGCYL**C**RQKRFKCE | 37 |
| M20 | FOXA1 | H247Q | 0.1974 | GKGSYWTL**Q**PDSGNMFE | 39 |
| M21 | FOXA1 | H247L | 0.0987 | GKGSYWTL**L**PDSGNMFE | 41 |
| M22 | FOXA1 | H247N | 0.0987 | GKGSYWTL**N**PDSGNMFE | 43 |

TABLE 1-continued

| Neo-epitope ID | Gene | Mutation | Patient Frequency (%) | Amino acid sequence | SEQ ID NO: |
|---|---|---|---|---|---|
| M23 | FOXA1 | H247Y | 0.0987 | GKGSYWTLYPDSG NMFE | 45 |
| M24 | FOXA1 | F266C | 0.0987 | CYLRRQKRCKCEK QPGA | 47 |
| M25 | FOXA1 | F266S | 0.0987 | CYLRRQKRSKCEK QPGA | 49 |
| M26 | FOXA1 | D226G | 0.0987 | IRHSLSFNGCFVK VARS | 51 |
| M27 | FOXA1 | D226N | 0.1974 | IRHSLSFNNCFVK VARS | 53 |
| M28 | FOXA1 | R219C | 0.0987 | QQRWQNSICHSLS FNDC | 55 |
| M29 | FOXA1 | R219S | 0.1974 | QQRWQNSISHSLS FNDC | 57 |
| M30 | FOXA1 | M253K | 0.1974 | TLHPDSGNKFENG CYLR | 59 |
| M31 | FOXA1 | M253R | 0.0987 | TLHPDSGNRFENG CYLR | 61 |
| M32 | CDK12 | R858W | 0.1974 | CHKKNFLHWDIKC SNIL | 63 |
| M33 | PTEN | R130Q | 0.2962 | IHCKAGKGQTGVM ICAY | 65 |
| M34 | PTEN | V119F | 0.1974 | WLSEDDNHFAAIH CKAG | 67 |
| M35 | ATM | N2875S | 0.0987 | GLGDRHVQSILIN EQSA | 69 |
| M36 | ATM | N2875K | 0.0987 | GLGDRHVQKILIN EQSA | 71 |
| M37 | KDM6A | C1164S | 0.0987 | NINIGPGDSEWFV VPEG | 73 |
| M38 | KDM6A | C1164Y | 0.0987 | NINIGPGDYEWFV VPEG | 75 |
| M39 | PIK3CA | H1047R | 0.4936 | FMKQMNDARHGGW TTKM | 77 |
| M40 | PIK3CA | E545K | 0.2962 | RDPLSEITKQEKD FLWS | 79 |
| M41 | PIK3CA | E545G | 0.0987 | RDPLSEITGQEKD FLWS | 81 |
| M42 | PIK3CA | E545A | 0.0987 | RDPLSEITAQEKD FLWS | 83 |
| M43 | CTNNB1 | T41A | 0.4936 | SGIHSGATATAPS LSGK | 85 |
| M44 | CTNNB1 | D32A | 0.0987 | HWQQQSYLASGIH SGAT | 87 |
| M45 | CTNNB1 | D32H | 0.0987 | HWQQQSYLHSGIH SGAT | 89 |
| M46 | CTNNB1 | D32V | 0.0987 | HWQQQSYLVSGIH SGAT | 91 |
| M47 | CTNNB1 | D32Y | 0.1974 | HWQQQSYLYSGIH SGAT | 93 |

TABLE 1-continued

| Neo-epitope ID | Gene | Mutation | Patient Frequency (%) | Amino acid sequence | SEQ ID NO: |
|---|---|---|---|---|---|
| M48 | CTNNB1 | S37A | 0.0987 | SYLDSGIHAGATT TAPS | 95 |
| M49 | CTNNB1 | S37C | 0.0987 | SYLDSGIHCGATT TAPS | 97 |
| M50 | CTNNB1 | S37F | 0.0987 | SYLDSGIHFGATT TAPS | 99 |
| M51 | CTNNB1 | S37Y | 0.0987 | SYLDSGIHYGATT TAPS | 101 |
| M52 | CTNNB1 | S45C | 0.0987 | SGATTTAPCLSGK GNPE | 103 |
| M53 | CTNNB1 | S45F | 0.0987 | SGATTTAPFLSGK GNPE | 105 |
| M54 | CTNNB1 | S45P | 0.0987 | SGATTTAPPLSGK GNPE | 107 |
| M55 | COL5A1 | T348K | 0.1974 | YVPSEDYYKPSPY DDLT | 109 |
| M56 | TAF1L | A869T | 0.1974 | IRKRLKLCTDFKR TGMD | 111 |
| M57 | MED12 | L1224F | 0.7897 | VDGAVFAVFKAVF VLGD | 113 |
| M58 | MED12 | V1223G | 0.0987 | IVDGAVFAGLKAV FVLG | 115 |
| M59 | MED12 | V1223L | 0.0987 | IVDGAVFALLKAV FVLG | 117 |
| M60 | MGA | R2435W | 0.1974 | THTANERRWRGEM RDLF | 119 |
| M61 | ARID1A | P1756R | 0.1974 | GRFSKVSSRAPME GGEE | 121 |
| M62 | CUL3 | M299R | 0.4936 | GKTEDLGCRYKLF SRVP | 123 |
| M63 | USP7 | Q4H | 0.4936 | MNHHQQQQQQKA | 125 |
| M64 | SF3B1 | K700E | 0.1974 | HGLVDEQQEVRTI SALA | 127 |
| M65 | U2AF1 | S34F | 0.2962 | VCRHGDRCFRLHN KPTF | 129 |
| M66 | CDC27 | Y73C | 0.1974 | SCTTPQCKCLLAK CCVD | 131 |
| M67 | CDC27 | N260H | 0.1974 | SILSKQVQHKPKT GRSL | 133 |
| M68 | BRAF | G469A | 0.2962 | QRIGSGSFATVYK GKWH | 135 |
| M69 | BRAF | K601E | 0.1974 | GDFGLATVESRWS GSHQ | 137 |
| M70 | RAG1 | R112C | 0.0987 | QANLRHLCCICGN SFRA | 139 |
| M71 | RAG1 | R112H | 0.1974 | QANLRHLCHICGN SFRA | 141 |
| M72 | CNOT3 | E20K | 0.3949 | DRCLKKVSKGVEQ FEDI | 143 |
| M73 | CNOT3 | E70K | 0.2962 | IKTWVASNKIKDK RQLI | 145 |

TABLE 1-continued

| Neo-epitope ID | Gene | Mutation | Patient Frequency (%) | Amino acid sequence | SEQ ID NO: |
|---|---|---|---|---|---|
| M74 | PIK3CB | E1051K | 0.2962 | QKFDEALR**K**SWTTKVNW | 147 |
| M75 | IDH1 | R132C | 0.1974 | WVKPIIIG**C**HAYGDQYR | 149 |
| M76 | IDH1 | R132G | 0.0987 | WVKPIIIG**G**HAYGDQYR | 151 |
| M77 | IDH1 | R132H | 0.4936 | WVKPIIIG**H**HAYGDQYR | 153 |
| M78 | KRAS | G12D | 0.1974 | YKLVVVGA**D**GVGKSALT | 155 |
| M79 | KRAS | G12R | 0.2962 | YKLVVVGA**R**GVGKSALT | 157 |
| M80 | KRAS | Q61K | 0.2962 | LDILDTAG**K**EEYSAMRD | 159 |
| M81 | KRAS | Q61L | 0.0987 | LDILDTAG**L**EEYSAMRD | 161 |
| M82 | KRAS | Q61R | 0.0987 | LDILDTAG**R**EEYSAMRD | 163 |
| M83 | AKT1 | E17K | 0.4936 | EGWLHKRG**K**YIKTWRPR | 165 |
| M84 | AR | T878A | 1.2833 | IARELHQF**A**FDLLIKSH | 167 |
| M85 | AR | T878G | 0.0987 | IARELHQF**G**FDLLIKSH | 169 |
| M86 | AR | L702H | 1.0859 | QPDSFAAL**H**SSLNELGE | 171 |
| M87 | AR | W742L | 0.1974 | QMAVIQYS**L**MGLMVFAM | 173 |
| M88 | AR | W742F | 0.0987 | QMAVIQYS**F**MGLMVFAM | 175 |

TABLE 2

| Neoepitope ID | Polynucleotide sequence | SEQ ID NO: |
|---|---|---|
| M1 | agttcctgcatgggcggcatgaaccAgaggcccatcctcaccatcatcaca | 2 |
| M2 | agttcctgcatgggcggcatgaaTTggaggcccatcctcaccatcatcaca | 4 |
| M3 | ctgggacggaacagctttgaggtgTgtgtttgtgcctgtcctgggagagac | 6 |
| M4 | ctgggacggaacagctttgaggtgcTtgtttgtgcctgtcctgggagagac | 8 |
| M5 | atgtgtaacagttcctgcatgggcAgcatgaaccggaggcccatcctcacc | 10 |
| M6 | tttcgacatagtgtggtggtgccctGtgagccgcctgaggttggctctgac | 12 |
| M7 | gtttgtgcctgtcctgggagagaTTggcgcacagaggaagagaatctccgc | 14 |
| M8 | tttgtgcaaggcaaagactggggatGcaagaaattcatccgtagagatttt | 16 |
| M9 | tttgtgcaaggcaaagactggggaAtcaagaaattcatccgtagagatttt | 18 |
| M10 | tttgtgcaaggcaaagactggggattAaagaaattcatccgtagagatttt | 20 |
| M11 | tttgtgcaaggcaaagactggggatCcaagaaattcatccgtagagatttt | 22 |
| M12 | tttgtgcaaggcaaagactggggaGtcaagaaattcatccgtagagatttt | 24 |
| M13 | tataggtttgtgcaaggcaaagactgTggattcaagaaattcatccgtaga | 26 |
| M14 | tataggtttgtgcaaggcaaagacGggggattcaagaaattcatccgtaga | 28 |
| M15 | tataggtttgtgcaaggcaaagactggggattcaagaaattcatccgtaga | 30 |
| M16 | tataggtttgtgcaaggcaaagacCggggattcaagaaattcatccgtaga | 32 |
| M17 | tataggtttgtgcaaggcaaagactCgggattcaagaaattcatccgtaga | 34 |
| M18 | tatcccgtgggctacgaggccacgcAcatctattggagcctccgcaccaac | 36 |
| M19 | atgttcgagaacggctgctacttgTgccgccagaagcgcttcaagtgcgag | 38 |
| M20 | ggcaagggctcctactggacgctgcaGccggactccggcaacatgttcgag | 40 |
| M21 | ggcaagggctcctactggacgctgcTcccggactccggcaacatgttcgag | 42 |
| M22 | ggcaagggctcctactggacgctgAacccggactccggcaacatgttcgag | 44 |

TABLE 2-continued

| Neoepitope ID | Polynucleotide sequence | SEQ ID NO: |
|---|---|---|
| M23 | ggcaagggctcctactggacgctgTacccggactccggcaacatgttcgag | 46 |
| M24 | tgctacttgcgccgccagaagcgctGcaagtgcgagaagcagccgggggcc | 48 |
| M25 | tgctacttgcgccgccagaagcgctCcaagtgcgagaagcagccgggggcc | 50 |
| M26 | atccgccactcgctgtccttcaatgGctgcttcgtcaaggtggcacgctcc | 52 |
| M27 | atccgccactcgctgtccttcaatAactgcttcgtcaaggtggcacgctcc | 54 |
| M28 | cagcagcgctggcagaactccatcTgccactcgctgtccttcaatgactgc | 56 |
| M29 | cagcagcgctggcagaactccatcAgccactcgctgtccttcaatgactgc | 58 |
| M30 | acgctgcacccggactccggcaacaAgttcgagaacggctgctacttgcgc | 60 |
| M31 | acgctgcacccggactccggcaacaGgttcgagaacggctgctacttgcgc | 62 |
| M32 | tgtcacaaaaagaatttcctgcatTgggatattaagtgttctaacattttg | 64 |
| M33 | attcactgtaaagctggaaagggacAaactggtgtaatgatatgtgcatat | 66 |
| M34 | tggctaagtgaagatgacaatcatTttgcagcaattcactgtaaagctgga | 68 |
| M35 | ggacttggtgatagacatgtacagaGtatcttgataaatgagcagtcagca | 70 |
| M36 | ggacttggtgatagacatgtacagaaAatcttgataaatgagcagtcagca | 72 |
| M37 | aacataaatattggcccaggtgactCtgaatggtttgttgttcctgaaggt | 74 |
| M38 | aacataaatattggcccaggtgactAtgaatggtttgtttcctgaaggt | 76 |
| M39 | ttcatgaaacaaatgaatgatgcacGtcatggtggctggacaacaaaaatg | 78 |
| M40 | cgagatcctctctctgaaatcactAagcaggagaaagattttctatggagt | 80 |
| M41 | cgagatcctctctctgaaatcactgGgcaggagaaagattttctatggagt | 82 |
| M42 | cgagatcctctctctgaaatcactgCgcaggagaaagattttctatggagt | 84 |
| M43 | tctggaatccattctggtgccactGccacagctccttctctgagtggtaaa | 86 |
| M44 | cactggcagcaacagtcttacctggCctctggaatccattctggtgccact | 88 |
| M45 | cactggcagcaacagtcttacctgCactctggaatccattctggtgccact | 90 |
| M46 | cactggcagcaacagtcttacctggTctctggaatccattctggtgccact | 92 |
| M47 | cactggcagcaacagtcttacctgTactctggaatccattctggtgccact | 94 |
| M48 | tcttacctggactctggaatccatGctggtgccactaccacagctccttct | 96 |
| M49 | tcttacctggactctggaatccattGtggtgccactaccacagctccttct | 98 |
| M50 | tcttacctggactctggaatccattTtggtgccactaccacagctccttct | 100 |
| M51 | tcttacctggactctggaatccattAtggtgccactaccacagctccttct | 102 |
| M52 | tctggtgccactaccacagctccttGtctgagtggtaaaggcaatcctgag | 104 |
| M53 | tctggtgccactaccacagctccttTtctgagtggtaaaggcaatcctgag | 106 |
| M54 | tctggtgccactaccacagctcctCctctgagtggtaaaggcaatcctgag | 108 |
| M55 | tacgtgcccagtgaggactactacaAgccctcaccgtatgatgacctcacc | 110 |
| M56 | atccggaagaggctaaagctctgcActgacttcaaacgcacagggatggat | 112 |
| M57 | gtggatggagccgtgtttgctgttTtcaaggctgtgtttgtacttggggat | 114 |
| M58 | atcgtggatggagccgtgtttgctgGtctcaaggctgtgtttgtacttggg | 116 |
| M59 | atcgtggatggagccgtgtttgctCttctcaaggctgtgtttgtacttggg | 118 |
| M60 | acacacactgccaatgagcggcggTggcgtggtgaaatgagggatctcttt | 120 |

TABLE 2-continued

| Neoepitope ID | Polynucleotide sequence | SEQ ID NO: |
|---|---|---|
| M61 | gggaggttcagcaaggtgtctagtcGagctcccatggagggtggggaagaa | 122 |
| M62 | ggaaagacagaagaccttggttgcaGgtacaagttatttagtcgtgtgcca | 124 |
| M63 | atgaaccaccaCcagcagcagcagcagcagaaagcg | 126 |
| M64 | catggtcttgtggatgagcagcagGaagttcggaccatcagtgctttggcc | 128 |
| M65 | gcatgtcgtcatggagacaggtgctTtcggttgcacaataaaccgacgttt | 130 |
| M66 | agttgtactacaccgcaatgcaaatGcctgcttgcaaaatgttgtgttgat | 132 |
| M67 | tccatattatctaaacaggttcaaCataaaccaaaaactggtcgaagttta | 134 |
| M68 | caaagaattggatctggatcatttgCaacagtctacaagggaaagtggcat | 136 |
| M69 | ggtgattttggtctagctacagtgGaatctcgatggagtgggtcccatcag | 138 |
| M70 | caagccaaccttcgacatctctgcTgcatctgtgggaattcttttagagct | 140 |
| M71 | caagccaaccttcgacatctctgccAcatctgtgggaattcttttagagct | 142 |
| M72 | gatcgctgcctcaagaaggtgtccAagggcgtggagcagtttgaagatatt | 144 |
| M73 | atcaagacatgggtagcgtccaacAagatcaaggacaagaggcagcttata | 146 |
| M74 | caaaaatttgatgaggcgctcaggAaaagctggactactaaagtgaactgg | 148 |
| M75 | tgggtaaaacctatcatcataggtTgtcatgcttatggggatcaatacaga | 150 |
| M76 | tgggtaaaacctatcatcataggtGgtcatgcttatggggatcaatacaga | 152 |
| M77 | tgggtaaaacctatcatcataggtcAtcatgcttatggggatcaatacaga | 154 |
| M78 | tataagctggtggtggtgggcgccgAcggtgtgggcaagagtgcgctgacc | 156 |
| M79 | tataagctggtggtggtgggcgccCgcggtgtgggcaagagtgcgctgacc | 158 |
| M80 | ttggacatcctggataccgccggAAaggaggagtacagcgccatgcgggac | 160 |
| M81 | ttggacatcctggataccgccggccTggaggagtacagcgccatgcgggac | 162 |
| M82 | ttggacatcctggataccgccggccGggaggagtacagcgccatgcgggac | 164 |
| M83 | gagggttggctgcacaaacgagggAagtacatcaagacctggcggccacgc | 166 |
| M84 | attgcgagagagctgcatcagttcGcttttgacctgctaatcaagtcacac | 168 |
| M85 | attgcgagagagctgcatcagttcGGttttgacctgctaatcaagtcacac | 170 |
| M86 | cagcccgactcctttgcagccttgcActctagcctcaatgaactgggagag | 172 |
| M87 | cagatggctgtcattcagtactcctTgatggggctcatggtgtttgccatg | 174 |
| M88 | cagatggctgtcattcagtactcctTTatggggctcatggtgtttgccatg | 176 |

Table 3 shows the gene origin, the specific frameshift mutation (FR), the amino acid sequences of the identified neoantigens that arose from frameshift events and frequency of the mutation in patients. The wild-type sequence is bolded in Table 3, followed by the novel sequence due to frameshift. Table 4 shows their corresponding polynucleotide sequences. The mutant sequences are capitalized in Table 4. Patient frequency (%) in Table 3 was obtained from Armenia et al., *Nat Genet* 50(5): 645-651, 2018.

TABLE 3

| Neoepitope ID | Gene | Frameshift | Patient Frequency (%) | Amino acid sequence | SEQ ID NO: |
|---|---|---|---|---|---|
| FR1 | ZFHX3 | E763Sfs*61 | 0.2962 | **QNLQNGGG**SRSSATLPGRRRRRRWLRRRRQPISVAPAGPPRPNQKPNPPGGARCVIMRPTWPGTSAFT | 177 |
| FR2 | ZFHX3 | E763Gfs*26 | 0.0987 | **QNLQNGGG**GAGLQPHCRGGGGGGGCGGGGSQYQ | 179 |
| FR3 | APC | T1556Nfs*3 | 0.3949 | **NQEKEAEK**NY | 181 |
| FR4 | SPEN | A2105Lfs*33 | 0.1974 | **DAAVSPRG**LQHRQGRGNLGWWQSPLRKVRVPKRRMVYHPS | 183 |
| FR5 | BRCA2 | T3085Nfs*26 | 0.1974 | **FVVSVVKK**NRTCPFRLFVRRMLQFTGNKVLDRP | 185 |
| FR6 | BRCA2 | K2674Rfs*2 | 0.1974 | **RSRRSAIK**R | 187 |
| FR7 | ARID4A | S1067Rfs*16 | 0.2962 | **SIIVQERE**RAERRVRRGQVMEIVD | 189 |
| FR8 | SMARCAD1 | N770Kfs*28 | 0.1974 | **NNLVTEKK**HRNVQCHDAVEENGQSSFITSPILHS | 191 |
| FR9 | RNF43 | G659Vfs*41 | 0.3949 | **HPQRKRRG**VPPSPPLALGPRMQLCTQLARFFPITPPVWHILGPQRHTP | 193 |
| FR10 | AXIN2 | G665Afs*24 | 0.1974 | **ASRHHLWG**ATAGTPAPPPVPTCSPRTLRCLP | 195 |
| FR11 | ERF | L525Sfs*6 | 0.2962 | **GPGEAGGP**SPQGG | 197 |
| FR12 | ERF | G299Efs*12 | 0.2962 | **GGGPSGSG**EAPTSPSALRT | 199 |
| FR13 | CHD3 | R599Vfs*16 | 0.3949 | **GNPDVPPP**VLFKADQSESSLSSG | 201 |
| FR14 | KMT2C | S143Vfs*3 | 0.2962 | **AFCYCGEK**VP | 203 |
| FR15 | FOXA1 | M253_N256del | 0.0987 | **TLHPDSGN**GCYLRRQK | 205 |
| FR16 | FOXA1 | F254_N256delinsY | 0.2962 | **LHPDSGNM**YGCYLRRQ | 207 |
| FR17 | FOXA1 | F254_G257delinsC | 0.0987 | **LHPDSGNM**CCYLRRQKR | 209 |

TABLE 4

| Neoantigen ID | Polynucleotide sequence | SEQ ID NO: |
|---|---|---|
| FR1 | Cagaacctgcagaatggaggggggagcaggtcttcagccacactgccggggcggcggcggcg gcggtggctgcggcggcggcggcagccaatatcagtagctcctgcggggcccctcgccgac caaaccaaaaaccaaacccacctggcggtgcgaggtgtgtgattatgagaccaacgtggcca ggaacctccgcattcaca | 178 |
| FR2 | cagaacctgcagaatggaggggggGgagcaggtcttcagccacactgccggggcggcggcgg cggcggtggctgcggcggcggcggcagccaatatcagtag | 180 |
| FR3 | aaccaagagaaagaggcagAaaaaaactattga | 182 |
| FR4 | gatgctgctgtcagtcccagggggctgcagcacaggcaggggagagggaatctggggtggtg gcagtctcccctgagaaaagtgagagtccccaaaaggaggatggtttatcatcccagttga | 184 |
| FR5 | tttgtcgtttctgttgtgaAaaaaaacaggacttgcccctttcgtctatttgtcagacgaat gttacaatttactggcaataaagttttggatagaccttaa | 186 |
| FR6 | agaagcagaagatcggctataaaaagataatg | 188 |
| FR7 | agtataattgtacaAGagagagagagagcagagagaagggtcagaagaggccaagtgatgga aatagtggattaa | 190 |
| FR8 | aataacttggtcacagAaaaaaaacacagaaatgtgcaatgtcatgatgcagttgaggaaaa tggccaatcatcctttattacatcgccaatattacacagctgaaa | 192 |
| FR9 | cacccacagaggaaaaggcggggggtccctccgagcccacccctggctctcggccccaggat gcaactgtgcacccagcttgccagattttttccccattacaccccagtgtggcatatccttg gtccccagaggcacaccccttgatc | 194 |
| FR10 | gccagccggcaccatctgtgggggggcaacagcgggcacccccgcaccaccccccgtgcccac ctgttcacccaggaccctgcgatgcctcccctgacc | 196 |
| FR11 | gggcctggggaggctgggggcccctcaccccaaggcgggtgagc | 198 |
| FR12 | ggcggggggcccagcggctcaggggaggctcccacttctccttcagccctgaggacatgaaa | 200 |
| FR13 | ggaaatccagatgtcccacccccccgtcctcttcaaggcagatcagagcgagagttctttgtc aagtgggtag | 202 |
| FR14 | gctttttgttactgtggggaaaaagttccttagga | 204 |
| FR15 | acgctgcacccggactccggcaacggctgctacttgcgccgccagaagcg | 206 |
| FR16 | acgctgcacccggactccggcaacatgtacggctgctacttgcgccgccagaa | 208 |
| FR17 | ctgcacccggactccggcaacatgtgctgctacttgcgccgccagaagcgc | 210 |

Table 5 shows the gene origin and amino acid sequences of the identified neoantigens that arose from gene fusion (FUS) events. Table 6 shows their corresponding polynucleotide sequences. Table 7 shows the prevalence of the FUS neoantigens in analyzed databases.

TABLE 5

| Neo-antigen ID | Fusion Gene | Amino acid sequence | SEQ ID NO: |
|---|---|---|---|
| FUS1 | SLC45A3->ELK4 | CGASACDVSLIAMDSA | 211 |
| FUS2 | ARHGEF38->ARHGEF38-IT1 | TEYNQKLQVNQFSESK | 213 |
| FUS3 | MSMB->NCOA4 | TEISCCTLSSEENEY LPRPEWQLQ | 215 |

TABLE 5-continued

| Neo-antigen ID | Fusion Gene | Amino acid sequence | SEQ ID NO: |
|---|---|---|---|
| FUS4 | LIPE->CNFN | GLVSFGEHFCLPCALC | 217 |
| FUS5 | TMPRSS2->ERG | NSKMALNSEALSVVSE | 219 |
| FUS6 | TMPRSS2->ERG | CEERGAAGSLISCE | 221 |
| FUS7 | NME4->DECR2 | LWFQSSELSPTGAPWP SRRPTWRGTTVSPRTA TSSARTCCGTKWPSSQ EAALGLGSGLLRFSCG TAAIR | 223 |
| FUS8 | INCA1->CAMTA2 | WGMELAASRRFSWDHH SAGGPPRVPSVRSGAA QVQPKDPLPLRTLAGC LARTAHLRPGAESLPQ PQLHCT | 225 |

TABLE 5-continued

| Neo-antigen ID | Fusion Gene | Amino acid sequence | SEQ ID NO: |
|---|---|---|---|
| FUS9 | AP5S1->MAVS | KEQILAVASLVSSQSIHPSWGQSPLSRI | 227 |
| FUS10 | DIP2A->DIP2A-IT1 | LELELSEGVCFRLR | 229 |
| FUS11 | MBTPS2->YY2 | QQLRIFCAAMASNEDFS | 231 |
| FUS15 | D2HGDH->GAL3ST2 | HVVGYGHLDTSGSSSSSSWP | 345 |
| FUS18 | OPN3->CHML | DGFSGSLFAVVTRRCYFLKWRTIFPQSLMWL | 233 |
| FUS19 | GTF2F1->PSPN | KMHFSLKEHPPPPCPP | 235 |
| FUS23 | NUDT14->JAG2 | DLRRVATYCAPLPSSWRPGTGTTIPPRMRSC | 237 |
| FUS24 | DMPK->SIX5 | LQERMELLACGAERGAGGWGGGGGGGGDRRGGGGSAPALADFAGGRG | 239 |

TABLE 6

| Neo-antigen ID | Polynucleotide sequence | SEQ ID NO: |
|---|---|---|
| FUS1 | TGCGGGGCCTCTGCCTGTGATGTCTCCCTCATTGCTATGGACAGTGCT | 212 |
| FUS2 | ACCGAATACAACCAGAAATTACAAGTGAATCAATTTAGTGAATCCAAA | 214 |
| FUS3 | ACAGAAATTTCATGTTGCACCCTGAGCAGTGAGGAGAATGAATACCTTCCAAGACCAGAGTGGCAGCTCCAG | 216 |
| FUS4 | GGGCTGGTGTCCTTCGGGGAGCACTTTTGTCTGCCCTGCGCCCTCTGCCA | 218 |
| FUS5 | AACAGCAAGATGGCTTTGAACTCAGAAGCCTTATCAGTTGTGAGTGAG | 220 |
| FUS6 | TGTGAGGAGCGCGGCGCGGCAGGAAGCCTTATCAGTTGTGAG | 222 |
| FUS7 | CTGTGGTTCCAGAGCAGTGAGCTGTCCCCGACGGAGCGCCATGGCCCAGCCGCCGCCCGACGTGGAGGGGGACGACTGTCTCCCCGCGTACCGCCACCTCTTCTGCCCGGACCTGCTGCGGGACAAAGTGGCCTTCATCACAGGAGGCGGCTCTGGGATTGGGTTCCGGATTGCTGAGATTTTCATGCGGCACGGCTGCCATACGG | 224 |
| FUS8 | TGGGGGATGGAGTTGGCAGCGTCTCGGAGGTTCTCCTGGGACCACCACTCCGCCGGGGGGCCGCCCAGAGTGCCAAGCGTCCGATCCGGCGCCGCCCAAGTGCAGCCCAAGGACCCGCTCCCGCTCCGCACCCTGGCAGGCTGCCTAGCCAGGACTGCGCACCTGCGCCCTGGGGCGGAGTCCTTACCCCAACCCCAGCTTCACTGCACA | 226 |
| FUS9 | AAGGAACAGATTTTAGCTGTGGCCAGTCTCGTTTCCTCTCAGTCCATCCACCCTTCATGGGGCCAGAGCCCTCTCTCCAGAATC | 228 |
| FUS10 | CTGGAGCTGGAGCTGTCGGAAGGAGTCTGCTTCAGATTAAGA | 230 |
| FUS11 | CAGCAGCTAAGGATATTTGTGCAGCCATGGCCTCCAACGAAGATTTCTCCA | 232 |

TABLE 6-continued

| Neo-antigen ID | Polynucleotide sequence | SEQ ID NO: |
|---|---|---|
| FUS15 | CACGTGGTGGGCTATGGCCACCTTGATACTTCCGGGTCATCCTCCTCCTCCTCCTGGCCC | 346 |
| FUS18 | GACGGGTTTAGCGGCAGCCTCTTCGCAGTTGTCACCAGACGCTGTTACTTCCTAAAATGGCGGACAATCTTCCCACAGAGTTTGATGTGGTTA | 234 |
| FUS19 | AAAATGCACTTCTCCCTCAAGGAGCACCCACCGCCCCCTTGCCCGCCT | 236 |
| FUS23 | GATCTGCGCCGGGTCGCCACATACTGCGCTCCTTTACCCTCATCGTGGAGGCCTGGGACTGGGACAACGATACCACCCCGAATGAGGAGCTGC | 238 |
| FUS24 | TTGCAGGAGCGGATGGAGTTGCTTGCCTGCGGAGCCGAGCGCGGGGCCGGCGGCTGGGGGGGAGGCGGTGGCGGCGGCGGCGGCGACCGAAGAGGAGGAGGAGGAAGCGCGCCAGCTCTTGCAGACTTTGCAGGCGGCCGAGGG | 240 |

TABLE 7

| Neoantigen ID | TCGA (%) | SU2C (%) |
|---|---|---|
| FUS1 | 30.51 | 23.26 |
| FUS2 | 63.58 | 46.51 |
| FUS3 | 35.04 | 23.26 |
| FUS4 | 12.20 | 11.63 |
| FUS5 | 12.40 | 18.60 |
| FUS6 | 21.46 | 32.56 |
| FUS7 | 3.35 | 16.28 |
| FUS8 | 1.18 | 32.56 |
| FUS9 | N.O. | 18.60 |
| FUS10 | N.O. | 13.95 |
| FUS11 | 1.57 | 13.95 |
| FUS15 | 0.39 | 9.30 |
| FUS18 | 0.39 | 9.30 |
| FUS19 | 8.86 | 30.23 |
| FUS23 | N.O. | 9.30 |
| FUS24 | N.O. | 9.30 |

N.O. not observed

Table 8 shows the gene origin and amino acid sequences of the identified neoantigens that arose from alternative splicing (AS) events. Table 9 shows their corresponding polynucleotide sequences. Table 10 shows the prevalence of the AS neoantigens in analyzed databases.

TABLE 8

| Neo epitope ID | Gene | Amino acid sequence | SEQ ID NO: |
|---|---|---|---|
| AS1 | ABCC4 | **LTFLDFIQ**VTLRVMSGSQMENGSSYFFKPFSWGLGVGLSAWLCVMLT | 241 |
| AS2 | SLC30A4 | **FMIGELVG**ELCCQLTFRLPFLESLCQAVVTQALRFNPSFQEVCIYQDTDLM | 243 |
| AS3 | DNAH8 | **VAMMVPDR**QVHYDFGL | 245 |
| AS4 | NCAPD3 | **WCPLDLRL**GSTGCLTCRHHQTSHE | 247 |
| AS5 | DHDH | **VVGRRHET**APQPLLVPDRAGGEGGA | 249 |
| AS6 | ACSM1 | **DYWAQKEK**ISIPRTHLC | 251 |
| AS7 | ACSM1 | **DYWAQKEK**GSSSFLRPSC | 253 |
| AS8 | CACNA1D | **LVLGVLSG**HSGSRL | 255 |

TABLE 8-continued

| Neo epitope ID | Gene | Amino acid sequence | SEQ ID NO: |
|---|---|---|---|
| AS9 | CACNA1D | **PVPTATPG**VRSVTSPQGLGLFLKFI | 257 |
| AS10 | CHRNA5 | **KENDVREV**CDVYLQMQIFFHFKFRSYFH | 259 |
| AS11, AS33 | CPNE7 | **VPFRELKN**QRTAQGAPGIHHAASPVAANLCDPARHAQHTRIPCGAGQVRAGRGPEAGGGVLQPQRPAPEKPGCPCRRGQPRLHTVKMWRA | 261 |
| AS12 | EVPL | **FARKMLEK**VHRQHLQLSHNSQE | 263 |
| AS13 | GRIN3A | **KRSFAVTE**RII | 265 |
| AS14 | IQCG | **MFLRKEQQ**VGPHSFSML | 267 |
| AS15 | LRRC45 | **VLRFLDLK**VRYLHS | 269 |
| AS16 | LRRC45 | **GNTTLQQL**GEASQAPSGSLIPLRLPLLWEVRG | 271 |
| AS17 | MPHOSPH9 | **GLNLNTDR**PGGYSYSIWWKNNAKNR | 273 |
| AS18 | NWD1 | **WKFEMSYT**VGGPPPHVHARPRHWKTDR | 275 |
| AS19 | NWD1 | **QWQHYHRS**GEAAGTPLWRPTRN | 277 |
| AS20 | PFKFB4 | **KVLNEIDA**VVTVPPSLSTSQIPQGCCIIL | 279 |
| AS21 | RECQL4 | **ANLKGTLQ**VRSGQAVSPR | 281 |
| AS22 | TONSL | **LQAAASGQ**GKQGVPCPWGCCAYAESPRALISGDAPSQVEREVPGPCLNTHSLSHRSPQLPGLPHPKQPSV | 283 |
| AS23 | ZNF614 | **KIQNKNCPD** | 285 |
| AS32 | TONSL | **GEVELSEG**GEGQRHLAFPWACSGPGWRGVCCAAVEPA | 287 |
| AS63 | TDRD1 | **IEMKKLLKS** | 289 |
| AS34 | LRRC45 | **KMRAIQAE**GGHGQACCGGAWGWAPGDGGPQGMLTHTLPTLGFQSAWTWRREDADRAWRTPKACASRRWSI | 291 |
| AS35 | AMACR | **LLEPFRR**GEPGPRGLLSGSSRGGEGPGRSIEAAPATPLPCCRKNPCRPQPSRFLPPRVLLVIILPKLDCPKLGF | 293 |
| AS36 | CCNF | **PSGRRTKR**LVTLRSGCAIQCWHPRAGPVPSALPHTERPPRLVRGAADPRTVTLGRSPAVMPRAPA | 295 |
| AS37 | RECQL4 | **CHLFLQPQ**VGTPPPHTASARAPSGPPHPHESCPAGRRPARAAQTCARRQHGLPGCEEAGTARVPSLHLHLHQAALGAGRGRGWGEACAQVPPSRG | 297 |
| AS38 | LRRC45 | **KELKLEQQ**VGGQGLRGVGQGVRGGFVTLTTHTPFPSQ**EAAERESK** | 299 |
| AS39 | CCNF | **GEISQEEV**PPSRHLGVSWGAGVWAGLTLGASAPPNSSFPSGAELQPVVCCIRSDTRQPRPPDFPQHRGDPRLPQLSLGAENQTVSYPAFWLRHTMLASSCRPSSLSASSHREAPKACQGSSRSQDSDPGTEPCSHASGPCVTSTVSSPGLLPQRLLPLALTGLPVEEDGFEHAGA | 301 |
| AS40 | LRRC45 | **DCMLSEEG**GQARRGGSLCSLAAHTIASAARGRFLSRLSNFCAVVKASRGAPSCTWE | 303 |

TABLE 8-continued

| Neo epitope ID | Gene | Amino acid sequence | SEQ ID NO: |
|---|---|---|---|
| AS41 | RHPN1 | **EAFQRAAG**EGGPGRGGARRGARVLQSPFCRAGAGEWLGHQSLR | 305 |
| AS42 | 5LC39A4 | **PEPRRLSP**GEPRGRPRKGWGIWGLCGARVGPKAWR | 307 |
| AS43 | CPNE7 | **VPFRELKN**VSVLEGLRQGRLGGPCSCHCPRPSQARLTPVDVAGPFLCLGDPGLFPPVKSSI | 309 |
| AS44 | FASN | **FVSLTAIQ**MASSATPWGRWPVATPTAACPRRRPSSLPTGGDSASKKPISRRAPWQPWACPGRSVNSAAPRAWCPPATTPRTQSPSRDLRPRCLSSWSS | 311 |
| AS45 | RBM47 | **PVAIKPGT**GPPNNSSIHGGSKRSENSYCRDLRGQLRAICCSSYSHDRHTTEERGSRGRHVWRIRRLHTSGLPCCCHSGPHPRRLPDILRLVTSTKTDHTNTTEGTLDYL | 313 |
| AS46 | SERINC5 | **KWNKNWTA**TLGALTIRGHKLLCHLPHLLSSVQQTCRSSSR | 315 |
| AS47 | AGRN | **FKKFDGPC**GERGGGRTARALWARGDSVLTPALDPQTPVRAPSLTRAAAAV | 317 |
| AS48 | SYT17 | **ENASLVFT**GSNSPIPACELSSHPAHGISPWIPSPGNEHFHGIKKQVKAIKVE | 319 |
| AS49 | PDF | **RLTQRLVQ**GWTPMENRWCGRRAGGQPASSSTRWTTCRAACLLTKWTAGRSQTSIG | 321 |
| AS50 | LRIF1 | **ENSGNASR**WLHVPSSSDDWLGWKKSSAITSNS | 323 |
| AS51 | CPNE7 | **GMECTLGQ**VGAPSPRREEDGWRGGHSRFKADVPAPQGPCWGGQPGSAPSSAPPEQSLLD | 325 |
| AS52 | ILDR1 | **KGSVERRS**VSLGHPAEGWAWAERSLQPGMTTANTGCLSFHHRGCLLPVLPKLHCGLGGLPLVRAKEIKRVQRAGESSLPVKGLLTVASAVIAVLWGRPSEVTGENEAQHD | 327 |
| AS53 | PEX10 | **FGLTTLAG**RSSHGTSGLRAATHTKSGDGGQGAARQCEKLLELARATRPWGRSTSASSRWTHRGYMCPPRCAVACW | 329 |
| AS54 | ABCC4 | **IIDSDKIM**AVCMGCLLTRHVQCQAMEMQQ | 331 |
| AS55 | SPOCK1 | **DGHSYTSK**VNCLLLQDGFHGCVSITGAAGRRNLSIFLFL**MLCKLEFHAC** | 333 |
| AS56 | TM9SF3 | **LLNAEDYR**CAIHSKEIYLLSPSPHQAMDKFSLCCINCNLCLHVFLLLLFFQNKDVWLISNIILLWIYGGI | 335 |
| AS57 | KLK3 | **TGGKSTCS**APGPQSLPSTPFSTYPQ**WVILITEL** | 337 |
| AS58 | CREB3L1 | **VETLENAN**SFSSGIQPLLCSLIGLENPT | 339 |
| AS59 | ACSL3 | **AGAGTISE**GSVLHGQRLECDARRFFGCGTTILAEWEHH | 341 |
| AS55.1 | SPOCK1 | **DGHSYTSK**VNCLLLQDGFHGCVSITGAAGRRNLSIFLFLMLCKLEFHA | 385 |

TABLE 9

| Neo-epi-tope ID | Polynucleotide sequence | SEQ ID NO: |
|---|---|---|
| AS1 | CTGACGTTTTTAGATTTCATCCAGGTAACGTTGAGAGTAATGTCAGGATCTCAAATGGAAAACGGAAGTTCCTATTTTTTCAAGCCCTTTTCATGGGGTCTGGGGGTGGGACTCTCGGCCTGGCTGTGTGTAATGTTAACT | 242 |
| AS2 | TTCATGATTGGAGAACTTGTAGGTGAGTTGTGTTGCCAACTCACTTTCCGTTTACCTTTCCTCGAGAGTCTTTGTCAAGCTGTAGTTACACAGGCTTTGAGGTTTAACCCATCTTTTCAGGAAGTTTGTATTTATCAAGACACTGATCTCATG | 244 |
| AS3 | GTTGCTATGATGGTTCCTGATAGACAGGTTCATTATGACTTTGGATTG | 246 |
| AS4 | TGGTGTCCGCTGGATCTTAGACTCGGTTCCACTGGATGTCTCACATGCAGACATCATCAAACGTCACATGAG | 248 |
| AS5 | GTCGTGGGAAGGCGTCATGAAACAGCTCCTCAACCCCTGCTGGTGCCCGACCGAGCTGGTGGTGAAGGGGGAGCA | 250 |
| AS6 | GACTACTGGGCTCAAAAGGAGAAGATCAGCATCCCCAGAACACACCTGTGT | 252 |
| AS7 | GACTACTGGGCTCAAAAGGAGAAGGGATCATCTTCATTCCTGCGACCATCCTGT | 254 |
| AS8 | CTTGTACTTGGTGTATTGAGCGGGCACAGTGGCTCACGCCTA | 256 |
| AS9 | CCTGTCCCAACTGCTACACCTGGGGTAAGATCAGTGACTAGTCCCCAGGGGCTGGGCCTTTTCCTTAAGTTTATT | 258 |
| AS10 | AAGGAAAATGATGTCCGTGAGGTCTGTGATGTGTATTTACAAATGCAGATCTTCTTCCATTTTAAGTTCAGAAGTTACTTTCAT | 260 |
| AS11, AS33 | GTGCCCTTCCGGGAGCTCAAGAACCAGAGAACAGCACAAGGGGCTCCTGGGATCCACCACGCGGCTTCCCCCGTTGCTGCCAACCTCTGCGACCCGGCGAGACACGCACAGCACACACGCATCCCCTGCGGCGCTGGCCAAGTGCGTGCTGGCCGAGGTCCCGAAGCAGGTGGTGGAGTACTACAGCCACAGAGGCCTGCCCCCGAGAAGCCTGGGTGTCCCTGCCGGAGAGGCCAGCCCAGGCTGCACACCGTGAAGATGTGGAGGGCG | 262 |
| AS12 | TTTGCTAGAAAAATGCTGGAGAAGGTACACAGACAACACCTACAGCTTTCCCACAATAGCCAGGAA | 264 |
| AS13 | AAGAGAAGTTTTGCTGTCACGGAGAGGATCATC | 266 |
| AS14 | ATGTTCCTTAGAAAGGAGCAGCAGGTGGGTCCCCACAGCTTTTCTATGCTT | 268 |
| AS15 | GTGCTGCGCTTTCTGGACTTAAAGGTGAGATACCTGCACTCT | 270 |
| AS16 | GGCAACACCACCCTCCAGCAGCTGGGTGAGGCCTCCCAGGCGCCCTCAGGCTCCCTCATCCCTCTGAGGCTGCCTCTGCTCTGGGAAGTGAGGGGC | 272 |
| AS17 | GGACTGAACTTAAATACTGATAGACCAGGTGGTTACAGCTATTCAATTTGGTGGAAAAACAATGCCAAGAACAGA | 274 |
| AS18 | TGGAAATTCGAGATGAGCTACACGGTGGGTGGCCCGCCTCCCCATGTTCATGCTAGACCCAGGCATTGGAAAACTGATAGA | 276 |
| AS19 | CAGTGGCAGCACTACCACCGGTCAGGTGAGGCCGCAGGGACTCCCCTCTGGAGACCCACAAGAAAC | 278 |
| AS20 | AAGGTCCTCAACGAGATCGATGCGGTAGTTACCGTCCCTCCCTCCCTGTCTACCTCCCAGATACCGCAGGGCTGCTGCATCATATTG | 280 |
| AS21 | GCCAATCTGAAAGGCACCCTGCAGGTGAGGAGTGGGCAGGCAGTGAGTCCACGC | 282 |

TABLE 9-continued

| Neo-epi-tope ID | Polynucleotide sequence | SEQ ID NO: |
|---|---|---|
| AS22 | CTCCAGGCGGCTGCCTCGGGCCAAGGCAAGCAGGGCGTCCCTTGTCCCTGGGGTTGCTGTGCCTACGCTGAGAGTCCCCGGGCCCTGATTTCGGGAGATGCTCCATCACAGGTGGAGCGGGAGGTGCCGGGCCCCTGCCTCAACACGCATTCTCTCTCCCACAGATCCCCACAGCTCCCAGGCCTTCCACACCCCAAGCAGCCTTCTGTT | 284 |
| AS23 | AAAATTCAGAATAAAAATTGTCCAGAC | 286 |
| AS32 | GGCGAGGTGGAGCTCTCAGAGGGCGGTGAGGGCCAGCGGCACCTTGCATTTCCCTGGGCCTGCTCTGGGCCGGGCTGGAGAGGGGTGTGCTGTGCTGCTGTGGAGCCTGCT | 288 |
| AS63 | ATTGAAATGAAAAAACTGTTAAAAAGT | 290 |
| AS34 | AAGATGCGGGCCATCCAGGCCGAGGGTGGGCACGGGCAGGCCTGCTGTGGAGGGGCCTGGGGATGGGCACCGGGGGACGGGGGCCCCCAGGGGATGCTCACGCATACTCTGCCCACCCTGGGCTTCCAGAGCGCCTGGACATGGAGAAGAGAAGATGCAGACAGAGCCTGGAGGACTCCGAAAGCCTGCGCATCAAGGAGGTGGAGCATA | 292 |
| AS35 | CTGCTGGAGCCCTTCCGCCGCGGTGAGCCCGGGCCCCGCGGGCTGCTCTCGGGAAGTTCCCGCGGAGGGGAGGGGCCTGGCCGTTCGATCGAGGCTGCACCCGCCACACCTTTGCCCTGTTGCCGCAAGAACCCTTGTCGGCCCCAGCCTTCCAGATTTTTGCCTCCTAGGGTATTGTTAGTGATCATTCTTCCCAAACTGGATTGTCCAAAACTTGGGTTC | 294 |
| AS36 | CCCTCGGGGCGGAGAACCAAACGGTTAGTTACCCTGCGTTCTGGCTGCGCCATACAATGCTGGCATCCTCGTGCCGGCCCAGTTCCCTCAGCGCTTCCTCACACAGAGAGGCCCCCAAGGCTTGTCAGGGGAGCAGCAGATCCCAGGACAGTGACCCTGGGACGGAGCCCTGCAGTCATGCCTCGGGCCCCTGCG | 296 |
| AS37 | TGCCACCTCTTCCTGCAGCCCCAGGTTGGCACCCCCCCCCCCACACTGCCAGTGCTCGAGCCCCCAGTGGTCCACCCCACCCTCATGAAAGTTGCCCTGCAGGGCGAAGACCTGCGAGAGCTGCGCAGACATGTGCACGCCGACAGCACGGACTTCCTGGCTGTGAAGAGGCTGGTACAGCGCGTGTTCCCAGCCTGCACCTGCACCTGCACCAGGCCGCCCTCGGAGCAGGAAGGGGCCGTGGGTGGGGAGAGGCCTGTGCCCAAGTACCCCCCTCAAGAGGC | 298 |
| AS38 | AAGGAGCTCAAGCTGGAGCAGCAGGTGGGTGGGCAGGGCTTGAGAGGGGTGGGCCAAGGGGTGCGTGGCGGCTTCGTGACCCTCACTACCCATACCCCGTTCCCCTCCCAGGAAGCTGCAGAGCGGGAGTCTAAA | 300 |
| AS39 | GGAGAAATCAGCCAGGAAGAGGTGCCTCCCTCCCGCCACCTGGGCGTCTCATGGGGTGCTGGGGTGTGGGCGGGCCTCACCCTCGGGGCCTCTGCACCCCCTAACTCTAGCTTCCCCTCAGGTGCTGAGCTACAGCCAGTTGTGTGCTGCATTAGGAGTGACACAAGACAGCCCCGACCCCCCGACTTTCCTCAGCACAGGGGAGATCCACGCCTTCCTCAGCTCTCCCTCGGGGCGGAGAACCAAACGGTTAGTTACCCTGCGTTCTGGCTGCGCCATACAATGCTGGCATCCTCGTGCCGGCCCAGTTCCCTCAGCGCTTCCTCACACAGAGAGGCCCCCAAGGCTTGTCAGGGGAGCAGCAGATCCCAGGACAGTGACCCTGGGACGGAGCCCTGCAGTCATGCCTCGGGCCCCTGCGTAACCTCCACTGTCTCCAGCCCAGGTCTCCTTCCTCAGAGGCTATTGCCTCTCGCTCTGACTGGGCTCCCTGTGGAGGAAGATGGTTTCGAGCACGCGGGAGCC | 302 |
| AS40 | GACTGCATGCTCAGCGAGGAAGGTGGGCAGGCGCGGCGGGGTGGATCCCTCTGCTCCTTAGCTGCCCACACCATTGCCTCGGCAGCCCGAGGTCGCTTCCTCTCCAGGCTCTCCAATTTCTGTGCCGTAGTTAAAGCGAGCAGGGGCGCCCCTTCCTGCACCTGGGAG | 304 |
| AS41 | GAGGCCTTCCAGAGGGCCGCTGGTGAGGGCGGCCCGGGCCGCGGTGGGGCACGGCGCGGTGCCAGGGTGTTGCAGAGCCCCTTTTGCAGGGCAGGAGCTGGGGAGTGGTTAGGACATCAGTCCCTCAGG | 306 |

TABLE 9-continued

| Neo-epi-tope ID | Polynucleotide sequence | SEQ ID NO: |
|---|---|---|
| AS42 | CCTGAGCCCAGGAGACTGAGCCCAGGTGAGCCCAGGGGG CGACCCCGGAAGGGCTGGGGGATCTGGGGTTTGTGTGGA GCGCGGGTGGGGCCCAAGGCTTGGCGG | 308 |
| AS43 | GTGCCCTTCCGGGAGCTCAAGAACGTGAGTGTCCTGGAG GGGCTCCGTCAAGGCCGGCTTGGGGTCCCTGTTCATGTC ACTGCCCAAGACCTTCCCAGGCCAGGCTCACGCCAGTGG ATGTGGCAGGTCCCTTCTTGTGTCTGGGGGATCCTGGGCT GTTCCCCCCAGTCAAGAGCAGTATC | 310 |
| AS44 | TTTGTGAGCCTGACTGCCATCCAGATGGCATCGTCGGCCA CTCCCTGGGGGAGGTGGCCTGTGGCTACGCCGACGGCTG CCTGTCCCAGGAGGAGGCCGTCCTCGCTGCCTACTGGAG GGGACAGTGCATCAAAGAAGCCCATCTCCCGCCGGGCGC CATGGCAGCCGTGGGCTTGTCCTGGGAGGAGTGTAAACA GCGCTGCCCCCCGGGCGTGGTGCCCGCCTGCCACAACTCC AAGGACACAGTCACCATCTCGGGACCTCAGGCCCCGGTG TTTGAGTTCGTGGAGCAGC | 312 |
| AS45 | CCAGTTGCCATTAAACCTGGTACAGGGCCGCCCAATAAC TCCAGTATACACGGTGGCTCCAAACGTTCAGAGAATTCCT ACTGCCGGGATCTACGGGGCCAGTTACGTGCCATTTGCTG CTCCAGCTACAGCCACGATCGCCACACTACAGAAGAACG CGGCAGCCGCGGCCGCCATGTATGGAGGATACGCAGGCT ACATACCTCAGGCCTTCCCTGCTGCTGCCATTCAGGTCCC CATCCCCGACGTCTACCAGACATACTGAGGCTGGTGACC AGCACGAAGACAGACCACACAAACACCACTGAAGGAAC GCTTGACTATTTA | 314 |
| AS46 | AAGTGGAACAAGAACTGGACAGCCACACTCGGGGCTCTT ACAATCAGGGGTCATAAGCTGCTATGTCACCTACCTCACC TTCTCAGCTCTGTCCAGCAAACCTGCAGAAGTAGTTCTAG A | 316 |
| AS47 | TTCAAGAAGTTCGACGGCCCTTGTGGTGAGCGCGGCGGC GGGCGCACGGCTCGAGCTCTGTGGGCGCGCGGCGACAGC GTCCTGACTCCTGCCCTCGACCCCCAGACCCCTGTCAGGG CGCCCTCCCTGACCCGAGCCGCAGCTGCCGTG | 318 |
| AS48 | GAAAATGCCAGCCTAGTGTTTACAGGATCCAACAGCCCC ATACCAGCCTGCGAACTGAGTAGTCACCCAGCTCATGGT ATCAGTCCTTGGATACCCTCACCTGGAAATGAACATTTCC ATGGCATAAAGAAGCAAGTAAAGGCAATAAAAGTAGAA | 320 |
| AS49 | CGGCTGACGCAACGGCTGGTCCAGGGCTGGACCCCAATG GAGAACAGGTGGTGTGGCAGGCGAGCGGGTGGGCAGCC CGCATCATCCAGCACGAGATGGACCACCTGCAGGGCTGC CTGTTTATTGACAAAATGGACAGCAGGACGTTCACAAAC GTCTATTGGA | 322 |
| AS50 | GAAAATTCAGGCAACGCCTCGCGTTGGCTGCATGTACCA AGTAGTTCAGACGATTGGCTCGGATGGAAAAAATCTTCT GCAATTACTTCCAATTCC | 324 |
| AS51 | GGCATGGAGTGCACCCTGGGGCAGGTGGGTGCCCCGTCC CCTCGGAGGGAGGAGGACGGTTGGCGTGGGGGCCACAGC CGATTCAAGGCTGATGTACCAGCACCGCAGGGACCCTGC TGGGGTGGCCAACCTGGCTCTGCCCCCTCCTCAGCTCCTC CTGAACAGTCATTATTAGAT | 326 |
| AS52 | AAAGGGAGTGTGGAGAGGCGCTCGGTGAGCCTGGGGCAT CCTGCTGAGGGTTGGGCATGGGCAGAGAGGAGCCTCCAG CCAGGCATGACCACAGCCAACACAGGCTGCCTCTCATTC CACCACAGAGGGTGCCTCCTCCCTGTTTTGCCCAAATTAC ACTGTGGGCTAGGTGGACTACCTCTTGTCAGAGCTAAAG AAATCAAGCGAGTGCAGAGGGCAGGGGAGAGTTCGCTGC CTGTGAAGGGCCTTCTCACCGTCGCTTCGGCTGTCATCGC AGTCCTGTGGGGTAGGCCAAGCGAGGTCACAGGAGAAAA TGAGGCTCAGCATGAT | 328 |
| AS53 | TTTGGCCTCACCACACTTGCAGGTAGAAGCTCCCACGGG ACCTCAGGACTGAGGGCAGCCACACACACCAAGTCTGGG GACGGTGGCCAGGGGGCTGCCAGGCAGTGTGAGAAGCTC CTGGAGCTGGCCCGGGCTACCAGACCCTGGGGGAGGAGT ACGTCAGCATCATCCAGGTGGACCCATCGCGGATACATG TGCCCTCCTCGCTGCGCCGTGGCGTGCTGG | 330 |
| AS54 | ATTATTGACAGCGACAAGATAATGGCAGTGTGCATGGGG TGCCTGCTCACACGTCATGTGCAATGCCAGGCCATGGAG ATGCAACAG | 332 |
| AS55 | GATGGCCACTCCTACACATCCAAGGTGAATTGTTTACTCC TTCAAGATGGGTTCCATGGCTGTGTGAGCATCACCGGGG CAGCTGGAAGAAGAAACCTGAGCATCTTCCTGTTCTTGAT GCTGTGCAAATTGGAGTTCCATGCTTGT | 334 |
| AS56 | CTACTAAATGCAGAAGATTACCGGTGTGCCATTCATTCAA AAGAGATTTATCTTCTTTCCCCCTCCCCCCACCAGGCAAT GGACAAGTTTTCTCTCTGCTGCATCAACTGCAATCTATGT TTACATGTATTCCTTTTACTACTATTTTTTCAAAACAAAGA TGTATGGCTTATTTCAAACATCATTTTACTTTGGATATATG GCGGTATT | 336 |
| AS57 | ACAGGGGGCAAAAGCACCTGCTCGGCTCCTGGCCCTCAG TCTCTCCCCTCCACTCCATTCTCCACCTACCCACAGTGGG TCATTCTGATCACCGAACTG | 338 |
| AS58 | GTGGAGACCCTGGAGAATGCCAACAGCTTCTCCAGCGGG ATCCAGCCACTCCTCTGTTCCCTGATTGGCCTGGAGAATC CCACC | 340 |
| AS59 | GCTGGGGCTGGAACAATTTCCGAAGGTAGTGTTCTCCATG GTCAGAGGCTGGAGTGTGATGCCAGACGTTTTTTTGGGTG TGGGACTACAATACTGGCAGAGTGGGAGCACCAT | 342 |
| AS55.1 | GATGGCCACTCCTACACATCCAAGGTGAATTGTTTACTCC TTCAAGATGGGTTCCATGGCTGTGTGAGCATCACCGGGG CAGCTGGAAGAAGAAACCTGAGCATCTTCCTGTTCTTGAT GCTGTGCAAATTGGAGTTCCATGCT | 386 |

TABLE 10

| Neoepitope ID | TCGA (%) | SU2C (%) |
|---|---|---|
| AS1 | 28.5 | 2.3 |
| AS2 | 18.5 | N.O. |
| AS3 | 10.4 | 25.6 |
| AS4 | 27.4 | 41.9 |
| AS5 | 18.7 | 9.3 |
| AS6 | 5.1 | 16.3 |
| AS7 | 5.1 | 16.3 |
| AS8 | N.O. | 14.0 |
| AS9 | 1.2 | 18.6 |
| AS10 | 8.9 | 27.9 |
| AS11 | 1.2 | 48.8 |
| AS12 | 0.4 | 34.9 |
| AS13 | 5.7 | 32.6 |
| AS14 | N.O. | 30.2 |
| AS15 | 4.5 | 46.5 |
| AS16 | 0.6 | 18.6 |
| AS17 | N.O. | 37.2 |
| AS18 | 12.6 | 20.9 |
| AS19 | 12.6 | 20.9 |
| AS20 | 0.2 | 16.3 |
| AS21 | N.O. | 11.6 |
| AS22 | 0.2 | 20.9 |
| AS23 | 3.1 | 18.6 |
| AS32 | 57.1 | N.O. |
| AS33 | 47.6 | N.O. |
| AS34 | N.O. | 42.9 |
| AS35 | N.O. | 42.9 |
| AS36 | N.O. | 40.5 |
| AS37 | N.O. | 38.1 |
| AS38 | N.O. | 35.7 |
| AS39 | N.O. | 33.3 |
| AS40 | N.O. | 33.3 |
| AS41 | N.O. | 33.3 |

TABLE 10-continued

| Neoepitope ID | TCGA (%) | SU2C (%) |
|---|---|---|
| AS42 | N.O. | 33.3 |
| AS43 | N.O. | 31 |
| AS44 | N.O. | 28.6 |
| AS45 | N.O. | 26.2 |
| AS46 | N.O. | 26.2 |
| AS47 | N.O. | 23.8 |
| AS48 | N.O. | 23.8 |
| AS49 | N.O. | 23.8 |
| AS50 | N.O. | 23.8 |
| AS51 | N.O. | 23.8 |
| AS52 | 15.9 | 38.1 |
| AS53 | 16 | 9.5 |
| AS54 | 11.9 | N.O. |
| AS55 | 12.1 | N.O. |
| AS56 | 14.7 | N.O. |
| AS57 | 14.9 | N.O. |
| AS58 | 16.6 | N.O. |
| AS59 | 17.6 | N.O. |
| AS63 | 18.0 | |

N.O. not observed

Example 3: Identification of Additional Neoantigens Using Bioinformatics

Additional neoantigen sequences were identified by further queries as described in Example 2. Table 11 shows the amino acid sequences of the additional neoantigens. Table 12 shows the corresponding polynucleotide sequences.

TABLE 11

| Neoantigen ID | Gene(s) | Amino acid sequence | SEQ ID NO: |
|---|---|---|---|
| P16 | MSMB-NCOA4 | GVPGD**STRRAVRRM**NTF | 343 |
| P17 | MSMB-NOCA4 | GVPGDSTR**RAVRRMNTF** | 343 |
| P19 | TMEM222-LOC644961 | WTP**IPVLTRWPL**PHPPPWRRATSCRMARSSPSATSGSSVRRRCSSLPSWVWNLAASTRPRSTPS | 347 |
| P22 | 5LC45A3-ELK4 | SLYHREK**QLIAMDSAI** | 349 |
| P27 | FAM126B-ORC2 | LHPQRETFTPRWSGANYWKLA**FPVGAEGTF**PAAATQRGVVRPA | 351 |
| P35 | TMPRSS2-ERG | **NSKMALNS**LNSIDDAQLTRIAPPRSHCCFWEVNAP | 353 |
| P37 | TSTD1-F11R | MAG**GVLRRLLCR**EPDRDGDKGASREETVVPLHIGDPVVLPGIGQCYSALF | 355 |
| P46 | TP53 (R213D) | DDRNTFDIVWW**CPMSRLRLAL**TVPPSTTTTCVTVPAWAA | 357 |
| P48 | AR.p.H875Y | VQPIAREL**YQFTFDLLI** | 359 |
| P50 | AR (W742C) | QMAV**IQYSCMGLM**VFAM | 361 |
| P56 | SPOP (F102C) | PKSEV**RAKCKFSIL**NAK | 363 |
| P58 | AR (Q903H) | MMAEHSV**HVPKILSGK** | 365 |
| P59 | FOXA1 (F254V) | LHPDSG**NMVENGCYL**RR | 367 |
| P60 | FOXA1.p.F266L | C**YLRRQKRLK**CEKQPGA | 369 |
| P61 | FOXA1.p.R261G | MFENG**CYLGRQKRF**KCE | 371 |

TABLE 11-continued

| Neoantigen ID | Gene(s) | Amino acid sequence | SEQ ID NO: |
|---|---|---|---|
| P73 | TP53 (G266E) | DSSGN**LLERNSFEV**RV | 373 |
| P76 | AR-V3 | VFFKRAAEGFFRMNKLKESSDTNPKP**YCMAAPMGL**TENNRNRKKSYRETNLKAVSWPLNHT | 375 |
| P77 | AR-V3 | V**FFKRAAEGF**FRMNKLKESSDTNPKPYCMAAPMGLTENNRNRKKSYRETNLKAVSWPLNHT | 375 |
| P82 | AR-V7 | YEAGMTLGEKF**RVGNCKHLK**MTRP | 379 |
| P87 | AR-Intron | YEAGMTLGGKILF**FLFLLLPLS**PFSLIF | 381 |
| P97 | FOXRED2-TXN2 | GYLRMQG**LMAQRLLLR** | 383 |
| P98 | TP53 (R213D) | DDRNTFD**IVWWCPMSR**LRLALTVPPSTTTTCVTVPAWAA | 357 |

TABLE 12

| Neoantigen ID | Gene(s) | Nucleotide sequence | SEQ ID NO: |
|---|---|---|---|
| P16 | MSMB-NCOA4 | GGAGTTCCAGGAGATTCAACCAGGAGAGCAGTGAGGAGAATGAATACCTTC | 344 |
| P17 | MSMB-NOCA4 | GGAGTTCCAGGAGATTCAACCAGGAGAGCAGTGAGGAGAATGAATACCTTC | 344 |
| P19 | TMEM222-LOC644961 | TGGACGCCCATCCCGGTGCTCACGAGATGGCCACTACCACATCCTCCTCCCTGGAGAAGAGCTACAAGCTGCCGGATGGCCAGGTCATCACCATCAGCAACAAGCGGTTCCAGTGTCCGGAGGCGCTGTTCCAGCCTTCCTTCCTGGGTATGGAATCTTGCGGCATCCACGAGACCACGTTCAACTCCATCATGAA | 348 |
| P22 | 5LC45A3-ELK4 | TCCCTCTACCACCGGGAGAAGCAGCTCATTGCTATGGACAGTGCTATC | 350 |
| P27 ORC2 | FAM126B- | CTTCATCCTCAGAGGGAAACATTCACTCCCCGGTGGTCGGGCGCGAATTACTGGAAATTGGCTTTTCCCGTTGGGGCCGAAGGTACCTTCCCTGCGGCGGCGACTCAGCGGGGTGTCGTTCGGCCGGCGTG | 352 |
| P35 | TMPRSS2-ERG | AACAGCAAGATGGCTTTGAACTCATTAAACTCCATTGATGATGCACAGTTGACAAGAATTGCCCCTCCAAGATCTCATTGCTGTTTCTGGGAAGTAAACGCTCCT | 354 |
| P37 | TSTD1-F11R | ATGGCTGGAGGAGTCCTTCGGCGGCTGTTGTGTCGGGAGCCTGATCGCGATGGGGACAAAGGCGCAAGTCGAGAGGAAACTGTTGTGCCTCTTCATATTGGCGATCCTGTTGTGCTCCCTGGCATTGGGCAGTGTTACAGTGCACTCTTCT | 356 |
| P46 | TP53 (R213D) | GATGACAGAAACACTTTCGACATAGTGTGGTGGTGCCCTATGAGCCGCCTGAGGTTGGCTCTGACTGTACCACCATCCACTACAACTACATGTGTAACAGTTCCTGCATGGGCGGCATGA | 358 |

TABLE 12-continued

| Neo-anti-gen ID | Gene(s) | Nucleotide sequence | SEQ ID NO: |
|---|---|---|---|
| P48 | AR.p.H875Y | GTGCAGCCTATTGCGAGAGAGCTGC ATCAGTTCACTTTTGACCTGCTAATC | 360 |
| P50 | AR (W742C) | CAGATGGCTGTCATTCAGTACTCCTG CATGGGGCTCATGGTGTTTGCCATG | 362 |
| P56 | SPOP (F102C) | CAAAGAGTGAAGTTCGGGCAAAATT CAAATGCTCCATCCTGAATGCCAAG | 364 |
| P58 | AR (Q903H) | ATGATGGCAGAGATCATCTCTGTGCA CGTGCCCAAGATCCTTTCTGGGAAA | 366 |
| P59 | FOXA1 (F254V) | CTGCACCCGGACTCCGGCAACATGG TCGAGAACGGCTGCTACTTGCGCCGC | 368 |
| P60 | FOXA1.p. F266L | TGCTACTTGCGCCGCCAGAAGCGCTT GAAGTGCGAGAAGCAGCCGGGGGCC | 370 |
| P61 | FOXA1.p. R261G | ATGTTCGAGAACGGCTGCTACTTGGG CCGCCAGAAGCGCTTCAAGTGCGAG | 372 |
| P73 | TP53 (G266E) | GACTCCAGTGGTAATCTACTGGAAC GGAACAGCTTTGAGGTGCGTGTT | 374 |
| P76 | AR-V3 | GTCTTCTTCAAAAGAGCCGCTGAAG GATTTTTCAGAATGAACAAATTAAA AGAATCATCAGACACTAACCCCAAG CCATACTGCATGGCAGCACCAATGG GACTGACAGAAAACAACAGAAATAG GAAGAAATCCTACAGAGAAACAAAC TTGAAAGCTGTCTCATGGCCTTTGAA TCATACT | 376 |
| P77 | AR-V3 | GTCTTCTTCAAAAGAGCCGCTGAAG GATTTTTCAGAATGAACAAATTAAA AGAATCATCAGACACTAACCCCAAG CCATACTGCATGGCAGCACCAATGG GACTGACAGAAAACAACAGAAATAG GAAGAAATCCTACAGAGAAACAAAC TTGAAAGCTGTCTCATGGCCTTTGAA TCATACT | 376 |
| P82 | AR-V7 | TATGAAGCAGGGATGACTCTGGGAG AAAAATTCCGGGTTGGCAATTGCAA GCATCTCAAAATGACCAGACCC | 380 |
| P87 | AR-Intron | TATGAAGCAGGGATGACTCTGGGAG GTAAGATACTTTTCTTTCTCTTCCTCC TCCTTCCTCTCTCCCCCTTCTCCCTCA TTTTC | 382 |
| P97 | FOXRED2-TXN2 | GGGTACCTGAGGATGCAGGGACTCA TGGCTCAGCGACTTCTTCTGAGG | 384 |
| P98 | TP53 (R213D) | GATGACAGAAACACTTTCGACATAG TGTGGTGGTGCCCTATGAGCCGCCTG AGGTTGGCTCTGACTGTACCACCATC CACTACAACTACATGTGTAACAGTTC CTGCATGGGCGGCATGA | 358 |

Example 4: HLA Binding Predictions

The amino acid sequences of the neoantigens identified using the various approaches as described in Example 3 were split into all possible unique, contiguous 9 mer amino acid fragments and HLA binding predictions to six common HLA alleles (HLA-A*01:01, HLA-A*02:01, HLA-A*03:01, HLA-A*24:02, HLA-B*07:02, HLA-B*08:01) were performed for each of these 9mers using netMHCpan4.0. Several 9 mer fragments were selected for further analysis based on ranking by likelihood of binding to one or more of the tested HLA alleles and their prevalence in prostate cancer patients.

Table 13 shows the amino acid sequences of select 9 mer fragments and their neoantigen origin. Table 14 shows the prevalence of neoantigens in the analyzed cohorts.

TABLE 13

| Neoantigen ID | Gene(s) | Type | Amino acid sequence or 9-mer | SEQ ID NO: of the 9 mer |
|---|---|---|---|---|
| P16 | MSMB-NCOA4 | Fusion | STRRAVRRM | 387 |
| P17 | MSMB-NOCA4 | Fusion | RAVRRMNTF | 388 |
| P19 | TMEM222- | Fusion | IPVLTRWPL | 389 |
| P22 | SLC45A3-ELK4 | Fusion | QLIAMDSAI | 390 |
| P27 | FAM126B-ORC2 | Fusion | FPVGAEGTF | 391 |
| P35 | TMPRSS2-ERG | Fusion | NSKMALNSL | 392 |
| P37 | TSTD1-F11R | Fusion | GVLRRLLCR | 393 |
| P46 | TP53 (R213D) | Frameshift | CPMSRLRLA | 394 |
| P48 | AR.p.H875Y | Missense | YQFTFDLLI | 395 |
| P50 | AR (W742C) | Missense | IQYSCMGLM | 396 |
| P56 | SPOP(F102C) | Missense | RAKCKFSIL | 397 |
| P58 | AR (Q903H) | Missense | HVPKILSGK | 398 |
| P59 | FOXA1 (F254V) | Missense | NMVENGCYL | 399 |

TABLE 13-continued

| Neoantigen ID | Gene(s) | Type | Amino acid sequence or 9-mer | SEQ ID NO: of the 9 mer |
|---|---|---|---|---|
| P60 | FOXA1.p.F266L | Missense | YLRRQKRLK | 400 |
| P61 | FOXA1.p.R261G | Missense | CYLGRQKRF | 401 |
| P73 | TP53 (G266E) | Missense | LLERNSFEV | 402 |
| P76 | AR-V3 | Splice Variant | YCMAAPMGL | 403 |
| P77 | AR-V3 | Splice Variant | FFKRAAEGF | 404 |
| P82 | AR-V7 | Splice Variant | RVGNCKHLK | 405 |
| P87 | AR-Intron | Splice Variant | FLFLLLPLS | 406 |
| P97 | FOXRED2-TXN2 | Fusion | LMAQRLLLR | 407 |
| P98 | TP53 (R213D) | Frameshift | IVWWCPMSR | 408 |

TABLE 14

| Neoantigen | | Prevalence | |
|---|---|---|---|
| ID | Gene | TCGA | SU2C |
| P16 | MSMB-NCOA4 | 27.16% | 23.25% |
| P17 | MSMB-NOCA4 | 27.16% | 23.25% |
| P19 | TMEM222-LOC644961 | N.O. | 13.95% |
| P22 | SLC45A3-ELK4 | 17.71% | 13.95% |
| P27 | FAM126B-ORC2 | 5.11% | 18.60% |
| P35 | TMPRSS2-ERG | 2.75% | 11.62% |
| P37 | TSTD1-F11R | 16.33% | 9.30% |
| P46 | TP53 (R213D) | N.O. | 1% |
| P48 | AR.p.H875Y | N.O. | 1% |
| P50 | AR (W742C) | N.O. | 1.25% |
| P56 | SPOP (F102C) | 0.40% | 2.00% |
| P58 | AR (Q903H) | N.O. | 1.00% |
| P59 | FOXA1 (F254V) | 0.20% | 1.00% |
| P60 | FOXA1.p.F266L | 0.20% | 1% |
| P61 | FOXA1.p.R261G | 0.20% | 1% |
| P73 | TP53 (G266E) | N.O. | 1% |
| P76 | AR-V3 | Present | Present |
| P77 | AR-V3 | Present | Present |
| P82 | AR-V7 | Present | Present |
| P87 | AR-Intron | Present | Present |
| P97 | FOXRED2-TXN2 | 3.74% | 11.62% |
| P98 | TP53 (R213D) | 0.00% | 1.00% |

N.O: not observed;
Present: AR splice variants were expressed at variable levels and hence prevalence was not determined

Example 5: Immunogenicity Assessment of Neoantigens

Figure 5A:
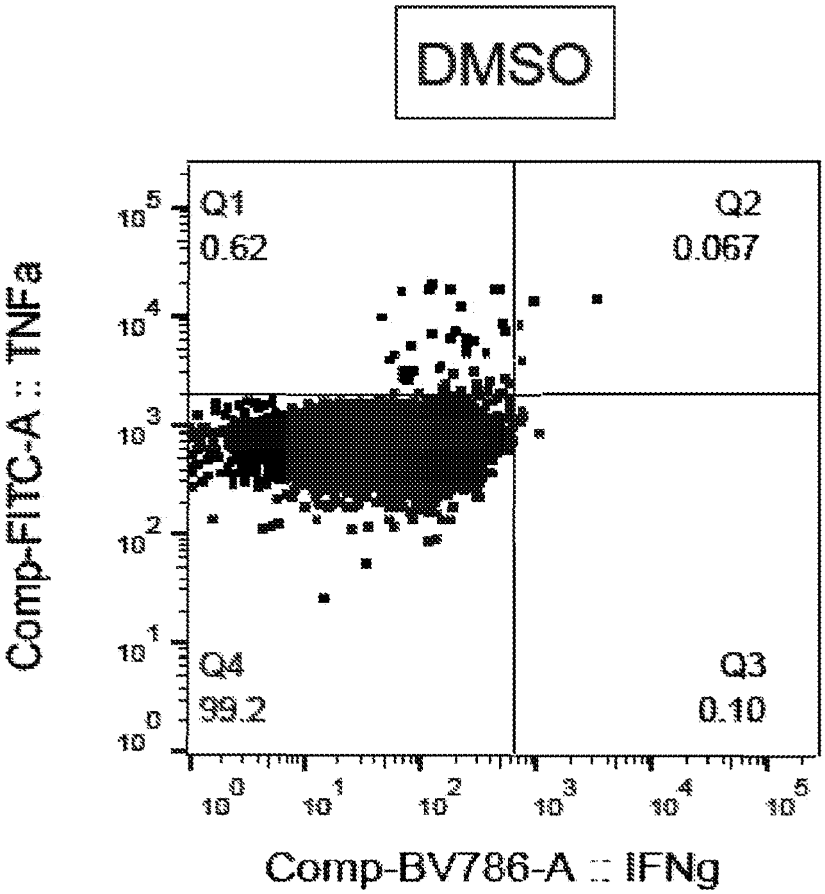
FIG. 5A shows a flow cytometry dot plot depicting $TNF\alpha^+IFN\gamma^+CD8^+$ T cell frequencies in PBMC samples after no stimulation (DMSO).
Figure 5B:
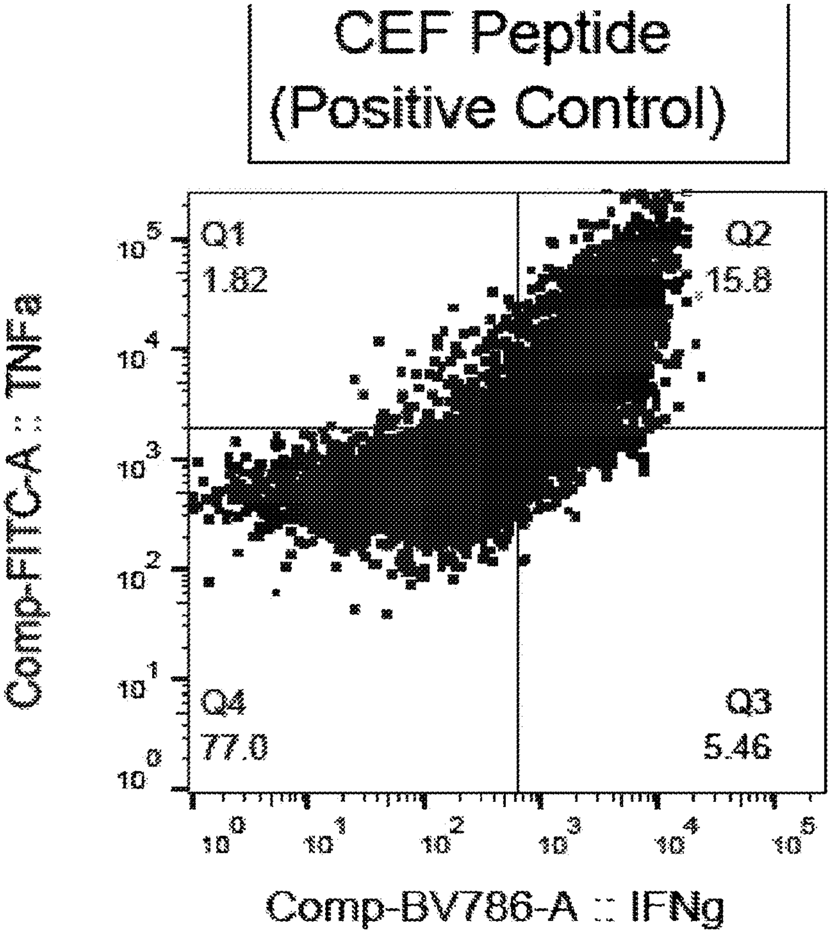
FIG. 5B shows a flow cytometry dot plot depicting $TNF\alpha^+IFN\gamma^+CD8^+$ T cell frequencies in PBMC samples after stimulating with CEF peptide.
Figure 5C:
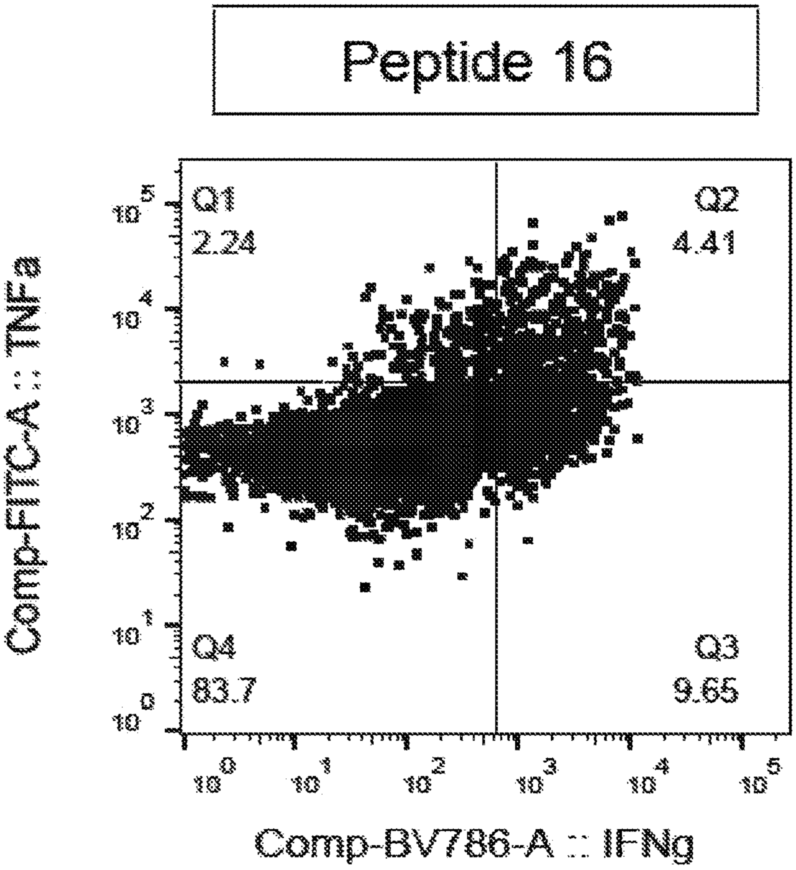
FIG. 5C shows a flow cytometry dot plot depicting $TNF\alpha^+IFN\gamma^+CD8^+$ T cell frequencies in PBMC samples after stimulation with P16.
Figure 5D:
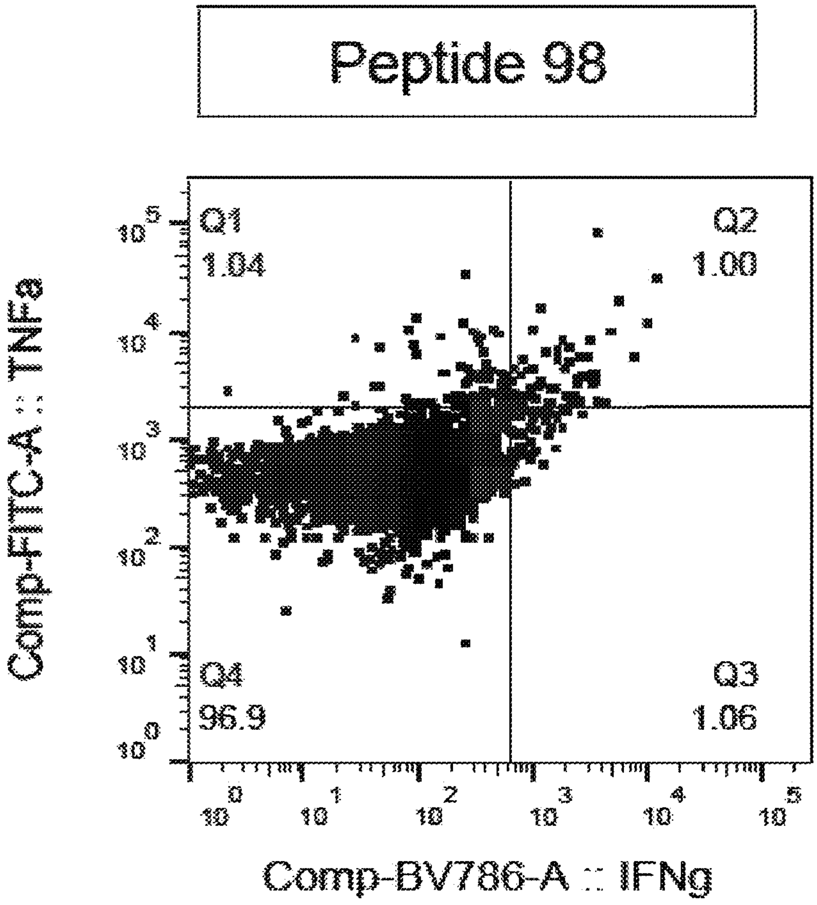
FIG. 5D shows a flow cytometry dot plot depicting $TNF\alpha^+IFN\gamma^+CD8^+$ T cell frequencies in PBMC samples after stimulation with P98.
Figure 5E:
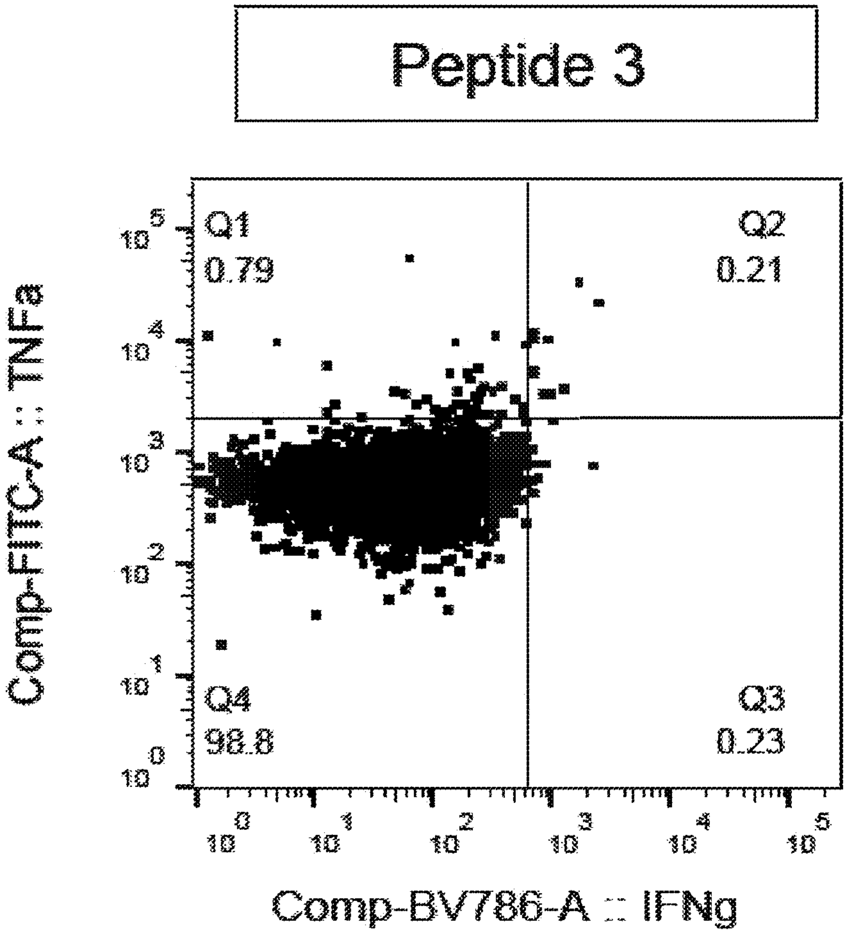
FIG. 5E shows a flow cytometry dot plot depicting $TNF\alpha^+IFN\gamma^+CD8^+$ T cell frequencies in PBMC samples after stimulation with P3 self-antigen.
Figure 6:
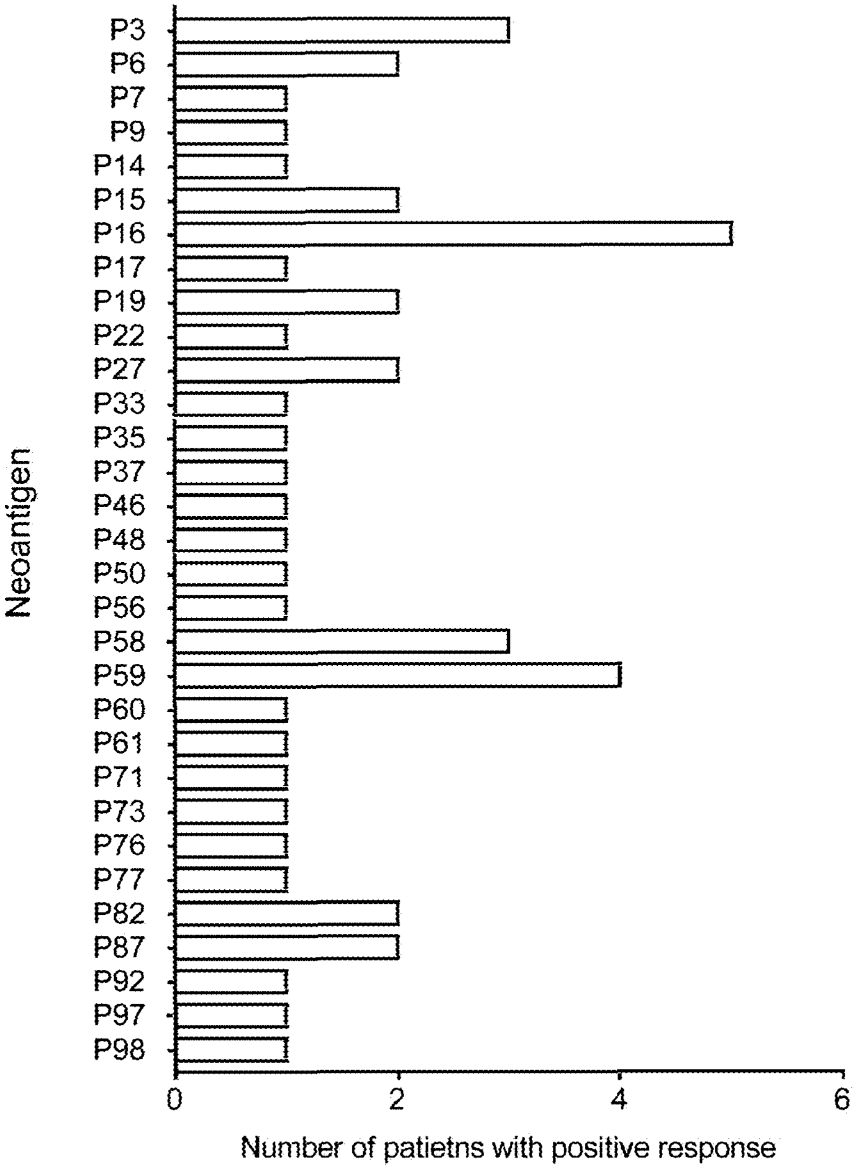
FIG. 6 shows the number of prostate cancer patients whose PBMC samples demonstrated a positive immune response to the specified neoantigens. P3, P6, P7, P9 and P92 represent self-antigens.

The 9 mer fragments shown in Table 13 were assessed for their ability to activate T cells using the Patient PBMC restimulation assay described in Example 1 using TNFα and IFNγ production by $CD8^+$ T cells as a readout. Self-antigens shown in Table 15 were also used in the assays. FIG. 5A, FIG. 5B, FIG. 5C, FIG. 5D and FIG. 5E show flow cytometry dot plots depicting $TNF\alpha^+IFN\gamma^+CD8^+$ T cell frequencies in PBMC samples after no stimulation (DMSO negative control) (FIG. 5A), after stimulation with CEF peptide (positive control (FIG. 5B), after stimulation with P16 (FIG. 5C), after stimulation with P98 (FIG. 5D), and after stimulation with P3 (FIG. 5E). Table 16 shows the maximum frequency of $TNF\alpha^+IFN\gamma^+CD8^+$ T cells and maximum fold change over negative control for each peptide analyzed, indicating the highest frequency of $TNF\alpha^+IFN\gamma^+CD8^+$ T cells and resulting fold change across the PBMC donors evaluated for the peptide. All neoantigens evaluated were found to stimulate $CD8^+$ T cells. FIG. 6 shows the number of prostate cancer patients whose PBMC samples demonstrated a positive immune response to the specified neoantigens. PBMCs from ten patients were evaluated.

TABLE 15

| Peptide ID | Gene name | Amino Acid Sequence of the 9-mer | SEQ ID NO: |
|---|---|---|---|
| P3 | ERG | KLSRALRYY | 421 |
| P6 | FOLH1 | MVFELANSI | 422 |
| P7 | ERG | ILFQNIDGK | 423 |
| P9 | FOLH1 | KIVIARYGK | 424 |
| P92 | ERG | FLLELLSDS | 425 |

TABLE 16

| Peptide Name | Maximum fold change over | Maximum frequency of $TNF\alpha^+IFN\gamma^+CD8^+$ T cells | Immunogenic |
|---|---|---|---|
| Negative control | n/a | 0.011-0.8 (depending on | n/a |
| P16 | 65.82 | 4.620 | Yes |
| P17 | 2.17 | 0.130 | Yes |
| P19 | 5.00 | 0.480 | Yes |
| P22 | 5.00 | 0.120 | Yes |
| P27 | 3.43 | 0.430 | Yes |
| P35 | 2.67 | 0.064 | Yes |
| P37 | 3.13 | 1.160 | Yes |
| P46 | 2.33 | 0.140 | Yes |
| P48 | 2.33 | 0.220 | Yes |
| P50 | 5.14 | 0.190 | Yes |
| P56 | 11.57 | 1.620 | Yes |
| P58 | 19.18 | 5.370 | Yes |
| P59 | 10.75 | 3.010 | Yes |
| P60 | 2.08 | 0.340 | Yes |
| P61 | 2.27 | 0.084 | Yes |
| P73 | 2.97 | 0.110 | Yes |
| P76 | 2.30 | 0.170 | Yes |
| P77 | 3.24 | 0.160 | Yes |
| P82 | 3.46 | 0.970 | Yes |
| P87 | 3.24 | 0.120 | Yes |

TABLE 16-continued

| Peptide Name | Maximum fold change over | Maximum frequency of TNFα$^+$IFNγ$^+$CD8$^+$ T cells | Immuno-genic |
|---|---|---|---|
| P97 | 4.55 | 0.160 | Yes |
| P98 | 14.93 | 1.000 | Yes |

Maximum frequency refers to the greatest frequency of TNFα$^+$IFNγ$^+$CD8$^+$ T cells among all tested PBMC donors Example 6: Binding of Neoantigens to HLA Binding of select neoepitopes to HLA-A*01:01, HLA-A* 02:01, HLA-A* 03:01, HLA-A*24:02, HLA-1B*07:02 and HLA-1B*08:01 was evaluated using the assay described in Example 1. The results of binding the various neoantigens to HLA is shown in Table 17. Each HLA allele tested had a corresponding positive control (Pos) and a negative control (Neg) peptide against which the peptide of interest was exchanged. An exchange rate of 100% with Pos, thus means that the peptide of interest has the same binding affinity to the HLA allele as the positive 10 control peptide. As a criterion for further evaluation, peptides with an exchange rate of at least 10% with the corresponding Pos peptide for at least one of the 6 HLA alleles that we considered for further evaluation. The exchange rates with the allele specific Pos peptides, of the 24 neoantigens so identified are summarized below in Table 17. Higher percentages correspond to stronger binding to the HLA allele.

TABLE 17

| Peptide Name | HLA-A*01:01 | HLA-A*02:01 | HLA-A*03:01 | HLA-A*24:02 | HLA-B*07:02 | HLA-B*08:01 |
|---|---|---|---|---|---|---|
| P16 | 5.5 | 10.4 | 6.1 | 0.8 | 13.7 | 6.2 |
| P17 | 4.9 | 9.3 | 3.8 | 0.1 | 38.7 | 9 |
| P19 | 5.2 | 8.2 | 4.1 | 0.1 | 91.3 | 14.5 |
| P22 | 4.4 | 46.9 | 4.8 | 0 | 8.3 | 3.9 |
| P27 | 4.8 | 10 | 4.5 | 0.7 | 7.8 | 6.4 |
| P35 | 2.5 | 12.5 | 4.2 | 0.2 | 12.1 | 13.7 |
| P37 | 1.4 | 12.5 | 6.4 | −0.1 | 9.4 | 3.3 |
| P46 | 2.4 | 14.4 | 10.3 | −0.4 | 64.8 | 14.5 |
| P48 | 4.3 | 99.3 | 4.4 | 0.1 | 12.8 | 8.9 |
| P50 | 2.3 | 8.8 | 5.5 | 0.1 | 10.4 | 4.7 |
| P56 | 2.6 | 8.4 | 6.8 | 0.5 | 82.5 | 38 |
| P58 | 2.5 | 11.8 | 32.5 | 0.2 | 9.7 | 5.3 |
| P59 | 2.2 | 11.9 | 4.5 | −0.5 | 7.5 | 5.5 |
| P60 | 3.1 | 7.9 | 36.6 | 0.9 | 6.1 | 10.2 |
| P61 | 1.7 | 5.8 | 2.1 | 90.3 | 9.6 | 3.6 |
| P73 | 2.1 | 89.2 | 3.5 | 0.5 | 8.7 | 2.6 |
| P76 | 0.1 | 85.9 | 6 | −0.5 | 91.5 | 8.5 |
| P77 | 1.9 | 9.6 | 2.8 | 1.7 | 14.2 | 3.4 |
| P82 | 1.5 | 6.3 | 58.1 | −0.1 | 12.9 | 1.4 |
| P87 | 1.1 | 64 | 2.4 | 0.2 | 5 | 3.1 |
| P97 | 2.5 | 4.6 | 39 | 0.1 | 7 | 2.7 |
| P98 | 2.5 | 7.9 | 51.1 | −0.1 | 6.7 | 2.4 |

Example 7: MHC I-Peptide Complex Profiling of Prostate Cancer Tissues Identified Unique MHC I-Presented Peptides in Prostate Cancer MHC I-peptide complexes were isolated from samples of 11 human prostate cancer and peptides presented by MHC I were identified using unbiased mass spectrometry. At collection, the subjects were diagnosed with grade 7 adenocarcinoma or stromal sarcoma with two subject having invasive adenocarcinoma.

Frozen human prostate cancer tissues with HLA-A*02:01, HLA-A*03:03, HLA-B*27:0 and HLA-B*08:01 haplotypes were mechanically disrupted in non-ionic detergent including protease inhibitors and processed. A pan-MHC allele monoclonal antibody was used to immunopurify MHC I-peptide complexes from the samples. After acid elution, recovery of the MHC I-peptide complexes was assessed by ELISA and recovered peptides desalted and subjected to LC-MS/MS analyses.

The raw LC-MS/MS data files from prostate tumors were analyzed to search against the neoantigen database that was created from corresponding RNAseq data obtained from the 11 human prostate cancer samples. These peptides had a theoretical mass for parent ions (MS1) and a list of theoretical fragment ions (MS2). A list of MS1 ions that had triggered MS2 scans were searched against the theoretical list of peptides and matched by mass. All theoretical peptides within a set MS1 ppm mass accuracy (5 ppm) then had their in silico MS2 spectrum compared to the empirical MS2 for that parent ion (peptide spectral matches or PSMs). A score was computed based on how closely the empirical spectrum matched the theoretical spectrum. Each LC-MS/MS run (one file per tumor sample) produced thousands of PSMs. However, the vast majority of these peptides were canonical sequences that were found in the human reference database (Swissprot). These were filtered out and peptides of interest (putative neoantigens) were compiled. From this list, peptides that had sufficient evidence for being positive were selected.

Table 18 shows the amino acid sequences of the peptides identified in complex with MHC I using LC-MS/MS and the gene origin of the peptides.

Table 19 shows the amino acid sequences of the corresponding longer neoantigens of the peptides identified in complex with MHC I using LC/MS/MS.

Table 20 shows the polynucleotide sequences encoding the corresponding longer neoantigens.

The MHC I complexed peptides described herein confirmed the expression, processing, and presentation of immunogenic epitopes specific to prostate cancer aberrant gene alterations. Evaluation of RNAseq databases mapped the identified MHC I complexed peptides within longer aberrant transcripts present in prostate cancer. Hence, these data identified prostate cancer neoantigens that contained at least one MHC class I epitope that is immunologically relevant and capable of eliciting an adaptive T cell response.

TABLE 18

| Neoantigen ID | Amino acid sequence | SEQ ID NO: | Gene | type |
|---|---|---|---|---|
| MS1 | VTFLKPCFLL | 426 | TTLL7 | Alternative 5' SS |
| MS2 | TDIVKQSV | 427 | CHD7 | Alternative Last Exon |
| MS3 | SPAFPKPVRP | 428 | TESK1 | Alternative Last Exon |
| MS4 | SYFSLTNIFNFV | 429 | PPIP5K2 | Alternative Last Exon |
| MS5 | EFSPETCAFRLS | 430 | SRPK2 | Alternative Last Exon |
| MS6 | FLSRALRAL | 431 | SOAT1 | Alternative 5' SS |
| MS7 | KKDLELIL | 432 | PDE4D | Alternative Last Exon |
| MS8 | KLQKNCLL | 433 | ZYG11A | Exon Skip |
| MS9 | SALSGNSWV | 434 | SYNE2 | Alternative Last Exon |
| MS10 | TVRAILL | 435 | USP21 | Intron Retention |
| MS11 | GSLHFHEVLK | 436 | TDG | Novel Cassette |

TABLE 19

| Neoantigen ID | Gene ID | Peptide Sequence | Peptide SEQ ID |
|---|---|---|---|
| MS1 | TTLL7 | **HYKLIQQP**ISLFSITDRLHKTFSQLPSVHLCSITFQWGHPPIFCSTNDICVTANFCISVTFLKPCFLLHEASASQ | 437 |
| MS2 | CHD7 | **WTDIVKQS**VSTNCISIKKGSYTKLFSLVFLIFCWPLIIQL | 438 |
| MS3 | TESK1 | **RTALTHNQ**DFSIYRLCCKRGSLCHASQARSPAFPKPVRPLPAPITRITPQLGGQSDSSQPLLTTGRPQGWQDQALRHTQQASPASCATITIPIHSAALGDHSGDPGPAWDTCPPLPLTTLIPRAPPPYGDSTARSWPSRCGPLG | 439 |
| MS4 | PPIP5K2 | **LRYGALCN**VSRISYFSLTNIFNFVIKSLTAIFTVKF | 440 |
| MS5 | SRPK2 | **RKERNIRK**SESTLRLSPFPTPAPSGAPAAAQGKVVRVPGPAGGLVPRDAGARLLPPAGGPGGGAAAGEGRAGRGRFPSITEPRPRDLPPRVATGRRAGGRRKGAGQGVRTRPLPASWPGGRGPFRKGPRRLPLGSGPPAAGVQRLRCSHLSRGPRRRRGRVCGRACVSPPLPPRPPPVGLSAENLSWLSSGLPRACSWREFSPETCAFRLSGLDSKLSARVERDLGALRAPGSRAAQGGGRVRGSRSEWKTRPWRPPPAWPLTRAGGPLPKNPFLESCSETAQRRRVFSFSTPLS | 441 |
| MS6 | SOAT1 | **YAYKDFLW**CFPFSLVFLQEIQICCHVSCLCCICCSTRICLGCLLELFLSRALRALHVLWNGFQLHCQ | 442 |
| MS7 | PDE4D | **SINKATIT**GKKDLELILHVSRKKPFLPRVNITPTPISCCNLKMLKKFFLLYIIISIIDLTNCLSCYLEHFYRFTFFTDVHYF | 443 |
| MS8 | ZYG11A | **TMPAILKL**QKNCLLSL | 444 |
| MS9 | SYNE2 | **PYYSALSG**NSWVPSTLESDPFGYVFSPLATRPALNDQESILWPTLTSVVSCALSCPSLNLPENWLTLITGGMKGGKKMKFTFRH | 445 |
| MS10 | USP21 | **GLRNLGNT**VRAILLSFLSKRNVKWCWGWGKPTSLGKACGRRALKLF | 446 |
| MS11 | TDG | **MEAENAGS**LHFHEVLKMGHVKF | 447 |

TABLE 20

| Neoantigen ID | Gene ID | Polynucleotide sequence | DNA SEQ ID NO: |
|---|---|---|---|
| MS1 | TTLL7 | **CACTACAAATTAATTCAACAACCCA**TATCCCTCTT CTCCATCACTGATAGGCTCCATAAGACGTTCAGTC AGCTGCCCTCGGTCCATCTCTGCTCAATCACCTTCC AGTGGGGACACCCGCCCATTTTCTGCTCAACAAAT GATATCTGTGTCACGGCCAACTTCTGCATCTCGGTC ACATTCCTTAAACCGTGCTTCCTCCTACATGAGGCA TCTGCCTCACAG | 448 |
| MS2 | CHD7 | **TGGACTGATATAGTTAAGCAGTCT**GTAAGTACAA ACTGCATTTCTATCAAGAAAGGTAGCTATACAAAA CTGTTTTCCTTAGTCTTTCTTATTTTCTGTTGGCCAT TAATTATTCAGTTG | 449 |
| MS3 | TESK1 | **AGGACCGCCCTGACACACAATCAGG**ACTTCTCTA TCTACAGGCTCTGTTGCAAGAGGGGGTCCCTCTGC CACGCTTCCCAGGCCAGATCCCCGGCTTTCCCGAA GCCGGTCAGACCTCTTCCTGCCCCCATCACCAGAAT CACCCCCCAACTGGGGGACAATCTGACTCGAGTC AACCCCTTCTCACTACGGAAGACCTCAGGGGTGG CAAGATCAAGCTCTTAGACACACCCAGCAAGCCAG TCCTGCCTCTTGTGCCACCATCACCATTCCCATCCA CTCAGCTGCCCTTGGTGACCACTCCGGAGACCCTG GTCCAGCCTGGGACACCTGCCCGCCGCTGCCGCTC ACTACCCTCATCCCCCGAGCTCCCCCGCCGTATGGA GACAGCACTGCCAGGTCCTGGCCCTCCCGCTGTGG GCCCCTCGGC | 450 |
| MS4 | PPIP5 K2 | **CTTCGCTATGGTGCCTTATGCAAT**GTAAGTAGAA TAAGTTATTTCAGTCTAACAAATATATTTAATTTTG TAATTAAATCACTAACTGCTATTTTTACTGTGAAAT TT | 451 |
| MS5 | SRPK2 | **CGAAAAGAGAGAAACATCCGAAAAA**GTGAGTCC ACGCTGCGCCTGTCCCCGTTCCCCACCCCCGCCCCG TCGGGGGCGCCCGCGGCCGCGCAGGGGAAAGTTGT CCGGGTCCCCGGGCCGGCGGGCGGGCTGGTCCCCC GGGACGCTGGCGCTCGGCTCCTGCCCCCGGCGGGC GGCCCGGGGGGAGGGGCGGCGGCGGGGGAGGGGC GCGCGGGCCGCGGCCGGTTCCCTAGCATCACGGAG CCTCGACCCCGCGACCTCCCGCCCCGGGTCGCCAC CGGCCGGCGGGCGGGAGGCCGGCGGAAAGGCGCC GGGCAGGGCGTGCGCACCCGTCCCTTGCCCGCGAG CTGGCCCGGGGGTCGCGGCCCTTTCCGGAAGGGGC CCCGGCGTCTGCCGCTGGGCTCCGGCCCGCCCGCT GCGGGAGTGCAGCGGCTGCGTTGCTCCCACCTGAG CCGCGGGCCGAGGAGGCGGAGGGGCCGAGTGTGC GGGAGGGCGTGTGTCTCGCCTCCCCTTCCTCCCCGG CCCCCGCCTGTCGGCCTTTCTGCTGAGAACCTAAGC TGGTTGTCAAGTGGTTTGCCTCGGGCGTGTTCCTGG CGCGAGTTCAGCCCCGAGACCTGTGCGTTTCGGCT CTCGGGTTTGGATTCGAAACTTTCCGCTCGGGTTGA GCGTGACTTGGGTGCGCTGCGGGCGCCGGGGTCGC GGGCTGCGCAGGGCGGTGGGCGTGTGCGCGGGAG CCGGTCGGAGTGGAAAACGCGCCCGTGGCGGCCAC CTCCAGCCTGGCCGCTCACCCGAGCAGGGGGGCCG CTGCCCAAGAACCCTTTCCTGGAGAGCTGCTCCGA GACCGCACAGCGCCGCCGCGTCTTCTCCTTTTCCAC TCCTCTCTCC | 452 |
| MS6 | SOAT 1 | **TATGCTTACAAGGACTTTCTCTGG**TGTTTTCCTTT TTCTTTAGTTTTTCTCCAAGAGATTCAAATCTGCTG CCATGTTAGCTGTCTTTGCTGTATCTGCTGTAGTAC ACGAATATGCCTTGGCTGTTTGCTTGAGCTTTTTCT ATCCCGTGCTCTTCGTGCTCTTCATGTTCTTTGGAA TGGCTTTCAACTTCATTGTCAA | 453 |
| MS7 | PDE4 D | **TCCATCAACAAAGCCACCATAACAG**GTAAGAAA GATCTGGAGCTTATTCTTCATGTGTCTAGGAAGAA ACCATTTCTGCCAAGAGTCAATATAACACCAACAC CAATTTCATGCTGCAATTTGAAAATGTTAAAGAAA TTCTTTCTTCTCTACATTATCATTTCTATCATTGATC TCACAAATTGTCTAAGCTGTTATTTGGAACATTTTT ACCGATTTACGTTTTTTACTGATGTACATTATTTT | 454 |
| MS8 | ZYG11 A | **ACCATGCCTGCTATTTTAAAG**TTACAGAAGAATT GTCTTCTCTCCTTA | 455 |

TABLE 20-continued

| Neoantigen ID | Gene ID | Polynucleotide sequence | DNA SEQ ID NO: |
|---|---|---|---|
| MS9 | SYNE 2 | **CCATACTACAGCGCACTGTCAG**GTAACAGCTGGG TTCCCAGCACCCTGGAAAGTGACCCGTTTGGCTAT GTTTTTAGCCCCTTAGCAACACGGCCAGCTCTCAAT GACCAAGAGTCCATCTTGTGGCCGACCCTGACTTCT GTGGTTTCCTGTGCTCTATCCTGCCCATCTCTTAAC TTACCTGAGAATTGGCTCACTCTCATCACAGGTGG AATGAAAGGGGGAAAAAAAATGAAATTCACATTC AGACAC | 456 |
| MS10 | USP21 | **GGCCTTCGAAACCTGGGAAACACG**GTGAGAGCT ATTCTCCTATCTTTCCTCTCTAAAAGGAATGTGAAA TGGTGCTGGGGGTGGGGAAAACCCACGAGCTTGGG GAAGGCATGTGGAAGGAGAGCTCTGAAGCTCTTC | 457 |
| MS11 | TDG | **ATGGAAGCGGAGAACGCGGGCAGT**TTGCATTTTC ATGAAGTGCTCAAAATGGGACATGTGAAATTC | 458 |

Example 8 Expression Profiling of Prostate Neoantigens in Tumor and Normal Tissues The identified prostate neoantigens were profiled for their expression in about 90 FFPE tissue samples from prostate cancer (adenocarcinoma, clinical stages II-IV, Gleason score 8-9, subjects were treatment naïve or treated with CASODEX® (bicalutamide), LUPRON DEPOT® (leuprolide acetate for depot suspension) or FIRMAGON® (degarelix)) and a panel of normal tissues including liver, kidney, pancreas, ovary, prostate, mammary gland, colon, stomach, skeletal muscle and lung, in PBMCs obtained from healthy subjects and in prostate cancer cell lines including DU145-1, MDA-MB-436-1, LREX-1, 22RV1-1, H660-1. And other tissue cell lines including NCI-H2106-1, L-363-1, HC1-N87-1, OCI-AML5-1, MDA-PCa-2b-1 and GDM-1-1. Total RNA was extracted from formalin fixed paraffin embedded tissue samples using CELLDATA's RNAstorm-RNA isolation kit following kit protocol. RNA from cultured cell lines and PBMCs were isolated using Qiagen RNA isolation kits using standard methods. 200 ng of Total RNA from FFPE samples was used to prepare cDNA using High-capacity cDNA reverse transcription kit (ABI) and standard protocols. 37.5 ng cDNA was preamplified with gene markers in 15 μl preamplification mix using TaqMan preamplification kit (ThermoFisher Scientific) and standard protocols. To test gene expression of the identified neoantigens in the various samples, primers spanning the breakpoint sequences were designed for each of the identified prostate neoantigens and expression was assessed using Fluidigm Biomark™ HD. Percent (%) of expression positive FFPE prostate cancer samples were recorded for each neoantigen with relative average CT calculated in the prostate cancer samples. The results of the expression profiling of select neoantigens is shown in Table 21. The prevalence of each neoantigen in TCGA, SU2C and GTEx database is shown in Table 22.

TABLE 21

| Neoantigen ID | Amino acid SEQ ID NO: | Polynucleotide SEQ ID NO: | qPCR % Positive FFPE | qPCR Relative Average Ct | qPCR Normal Tissue Expression |
|---|---|---|---|---|---|
| AS18 | 275 | 276 | 95.6 | 6.3 | Ovary, Prostate |
| P87 | 381 | 382 | 85.6 | 8.3 | Ovary, Prostate |

TABLE 21-continued

| Neoantigen ID | Amino acid SEQ ID NO: | Polynucleotide SEQ ID NO: | qPCR % Positive FFPE | qPCR Relative Average Ct | qPCR Normal Tissue Expression |
|---|---|---|---|---|---|
| AS55 | 333 | 334 | 83.3 | 8.2 | Prostate |
| AS57 | 337 | 338 | 83.3 | 7.9 | Prostate |
| AS15 | 269 | 270 | 68.9 | 11.4 | Ovary, Mammary Gland |
| AS7 | 253 | 254 | 57.8 | 11.0 | None |
| AS43 | 309 | 310 | 52.2 | 11.2 | Mammary Gland |
| AS51 | 325 | 326 | 47.8 | 10.5 | Ovary |
| AS16 | 271 | 272 | 47.8 | 10.8 | Ovary |
| AS41 | 305 | 306 | 45.6 | 11.6 | Ovary |
| AS6 | 251 | 252 | 33.3 | 10.0 | None |
| AS3 | 245 | 246 | 26.7 | 10.8 | None |
| AS11 | 261 | 262 | 25.6 | 12.1 | None |
| AS13 | 265 | 266 | 21.1 | 11.1 | None |
| AS47 | 317 | 318 | 16.7 | 12.3 | Ovary |
| AS8 | 255 | 256 | 13.3 | 12.5 | None |
| AS19 | 277 | 278 | 95.6 | 6.3 | Ovary, Prostate |
| AS37 | 297 | 298 | 0.0 | N/A | None |
| AS23 | 285 | 286 | 22.0 | 13.0 | Ovary, Prostate, Mammary Gland |
| MS1 | 437 | 448 | N/A | N/A | None |
| MS3 | 439 | 450 | N/A | N/A | None |
| MS6 | 442 | 453 | N/A | N/A | None |
| MS8 | 444 | 455 | N/A | N/A | None |
| P82 | 379 | 380 | 37.0 | 11 | |
| P16 | 343 | 344 | 76 | 9 | Prostate |
| FUS1 | 211 | 212 | 72 | 9 | Prostate |
| P22 | 349 | 350 | 70 | 9 | Prostate |
| FUS2 | 213 | 214 | 55 | 11 | Mammary Gland |
| FUS3 | 215 | 216 | 43 | 11 | Prostate |
| FUS6 | 221 | 222 | 19 | 11 | None |
| FUS5 | 219 | 220 | 14 | 7 | None |
| FUS8 | 225 | 226 | 11 | 14 | None |
| FUS15 | 345 | 346 | 8 | 13 | None |
| P35 | 353 | 354 | 5 | 13 | None |
| FUS19 | 235 | 236 | 4 | 13 | None |
| FUS7 | 223 | 224 | 0 | N/A | None |
| M84 | 167 | 168 | N/A | N/A | N/A |
| M86 | 171 | 172 | N/A | N/A | N/A |
| M10 | 19 | 20 | N/A | N/A | N/A |
| M12 | 23 | 24 | N/A | N/A | N/A |
| FR1 | 177 | 178 | N/A | N/A | N/A |

TABLE 22

| Neo-antigen ID | Amino acid SEQ ID NO: | Frozen prostate cancer tissues* (n = 11) | TCGA % | SU2C % | GTEx % |
|---|---|---|---|---|---|
| AS18 | 275 | 54.5 | 12.6 | 20.9 | 0.03 |
| P87 | 381 | 0.0 | 0 | 20.9 | 0 |
| AS55 | 333 | 18.2 | 12.1 | 0 | 0 |
| AS57 | 337 | 36.4 | 14.9 | 0 | 0 |
| AS15 | 269 | 36.4 | 4.5 | 46.5 | 0 |
| AS7 | 253 | 27.3 | 5.1 | 16.3 | 0 |
| AS43 | 309 | 0.0 | 0 | 31 | 0.4 |
| AS51 | 325 | 9.1 | 0 | 23.8 | 0.52 |
| AS16 | 271 | 45.5 | 0.6 | 18.6 | 0 |
| AS41 | 305 | 0.0 | 0 | 33.3 | 0.16 |
| AS6 | 251 | 27.3 | 5.1 | 16.3 | 0 |
| AS3 | 245 | 27.3 | 10.4 | 25.6 | 0.03 |
| AS11 | 261 | 9.1 | 1.2 | 48.8 | 0.07 |
| AS13 | 265 | 27.3 | 5.7 | 32.6 | 0 |
| AS47 | 317 | 0.0 | 0 | 23.8 | 0.05 |
| AS8 | 255 | 0.0 | 0 | 14 | 0 |
| AS19 | 277 | 54.5 | 12.6 | 20.9 | 0.03 |
| AS37 | 297 | 0.0 | 0 | 38.1 | 0 |
| AS23 | 285 | 45.5 | 3.1 | 18.6 | 0.09 |
| MS1 | 437 | 18.2 | 0 | 0 | 0 |
| MS3 | 439 | 9.1 | 0.197 | 0 | 0.13 |
| MS6 | 442 | 9.1 | 0.197 | 0 | 0 |
| MS8 | 444 | 18.2 | 0 | 0 | 0.016 |
| P82 | 379 | | Varied Expression | | |
| P16 | 343 | | 27.17 | 2.33 | 0.02 |
| FUS1 | 211 | | 17.72 | 13.95 | #N/A |
| P22 | 349 | | 30.51 | 23.26 | 0.03 |
| FUS2 | 213 | | 63.58 | 46.51 | 1.78 |
| FUS3 | 215 | | 35.04 | 23.26 | 0.02 |
| FUS6 | 221 | | 21.46 | 32.56 | #N/A |
| FUS5 | 219 | | 12.40 | 18.60 | #N/A |
| FUS8 | 225 | | 1.18 | 32.56 | 0.54 |
| FUS15 | 345 | | 0.39 | 9.30 | 0.11 |
| P35 | 353 | | 1.38 | 6.98 | #N/A |
| FUS19 | 235 | | 8.86 | 30.23 | 1.04 |
| FUS7 | 223 | | 3.35 | 16.28 | 0.51 |
| M84 | 167 | | | 1.28 | |
| M86 | 171 | | | 1.09 | |
| M10 | 19 | | | 1.18 | |
| M12 | 23 | | | 0.99 | |
| FR1 | 177 | | | 0.30 | |

Example 10 Generation of Viral Vectors Encoding the Identified Neoantigens

The identified neoantigens were validated and prioritized for their inclusion into a universal prostate cancer vaccine. 41 of the identified neoantigens were selected to be included into the expression cassettes based on their expression across prostate cancer samples, low expression in normal tissues, binding to HLA, and immunogenicity. The selected 41 neoantigens are shown in Table 21 and Table 22 and include

```
AS18
(WKFEMSYTVGGPPPHVHARPRHWKTDR; SEQ ID NO: 275),

P87
(YEAGMTLGGKILFFLFLLLPLSPFSLIF; SEQ ID NO: 381),

AS55
(DGHSYTSKVNCLLLQDGFHGCVSITGAAGRRNLSIFLFLMLCKLEFHA

C; SEQ ID NO: 333),
```

-continued

```
AS57
(TGGKSTCSAPGPQSLPSTPFSTYPQWVILITEL; SEQ ID NO:
337),

AS15
(VLRFLDLKVRYLHS; SEQ ID NO: 269),

AS7
(DYWAQKEKGSSSFLRPSC; SEQ ID NO: 253),

AS43
(VPFRELKNVSVLEGLRQGRLGGPCSCHCPRPSQARLTPVDVAGPFLCLG

DPGLFPPVKSSI; SEQ ID NO: 309),

AS51
(GMECTLGQVGAPSPRREEDGWRGGHSRFKADVPAPQGPCWGGQPGSAPS

SAPPEQSLLD; SEQ ID NO: 325),

AS16
(GNTTLQQLGEASQAPSGSLIPLRLPLLWEVRG; SEQ ID NO: 271),

AS41
(EAFQRAAGEGGPGRGGARRGARVLQSPFCRAGAGEWLGHQSLR;
SEQ ID NO: 305),

AS6
(DYWAQKEKISIPRTHLC (SEQ ID NO: 251),

AS3
(VAMMVPDRQVHYDFGL (SEQ ID NO: 245),

AS11
(VPFRELKNQRTAQGAPGIHHAASPVAANLCDPARHAQHTRIPCGAGQVR

AGRGPEAGGGVLQPQRPAPEKPGCPCRRGQPRLHTVKMWRA; SEQ ID
NO: 261),

AS13
(KRSFAVTERII; SEQ ID NO: 265),

AS47
(FKKFDGPCGERGGGRTARALWARGDSVLTPALDPQTPVRAPSLTRAAAA

V; SEQ ID NO: 317),

AS8
(LVLGVLSGHSGSRL; SEQ ID NO: 255),

AS19
(QWQHYHRSGEAAGTPLWRPTRN; SEQ ID NO: 277),

AS37
(CHLFLQPQVGTPPPHTASARAPSGPPHPHESCPAGRRPARAAQTCARRQ

HGLPGCEEAGTARVPSLHLHLHQAALGAGRGRGWGEACAQVPPSRG;
SEQ ID NO: 297),

AS23
(KIQNKNCPD; SEQ ID NO: 285),

MS1
(HYKLIQQPISLFSITDRLHKTFSQLPSVHLCSITFQWGHPPIFCSTNDI

CVTANFCISVTFLKPCFLLHEASASQ; SEQ ID NO: 437),

MS3
(RTALTHNQDFSIYRLCCKRGSLCHASQARSPAFPKPVRPLPAPITRITP

QLGGQSDSSQPLLTTGRPQGWQDQALRHTQQASPASCATITIPIHSAALG

DHSGDPGPAWDTCPPLPLTTLIPRAPPPYGDSTARSWPSRCGPLG; SEQ
ID NO: 439),

MS6
(YAYKDFLWCFPFSLVFLQEIQICCHVSCLCCICCSTRICLGCLLELFLS

RALRALHVLWNGFQLHCQ; SEQ ID NO: 442),
```

-continued

MS8
(TMPAILKLQKNCLLSL; SEQ ID NO: 444),

P82
(YEAGMTLGEKFRVGNCKHLKMTRP; SEQ ID NO: 379).

P16
(GVPGDSTRRAVRRMNTF; SEQ ID NO: 343),

FUS1
(CGASACDVSLIAMDSA; SEQ ID NO: 211),

P22
(SLYHREKQLIAMDSAI; SEQ ID NO: 349),

FUS2
(TEYNQKLQVNQFSESK; SEQ ID NO: 213),

FUS3
(TEISCCTLSSEENEYLPRPEWQLQ; SEQ ID NO: 215),

FUS6
(CEERGAAGSLISCE; SEQ ID NO: 221),

FUS6
(NSKMALNSEALSVVSE; SEQ ID NO: 219),

FUS8
(WGMELAASRRFSWDHHSAGGPPRVPSVRSGAAQVQPKDPLPLRTLAGCL

ARTAHLRPGAESLPQPQLHCT; SEQ ID NO: 225),

FUS15
(HVVGYGHLDTSGSSSSSSWP; SEQ ID NO: 345),

-continued

P35
(NSKMALNSLNSIDDAQLTRIAPPRSHCCFWEVNAP; SEQ ID NO: 353),

FUS19
(KMHFSLKEHPPPPCPP; SEQ ID NO: 235),
and

FUS7
(LWFQSSELSPTGAPWPSRRPTWRGTTVSPRTATSSARTCCGTKWPSSQE

AALGLGSGLLRFSCGTAAIR; SEQ ID NO: 223),

M84
(IARELHQFAFDLLIKSH; SEQ ID NO: 167),

M86
(QPDSFAALHSSLNELGE; SEQ ID NO: 171),

M10
(FVQGKDWGLKKFIRRDF; SEQ ID NO: 19),

M12
(FVQGKDWGVKKFIRRDF; SEQ ID NO: 23),
and

FR1
(QNLQNGGGSRSSATLPGRRRRRWLRRRRQPISVAPAGPPRRPNQKPNPP

GGARCVIMRPTWPGTSAFT; SEQ ID NO: 177).

Expression cassettes were designed for cloning into viral backbones Modified Vaccinia Ankara (MVA) and Great Ape Adenovirus 20 (GAd20) by joining the 41 neoantigen sequences one after the other without any linker. Each neoantigen sequences was codon-optimized for expression in either MVA or GAd20. The optimized polynucleotide sequences are shown in Table 23 for GAd20 and Table 24 for MVA expression.

TABLE 23

| Neoantigen ID | Gene ID | Amino acid SEQ ID NO: | Codon-optimized polynucleo-tide for GAd20 expression; SEQ ID NO: | Codon-optimized polynucleotide sequence for GAd20 expression |
|---|---|---|---|---|
| AS18 | NWD1 | 275 | 459 | TGGAAGTTCGAGATGAGCTACACCGTCGGC GGACCTCCACCTCATGTTCATGCCAGACCTC GGCACTGGAAAACCGACAGA |
| P87 | AR-Intron | 381 | 460 | TATGAGGCCGGCATGACACTCGGCGGCAAG ATCCTGTTCTTCCTGTTCCTGCTGCTCCCTCT GAGCCCCTTCAGCCTGATCTTC |
| AS55 | SPOC | 333 | 461 | GATGGCCACAGCTACACCAGCAAAGTGAAC TGCCTCCTGCTGCAGGATGGCTTCCACGGCT GTGTGTCTATTACTGGCGCCGCTGGCAGAC GGAACCTGAGCATCTTTCTGTTTCTGATGCT GTGCAAGCTCGAGTTCCACGCCTGC |
| AS57 | KLK3 | 337 | 462 | ACAGGCGGCAAGTCCACATGTTCTGCCCCT GGACCTCAGAGCCTGCCTAGCACACCCTTC AGCACATACCCTCAGTGGGTCATCCTGATC ACCGAACTC |
| AS15 | LRRC45 | 269 | 463 | GTGCTGAGATTCCTGGACCTGAAAGTGCGC TACCTGCACAGC |
| AS7 | ACSM1 | 253 | 464 | GACTATTGGGCTCAAAAAGAGAAGGGCAGC AGCAGCTTCCTGCGGCCTAGCTGT |
| AS43 | CPNE7 | 309 | 465 | GTCCCCTTCAGAGAGCTGAAGAACGTTTCC GTGCTGGAAGGCCTGAGACAGGGCAGACTT |

TABLE 23-continued

| Neoantigen ID | Gene ID | Amino acid SEQ ID NO: | Codon-optimized polynucleotide for GAd20 expression; SEQ ID NO: | Codon-optimized polynucleotide sequence for GAd20 expression |
|---|---|---|---|---|
| | | | | GGCGGCCCTTGTAGCTGTCACTGCCCCAGACCTAGTCAGGCCAGACTGACACCTGTGGATGTGGCCGGACCTTTCCTGTGTCTGGGAGATCCTGGCCTGTTTCCACCTGTGAAGTCCAGCATC |
| AS51 | CPNE7 | 325 | 466 | GGCATGGAATGCACCCTGGGACAAGTGGGAGCCCCATCTCCTAGAAGAGAAGAGGATGGCTGGCGCGGAGGCCACTCTAGATTCAAAGCTGATGTGCCCGCTCCTCAGGGCCCTTGTTGGGGAGGACAACCTGGATCTGCCCCATCTTCTGCCCCACCTGAACAGTCCCTGCTGGAT |
| AS16 | LRRC45 | 271 | 467 | GGCAACACAACCCTCCAGCAACTGGGAGAAGCCTCTCAGGCTCCTAGCGGCTCTCTGATCCCTCTCAGACTGCCTCTCCTGTGGGAAGTTCGGGGC |
| AS41 | RHPN1 | 305 | 468 | GAGGCTTTCCAAAGAGCTGCTGGCGAAGGCGGACCTGGTAGAGGTGGTGCTAGAAGAGGTGCTAGGGTGCTGCAGAGCCCATTCTGTAGAGCAGGCGCAGGCGAATGGCTGGGCCATCAGAGTCTGAGA |
| AS6 | ACSM1 | 251 | 469 | GATTATTGGGCCCAGAAAGAAAAGATCAGCATCCCCAGAACACACCTGTGC |
| AS3 | DNAH8 | 245 | 470 | GTGGCCATGATGGTGCCCGATAGACAGGTCCACTACGACTTTGGACTG |
| AS11 | CPNE7 | 261 | 471 | GTGCCCTTCCGGGAACTGAAGAACCAGAGAACAGCTCAGGGCGCTCCTGGAATCCACCATGCTGCTTCTCCAGTGGCCGCCAACCTGTGTGATCCTGCCAGACATGCCCAGCACACCAGGATTCCTTGTGGCGCTGGACAAGTGCGCGCTGGAAGAGGACCTGAAGCAGGCGGAGGTGTTCTGCAACCTCAAAGACCCGCTCCTGAGAAGCCTGGCTGCCCTTGCAGAAGAGGACAGCCTAGACTGCACACCGTGAAAATGTGGCGAGCC |
| AS13 | GRIN3A | 265 | 472 | AAGAGAAGCTTTGCCGTGACCGAGCGGATCATC |
| AS47 | AGRN | 317 | 473 | TTCAAGAAGTTCGACGGCCCTTGCGGAGAAAGAGGCGGAGGCAGAACAGCTAGAGCCCTTTGGGCTAGAGGCGACAGCGTTCTGACACCAGCTCTGGACCCTCAGACACCTGTTAGGGCCCCTAGCCTGACAAGAGCTGCCGCCGCTGTG |
| AS8 | CACNA1D | 255 | 474 | CTGGTGCTGGGAGTGCTGTCTGGACACTCTGGCAGCAGACTG |
| AS19 | NWD1 | 277 | 475 | CAGTGGCAGCACTATCACAGATCTGGCGAAGCCGCCGGAACACCCCTTTGGAGGCCAACAAGAAAC |
| AS37 | RECQL4 | 297 | 476 | TGCCACTTGTTTCTGCAGCCCCAAGTGGGCACACCTCCTCCACATACAGCCTCTGCTAGAGCACCTAGCGGCCCTCCACATCCTCACGAATCTTGTCCTGCCGGAAGAAGGCCTGCCAGAGCCGCTCAAACATGTGCCAGACGACAGCACGGACTGCCTGGATGTGAAGAGGCTGGAACAGCCAGAGTGCCTAGCCTGCACCTCCATCTGCATCAGGCTGCTCTTGGAGCCGGAAGAGGTAGAGGATGGGGCGAAGCTTGTGCTCAGGTGCCACCTTCTAGAGGC |
| AS23 | ZNF614 | 285 | 477 | AAGATCCAGAACAAGAACTGCCCCGAC |
| MS1 | TTLL7 | 437 | 478 | CACTACAAGCTGATCCAGCAGCCAATCAGCCTGTTCAGCATCACCGACCGGCTGCACAAG |

TABLE 23-continued

| Neoantigen ID | Gene ID | Amino acid SEQ ID NO: | Codon-optimized polynucleotide for GAd20 expression; SEQ ID NO: | Codon-optimized polynucleotide sequence for GAd20 expression |
|---|---|---|---|---|
| | | | | ACATTCAGCCAGCTGCCAAGCGTGCACCTG TGCTCCATCACCTTCCAGTGGGGACACCCTC CTATCTTTTGCTCCACCAACGACATCTGCGT GACCGCCAACTTCTGTATCAGCGTGACCTTC CTGAAGCCTTGCTTTCTGCTGCACGAGGCCA GCGCCTCTCAG |
| MS3 | TESK1 | 439 | 479 | CGAACCGCTCTGACACACAACCAGGACTTC AGCATCTACAGACTGTGTTGCAAGCGGGGC TCCCTGTGCCATGCAAGCCAAGCTAGAAGC CCCGCCTTTCCTAAACCTGTGCGACCTCTGC CAGCTCCAATCACCAGAATTACCCCTCAGCT CGGCGGCCAGAGCGATTCATCTCAACCTCT GCTGACCACCGGCAGACCTCAAGGCTGGCA AGACCAAGCTCTGAGACACACCCAGCAGGC TAGCCCTGCCTCTTGTGCCACCATCACAATC CCCATCCACTCTGCCGCTCTGGGCGATCATT CTGGCGATCCTGGACCAGCCTGGGACACAT GTCCTCCACTGCCACTCACAACACTGATCCC TAGGGCTCCTCCACCTTACGGCGATTCTACC GCTAGAAGCTGGCCCAGCAGATGTGGACCA CTCGGA |
| MS6 | SOAT1 | 442 | 480 | TACGCCTACAAGGACTTCCTGTGGTGCTTCC CCTTCTCTCTGGTGTTCCTGCAAGAGATCCA GATCTGCTGTCATGTGTCCTGCCTGTGCTGC ATCTGCTGTAGCACCAGAATCTGCCTGGGCT GTCTGCTGGAACTGTTCCTGAGCAGAGCCCT GAGAGCACTGCACGTGCTGTGGAACGGATT CCAGCTGCACTGCCAG |
| MS8 | ZYG11A | 444 | 481 | ACAATGCCCGCCATCCTGAAGCTGCAGAAG AATTGCCTCCTAAGCCTG |
| P82 | AR-V7 | 379 | 482 | TACGAAGCCGGGATGACCCTGGGCGAGAAG TTCAGAGTGGGCAACTGCAAGCACCTGAAG ATGACCCGGCCT |
| P16 | MSMB-NCOA4-1 | 343 | 483 | GGCGTGCCAGGCGATAGCACTCGGAGAGCC GTCAGACGGATGAACACCTTT |
| FUS1 | SLC45A3 -> ELK4-1 | 211 | 484 | TGTGGCGCCTCTGCCTGTGACGTGTCCCTGA TCGCTATGGACTCCGCC |
| P22 | SLC45A3 -ELK4-2 | 349 | 485 | AGCCTGTACCACCGGGAAAAGCAGCTCATT GCCATGGACAGCGCCATC |
| FUS2 | ARHGEF 38-> ARHGEF 38-IT1 | 213 | 486 | ACCGAGTACAACCAGAAACTGCAAGTGAAC CAGTTCAGCGAGAGCAAG |
| FUS3 | MSMB-> NCOA4-2 | 215 | 487 | ACCGAGATCAGCTGCTGCACCCTGAGCAGC GAGGAAAACGAGTACCTGCCTAGACCTGAG TGGCAGCTGCAG |
| FUS6 | TMPRSS 2-> ERG | 221 | 488 | TGCGAAGAGAGAGGCGCCGCAGGATCTCTG ATCTCCTGCGAA |
| FUS5 | TMPRSS 2-> ERG | 219 | 489 | AACAGCAAGATGGCCCTGAATAGCGAGGCC CTGTCTGTGGTGTCTGAA |
| FUS8 | INCA1-> CAMTA 2 | 225 | 490 | TGGGGCATGGAACTGGCCGCCAGCAGAAGA TTCAGCTGGGATCATCATAGCGCAGGCGGC CCACCTAGAGTGCCATCTGTTAGAAGCGGA GCTGCCCAGGTGCAGCCTAAAGATCCTCTG |

TABLE 23-continued

| Neoantigen ID | Gene ID | Amino acid SEQ ID NO: | Codon-optimized polynucleotide for GAd20 expression; SEQ ID NO: | Codon-optimized polynucleotide sequence for GAd20 expression |
|---|---|---|---|---|
| | | | | CCACTGAGAACACTGGCCGGCTGCCTTGCT AGAACAGCCCATCTTAGACCTGGCGCCGAG TCTCTGCCTCAGCCACAACTGCACTGTACC |
| FUS15 | D2HGD H-> GAL3ST 2 | 345 | 491 | CATGTCGTCGGCTACGGCCACCTGGATACA AGCGGAAGCAGCTCTAGCTCCAGCTGGCCT |
| P35 | TMPRSS 2-ERG | 353 | 492 | AACTCAAAAATGGCTCTGAACAGCCTGAAC TCCATCGACGACGCCCAGCTGACAAGAATC GCCCCTCCTAGATCTCACTGCTGCTTTTGGG AAGTGAACGCCCCA |
| FUS19 | GTF2F1->PSPN | 235 | 493 | AAGATGCACTTTAGCCTGAAAGAACACCCT CCACCACCTTGTCCTCCA |
| FUS7 | NME4->DECR2 | 223 | 494 | CTGTGGTTCCAGTCCAGCGAGCTGTCTCCTA CTGGTGCCCCTTGGCCATCTAGACGCCCTAC TTGGAGAGGCACCACCGTGTCACCAAGAAC CGCCACAAGCAGCGCCAGAACCTGTTGTGG CACAAAGTGGCCCTCCAGCCAAGAAGCCGC TCTCGGACTTGGAAGCGGACTGCTGAGGTT CTCTTGTGGAACCGCCGCCATTCGG |
| M84 | AR-T878A | 167 | 495 | ATCGCTAGAGAGCTGCACCAGTTCGCCTTC GACCTGCTGATCAAGAGCCAC |
| M86 | AR-L702H | 171 | 496 | CAGCCTGATTCTTTTGCCGCACTGCACAGCT CCCTGAACGAGCTGGGAGAG |
| M10 | SPOP-F133L | 19 | 497 | TTCGTGCAAGGCAAGGATTGGGGCCTCAAA AAGTTTATCCGCAGAGACTTC |
| M12 | SPOP-W133V | 23 | 498 | TTTGTGCAGGGCAAAGACTGGGGCGTGAAG AAGTTCATCCGGCGGGACTTC |
| FR1 | ZFHX3 | 177 | 499 | CAGAACCTGCAGAACGGCGGAGGCTCTAGA AGCTCTGCTACACTTCCTGGCAGGCGGCGG AGAAGATGGCTGAGAAGAAGGCGGCAGCC TATCTCTGTGGCTCCTGCTGGACCTCCTAGA CGGCCCAACCAGAAGCCTAATCCTCCTGGC GGAGCCAGATGCGTGATCATGAGGCCTACA TGGCCTGGCACCAGCGCCTTCACC |

TABLE 24

| Neoantigen ID | Gene ID | Amino acid SEQ ID NO: | Codon-optimized polynucleotide for MVA expression; SEQ ID NO: | Codon-optimized polynucleotide sequence for MVA expression |
|---|---|---|---|---|
| AS18 | NWD1 | 275 | 500 | TGGAAGTTCGAGATGAGCTACACCGTTGG CGGCCCTCCACCACATGTTCACGCCAGAC CTAGACACTGGAAAACCGACAGA |
| P87 | AR-Intron | 381 | 501 | TACGAGGCCGGCATGACACTCGGAGGCAA GATCCTGTTCTTCCTGTTCCTGCTGCTCCCT CTGAGCCCCTTCAGCCTGATCTTT |
| AS55 | SPOC | 333 | 461 | GATGGCCACAGCTACACCAGCAAAGTGAA CTGCCTCCTGCTGCAGGATGGCTTCCACGG CTGTGTGTCTATTACTGGCGCCGCTGGCAG ACGGAACCTGAGCATCTTTCTGTTTCTGAT GCTGTGCAAGCTCGAGTTCCACGCCTGC |

TABLE 24-continued

| Neoantigen ID | Gene ID | Amino acid SEQ ID NO: | Codon-optimized polynucleotide for MVA expression; SEQ ID NO: | Codon-optimized polynucleotide sequence for MVA expression |
|---|---|---|---|---|
| AS57 | KLK3 | 337 | 503 | ACAGGCGGCAAGAGCACATGTTCTGCCCCTGGACCTCAGTCTCTGCCCAGCACACCCTTCAGCACATACCCTCAGTGGGTCATCCTGATCACCGAGCTG |
| AS15 | LRRC45 | 269 | 504 | GTGCTGCGGTTCCTGGATCTCAAAGTGCGCTACCTGCACAGC |
| AS7 | ACSM1 | 253 | 505 | GATTATTGGGCCCAGAAAGAAAAGGGCAGCAGCAGCTTCCTGCGGCCTAGCTGT |
| AS43 | CPNE7 | 309 | 506 | GTGCCCTTCCGGGAACTGAAGAACGTGTCCGTTCTGGAAGGCCTGAGGCAGGGCAGACTTGGCGGACCTTGTAGCTGCCACTGTCCTAGACCAAGCCAGGCCAGACTGACCCCTGTGGATGTGGCTGGCCCATTTCTGTGTCTGGGCGACCCTGGACTGTTCCCTCCAGTGAAGTCTAGCATC |
| AS51 | CPNE7 | 325 | 507 | GGCATGGAATGTACACTGGGCCAAGTGGGAGCCCCATCTCCTAGAAGAGAAGAGGATGGCTGGCGCGGAGGCCACTCTAGATTCAAAGCTGATGTGCCCGCTCCTCAGGGCCCTTGTTGGGGAGGACAACCTGGATCTGCCCCATCTTCTGCCCCACCTGAACAGAGCCTGCTGGAT |
| AS16 | LRRC45 | 271 | 508 | GGCAACACCACACTGCAACAGCTGGGAGAAGCCTCTCAGGCCCCAAGCGGTTCTCTGATCCCTCTCAGACTGCCCCTCCTGTGGGAAGTGCGGGGC |
| AS41 | RHPN1 | 305 | 509 | GAGGCTTTCCAGAGAGCAGCTGGCGAAGGCGGACCTGGCAGAGGTGGTGCTAGAAGAGGTGCTAGAGTGCTGCAGAGCCCATTCTGTAGAGCTGGCGCTGGCGAATGGCTGGGCCACCAATCTCTTAGA |
| AS6 | ACSM1 | 251 | 510 | GACTATTGGGCTCAAAAAGAGAAGATCAGCATCCCCAGAACACACCTGTGC |
| AS3 | DNAH8 | 245 | 511 | GTGGCCATGATGGTGCCCGACAGACAGGTGCACTACGACTTCGGCCTG |
| AS11 | CPNE7 | 261 | 512 | GTGCCCTTCAGAGAGCTGAAAAACCAGAGAACAGCCCAGGGCGCTCCTGGAATCCATCATGCTGCTTCTCCAGTGGCCGCCAATCTGTGCGATCCTGCCAGACATGCCCAGCATACCAGGATTCCTTGTGGCGCTGGACAAGTGCGCGCTGGAAGAGGACCTGAAGCTGGTGGCGGAGTTCTGCAGCCTCAAAGACCTGCTCCTGAGAAGCCTGGCTGCCCCTGTAGAAGAGGACAGCCTAGACTGCACACCGTGAAGATGTGGCGGGCC |
| AS13 | GRIN3A | 265 | 513 | AAGAGAAGCTTCGCCGTGACCGAGCGGATCATC |
| AS47 | AGRN | 317 | 514 | TTTAAGAAGTTTGACGGCCCCTGCGGCGAGAGAGGCGGAGGAAGAACTGCAAGAGCCCTTTGGGCCAGAGGCGACTCTGTTCTGACACCAGCTCTGGACCCTCAGACACCTGTTAGGGCCCCTAGCCTGACAAGAGCTGCCGCTGCTGTT |
| AS8 | CACNA1D | 255 | 515 | CTGGTGCTGGGCGTGCTGTCTGGCCACTCTGGAAGCAGACTG |
| AS19 | NWD1 | 277 | 516 | CAATGGCAGCACTACCACAGATCTGGCGAAGCCGCTGGAACCCCACTTTGGAGGCCTACCAGAAAC |

TABLE 24-continued

| Neoantigen ID | Gene ID | Amino acid SEQ ID NO: | Codon-optimized polynucleotide for MVA expression; SEQ ID NO: | Codon-optimized polynucleotide sequence for MVA expression |
|---|---|---|---|---|
| AS37 | RECQL4 | 297 | 517 | TGCCACTTGTTTCTCCAGCCACAAGTGGGC ACCCCTCCACCTCATACAGCCTCTGCTAGA GCACCTAGCGGCCCACCTCATCCTCACGA ATCTTGTCCTGCCGGAAGAAGGCCTGCCA GAGCCGCTCAAACATGTGCCAGACGACAG CACGGACTGCCCGGATGTGAAGAAGCCGG AACAGCCAGAGTGCCTAGCCTGCACCTTC ATCTGCATCAGGCCGCTCTTGGAGCCGGA AGAGGTAGAGGATGGGGAGAAGCTTGTGC CCAGGTGCCACCTTCTAGAGGC |
| AS23 | ZNF614 | 285 | 477 | AAGATCCAGAACAAGAACTGCCCCGAC |
| MS1 | TTLL7 | 437 | 519 | CACTACAAGCTGATCCAGCAGCCAATCAG CCTGTTCTCCATCACCGACCGGCTGCACAA GACATTCAGCCAGCTGCCTTCCGTGCATCT GTGCAGCATCACCTTCCAGTGGGGACACC CTCCTATCTTTTGCTCCACCAACGACATCT GCGTGACCGCCAACTTCTGTATCAGCGTG ACCTTCCTGAAGCCTTGCTTTCTGCTGCAC GAGGCCTCCGCCAGCCAG |
| MS3 | TESK1 | 439 | 520 | CGGACCGCTCTGACCCACAACCAGGACTT CAGCATCTACCGGCTGTGCTGCAAGAGGG GCTCTCTGTGTCATGCTAGCCAGGCTAGA AGCCCCGCCTTTCCTAAGCCTGTCAGACCT CTGCCTGCTCCTATCACCAGAATCACCCCT CAGCTCGGCGGCCAGTCTGATTCATCTCA GCCACTGCTGACCACCGGCAGACCTCAAG GATGGCAAGACCAGGCTCTGAGACACACA CAGCAGGCTAGCCCAGCCTCTTGCGCCAC CATCACAATACCAATACATTCTGCCGCTCT GGGCGATCACAGCGGAGATCCTGGACCTG CCTGGGATACTTGTCCTCCTCTGCCCCTAA CTACACTGATCCCTAGGGCTCCTCCACCTT ACGGCGATAGCACAGCCAGATCCTGGCCT AGCAGATGTGGCCCTCTGGGC |
| MS6 | SOAT1 | 442 | 521 | TACGCCTACAAGGACTTCCTGTGGTGCTTC CCCTTCTCTCTGGTGTTCCTGCAAGAAATC CAGATCTGCTGTCACGTGTCCTGCCTGTGC TGTATCTGCTGTAGCACCCGGATCTGTCTG GGCTGTCTGCTGGAACTGTTCCTGAGCAG AGCCCTGAGAGCACTGCACGTGCTGTGGA ACGGATTCCAGCTGCACTGCCAG |
| MS8 | ZYG11A | 444 | 522 | ACCATGCCTGCCATTCTGAAGCTGCAGAA GAATTGTCTTCTAAGCCTG |
| P82 | AR-V7 | 379 | 523 | TATGAGGCTGGAATGACCCTGGGCGAGAA GTTCAGAGTGGGCAACTGCAAGCACCTGA AGATGACCCGGCCT |
| P16 | MSMB-NCOA4-1 | 343 | 524 | GGAGTGCCTGGCGATTCTACTAGAAGGGC CGTGCGGCGGATGAACACCTTT |
| FUS1 | SLC45A3-> ELK4 - 1 | 211 | 525 | TGTGGCGCATCTGCCTGCGACGTGTCCCTG ATCGCTATGGATAGCGCC |
| P22 | SLC45A3-ELK4 - 2 | 349 | 485 | AGCCTGTACCACCGGGAAAAGCAGCTCAT TGCCATGGACAGCGCCATC |
| FUS2 | ARHGEF38-> ARHGEF38-IT1 | 213 | 486 | ACCGAGTACAACCAGAAACTGCAAGTGAA CCAGTTCAGCGAGAGCAAG |
| FUS3 | MSMB-> NCOA4-2 | 215 | 528 | ACCGAGATCAGCTGCTGCACCCTGAGCAG CGAGGAAAACGAGTACCTGCCTAGACCTG AATGGCAGCTGCAG |

TABLE 24-continued

| Neoantigen ID | Gene ID | Amino acid SEQ ID NO: | Codon-optimized polynucleotide for MVA expression; SEQ ID NO: | Codon-optimized polynucleotide sequence for MVA expression |
|---|---|---|---|---|
| FUS6 | TMPRSS2-> ERG | 221 | 529 | TGCGAGGAAAGAGGCGCAGCCGGATCTCT GATCTCTTGCGAG |
| FUS8 | TMPRSS2-> ERG | 219 | 530 | AACAGCAAGATGGCCCTGAATAGCGAGGC CCTGTCTGTGGTGTCCGAG |
| FUS8 | INCA1-> CAMTA2 | 225 | 531 | TGGGGAATGGAACTGGCCGCTAGCAGGCG GTTTAGCTGGGATCATCATTCTGCCGGCGG ACCTCCAAGAGTGCCAAGCGTTAGAAGCG GAGCAGCCCAGGTCCAGCCTAAAGATCCA CTGCCACTGAGAACACTGGCCGGCTGCCT TGCCAGAACAGCTCATCTTAGACCTGGCG CCGAAAGCCTGCCTCAACCTCAGCTGCAT TGCACA |
| FUS15 | D2HGDH-> GAL3ST2 | 345 | 532 | CACGTTGTCGGCTATGGCCACCTGGATAC AAGCGGCTCCTCTAGCAGTAGCTCCTGGC CT |
| P35 | TMPRSS2- ERG | 353 | 533 | AATTCTAAGATGGCTCTCAACAGCCTGAA CTCCATCGACGACGCCCAGCTGACAAGAA TCGCCCCTCCAAGAAGCCACTGTTGCTTTT GGGAAGTGAACGCCCCT |
| FUS19 | GTF2F1-> PSPN | 235 | 534 | AAGATGCACTTCTCACTGAAAGAGCACCC GCCACCGCCGTGCCCACCG |
| FUS7 | NME4-> DECR2 | 223 | 535 | CTGTGGTTCCAGTCCAGCGAACTGTCTCCT ACTGGCGCTCCATGGCCAAGCAGAAGGCC TACTTGGAGAGGCACCACCGTGTCTCCAA GAACCGCTACAAGCAGCGCCAGAACCTGT TGCGGCACAAAATGGCCCTCCAGCCAAGA AGCTGCCCTCGGACTTGGAAGCGGACTGC TGAGATTCAGCTGTGGCACAGCCGCCATC AGA |
| M84 | AR-T878A | 167 | 536 | ATCGCCAGAGAACTGCACCAGTTCGCCTT CGACCTGCTGATCAAGAGCCAC |
| M86 | AR-L702H | 171 | 537 | CAGCCTGACAGCTTTGCTGCCCTGCATAGC TCCCTGAATGAGCTGGGCGAA |
| M10 | SPOP-F133L | 19 | 538 | TTTGTGCAGGGTAAAGATTGGGGCCTCAA AAAGTTTATCAGACGGGACTTC |
| M12 | SPOP-W133V | 23 | 539 | TTCGTGCAGGGCAAAGACTGGGGCGTGAA GAAGTTCATCCGGCGGGACTTT |
| FR1 | ZFHX3 | 177 | 540 | CAGAACCTGCAGAACGGCGGAGGCTCTAG AAGCTCTGCTACACTTCCTGGCAGGCGGC GGAGAAGATGGCTGAGAAGAAGGCGGCA GCCTATCTCTGTGGCTCCTGCTGGACCTCC TAGACGGCCCAACCAGAAGCCTAATCCTC CTGGCGGAGCCAGATGCGTGATCATGAGG CCTACATGGCCTGGCACCAGCGCCTTTACC |

Synthetic Gene Design

The 41 neoantigen amino acidic sequences were joined head to tail. The order of the neoantigens sequences was determined according to a strategy that minimized the formation of predicted junctional epitopes that may be generated by the juxtaposition of two adjacent neoantigen peptides.

To this purpose, custom tools were developed to split the 41 neoantigens into 4 smaller lists (sublists) of similar cumulative length and to generate, for each sublist, 2 million scrambled layouts of the synthetic gene with a different neoantigen order. The tool proceeded iteratively. At each loop a scrambled layout was generated and compared to the layouts already generated. If the number of predicted junctional epitopes in the new layout was lower than the number of the previously best layout, the new layout was considered as the best. Each scrambled layout was analyzed estimating the number of potential junctional epitopes predicted to bind one out of a subset of 9 class I HLA haplotypes with an $IC_{50}$<=1500 nM (considering only 9mer epitopes predicted by the IEDB_recommended method included in the IEDB 2.17 software). The 9 class I HLA haplotypes cumulatively cover 82% of the world population as estimated by analyzing haplotypes annotated for subjects in the 1000 genomes project. Scrambled layouts with neoantigens that formed predicted junctional epitopes with the N-terminal T-cell enhancer or the C-terminal TAG sequence were excluded. As an additional constraint, in each layout junctions that contained a 9mer peptide that matched a protein annotated in the human wildtype proteome were also excluded.

The best layouts obtained after scrambling 2 million times each of the 4 sublists were then joined to generate an overall layout comprising all 41 neoantigens. Out of all possible combinations of the best 4 layouts the one with the minimal number of predicted epitopes formed by the newly formed junctions was selected.

The whole procedure described was applied two times independently to generate two artificial genes to be encoded alternatively by the GAd20 or MVA vector. For the MVA vector the scrambled layouts were designed with the additional constraint of avoiding the junctions with predicted junctional epitopes that were already present in the layout selected for the Adenoviral transgene.

Amino acid sequences of the optimized layout for the GAd20 is shown in SEQ ID NO: 541 and for MVA SEQ ID NO: 543. Neoantigens in the GAd20 insert of SEQ ID NO: 541 were in the following order: FR1-AS13-AS7-AS6-AS8-P87-FUS3-AS43-AS57-AS51-AS18-AS55-AS23-AS47-MS1-AS37-AS15-AS19-AS11-AS3-P16-P82-FUS5-FUS1-M12-MS6-FUS2-P22-FUS6-MS8-MS3-AS16-M86-M84-M10-FUS8-FUS7-FUS19-AS41-FUS15-P35. Neoantigens in the MVA insert of SEQ DID NO: 543 were in the following order: FR1-AS51-AS6-AS18-AS7-AS43-FUS3-P87-AS8-AS13-AS57-AS55-AS19-AS3-AS23-AS15-AS11-AS37-MS1-AS47-P16-FUS1-FUS6-P22-M12-MS8-FUS5-P82-FUS2-MS3-MS6-AS16-P35-M10-AS41-FUS8-M84-FUS19-FUS15-M86-FUS7

Five additional alternative optimized layouts of scrambled neoantigens were assessed for each vector. The five alternative layouts had the same number of predicted junctional epitopes compared to SEQ ID NO: 541 and SEQ ID NO: 543. The five alternative layouts for Gad20 are shown in SEQ ID NO: 554, SEQ ID NO; 555, SEQ ID NO: 556, SEQ ID NO: 623 and SEQ ID NO: 624. The five alternative layouts for MVA are shown in SEQ ID NO: 557, SEQ ID NO: 558, SEQ ID NO: 559, SEQ ID NO: 625 and SEQ ID NO: 626. The neoantigens in the alternative optimized layouts were in the following order:

SEQ ID NO: 554: FR1-AS13-AS8-P87-FUS3-AS43-AS57-AS51-AS7-AS6-AS18-P16-P82-FUS5-FUS1-M12-MS6-FUS2-P22-FUS6-MS8-MS3-AS55-AS23-AS47-MS1-AS37-AS15-AS19-AS11-AS3-AS16-M86-M84-M10-FUS8-FUS7-FUS19-AS41-FUS15-P35

SEQ ID NO: 555: FR1-AS13-FUS3-P87-AS7-AS43-AS57-AS51-AS6-AS8-AS18-AS55-AS23-AS47-MS1-AS37-AS15-AS19-AS 11-AS3-P16-P82-FUS5-FUS1-M12-MS6-FUS2-P22-FUS6-MS8-MS3-AS16-M86-M84-M10-FUS8-FUS7-FUS19-AS41-FUS15-P35

SEQ ID NO: 556: FRI-AS13-AS7-AS43-AS8-P87-FUS3-AS57-AS51-AS6-AS18-AS55-AS23-AS47-MS1-AS37-AS15-AS19-AS 11-AS3-P16-P82-FUS5-FUS1-M12-MS6-FUS2-P22-FUS6-MS8-MS3-AS16-M86-M84-M10-FUS8-FUS7-FUS19-AS41-FUS15-P35

ID NO: 623: P16-P82-FUS5-FUS1-M12-MS6-FUS2-P22-FUS6-MS8-MS3-AS16-M86-M84-M10-FUS8-FUS7-FUS19-AS41-FUS15-P35-AS55-AS23-AS47-MS1-AS37-AS15-AS19-AS11-AS3-FR1-AS13-AS8-P87-FUS3-AS43-AS57-AS51-AS7-AS6-AS18

SEQ ID NO: 624: AS16-M86-M84-M10-FUS8-FUS7-FUS19-AS41-FUS15-P35-P16-P82-FUS5-FUS1-M12-MS6-FUS2-P22-FUS6-MS8-MS3-AS55-AS23-AS47-MS1-AS37-AS15-AS19-AS11-AS3-FR1-AS13-FUS3-P87-AS7-AS43-AS57-AS51-AS6-AS8-AS18

SEQ ID NO: 557: FR1-AS51-AS6-AS18-AS7-AS43-FUS3-P87-AS8-AS13-AS57-AS55-AS37-MS1-AS3-AS23-AS15-AS11-AS19-AS47-P16-FUS1-FUS6-P22-M12-MS8-FUS5-P82-FUS2-MS3-MS6-AS16-P35-M10-AS41-FUS8-M84-FUS19-FUS15-M86-FUS7

SEQ ID NO: 558: AS55-AS19-AS3-AS15-AS23-AS11-AS37-MS1-AS47-FR1-AS51-AS6-AS18-AS7-AS43-FUS3-P87-AS8-AS13-AS57-P16-FUS1-FUS6-P22-M12-MS8-FUS5-P82-FUS2-MS3-MS6-AS16-P35-M10-AS41-FUS8-M84-FUS19-FUS15-M86-FUS7

ID NO: 559: AS16-P35-M10-AS41-FUS8-M84-FUS19-FUS15-M86-FUS7-AS55-AS19-AS3-AS23-AS15-AS11-AS37-MS1-AS47-P16-FUS1-FUS2-P82-MS8-FUS5-FUS6-P22-M12-MS3-MS6-FR1-AS51-AS6-AS18-AS7-AS43-FUS3-P87-AS8-AS13-AS57

ID NO: 625: AS16-P35-M10-AS41-FUS8-M84-FUS19-FUS15-M86-FUS7-FR1-AS51-AS6-AS18-AS7-AS43-FUS3-P87-AS8-AS13-AS57-AS55-AS19-AS3-AS15-AS23-AS11-AS37-MS1-AS47-P16-FUS1-FUS6-P22-M12-MS8-FUS5-P82-FUS2-MS3-MS6

SEQ ID NO: 626: AS55-AS11-AS19-AS23-AS3-AS15-AS37-MS1-AS47-FR1-AS51-AS6-AS18-AS7-AS43-FUS3-P87-AS8-AS13-AS57-AS16-P35-M10-AS41-FUS8-M84-FUS19-FUS15-M86-FUS7-P16-FUS1-FUS6-P22-M12-P82-MS8-FUS5-FUS2-MS3-MS6

Insertion of T-Cell Enhancer and TAG Sequences

A small peptide fragment with length of 28aa from the mandarin fish invariant chain (MGQKEQIHTLQKNSERMSKQLTRSSQAV; SEQ ID NO: 549) was placed at the N-terminus of each transgene encoding the 41 neoantigens. Preclinical data has shown this sequence to increase the immunological response of the viral vector. A small segment of 7 amino acids (TAG sequence; seq: SHHHHHH; SEQ ID NO: 627) was added at the C-terminus of the transgene for the purpose of monitoring the expression of the encoded transgene.

Amino acid sequences of the optimized layout for the GAd20 that includes the TCE sequence and omits the tag sequence are shown in SEQ ID NO: 550 and for MVA SEQ ID NO: 551.

Conversion into Nucleotide Sequence and Optimization to Remove Predicted miRNA Binding Sites.

The conversion from amino acid sequence into nucleotide sequence was performed using codon optimizing according to the human codon usage applying additional constraints to avoid as much as possible the following features:

internal TATA-boxes, chi-sites and ribosomal entry sites

AT-rich or GC-rich sequence stretches

RNA instability motifs repeat sequences and RNA secondary structures (cryptic) splice donor and acceptor sites in higher eukaryotes TTTTTnT termination motifs for the MVA vector EcoR1, BamH1 restriction sites and a KOZAK sequence were then added upstream the optimized nucleotide sequence. 2 STOP codons followed by Asc1 and Notl restriction sites were added downstream the optimized nucleotide sequence.

The optimized nucleotide sequence of each transgene was then further analyzed with the PITA and miranda software to detect predicted miRNA target sites that might downregulate the expression of the synthetic transgene. 9 miRNA binding sites detected by both methods were removed by modifying the nucleotide sequence of the regions that are predicted to bind the miRNA "seed" by introducing synonymous changes in the corresponding codons. The synthesis of GAd20 and MVA transgenes, was performed using standard methods.

The codon optimized polynucleotide sequence encoding the GAd20 neoantigen layout of SEQ ID NO: 541 is shown in SEQ ID NO: 542.

The codon optimized polynucleotide sequence encoding the MVA (neoMVA) neoantigen layout of SEQ ID NO: 543 is shown in SEQ ID NO: 544.

The codon optimized polynucleotide sequence encoding the GAd20 neoantigen layout including the TCE sequence and excluding the TAG sequence of SEQ ID NO: 550 is shown in SEQ ID NO: 551.

The codon optimized polynucleotide sequence encoding the MVA neoantigen layout including the TCE sequence and excluding the TAG sequence of SEQ ID NO: 552 is shown in SEQ ID NO: 553.

```
Kozak sequence:
                                        SEQ ID NO: 545
CGCGACTTCGCCGCC;

Polynucleotide encoding the TCE:
                                        SEQ ID NO: 546
ATGGGCCAGAAAGAGCAGATCCACACACTGCAGAAAAACAGCGAGCGGAT

GAGCAAGCAGCTGACCAGATCTTCTCAGGCCGTG;

Polynucleotide encoding the serine-histidine tag:
                                        SEQ ID NO: 547
AGCCATCACCATCACCACCAT;

Two stop codons (TAGTAA)
Polypeptide sequence of the TCE:
                                        SEQ ID NO: 549
MGQKEQIHTLQKNSERMSKQLTRSSQAV;
```

Viral Vector Production

GAd20 Viral Vector Production

The GAd20 transgene was subcloned into a shuttle plasmid between CMV promoter with two TetO repeats and a BGH polyA via ECOR1-NOT1 restriction sites.

The resulting expression cassette was transferred into the GAd20 genome by homologous recombination in suitable *E. coli* strains, transformed with the CMV-transgene-BGH DNA fragment and with a construct carrying the GAd20 genome.

Recombination involved CMV and BGH as homology arms, that were already present in the GAd20 construct in place of the E1 deletion (insertion site of the transgene). Recombinant GAd20 vectors were then rescued by transfection of the E1 complementing, TetR expressing M9 cells and amplified by subsequent re-infection of fresh M9 cells.

```
CMV promoter with TetO sites:
                                        SEQ ID NO: 628
Ccattgcatacgttgtatccatatcataatatgtacatttatattggctc

atgtccaacattaccgccatgttgacattgattattgactagttattaat

agtaatcaattacggggtcattagttcatagcccatatatggagttccgc

gttacataacttacggtaaatggcccgcctggctgaccgcccaacgaccc

ccgcccattgacgtcaataatgacgtatgttcccatagtaacgccaatag
```

-continued

```
ggactttccattgacgtcaatgggtggagtatttacggtaaactgcccac

ttggcagtacatcaagtgtatcatatgccaagtacgccccctattgacgt

caatgacggtaaatggcccgcctggcattatgcccagtacatgaccttat

gggactttcctacttggcagtacatctacgtattagtcatcgctattacc

atggtgatgcggttttggcagtacatcaatgggcgtggatagcggtttga

ctcacggggatttccaagtctccaccccattgacgtcaatgggagtttgt

tttggcaccaaaatcaacgggactttccaaaatgtcgtaacaactccgcc

ccattgacgcaaatgggcggtaggcgtgtacggtgggaggtctatataag

cagagctctccctatcagtgatagagatctccctatcagtgatagagatc

gtcgacgagctcgtttagtgaaccgtcagatcgcctggagacgccatcca

cgctgttttgacctccatagaagacaccgggaccgatccagcctccgcgg

ccgggaacggtgcattggaacgcggattccccgtgccaagagtga

BGH poly A
                                        SEQ ID NO: 629
ctgtgccttctagttgccagccatctgttgtttgcccctcccccgtgcct

tccttgaccctggaaggtgccactcccactgtcctttcctaataaaatga

ggaaattgcatcgcattgtctgagtaggtgtcattctattctggggggtg

gggtggggcaggacagcaagggggaggattgggaagacaatagcaggcat

gctggggatgcggtgggctctatggcc
```

MVA Viral Vector Production

The MVA transgene was subcloned into the p94 shuttle plasmid via BAMH1-ASC1 restriction sites, under the control of the vaccinia P7.5 early/late promoter (SEQ ID NO: 630), between sequences homologous to the deletion III locus of MVA (FlankIII-1 and -2 regions). An additional expression cassette for eGFP protein, flanked by a repeated sequence named "Z", was present in the p94 shuttle plasmid, between Flank III regions.

The parental MVA vector used for recombinant vaccine viruses' generation carried the HcRed1-1 fluorescent protein transgene at the Deletion III locus and was indicated as MVA-RED 476 MG.

Recombinant MVA, with transgene insertion at the Deletion III locus, were generated by two events of in vivo recombination in Chicken embryo fibroblasts (CEF) cells. The first recombination event occurred in cells infected with MVA-RED 476 MG and transfected with the p94 shuttle plasmid, and resulted in replacement of the HcRed protein gene with the transgene/eGFP cassette. Infected cells containing MVA-Green intermediate were isolated by FACS sorting of green cells. The intermediate recombinant MVA resulting from first recombination carried both the transgene and the eGFP cassette but was unstable due to the presence of repeated Z regions. Thus, a spontaneous second recombination event occured involving Z regions and removed the eGFP cassette. The resulting recombinant MVA was colorless and carried the transgene cassette at the Deletion III locus (insertion site) of MVA-RED 476 MG. This was isolated by FACS sorting of colorless infected cells and amplified by re-infection of fresh CEF cells. The obtained lysate was used to infect Age l cells to produce the research batch.

P7.5 early/late promoter

SEQ ID NO: 630

GATCACTAATTCCAAACCCACCCGCTTTTTATAGTAAGTTTTTCACCCATAAATAATA

AATACAATAATTAATTTCTCGTAAAAGTAGAAAATATATTCTAATTTATTGCACGGT

AAGGAAGTAGAATCATAAAGAACAGTGACGGATC neoGAd20 protein (no TCE, no HIS tag)

SEQ ID NO: 541

QNLQNGGGSRSSATLPGRRRRRWLRRRRQPISVAPAGPPRRPNQKPNPPGGARCVIMRP

TWPGTSAFTKRSFAVTERIIDYWAQKEKGSSSFLRPSCDYWAQKEKISIPRTHLCLVLGV

LSGHSGSRLYEAGMTLGGKILFFLFLLLPLSPFSLIFTEISCCTLSSEENEYLPRPEWQLQVP

FRELKNVSVLEGLRQGRLGGPCSCHCPRPSQARLTPVDVAGPFLCLGDPGLFPPVKSSIT

GGKSTCSAPGPQSLPSTPFSTYPQWVILITELGMECTLGQVGAPSPRREEDGWRGGHSRF

KADVPAPQGPCWGGQPGSAPSSAPPEQSLLDWKFEMSYTVGGPPPHVHARPRHWKTDR

DGHSYTSKVNCLLLQDGFHGCVSITGAAGRRNLSIFLFLMLCKLEFHACKIQNKNCPDFK

KFDGPCGERGGGRTARALWARGDSVLTPALDPQTPVRAPSLTRAAAAVHYKLIQQPISL

FSITDRLHKTFSQLPSVHLCSITFQWGHPPIFCSTNDICVTANFCISVTFLKPCFLLHEASAS

QCHLFLQPQVGTPPPHTASARAPSGPPHPHESCPAGRRPARAAQTCARRQHGLPGCEEA

GTARVPSLHLHLHQAALGAGRGRGWGEACAQVPPSRGVLRFLDLKVRYLHSQWQHYH

RSGEAAGTPLWRPTRNVPFRELKNQRTAQGAPGIHHAASPVAANLCDPARHAQHTRIPC

GAGQVRAGRGPEAGGGVLQPQRPAPEKPGCPCRRGQPRLHTVKMWRAVAMMVPDRQ

VHYDFGLGVPGDSTRRAVRRMNTFYEAGMTLGEKFRVGNCKHLKMTRPNSKMALNSE

ALSVVSECGASACDVSLIAMDSAFVQGKDWGVKKFIRRDFYAYKDFLWCFPFSLVFLQE

IQICCHVSCLCCICCSTRICLGCLLELFLSRALRALHVLWNGFQLHCQTEYNQKLQVNQF

SESKSLYHREKQLIAMDSAICEERGAAGSLISCETMPAILKLQKNCLLSLRTALTHNQDFS

IYRLCCKRGSLCHASQARSPAFPKPVRPLPAPITRITPQLGGQSDSSQPLLTTGRPQGWQD

QALRHTQQASPASCATITIPIHSAALGDHSGDPGPAWDTCPPLPLTTLIPRAPPPYGDSTA

RSWPSRCGPLGGNTTLQQLGEASQAPSGSLIPLRLPLLWEVRGQPDSFAALHSSLNELGEI

ARELHQFAFDLLIKSHFVQGKDWGLKKFIRRDFWGMELAASRRFSWDHHSAGGPPRVP

SVRSGAAQVQPKDPLPLRTLAGCLARTAHLRPGAESLPQPQLHCTLWFQSSELSPTGAP

WPSRRPTWRGTTVSPRTATSSARTCCGTKWPSSQEAALGLGSGLLRFSCGTAAIRKMHF

SLKEHPPPPCPPEAFQRAAGEGGPGRGGARRGARVLQSPFCRAGAGEWLGHQSLRHVV

GYGHLDTSGSSSSSSWPNSKMALNSLNSIDDAQLTRIAPPRSHCCFWEVNAP neoGAd20 polynucleotide (no TCE, no HIS tag)

SEQ ID NO: 542

CAGAACCTGCAGAACGGCGGAGGCTCTAGAAGCTCTGCTACACTTCCTGGCAGGCG

GCGGAGAAGATGGCTGAGAAGAAGGCGGCAGCCTATCTCTGTGGCTCCTGCTGGAC

CTCCTAGACGGCCCAACCAGAAGCCTAATCCTCCTGGCGGAGCCAGATGCGTGATCA

TGAGGCCTACATGGCCTGGCACCAGCGCCTTCACCAAGAGAAGCTTTGCCGTGACCG

AGCGGATCATCGACTATTGGGCTCAAAAAGAGAAGGGCAGCAGCAGCTTCCTGCGG

CCTAGCTGTGATTATTGGGCCCAGAAAGAAAAGATCAGCATCCCCAGAACACACCT

GTGCCTGGTGCTGGGAGTGCTGTCTGGACACTCTGGCAGCAGACTGTATGAGGCCGG

CATGACACTCGGCGGCAAGATCCTGTTCTTCCTGTTCCTGCTGCTCCCTCTGAGCCCC

TTCAGCCTGATCTTCACCGAGATCAGCTGCTGCACCCTGAGCAGCGAGGAAAACGA

GTACCTGCCTAGACCTGAGTGGCAGCTGCAGGTCCCCTTCAGAGAGCTGAAGAACGT

```
TTCCGTGCTGGAAGGCCTGAGACAGGGCAGACTTGGCGGCCCTTGTAGCTGTCACTG

CCCCAGACCTAGTCAGGCCAGACTGACACCTGTGGATGTGGCCGGACCTTTCCTGTG

TCTGGGAGATCCTGGCCTGTTTCCACCTGTGAAGTCCAGCATCACAGGCGGCAAGTC

CACATGTTCTGCCCCTGGACCTCAGAGCCTGCCTAGCACACCCTTCAGCACATACCC

TCAGTGGGTCATCCTGATCACCGAACTCGGCATGGAATGCACCCTGGGACAAGTGG

GAGCCCCATCTCCTAGAAGAGAAGAGGATGGCTGGCGCGGAGGCCACTCTAGATTC

AAAGCTGATGTGCCCGCTCCTCAGGGCCCTTGTTGGGGAGGACAACCTGGATCTGCC

CCATCTTCTGCCCCACCTGAACAGTCCCTGCTGGATTGGAAGTTCGAGATGAGCTAC

ACCGTCGGCGGACCTCCACCTCATGTTCATGCCAGACCTCGGCACTGGAAAACCGAC

AGAGATGGCCACAGCTACACCAGCAAAGTGAACTGCCTCCTGCTGCAGGATGGCTT

CCACGGCTGTGTGTCTATTACTGGCGCCGCTGGCAGACGGAACCTGAGCATCTTTCT

GTTTCTGATGCTGTGCAAGCTCGAGTTCCACGCCTGCAAGATCCAGAACAAGAACTG

CCCCGACTTCAAGAAGTTCGACGGCCCTTGCGGAGAAAGAGGCGGAGGCAGAACAG

CTAGAGCCCTTTGGGCTAGAGGCGACAGCGTTCTGACACCAGCTCTGGACCCTCAGA

CACCTGTTAGGGCCCCTAGCCTGACAAGAGCTGCCGCCGCTGTGCACTACAAGCTGA

TCCAGCAGCCAATCAGCCTGTTCAGCATCACCGACCGGCTGCACAAGACATTCAGCC

AGCTGCCAAGCGTGCACCTGTGCTCCATCACCTTCCAGTGGGGACACCCTCCTATCT

TTTGCTCCACCAACGACATCTGCGTGACCGCCAACTTCTGTATCAGCGTGACCTTCCT

GAAGCCTTGCTTTCTGCTGCACGAGGCCAGCGCCTCTCAGTGCCACTTGTTTCTGCAG

CCCCAAGTGGGCACACCTCCTCCACATACAGCCTCTGCTAGAGCACCTAGCGGCCCT

CCACATCCTCACGAATCTTGTCCTGCCGGAAGAAGGCCTGCCAGAGCCGCTCAAACA

TGTGCCAGACGACAGCACGGACTGCCTGGATGTGAAGAGGCTGGAACAGCCAGAGT

GCCTAGCCTGCACCTCCATCTGCATCAGGCTGCTCTTGGAGCCGGAAGAGGTAGAGG

ATGGGGCGAAGCTTGTGCTCAGGTGCCACCTTCTAGAGGCGTGCTGAGATTCCTGGA

CCTGAAAGTGCGCTACCTGCACAGCCAGTGGCAGCACTATCACAGATCTGGCGAAG

CCGCCGGAACACCCCTTTGGAGGCCAACAAGAAACGTGCCCTTCCGGGAACTGAAG

AACCAGAGAACAGCTCAGGGCGCTCCTGGAATCCACCATGCTGCTTCTCCAGTGGCC

GCCAACCTGTGTGATCCTGCCAGACATGCCCAGCACACCAGGATTCCTTGTGGCGCT

GGACAAGTGCGCGCTGGAAGAGGACCTGAAGCAGGCGGAGGTGTTCTGCAACCTCA

AAGACCCGCTCCTGAGAAGCCTGGCTGCCCTTGCAGAAGAGGACAGCCTAGACTGC

ACACCGTGAAAATGTGGCGAGCCGTGGCCATGATGGTGCCCGATAGACAGGTCCAC

TACGACTTTGGACTGGGCGTGCCAGGCGATAGCACTCGGAGAGCCGTCAGACGGAT

GAACACCTTTTACGAAGCCGGGATGACCCTGGGCGAGAAGTTCAGAGTGGGCAACT

GCAAGCACCTGAAGATGACCCGGCCTAACAGCAAGATGGCCCTGAATAGCGAGGCC

CTGTCTGTGGTGTCTGAATGTGGCGCCTCTGCCTGTGACGTGTCCCTGATCGCTATGG

ACTCCGCCTTTGTGCAGGGCAAAGACTGGGGCGTGAAGAAGTTCATCCGGCGGGAC

TTCTACGCCTACAAGGACTTCCTGTGGTGCTTCCCCTTCTCTCTGGTGTTCCTGCAAG

AGATCCAGATCTGCTGTCATGTGTCCTGCCTGTGCTGCATCTGCTGTAGCACCAGAA

TCTGCCTGGGCTGTCTGCTGGAACTGTTCCTGAGCAGAGCCCTGAGAGCACTGCACG

TGCTGTGGAACGGATTCCAGCTGCACTGCCAGACCGAGTACAACCAGAAACTGCAA
```

-continued

GTGAACCAGTTCAGCGAGAGCAAGAGCCTGTACCACCGGGAAAAGCAGCTCATTGC

CATGGACAGCGCCATCTGCGAAGAGAGAGGCGCCGCAGGATCTCTGATCTCCTGCG

AAACAATGCCCGCCATCCTGAAGCTGCAGAAGAATTGCCTCCTAAGCCTGCGAACC

GCTCTGACACACAACCAGGACTTCAGCATCTACAGACTGTGTTGCAAGCGGGGCTCC

CTGTGCCATGCAAGCCAAGCTAGAAGCCCCGCCTTTCCTAAACCTGTGCGACCTCTG

CCAGCTCCAATCACCAGAATTACCCCTCAGCTCGGCGGCCAGAGCGATTCATCTCAA

CCTCTGCTGACCACCGGCAGACCTCAAGGCTGGCAAGACCAAGCTCTGAGACACAC

CCAGCAGGCTAGCCCTGCCTCTTGTGCCACCATCACAATCCCCATCCACTCTGCCGCT

CTGGGCGATCATTCTGGCGATCCTGGACCAGCCTGGGACACATGTCCTCCACTGCCA

CTCACAACACTGATCCCTAGGGCTCCTCCACCTTACGGCGATTCTACCGCTAGAAGC

TGGCCCAGCAGATGTGGACCACTCGGAGGCAACACAACCCTCCAGCAACTGGGAGA

AGCCTCTCAGGCTCCTAGCGGCTCTCTGATCCCTCTCAGACTGCCTCTCCTGTGGGAA

GTTCGGGGCCAGCCTGATTCTTTTGCCGCACTGCACAGCTCCCTGAACGAGCTGGGA

GAGATCGCTAGAGAGCTGCACCAGTTCGCCTTCGACCTGCTGATCAAGAGCCACTTC

GTGCAAGGCAAGGATTGGGGCCTCAAAAAGTTTATCCGCAGAGACTTCTGGGGCAT

GGAACTGGCCGCCAGCAGAAGATTCAGCTGGGATCATCATAGCGCAGGCGGCCCAC

CTAGAGTGCCATCTGTTAGAAGCGGAGCTGCCCAGGTGCAGCCTAAAGATCCTCTGC

CACTGAGAACACTGGCCGGCTGCCTTGCTAGAACAGCCCATCTTAGACCTGGCGCCG

AGTCTCTGCCTCAGCCACAACTGCACTGTACCCTGTGGTTCCAGTCCAGCGAGCTGT

CTCCTACTGGTGCCCCTTGGCCATCTAGACGCCCTACTTGGAGAGGCACCACCGTGT

CACCAAGAACCGCCACAAGCAGCGCCAGAACCTGTTGTGGCACAAAGTGGCCCTCC

AGCCAAGAAGCCGCTCTCGGACTTGGAAGCGGACTGCTGAGGTTCTCTTGTGGAACC

GCCGCCATTCGGAAGATGCACTTTAGCCTGAAAGAACACCCTCCACCACCTTGTCCT

CCAGAGGCTTTCCAAAGAGCTGCTGGCGAAGGCGGACCTGGTAGAGGTGGTGCTAG

AAGAGGTGCTAGGGTGCTGCAGAGCCCATTCTGTAGAGCAGGCGCAGGCGAATGGC

TGGGCCATCAGAGTCTGAGACATGTCGTCGGCTACGGCCACCTGGATACAAGCGGA

AGCAGCTCTAGCTCCAGCTGGCCTAACTCAAAAATGGCTCTGAACAGCCTGAACTCC

ATCGACGACGCCCAGCTGACAAGAATCGCCCCTCCTAGATCTCACTGCTGCTTTTGG

GAAGTGAACGCCCCA neoMVA protein (no TCE, no HIS Tag)

SEQ ID NO: 543

QNLQNGGGSRSSATLPGRRRRRWLRRRRQPISVAPAGPPRRPNQKPNPPGGARCVIMRP

TWPGTSAFTGMECTLGQVGAPSPRREEDGWRGGHSRFKADVPAPQGPCWGGQPGSAPS

SAPPEQSLLDDYWAQKEKISIPRTHLCWKFEMSYTVGGPPPHVHARPRHWKTDRDYWA

QKEKGSSSFLRPSCVPFRELKNVSVLEGLRQGRLGGPCSCHCPRPSQARLTPVDVAGPFL

CLGDPGLFPPVKSSITEISCCTLSSEENEYLPRPEWQLQYEAGMTLGGKILFFLFLLLPLSP

FSLIFLVLGVLSGHSGSRLKRSFAVTERIITGGKSTCSAPGPQSLPSTPFSTYPQWVILITEL

DGHSYTSKVNCLLLQDGFHGCVSITGAAGRRNLSIFLFLMLCKLEFHACQWQHYHRSGE

AAGTPLWRPTRNVAMMVPDRQVHYDFGLKIQNKNCPDVLRFLDLKVRYLHSVPFRELK

NQRTAQGAPGIHHAASPVAANLCDPARHAQHTRIPCGAGQVRAGRGPEAGGGVLQPQR

PAPEKPGCPCRRGQPRLHTVKMWRACHLFLQPQVGTPPPHTASARAPSGPPHPHESCPA

GRRPARAAQTCARRQHGLPGCEEAGTARVPSLHLHLHQAALGAGRGRGWGEACAQVP

-continued

PSRGHYKLIQQPISLFSITDRLHKTFSQLPSVHLCSITFQWGHPPIFCSTNDICVTANFCISV

TFLKPCFLLHEASASQFKKFDGPCGERGGGRTARALWARGDSVLTPALDPQTPVRAPSL

TRAAAAVGVPGDSTRRAVRRMNTFCGASACDVSLIAMDSACEERGAAGSLISCESLYHR

EKQLIAMDSAIFVQGKDWGVKKFIRRDFTMPAILKLQKNCLLSLNSKMALNSEALSVVS

EYEAGMTLGEKFRVGNCKHLKMTRPTEYNQKLQVNQFSESKRTALTHNQDFSIYRLCC

KRGSLCHASQARSPAFPKPVRPLPAPITRITPQLGGQSDSSQPLLTTGRPQGWQDQALRH

TQQASPASCATITIPIHSAALGDHSGDPGPAWDTCPPLPLTTLIPRAPPPYGDSTARSWPSR

CGPLGYAYKDFLWCFPFSLVFLQEIQICCHVSCLCCICCSTRICLGCLLELFLSRALRALH

VLWNGFQLHCQGNTTLQQLGEASQAPSGSLIPLRLPLLWEVRGNSKMALNSLNSIDDAQ

LTRIAPPRSHCCFWEVNAPFVQGKDWGLKKFIRRDFEAFQRAAGEGGPGRGGARRGAR

VLQSPFCRAGAGEWLGHQSLRWGMELAASRRFSWDHHSAGGPPRVPSVRSGAAQVQP

KDPLPLRTLAGCLARTAHLRPGAESLPQPQLHCTIARELHQFAFDLLIKSHKMHFSLKEH

PPPPCPPHVVGYGHLDTSGSSSSSSWPQPDSFAALHSSLNELGELWFQSSELSPTGAPWPS

RRPTWRGTTVSPRTATSSARTCCGTKWPSSQEAALGLGSGLLRFSCGTAAIR neoMVA polynucleotide

SEQ ID NO: 544

CAGAACCTGCAGAACGGCGGAGGCTCTAGAAGCTCTGCTACACTTCCTGGCAGGCG

GCGGAGAAGATGGCTGAGAAGAAGGCGGCAGCCTATCTCTGTGGCTCCTGCTGGAC

CTCCTAGACGGCCCAACCAGAAGCCTAATCCTCCTGGCGGAGCCAGATGCGTGATCA

TGAGGCCTACATGGCCTGGCACCAGCGCCTTTACCGGCATGGAATGTACACTGGGCC

AAGTGGGAGCCCCATCTCCTAGAAGAGAAGAGGATGGCTGGCGCGGAGGCCACTCT

AGATTCAAAGCTGATGTGCCCGCTCCTCAGGGCCCTTGTTGGGGAGGACAACCTGGA

TCTGCCCCATCTTCTGCCCCACCTGAACAGAGCCTGCTGGATGACTATTGGGCTCAA

AAAGAGAAGATCAGCATCCCCAGAACACACCTGTGCTGGAAGTTCGAGATGAGCTA

CACCGTTGGCGGCCCTCCACCACATGTTCACGCCAGACCTAGACACTGGAAAACCGA

CAGAGATTATTGGGCCCAGAAAGAAAAGGGCAGCAGCAGCTTCCTGCGGCCTAGCT

GTGTGCCCTTCCGGGAACTGAAGAACGTGTCCGTTCTGGAAGGCCTGAGGCAGGGC

AGACTTGGCGGACCTTGTAGCTGCCACTGTCCTAGACCAAGCCAGGCCAGACTGACC

CCTGTGGATGTGGCTGGCCCATTTCTGTGTCTGGGCGACCCTGGACTGTTCCCTCCAG

TGAAGTCTAGCATCACCGAGATCAGCTGCTGCACCCTGAGCAGCGAGGAAAACGAG

TACCTGCCTAGACCTGAATGGCAGCTGCAGTACGAGGCCGGCATGACACTCGGAGG

CAAGATCCTGTTCTTCCTGTTCCTGCTGCTCCCTCTGAGCCCCTTCAGCCTGATCTTTC

TGGTGCTGGGCGTGCTGTCTGGCCACTCTGGAAGCAGACTGAAGAGAAGCTTCGCCG

TGACCGAGCGGATCATCACAGGCGGCAAGAGCACATGTTCTGCCCCTGGACCTCAGT

CTCTGCCCAGCACACCCTTCAGCACATACCCTCAGTGGGTCATCCTGATCACCGAGC

TGGATGGCCACAGCTACACCAGCAAAGTGAACTGCCTCCTGCTGCAGGATGGCTTCC

ACGGCTGTGTGTCTATTACTGGCGCCGCTGGCAGACGGAACCTGAGCATCTTTCTGT

TTCTGATGCTGTGCAAGCTCGAGTTCCACGCCTGCCAATGGCAGCACTACCACAGAT

CTGGCGAAGCCGCTGGAACCCCACTTTGGAGGCCTACCAGAAACGTGGCCATGATG

GTGCCCGACAGACAGGTGCACTACGACTTCGGCCTGAAGATCCAGAACAAGAACTG

CCCCGACGTGCTGCGGTTCCTGGATCTCAAAGTGCGCTACCTGCACAGCGTGCCCTT

-continued
CAGAGAGCTGAAAAACCAGAGAACAGCCCAGGGCGCTCCTGGAATCCATCATGCTG
CTTCTCCAGTGGCCGCCAATCTGTGCGATCCTGCCAGACATGCCCAGCATACCAGGA
TTCCTTGTGGCGCTGGACAAGTGCGCGCTGGAAGAGGACCTGAAGCTGGTGGCGGA
GTTCTGCAGCCTCAAAGACCTGCTCCTGAGAAGCCTGGCTGCCCCTGTAGAAGAGGA
CAGCCTAGACTGCACACCGTGAAGATGTGGCGGGCCTGCCACTTGTTTCTCCAGCCA
CAAGTGGGCACCCCTCCACCTCATACAGCCTCTGCTAGAGCACCTAGCGGCCCACCT
CATCCTCACGAATCTTGTCCTGCCGGAAGAAGGCCTGCCAGAGCCGCTCAAACATGT
GCCAGACGACAGCACGGACTGCCCGGATGTGAAGAAGCCGGAACAGCCAGAGTGCC
TAGCCTGCACCTTCATCTGCATCAGGCCGCTCTTGGAGCCGGAAGAGGTAGAGGATG
GGGAGAAGCTTGTGCCCAGGTGCCACCTTCTAGAGGCCACTACAAGCTGATCCAGC
AGCCAATCAGCCTGTTCTCCATCACCGACCGGCTGCACAAGACATTCAGCCAGCTGC
CTTCCGTGCATCTGTGCAGCATCACCTTCCAGTGGGGACACCCTCCTATCTTTTGCTC
CACCAACGACATCTGCGTGACCGCCAACTTCTGTATCAGCGTGACCTTCCTGAAGCC
TTGCTTTCTGCTGCACGAGGCCTCCGCCAGCCAGTTTAAGAAGTTTGACGGCCCCTG
CGGCGAGAGAGGCGGAGGAAGAACTGCAAGAGCCCTTTGGGCCAGAGGCGACTCTG
TTCTGACACCAGCTCTGGACCCTCAGACACCTGTTAGGGCCCCTAGCCTGACAAGAG
CTGCCGCTGCTGTTGGAGTGCCTGGCGATTCTACTAGAAGGGCCGTGCGGCGGATGA
ACACCTTTTGTGGCGCATCTGCCTGCGACGTGTCCCTGATCGCTATGGATAGCGCCT
GCGAGGAAAGAGGCGCAGCCGGATCTCTGATCTCTTGCGAGAGCCTGTACCACCGG
GAAAAGCAGCTCATTGCCATGGACAGCGCCATCTTCGTGCAGGGCAAAGACTGGGG
CGTGAAGAAGTTCATCCGGCGGGACTTTACCATGCCTGCCATTCTGAAGCTGCAGAA
GAATTGTCTTCTAAGCCTGAACAGCAAGATGGCCCTGAATAGCGAGGCCCTGTCTGT
GGTGTCCGAGTATGAGGCTGGAATGACCCTGGGCGAGAAGTTCAGAGTGGGCAACT
GCAAGCACCTGAAGATGACCCGGCCTACCGAGTACAACCAGAAACTGCAAGTGAAC
CAGTTCAGCGAGAGCAAGCGGACCGCTCTGACCCACAACCAGGACTTCAGCATCTA
CCGGCTGTGCTGCAAGAGGGGCTCTCTGTGTCATGCTAGCCAGGCTAGAAGCCCCGC
CTTTCCTAAGCCTGTCAGACCTCTGCCTGCTCCTATCACCAGAATCACCCCTCAGCTC
GGCGGCCAGTCTGATTCATCTCAGCCACTGCTGACCACCGGCAGACCTCAAGGATGG
CAAGACCAGGCTCTGAGACACACACAGCAGGCTAGCCCAGCCTCTTGCGCCACCAT
CACAATACCAATACATTCTGCCGCTCTGGGCGATCACAGCGGAGATCCTGGACCTGC
CTGGGATACTTGTCCTCCTCTGCCCCTAACTACACTGATCCCTAGGGCTCCTCCACCT
TACGGCGATAGCACAGCCAGATCCTGGCCTAGCAGATGTGGCCCTCTGGGCTACGCC
TACAAGGACTTCCTGTGGTGCTTCCCCTTCTCTCTGGTGTTCCTGCAAGAAATCCAGA
TCTGCTGTCACGTGTCCTGCCTGTGCTGTATCTGCTGTAGCACCCGGATCTGTCTGGG
CTGTCTGCTGGAACTGTTCCTGAGCAGAGCCCTGAGAGCACTGCACGTGCTGTGGAA
CGGATTCCAGCTGCACTGCCAGGGCAACACCACACTGCAACAGCTGGGAGAAGCCT
CTCAGGCCCCAAGCGGTTCTCTGATCCCTCTCAGACTGCCCCTCCTGTGGGAAGTGC
GGGGCAATTCTAAGATGGCTCTCAACAGCCTGAACTCCATCGACGACGCCCAGCTGA
CAAGAATCGCCCCTCCAAGAAGCCACTGTTGCTTTTGGGAAGTGAACGCCCCTTTTG
TGCAGGGTAAAGATTGGGGCCTCAAAAAGTTTATCAGACGGGACTTCGAGGCTTTCC
AGAGAGCAGCTGGCGAAGGCGGACCTGGCAGAGGTGGTGCTAGAAGAGGTGCTAG -continued AGTGCTGCAGAGCCCATTCTGTAGAGCTGGCGCTGGCGAATGGCTGGGCCACCAATC
TCTTAGATGGGGAATGGAACTGGCCGCTAGCAGGCGGTTTAGCTGGGATCATCATTC
TGCCGGCGGACCTCCAAGAGTGCCAAGCGTTAGAAGCGGAGCAGCCCAGGTCCAGC
CTAAAGATCCACTGCCACTGAGAACACTGGCCGGCTGCCTTGCCAGAACAGCTCATC
TTAGACCTGGCGCCGAAAGCCTGCCTCAACCTCAGCTGCATTGCACAATCGCCAGAG
AACTGCACCAGTTCGCCTTCGACCTGCTGATCAAGAGCCACAAGATGCACTTCTCAC
TGAAAGAGCACCCGCCACCGCCGTGCCCACCGCACGTTGTCGGCTATGGCCACCTGG
ATACAAGCGGCTCCTCTAGCAGTAGCTCCTGGCCTCAGCCTGACAGCTTTGCTGCCC
TGCATAGCTCCCTGAATGAGCTGGGCGAACTGTGGTTCCAGTCCAGCGAACTGTCTC
CTACTGGCGCTCCATGGCCAAGCAGAAGGCCTACTTGGAGAGGCACCACCGTGTCTC
CAAGAACCGCTACAAGCAGCGCCAGAACCTGTTGCGGCACAAAATGGCCCTCCAGC
CAAGAAGCTGCCCTCGGACTTGGAAGCGGACTGCTGAGATTCAGCTGTGGCACAGC
CGCCATCAGA neoGAd20 expression cassette protein

SEQ ID NO: 550

MGQKEQIHTLQKNSERMSKQLTRSSQAVQNLQNGGGSRSSATLPGRRRRRWLRRRRQP
ISVAPAGPPRRPNQKPNPPGGARCVIMRPTWPGTSAFTKRSFAVTERIIDYWAQKEKGSS
SFLRPSCDYWAQKEKISIPRTHLCLVLGVLSGHSGSRLYEAGMTLGGKILFFLFLLLPLSP
FSLIFTEISCCTLSSEENEYLPRPEWQLQVPFRELKNVSVLEGLRQGRLGGPCSCHCPRPS
QARLTPVDVAGPFLCLGDPGLFPPVKSSITGGKSTCSAPGPQSLPSTPFSTYPQWVILITEL
GMECTLGQVGAPSPRREEDGWRGGHSRFKADVPAPQGPCWGGQPGSAPSSAPPEQSLL
DWKFEMSYTVGGPPPHVHARPRHWKTDRDGHSYTSKVNCLLLQDGFHGCVSITGAAG
RRNLSIFLFLMLCKLEFHACKIQNKNCPDFKKFDGPCGERGGGRTARALWARGDSVLTP
ALDPQTPVRAPSLTRAAAAVHYKLIQQPISLFSITDRLHKTFSQLPSVHLCSITFQWGHPPI
FCSTNDICVTANFCISVTFLKPCFLLHEASASQCHLFLQPQVGTPPPHTASARAPSGPPHP
HESCPAGRRPARAAQTCARRQHGLPGCEEAGTARVPSLHLHLHQAALGAGRGRGWGE
ACAQVPPSRGVLRFLDLKVRYLHSQWQHYHRSGEAAGTPLWRPTRNVPFRELKNQRTA
QGAPGIHHAASPVAANLCDPARHAQHTRIPCGAGQVRAGRGPEAGGGVLQPQRPAPEK
PGCPCRRGQPRLHTVKMWRAVAMMVPDRQVHYDFGLGVPGDSTRRAVRRMNTFYEA
GMTLGEKFRVGNCKHLKMTRPNSKMALNSEALSVVSECGASACDVSLIAMDSAFVQG
KDWGVKKFIRRDFYAYKDFLWCFPFSLVFLQEIQICCHVSCLCCICCSTRICLGCLLELFL
SRALRALHVLWNGFQLHCQTEYNQKLQVNQFSESKSLYHREKQLIAMDSAICEERGAA
GSLISCETMPAILKLQKNCLLSLRTALTHNQDFSIYRLCCKRGSLCHASQARSPAFPKPVR
PLPAPITRITPQLGGQSDSSQPLLTTGRPQGWQDQALRHTQQASPASCATITIPIHSAALGD
HSGDPGPAWDTCPPLPLTTLIPRAPPPYGDSTARSWPSRCGPLGGNTTLQQLGEASQAPS
GSLIPLRLPLLWEVRGQPDSFAALHSSLNELGEIARELHQFAFDLLIKSHFVQGKDWGLK
KFIRRDFWGMELAASRRFSWDHHSAGGPPRVPSVRSGAAQVQPKDPLPLRTLAGCLAR
TAHLRPGAESLPQPQLHCTLWFQSSELSPTGAPWPSRRPTWRGTTVSPRTATSSARTCCG
TKWPSSQEAALGLGSGLLRFSCGTAAIRKMHFSLKEHPPPPCPPEAFQRAAGEGGPGRG
GARRGARVLQSPFCRAGAGEWLGHQSLRHVVGYGHLDTSGSSSSSSWPNSKMALNSLN
SIDDAQLTRIAPPRSHCCFWEVNAP

-continued neoGAd20 expression cassette polynucleotide

SEQ ID NO: 551

Ccattgcatacgttgtatccatatcataatatgtacatttatattggctcatgtccaacattaccgccatgttgacattgattattgactagttattaat agtaatcaattacggggtcattagttcatagcccatatatggagttccgcgttacataacttacggtaaatggcccgcctggctgaccgcccaa cgacccccgcccattgacgtcaataatgacgtatgttcccatagtaacgccaatagggactttccattgacgtcaatgggtggagtatttacgg taaactgcccacttggcagtacatcaagtgtatcatatgccaagtacgccccctattgacgtcaatgacggtaaatggcccgcctggcattatg cccagtacatgaccttatgggactttcctacttggcagtacatctacgtattagtcatcgctattaccatggtgatgcggttttggcagtacatcaa tgggcgtggatagcggtttgactcacggggatttccaagtctccaccccattgacgtcaatgggagtttgttttggcaccaaaatcaacggga ctttccaaaatgtcgtaacaactccgccccattgacgcaaatgggcggtaggcgtgtacggtgggaggtctatataagcagagctctccctat cagtgatagagatctccctatcagtgatagagatcgtcgacgagctcgtttagtgaaccgtcagatcgcctggagacgccatccacgctgttt tgacctccatagaagacaccgggaccgatccagcctccgcggccgggaacggtgcattggaacgcggattccccgtgccaagagtgag atcttccgtttatctaggtaccagatatcaGAATTCGGATCCCGCGACTTCGCCGCCATGGGCCAGAAA

GAGCAGATCCACACACTGCAGAAAAACAGCGAGCGGATGAGCAAGCAGCTGACCA

GATCTTCTCAGGCCGTGCAGAACCTGCAGAACGGCGGAGGCTCTAGAAGCTCTGCTA

CACTTCCTGGCAGGCGGCGGAGAAGATGGCTGAGAAGAAGGCGGCAGCCTATCTCT

GTGGCTCCTGCTGGACCTCCTAGACGGCCCAACCAGAAGCCTAATCCTCCTGGCGGA

GCCAGATGCGTGATCATGAGGCCTACATGGCCTGGCACCAGCGCCTTCACCAAGAG

AAGCTTTGCCGTGACCGAGCGGATCATCGACTATTGGGCTCAAAAAGAGAAGGGCA

GCAGCAGCTTCCTGCGGCCTAGCTGTGATTATTGGGCCCAGAAAGAAAAGATCAGC

ATCCCCAGAACACACCTGTGCCTGGTGCTGGGAGTGCTGTCTGGACACTCTGGCAGC

AGACTGTATGAGGCCGGCATGACACTCGGCGGCAAGATCCTGTTCTTCCTGTTCCTG

CTGCTCCCTCTGAGCCCCTTCAGCCTGATCTTCACCGAGATCAGCTGCTGCACCCTGA

GCAGCGAGGAAAACGAGTACCTGCCTAGACCTGAGTGGCAGCTGCAGGTCCCCTTC

AGAGAGCTGAAGAACGTTTCCGTGCTGGAAGGCCTGAGACAGGGCAGACTTGGCGG

CCCTTGTAGCTGTCACTGCCCCAGACCTAGTCAGGCCAGACTGACACCTGTGGATGT

GGCCGGACCTTTCCTGTGTCTGGGAGATCCTGGCCTGTTTCCACCTGTGAAGTCCAG

CATCACAGGCGGCAAGTCCACATGTTCTGCCCCTGGACCTCAGAGCCTGCCTAGCAC

ACCCTTCAGCACATACCCTCAGTGGGTCATCCTGATCACCGAACTCGGCATGGAATG

CACCCTGGGACAAGTGGGAGCCCCATCTCCTAGAAGAGAAGAGGATGGCTGGCGCG

GAGGCCACTCTAGATTCAAAGCTGATGTGCCCGCTCCTCAGGGCCCTTGTTGGGGAG

GACAACCTGGATCTGCCCCATCTTCTGCCCCACCTGAACAGTCCCTGCTGGATTGGA

AGTTCGAGATGAGCTACACCGTCGGCGGACCTCCACCTCATGTTCATGCCAGACCTC

GGCACTGGAAAACCGACAGAGATGGCCACAGCTACACCAGCAAAGTGAACTGCCTC

CTGCTGCAGGATGGCTTCCACGGCTGTGTGTCTATTACTGGCGCCGCTGGCAGACGG

AACCTGAGCATCTTTCTGTTTCTGATGCTGTGCAAGCTCGAGTTCCACGCCTGCAAG

ATCCAGAACAAGAACTGCCCCGACTTCAAGAAGTTCGACGGCCCTTGCGGAGAAAG

AGGCGGAGGCAGAACAGCTAGAGCCCTTTGGGCTAGAGGCGACAGCGTTCTGACAC

CAGCTCTGGACCCTCAGACACCTGTTAGGGCCCCTAGCCTGACAAGAGCTGCCGCCG

CTGTGCACTACAAGCTGATCCAGCAGCCAATCAGCCTGTTCAGCATCACCGACCGGC

TGCACAAGACATTCAGCCAGCTGCCAAGCGTGCACCTGTGCTCCATCACCTTCCAGT

GGGGACACCCTCCTATCTTTTGCTCCACCAACGACATCTGCGTGACCGCCAACTTCT

GTATCAGCGTGACCTTCCTGAAGCCTTGCTTTCTGCTGCACGAGGCCAGCGCCTCTC

-continued

AGTGCCACTTGTTTCTGCAGCCCCAAGTGGGCACACCTCCTCCACATACAGCCTCTG

CTAGAGCACCTAGCGGCCCTCCACATCCTCACGAATCTTGTCCTGCCGGAAGAAGGC

CTGCCAGAGCCGCTCAAACATGTGCCAGACGACAGCACGGACTGCCTGGATGTGAA

GAGGCTGGAACAGCCAGAGTGCCTAGCCTGCACCTCCATCTGCATCAGGCTGCTCTT

GGAGCCGGAAGAGGTAGAGGATGGGGCGAAGCTTGTGCTCAGGTGCCACCTTCTAG

AGGCGTGCTGAGATTCCTGGACCTGAAAGTGCGCTACCTGCACAGCCAGTGGCAGC

ACTATCACAGATCTGGCGAAGCCGCCGGAACACCCCTTTGGAGGCCAACAAGAAAC

GTGCCCTTCCGGGAACTGAAGAACCAGAGAACAGCTCAGGGCGCTCCTGGAATCCA

CCATGCTGCTTCTCCAGTGGCCGCCAACCTGTGTGATCCTGCCAGACATGCCCAGCA

CACCAGGATTCCTTGTGGCGCTGGACAAGTGCGCGCTGGAAGAGGACCTGAAGCAG

GCGGAGGTGTTCTGCAACCTCAAAGACCCGCTCCTGAGAAGCCTGGCTGCCCTTGCA

GAAGAGGACAGCCTAGACTGCACACCGTGAAAATGTGGCGAGCCGTGGCCATGATG

GTGCCCGATAGACAGGTCCACTACGACTTTGGACTGGGCGTGCCAGGCGATAGCACT

CGGAGAGCCGTCAGACGGATGAACACCTTTTACGAAGCCGGGATGACCCTGGGCGA

GAAGTTCAGAGTGGGCAACTGCAAGCACCTGAAGATGACCCGGCCTAACAGCAAGA

TGGCCCTGAATAGCGAGGCCCTGTCTGTGGTGTCTGAATGTGGCGCCTCTGCCTGTG

ACGTGTCCCTGATCGCTATGGACTCCGCCTTTGTGCAGGGCAAAGACTGGGGCGTGA

AGAAGTTCATCCGGCGGGACTTCTACGCCTACAAGGACTTCCTGTGGTGCTTCCCCT

TCTCTCTGGTGTTCCTGCAAGAGATCCAGATCTGCTGTCATGTGTCCTGCCTGTGCTG

CATCTGCTGTAGCACCAGAATCTGCCTGGGCTGTCTGCTGGAACTGTTCCTGAGCAG

AGCCCTGAGAGCACTGCACGTGCTGTGGAACGGATTCCAGCTGCACTGCCAGACCG

AGTACAACCAGAAACTGCAAGTGAACCAGTTCAGCGAGAGCAAGAGCCTGTACCAC

CGGGAAAAGCAGCTCATTGCCATGGACAGCGCCATCTGCGAAGAGAGAGGCGCCGC

AGGATCTCTGATCTCCTGCGAAACAATGCCCGCCATCCTGAAGCTGCAGAAGAATTG

CCTCCTAAGCCTGCGAACCGCTCTGACACACAACCAGGACTTCAGCATCTACAGACT

GTGTTGCAAGCGGGGCTCCCTGTGCCATGCAAGCCAAGCTAGAAGCCCCGCCTTTCC

TAAACCTGTGCGACCTCTGCCAGCTCCAATCACCAGAATTACCCCTCAGCTCGGCGG

CCAGAGCGATTCATCTCAACCTCTGCTGACCACCGGCAGACCTCAAGGCTGGCAAGA

CCAAGCTCTGAGACACACCCAGCAGGCTAGCCCTGCCTCTTGTGCCACCATCACAAT

CCCCATCCACTCTGCCGCTCTGGGCGATCATTCTGGCGATCCTGGACCAGCCTGGGA

CACATGTCCTCCACTGCCACTCACAACACTGATCCCTAGGGCTCCTCCACCTTACGG

CGATTCTACCGCTAGAAGCTGGCCCAGCAGATGTGGACCACTCGGAGGCAACACAA

CCCTCCAGCAACTGGGAGAAGCCTCTCAGGCTCCTAGCGGCTCTCTGATCCCTCTCA

GACTGCCTCTCCTGTGGGAAGTTCGGGGCCAGCCTGATTCTTTTGCCGCACTGCACA

GCTCCCTGAACGAGCTGGGAGAGATCGCTAGAGAGCTGCACCAGTTCGCCTTCGACC

TGCTGATCAAGAGCCACTTCGTGCAAGGCAAGGATTGGGGCCTCAAAAAGTTTATCC

GCAGAGACTTCTGGGGCATGGAACTGGCCGCCAGCAGAAGATTCAGCTGGGATCAT

CATAGCGCAGGCGGCCCACCTAGAGTGCCATCTGTTAGAAGCGGAGCTGCCCAGGT

GCAGCCTAAAGATCCTCTGCCACTGAGAACACTGGCCGGCTGCCTTGCTAGAACAGC

CCATCTTAGACCTGGCGCCGAGTCTCTGCCTCAGCCACAACTGCACTGTACCCTGTG

-continued

GTTCCAGTCCAGCGAGCTGTCTCCTACTGGTGCCCCTTGGCCATCTAGACGCCCTACT

TGGAGAGGCACCACCGTGTCACCAAGAACCGCCACAAGCAGCGCCAGAACCTGTTG

TGGCACAAAGTGGCCCTCCAGCCAAGAAGCCGCTCTCGGACTTGGAAGCGGACTGC

TGAGGTTCTCTTGTGGAACCGCCGCCATTCGGAAGATGCACTTTAGCCTGAAAGAAC

ACCCTCCACCACCTTGTCCTCCAGAGGCTTTCCAAAGAGCTGCTGGCGAAGGCGGAC

CTGGTAGAGGTGGTGCTAGAAGAGGTGCTAGGGTGCTGCAGAGCCCATTCTGTAGA

GCAGGCGCAGGCGAATGGCTGGGCCATCAGAGTCTGAGACATGTCGTCGGCTACGG

CCACCTGGATACAAGCGGAAGCAGCTCTAGCTCCAGCTGGCCTAACTCAAAAATGG

CTCTGAACAGCCTGAACTCCATCGACGACGCCCAGCTGACAAGAATCGCCCCTCCTA

GATCTCACTGCTGCTTTTGGGAAGTGAACGCCCCAAGCCATCACCATCACCACCATT

AGTAAAGGCGCGCCTAGCGGCCGCgatctgctgtgccttctagttgccagccatctgttgtttgcccctcccccgtgcct tccttgaccctggaaggtgccactcccactgtcctttcctaataaaatgaggaaattgcatcgcattgtctgagtaggtgtcattctattctgggg ggtggggtggggcaggacagcaaggggaggattgggaagacaatagcaggcatgctggggatgcggtgggctctatggcc neoMVA expression cassette protein

SEQ ID NO: 552

MGQKEQIHTLQKNSERMSKQLTRSSQAVQNLQNGGGSRSSATLPGRRRRRWLRRRRQP

ISVAPAGPPRRPNQKPNPPGGARCVIMRPTWPGTSAFTGMECTLGQVGAPSPRREEDGW

RGGHSRFKADVPAPQGPCWGGQPGSAPSSAPPEQSLLDDYWAQKEKISIPRTHLCWKFE

MSYTVGGPPPHVHARPRHWKTDRDYWAQKEKGSSSFLRPSCVPFRELKNVSVLEGLRQ

GRLGGPCSCHCPRPSQARLTPVDVAGPFLCLGDPGLFPPVKSSITEISCCTLSSEENEYLPR

PEWQLQYEAGMTLGGKILFFLFLLLPLSPFSLIFLVLGVLSGHSGSRLKRSFAVTERIITGG

KSTCSAPGPQSLPSTPFSTYPQWVILITELDGHSYTSKVNCLLLQDGFHGCVSITGAAGRR

NLSIFLFLMLCKLEFHACQWQHYHRSGEAAGTPLWRPTRNVAMMVPDRQVHYDFGLKI

QNKNCPDVLRFLDLKVRYLHSVPFRELKNQRTAQGAPGIHHAASPVAANLCDPARHAQ

HTRIPCGAGQVRAGRGPEAGGGVLQPQRPAPEKPGCPCRRGQPRLHTVKMWRACHLFL

QPQVGTPPPHTASARAPSGPPHPHESCPAGRRPARAAQTCARRQHGLPGCEEAGTARVP

SLHLHLHQAALGAGRGRGWGEACAQVPPSRGHYKLIQQPISLFSITDRLHKTFSQLPSVH

LCSITFQWGHPPIFCSTNDICVTANFCISVTFLKPCFLLHEASASQFKKFDGPCGERGGGR

TARALWARGDSVLTPALDPQTPVRAPSLTRAAAAVGVPGDSTRRAVRRMNTFCGASAC

DVSLIAMDSACEERGAAGSLISCESLYHREKQLIAMDSAIFVQGKDWGVKKFIRRDFTM

PAILKLQKNCLLSLNSKMALNSEALSVVSEYEAGMTLGEKFRVGNCKHLKMTRPTEYN

QKLQVNQFSESKRTALTHNQDFSIYRLCCKRGSLCHASQARSPAFPKPVRPLPAPITRITP

QLGGQSDSSQPLLTTGRPQGWQDQALRHTQQASPASCATITIPIHSAALGDHSGDPGPA

WDTCPPLPLTTLIPRAPPPYGDSTARSWPSRCGPLGYAYKDFLWCFPFSLVFLQEIQICCH

VSCLCCICCSTRICLGCLLELFLSRALRALHVLWNGFQLHCQGNTTLQQLGEASQAPSGS

LIPLRLPLLWEVRGNSKMALNSLNSIDDAQLTRIAPPRSHCCFWEVNAPFVQGKDWGLK

KFIRRDFEAFQRAAGEGGPGRGGARRGARVLQSPFCRAGAGEWLGHQSLRWGMELAA

SRRFSWDHHSAGGPPRVPSVRSGAAQVQPKDPLPLRTLAGCLARTAHLRPGAESLPQPQ

LHCTIARELHQFAFDLLIKSHKMHFSLKEHPPPPCPPHVVGYGHLDTSGSSSSSSWPQPDS

FAALHSSLNELGELWFQSSELSPTGAPWPSRRPTWRGTTVSPRTATSSARTCCGTKWPSS

QEAALGLGSGLLRFSCGTAAIR

-continued neoMVA expression cassette polynucleotide

SEQ ID NO: 553 gatcactaattccaaacccacccgctttttatagtaagtttttcacccataaataataaatacaataattaatttctcgtaaaagtagaaaatatattc taatttattgcacggtaaggaagtagaatcataaagaacagtgacGGATCCCGCGACTTCGCCGCCATGGGCCA

GAAAGAGCAGATCCACACACTGCAGAAAAACAGCGAGCGGATGAGCAAGCAGCTG

ACCAGATCTTCTCAGGCCGTGCAGAACCTGCAGAACGGCGGAGGCTCTAGAAGCTC

TGCTACACTTCCTGGCAGGCGGCGGAGAAGATGGCTGAGAAGAAGGCGGCAGCCTA

TCTCTGTGGCTCCTGCTGGACCTCCTAGACGGCCCAACCAGAAGCCTAATCCTCCTG

GCGGAGCCAGATGCGTGATCATGAGGCCTACATGGCCTGGCACCAGCGCCTTTACCG

GCATGGAATGTACACTGGGCCAAGTGGGAGCCCCATCTCCTAGAAGAGAAGAGGAT

GGCTGGCGCGGAGGCCACTCTAGATTCAAAGCTGATGTGCCCGCTCCTCAGGGCCCT

TGTTGGGGAGGACAACCTGGATCTGCCCCATCTTCTGCCCCACCTGAACAGAGCCTG

CTGGATGACTATTGGGCTCAAAAAGAGAAGATCAGCATCCCCAGAACACACCTGTG

CTGGAAGTTCGAGATGAGCTACACCGTTGGCGGCCCTCCACCACATGTTCACGCCAG

ACCTAGACACTGGAAAACCGACAGAGATTATTGGGCCCAGAAAGAAAAGGGCAGC

AGCAGCTTCCTGCGGCCTAGCTGTGTGCCCTTCCGGGAACTGAAGAACGTGTCCGTT

CTGGAAGGCCTGAGGCAGGGCAGACTTGGCGGACCTTGTAGCTGCCACTGTCCTAG

ACCAAGCCAGGCCAGACTGACCCCTGTGGATGTGGCTGGCCCATTTCTGTGTCTGGG

CGACCCTGGACTGTTCCCTCCAGTGAAGTCTAGCATCACCGAGATCAGCTGCTGCAC

CCTGAGCAGCGAGGAAAACGAGTACCTGCCTAGACCTGAATGGCAGCTGCAGTACG

AGGCCGGCATGACACTCGGAGGCAAGATCCTGTTCTTCCTGTTCCTGCTGCTCCCTCT

GAGCCCCTTCAGCCTGATCTTTCTGGTGCTGGGCGTGCTGTCTGGCCACTCTGGAAG

CAGACTGAAGAGAAGCTTCGCCGTGACCGAGCGGATCATCACAGGCGGCAAGAGCA

CATGTTCTGCCCCTGGACCTCAGTCTCTGCCCAGCACACCCTTCAGCACATACCCTCA

GTGGGTCATCCTGATCACCGAGCTGGATGGCCACAGCTACACCAGCAAAGTGAACT

GCCTCCTGCTGCAGGATGGCTTCCACGGCTGTGTGTCTATTACTGGCGCCGCTGGCA

GACGGAACCTGAGCATCTTTCTGTTTCTGATGCTGTGCAAGCTCGAGTTCCACGCCT

GCCAATGGCAGCACTACCACAGATCTGGCGAAGCCGCTGGAACCCCACTTTGGAGG

CCTACCAGAAACGTGGCCATGATGGTGCCCGACAGACAGGTGCACTACGACTTCGG

CCTGAAGATCCAGAACAAGAACTGCCCCGACGTGCTGCGGTTCCTGGATCTCAAAGT

GCGCTACCTGCACAGCGTGCCCTTCAGAGAGCTGAAAAACCAGAGAACAGCCCAGG

GCGCTCCTGGAATCCATCATGCTGCTTCTCCAGTGGCCGCCAATCTGTGCGATCCTGC

CAGACATGCCCAGCATACCAGGATTCCTTGTGGCGCTGGACAAGTGCGCGCTGGAA

GAGGACCTGAAGCTGGTGGCGGAGTTCTGCAGCCTCAAAGACCTGCTCCTGAGAAG

CCTGGCTGCCCCTGTAGAAGAGGACAGCCTAGACTGCACACCGTGAAGATGTGGCG

GGCCTGCCACTTGTTTCTCCAGCCACAAGTGGGCACCCCTCCACCTCATACAGCCTCT

GCTAGAGCACCTAGCGGCCCACCTCATCCTCACGAATCTTGTCCTGCCGGAAGAAGG

CCTGCCAGAGCCGCTCAAACATGTGCCAGACGACAGCACGGACTGCCCGGATGTGA

AGAAGCCGGAACAGCCAGAGTGCCTAGCCTGCACCTTCATCTGCATCAGGCCGCTCT

TGGAGCCGGAAGAGGTAGAGGATGGGGAGAAGCTTGTGCCCAGGTGCCACCTTCTA

GAGGCCACTACAAGCTGATCCAGCAGCCAATCAGCCTGTTCTCCATCACCGACCGGC

-continued

TGCACAAGACATTCAGCCAGCTGCCTTCCGTGCATCTGTGCAGCATCACCTTCCAGT

GGGGACACCCTCCTATCTTTTGCTCCACCAACGACATCTGCGTGACCGCCAACTTCT

GTATCAGCGTGACCTTCCTGAAGCCTTGCTTTCTGCTGCACGAGGCCTCCGCCAGCC

AGTTTAAGAAGTTTGACGGCCCCTGCGGCGAGAGAGGCGGAGGAAGAACTGCAAGA

GCCCTTTGGGCCAGAGGCGACTCTGTTCTGACACCAGCTCTGGACCCTCAGACACCT

GTTAGGGCCCCTAGCCTGACAAGAGCTGCCGCTGCTGTTGGAGTGCCTGGCGATTCT

ACTAGAAGGGCCGTGCGGCGGATGAACACCTTTTGTGGCGCATCTGCCTGCGACGTG

TCCCTGATCGCTATGGATAGCGCCTGCGAGGAAAGAGGCGCAGCCGGATCTCTGATC

TCTTGCGAGAGCCTGTACCACCGGGAAAAGCAGCTCATTGCCATGGACAGCGCCATC

TTCGTGCAGGGCAAAGACTGGGGCGTGAAGAAGTTCATCCGGCGGGACTTTACCAT

GCCTGCCATTCTGAAGCTGCAGAAGAATTGTCTTCTAAGCCTGAACAGCAAGATGGC

CCTGAATAGCGAGGCCCTGTCTGTGGTGTCCGAGTATGAGGCTGGAATGACCCTGGG

CGAGAAGTTCAGAGTGGGCAACTGCAAGCACCTGAAGATGACCCGGCCTACCGAGT

ACAACCAGAAACTGCAAGTGAACCAGTTCAGCGAGAGCAAGCGGACCGCTCTGACC

CACAACCAGGACTTCAGCATCTACCGGCTGTGCTGCAAGAGGGGCTCTCTGTGTCAT

GCTAGCCAGGCTAGAAGCCCCGCCTTTCCTAAGCCTGTCAGACCTCTGCCTGCTCCT

ATCACCAGAATCACCCCTCAGCTCGGCGGCCAGTCTGATTCATCTCAGCCACTGCTG

ACCACCGGCAGACCTCAAGGATGGCAAGACCAGGCTCTGAGACACACACAGCAGGC

TAGCCCAGCCTCTTGCGCCACCATCACAATACCAATACATTCTGCCGCTCTGGGCGA

TCACAGCGGAGATCCTGGACCTGCCTGGGATACTTGTCCTCCTCTGCCCCTAACTAC

ACTGATCCCTAGGGCTCCTCCACCTTACGGCGATAGCACAGCCAGATCCTGGCCTAG

CAGATGTGGCCCTCTGGGCTACGCCTACAAGGACTTCCTGTGGTGCTTCCCCTTCTCT

CTGGTGTTCCTGCAAGAAATCCAGATCTGCTGTCACGTGTCCTGCCTGTGCTGTATCT

GCTGTAGCACCCGGATCTGTCTGGGCTGTCTGCTGGAACTGTTCCTGAGCAGAGCCC

TGAGAGCACTGCACGTGCTGTGGAACGGATTCCAGCTGCACTGCCAGGGCAACACC

ACACTGCAACAGCTGGGAGAAGCCTCTCAGGCCCCAAGCGGTTCTCTGATCCCTCTC

AGACTGCCCCTCCTGTGGGAAGTGCGGGGCAATTCTAAGATGGCTCTCAACAGCCTG

AACTCCATCGACGACGCCCAGCTGACAAGAATCGCCCCTCCAAGAAGCCACTGTTGC

TTTTGGGAAGTGAACGCCCCTTTTGTGCAGGGTAAAGATTGGGGCCTCAAAAAGTTT

ATCAGACGGGACTTCGAGGCTTTCCAGAGAGCAGCTGGCGAAGGCGGACCTGGCAG

AGGTGGTGCTAGAAGAGGTGCTAGAGTGCTGCAGAGCCCATTCTGTAGAGCTGGCG

CTGGCGAATGGCTGGGCCACCAATCTCTTAGATGGGGAATGGAACTGGCCGCTAGC

AGGCGGTTTAGCTGGGATCATCATTCTGCCGGCGGACCTCCAAGAGTGCCAAGCGTT

AGAAGCGGAGCAGCCCAGGTCCAGCCTAAAGATCCACTGCCACTGAGAACACTGGC

CGGCTGCCTTGCCAGAACAGCTCATCTTAGACCTGGCGCCGAAAGCCTGCCTCAACC

TCAGCTGCATTGCACAATCGCCAGAGAACTGCACCAGTTCGCCTTCGACCTGCTGAT

CAAGAGCCACAAGATGCACTTCTCACTGAAAGAGCACCCGCCACCGCCGTGCCCAC

CGCACGTTGTCGGCTATGGCCACCTGGATACAAGCGGCTCCTCTAGCAGTAGCTCCT

GGCCTCAGCCTGACAGCTTTGCTGCCCTGCATAGCTCCCTGAATGAGCTGGGCGAAC

TGTGGTTCCAGTCCAGCGAACTGTCTCCTACTGGCGCTCCATGGCCAAGCAGAAGGC

CTACTTGGAGAGGCACCACCGTGTCTCCAAGAACCGCTACAAGCAGCGCCAGAACC

-continued

TGTTGCGGCACAAAATGGCCCTCCAGCCAAGAAGCTGCCCTCGGACTTGGAAGCGG

ACTGCTGAGATTCAGCTGTGGCACAGCCGCCATCAGAAGCCATCACCATCACCACCA

TTAGTAAAGGCGCGCC

The amino acid sequence of additional five neoantigen layouts for GAd20 expression are shown in SEQ ID NOs: 554, 555, 556, 623 and 624.

SEQ ID NO: 554

MGQKEQIHTLQKNSERMSKQLTRSSQAVQNLQNGGGSRSSATLPGRRRRRWLRRRRQP

ISVAPAGPPRRPNQKPNPPGGARCVIMRPTWPGTSAFTKRSFAVTERIILVLGVLSGHSGS

RLYEAGMTLGGKILFFLFLLLPLSPFSLIFTEISCCTLSSEENEYLPRPEWQLQVPFRELKN

VSVLEGLRQGRLGGPCSCHCPRPSQARLTPVDVAGPFLCLGDPGLFPPVKSSITGGKSTC

SAPGPQSLPSTPFSTYPQWVILITELGMECTLGQVGAPSPRREEDGWRGGHSRFKADVPA

PQGPCWGGQPGSAPSSAPPEQSLLDDYWAQKEKGSSSFLRPSCDYWAQKEKISIPRTHLC

WKFEMSYTVGGPPPHVHARPRHWKTDRGVPGDSTRRAVRRMNTFYEAGMTLGEKFRV

GNCKHLKMTRPNSKMALNSEALSVVSECGASACDVSLIAMDSAFVQGKDWGVKKFIRR

DFYAYKDFLWCFPFSLVFLQEIQICCHVSCLCCICCSTRICLGCLLELFLSRALRALHVLW

NGFQLHCQTEYNQKLQVNQFSESKSLYHREKQLIAMDSAICEERGAAGSLISCETMPAIL

KLQKNCLLSLRTALTHNQDFSIYRLCCKRGSLCHASQARSPAFPKPVRPLPAPITRITPQL

GGQSDSSQPLLTTGRPQGWQDQALRHTQQASPASCATITIPIHSAALGDHSGDPGPAWD

TCPPLPLTTLIPRAPPPYGDSTARSWPSRCGPLGDGHSYTSKVNCLLLQDGFHGCVSITGA

AGRRNLSIFLFLMLCKLEFHACKIQNKNCPDFKKFDGPCGERGGGRTARALWARGDSVL

TPALDPQTPVRAPSLTRAAAAVHYKLIQQPISLFSITDRLHKTFSQLPSVHLCSITFQWGH

PPIFCSTNDICVTANFCISVTFLKPCFLLHEASASQCHLFLQPQVGTPPPHTASARAPSGPP

HPHESCPAGRRPARAAQTCARRQHGLPGCEEAGTARVPSLHLHLHQAALGAGRGRGW

GEACAQVPPSRGVLRFLDLKVRYLHSQWQHYHRSGEAAGTPLWRPTRNVPFRELKNQR

TAQGAPGIHHAASPVAANLCDPARHAQHTRIPCGAGQVRAGRGPEAGGGVLQPQRPAP

EKPGCPCRRGQPRLHTVKMWRAVAMMVPDRQVHYDFGLGNTTLQQLGEASQAPSGSL

IPLRLPLLWEVRGQPDSFAALHSSLNELGEIARELHQFAFDLLIKSHFVQGKDWGLKKFIR

RDFWGMELAASRRFSWDHHSAGGPPRVPSVRSGAAQVQPKDPLPLRTLAGCLARTAHL

RPGAESLPQPQLHCTLWFQSSELSPTGAPWPSRRPTWRGTTVSPRTATSSARTCCGTKWP

SSQEAALGLGSGLLRFSCGTAAIRKMHFSLKEHPPPPCPPEAFQRAAGEGGPGRGGARRG

ARVLQSPFCRAGAGEWLGHQSLRHVVGYGHLDTSGSSSSSSWPNSKMALNSLNSIDDA

QLTRIAPPRSHCCFWEVNAP

SEQ ID NO: 555

MGQKEQIHTLQKNSERMSKQLTRSSQAVQNLQNGGGSRSSATLPGRRRRRWLRRRRQP

ISVAPAGPPRRPNQKPNPPGGARCVIMRPTWPGTSAFTKRSFAVTERIITEISCCTLSSEEN

EYLPRPEWQLQYEAGMTLGGKILFFLFLLLPLSPFSLIFDYWAQKEKGSSSFLRPSCVPFR

ELKNVSVLEGLRQGRLGGPCSCHCPRPSQARLTPVDVAGPFLCLGDPGLFPPVKSSITGG

KSTCSAPGPQSLPSTPFSTYPQWVILITELGMECTLGQVGAPSPRREEDGWRGGHSRFKA

DVPAPQGPCWGGQPGSAPSSAPPEQSLLDDYWAQKEKISIPRTHLCLVLGVLSGHSGSRL

WKFEMSYTVGGPPPHVHARPRHWKTDRDGHSYTSKVNCLLLQDGFHGCVSITGAAGR

-continued

RNLSIFLFLMLCKLEFHACKIQNKNCPDFKKFDGPCGERGGGRTARALWARGDSVLTPA
LDPQTPVRAPSLTRAAAAVHYKLIQQPISLFSITDRLHKTFSQLPSVHLCSITFQWGHPPIF
CSTNDICVTANFCISVTFLKPCFLLHEASASQCHLFLQPQVGTPPPHTASARAPSGPPHPH
ESCPAGRRPARAAQTCARRQHGLPGCEEAGTARVPSLHLHLHQAALGAGRGRGWGEA
CAQVPPSRGVLRFLDLKVRYLHSQWQHYHRSGEAAGTPLWRPTRNVPFRELKNQRTAQ
GAPGIHHAASPVAANLCDPARHAQHTRIPCGAGQVRAGRGPEAGGGVLQPQRPAPEKP
GCPCRRGQPRLHTVKMWRAVAMMVPDRQVHYDFGLGVPGDSTRRAVRRMNTFYEAG
MTLGEKFRVGNCKHLKMTRPNSKMALNSEALSVVSECGASACDVSLIAMDSAFVQGK
DWGVKKFIRRDFYAYKDFLWCFPFSLVFLQEIQICCHVSCLCCICCSTRICLGCLLELFLS
RALRALHVLWNGFQLHCQTEYNQKLQVNQFSESKSLYHREKQLIAMDSAICEERGAAG
SLISCETMPAILKLQKNCLLSLRTALTHNQDFSIYRLCCKRGSLCHASQARSPAFPKPVRP
LPAPITRITPQLGGQSDSSQPLLTTGRPQGWQDQALRHTQQASPASCATITIPIHSAALGD
HSGDPGPAWDTCPPLPLTTLIPRAPPPYGDSTARSWPSRCGPLGGNTTLQQLGEASQAPS
GSLIPLRLPLLWEVRGQPDSFAALHSSLNELGEIARELHQFAFDLLIKSHFVQGKDWGLK
KFIRRDFWGMELAASRRFSWDHHSAGGPPRVPSVRSGAAQVQPKDPLPLRTLAGCLAR
TAHLRPGAESLPQPQLHCTLWFQSSELSPTGAPWPSRRPTWRGTTVSPRTATSSARTCCG
TKWPSSQEAALGLGSGLLRFSCGTAAIRKMHFSLKEHPPPPCPPEAFQRAAGEGGPGRG
GARRGARVLQSPFCRAGAGEWLGHQSLRHVVGYGHLDTSGSSSSSSWPNSKMALNSLN
SIDDAQLTRIAPPRSHCCFWEVNAP

SEQ ID NO: 556

MGQKEQIHTLQKNSERMSKQLTRSSQAVQNLQNGGGSRSSATLPGRRRRRWLRRRRQP
ISVAPAGPPRRPNQKPNPPGGARCVIMRPTWPGTSAFTKRSFAVTERIIDYWAQKEKGSS
SFLRPSCVPFRELKNVSVLEGLRQGRLGGPCSCHCPRPSQARLTPVDVAGPFLCLGDPGL
FPPVKSSILVLGVLSGHSGSRLYEAGMTLGGKILFFLFLLLPLSPFSLIFTEISCCTLSSEENE
YLPRPEWQLQTGGKSTCSAPGPQSLPSTPFSTYPQWVILITELGMECTLGQVGAPSPRREE
DGWRGGHSRFKADVPAPQGPCWGGQPGSAPSSAPPEQSLLDDYWAQKEKISIPRTHLC
WKFEMSYTVGGPPPHVHARPRHWKTDRDGHSYTSKVNCLLLQDGFHGCVSITGAAGR
RNLSIFLFLMLCKLEFHACKIQNKNCPDFKKFDGPCGERGGGRTARALWARGDSVLTPA
LDPQTPVRAPSLTRAAAAVHYKLIQQPISLFSITDRLHKTFSQLPSVHLCSITFQWGHPPIF
CSTNDICVTANFCISVTFLKPCFLLHEASASQCHLFLQPQVGTPPPHTASARAPSGPPHPH
ESCPAGRRPARAAQTCARRQHGLPGCEEAGTARVPSLHLHLHQAALGAGRGRGWGEA
CAQVPPSRGVLRFLDLKVRYLHSQWQHYHRSGEAAGTPLWRPTRNVPFRELKNQRTAQ
GAPGIHHAASPVAANLCDPARHAQHTRIPCGAGQVRAGRGPEAGGGVLQPQRPAPEKP
GCPCRRGQPRLHTVKMWRAVAMMVPDRQVHYDFGLGVPGDSTRRAVRRMNTFYEAG
MTLGEKFRVGNCKHLKMTRPNSKMALNSEALSVVSECGASACDVSLIAMDSAFVQGK
DWGVKKFIRRDFYAYKDFLWCFPFSLVFLQEIQICCHVSCLCCICCSTRICLGCLLELFLS
RALRALHVLWNGFQLHCQTEYNQKLQVNQFSESKSLYHREKQLIAMDSAICEERGAAG
SLISCETMPAILKLQKNCLLSLRTALTHNQDFSIYRLCCKRGSLCHASQARSPAFPKPVRP
LPAPITRITPQLGGQSDSSQPLLTTGRPQGWQDQALRHTQQASPASCATITIPIHSAALGD
HSGDPGPAWDTCPPLPLTTLIPRAPPPYGDSTARSWPSRCGPLGGNTTLQQLGEASQAPS
GSLIPLRLPLLWEVRGQPDSFAALHSSLNELGEIARELHQFAFDLLIKSHFVQGKDWGLK

-continued

KFIRRDFWGMELAASRRFSWDHHSAGGPPRVPSVRSGAAQVQPKDPLPLRTLAGCLAR

TAHLRPGAESLPQPQLHCTLWFQSSELSPTGAPWPSRRPTWRGTTVSPRTATSSARTCCG

TKWPSSQEAALGLGSGLLRFSCGTAAIRKMHFSLKEHPPPPCPPEAFQRAAGEGGPGRG

GARRGARVLQSPFCRAGAGEWLGHQSLRHVVGYGHLDTSGSSSSSSWPNSKMALNSLN

SIDDAQLTRIAPPRSHCCFWEVNAP

SEQ ID NO: 623

MGQKEQIHTLQKNSERMSKQLTRSSQAVGVPGDSTRRAVRRMNTFYEAGMTLGEKFR

VGNCKHLKMTRPNSKMALNSEALSVVSECGASACDVSLIAMDSAFVQGKDWGVKKFI

RRDFYAYKDFLWCFPFSLVFLQEIQICCHVSCLCCICCSTRICLGCLLELFLSRALRALHV

LWNGFQLHCQTEYNQKLQVNQFSESKSLYHREKQLIAMDSAICEERGAAGSLISCETMP

AILKLQKNCLLSLRTALTHNQDFSIYRLCCKRGSLCHASQARSPAFPKPVRPLPAPITRITP

QLGGQSDSSQPLLTTGRPQGWQDQALRHTQQASPASCATITIPIHSAALGDHSGDPGPA

WDTCPPLPLTTLIPRAPPPYGDSTARSWPSRCGPLGGNTTLQQLGEASQAPSGSLIPLRLP

LLWEVRGQPDSFAALHSSLNELGEIARELHQFAFDLLIKSHFVQGKDWGLKKFIRRDFW

GMELAASRRFSWDHHSAGGPPRVPSVRSGAAQVQPKDPLPLRTLAGCLARTAHLRPGA

ESLPQPQLHCTLWFQSSELSPTGAPWPSRRPTWRGTTVSPRTATSSARTCCGTKWPSSQE

AALGLGSGLLRFSCGTAAIRKMHFSLKEHPPPPCPPEAFQRAAGEGGPGRGGARRGARV

LQSPFCRAGAGEWLGHQSLRHVVGYGHLDTSGSSSSSSWPNSKMALNSLNSIDDAQLTR

IAPPRSHCCFWEVNAPDGHSYTSKVNCLLLQDGFHGCVSITGAAGRRNLSIFLFLMLCKL

EFHACKIQNKNCPDFKKFDGPCGERGGGRTARALWARGDSVLTPALDPQTPVRAPSLTR

AAAAVHYKLIQQPISLFSITDRLHKTFSQLPSVHLCSITFQWGHPPIFCSTNDICVTANFCIS

VTFLKPCFLLHEASASQCHLFLQPQVGTPPPHTASARAPSGPPHPHESCPAGRRPARAAQ

TCARRQHGLPGCEEAGTARVPSLHLHLHQAALGAGRGRGWGEACAQVPPSRGVLRFLD

LKVRYLHSQWQHYHRSGEAAGTPLWRPTRNVPFRELKNQRTAQGAPGIHHAASPVAA

NLCDPARHAQHTRIPCGAGQVRAGRGPEAGGGVLQPQRPAPEKPGCPCRRGQPRLHTV

KMWRAVAMMVPDRQVHYDFGLQNLQNGGGSRSSATLPGRRRRRWLRRRRQPISVAPA

GPPRRPNQKPNPPGGARCVIMRPTWPGTSAFTKRSFAVTERIILVLGVLSGHSGSRLYEA

GMTLGGKILFFLFLLLPLSPFSLIFTEISCCTLSSEENEYLPRPEWQLQVPFRELKNVSVLE

GLRQGRLGGPCSCHCPRPSQARLTPVDVAGPFLCLGDPGLFPPVKSSITGGKSTCSAPGP

QSLPSTPFSTYPQWVILITELGMECTLGQVGAPSPRREEDGWRGGHSRFKADVPAPQGPC

WGGQPGSAPSSAPPEQSLLDDYWAQKEKGSSSFLRPSCDYWAQKEKISIPRTHLCWKFE

MSYTVGGPPPHVHARPRHWKTDR

SEQ ID NO: 624

MGQKEQIHTLQKNSERMSKQLTRSSQAVGNTTLQQLGEASQAPSGSLIPLRLPLLWEVR

GQPDSFAALHSSLNELGEIARELHQFAFDLLIKSHFVQGKDWGLKKFIRRDFWGMELAA

SRRFSWDHHSAGGPPRVPSVRSGAAQVQPKDPLPLRTLAGCLARTAHLRPGAESLPQPQ

LHCTLWFQSSELSPTGAPWPSRRPTWRGTTVSPRTATSSARTCCGTKWPSSQEAALGLG

SGLLRFSCGTAAIRKMHFSLKEHPPPPCPPEAFQRAAGEGGPGRGGARRGARVLQSPFCR

AGAGEWLGHQSLRHVVGYGHLDTSGSSSSSSWPNSKMALNSLNSIDDAQLTRIAPPRSH

CCFWEVNAPGVPGDSTRRAVRRMNTFYEAGMTLGEKFRVGNCKHLKMTRPNSKMAL

NSEALSVVSECGASACDVSLIAMDSAFVQGKDWGVKKFIRRDFYAYKDFLWCFPFSLVF

-continued

LQEIQICCHVSCLCCICCSTRICLGCLLELFLSRALRALHVLWNGFQLHCQTEYNQKLQV
NQFSESKSLYHREKQLIAMDSAICEERGAAGSLISCETMPAILKLQKNCLLSLRTALTHN
QDFSIYRLCCKRGSLCHASQARSPAFPKPVRPLPAPITRITPQLGGQSDSSQPLLTTGRPQG
WQDQALRHTQQASPASCATITIPIHSAALGDHSGDPGPAWDTCPPLPLTTLIPRAPPPYGD
STARSWPSRCGPLGDGHSYTSKVNCLLLQDGFHGCVSITGAAGRRNLSIFLFLMLCKLEF
HACKIQNKNCPDFKKFDGPCGERGGGRTARALWARGDSVLTPALDPQTPVRAPSLTRA
AAAVHYKLIQQPISLFSITDRLHKTFSQLPSVHLCSITFQWGHPPIFCSTNDICVTANFCISV
TFLKPCFLLHEASASQCHLFLQPQVGTPPPHTASARAPSGPPHPHESCPAGRRPARAAQT
CARRQHGLPGCEEAGTARVPSLHLHLHQAALGAGRGRGWGEACAQVPPSRGVLRFLDL
KVRYLHSQWQHYHRSGEAAGTPLWRPTRNVPFRELKNQRTAQGAPGIHHAASPVAAN
LCDPARHAQHTRIPCGAGQVRAGRGPEAGGGVLQPQRPAPEKPGCPCRRGQPRLHTVK
MWRAVAMMVPDRQVHYDFGLQNLQNGGGSRSSATLPGRRRRRWLRRRRQPISVAPAG
PPRRPNQKPNPPGGARCVIMRPTWPGTSAFTKRSFAVTERIITEISCCTLSSEENEYLPRPE
WQLQYEAGMTLGGKILFFLFLLLPLSPFSLIFDYWAQKEKGSSSFLRPSCVPFRELKNVSV
LEGLRQGRLGGPCSCHCPRPSQARLTPVDVAGPFLCLGDPGLFPPVKSSITGGKSTCSAP
GPQSLPSTPFSTYPQWVILITELGMECTLGQVGAPSPRREEDGWRGGHSRFKADVPAPQG
PCWGGQPGSAPSSAPPEQSLLDDYWAQKEKISIPRTHLCLVLGVLSGHSGSRLWKFEMS
YTVGGPPPHVHARPRHWKTDR

The amino acid sequence of additional five neoantigen layouts for MVA expression are shown in SEQ ID NOs: 557, 558, 559, 625 and 626.

SEQ ID NO: 557

MGQKEQIHTLQKNSERMSKQLTRSSQAVQNLQNGGGSRSSATLPGRRRRRWLRRRRQP
ISVAPAGPPRRPNQKPNPPGGARCVIMRPTWPGTSAFTGMECTLGQVGAPSPRREEDGW
RGGHSRFKADVPAPQGPCWGGQPGSAPSSAPPEQSLLDDYWAQKEKISIPRTHLCWKFE
MSYTVGGPPPHVHARPRHWKTDRDYWAQKEKGSSSFLRPSCVPFRELKNVSVLEGLRQ
GRLGGPCSCHCPRPSQARLTPVDVAGPFLCLGDPGLFPPVKSSITEISCCTLSSEENEYLPR
PEWQLQYEAGMTLGGKILFFLFLLLPLSPFSLIFLVLGVLSGHSGSRLKRSFAVTERIITGG
KSTCSAPGPQSLPSTPFSTYPQWVILITELDGHSYTSKVNCLLLQDGFHGCVSITGAAGRR
NLSIFLFLMLCKLEFHACCHLFLQPQVGTPPPHTASARAPSGPPHPHESCPAGRRPARAA
QTCARRQHGLPGCEEAGTARVPSLHLHLHQAALGAGRGRGWGEACAQVPPSRGHYKLI
QQPISLFSITDRLHKTFSQLPSVHLCSITFQWGHPPIFCSTNDICVTANFCISVTFLKPCFLL
HEASASQVAMMVPDRQVHYDFGLKIQNKNCPDVLRFLDLKVRYLHSVPFRELKNQRTA
QGAPGIHHAASPVAANLCDPARHAQHTRIPCGAGQVRAGRGPEAGGGVLQPQRPAPEK
PGCPCRRGQPRLHTVKMWRAQWQHYHRSGEAAGTPLWRPTRNFKKFDGPCGERGGGR
TARALWARGDSVLTPALDPQTPVRAPSLTRAAAAVGVPGDSTRRAVRRMNTFCGASAC
DVSLIAMDSACEERGAAGSLISCESLYHREKQLIAMDSAIFVQGKDWGVKKFIRRDFTM
PAILKLQKNCLLSLNSKMALNSEALSVVSEYEAGMTLGEKFRVGNCKHLKMTRPTEYN
QKLQVNQFSESKRTALTHNQDFSIYRLCCKRGSLCHASQARSPAFPKPVRPLPAPITRITP
QLGGQSDSSQPLLTTGRPQGWQDQALRHTQQASPASCATITIPIHSAALGDHSGDPGPA
WDTCPPLPLTTLIPRAPPPYGDSTARSWPSRCGPLGYAYKDFLWCFPFSLVFLQEIQICCH

-continued

VSCLCCICCSTRICLGCLLELFLSRALRALHVLWNGFQLHCQGNTTLQQLGEASQAPSGS
LIPLRLPLLWEVRGNSKMALNSLNSIDDAQLTRIAPPRSHCCFWEVNAPFVQGKDWGLK
KFIRRDFEAFQRAAGEGGPGRGGARRGARVLQSPFCRAGAGEWLGHQSLRWGMELAA
SRRFSWDHHSAGGPPRVPSVRSGAAQVQPKDPLPLRTLAGCLARTAHLRPGAESLPQPQ
LHCTIARELHQFAFDLLIKSHKMHFSLKEHPPPPCPPHVVGYGHLDTSGSSSSSSWPQPDS
FAALHSSLNELGELWFQSSELSPTGAPWPSRRPTWRGTTVSPRTATSSARTCCGTKWPSS
QEAALGLGSGLLRFSCGTAAIR

SEQ ID NO: 558

MGQKEQIHTLQKNSERMSKQLTRSSQAVDGHSYTSKVNCLLLQDGFHGCVSITGAAGR
RNLSIFLFLMLCKLEFHACQWQHYHRSGEAAGTPLWRPTRNVAMMVPDRQVHYDFGL
VLRFLDLKVRYLHSKIQNKNCPDVPFRELKNQRTAQGAPGIHHAASPVAANLCDPARHA
QHTRIPCGAGQVRAGRGPEAGGGVLQPQRPAPEKPGCPCRRGQPRLHTVKMWRACHLF
LQPQVGTPPPHTASARAPSGPPHPHESCPAGRRPARAAQTCARRQHGLPGCEEAGTARV
PSLHLHLHQAALGAGRGRGWGEACAQVPPSRGHYKLIQQPISLFSITDRLHKTFSQLPSV
HLCSITFQWGHPPIFCSTNDICVTANFCISVTFLKPCFLLHEASASQFKKFDGPCGERGGG
RTARALWARGDSVLTPALDPQTPVRAPSLTRAAAAVQNLQNGGGSRSSATLPGRRRRR
WLRRRRQPISVAPAGPPRRPNQKPNPPGGARCVIMRPTWPGTSAFTGMECTLGQVGAPS
PRREEDGWRGGHSRFKADVPAPQGPCWGGQPGSAPSSAPPEQSLLDDYWAQKEKISIPR
THLCWKFEMSYTVGGPPPHVHARPRHWKTDRDYWAQKEKGSSSFLRPSCVPFRELKNV
SVLEGLRQGRLGGPCSCHCPRPSQARLTPVDVAGPFLCLGDPGLFPPVKSSITEISCCTLSS
EENEYLPRPEWQLQYEAGMTLGGKILFFLFLLLPLSPFSLIFLVLGVLSGHSGSRLKRSFA
VTERIITGGKSTCSAPGPQSLPSTPFSTYPQWVILITELGVPGDSTRRAVRRMNTFCGASA
CDVSLIAMDSACEERGAAGSLISCESLYHREKQLIAMDSAIFVQGKDWGVKKFIRRDFT
MPAILKLQKNCLLSLNSKMALNSEALSVVSEYEAGMTLGEKFRVGNCKHLKMTRPTEY
NQKLQVNQFSESKRTALTHNQDFSIYRLCCKRGSLCHASQARSPAFPKPVRPLPAPITRIT
PQLGGQSDSSQPLLTTGRPQGWQDQALRHTQQASPASCATITIPIHSAALGDHSGDPGPA
WDTCPPLPLTTLIPRAPPPYGDSTARSWPSRCGPLGYAYKDFLWCFPFSLVFLQEIQICCH
VSCLCCICCSTRICLGCLLELFLSRALRALHVLWNGFQLHCQGNTTLQQLGEASQAPSGS
LIPLRLPLLWEVRGNSKMALNSLNSIDDAQLTRIAPPRSHCCFWEVNAPFVQGKDWGLK
KFIRRDFEAFQRAAGEGGPGRGGARRGARVLQSPFCRAGAGEWLGHQSLRWGMELAA
SRRFSWDHHSAGGPPRVPSVRSGAAQVQPKDPLPLRTLAGCLARTAHLRPGAESLPQPQ
LHCTIARELHQFAFDLLIKSHKMHFSLKEHPPPPCPPHVVGYGHLDTSGSSSSSSWPQPDS
FAALHSSLNELGELWFQSSELSPTGAPWPSRRPTWRGTTVSPRTATSSARTCCGTKWPSS
QEAALGLGSGLLRFSCGTAAIR

SEQ ID NO: 559

MGQKEQIHTLQKNSERMSKQLTRSSQAVGNTTLQQLGEASQAPSGSLIPLRLPLLWEVR
GNSKMALNSLNSIDDAQLTRIAPPRSHCCFWEVNAPFVQGKDWGLKKFIRRDFEAFQRA
AGEGGPGRGGARRGARVLQSPFCRAGAGEWLGHQSLRWGMELAASRRFSWDHHSAG
GPPRVPSVRSGAAQVQPKDPLPLRTLAGCLARTAHLRPGAESLPQPQLHCTIARELHQFA
FDLLIKSHKMHFSLKEHPPPPCPPHVVGYGHLDTSGSSSSSSWPQPDSFAALHSSLNELGE
LWFQSSELSPTGAPWPSRRPTWRGTTVSPRTATSSARTCCGTKWPSSQEAALGLGSGLL

-continued

RFSCGTAAIRDGHSYTSKVNCLLLQDGFHGCVSITGAAGRRNLSIFLFLMLCKLEFHACQ

WQHYHRSGEAAGTPLWRPTRNVAMMVPDRQVHYDFGLKIQNKNCPDVLRFLDLKVR

YLHSVPFRELKNQRTAQGAPGIHHAASPVAANLCDPARHAQHTRIPCGAGQVRAGRGP

EAGGGVLQPQRPAPEKPGCPCRRGQPRLHTVKMWRACHLFLQPQVGTPPPHTASARAP

SGPPHPHESCPAGRRPARAAQTCARRQHGLPGCEEAGTARVPSLHLHLHQAALGAGRG

RGWGEACAQVPPSRGHYKLIQQPISLFSITDRLHKTFSQLPSVHLCSITFQWGHPPIFCSTN

DICVTANFCISVTFLKPCFLLHEASASQFKKFDGPCGERGGGRTARALWARGDSVLTPAL

DPQTPVRAPSLTRAAAAVGVPGDSTRRAVRRMNTFCGASACDVSLIAMDSATEYNQKL

QVNQFSESKYEAGMTLGEKFRVGNCKHLKMTRPTMPAILKLQKNCLLSLNSKMALNSE

ALSVVSECEERGAAGSLISCESLYHREKQLIAMDSAIFVQGKDWGVKKFIRRDFRTALTH

NQDFSIYRLCCKRGSLCHASQARSPAFPKPVRPLPAPITRITPQLGGQSDSSQPLLTTGRPQ

GWQDQALRHTQQASPASCATITIPIHSAALGDHSGDPGPAWDTCPPLPLTTLIPRAPPPYG

DSTARSWPSRCGPLGYAYKDFLWCFPFSLVFLQEIQICCHVSCLCCICCSTRICLGCLLEL

FLSRALRALHVLWNGFQLHCQQNLQNGGGSRSSATLPGRRRRRWLRRRRQPISVAPAG

PPRRPNQKPNPPGGARCVIMRPTWPGTSAFTGMECTLGQVGAPSPRREEDGWRGGHSRF

KADVPAPQGPCWGGQPGSAPSSAPPEQSLLDDYWAQKEKISIPRTHLCWKFEMSYTVG

GPPPHVHARPRHWKTDRDYWAQKEKGSSSFLRPSCVPFRELKNVSVLEGLRQGRLGGP

CSCHCPRPSQARLTPVDVAGPFLCLGDPGLFPPVKSSITEISCCTLSSEENEYLPRPEWQLQ

YEAGMTLGGKILFFLFLLLPLSPFSLIFLVLGVLSGHSGSRLKRSFAVTERIITGGKSTCSAP

GPQSLPSTPFSTYPQWVILITEL

SEQ ID NO: 625

MGQKEQIHTLQKNSERMSKQLTRSSQAVGNTTLQQLGEASQAPSGSLIPLRLPLLWEVR

GNSKMALNSLNSIDDAQLTRIAPPRSHCCFWEVNAPFVQGKDWGLKKFIRRDFEAFQRA

AGEGGPGRGGARRGARVLQSPFCRAGAGEWLGHQSLRWGMELAASRRFSWDHHSAG

GPPRVPSVRSGAAQVQPKDPLPLRTLAGCLARTAHLRPGAESLPQPQLHCTIARELHQFA

FDLLIKSHKMHFSLKEHPPPPCPPHVVGYGHLDTSGSSSSSSWPQPDSFAALHSSLNELGE

LWFQSSELSPTGAPWPSRRPTWRGTTVSPRTATSSARTCCGTKWPSSQEAALGLGSGLL

RFSCGTAAIRQNLQNGGGSRSSATLPGRRRRRWLRRRRQPISVAPAGPPRRPNQKPNPPG

GARCVIMRPTWPGTSAFTGMECTLGQVGAPSPRREEDGWRGGHSRFKADVPAPQGPC

WGGQPGSAPSSAPPEQSLLDDYWAQKEKISIPRTHLCWKFEMSYTVGGPPPHVHARPRH

WKTDRDYWAQKEKGSSSFLRPSCVPFRELKNVSVLEGLRQGRLGGPCSCHCPRPSQARL

TPVDVAGPFLCLGDPGLFPPVKSSITEISCCTLSSEENEYLPRPEWQLQYEAGMTLGGKIL

FFLFLLLPLSPFSLIFLVLGVLSGHSGSRLKRSFAVTERIITGGKSTCSAPGPQSLPSTPFSTY

PQWVILITELDGHSYTSKVNCLLLQDGFHGCVSITGAAGRRNLSIFLFLMLCKLEFHACQ

WQHYHRSGEAAGTPLWRPTRNVAMMVPDRQVHYDFGLVLRFLDLKVRYLHSKIQNKN

CPDVPFRELKNQRTAQGAPGIHHAASPVAANLCDPARHAQHTRIPCGAGQVRAGRGPE

AGGGVLQPQRPAPEKPGCPCRRGQPRLHTVKMWRACHLFLQPQVGTPPPHTASARAPS

GPPHPHESCPAGRRPARAAQTCARRQHGLPGCEEAGTARVPSLHLHLHQAALGAGRGR

GWGEACAQVPPSRGHYKLIQQPISLFSITDRLHKTFSQLPSVHLCSITFQWGHPPIFCSTND

ICVTANFCISVTFLKPCFLLHEASASQFKKFDGPCGERGGGRTARALWARGDSVLTPALD

PQTPVRAPSLTRAAAAVGVPGDSTRRAVRRMNTFCGASACDVSLIAMDSACEERGAAG

-continued

SLISCESLYHREKQLIAMDSAIFVQGKDWGVKKFIRRDFTMPAILKLQKNCLLSLNSKMA

LNSEALSVVSEYEAGMTLGEKFRVGNCKHLKMTRPTEYNQKLQVNQFSESKRTALTHN

QDFSIYRLCCKRGSLCHASQARSPAFPKPVRPLPAPITRITPQLGGQSDSSQPLLTTGRPQG

WQDQALRHTQQASPASCATITIPIHSAALGDHSGDPGPAWDTCPPLPLTTLIPRAPPPYGD

STARSWPSRCGPLGYAYKDFLWCFPFSLVFLQEIQICCHVSCLCCICCSTRICLGCLLELFL

SRALRALHVLWNGFQLHCQ

SEQ ID NO: 626

MGQKEQIHTLQKNSERMSKQLTRSSQAVDGHSYTSKVNCLLLQDGFHGCVSITGAAGR

RNLSIFLFLMLCKLEFHACVPFRELKNQRTAQGAPGIHHAASPVAANLCDPARHAQHTRI

PCGAGQVRAGRGPEAGGGVLQPQRPAPEKPGCPCRRGQPRLHTVKMWRAQWQHYHR

SGEAAGTPLWRPTRNKIQNKNCPDVAMMVPDRQVHYDFGLVLRFLDLKVRYLHSCHLF

LQPQVGTPPPHTASARAPSGPPHPHESCPAGRRPARAAQTCARRQHGLPGCEEAGTARV

PSLHLHLHQAALGAGRGRGWGEACAQVPPSRGHYKLIQQPISLFSITDRLHKTFSQLPSV

HLCSITFQWGHPPIFCSTNDICVTANFCISVTFLKPCFLLHEASASQFKKFDGPCGERGGG

RTARALWARGDSVLTPALDPQTPVRAPSLTRAAAAVQNLQNGGGSRSSATLPGRRRRR

WLRRRRQPISVAPAGPPRRPNQKPNPPGGARCVIMRPTWPGTSAFTGMECTLGQVGAPS

PRREEDGWRGGHSRFKADVPAPQGPCWGGQPGSAPSSAPPEQSLLDDYWAQKEKISIPR

THLCWKFEMSYTVGGPPPHVHARPRHWKTDRDYWAQKEKGSSSFLRPSCVPFRELKNV

SVLEGLRQGRLGGPCSCHCPRPSQARLTPVDVAGPFLCLGDPGLFPPVKSSITEISCCTLSS

EENEYLPRPEWQLQYEAGMTLGGKILFFLFLLLPLSPFSLIFLVLGVLSGHSGSRLKRSFA

VTERIITGGKSTCSAPGPQSLPSTPFSTYPQWVILITELGNTTLQQLGEASQAPSGSLIPLRL

PLLWEVRGNSKMALNSLNSIDDAQLTRIAPPRSHCCFWEVNAPFVQGKDWGLKKFIRRD

FEAFQRAAGEGGPGRGGARRGARVLQSPFCRAGAGEWLGHQSLRWGMELAASRRFSW

DHHSAGGPPRVPSVRSGAAQVQPKDPLPLRTLAGCLARTAHLRPGAESLPQPQLHCTIA

RELHQFAFDLLIKSHKMHFSLKEHPPPPCPPHVVGYGHLDTSGSSSSSSWPQPDSFAALH

SSLNELGELWFQSSELSPTGAPWPSRRPTWRGTTVSPRTATSSARTCCGTKWPSSQEAAL

GLGSGLLRFSCGTAAIRGVPGDSTRRAVRRMNTFCGASACDVSLIAMDSACEERGAAGS

LISCESLYHREKQLIAMDSAIFVQGKDWGVKKFIRRDFYEAGMTLGEKFRVGNCKHLK

MTRPTMPAILKLQKNCLLSLNSKMALNSEALSVVSETEYNQKLQVNQFSESKRTALTHN

QDFSIYRLCCKRGSLCHASQARSPAFPKPVRPLPAPITRITPQLGGQSDSSQPLLTTGRPQG

WQDQALRHTQQASPASCATITIPIHSAALGDHSGDPGPAWDTCPPLPLTTLIPRAPPPYGD

STARSWPSRCGPLGYAYKDFLWCFPFSLVFLQEIQICCHVSCLCCICCSTRICLGCLLELFL

SRALRALHVLWNGFQLHCQ

SEQ ID NO: 713

The polynucleotide sequence of the full GAd20 incorporating the GAd20 expression cassette catcatcaataatataccttattttggattgaggccaatatgataatgaggtgggcggggcgaggcggggcgggtgacgtagga cgcgcgagtagggttgggaggtgtggcggaagtgtggcatttgcaagtgggaggagctgacatgcaatcttccgtcgcggaa aatgtgacgcgtttttgatgagcgccgcctacctccggaagtgccaattttcgcgcgcttttcaccggatatcgtagtaattttgggcg ggaccatgtaagatttggccattttcgcgcgaaaagtgaaacggggaagtgaaaactgaataatagggcgttagtcatagcgcg taatatttaccgagggccgagggactttgaccgattacgtggaggactcgcccaggtgtttttttacgtgaatttccgcgttccgggt caaagtctccgtttttattgtcgccgtcatctgacgggccgccattgcatacgttgtatccatatcataatatgtacatttatattggctc atgtccaacattaccgccatgttgacattgattattgactagttattaatagtaatcaattacggggtcattagttcatagcccatatat -continued ggagttccgcgttacataacttacggtaaatggcccgcctggctgaccgcccaacgacccccgcccattgacgtcaataatgac gtatgttcccatagtaacgccaatagggactttccattgacgtcaatgggtggagtatttacggtaaactgcccacttggcagtaca tcaagtgtatcatatgccaagtacgccccctattgacgtcaatgacggtaaatggcccgcctggcattatgcccagtacatgacct tatgggactttcctacttggcagtacatctacgtattagtcatcgctattaccatggtgatgcggttttggcagtacatcaatgggcgt ggatagcggtttgactcacggggatttccaagtctccaccccattgacgtcaatgggagtttgttttggcaccaaaatcaacggga ctttccaaaatgtcgtaacaactccgccccattgacgcaaatgggcggtaggcgtgtacggtgggaggtctatataagcagagc tctccctatcagtgatagagatctccctatcagtgatagagatcgtcgacgagctcgtttagtgaaccgtcagatcgcctggagac gccatccacgctgttttgacctccatagaagacaccgggaccgatccagcctccgcggccgggaacggtgcattggaacgcg gattccccgtgccaagagtgagatcttccgtttatctaggtaccagatatcagaattcggatcccgcgacttcgccgccatgggc cagaaagagcagatccacacactgcagaaaaacagcgagcggatgagcaagcagctgaccagatcttctcaggccgtgcag aacctgcagaacggcggaggctctagaagctctgctacacttcctggcaggcggcggagaagatggctgagaagaaggcgg cagcctatctctgtggctcctgctggacctcctagacggcccaaccagaagcctaatcctcctggcggagccagatgcgtgatc atgaggcctacatggcctggcaccagcgccttcaccaagagaagctttgccgtgaccgagcggatcatcgactattgggctca aaaagagaagggcagcagcagcttcctgcggcctagctgtgattattgggcccagaaagaaaagatcagcatccccagaaca cacctgtgcctggtgctgggagtgctgtctggacactctggcagcagactgtatgaggccggcatgacactcggcggcaagat cctgttcttcctgttcctgctgctccctctgagccccttcagcctgatcttcaccgagatcagctgctgcaccctgagcagcgagg aaaacgagtacctgcctagacctgagtggcagctgcaggtccccttcagagagctgaagaacgtttccgtgctggaaggcctg agacagggcagacttggcggcccttgtagctgtcactgccccagacctagtcaggccagactgacacctgtggatgtggccg gacctttcctgtgtctgggagatcctggcctgtttccacctgtgaagtccagcatcacaggcggcaagtccacatgttctgcccct ggacctcagagcctgcctagcacacccttcagcacataccctcagtgggtcatcctgatcaccgaactcggcatggaatgcacc ctgggacaagtgggagccccatctcctagaagagaagaggatggctggcgcggaggccactctagattcaaagctgatgtgc ccgctcctcagggcccttgttggggaggacaacctggatctgccccatcttctgcccccacctgaacagtccctgctggattggaa gttcgagatgagctacaccgtcggcggacctccacctcatgttcatgccagacctcggcactggaaaaccgacagagatggcc acagctacaccagcaaagtgaactgcctcctgctgcaggatggcttccacggctgtgtgtctattactggcgccgctggcagac ggaacctgagcatctttctgtactgatgctgtgcaagctcgagttccacgcctgcaagatccagaacaagaactgccccgacttc aagaagttcgacggcccttgcggagaaagaggcggaggcagaacagctagagccctttgggctagaggcgacagcgttctg acaccagctctggaccctcagacacctgttagggcccctagcctgacaagagctgccgccgctgtgcactacaagctgatcca gcagccaatcagcctgttcagcatcaccgaccggctgcacaagacattcagccagctgccaagcgtgcacctgtgctccatca ccttccagtggggacaccctcctatcttttgctccaccaacgacatctgcgtgaccgccaacttctgtatcagcgtgaccttcctga agccttgctttctgctgcacgaggccagcgcctctcagtgccacttgtttctgcagccccaagtgggcacacctcctccacatac agcctctgctagagcacctagcggccctccacatcctcacgaatcttgtcctgccggaagaaggcctgccagagccgctcaaa catgtgccagacgacagcacggactgcctggatgtgaagaggctggaacagccagagtgcctagcctgcacctccatctgca tcaggctgctcttggagccggaagaggtagaggatggggcgaagcttgtgctcaggtgccaccttctagaggcgtgctgagat tcctggacctgaaagtgcgctacctgcacagccagtggcagcactatcacagatctggcgaagccgccggaacacccctttgg aggccaacaagaaacgtgcccttccgggaactgaagaaccagagaacagctcagggcgctcctggaatccaccatgctgctt ctccagtggccgccaacctgtgtgatcctgccagacatgcccagcacaccaggattccttgtggcgctggacaagtgcgcgct ggaagaggacctgaagcaggcggaggtgttctgcaacctcaaagacccgctcctgagaagcctggctgcccttgcagaaga ggacagcctagactgcacaccgtgaaaatgtggcgagccgtggccatgatggtgcccgatagacaggtccactacgactttgg actgggcgtgccaggcgatagcactcggagagccgtcagacggatgaacaccttttacgaagccgggatgaccctgggcga gaagttcagagtgggcaactgcaagcacctgaagatgacccggcctaacagcaagatggccctgaatagcgaggccctgtct -continued gtggtgtctgaatgtggcgcctctgcctgtgacgtgtccctgatcgctatggactccgcctttgtgcagggcaaagactggggcg tgaagaagttcatccggcgggacttctacgcctacaaggacttcctgtggtgcttccccttctctctggtgttcctgcaagagatcc agatctgctgtcatgtgtcctgcctgtgctgcatctgctgtagcaccagaatctgcctgggctgtctgctggaactgttcctgagca gagccctgagagcactgcacgtgctgtggaacggattccagctgcactgccagaccgagtacaaccagaaactgcaagtgaa ccagttcagcgagagcaagagcctgtaccaccgggaaaagcagctcattgccatggacagcgccatctgcgaagagagagg cgccgcaggatctctgatctcctgcgaaacaatgcccgccatcctgaagctgcagaagaattgcctcctaagcctgcgaaccg ctctgacacacaaccaggacttcagcatctacagactgtgttgcaagcggggctccctgtgccatgcaagccaagctagaagc cccgcctttcctaaacctgtgcgacctctgccagctccaatcaccagaattacccctcagctcggcggccagagcgattcatctc aacctctgctgaccaccggcagacctcaaggctggcaagaccaagctctgagacacacccagcaggctagccctgcctcttgt gccaccatcacaatccccatccactctgccgctctgggcgatcattctggcgatcctggaccagcctgggacacatgtcctcca ctgccactcacaacactgatccctagggctcctccaccttacggcgattctaccgctagaagctggcccagcagatgtggacca ctcggaggcaacacaaccctccagcaactgggagaagcctctcaggctcctagcggctctctgatccctctcagactgcctctc ctgtgggaagttcggggccagcctgattcttttgccgcactgcacagctccctgaacgagctgggagagatcgctagagagct gcaccagttcgccttcgacctgctgatcaagagccacttcgtgcaaggcaaggattggggcctcaaaaagtttatccgcagaga cttctggggcatggaactggccgccagcagaagattcagctgggatcatcatagcgcaggcggcccacctagagtgccatctg ttagaagcggagctgcccaggtgcagcctaaagatcctctgccactgagaacactggccggctgccttgctagaacagcccat cttagacctggcgccgagtctctgcctcagccacaactgcactgtaccctgtggttccagtccagcgagctgtctcctactggtg ccccttggccatctagacgccctacttggagaggcaccaccgtgtcaccaagaaccgccacaagcagcgccagaacctgttgt ggcacaaagtggccctccagccaagaagccgctctcggacttggaagcggactgctgaggttctcttgtggaaccgccgccat tcggaagatgcactttagcctgaaagaacaccctccaccaccttgtcctccagaggctttccaaagagctgctggcgaaggcgg acctggtagaggtggtgctagaagaggtgctagggtgctgcagagcccattctgtagagcaggcgcaggcgaatggctgggc catcagagtctgagacatgtcgtcggctacggccacctggatacaagcggaagcagctctagctccagctggcctaactcaaa aatggctctgaacagcctgaactccatcgacgacgcccagctgacaagaatcgcccctcctagatctcactgctgcttttgggaa gtgaacgccccaagccatcaccatcaccaccattagtaaaggcgcgcctagcggccgcgatctgctgtgccttctagttgccag ccatctgttgtttgcccctcccccgtgccttccttgaccctggaaggtgccactcccactgtcctttcctaataaaatgaggaaattg catcgcattgtctgagtaggtgtcattctattctggggggtggggtggggcaggacagcaagggggaggattgggaagacaat agcaggcatgctggggatgcggtgggctctatggccgggccgcgatcgcgcttaggcctgaccatctggtgctggcctgcac cagggccgagtttgggtctagcgatgaggataccgattgaggtgggtaaggtgggcgtggctagcagggtgggcgtgtataa attgggggtctaaggggtctctctgtttgtcttgcaacagccgccgccatgagcgacaccggcaacagctttgatggaagcatct ttagtccctatctgacagtgcgcatgcctcactgggccggagtgcgtcagaatgtgatgggttccaacgtggatggacgtcccgt tctgccttcaaattcgtctactatggcctacgcgaccgtgggaggaactccgctggacgccgcgacctccgccgccgcctccg ccgccgccgcgaccgcgcgcagcatggctacggacctttacagctctttggtggcgagcagcgcggcctctcgcgcgtctgc tcgggatgagaaactgactgctctgctgcttaaactggaagacttgacccgggagctgggtcaactgacccagcaggtttccag cttgcgtgagagcagccttgcctccccctaatggcccataatataaataaaagccagtctgtttggattaagcaagtgtatgttcttt atttaactctccgcgcgcggtaagcccgggaccagcggtctcggtcgtttagggtgcggtggatttttttccaacacgtggtacag gtggctctggatgtttagatacatgggcatgagtccatccctggggtggaggtagcaccactgcagagcttcgtgctcgggggt ggtgttgtatatgatccagtcgtagcaggagcgctgggcgtggtgctgaaaaatgtccttaagcaagaggcttatagctagggg gaggcccttggtgtaagtgtttacaaatctgcttagctgggagggggtgcatccgggggggatatgatgtgcatcttggactggattt ttaggttggctatgttcccgcccagatcccttctgggattcatgttgtgcaggaccaccagcacggtatatccagtgcacttggga aatttatcgtggagcttagacgggaatgcatggaagaacttggagacgcccttgtggcctcccagattttccatacattcgtccat gatgatggcaatgggcccgtgggaagctgcctgagcaaaaacgtttctggcatcgctcacatcgtagttatgttccagggtgag -continued gtcatcataggacatctttacgaatcgggggcgaagggtcccggactgggggatgatggtaccctcgggcccccggggcgtag ttcccctcacagatctgcatctcccaggctttcatttcagagggagggatcatatccacctgcggggcgatgaaaaagacagtttc tggcgcaggggagattaactgggatgagagcaggtttctgagcagctgtgactttccacagccggtgggcccatatatcacgc ctatcaccggctgcagctggtagttaagagagctgcagctgccgtcctcccggagcagggggccacctcgttgagcatatcc ctgacgtggatgttctccctgaccagttccgccagaaggcgctcgccgcccagcgaaagcagctcttgcaaggaagcaaaatt tttcagcggtttcaggccatcggccgtgggcatgtttttcagcgtctgggtcagcagctccagcctgtcccagagctcggtgatgt gctctacggcatctcgatccagcagatctcctcgtttcgcgggttggggcggctttcgctgtagggcaccagccgatgggcgtc cagcggggccagagtcatgtccttccatgggcgcagggtcctcgtcagggtggtctgggtcacggtgaaggggtgcgctccg ggttgggcactggccagggtgcgcttgaggctggttctgctggtgctgaatcgctgccgctcttcgccctgcgcgtcggccagg tagcatttgaccatggtctcgtagtcgagaccctcggcggcgtgccccttggcgcggagctttcccttggaggtggcgccgcac gaggggcactgcaggctcttcagggcgtagagcttgggagcgagaaacacggactctggggagtaggcgtccgcgccgca ggccgagcagaccgtctcgcattccaccagccaagtgagttccgggcggtcagggtcaaaaaccaggttgcccccatgcttttt gatgcgtttcttaccttggctctccatgaggcggtgtcccttctcggtgacgaagaggctgtccgtgtccccgtagaccgacttca ggggcctgtcttccagcggagtgcctctgtcctcctcgtagagaaactctgaccactctgagacgaaggcccgcgtccaggcc aggacgaaggaggccacgtgggaggggtagcggtcgttgtccactagcgggtccaccttctccagggtgtgcaggcacatgt ccccctcctccgcgtccagaaaagtgattggcttgtaggtgtaggacacgtgaccgggggttcccaacgggggggtataaaag gggtgggtgccctttcatcttcactctcttccgcatcgctgtctgcgagagccagctgctggggtaagtattccctctcgaaggc gggcatgacctcagcgctcaggttgtcagtttctaaaaatgaggaggatttgatgttcacctgtccggaggtgatacctttgaggg tacctgggtccatctggtcagaaaacactatttttttgttatcaagcttggtggcgaatgacccgtagagggcgttggagagcagc ttggcgatggagcgcagggtctggtttttgtcgcggtcggctcgctccttggccgcgatgttgagttgcacgtactcgcgggcca cgcacttccactcggggaacacggtggtgcgctcgtctgggatcaggcgcaccctccagccgcggttgtgcagggtgaccat gtcgacgctggtggcgacctcaccgcgcagacgctcgttggtccagcagaggcggccgcccttgcgcgagcagaagggggg gtagggggtccagctggtcctcgtttgggggggtccgcgtcgatggtaaagaccccggggagcaggcgcgggtcaaagtagt cgatcttgcaagcttgcatgtccagagcccgctgccattcgcgggcggcgagcgcgcgctcgtaggggttgaggggcgggc cccagggcatggggtgggtgagcgcggaggcgtacatgccgcagatgtcatacacgtacaggggttccctgaggataccga ggtaggtggggtagcagcgcccccccgcggatgctggcgcgcacgtagtcatagagctcgtgggagggggccagcatgttgg gcccgaggttggtgcgctgggggcgctcggcgcggaagacgatctgcctgaagatggcgtgggagttggaggagatggtg ggccgctggaagacgttgaagcttgcttcttgcaagcccacggagtccctgacgaaggaggcgtaggactcgcgcagcttgtg caccagctcggcggtgacctggacgtcgagcgcacagtagtcgagggtctcgcggatgatgtcatacctatcctccccccttcttt ttccacagctcgcggttgaggacgaactcttcgcggtctttccagtactcttggaggggaaacccgtccgtgtccgaacggtaag agcctagcatgtagaactggttgacggcctggtaggggcagcagcccttctccacgggcagcgcgtaggcctgcgccgcctt gcggagggaggtgtgggtgagggcgaaagtgtccctgaccatgactttgaggtattgatgtctgaagtctgtgtcatcgcagcc gccctgttcccacagggtgtagtccgtgcgctttttggagcgcgggttgggcagggagaaggtgaggtcattgaagaggatctt ccccgctcgaggcatgaagtttctggtgatgcgaaagggccctgggaccgaggagcggttgttgatgacctgggcggccagg acgatctcgtcaaagccgtttatgttgtgtcccacgatgtagagctccaggaagcggggctggcccttgatggaggggagctttt taagttcctcgtaggtaagctcctcgggcgattccaggccgtgctcctccagggcccagtcttgcaagtgagggttggccgcca ggaaggatcgccagaggtcgcgggccatgagggtctgcaggcggtcgcggaaggttctgaactgccgccccacggccatttt ttcgggggtgatgcagtagaaggtgagggggtctttctcccaggggtcccatctgagctctcgggcgaggtcgcgcgcggca gcgaccagagcctcgtcgccccccagtttcatgaccagcatgaagggcacgagttgcttgccaaaggctcccatccaagtgta ggtttctacatcgtaggtgacaaagaggcgctccgtgcgaggatgagagccgattgggaagaactggatctcccgccaccagt -continued tggaggattggctgttgatgtggtgaaagtagaagtcccgtctgcgggccgagcactcgtgctggcttttgtaaaagcgaccgc
agtactggcagcgctgcacgggttgtatatcttgcacgaggtgaacctggcgacctctgacgaggaagcgcagcgggaatcta
agtcccccgcctggggtcccgtgtggctggtggtcttttactttggttgtctggccgccagcatctgtctcctggagggcgatggt
ggaacagaccaccacgccgcgagagccgcaggtccagatctcggcgctcggcgggcggagtttgatgacgacatcgcgca
cattggagctgtccatggtctccagctcccgcggcggcaggtcagccgggagttccctggaggttcacctcgcagagacgggt
caaggcgcggacagtgttgagatggtatctgatttcaaggggcatgttggaggcggagtcgatggcttgcaggaggccgcag
ccccgggggggccacgatggttccccgcggggcgcgaggggaggcggaagctgggggtgtgttcagaagcggtgacgcgg
gcgggcccccggaggtagggggggttccggccccacaggcatgggcggcaggggcacgtcttcgccgcgcgcgggcag
gggctggtgctggctccgaagagcgcttgcgtgcgcgacgacgcgacggttggtgttcctgtatctggcgcctctgagtgaag
accacgggtcccgtgaccttgaacctgaaagagagttcgacagaatcaatctcggcatcgttgacagcggcctggcgcaggat
ctcctgcacgtcgcccgagttgtcctggtaggcgatttctgccatgaactgctcgatctcttcctcctggagatctcctcgtccggc
gcgctccacggtggccgccaggtcgttggagatgcgacccatgagctgcgagaaggcgttgagtccgccctcgttccagacc
cggctgtagaccacgcccccctcggcgtcgcgggcgcgcatgaccacctgggccaggttgagctccacgtgtcgcgtgaag
acggcgtagttgcgcaggcgctggaaaaggtagttcagggtggtggcggtgtgctcggcgacgaagaagtacatgacccag
cgccgcaacgtggattcattgatgtcccccaaggcctccaggcgctccatggcctcgtagaagtccacggcgaagttgaaaaa
ctgggagttgcgagcggacacggtcaactcctcctccagaagaacggatgagctcggcgacagtgtcgcgcacctcgcgctc
gaaggccacggggggcgcttcttcctcttccacctcttcttccatgattgcttcttcttcttcctcagccgggacgggagggggcg
gcggcgggggagggggcgcggcggcggcggcggcgcaccgggaggcggtcgatgaagcgctcgatcatctccccccgca
tgcggcgcatggtctcggtgacggcgcggccgttctcccgggggcgcagctcgaagacgccgcctctcatttcgccgcggg
gcgggcggccgtgaggtagcgagacggcgctgactatgcatcttaacaattgctgtgtaggtacgccgccaagggacctgatt
gagtccagatccaccggatccgaaaacctttggaggaaagcgtctatccagtcgcagtcgcaaggtaggctgagcaccgtgg
cgggcgggggcgggtcgggagagttcctggcggagatgctgctgatgatgtaattaaagtaggcggtcttgagaaggcggat
ggtggacaggagcaccatgtctttgggtccggcctgttggatgcggaggcggtcggccatgccccaggcctcgttctgacacc
ggcgcaggtctttgtagtaatcttgcatgagtctttccaccggcacttcttctccttcctcttcttcatctcgccggtggtttctcgcgc
cgcccatgcgcgtgaccccaaagcccctgagcggctgcagcagggccaggtcggcgaccacgcgctcggccaagatggc
ctgctgtacctgagtgagggtcctctcgaagtcatccatgtccacgaagcggtggtaggcacccgtgttgatggtgtaggtgca
gttggccatgacggaccagttgacggtctggtgtcccggctgcgagagctccgtgtaccgcaggcgcgagaaggcgcggga
atcgaacacgtagtcgttgcaagtccgcaccagatactggtagcccaccaggaagtgcggcggaggttggcgatagagggg
ccagcgctgggtggcgggggcgccgggcgccaggtcttccagcatgaggcggtggtatccgtagatgtacctggacatcca
ggtgatgcctgcggcggtggtggtggcgcgcgcgtagtcgcggacccggttccagatgtttcgcaggggcgagaagtgttcc
atggtcggcacgctctggccggtgaggcgcgcgcagtcgttgacgctctatacacacacaaaaacgaaagcgtttacagggct
ttcgttctgtagcctggaggaaagtaaatgggttgggttgcggtgtgccccggttcgagaccaagctgagctcagccggctgaa
gccgcagctaacgtggtattggcagtcccgtctcgacccaggccctgtatcctccaggatacggtcgagagcccttttgctttctt
ggccaagcgcccgtggcgcgatctgggatagatggtcgcgatgagaggacaaaagcggctcgcttccgtagtctggagaaa
caatcgccagggttgcgttgcggcgtaccccggttcgagcccctatggcggcttggatcggccggaaccgcggctaacgtgg
gctgtggcagccccgtcctcaggaccccgccagccgacttctccagttacgggagcgagccccttttgtttttttatttttagatgc
atcccgtgctgcggcagatgcgcccctcgccccggcccgatcagcagcagcaacagcaggcatgcagaccccccctctcctct
ccccgccccggtcaccacggccgcggcggccgtgtccggtgcgggggggcgcgctggagtcagatgagccaccgcggcgg
cgacctaggcagtatctggacttggaagagggcgagggactggcgcggctgggggcgagctctccagagcgcccacccgcg
ggtgcagttgaaaagggacgcgcgtgaggcgtacctgccgcggcaaaacctgtttcgcgaccgcgggggcgaggagcccg
aggagatgcgggactgcaggttccaagcggggcgcgagctgcgccgcggcttggacagacagcgcctgctgcgcgagga -continued ggactttgagcccgacacgcagacgggcatcagccccgcgcgcgcgcacgtggccgcggccgacctggtgaccgcctacg agcagacggtgaaccaggagcgcaacttccaaaaaagcttcaacaaccacgtgcgcacgctggtggcgcgcgaggaggtg accctgggtctcatgcatctgtgggacctggtggaggcgatcgtgcagaaccccagcagcaagcccctgaccgcgcagctgtt cctggtggtgcagcacagcagggacaacgaggccttcagggaggcgctgctgaacatcaccgagccggaggggcgctggc tcctggacctgataaacatcctgcagagcatagtggtgcaggagcgcagcctgagcctggccgagaaggtggcggccattaa ctattctatgctgagcctgggcaagttctacgctcgcaagatctacaagacccccctacgtgcccatagacaaggaggtgaagat agacagcttctacatgcgcatggcgctgaaggtgctaaccctgagcgacgacctgggagtgtaccgcaacgagcgcatccac aaggccgtgagcgccagccggcggcgcgagctgagcgaccgcgaactgatgcacagtctgcagcgcgcgctgaccggcg cgggcgagggcgacagggaggtcgagtcctactttgacatgggggccgacctgcactggcagccgagccgccgcgccctg gaagcggcgggggcgtacggcggcccccctggcggccgatgacgaggaagaggaggactatgagctagaggagggcgag tacctggaggactgacctggctggtggtgttttggtatagatgcaagatccgaacgtggcggacccggcggtccgggcggcg ctgcagagccagccgtccggcattaactcctctgacgactgggccgcggccatgggtcgcatcatggccctgaccgcgcgca accccgaggccttcaggcagcagcctcaggctaaccggctggcggccatcttggaagcggtagtgcccgcgcgctccaacc ccacccacgagaaggtgctggccatagtcaacgcgctggcggagagcagggccatccgggcagacgaggccggactggt gtacgatgcgctgctgcagcgggtggcgcggtacaacagcggcaacgtgcagaccaacctggaccgcctggtgacggacgt gcgcgaggccgtggcgcagcgcgagcgcttgcatcaggacggcaacctgggctcgctggtggcgctaaacgccttccttag cacccagccggccaacgtaccgcgggggcaggaggactacaccaacttcttgagcgcgctgcggctgatggtgaccgaggt ccctcagagcgaggtgtaccagtcggggcccgactacttcttccagaccagcagacagggcttgcaaaccgtgaacctgagc caggctttcaagaacctgcgggggctgtggggagtgaaggcgcccaccggcgaccgggctacggtgtccagcctgctaacc cccaactcgcgcctgctgctgctgctgatcgcgccctt cacggacagcgggagcgtctcgcgggagacctatctgggccacct gctgacgctgtaccgcgaggccatcgggcaggcgcaggtggacgagcacaccttccaggagatcaccagcgtgagccacg cgctggggcaggaggacacgggcagcctgcaggcgaccctgaactacctgctgaccaacaggcggcagaagattcccacg ctgcacagcctgacccaggaggaggagcgcatcttgcgctacgtgcagcagagcgtgagcctgaacctgatgcgcgacggc gtgacgcccagcgtggcgctggacatgaccgcgcgcaacatggaaccgggcatgtacgcttcccagcggccgttcatcaacc gcctgatggactacttgcatcgggcggcggccgtgaaccccgagtacttcaccaatgccattctgaatccccactggatgcccc ctccgggtttctacaacggggacttcgaggtgcctgaggtcaacgatgggttcctctgggatgacatggatgacagtgtgttctc ccccaacccgctgcgcgccgcgtctctgcgattgaaggagggctctgacagggaaggaccaaggagtctggcctcctccctg gctctgggggcggtgggcgccacgggcgcggcggcgcggggcagcagccccttccccagcctggcggactctctgaatag cgggcgggtgagcaggccccgcttgctaggcgaggaggagtatctgaacaactccctgctgcagcccgtgagggacaaaaa cgctcagcggcagcagtttcccaacaatgggatagagagcctggtggacaagatgtccagatggaagacgtatgcgcaggag tacaaggagtgggaggaccgccagccgcggcccctgccgcccccctagacagcgctggcagcggcgcgcgtccaaccgcc gctggaggcaggggcccgaggacgatgatgactctgcagatgacagcagcgtgttggacctgggcgggagcgggaacccc ttttcgcacctgcgcccacgcctgggcaagatgttttaaaagagaaaaataaaaactcaccaaggccatggcgacgagcgttgg tttttttgttcccttccttagtatgcggcgcgcggcgatgttcgaggaggggcctcccccctcttacgagagcgcgatgggaatttct cctgcggcgcccctgcagcctccctacgtgcctcctcggtacctgcaacctacagggggggagaaatagcatctgttactctgag ctgcagcccctgtacgataccaccagactgtacctggtggacaacaagtccgcggacgtggcctccctgaactaccagaacga ccacagcgatttttttgaccacggtgatccaaaacaacgacttcaccccaaccgaggccagtacccagaccataaacctggaca acaggtcgaactggggcggcgacctgaagactatcctgcacaccaatatgcccaacgtgaacgagttcatgttcaccaactcttt taaggcgcgggtgatggtggcgcgcgagcagggggaggcgaagtacgagtgggtggacttcacgctgcccgagggcaact actcagagaccatgactctcgacctgatgaacaatgcgatcgtggaacactatctgaaagtgggcaggcagaacggggtgaa -continued ggagagcgatatcggggtcaagtttgacaccagaaacttccgtctgggctgggaccctgtgaccgggctggtcatgccgggg gtctacaccaacgaggcctttcatcccgatatagtgctcctgcccggctgtggggtggacttcacccagagccggctgagcaac ctgctgggcgttcgcaagcggcaacctttccaggagggtttcaagatcacctatgaggatctggaggggggcaacattcccgc gctccttgatctggacgcctacgaggagagcttgaaacccgaggagagcgctggcgacagcggcgagagtggcgaggagc aagccggcggcggcggcagcgcgtcggtagaaaacgaaagtactcccgcagtggcggcggacgctgcggaggtcgagcc ggaggccatgcagcaggacgcagaggagggcgcgcaggaggacatgaacaatggggagatcaggggcgacactttcgcc acccggggcgaagaaaaagaggcagaggcggcggcggcgacggcggaagccgaaaccgaggcagaggcagagcccg agaccgaagttatggaagacatgaatgatggagaacgtaggggtgacacgtttgccacccggggcgaagagaaggcggcg gaggcagaagccgcggctgaggaggcggctgcggctgcggccaaggctgaggctgcggctgaggctaaggtcgaagccg atgttgcggttgaggctcaggctgaggaggaggcggcggctgaagcagttaaggaaaaggcccaggcagagcaggaagag aaaaaacctgtcattcaacctctaaaagaagatagcaaaaagcgcagttacaacgtcattgagggcagcacctttacccaatacc gcagctggtacctggcttacaactacggcgacccggtcaaggggggtgcgctcgtggaccctgctctgcacgccggacgtcac ctgcggctccgagcagatgtactggtcgctgccaaacatgatgcaagacccggtgaccttccgttccacgcggcaggttagca actttccggtggtgggcgccgaactgctgccagtacactccaagagtttttacaacgagcaggccgtctactcccagctgatccg ccaggccacctctctgacccacgtgttcaatcgctttcccgagaaccagattttggcgcgcccgccggcccccaccatcaccac cgtcagtgaaaacgttcctgccctcacagatcacgggacgctaccgctgcgcaacagcatctcaggagtccagcgagtgacc attactgacgccagacgccggacctgcccctacgtttacaaggccttgggcatagtctcgccgcgcgtcctctccagtcgcactt tttaaaacacatccacccacacgctccaaaatcatgtccgtactcatctcgcccagcaacaacaccggctgggggctgcgcgca cccagcaagatgtttggaggggcaaggaagcgctccgaccagcaccccgtgcgcgtgcgcggccactaccgcgcgccctg gggtgcgcacaagcgcgggcgcacagggcgcaccactgtggatgatgtcattgactccgtagtggagcaggcgcgccacta cacacccggcgcgccgaccgcctccgccgtgtccaccgtggaccaggcgatcgaaagcgtggtacagggggcgcggcact atgccaaccttaaaagtcgccgccgccgcgtggcgcgccgccgccatcgccggagaccccgggctactgccgccgcgcgccttaa ccaaggctctgctcaagcgcgccaggcgaactggccaccgggccgccatgagggccgcacggcgggctgccgctgccgc gagcgccgtggccccgcgggcacgaaggcgcgcggccgctgccgccgccgccgccatttccagcttggcctcgacgcgg cgcggtaacatatactgggtgcgcgactcggtgagcggcacacgtgtgcccgtgcgctttcgcccccccacggaattagcacaa gacaacatacacactgagtctcctgctgttgtgtatcccagcggcgaccgtcagcagcggcgacatgtccaagcgcaaaattaa agaagagatgctccaggtcatcgcgccggagatctatgggcccccgaagaaggaggaggaggattacaagccccgcaagct aaagcgggtcaaaaagaaaaagaaagatgatgacgttgacgaggcggtggagtttgtccgccgcatggcgcccaggcgccc tgtgcagtggaagggtcggcgcgtgcagcgagtcctgcgccccggcaccgcggtggtctttacgcccggcgagcgttccac gcgcactttcaagcgggtgtacgatgaggtgtacggcgacgaggatctgttggagcaggccaaccatcgatttggggagtttg catatgggaaacggcctcgcgagagtctaaaagaggacctgctggcgctaccgctggacgagggcaatcccaccccgagtct gaagccggtgaccctgcaacaggtgctgcctttgagcgcgcccagcgagcagaagcgagggttaaagcgcgagggcggg gacctggcacccaccgtgcagttgatggtgcccaagcggcagaagctggaggacgtgctggagaaaatgaaagtagagccc gggatccagcccgagatcaaggtccgccctatcaagcaggtggcgcccggcgtgggagtccagaccgtggacgttaggatt cccacggaggagatggaaacccaaaccgccactccctcttcggcagcaagcgccaccaccggcgccgcttcggtagaggtg cagacggacccctggctacccgccgccactatcgccgtcgccgccgccccccgttcgcgcggacgcaagagaaattatcca gcggccagcgcgcttatgccccagtatgcgctgcatccatccatcgcgcccacccccggctaccgcgggtactcgtaccgcc cgcgcagatcagccggcactcgcggccgccgccgccgtgcgaccacaaccagccgccgccgtcgccgccgccgccagcc agtgctgacccccgtgtctgtaaggaaggtggctcgctcggggagcacgctggtggtgcccagagcgcgctaccaccccag catcgtttaaagccggtctctgtatggttcttgcagatatggccctcacttgtcgccttcgcttcccggtgccgggataccgaggaa gaactcaccgccgcaggggcatggcgggcagcggtctccgcggcggccgtcgccatcgccggcgcgcaaagagcaggc -continued gcatgcgcggcggtgtgttgcccctgctggtcccgctactcgccgcggcgatcggcgccgtgcccgggatcgcctccgtggc cctgcaggcgtcccagaaacattgactcttgcaaccttgcaagcttgcattttggaggaaaaaataaaaaagtctagactctcac gctcgcttggtcctgtgactattttgtagaaaaaagatggaagacatcaactttgcgtcgctggccccgcgtcacggctcgcgcc cgttcatgggagactggacagatatcggcaccagcaatatgagcggtggcgccttcagctggggcagtctgtggagcggcctt aaaaattttggttccaccattaagaactatggcaacaaagcgtggaacagcagcacgggtcagatgctgagagacaagttgaaa gagcagaacttccaggagaaggtggcgcagggcctggcctctggcatcagcggggtggtggacatagctaaccaggccgtg cagaaaaagataaacagtcatctggaccccgccctcaggtggaggaaacgcctccagccatggagacggtgtctcccgag ggcaaaggcgaaaagcgcccgcggcccgacagggaagagaccctggtgtcacacaccgaggagccgccctcttacgagg aggcagtcaaggccggcctgcccaccactcgccccatagctcccatggccaccggtgtggtgggtcacaggcaacacaccc ccgcaacactagatctgcccccgccgtccgagccgactcgccagccaaaggcggtgacggtgtccgctccctccacttccgc cgccaacagagtgcctctgcgccgcgctgcgagcggcccccgggcctcgcgagtcagcggcaactggcagagcacactga acagcatcgtgggcctgggagtgaggagtgtgaagcgccgccgttgctactgaatgagcaagctagctaacgtgttgtatgtgt gtatgcgtcctatgtcgccgccagaggagctgttgagccgccggcgccgtctgcactccagcgaatttcaagatggcgacccc atcgatgatgcctcagtggtcgtacatgcacatctcgggccaggacgcttcggagtacctgagccccgggctggtgcagttcgc ccgcgccacagacacctacttcaacatgagtaacaagttcaggaaccccactgtggcgcccacccacgatgtgaccacggac cggtcgcagcgcctgacgctgcggttcatccccgtggatcgggaggacaccgcttactcttacaaggcgcggttcacgctggc cgtgggcgacaaccgcgtgctggacatggcctccacttactttgacatccgggggtgctggacaggggccccacttttaagc cctactcgggcactgcctacaacccccctggcccccaagggcgcccccaattcttgtgagtgggaacaagaggaaaatcaggt ggtcgctgcagatgatgaacttgaagatgaagaagcgcaagcacaagaggaagcccctgtgaaaaaaattcatgtatatgctc aggcgcctctttctggcgaaaagatttccaaggatggtatccaaataggtactgaagtcgtaggagatacatctaaggacactttt gcagataaaacattccaacccgaacctcagataggcgagtctcagtggaacgaggctgatgccacagcagcaggaggtaga gttttgaaaaagactacccctatgagaccttgctatggatcctatgccaggcctaccaatgccaacgggggtcaaggaattatgg ttgccaatgaacaaggagtgttggagtctaaagtagaaatgcaatttttctctaacaccacaacccttaatgcgcgggatggaacc ggcaatcccgaaccaaaggtggtgttgtacagcgaagatgtccacttggaatctcccgatactcatctgtcttacaagcccaaaa aggatgatgttaatgccaaaatcatgttgggtcagcaagccatgcccaacagacccaacctcattggatttagagataatttcattg ggcttatgttttacaacagcaccggtaacatgggagtgctggcgggtcaggcctctcagttgaatgctgtggtggacttgcagga tagaaacacagaactgtcatatcagcttctgcttgattcaattggggatagaaccagatacttctccatgtggaaccaggcagtgg atagctatgatccagatgtcagaattattgaaaaccatgggactgaggatgaactgcccaactactgcttccctttgggcggcata ggagttactgatacttatcaagggataaaaaataccaatggcaatggtcagtggaccaaagatgatcagttcgcggaccgcaac gaaataggggtgggaaacaacttcgccatggagatcaacatccaggccaacctttggagaaacttcctctatgcaaacgtggg gctctacctgccagacaagctcaagtacaaccccaccaacgtggacatctctgacaaccccaacacctatgactacatgaacaa gcgggtggtggcccctggcctggtggactgctttgtcaatgtgggagccaggtggtccctggactacatggacaacgtcaacc ccttcaaccaccaccgcaatgcgggtctgcgctaccgctccatgatcctgggcaacgggcgctatgtgccctttcacatccagg taccccagaagttctttgccatcaagaacctcctgctcctgcccggctcctacacctacgagtggaacttcaggaaggatgtgaa catggtcctacagagctctctgggcaatgaccttagggtggatggggccagcatcaagtttgacagcatcaccctctatgctaca tttttccccatggcccacaacaccgcctccacgcttgaggccatgctgagaaacgacaccaacgaccagtcctttaatgactacc tctctggggccaacatgctctacccaatcccagccaaggccaccaacgtgcccatctccatcccctctcgcaactgggccgcct ttagaggctgggcctttacccgccttaagaccaaggagacccccctccctgggctcgggttttgatccctactttgtttactcgggat ccatcccctacctggatggcaccttctacctcaaccacactttcaagaagatatccatcatgtatgactcctccgtcagctggccg ggcaacgaccgcttgctcacccccaatgagttcgaggtcaagcgcgccgtggacggcgagggctacaacgtggcccagtgc -continued aacatgaccaaggactggttcctggtgcagatgctggccaactacaacataggctaccagggcttttacatcccagagagctac aaggacaggatgtactccttcttcagaaatttccaacccatgagccgacaggtggtggacgagaccaattacaaggactatcaa gccattggcatcacccaccagcacaacaactcgggtttcgtgggctacctggcgcccaccatgcgcgagggtcaggcctacc ccgccaacttcccctaccccttgataggcaagaccgcggtcgacagcgtcacccagaaaaagttcctctgcgaccgcaccctc tggcgcatccccttctctagcaacttcatgtccatgggtgcgctcacggacctgggccaaaacctgctttatgccaactctgccca tgcgctggacatgacttttgaggtggaccccatggacgagcccacccttctctatattgtgtttgaagtgttcgacgtggtcagagt gcaccagccgcaccgcggtgtcatcgagaccgtgtacctgcgtacgcccttctcagccggcaacgccaccacctaaggagac agcgccgccgccgcctgcatgacgggttccaccgagcaagagctcagggccattgccagagacctgggatgcggaccctat tttttgggcacctatgacaaacgcttcccgggctttatctcccgagacaagctcgcctgcgccattgtcaacacggccgcgcgcg agaccgggggcgtgcactggctggcctttggctgggacccgcgctccaaaacttgctacctctttgaccccttggcttctccga tcagcgcctcaggcagatttatgagtttgagtacgaggggctgctgcgccgcagcgcgctcgcctcctcgcccgaccgctgca tcacccttgagaagtccaccgaaaccgtgcaggggccccactcggccgcctgcggtctcttctgttgcatgtttttgcacgccttt gtgcactggcctcagagtcccatggattgcaaccccaccatgaacttgctaaagggagtgcccaacgccatgctccagagccc ccaggtccagcccaccctgcgccgcaaccaggaacagctttaccgcttcctggagcgccactcccccctacttccgcagccaca gcgcgcgcatccgggggggccacctctttttgccacttgcaagaaaacatgcaagacggaaaatgatgtacagcatgcttttaata aatgtaaagactgtgcactttaattatacacgggctctttctggttatttattcaacaccgccgtcgccatttagaaatcgaaagggtt ctgccgtgcgtcgccgtgcgccacgggcagagacacgttgcgatactggaagcggctcgcccacttgaactcgggcaccac catgcggggcagtggttcctcggggaagttctcgctccacagggtgcgggtcagctgcagcgcgctcaggaggtcgggagc cgagatcttgaagtcgcagttggggccggaaccctgcgcgcgcgagttgcggtacacggggttgcagcactggaacaccag cagggccggattattcacgctggccagcaggctctcgtcgctgatcatgtcgctgtccagatcctccgcgttgctcagggcgaat ggggtcatcttgcagacctgcctgcccaggaaaggcgggagcccaggcttgccgttgcagtcgcagcgcaggggcattagc aggtgcccacggcccgactgcgcctgcgggtacaacgcgcgcatgaaggcttcgatctgcctaaaagccacctgggtcttgg ctccctccgaaaagaacatcccacaggacttgctggagaactggttcgcgggacagctggcatcgtgcaggcagcagcgcgc gtcagtgttggcaatctgcaccacgttgcgaccccaccggtttttcactatcttggccttggaagcctgctcctttagcgcgcgctg gccgttctcgctggtcacatccatctctatcacctgttccttgttgatcatgtttgtcccgtgcagacactttaggtcgccctccgtctg ggtgcagcggtgctcccacagcgcgcaaccggtgggctcccaattcttgtgggtcacccccgcgtaggcctgcaggtaggcc tgcaggaagcgccccatcatggtcataaaggtcttctggctcgtaaaggtcagctgcaggccgcgatgctcttcgttcagccag gtcttgcagatggcggccagcgcctcggtctgctcgggcagcatcttaaaatttgtcttcaggtcgttatccacgtggtacttgtcc atcatggcacgcgccgcctccatgcccttctcccaggcggacaccatgggcaggcttagggggtttatcacttccagcggcga ggacaccgtactttcgatacttcttcctcccccctcttcccggcgcgcgcccccgctgttgcgcgctcttaccgcctgcaccaagg ggtcgtcttcaggcaagcgccgcaccgagcgcttgccgcccttgacctgcttgatcagtaccggcgggttgctgaagcccacc atggtcagcgccgcctgctcttcttcgtcttcgctgtctaccactatttctggggaggggcttctccgctctgcggcaaaggcggc ggatcgcttcttttttttcttgggagccgccgcgatggagtccgccacggcgaccgaggtcgagggcgtggggctgggggtgc gcggtaccagggcctcgtcgccctcggactcttcctctgactccaggcggcggcggagtcgcttctttgggggcgcgcgcgtc agcggcggcggagacggggacggggacggggacgggacgccctccacagggggtggtcttcgcgcagacccgcggcc gcgctcgggggtcttctcgcgctggtcttggtcccgactggccattgtatcctcctcctcctaggcagagagacataaggagtct atcatgcaagtcgagaaggaggagagcttaaccacccccctcagagaccgccgatgcgcccgccgtcgccgtcgccccccgct accgccgacgcgcccgccacaccgagcgacacccccacggacccccccgccgacgcacccctgttcgaggaagcggccg tggagcaggacccgggctttgtctcggcagaggaggatttgcaagaggaggagaataaggaggagaagccctcagtgccaa aagatcataaagagcaagacgagcacgacgcagacgcacaccagggtgaagtcgggcggggggacggagggcatggcg gcgccgactacctagacgaaggaaacgacgtgctcttgaagcacctgcatcgtcagtgcgccatcgtctgcgacgctctgcag -continued gagcgcagcgaggtgcccctcagcgtggcggaggtcagccgcgcctacgagctcagcctcttttcccccgggtgcccccc
cgccgccgcgaaaacggcacatgcgagcccaacccgcgcctcaacttctaccccgcctttgtggtgcccgaggtcctggcca
cctatcacatcttctttcaaaattgcaagatccccatctcgtgccgcgccaaccgtagccgcgccgataagatgctggccctgcg
ccagggcgaccacatacctgatatcgccgctttggaagatgtgccaaagatcttcgagggtctggggcgcaacgagaagcgg
gcagcaaactctctgcaacaggaaaacagcgaaaatgagagtcacactggagcgctggtggagctggagggcgacaacgc
ccgcctggcggtgctcaagcgcagcatcgaggtcacccactttgcctaccccgcgctcaacctgccccccaaagtcatgaacg
cggtcatggacgggctgatcatgcgccgcggccggcccctcgctccagatgcaaacttgcatgaggagaccgaggacggtc
agcccgtggtcagcgacgagcagctgacgcgctggctggagagcgcggaccccgccgaactggaggagcggcgcaagat
gatgatggccgcggtgctggtcaccgtagagctggagtgtctgcagcgcttcttcggtgaccccgagatgcagagaaaggtcg
aggagaccctacactacaccttccgccagggctacgtgcgccaggcttgcaagatctccaacgtggagctcagcaacctggtg
tcctacctgggcatcttgcatgaaaaccgccttgggcagagcgtgctacactccaccctgcgcggggaggcgcgccgcgact
acgtgcgcgactgcgtttacctcttcctctgctacacctggcagacggccatgggggtctggcagcagtgcctggaggagcgc
aacctcaaggagctggagaagcttctgcagcgcgcgctcaaagacctctggacgggcttcaacgagcgctcggtggccgcc
gcgctagccgacctcatcttccccgagcgcctgctcaaaaccctccagcaggggctgcccgacttcaccagccaaagcatgtt
gcaaaattttaggaactttatcctggagcgttctggcatcctacccgccacctgctgcgccctgcccagcgactttgtcccccctcgt
gtaccgcgagtgcccccccgccgctgtggggccactgctacctgttccaactggccaactacctgtcctaccacgcggacctcat
ggaggactccagcggcgaggggctcatggagtgccactgccgctgcaacctctgcacgccccaccgctccctggtctgcaac
acccaactgctcagcgagagtcagattatcggtaccttcgagctacagggtccgtcctcctcagacgagaagtccgcggctcc
ggggctaaaactcactccggggctgtggacttccgcctacctgcgcaaatttgtacctgaagactaccacgcccacgaaatcag
gttttacgaggaccaatcccgcccgcccaaggcggagctgaccgcctgcgtcatcacccagggcgagatcctaggccaattg
caagccatccaaaaagcccgccaagagtttttgctgaagaggggtcggggggtgtatctggaccccccagtcgggtgaggagc
tcaacccggttcccccgctgccaccgccgcgggaccttgcttcccaggataagcatcgccatggctcccagaaagaagcagc
agcggccgccgctgccgccgccccacatgctggaggaagaggaggaatactgggacagtcaggcagaggaggtttcggac
gaggaggagccggagacggagatggaagagtgggaggaggacagcttagacgaggaggcttccgaagccgaagaggca
ggcgcaacaccgtcaccctcggccgcagcccccctcgcaggcgcccccgaagtccgctcccagcatcagcagcaacagcag
cgctataacctccgctcctccaccgccgcgacccacggccgaccgcagacccaaccgtagatgggacaccaccggaaccg
gggccggtaagtcctccgggagaggcaagcaagcgcagcgccaaggctaccgctcgtggcgcgctcacaagaacgccata
gtcgcttgcttgcaagactgcgggggggaacatctccttcgcccgccgcttcctgctcttccaccacggtgtggccttcccccgta
acgtcctgcattactaccgtcatctctacagcccctactgcggcggcagtgagccagaggcggccagcggcggcggcgccc
gtttcggtgcctaggaagacccagggcaagacttcagccaagaaactcgcggcgaccgcggcgaacgcggtcgcgggggc
cctgcgcctgacggtgaacgaacccctgtcgacccgcgaactgaggaaccgaatcttccccactctctatgccatcttccagca
gagcagagggcaggatcaggaactgaaagtaaaaaacaggtctctgcgctccctcacccgcagctgtctgtatcacaagagc
gaagaccagcttcggcgcacgctggaggacgctgaggcactcttcagcaaatactgcgcgctcactcttaaggactagctccg
cgcccttctcgaatttaggcgggaacgcctacgtcatcgcagcgccgccgtcatgagcaaggacattcccacgccatacatgtg
gagctatcagccgcagatgggactcgcggcgggcgcctcccaagactactccacccgcatgaactggctcagtgccggccc
acacatgatctcacaggttaatgacatccgcacccatcgaaaccaaatattggtgaagcaggcggcaattaccaccacgcccc
gcaataatcccaaccccagggagtggcccgcgtccctggtgtatcaggaaattcccggccccaccaccgtactacttccgcgt
gattcccaggccgaagtccaaatgactaactcaggggcacagctcgcgggcggctgtcgtcacagggtgcggcctcctcgcc
agggtataactcacctggagatccgaggcagaggtattcagctcaacgacgagtcggtgagctcctcgctcggtctcagacct
gacgggaccttccagatagccggagccggccgatcttccttcacgccccgccaggcgtacctgactctgcagagctcgtcctc -continued ggcgccgcgctcgggcggcatcgggactctccagttcgtgcaggagtttgtgccctcggtctacttcaacccccttctcgggctct cccggtcgctacccggaccagtttatcccgaactttgacgccgcgagggactcggtggacggctacgactgaatgtcgggtgg acccggtgcagagcaacttcgcctgaagcaccttgaccactgccgccgccctcagtgctttgcccgctgtcagaccggtgagtt ccagtacttttccctgcccgactcgcacccggacggcccggcgcacggggtgcgctttttcatcccgagtcaggtccgctctac cctaatcagggagttcaccgcccgtcccctactggcggagttggaaaaggggccttctatcctaaccattgcctgcatttgctcta accctggattacaccaagatctttgctgtcatttgtgtgctgagtataataaaggctgagatcagaatctactcggaccttatcccttt caattgatcataactgtaatcaataaaaaatcacttacttgaaatctgatagcaagactctgtccaatttttttcagcaacacttccttcc cctcctcccaactctggtactctaggcgcctcctagctgcaaacttcctccacagtctgaagggaatgtcagattcctcctcctgtc cctccgcacccacgatcttcatgttgttacagatgaaacgcgcgagatcgtctgacgagaccttcaaccccgtgtacccctacga taccgagatcgctccgacttctgtccctttccttacccctccctttgtatcatccgcaggaatgcaagaaaatccagctggggtgct gtccctgcacctgtcagagccccttaccacccacaatggggccctgactctaaaaatggggggcggcctgaccctggacaag gaagggaatctcacttcccaaaacatcaccagtgtcgatccccctctcaaaaaaagcaagaacaacatcagccttcagaccgcc gcacccctcgccgtcagctccggggccctaacccttttgccactccccccctagcggtcagtggcgacaaccttactgtgcagt ctcaggcccctcttactttggaagactcaaaactaactctggccaccaaaggacccctaactgtgtccgaaggcaaacttgtcct agaaacagagcctcccctgcatgcaagtgacagcagtagcctgggccttagcgtcacggccccacttagcattaacaatgaca gcctaggactagacatgcaagcgcccatcagctctcgagatggaaaactggctctaacagtggcggccccccctaactgtggcc gagggtatcaatgctttggcagtagccacaggtaatggtattggactaaatgaaaccaacacacacctgcaggcaaaactggtc gcgcccctaggctttgataccaacggcaacattaagctaagcgtcgcaggaggcatgaggctaaacaataacacactgatact agatgtaaactacccatttgaggctcaaggccaactgagcctaagagtgggctcgggcccactatatgtagattctagtagtcat aacctaaccattagatgccttaggggattgtatgtaacatcttctaacaaccaaaacggtctagaggccaacattaaactaacaaa aggccttgtgtatgacggaaatgccatagcagttaatgttggcaaagggctggaatacagccctactggcacaacagaaaaac ctatacagactaaaataggtctaggcatggagtatgacactgagggagccatgatgacaaaactaggctctggactaagctttga caattcaggagccattgtggtgggaaacaaaaatgatgacaggcttactttgtggaccacaccggacccatcgcccaactgtca gatttactctgaaaaagatgctaaactaaccttggtactgactaaatgtggcagtcaggttgtaggcacagtatctattgccgctctt aaaggtagccttgtgccaatcactagtgcaatcagtgtggttcagatatacctaaggtttgatgaaaatggggtgctgatgagtaa ctcttcacttaatggcgaatactggaattttagaaacggagactcaactaatggcacaccatatacaaacgcagtgggttttatgcc taatctactggcctatcctaaaggtcaaactacaactgcaaaaagtaacattgtcagccaggtctacatgaacggggacgatact aaacccatgacatttacaatcaacttcaatggccttagtgaaacaggggatacccctgtcagtaaatattccatgacattctcatgg aggtggccaaatggaagctacatagggcacaattttgtaacaaactcctttactttctcctacatcgcccaagaataaagaaagca cagagatgcttgttttgatttcaaaattgtgtgcttttatttattttcaagcttacagtatttccagtagtcattagaatagagcttaattaa actgcatgagaacccttccacatagcttaaatactagtggagaagtactcgcctacatgggggtagagtcataatcgtgcatcag gatagggcggtggtgctgcagcagcgcgcgaataaactgctgccgccgccgctccgtcctgcaggaatacaacatggcagtg gtctcctcagcgatgattcgcaccgcccgcagcataaggcgccttgtcctccgggcacagcagcgcaccctgatctcacttaaa tcagcacagtaactgcagcacagcaccacaatattgttcaaaatcccacagtgcaaggcgctgtatccaaagctcatggcggg gaccacagaacccacgtggccatcataccacaagcgcaggtagattaagtggcgacccctcataaacacgctggacataaac attacctcttttggcatgttgtaattcaccacctcccggtaccatataaacctctgattaaacatggcgccatccaccaccatcctaa accagctggccaaaacctgcccgccggctatacactgcagggaaccgggactggaacaatgacagtggagagcccaggact cgtaaccatggatcatcatgctcgtcatgatatcaatgttggcacaacacaggcacacgtgcatacacttcctcaggattacaagc tcctcccgcgttagaaccatatcccagggaacaacccattcctgaatcagcgtaaatcccacactgcagggaagacctcgcac gtaactcacgttgtgcattgtcaaagtgttacattcgggcagcagcggatgatcctccagtatggtagcgcgggtttctgtctcaaa aggaggtagacgatccctactgtacggagtgcgccgagacaaccgagatcgtgttggtcgtagtgtcatgccaaatggaacgc -continued

```
cggacgtagtcatatttcctgaagtcttcactctcacagcaccagcactaatcagagtgtgaagagggccaagtgccgaacgag
tatatataggaattaaaaatgacgtaaatgtgtaaaggtcaaaaaacgcccagaaaaatacacagaccaacgcccgaaacgaa
aacccgcgaaaaaatacccagaagttcctcaacaaccgccacttccgctttcccacgatacgtcacttcctcaaaaatagcaaac
tacatttcccacatgtacaaaaccaaaacccctccccttgtcaccgcccacaacttacataatcacaaacgtcaaagcctacgtca
cccgccccgcctcgccccgcccacctcattatcatattggcctcaatccaaaataaggtatattattgatgatg
```

Figure 7:
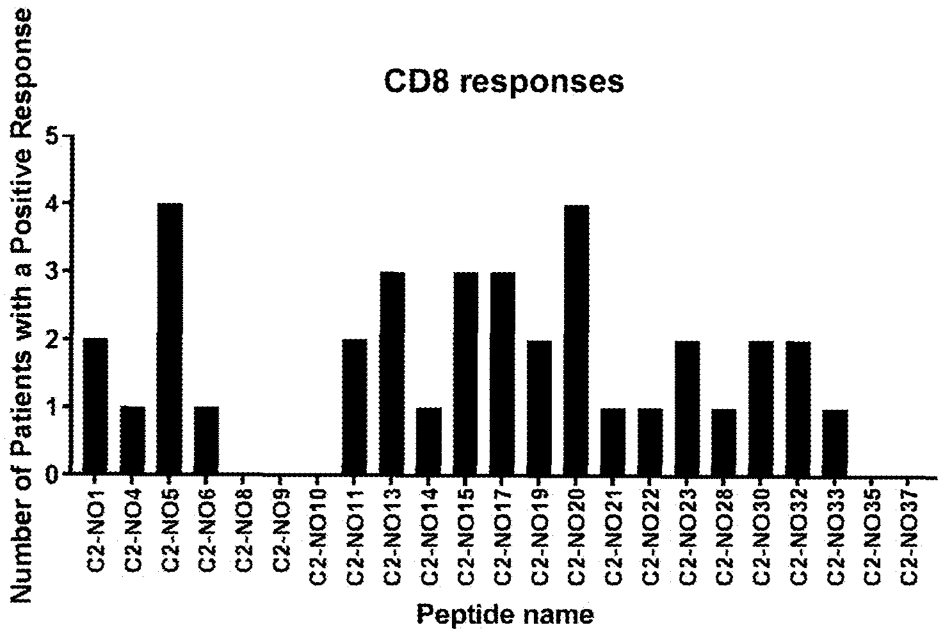
FIG. 7 shows the number of prostate cancer patients whose PBMC samples demonstrated a positive $CD4^+$ immune response to the specified neoantigens.
Figure 8:
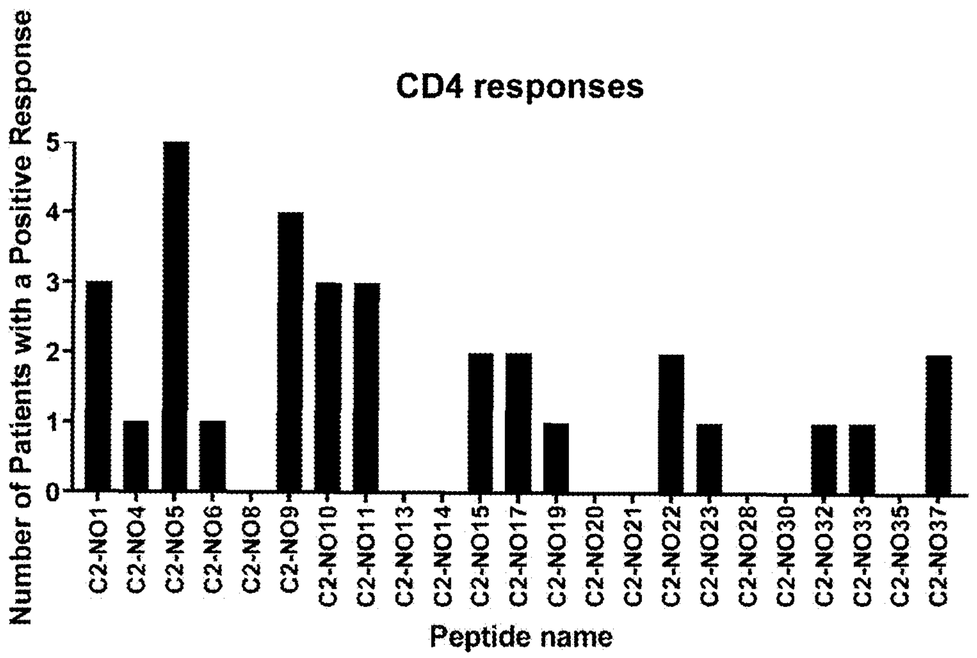
FIG. 8 shows the number of prostate cancer patients whose PBMC samples demonstrated a positive $CD8^+$ immune response to the specified neoantigens.

Example 11 Neoantigens Incorporated into NeoGAd20 and NeoMVA are Immunogenic In Vitro Overlapping 15-mer peptides were designed to span each neoantigen incorporated into NeoGAd20 and NeoMVA to assess their ability to activate T cells using the exogenous autologous normal donor restimulation assay described in Example 1 as pools using TNFα and IFNγ production by $CD8^+$ and $CD4^+$ T cells as a readout. Table 25 shows the maximum frequency of $TNF\alpha^+IFN\gamma+CD8^+$ and $TNF\alpha^+IFN\gamma+CD4^+$ T cells and maximum fold change over negative control for the pool of peptides analyzed, indicating the highest frequency of $TNF\alpha^+IFN\gamma^+CD8^+$ and $TNF\alpha^+IFN\gamma^+CD4^+$ T cells and resulting fold change across the normal donors evaluated for the peptide. Table 26 shows the peptide sequences used. FIG. 7 shows the number of patients with a positive CD8+ response for each tested peptide pool for select neoantigens. FIG. 8 shows the number of patients with a positive CD4+ response for each tested peptide pool for select neoantigens.

TABLE 25

| Neoantigen ID (Alternative name) | Maximum Fold Change Over Back-ground CD8+ cells | Maximum Frequency of TNFα/IFNγ Double Positive CD8+ T cells | Maximum Fold Change Over Back-ground CD4+ cells | Maximum Frequency of TNFα/IFNγ Double Positive CD4+ T cells |
|---|---|---|---|---|
| AS18 (C2-NO1) | 9.17 | 0.110 | 7.51 | 0.053 |
| P87 (C2-NO4) | 9.20 | 0.460 | 7.86 | 0.110 |
| AS55 (C2-NO5) | 1354.17 | 32.500 | 19.38 | 0.310 |
| AS57 (C2-NO6) | 4.67 | 0.056 | 11.00 | 0.110 |
| AS15 (C2-NO11) | 4.36 | 0.061 | 9.17 | 0.110 |
| AS7 (C2-NO13) | 52.60 | 2.630 | 2.50 | 0.045 |
| AS43 (C2-NO15) | 28.75 | 0.460 | 5.67 | 0.040 |
| AS51 (C2-NO17) | 33.13 | 0.530 | 8.75 | 0.140 |
| AS16 (C2-NO19) | 24.17 | 0.290 | 7.78 | 0.140 |
| AS41 (C2-NO20) | 190.60 | 9.530 | 2.20 | 0.022 |
| AS6 (C2-NO22) | 6.50 | 0.078 | 31.67 | 0.380 |
| AS3 (C2-NO23) | 7.92 | 0.095 | 3.86 | 0.054 |
| AS11 | 5.11 | 0.07 | 2.98 | 0.03 |
| AS13 | 1.67 | 0.10 | 1.96 | 0.05 |
| AS47 (C2-NO30) | 4.80 | 0.240 | 2.58 | 0.031 |
| AS8 (C2-NO33) | 54.55 | 0.600 | 4.08 | 0.049 |
| AS19 | 5.87 | 0.63 | 2.59 | 0.1 |
| AS37 | 19.47 | 0.74 | 7.51 | 0.04 |
| AS23 | 3.24 | 0.07 | 5.08 | 0.01 |
| MS1 | 5.56 | 0.1 | 50.19 | 0.39 |
| MS3 | 36.15 | 0.47 | 13.61 | 0.09 |
| MS6 | 4.17 | 0.08 | 111.97 | 0.87 |
| MS8 | 4.44 | 0.14 | 15.60 | 0.40 |
| P82 | 2.92 | 0.09 | 4.44 | 0.17 |
| P16 (C2-NO8) | 2.44 | 0.039 | 2.44 | 0.039 |
| FUS1 (C2-NO9) | 1.94 | 0.031 | 8.33 | 0.100 |
| P22 (C2-NO10) | 1.56 | 0.025 | 18.16 | 0.075 |
| FUS2 (C2-NO14) | 3.13 | 0.05 | 2.14 | 0.03 |
| FUS3 (C2-NO21) | 3.94 | 0.063 | 2.75 | 0.033 |
| FUS6 (C2-NO28) | 3.50 | 0.056 | 2.27 | 0.016 |

TABLE 25-continued

| Neoantigen ID (Alternative name) | Maximum Fold Change Over Back-ground CD8+ cells | Maximum Frequency of TNFα/IFNγ Double Positive CD8+ T cells | Maximum Fold Change Over Back-ground CD4+ cells | Maximum Frequency of TNFα/IFNγ Double Positive CD4+ T cells |
|---|---|---|---|---|
| FUS5 (C2-NO32) | 32.50 | 0.390 | 3.43 | 0.048 |
| FUS8 | 1.89 | 0.08 | 7.15 | 0.04 |
| FUS15 (C2-NO35) | 1.75 | 0.028 | 2.79 | 0.039 |
| P35 | 14.44 | 0.26 | 3.47 | 0.03 |
| FUS19(C2-NO37) | 1.88 | 0.030 | 3.15 | 0.013 |
| FUS7 | 8.89 | 0.16 | 36.13 | 0.04 |
| M84 | 1.39 | 0.03 | 35.84 | 0.31 |
| M86 | 4.22 | 0.08 | 6.18 | 0.05 |
| M10 | 1.89 | 0.09 | 14.14 | 0.1 |
| M12 | 6.67 | 0.12 | 8.94 | 0.05 |
| FR1 | 7.92 | 0.38 | 4.89 | 0.04 |

TABLE 26

| Neoantigen ID (alternative name) | Overlapping Peptide Sequences* (SEQ ID NO:) |
|---|---|
| AS18 (C2-NO1) | WKFEMSYTVGGPPPH (560)<br>VGGPPPHVHARPRHW (561)<br>PPHVHARPRHWKTD (562) |
| P87 (C2-NO4) | YEAGMTLGGKILFFL (563)<br>GKILFFLFLLLPLSP (564)<br>FFLFLLLPLSPFSLIF (565) |
| AS55 (C2-NO5) | DGHSYTSKVNCLLLQ (566)<br>VNCLLLQDGFHGCVS (567)<br>GFHGCVSITGAAGRR (568)<br>TGAAGRRNLSIFLFL (569)<br>LSIFLFLMLCKLEFH (570)<br>LFLMLCKLEFHAC (571) |
| AS57 (C2-NO6) | TGGKSTCSAPGPQSL (572)<br>APGPQSLPSTPFSTY (573)<br>STPFSTYPQWVILIT (574) |
| AS15 (C2-NO11) | VLRFLDLKVRYLHS (269) |
| AS7 (C2-NO13) | DYWAQKEKGSSSFLR (576)<br>QKEKGSSSFLRPSC (577) |
| AS43 (C2-NO15) | VPFRELKNVSVLEGL (578)<br>VSVLEGLRQGRLGGP (579)<br>QGRLGGPCSCHCPRP (580)<br>SCHCPRPSQARLTPV (581)<br>QARLTPVDVAGPFLC (582)<br>VAGPFLCLGDPGLFP (583)<br>GDPGLFPPVKSSI (584) |
| AS51 (C2-NO17) | GMECTLGQVGAPSPR (585)<br>VGAPSPRREEDGWRG (586)<br>EEDGWRGGHSRFKAD (587)<br>HSRFKADVPAPQGPC (588) |

TABLE 26-continued

| Neoantigen ID (alternative name) | Overlapping Peptide Sequences* (SEQ ID NO:) |
|---|---|
| | PAPQGPCWGGQPGSA (589) |
| | GGQPGSAPSSAPPEQ (590) |
| | GSAPSSAPPEQSLLD (591) |
| AS16 (C2-NO19) | GNTTLQQLGEASQAP (592) |
| | GEASQAPSGSLIPLR (593) |
| | GSLIPLRLPLLWEVRG (594) |
| AS41 (C2-NO20) | EAFQRAAGEGGPGRG (595) |
| | EGGPGRGGARRGARV (596) |
| | ARRGARVLQSPFCRA (597) |
| | QSPFCRAGAGEWLGH (598) |
| | CRAGAGEWLGHQSLR (599) |
| AS6 (C2-NO22) | DYWAQKEKISIPRTH (600) |
| | QKEKISIPRTHLC (601) |
| AS3 (C2-NO23) | VAMMVPDRQVHYDFG (602) |
| | VPDRQVHYDFGLR (603) |
| AS11 | VPFRELKNQRTAQGA (631) |
| | QRTAQGAPGIHHAAS (632) |
| | GIHHAASPVAANLCD (633) |
| | VAANLCDPARHAQHT (634) |
| | ARHAQHTRIPCGAGQ (635) |
| | IPCGAGQVRAGRGPE (636) |
| | RAGRGPEAGGGVLQP (637) |
| | GGGVLQPQRPAPEKP (638) |
| | RPAPEKPGCPCRRGQ (639) |
| | CPCRRGQPRLHTVKM (640) |
| | RGQPRLHTVKMWRA (641) |
| AS13 | KRSFAVTERII (265) |
| AS47 (C2-NO30) | FKKFDGPCGERGGGR (604) |
| | GERGGGRTARALWAR (605) |
| | ARALWARGDSVLTPA (606) |
| | DSVLTPALDPQTPVR (607) |
| | DPQTPVRAPSLTRAA (608) |
| | PVRAPSLTRAAAAV (609) |
| AS8 (C2-NO33) | LVLGVLSGHSGSRL (255) |
| AS19 | QWQHYHRSGEAAGTP (710) |
| | GEAAGTPLWRPTRN (711) |
| AS37 | CHLFLQPQVGTPPPH (642) |
| | VGTPPPHTASARAPS (643) |
| | ASARAPSGPPHPHES (644) |
| | PPHPHESCPAGRRPA (645) |
| | PAGRRPARAAQTCAR (646) |
| | AAQTCARRQHGLPGC (647) |
| | QHGLPGCEEAGTARV (648) |
| | EAGTARVPSLHLHLH (649) |
| | SLHLHLHQAALGAGR (650) |
| | AALGAGRGRGWGEAC (651) |
| | RGWGEACAQVPPSRG (652) |
| AS23 | KIQNKNCPD (285) |
| MS1 | HYKLIQQPISLFSIT (653) |
| | ISLFSITDRLHKTFS (654) |
| | RLHKTFSQLPSVHLC (655) |
| | LPSVHLCSITFQWGH (656) |
| | ITFQWGHPPIFCSTN (657) |
| | PIFCSTNDICVTANF (658) |
| | ICVTANFCISVTFLK (659) |
| | ISVTFLKPCFLLHEA (660) |
| | CFLLHEASASQ (661) |
| MS3 | RTALTHNQDFSIYRL (662) |
| | DFSIYRLCCKRGSLC (663) |
| | CKRGSLCHASQARSP (664) |
| | ASQARSPAFPKPVRP (665) |
| | FPKPVRPLPAPITRI (666) |
| | PAPITRITPQLGGQS (667) |
| | PQLGGQSDSSQPLLT (668) |
| | SSQPLLTTGRPQGWQ (669) |
| | GRPQGWQDQALRHTQ (670) |
| | QALRHTQQASPASCA (671) |
| | ASPASCATITIPIHS (672) |
| | ITIPIHSAALGDHSG (673) |
| | ALGDHSGDPGPAWDT (674) |
| | PGPAWDTCPPLPLTT (675) |
| | PPLPLTTLIPRAPPP (676) |
| | IPRAPPPYGDSTARS (677) |
| | GDSTARSWPSRCGPLG (678) |
| MS6 | YAYKDFLWCFPFSLV (679) |
| | CFPFSLVFLQEIQIC (680) |
| | LQEIQICCHVSCLCC (681) |
| | HVSCLCCICCSTRIC (682) |
| | CCSTRICLGCLLELF (683) |
| | GCLLELFLSRALRAL (684) |
| | SRALRALHVLWNGFQ (685) |
| | VLWNGFQLHCQ (686) |
| MS8 | TMPAILKLQKNCLLSL (444) |
| P82 | YEAGMTLGEKFRVGN (687) |
| | EKFRVGNCKHLKMTRP (688) |
| P16 (C2-NO8) | GVPGDSTRRAVRRMN (611) |
| | DSTRRAVRRMNTF (612) |
| FUS1 (C2-NO9) | CGASACDVSLIAMDSA (211) |
| P22 (C2-NO10) | SLYHREKQLIAMDSAI (349) |
| FUS2 | TEYNQKLQVNQFSESK (712) |
| FUS3 (C2-NO21) | TEISCCTLSSEENEY (615) |
| | SSEENEYLPRPEWQLQ (616) |
| FUS6 (C2-NO28) | CEERGAAGSLISCE (221) |
| FUS5 (C2-NO32) | NSKMALNSEALSVVSE (219) |
| FUS8 | WGMELAASRRFSWDH (689) |
| | RRFSWDHHSAGGPPR (690) |
| | SAGGPPRVPSVRSGA (691) |
| | PSVRSGAAQVQPKDP (692) |
| | QVQPKDPLPLRTLAG (693) |
| | PLRTLAGCLARTAHL (694) |
| | LARTAHLRPGAESLP (695) |
| | PGAESLPQPQLHCT (696) |
| FUS15 (C2-NO35) | HVVGYGHLDTSGSSS (619) |
| | YGHLDTSGSSSSSSWP (620) |
| P35 | NSKMALNSLNSIDDA (697) |
| | LNSIDDAQLTRIAPP (698) |
| | LTRIAPPRSHCCFWE (699) |
| | APPRSHCCFWEVNAP (700) |
| FUS19 (C2-NO37) | KMHFSLKEHPPPPCPP (235) |
| FUS7 | LWFQSSELSPTGAPW (701) |
| | SPTGAPWPSRRPTWR (702) |
| | SRRPTWRGTTVSPRT (703) |
| | TTVSPRTATSSARTC (704) |
| | TSSARTCCGTKWPSS (705) |
| | GTKWPSSQEAALGLG (706) |
| | EAALGLGSGLLRFSC(707) |
| | GLLRFSCGTAAIR (708) |
| M84 | IARELHQFAFDLLIKSH (167) |
| M86 | QPDSFAALHSSLNELGE (171) |
| M10 | FVQGKDWGLKKFIRRDF (19) |
| M12 | FVQGKDWGVKKFIRRDF (23) |

TABLE 26-continued

| Neoantigen ID (alternative name) | Overlapping Peptide Sequences* (SEQ ID NO:) |
|---|---|
| FR1 | QNLQNGGGSRSSATL (709)<br>SRSSATLPGRRRRRW (575)<br>GRRRRRWLRRRRQPI (610)<br>RRRRQPISVAPAGPP (613)<br>VAPAGPPRRPNQKPN (614)<br>RPNQKPNPPGGARCV (617)<br>PGGARCVIMRPTWPG (618)<br>MRPTWPGTSAFT (621) |

Example 12 Neoantigens Incorporated into NeoGAd20 and NeoMVA are Immunogenic when Expressed Endogenously In Vitro For three of the neoantigens, an Ad5 vector was designed to transduce normal Dendritic cells with the neoantigens. This assay assessed the ability of the endogenously expressed and presented neoantigens to activate autologous T cells following overlapping 15-mer peptide pools restimulation using the endogenous autologous normal donor restimulation assay described in Example 1 utilizing TNFα and IFNγ production by $CD8^+$ and $CD4^+$ T cells as a readout. Table 27 shows the maximum frequency of $TNF\alpha^+IFN\gamma^+$ $CD8^+$ and $TNF\alpha^+IFN\gamma^+CD4^+$ T cells and maximum fold change over negative control for the pool of peptides analyzed, indicating the highest frequency of $TNF\alpha^+IFN\gamma^+$ $CD8^+$ and $TNF\alpha^+IFN\gamma^+CD4^+$ T cells and resulting fold change across the normal donors evaluated for the peptide. Sixteen donors were used to assess endogenous immunogenicity.

TABLE 27

| Neoantigen ID | Overlapping Peptide Sequences* (SEQ ID NO:) | Maximum Fold Change Over Background CD8+ cells | Maximum Frequency of TNFα/IFNγ Double Positive CD8+ T cells | Maximum Fold Change Over Background CD4+ cells | Maximum Frequency of TNFα/IFNγ Double Positive CD4+30 T cells |
|---|---|---|---|---|---|
| AS18 (C2-NO1) | WKFEMSYTVGGPPPH (560)<br>VGGPPPHVHARPRHW (561)<br>PPHVHARPRHWKTD (562) | 4.09 | 0.36 | 1.90 | 0.046 |
| P87 (C2-NO4) | YEAGMTLGGKILFFL (563)<br>GKILFFLFLLLPLSP (564)<br>FFLFLLLPLSPFSLIF (565) | 2.47 | 0.39 | 2.41 | 0.079 |
| AS55 (C2-NO5) | DGHSYTSKVNCLLLQ (566)<br>VNCLLLQDGFHGCVS (567)<br>GFHGCVSITGAAGRR (568)<br>TGAAGRRNLSIFLFL (569)<br>LSIFLFLMLCKLEFH (570)<br>LFLMLCKLEFHAC (571) | 213.88 | 2.05 | 3.50 | 0.063 |

*All generated peptides had NH2 group at N-terminus and -OH group at C-terminus

Example 13: Neoantigens are Immunogenic in Vitro

Immunogenicity of various additional identified neoantigens was assessed. Overlapping 15-mer peptides were designed to span each neoantigen similarly to what was done in Example 11 to assess their ability to activate T cells using the exogenous autologous normal donor restimulation assay described in Example 1 as pools using TNFα and IFNγ production by $CD8^+$ and $CD4^+$ T cells as a readout. Table 28 shows the maximum frequency of $TNF\alpha^+IFN\gamma^+CD8^+$ and $TNF\alpha^+$ $IFN\gamma^+CD4^+$ T cells and maximum fold change over negative control for the pool of peptides analyzed, indicating the highest frequency of $TNF\alpha^+IFN\gamma^+CD8^+$ and $TNF\alpha^+$ $IFN\gamma^+CD4^+$ T cells and resulting fold change across the normal donors evaluated for the peptide. Table 29 shows the amino acid sequences of the peptides used in the assays for each neoantigen.

TABLE 28

| Neoantigen ID (Alternative name) | Max. Fold Change over background CD8+ TNFαINFγ double positive DP | Max. Frequency of CD8+ TNFαINFγ DP | Max. Fold Change over background CD4+ TNFαINFγ double positive DP | Max. Frequency of CD4+ TNFαINFγ DP |
|---|---|---|---|---|
| AS1 (Misc1-NO12) | 8.15 | 0.11 | 3.57 | 0.02 |
| AS2 (Misc1-NO13) | 5.06 | 0.09 | 110.68 | 0.86 |
| AS4 (Misc1-NO14) | 5.4 | 0.17 | 37.38 | 1.43 |
| AS5 (Misc1-NO15) | 2.13 | 0.16 | 8.71 | 0.1 |
| AS9 (Misc1-NO16) | 3.81 | 0.12 | 4.18 | 0.16 |
| AS10 (Misc1-NO17) | 4.33 | 0.08 | 3.97 | 0.23 |
| AS12 (Misc1-NO18) | 6.03 | 0.19 | 7.32 | 0.28 |
| AS14 (Misc1-NO19) | 3.81 | 0.12 | 1.49 | 0.06 |
| AS17 (Misc1-NO20) | 2.38 | 0.07 | 3.18 | 0.01 |
| AS20 (Misc1-NO21) | 3.81 | 0.12 | 1.36 | 0.05 |
| AS21 (Misc1-NO22) | 3.81 | 0.12 | 1.7 | 0.07 |
| AS22 (Misc1-NO23) | 2.61 | 0.1 | 7.86 | 0.11 |
| AS32 (Misc1-NO24) | 3.81 | 0.12 | 2.04 | 0.08 |
| AS34 (Misc1-NO26) | 16.25 | 0.26 | 9.48 | 0.01 |
| AS35 (Misc1-NO27) | 11.32 | 0.43 | 60.93 | 0.23 |
| AS36 (Misc2-NO1) | 1544.74 | 58.7 | 129.8 | 0.49 |
| AS40 (Misc2-NO3) | 178.52 | 2.41 | 15.34 | 0.89 |
| AS42 (Misc2-NO4) | 4.65 | 0.69 | 24.58 | 0.59 |
| AS44 (Misc2-NO5) | 4.72 | 0.09 | 293.94 | 1.48 |
| AS45 (Misc2-NO6) | 4.96 | 0.07 | 78.51 | 0.61 |
| AS46 (Misc2-NO7) | 11.6 | 0.87 | 157.98 | 0.29 |
| AS48 (Misc2-NO8) | 9.21 | 0.29 | 13.45 | 0.13 |
| AS49 (Misc2-NO9) | 8.67 | 0.65 | 184.87 | 0.14 |
| AS50 (Misc2-NO10) | 1.6 | 0.12 | 17.22 | 0.07 |
| AS52 (Misc2-NO11) | 6.85 | 0.1 | 184.87 | 0.63 |
| AS53 (Misc2-NO12) | 4.02 | 0.35 | 113.91 | 0.43 |
| AS54 | 88.15 | 8.33 | 17.87 | 0.18 |
| AS55.1 (Misc2-NO14) | 25.26 | 1.47 | 20.66 | 0.08 |
| AS56 | 6.35 | 0.6 | 128.76 | 0.18 |
| AS58 (Misc2-NO16) | 4.54 | 0.6 | 6.27 | 0.24 |
| AS59 (Misc2-NO17) | 4.22 | 0.08 | 59.58 | 0.3 |
| FUS9 (Misc1-NO2) | 1.82 | 0.07 | 203.97 | 0.77 |
| FUS10 (Misc1-NO3) | 2.42 | 0.09 | 10.86 | 0.04 |
| FUS11 (Misc1-NO4) | 2.63 | 0.1 | 28.57 | 0.16 |
| FUS18 | 42.33 | 0.91 | 31.76 | 0.04 |
| FUS23 (Misc1-NO6) | 11.05 | 0.62 | 12.77 | 0.12 |
| FUS24 (Misc1-NO7) | 8.53 | 0.64 | 4.4 | 0.05 |
| MS2 (Exc1-NO6) | 36.92 | 0.48 | 15.12 | 0.1 |
| MS4 (Exc1-NO8) | 24.13 | 0.76 | 367.35 | 2.43 |
| MS5 (Exc1-NO9) | 32.89 | 1.95 | 126.05 | 0.2 |
| MS7 (Exc1-NO11) | 6.67 | 0.12 | 10.52 | 0.09 |
| MS9 (Exc1-NO13) | 1.38 | 0.1 | 455.63 | 1.72 |
| MS10 (Exc1-NO14) | 3.42 | 0.13 | 74.17 | 0.28 |
| MS11 (Exc1-NO15) | 3.81 | 0.12 | 3.4 | 0.13 |
| P97 (Misc1-NO11) | 7.47 | 1.11 | 3.14 | 0.12 |
| P19 (Misc1-NO8) | 4.76 | 0.15 | 6.67 | 0.16 |
| P27 (Misc1-NO9) | 7.87 | 0.59 | 45.38 | 0.05 |
| P37 (Misc1-NO10) | 2.05 | 0.13 | 22.78 | 0.09 |
| P76, P77 (Misc2-NO18) | 4.56 | 0.08 | 53.18 | 0.36 |

TABLE 29

| Neoantigen ID (Alternative name) | Peptide sequences |
|---|---|
| AS1 (Misc1-NO12) | LTFLDFIQVTLRVMS (SEQ ID NO: 377)<br>VTLRVMSGSQMENGS (SEQ ID NO: 378)<br>SQMENGSSYFFKPFS (SEQ ID NO: 415)<br>YFFKPFSWGLGVGLS (SEQ ID NO: 417) |
| AS2 (Misc1-NO13) | FMIGELVGELCCQLT (SEQ ID NO: 418)<br>ELCCQLTFRLPFLES (SEQ ID NO: 419)<br>RLPFLESLCQAVVTQ (SEQ ID NO: 420)<br>CQAVVTQALRFNPSF (SEQ ID NO: 502)<br>LRFNPSFQEVCIYQD (SEQ ID NO: 518)<br>EVCIYQDTDLM (SEQ ID NO: 526) |
| AS4 (Misc1-NO14) | WCPLDLRLGSTGCLT (SEQ ID NO: 527)<br>GSTGCLTCRHHQTSHE (SEQ ID NO: 714) |
| AS5 (Misc1-NO15) | VVGRRHETAPQPLLV (SEQ ID NO: 715)<br>APQPLLVPDRAGGEG (SEQ ID NO: 716)<br>DRAGGEGGA (SEQ ID NO: 717) |
| AS9 (Misc1-NO16) | PVPTATPGVRSVTSP (SEQ ID NO: 718)<br>VRSVTSPQGLGLFLK (SEQ ID NO: 719)<br>GLGLFLKFI (SEQ ID NO: 720) |
| AS10 (Misc1-NO17) | KENDVREVCDVYLQM (SEQ ID NO: 721)<br>CDVYLQMQIFFHFKF (SEQ ID NO: 722)<br>IFFHFKFRSYFH (SEQ ID NO: 723) |
| AS12 (Misc1-NO18) | FARKMLEKVHRQHLQ (SEQ ID NO: 724)<br>VHRQHLQLSHNSQE (SEQ ID NO: 725) |
| AS14 (Misc1-NO19) | MFLRKEQQVGPHSFS (SEQ ID NO: 726)<br>VGPHSFSML (SEQ ID NO: 727) |
| AS17 (Misc1-NO20) | GLNLNTDRPGGYSYS (SEQ ID NO: 728)<br>PGGYSYSIWWKNNAK (SEQ ID NO: 729)<br>WWKNNAKNR (SEQ ID NO: 730) |
| AS20 (Misc1-NO21) | KVLNEIDAVVTVPPS (SEQ ID NO: 731)<br>VVTVPPSLSTSQIPQ (SEQ ID NO: 732)<br>STSQIPQGCCIIL (SEQ ID NO: 733) |
| AS21 (Misc1-NO22) | ANLKGTLQVRSGQAV (SEQ ID NO: 734)<br>VRSGQAVSPR (SEQ ID NO: 735) |
| AS22 (Misc1-NO23) | LQAAASGQGKQGVPC (SEQ ID NO: 736)<br>GKQGVPCPWGCCAYA (SEQ ID NO: 737)<br>WGCCAYAESPRALIS (SEQ ID NO: 738)<br>SPRALISGDAPSQVE (SEQ ID NO: 739)<br>DAPSQVEREVPGPCL (SEQ ID NO: 740)<br>EVPGPCLNTHSLSHR (SEQ ID NO: 741)<br>THSLSHRSPQLPGLP (SEQ ID NO: 742)<br>PQLPGLPHPKQPSV (SEQ ID NO: 743) |
| AS32 (Misc1-NO24) | GEVELSEGGEGQRHL (SEQ ID NO: 744)<br>GEGQRHLAFPWACSG (SEQ ID NO: 745)<br>FPWACSGPGWRGVCC (SEQ ID NO: 746)<br>GWRGVCCAAVEPA (SEQ ID NO: 980) |
| AS34 (Misc1-NO26) | KMRAIQAEGGHGQAC (SEQ ID NO: 747)<br>GGHGQACCGGAWGWA (SEQ ID NO: 748)<br>GGAWGWAPGDGGPQG (SEQ ID NO: 749)<br>GDGGPQGMLTHTLPT (SEQ ID NO: 750)<br>LTHTLPTLGFQSAWT (SEQ ID NO: 751)<br>GFQSAWTWRREDADR (SEQ ID NO: 752)<br>RREDADRAWRTPKAC (SEQ ID NO: 753)<br>WRTPKACASRRWSI (SEQ ID NO: 754) |
| AS35 (Misc1-NO27) | LLEPFRRGEPGPRGL (SEQ ID NO: 755)<br>EPGPRGLLSGSSRGG (SEQ ID NO: 756)<br>SGSSRGGEGPGRSIE (SEQ ID NO: 757)<br>GPGRSIEAAPATPLP (SEQ ID NO: 758)<br>APATPLPCCRKNPCR (SEQ ID NO: 759)<br>CRKNPCRPQPSRFLP (SEQ ID NO: 760)<br>QPSRFLPPRVLLVII (SEQ ID NO: 761)<br>RVLLVIILPKLDCPK (SEQ ID NO: 762)<br>PKLDCPKLGF (SEQ ID NO: 763) |

TABLE 29-continued

| Neoantigen ID (Alternative name) | Peptide sequences |
|---|---|
| AS36 (Misc2-NO1) | PSGRRTKRLVTLRSG (SEQ ID NO: 764)<br>LVTLRSGCAIQCWHP (SEQ ID NO: 765)<br>AIQCWHPRAGPVPSA (SEQ ID NO: 766)<br>AGPVPSALPHTERPP (SEQ ID NO: 767)<br>PHTERPPRLVRGAAD (SEQ ID NO: 768)<br>LVRGAADPRTVTLGR (SEQ ID NO: 769)<br>RTVTLGRSPAVMPRA (SEQ ID NO: 770)<br>PAVMPRAPA (SEQ ID NO: 771) |
| AS40 (Misc2-NO3) | DCMLSEEGGQARRGG (SEQ ID NO: 772)<br>GQARRGGSLCSLAAH (SEQ ID NO: 773)<br>LCSLAAHTIASAARG (SEQ ID NO: 774)<br>IASAARGRFLSRLSN (SEQ ID NO: 775)<br>FLSRLSNFCAVVKAS (SEQ ID NO: 776)<br>CAVVKASRGAPSCTWE (SEQ ID NO: 777) |
| AS42 (Misc2-NO4) | PEPRRLSPGEPRGRP (SEQ ID NO: 778)<br>GEPRGRPRKGWGIWG (SEQ ID NO: 779)<br>KGWGIWGLCGARVGP (SEQ ID NO: 780)<br>CGARVGPKAWR (SEQ ID NO: 781) |
| AS44 (Misc2-NO5) | FVSLTAIQMASSATP (SEQ ID NO: 782)<br>MASSATPWGRWPVAT (SEQ ID NO: 783)<br>GRWPVATPTAACPRR (SEQ ID NO: 784)<br>TAACPRRRPSSLPTG (SEQ ID NO: 785)<br>PSSLPTGGDSASKKP (SEQ ID NO: 786)<br>DSASKKPISRRAPWQ (SEQ ID NO: 787)<br>SRRAPWQPWACPGRS (SEQ ID NO: 788)<br>WACPGRSVNSAAPRA (SEQ ID NO: 789)<br>NSAAPRAWCPPATTP (SEQ ID NO: 790)<br>CPPATTPRTQSPSRD (SEQ ID NO: 791)<br>TQSPSRDLRPRCLSS (SEQ ID NO: 792)<br>RPRCLSSWSS (SEQ ID NO: 793) |
| AS45 (Misc2-NO6) | PVAIKPGTGPPNNSS (SEQ ID NO: 794)<br>GPPNNSSIHGGSKRS (SEQ ID NO: 795)<br>HGGSKRSENSYCRDL (SEQ ID NO: 796)<br>NSYCRDLRGQLRAIC (SEQ ID NO: 797)<br>GQLRAICCSSYSHDR (SEQ ID NO: 798)<br>SSYSHDRHTTEERGS (SEQ ID NO: 799)<br>TTEERGSRGRHVWRI (SEQ ID NO: 800)<br>GRHVWRIRRLHTSGL (SEQ ID NO: 801)<br>RLHTSGLPCCCHSGP (SEQ ID NO: 802)<br>CCCHSGPHPRRLPDI (SEQ ID NO: 803)<br>PRRLPDILRLVTSTK (SEQ ID NO: 804)<br>RLVTSTKTDHTNTTE (SEQ ID NO: 805)<br>DHTNTTEGTLDYL (SEQ ID NO: 806) |
| AS46 (Misc2-NO7) | KWNKNWTATLGALTI (SEQ ID NO: 807)<br>TLGALTIRGHKLLCH (SEQ ID NO: 808)<br>GHKLLCHLPHLLSSV (SEQ ID NO: 809)<br>PHLLSSVQQTCRSSSR (SEQ ID NO: 810) |
| AS48 (Misc2-NO8) | ENASLVFTGSNSPIP (SEQ ID NO: 811)<br>GSNSPIPACELSSHP (SEQ ID NO: 812)<br>CELSSHPAHGISPWI (SEQ ID NO: 813)<br>HGISPWIPSPGNEHF (SEQ ID NO: 814)<br>SPGNEHFHGIKKQVK (SEQ ID NO: 815)<br>GIKKQVKAIKVE (SEQ ID NO: 816) |
| AS49 (Misc2-NO9) | RLTQRLVQGWTPMEN (SEQ ID NO: 817)<br>GWTPMENRWCGRRAG (SEQ ID NO: 818)<br>WCGRRAGGQPASSST (SEQ ID NO: 819)<br>QPASSSTRWTTCRAA (SEQ ID NO: 820)<br>WTTCRAACLLTKWTA (SEQ ID NO: 821)<br>LLTKWTAGRSQTSIG (SEQ ID NO: 822) |
| AS50 (Misc2-NO10) | ENSGNASRWLHVPSS (SEQ ID NO: 823)<br>WLHVPSSSDDWLGWK (SEQ ID NO: 824)<br>DDWLGWKKSSAITSNS (SEQ ID NO: 825) |
| AS52 (Misc2-NO11) | KGSVERRSVSLGHPA (SEQ ID NO: 826)<br>VSLGHPAEGWAWAER (SEQ ID NO: 827)<br>GWAWAERSLQPGMTT (SEQ ID NO: 828)<br>LQPGMTTANTGCLSF (SEQ ID NO: 829) |

TABLE 29-continued

| Neoantigen ID (Alternative name) | Peptide sequences |
|---|---|
| | NTGCLSFHHRGCLLP (SEQ ID NO: 830)<br>HRGCLLPVLPKLHCG (SEQ ID NO: 831)<br>LPKLHCGLGGLPLVR (SEQ ID NO: 832)<br>GGLPLVRAKEIKRVQ (SEQ ID NO: 833)<br>KEIKRVQRAGESSLP (SEQ ID NO: 834)<br>AGESSLPVKGLLTVA (SEQ ID NO: 835)<br>KGLLTVASAVIAVLW (SEQ ID NO: 836)<br>AVIAVLWGRPSEVTG (SEQ ID NO: 837)<br>RPSEVTGENEAQHD (SEQ ID NO: 838) |
| AS53 (Misc2-NO12) | FGLTTLAGRSSHGTS (SEQ ID NO: 839)<br>RSSHGTSGLRAATHT (SEQ ID NO: 840)<br>LRAATHTKSGDGGQG (SEQ ID NO: 841)<br>SGDGGQGAARQCEKL (SEQ ID NO: 842)<br>ARQCEKLLELARATR (SEQ ID NO: 843)<br>ELARATRPWGRSTSA (SEQ ID NO: 844)<br>WGRSTSASSRWTHRG (SEQ ID NO: 845)<br>SRWTHRGYMCPPRCA (SEQ ID NO: 846)<br>MCPPRCAVACW (SEQ ID NO: 847) |
| AS54 | IIDSDKIMAVCMGCL (SEQ ID NO: 848)<br>DKIMAVCMGCLLTRH (SEQ ID NO: 849)<br>AVCMGCLLTRHVQCQ (SEQ ID NO: 850)<br>GCLLTRHVQCQAMEM (SEQ ID NO: 851)<br>TRHVQCQAMEMQQ (SEQ ID NO: 852) |
| AS55.1 (Misc2-NO14) | DGHSYTSKVNCLLLQ (SEQ ID NO: 566)<br>VNCLLLQDGFHGCVS (SEQ ID NO: 567)<br>GFHGCVSITGAAGRR (SEQ ID NO: 568)<br>TGAAGRRNLSIFLFL (SEQ ID NO: 569)<br>LSIFLFLMLCKLEFHA (SEQ ID NO: 853) |
| AS56 | LLNAEDYRCAIHSKE (SEQ ID NO: 854)<br>CAIHSKEIYLLSPSP (SEQ ID NO: 855)<br>YLLSPSPHQAMDKFS (SEQ ID NO: 856)<br>QAMDKFSLCCINCNL (SEQ ID NO: 857)<br>CCINCNLCLHVFLLL (SEQ ID NO: 858)<br>LHVFLLLLFFQNKDV (SEQ ID NO: 859)<br>FFQNKDVWLISNIIL (SEQ ID NO: 860)<br>LISNIILLWIYGGI (SEQ ID NO: 861) |
| AS58 (Misc2-NO16) | VETLENANSFSSGIQ (SEQ ID NO: 862)<br>SFSSGIQPLLCSLIG (SEQ ID NO: 863)<br>LLCSLIGLENPT (SEQ ID NO: 864) |
| AS59 (Misc2-NO17) | AGAGTISEGSVLHGQ (SEQ ID NO: 865)<br>GSVLHGQRLECDARR (SEQ ID NO: 866)<br>LECDARRFFGCGTTI (SEQ ID NO: 867)<br>FGCGTTILAEWEHH (SEQ ID NO: 868) |
| FUS9 (Misc1-NO2) | KEQILAVASLVSSQS (SEQ ID NO: 869)<br>SLVSSQSIHPSWGQS (SEQ ID NO: 870)<br>HPSWGQSPLSRI (SEQ ID NO: 871) |
| FUS10 (Misc1-NO3) | LELELSEGVCFRLR (SEQ ID NO: 229) |
| FUS11 (Misc1-NO4) | QQLRIFCAAMASNED (SEQ ID NO: 872)<br>AMASNEDFS (SEQ ID NO: 873) |
| FUS18 | DGFSGSLFAVVTRRC (SEQ ID NO: 874)<br>AVVTRRCYFLKWRTI (SEQ ID NO: 875)<br>FLKWRTIFPQSLMWL (SEQ ID NO: 876) |
| FUS23 (Misc1-NO6) | DLRRVATYCAPLPSS (SEQ ID NO: 877)<br>CAPLPSSWRPGTGTT (SEQ ID NO: 878)<br>RPGTGTTIPPRMRSC (SEQ ID NO: 879) |
| FUS24 (Misc1-NO7) | LQERMELLACGAERG (SEQ ID NO: 880)<br>ACGAERGAGGWGGGG (SEQ ID NO: 881)<br>GGWGGGGGGGGGDRR (SEQ ID NO: 882)<br>GGGGDRRGGGGSAPA (SEQ ID NO: 883)<br>GGGSAPALADFAGGRG (SEQ ID NO: 884) |
| MS2 (Exc1-NO6) | WTDIVKQSVSTNCIS (SEQ ID NO: 885)<br>VSTNCISIKKGSYTK (SEQ ID NO: 886)<br>KKGSYTKLFSLVFLI (SEQ ID NO: 887)<br>FSLVFLIFCWPLIIQL (SEQ ID NO: 888) |
| MS4 (Exc1-NO8) | LRYGALCNVSRISYF (SEQ ID NO: 889)<br>VSRISYFSLTNIFNF (SEQ ID NO: 890)<br>LTNIFNFVIKSLTAI (SEQ ID NO: 891)<br>IKSLTAIFTVKF (SEQ ID NO: 548) |
| MS5 (Exc1-NO9) | RKERNIRKSESTLRL (SEQ ID NO: 892)<br>SESTLRLSPFPTPAP (SEQ ID NO: 893)<br>PFPTPAPSGAPAAAQ (SEQ ID NO: 894)<br>GAPAAAQGKVVRVPG (SEQ ID NO: 895)<br>KVVRVPGPAGGLVPR (SEQ ID NO: 896)<br>AGGLVPRDAGARLLP (SEQ ID NO: 897)<br>AGARLLPPAGGPGGG (SEQ ID NO: 898)<br>AGGPGGGAAAGEGRA (SEQ ID NO: 899)<br>AAGEGRAGRGRFPSI (SEQ ID NO: 900)<br>RGRFPSITEPRPRDL (SEQ ID NO: 901)<br>EPRPRDLPPRVATGR (SEQ ID NO: 902)<br>PRVATGRRAGGRRKG (SEQ ID NO: 903)<br>AGGRRKGAGQGVRTR (SEQ ID NO: 904)<br>GQGVRTRPLPASWPG (SEQ ID NO: 905)<br>LPASWPGGRGPFRKG (SEQ ID NO: 906)<br>RGPFRKGPRRLPLGS (SEQ ID NO: 907)<br>RRLPLGSGPPAAGVQ (SEQ ID NO: 908)<br>PPAAGVQRLRCSHLS (SEQ ID NO: 909)<br>LRCSHLSRGPRRRRG (SEQ ID NO: 910)<br>GPRRRRGRVCGRACV (SEQ ID NO: 911)<br>VCGRACVSPPLPPRP (SEQ ID NO: 912)<br>PPLPPRPPPVGLSAE (SEQ ID NO: 913)<br>PVGLSAENLSWLSSG (SEQ ID NO: 914)<br>LSWLSSGLPRACSWR (SEQ ID NO: 915)<br>PRACSWREFSPETCA (SEQ ID NO: 916)<br>FSPETCAFRLSGLDS (SEQ ID NO: 917)<br>RLSGLDSKLSARVER (SEQ ID NO: 918)<br>LSARVERDLGALRAP (SEQ ID NO: 919)<br>LGALRAPGSRAAQGG (SEQ ID NO: 920)<br>SRAAQGGGRVRGSRS (SEQ ID NO: 921)<br>RVRGSRSEWKTRPWR (SEQ ID NO: 922)<br>WKTRPWRPPPAWPLT (SEQ ID NO: 923)<br>PPAWPLTRAGGPLPK (SEQ ID NO: 924)<br>AGGPLPKNPFLESCS (SEQ ID NO: 925)<br>PFLESCSETAQRRRV (SEQ ID NO: 926)<br>TAQRRRVFSFSTPLS (SEQ ID NO: 927) |
| MS7 (Exc1-NO11) | SINKATITGKKDLEL (SEQ ID NO: 928)<br>GKKDLELILHVSRKK (SEQ ID NO: 929)<br>LHVSRKKPFLPRVNI (SEQ ID NO: 930)<br>FLPRVNITPTPISCC (SEQ ID NO: 931)<br>PTPISCCNLKMLKKF (SEQ ID NO: 932)<br>LKMLKKFFLLYIIIS (SEQ ID NO: 933)<br>LLYIIISIIDLTNCL (SEQ ID NO: 934)<br>IDLTNCLSCYLEHFY (SEQ ID NO: 935)<br>CYLEHFYRFTFFTDV (SEQ ID NO: 936)<br>FTFFTDVHYF (SEQ ID NO: 937) |
| MS9 (Exc1-NO13) | PYYSALSGNSWVPST (SEQ ID NO: 938)<br>NSWVPSTLESDPFGY (SEQ ID NO: 939)<br>ESDPFGYVFSPLATR (SEQ ID NO: 940)<br>FSPLATRPALNDQES (SEQ ID NO: 941)<br>ALNDQESILWPTLTS (SEQ ID NO: 942)<br>LWPTLTSVVSCALSC (SEQ ID NO: 943)<br>VSCALSCPSLNLPEN (SEQ ID NO: 944)<br>SLNLPENWLTLITGG (SEQ ID NO: 945)<br>LTLITGGMKGGKKMK (SEQ ID NO: 946)<br>KGGKKMKFTFRH (SEQ ID NO: 947) |
| MS10 (Exc1-NO14) | GLRNLGNTVRAILLS (SEQ ID NO: 948)<br>VRAILLSFLSKRNVK (SEQ ID NO: 949)<br>LSKRNVKWCWGWGKP (SEQ ID NO: 950)<br>CWGWGKPTSLGKACG (SEQ ID NO: 951)<br>SLGKACGRRALKLF (SEQ ID NO: 952) |
| MS11 (Exc1-NO15) | MEAENAGSLHFHEVL (SEQ ID NO: 953)<br>LHFHEVLKMGHVKF (SEQ ID NO: 954) |

TABLE 29-continued

| Neoantigen ID (Alternative name) | Peptide sequences |
|---|---|
| P97 (Misc1-NO11) | GYLRMQGLMAQRLLLR (SEQ ID NO: 383) |
| P19 (Misc1-NO8) | WTPIPVLTRWPLPHP (SEQ ID NO: 955)<br>RWPLPHPPPWRRATS (SEQ ID NO: 956)<br>PWRRATSCRMARSSP (SEQ ID NO: 957)<br>RMARSSPSATSGSSV (SEQ ID NO: 958)<br>ATSGSSVRRRCSSLP (SEQ ID NO: 959)<br>RRCSSLPSWVWNLAA (SEQ ID NO: 960)<br>WVWNLAASTRPRSTPS (SEQ ID NO: 961) |
| P27 (Misc1-NO9) | LHPQRETFTPRWSGA (SEQ ID NO: 962)<br>TPRWSGANYWKLAFP (SEQ ID NO: 963)<br>YWKLAFPVGAEGTFP (SEQ ID NO: 964)<br>GAEGTFPAAATQRGV (SEQ ID NO: 965)<br>AATQRGVVRPA (SEQ ID NO: 966) |

TABLE 29-continued

| Neoantigen ID (Alternative name) | Peptide sequences |
|---|---|
| P37 (Misc1-NO10) | MAGGVLRRLLCREPD (SEQ ID NO: 967)<br>LLCREPDRDGDKGAS (SEQ ID NO: 968)<br>DGDKGASREETVVPL (SEQ ID NO: 969)<br>EETVVPLHIGDPVVL (SEQ ID NO: 970)<br>IGDPVVLPGIGQCYS (SEQ ID NO: 971)<br>GIGQCYSALF (SEQ ID NO: 972) |
| P76, P77 (Misc2-NO18) | VFFKRAAEGFFRMNK (SEQ ID NO: 973)<br>GFFRMNKLKESSDTN (SEQ ID NO: 974)<br>KESSDTNPKPYCMAA (SEQ ID NO: 975)<br>KPYCMAAPMGLTENN (SEQ ID NO: 976)<br>MGLTENNRNRKKSYR (SEQ ID NO: 977)<br>NRKKSYRETNLKAVS (SEQ ID NO: 978)<br>TNLKAVSWPLNHT (SEQ ID NO: 979) |

What is claimed:

1. A method of treating prostate cancer in a subject, the method comprising administering to the subject a therapeutically effective amount of a vaccine comprising:
   a) a heterologous polynucleotide encoding a heterologous polypeptide comprising SEQ ID NOs: 275, 381, 333, 337, 269, 253, 309, 325, 271, 305, 251, 245, 261, 265, 317, 255, 297, 285, 437, 439, 442, 444, 379, 343, 211, 349, 213, 215, 221, 219, 225, 345, 353, 235, 223, 167, 171, 19, 23, and 177; or
   b) a heterologous polynucleotide comprising SEQ ID NOs: 276, 382, 334, 338, 270, 254, 310, 326, 272, 306, 252, 246, 262, 266, 318, 256, 298, 286, 448, 450, 453, 455, 380, 344, 212, 350, 214, 216, 222, 220, 226, 346, 354, 236, 224, 168, 172, 20, 24, and 178.

2. The method of claim 1, wherein the subject is treatment naïve.

3. The method of claim 1, wherein the prostate cancer is a relapsed prostate cancer, a refractory prostate cancer, a metastatic prostate cancer, a castration resistant prostate cancer, or any combination thereof.

4. The method of claim 3, wherein the subject has received androgen deprivation therapy.

5. The method of claim 1, wherein the subject has an elevated level of prostate specific antigen (PSA).

6. The method of claim 1, further comprising administering an additional cancer therapeutic agent to the subject.

7. The method of claim 6, wherein the additional cancer therapeutic agent is a surgery, a chemotherapy, an androgen deprivation therapy, radiation, a checkpoint inhibitor, a targeted therapy, or any combination thereof.

8. The method of claim 7, wherein the additional cancer therapeutic agent is a CTLA-4 antibody, a CTLA-4 ligand, a PD-1 axis inhibitor, a PD-L1 axis inhibitor, a TLR agonist, a CD40 agonist, an OX40 agonist, hydroxyurea, ruxolitinib, fedratinib, a 4-1BB agonist, a CD28 agonist, a STING antagonist, a RIG-1 antagonist, a TCR-T therapy, a CAR-T therapy, a FLT3 ligand, aluminum sulfate, a BTK inhibitor, a CD38 antibody, a CDK inhibitor, a CD33 antibody, a CD37 antibody, a CD25 antibody, a GM-CSF inhibitor, IL-2, IL-15, IL-7, CD3 redirection molecules, pomalimib, IFNy, IFNa, TNFa, a VEGF antibody, a CD70 antibody, a CD27 antibody, a BCMA antibody, a GPRC5D antibody, or any combination thereof.

9. The method of claim 7, wherein the checkpoint inhibitor is ipilimumab, cetrelimab, pembrolizumab, nivolumab, sintilimab, cemiplimab, toripalimab, camrelizumab, tislelizumab, dostralimab, spartalizumab, prolgolimab, balstilimab, budigalimab, sasanlimab, avelumab, atezolizumab, durvalumab, envafolimab, iodapolimab, or any combination thereof.

10. The method of claim 1, wherein the vaccine comprises a heterologous polynucleotide encoding a heterologous polypeptide comprising SEQ ID NOs: 275, 381, 333, 337, 269, 253, 309, 325, 271, 305, 251, 245, 261, 265, 317, 255, 297, 285, 437, 439, 442, 444, 379, 343, 211, 349, 213, 215, 221, 219, 225, 345, 353, 235, 223, 167, 171, 19, 23, and 177.

11. The method of claim 1, wherein the vaccine comprises a heterologous polynucleotide comprising SEQ ID NOs: 276, 382, 334, 338, 270, 254, 310, 326, 272, 306, 252, 246, 262, 266, 318, 256, 298, 286, 448, 450, 453, 455, 380, 344, 212, 350, 214, 216, 222, 220, 226, 346, 354, 236, 224, 168, 172, 20, 24, and 178.

12. The method of claim 1, wherein the vaccine is a DNA vaccine.

13. The method of claim 1, wherein the vaccine is an RNA vaccine.

14. The method of claim 1, wherein the vaccine is a recombinant virus.

15. The method of claim 14, wherein the recombinant virus is derived from adenovirus, poxvirus, AAV, or retrovirus.

16. The method of claim 15, wherein the recombinant virus is derived from hAd5, hAd7, hAd11, hAd26, hAd34, hAd35, hAd48, hAd49, hAd50, GAd20, GAd19, GAd21, GAd25, GAd26, GAd27, GAd28, GAd29, GAd30, GAd31, ChAd3, ChAd4, ChAd5, ChAd6, ChAd7, ChAd8, ChAd9, ChAd10, ChAd11, ChAd16, ChAd17, ChAd19, ChAd20, ChAd22, ChAd24, ChAd26, ChAd30, ChAd31, ChAd37, ChAd38, ChAd44, ChAd55, ChAd63, ChAd73, ChAd82, ChAd83, ChAd146, ChAd147, PanAd1, PanAd2, PanAd3, Copenhagen vaccinia virus (W), New York Attenuated Vaccinia Virus (NYVAC), ALVAC, TROVAC, or MVA.

17. The method of claim 16, wherein the recombinant virus is derived from GAd20.

18. The method of claim 16, wherein the recombinant virus is derived from MVA.

19. The method of claim 1, wherein the vaccine is administered one or more times to the subject.

20. The method of claim 10, wherein the vaccine is a recombinant virus derived from MVA.

21. The method of claim 10, wherein the vaccine is a recombinant virus derived from GAd20.

22. The method of claim 11, wherein the vaccine is a recombinant virus derived from MVA.

23. The method of claim 11, wherein the vaccine is a recombinant virus derived from GAd20.

* * * * *

SEQUENCE LISTING

```
Sequence total quantity: 980
SEQ ID NO: 1            moltype = AA  length = 17
FEATURE                 Location/Qualifiers
source                  1..17
                        mol_type = protein
                        organism = Homo sapiens
SEQUENCE: 1
SSCMGGMNQR PILTIIT                                               17

SEQ ID NO: 2            moltype = DNA  length = 51
FEATURE                 Location/Qualifiers
source                  1..51
                        mol_type = genomic DNA
                        organism = Homo sapiens
SEQUENCE: 2
agttcctgca tgggcggcat gaaccagagg cccatcctca ccatcatcac a         51

SEQ ID NO: 3            moltype = AA  length = 17
FEATURE                 Location/Qualifiers
source                  1..17
                        mol_type = protein
                        organism = Homo sapiens
SEQUENCE: 3
SSCMGGMNWR PILTIIT                                               17

SEQ ID NO: 4            moltype = DNA  length = 51
FEATURE                 Location/Qualifiers
source                  1..51
                        mol_type = genomic DNA
                        organism = Homo sapiens
SEQUENCE: 4
agttcctgca tgggcggcat gaattggagg cccatcctca ccatcatcac a         51

SEQ ID NO: 5            moltype = AA  length = 17
FEATURE                 Location/Qualifiers
source                  1..17
                        mol_type = protein
                        organism = Homo sapiens
SEQUENCE: 5
LGRNSFEVCV CACPGRD                                               17

SEQ ID NO: 6            moltype = DNA  length = 51
FEATURE                 Location/Qualifiers
source                  1..51
                        mol_type = genomic DNA
                        organism = Homo sapiens
SEQUENCE: 6
ctgggacgga acagctttga ggtgtgtgtt tgtgcctgtc ctgggagaga c         51

SEQ ID NO: 7            moltype = AA  length = 17
FEATURE                 Location/Qualifiers
source                  1..17
                        mol_type = protein
```

```
                         organism = Homo sapiens
SEQUENCE: 7
LGRNSFEVLV CACPGRD                                                17

SEQ ID NO: 8             moltype = DNA  length = 51
FEATURE                  Location/Qualifiers
source                   1..51
                         mol_type = genomic DNA
                         organism = Homo sapiens
SEQUENCE: 8
ctgggacgga acagctttga ggtgcttgtt tgtgcctgtc ctgggagaga c          51

SEQ ID NO: 9             moltype = AA  length = 17
FEATURE                  Location/Qualifiers
source                   1..17
                         mol_type = protein
                         organism = Homo sapiens
SEQUENCE: 9
MCNSSCMGSM NRRPILT                                                17

SEQ ID NO: 10            moltype = DNA  length = 51
FEATURE                  Location/Qualifiers
source                   1..51
                         mol_type = genomic DNA
                         organism = Homo sapiens
SEQUENCE: 10
atgtgtaaca gttcctgcat gggcagcatg aaccggaggc ccatcctcac c          51

SEQ ID NO: 11            moltype = AA  length = 17
FEATURE                  Location/Qualifiers
source                   1..17
                         mol_type = protein
                         organism = Homo sapiens
SEQUENCE: 11
FRHSVVVPCE PPEVGSD                                                17

SEQ ID NO: 12            moltype = DNA  length = 51
FEATURE                  Location/Qualifiers
source                   1..51
                         mol_type = genomic DNA
                         organism = Homo sapiens
SEQUENCE: 12
tttcgacata gtgtggtggt gccctgtgag ccgcctgagg ttggctctga c          51

SEQ ID NO: 13            moltype = AA  length = 17
FEATURE                  Location/Qualifiers
source                   1..17
                         mol_type = protein
                         organism = Homo sapiens
SEQUENCE: 13
VCACPGRDWR TEEENLR                                                17

SEQ ID NO: 14            moltype = DNA  length = 51
FEATURE                  Location/Qualifiers
source                   1..51
                         mol_type = genomic DNA
                         organism = Homo sapiens
SEQUENCE: 14
gtttgtgcct gtcctgggag agattggcgc acagaggaag agaatctccg c          51

SEQ ID NO: 15            moltype = AA  length = 17
FEATURE                  Location/Qualifiers
source                   1..17
                         mol_type = protein
                         organism = Homo sapiens
SEQUENCE: 15
FVQGKDWGCK KFIRRDF                                                17

SEQ ID NO: 16            moltype = DNA  length = 51
FEATURE                  Location/Qualifiers
source                   1..51
                         mol_type = genomic DNA
                         organism = Homo sapiens
SEQUENCE: 16
tttgtgcaag gcaaagactg gggatgcaag aaattcatcc gtagagattt t          51

SEQ ID NO: 17            moltype = AA  length = 17
FEATURE                  Location/Qualifiers
source                   1..17
```

```
                        mol_type = protein
                        organism = Homo sapiens
SEQUENCE: 17
FVQGKDWGIK KFIRRDF                                                17

SEQ ID NO: 18           moltype = DNA  length = 51
FEATURE                 Location/Qualifiers
source                  1..51
                        mol_type = genomic DNA
                        organism = Homo sapiens
SEQUENCE: 18
tttgtgcaag gcaaagactg gggaatcaag aaattcatcc gtagagattt t          51

SEQ ID NO: 19           moltype = AA  length = 17
FEATURE                 Location/Qualifiers
source                  1..17
                        mol_type = protein
                        organism = Homo sapiens
SEQUENCE: 19
FVQGKDWGLK KFIRRDF                                                17

SEQ ID NO: 20           moltype = DNA  length = 51
FEATURE                 Location/Qualifiers
source                  1..51
                        mol_type = genomic DNA
                        organism = Homo sapiens
SEQUENCE: 20
tttgtgcaag gcaaagactg gggattaaag aaattcatcc gtagagattt t          51

SEQ ID NO: 21           moltype = AA  length = 17
FEATURE                 Location/Qualifiers
source                  1..17
                        mol_type = protein
                        organism = Homo sapiens
SEQUENCE: 21
FVQGKDWGSK KFIRRDF                                                17

SEQ ID NO: 22           moltype = DNA  length = 51
FEATURE                 Location/Qualifiers
source                  1..51
                        mol_type = genomic DNA
                        organism = Homo sapiens
SEQUENCE: 22
tttgtgcaag gcaaagactg gggatccaag aaattcatcc gtagagattt t          51

SEQ ID NO: 23           moltype = AA  length = 17
FEATURE                 Location/Qualifiers
source                  1..17
                        mol_type = protein
                        organism = Homo sapiens
SEQUENCE: 23
FVQGKDWGVK KFIRRDF                                                17

SEQ ID NO: 24           moltype = DNA  length = 51
FEATURE                 Location/Qualifiers
source                  1..51
                        mol_type = genomic DNA
                        organism = Homo sapiens
SEQUENCE: 24
tttgtgcaag gcaaagactg gggagtcaag aaattcatcc gtagagattt t          51

SEQ ID NO: 25           moltype = AA  length = 17
FEATURE                 Location/Qualifiers
source                  1..17
                        mol_type = protein
                        organism = Homo sapiens
SEQUENCE: 25
YRFVQGKDCG FKKFIRR                                                17

SEQ ID NO: 26           moltype = DNA  length = 51
FEATURE                 Location/Qualifiers
source                  1..51
                        mol_type = genomic DNA
                        organism = Homo sapiens
SEQUENCE: 26
tataggtttg tgcaaggcaa agactgtgga ttcaagaaat tcatccgtag a          51

SEQ ID NO: 27           moltype = AA  length = 17
FEATURE                 Location/Qualifiers
```

```
source                  1..17
                        mol_type = protein
                        organism = Homo sapiens
SEQUENCE: 27
YRFVQGKDGG FKKFIRR                                              17

SEQ ID NO: 28           moltype = DNA  length = 51
FEATURE                 Location/Qualifiers
source                  1..51
                        mol_type = genomic DNA
                        organism = Homo sapiens
SEQUENCE: 28
tataggtttg tgcaaggcaa agacggggga ttcaagaaat tcatccgtag a        51

SEQ ID NO: 29           moltype = AA  length = 17
FEATURE                 Location/Qualifiers
source                  1..17
                        mol_type = protein
                        organism = Homo sapiens
SEQUENCE: 29
YRFVQGKDLG FKKFIRR                                              17

SEQ ID NO: 30           moltype = DNA  length = 51
FEATURE                 Location/Qualifiers
source                  1..51
                        mol_type = genomic DNA
                        organism = Homo sapiens
SEQUENCE: 30
tataggtttg tgcaaggcaa agactgggga ttcaagaaat tcatccgtag a        51

SEQ ID NO: 31           moltype = AA  length = 17
FEATURE                 Location/Qualifiers
source                  1..17
                        mol_type = protein
                        organism = Homo sapiens
SEQUENCE: 31
YRFVQGKDRG FKKFIRR                                              17

SEQ ID NO: 32           moltype = DNA  length = 51
FEATURE                 Location/Qualifiers
source                  1..51
                        mol_type = genomic DNA
                        organism = Homo sapiens
SEQUENCE: 32
tataggtttg tgcaaggcaa agaccgggga ttcaagaaat tcatccgtag a        51

SEQ ID NO: 33           moltype = AA  length = 17
FEATURE                 Location/Qualifiers
source                  1..17
                        mol_type = protein
                        organism = Homo sapiens
SEQUENCE: 33
YRFVQGKDSG FKKFIRR                                              17

SEQ ID NO: 34           moltype = DNA  length = 51
FEATURE                 Location/Qualifiers
source                  1..51
                        mol_type = genomic DNA
                        organism = Homo sapiens
SEQUENCE: 34
tataggtttg tgcaaggcaa agactcggga ttcaagaaat tcatccgtag a        51

SEQ ID NO: 35           moltype = AA  length = 17
FEATURE                 Location/Qualifiers
source                  1..17
                        mol_type = protein
                        organism = Homo sapiens
SEQUENCE: 35
YPVGYEATHI YWSLRTN                                              17

SEQ ID NO: 36           moltype = DNA  length = 51
FEATURE                 Location/Qualifiers
source                  1..51
                        mol_type = genomic DNA
                        organism = Homo sapiens
SEQUENCE: 36
tatcccgtgg gctacgaggc cacgcacatc tattggagcc tccgcaccaa c        51

SEQ ID NO: 37           moltype = AA  length = 17
```

```
FEATURE                Location/Qualifiers
source                 1..17
                       mol_type = protein
                       organism = Homo sapiens
SEQUENCE: 37
MFENGCYLCR QKRFKCE                                              17

SEQ ID NO: 38          moltype = DNA  length = 51
FEATURE                Location/Qualifiers
source                 1..51
                       mol_type = genomic DNA
                       organism = Homo sapiens
SEQUENCE: 38
atgttcgaga acggctgcta cttgtgccgc cagaagcgct tcaagtgcga g           51

SEQ ID NO: 39          moltype = AA  length = 17
FEATURE                Location/Qualifiers
source                 1..17
                       mol_type = protein
                       organism = Homo sapiens
SEQUENCE: 39
GKGSYWTLQP DSGNMFE                                              17

SEQ ID NO: 40          moltype = DNA  length = 51
FEATURE                Location/Qualifiers
source                 1..51
                       mol_type = genomic DNA
                       organism = Homo sapiens
SEQUENCE: 40
ggcaagggct cctactggac gctgcagccg gactccggca acatgttcga g           51

SEQ ID NO: 41          moltype = AA  length = 17
FEATURE                Location/Qualifiers
source                 1..17
                       mol_type = protein
                       organism = Homo sapiens
SEQUENCE: 41
GKGSYWTLLP DSGNMFE                                              17

SEQ ID NO: 42          moltype = DNA  length = 51
FEATURE                Location/Qualifiers
source                 1..51
                       mol_type = genomic DNA
                       organism = Homo sapiens
SEQUENCE: 42
ggcaagggct cctactggac gctgctcccg gactccggca acatgttcga g           51

SEQ ID NO: 43          moltype = AA  length = 17
FEATURE                Location/Qualifiers
source                 1..17
                       mol_type = protein
                       organism = Homo sapiens
SEQUENCE: 43
GKGSYWTLNP DSGNMFE                                              17

SEQ ID NO: 44          moltype = DNA  length = 51
FEATURE                Location/Qualifiers
source                 1..51
                       mol_type = genomic DNA
                       organism = Homo sapiens
SEQUENCE: 44
ggcaagggct cctactggac gctgaacccg gactccggca acatgttcga g           51

SEQ ID NO: 45          moltype = AA  length = 17
FEATURE                Location/Qualifiers
source                 1..17
                       mol_type = protein
                       organism = Homo sapiens
SEQUENCE: 45
GKGSYWTLYP DSGNMFE                                              17

SEQ ID NO: 46          moltype = DNA  length = 51
FEATURE                Location/Qualifiers
source                 1..51
                       mol_type = genomic DNA
                       organism = Homo sapiens
SEQUENCE: 46
ggcaagggct cctactggac gctgtacccg gactccggca acatgttcga g           51
```

```
SEQ ID NO: 47          moltype = AA  length = 17
FEATURE                Location/Qualifiers
source                 1..17
                       mol_type = protein
                       organism = Homo sapiens
SEQUENCE: 47
CYLRRQKRCK CEKQPGA                                                17

SEQ ID NO: 48          moltype = DNA  length = 51
FEATURE                Location/Qualifiers
source                 1..51
                       mol_type = genomic DNA
                       organism = Homo sapiens
SEQUENCE: 48
tgctacttgc gccgccagaa gcgctgcaag tgcgagaagc agccgggggc c          51

SEQ ID NO: 49          moltype = AA  length = 17
FEATURE                Location/Qualifiers
source                 1..17
                       mol_type = protein
                       organism = Homo sapiens
SEQUENCE: 49
CYLRRQKRSK CEKQPGA                                                17

SEQ ID NO: 50          moltype = DNA  length = 51
FEATURE                Location/Qualifiers
source                 1..51
                       mol_type = genomic DNA
                       organism = Homo sapiens
SEQUENCE: 50
tgctacttgc gccgccagaa gcgctccaag tgcgagaagc agccgggggc c          51

SEQ ID NO: 51          moltype = AA  length = 17
FEATURE                Location/Qualifiers
source                 1..17
                       mol_type = protein
                       organism = Homo sapiens
SEQUENCE: 51
IRHSLSFNGC FVKVARS                                                17

SEQ ID NO: 52          moltype = DNA  length = 51
FEATURE                Location/Qualifiers
source                 1..51
                       mol_type = genomic DNA
                       organism = Homo sapiens
SEQUENCE: 52
atccgccact cgctgtcctt caatggctgc ttcgtcaagg tggcacgctc c          51

SEQ ID NO: 53          moltype = AA  length = 17
FEATURE                Location/Qualifiers
source                 1..17
                       mol_type = protein
                       organism = Homo sapiens
SEQUENCE: 53
IRHSLSFNNC FVKVARS                                                17

SEQ ID NO: 54          moltype = DNA  length = 51
FEATURE                Location/Qualifiers
source                 1..51
                       mol_type = genomic DNA
                       organism = Homo sapiens
SEQUENCE: 54
atccgccact cgctgtcctt caataactgc ttcgtcaagg tggcacgctc c          51

SEQ ID NO: 55          moltype = AA  length = 17
FEATURE                Location/Qualifiers
source                 1..17
                       mol_type = protein
                       organism = Homo sapiens
SEQUENCE: 55
QQRWQNSICH SLSFNDC                                                17

SEQ ID NO: 56          moltype = DNA  length = 51
FEATURE                Location/Qualifiers
source                 1..51
                       mol_type = genomic DNA
                       organism = Homo sapiens
SEQUENCE: 56
cagcagcgct ggcagaactc catctgccac tcgctgtcct tcaatgactg c          51
```

```
SEQ ID NO: 57          moltype = AA  length = 17
FEATURE                Location/Qualifiers
source                 1..17
                       mol_type = protein
                       organism = Homo sapiens
SEQUENCE: 57
QQRWQNSISH SLSFNDC                                                17

SEQ ID NO: 58          moltype = DNA  length = 51
FEATURE                Location/Qualifiers
source                 1..51
                       mol_type = genomic DNA
                       organism = Homo sapiens
SEQUENCE: 58
cagcagcgct ggcagaactc catcagccac tcgctgtcct tcaatgactg c          51

SEQ ID NO: 59          moltype = AA  length = 17
FEATURE                Location/Qualifiers
source                 1..17
                       mol_type = protein
                       organism = Homo sapiens
SEQUENCE: 59
TLHPDSGNKF ENGCYLR                                                17

SEQ ID NO: 60          moltype = DNA  length = 51
FEATURE                Location/Qualifiers
source                 1..51
                       mol_type = genomic DNA
                       organism = Homo sapiens
SEQUENCE: 60
acgctgcacc cggactccgg caacaagttc gagaacggct gctacttgcg c          51

SEQ ID NO: 61          moltype = AA  length = 17
FEATURE                Location/Qualifiers
source                 1..17
                       mol_type = protein
                       organism = Homo sapiens
SEQUENCE: 61
TLHPDSGNRF ENGCYLR                                                17

SEQ ID NO: 62          moltype = DNA  length = 51
FEATURE                Location/Qualifiers
source                 1..51
                       mol_type = genomic DNA
                       organism = Homo sapiens
SEQUENCE: 62
acgctgcacc cggactccgg caacaggttc gagaacggct gctacttgcg c          51

SEQ ID NO: 63          moltype = AA  length = 17
FEATURE                Location/Qualifiers
source                 1..17
                       mol_type = protein
                       organism = Homo sapiens
SEQUENCE: 63
CHKKNFLHWD IKCSNIL                                                17

SEQ ID NO: 64          moltype = DNA  length = 51
FEATURE                Location/Qualifiers
source                 1..51
                       mol_type = genomic DNA
                       organism = Homo sapiens
SEQUENCE: 64
tgtcacaaaa agaatttcct gcattgggat attaagtgtt ctaacatttt g          51

SEQ ID NO: 65          moltype = AA  length = 17
FEATURE                Location/Qualifiers
source                 1..17
                       mol_type = protein
                       organism = Homo sapiens
SEQUENCE: 65
IHCKAGKGQT GVMICAY                                                17

SEQ ID NO: 66          moltype = DNA  length = 51
FEATURE                Location/Qualifiers
source                 1..51
                       mol_type = genomic DNA
                       organism = Homo sapiens
SEQUENCE: 66
```

```
attcactgta aagctggaaa gggacaaact ggtgtaatga tatgtgcata t          51

SEQ ID NO: 67          moltype = AA  length = 17
FEATURE                Location/Qualifiers
source                 1..17
                       mol_type = protein
                       organism = Homo sapiens
SEQUENCE: 67
WLSEDDNHFA AIHCKAG                                                17

SEQ ID NO: 68          moltype = DNA  length = 51
FEATURE                Location/Qualifiers
source                 1..51
                       mol_type = genomic DNA
                       organism = Homo sapiens
SEQUENCE: 68
tggctaagtg aagatgacaa tcattttgca gcaattcact gtaaagctgg a          51

SEQ ID NO: 69          moltype = AA  length = 17
FEATURE                Location/Qualifiers
source                 1..17
                       mol_type = protein
                       organism = Homo sapiens
SEQUENCE: 69
GLGDRHVQSI LINEQSA                                                17

SEQ ID NO: 70          moltype = DNA  length = 51
FEATURE                Location/Qualifiers
source                 1..51
                       mol_type = genomic DNA
                       organism = Homo sapiens
SEQUENCE: 70
ggacttggtg atagacatgt acagagtatc ttgataaatg agcagtcagc a          51

SEQ ID NO: 71          moltype = AA  length = 17
FEATURE                Location/Qualifiers
source                 1..17
                       mol_type = protein
                       organism = Homo sapiens
SEQUENCE: 71
GLGDRHVQKI LINEQSA                                                17

SEQ ID NO: 72          moltype = DNA  length = 51
FEATURE                Location/Qualifiers
source                 1..51
                       mol_type = genomic DNA
                       organism = Homo sapiens
SEQUENCE: 72
ggacttggtg atagacatgt acagaaaatc ttgataaatg agcagtcagc a          51

SEQ ID NO: 73          moltype = AA  length = 17
FEATURE                Location/Qualifiers
source                 1..17
                       mol_type = protein
                       organism = Homo sapiens
SEQUENCE: 73
NINIGPGDSE WFVVPEG                                                17

SEQ ID NO: 74          moltype = DNA  length = 51
FEATURE                Location/Qualifiers
source                 1..51
                       mol_type = genomic DNA
                       organism = Homo sapiens
SEQUENCE: 74
aacataaata ttggcccagg tgactctgaa tggtttgttg ttcctgaagg t          51

SEQ ID NO: 75          moltype = AA  length = 17
FEATURE                Location/Qualifiers
source                 1..17
                       mol_type = protein
                       organism = Homo sapiens
SEQUENCE: 75
NINIGPGDYE WFVVPEG                                                17

SEQ ID NO: 76          moltype = DNA  length = 51
FEATURE                Location/Qualifiers
source                 1..51
                       mol_type = genomic DNA
                       organism = Homo sapiens
```

```
SEQUENCE: 76
aacataaata ttggcccagg tgactatgaa tggtttgttg ttcctgaagg t           51

SEQ ID NO: 77          moltype = AA  length = 17
FEATURE                Location/Qualifiers
source                 1..17
                       mol_type = protein
                       organism = Homo sapiens
SEQUENCE: 77
FMKQMNDARH GGWTTKM                                                 17

SEQ ID NO: 78          moltype = DNA  length = 51
FEATURE                Location/Qualifiers
source                 1..51
                       mol_type = genomic DNA
                       organism = Homo sapiens
SEQUENCE: 78
ttcatgaaac aaatgaatga tgcacgtcat ggtggctgga caacaaaaat g           51

SEQ ID NO: 79          moltype = AA  length = 17
FEATURE                Location/Qualifiers
source                 1..17
                       mol_type = protein
                       organism = Homo sapiens
SEQUENCE: 79
RDPLSEITKQ EKDFLWS                                                 17

SEQ ID NO: 80          moltype = DNA  length = 51
FEATURE                Location/Qualifiers
source                 1..51
                       mol_type = genomic DNA
                       organism = Homo sapiens
SEQUENCE: 80
cgagatcctc tctctgaaat cactaagcag gagaaagatt ttctatggag t           51

SEQ ID NO: 81          moltype = AA  length = 17
FEATURE                Location/Qualifiers
source                 1..17
                       mol_type = protein
                       organism = Homo sapiens
SEQUENCE: 81
RDPLSEITGQ EKDFLWS                                                 17

SEQ ID NO: 82          moltype = DNA  length = 51
FEATURE                Location/Qualifiers
source                 1..51
                       mol_type = genomic DNA
                       organism = Homo sapiens
SEQUENCE: 82
cgagatcctc tctctgaaat cactgggcag gagaaagatt ttctatggag t           51

SEQ ID NO: 83          moltype = AA  length = 17
FEATURE                Location/Qualifiers
source                 1..17
                       mol_type = protein
                       organism = Homo sapiens
SEQUENCE: 83
RDPLSEITAQ EKDFLWS                                                 17

SEQ ID NO: 84          moltype = DNA  length = 51
FEATURE                Location/Qualifiers
source                 1..51
                       mol_type = genomic DNA
                       organism = Homo sapiens
SEQUENCE: 84
cgagatcctc tctctgaaat cactgcgcag gagaaagatt ttctatggag t           51

SEQ ID NO: 85          moltype = AA  length = 17
FEATURE                Location/Qualifiers
source                 1..17
                       mol_type = protein
                       organism = Homo sapiens
SEQUENCE: 85
SGIHSGATAT APSLSGK                                                 17

SEQ ID NO: 86          moltype = DNA  length = 51
FEATURE                Location/Qualifiers
source                 1..51
                       mol_type = genomic DNA
```

```
                         organism = Homo sapiens
SEQUENCE: 86
tctggaatcc attctggtgc cactgccaca gctccttctc tgagtggtaa a            51

SEQ ID NO: 87            moltype = AA  length = 17
FEATURE                  Location/Qualifiers
source                   1..17
                         mol_type = protein
                         organism = Homo sapiens
SEQUENCE: 87
HWQQQSYLAS GIHSGAT                                                  17

SEQ ID NO: 88            moltype = DNA  length = 51
FEATURE                  Location/Qualifiers
source                   1..51
                         mol_type = genomic DNA
                         organism = Homo sapiens
SEQUENCE: 88
cactggcagc aacagtctta cctggcctct ggaatccatt ctggtgccac t            51

SEQ ID NO: 89            moltype = AA  length = 17
FEATURE                  Location/Qualifiers
source                   1..17
                         mol_type = protein
                         organism = Homo sapiens
SEQUENCE: 89
HWQQQSYLHS GIHSGAT                                                  17

SEQ ID NO: 90            moltype = DNA  length = 51
FEATURE                  Location/Qualifiers
source                   1..51
                         mol_type = genomic DNA
                         organism = Homo sapiens
SEQUENCE: 90
cactggcagc aacagtctta cctgcactct ggaatccatt ctggtgccac t            51

SEQ ID NO: 91            moltype = AA  length = 17
FEATURE                  Location/Qualifiers
source                   1..17
                         mol_type = protein
                         organism = Homo sapiens
SEQUENCE: 91
HWQQQSYLVS GIHSGAT                                                  17

SEQ ID NO: 92            moltype = DNA  length = 51
FEATURE                  Location/Qualifiers
source                   1..51
                         mol_type = genomic DNA
                         organism = Homo sapiens
SEQUENCE: 92
cactggcagc aacagtctta cctggtctct ggaatccatt ctggtgccac t            51

SEQ ID NO: 93            moltype = AA  length = 17
FEATURE                  Location/Qualifiers
source                   1..17
                         mol_type = protein
                         organism = Homo sapiens
SEQUENCE: 93
HWQQQSYLYS GIHSGAT                                                  17

SEQ ID NO: 94            moltype = DNA  length = 51
FEATURE                  Location/Qualifiers
source                   1..51
                         mol_type = genomic DNA
                         organism = Homo sapiens
SEQUENCE: 94
cactggcagc aacagtctta cctgtactct ggaatccatt ctggtgccac t            51

SEQ ID NO: 95            moltype = AA  length = 17
FEATURE                  Location/Qualifiers
source                   1..17
                         mol_type = protein
                         organism = Homo sapiens
SEQUENCE: 95
SYLDSGIHAG ATTTAPS                                                  17

SEQ ID NO: 96            moltype = DNA  length = 51
FEATURE                  Location/Qualifiers
source                   1..51
```

```
                        mol_type = genomic DNA
                        organism = Homo sapiens
SEQUENCE: 96
tcttacctgg actctggaat ccatgctggt gccactacca cagctccttc t           51

SEQ ID NO: 97           moltype = AA  length = 17
FEATURE                 Location/Qualifiers
source                  1..17
                        mol_type = protein
                        organism = Homo sapiens
SEQUENCE: 97
SYLDSGIHCG ATTTAPS                                                 17

SEQ ID NO: 98           moltype = DNA  length = 51
FEATURE                 Location/Qualifiers
source                  1..51
                        mol_type = genomic DNA
                        organism = Homo sapiens
SEQUENCE: 98
tcttacctgg actctggaat ccattgtggt gccactacca cagctccttc t           51

SEQ ID NO: 99           moltype = AA  length = 17
FEATURE                 Location/Qualifiers
source                  1..17
                        mol_type = protein
                        organism = Homo sapiens
SEQUENCE: 99
SYLDSGIHFG ATTTAPS                                                 17

SEQ ID NO: 100          moltype = DNA  length = 51
FEATURE                 Location/Qualifiers
source                  1..51
                        mol_type = genomic DNA
                        organism = Homo sapiens
SEQUENCE: 100
tcttacctgg actctggaat ccattttggt gccactacca cagctccttc t           51

SEQ ID NO: 101          moltype = AA  length = 17
FEATURE                 Location/Qualifiers
source                  1..17
                        mol_type = protein
                        organism = Homo sapiens
SEQUENCE: 101
SYLDSGIHYG ATTTAPS                                                 17

SEQ ID NO: 102          moltype = DNA  length = 51
FEATURE                 Location/Qualifiers
source                  1..51
                        mol_type = genomic DNA
                        organism = Homo sapiens
SEQUENCE: 102
tcttacctgg actctggaat ccattatggt gccactacca cagctccttc t           51

SEQ ID NO: 103          moltype = AA  length = 17
FEATURE                 Location/Qualifiers
source                  1..17
                        mol_type = protein
                        organism = Homo sapiens
SEQUENCE: 103
SGATTTAPCL SGKGNPE                                                 17

SEQ ID NO: 104          moltype = DNA  length = 51
FEATURE                 Location/Qualifiers
source                  1..51
                        mol_type = genomic DNA
                        organism = Homo sapiens
SEQUENCE: 104
tctggtgcca ctaccacagc tccttgtctg agtggtaaag gcaatcctga g           51

SEQ ID NO: 105          moltype = AA  length = 17
FEATURE                 Location/Qualifiers
source                  1..17
                        mol_type = protein
                        organism = Homo sapiens
SEQUENCE: 105
SGATTTAPFL SGKGNPE                                                 17

SEQ ID NO: 106          moltype = DNA  length = 51
FEATURE                 Location/Qualifiers
```

```
source                  1..51
                        mol_type = genomic DNA
                        organism = Homo sapiens
SEQUENCE: 106
tctggtgcca ctaccacagc tccttttctg agtggtaaag gcaatcctga g           51

SEQ ID NO: 107          moltype = AA  length = 17
FEATURE                 Location/Qualifiers
source                  1..17
                        mol_type = protein
                        organism = Homo sapiens
SEQUENCE: 107
SGATTTAPPL SGKGNPE                                                 17

SEQ ID NO: 108          moltype = DNA  length = 51
FEATURE                 Location/Qualifiers
source                  1..51
                        mol_type = genomic DNA
                        organism = Homo sapiens
SEQUENCE: 108
tctggtgcca ctaccacagc tcctcctctg agtggtaaag gcaatcctga g           51

SEQ ID NO: 109          moltype = AA  length = 17
FEATURE                 Location/Qualifiers
source                  1..17
                        mol_type = protein
                        organism = Homo sapiens
SEQUENCE: 109
YVPSEDYYKP SPYDDLT                                                 17

SEQ ID NO: 110          moltype = DNA  length = 51
FEATURE                 Location/Qualifiers
source                  1..51
                        mol_type = genomic DNA
                        organism = Homo sapiens
SEQUENCE: 110
tacgtgccca gtgaggacta ctacaagccc tcaccgtatg atgacctcac c           51

SEQ ID NO: 111          moltype = AA  length = 17
FEATURE                 Location/Qualifiers
source                  1..17
                        mol_type = protein
                        organism = Homo sapiens
SEQUENCE: 111
IRKRLKLCTD FKRTGMD                                                 17

SEQ ID NO: 112          moltype = DNA  length = 51
FEATURE                 Location/Qualifiers
source                  1..51
                        mol_type = genomic DNA
                        organism = Homo sapiens
SEQUENCE: 112
atccggaaga ggctaaagct ctgcactgac ttcaaacgca cagggatgga t           51

SEQ ID NO: 113          moltype = AA  length = 17
FEATURE                 Location/Qualifiers
source                  1..17
                        mol_type = protein
                        organism = Homo sapiens
SEQUENCE: 113
VDGAVFAVFK AVFVLGD                                                 17

SEQ ID NO: 114          moltype = DNA  length = 51
FEATURE                 Location/Qualifiers
source                  1..51
                        mol_type = genomic DNA
                        organism = Homo sapiens
SEQUENCE: 114
gtggatggag ccgtgtttgc tgttttcaag gctgtgtttg tacttgggga t           51

SEQ ID NO: 115          moltype = AA  length = 17
FEATURE                 Location/Qualifiers
source                  1..17
                        mol_type = protein
                        organism = Homo sapiens
SEQUENCE: 115
IVDGAVFAGL KAVFVLG                                                 17

SEQ ID NO: 116          moltype = DNA  length = 51
```

```
FEATURE                Location/Qualifiers
source                 1..51
                       mol_type = genomic DNA
                       organism = Homo sapiens
SEQUENCE: 116
atcgtggatg gagccgtgtt tgctggtctc aaggctgtgt ttgtacttgg g          51

SEQ ID NO: 117         moltype = AA  length = 17
FEATURE                Location/Qualifiers
source                 1..17
                       mol_type = protein
                       organism = Homo sapiens
SEQUENCE: 117
IVDGAVFALL KAVFVLG                                                17

SEQ ID NO: 118         moltype = DNA  length = 51
FEATURE                Location/Qualifiers
source                 1..51
                       mol_type = genomic DNA
                       organism = Homo sapiens
SEQUENCE: 118
atcgtggatg gagccgtgtt tgctcttctc aaggctgtgt ttgtacttgg g          51

SEQ ID NO: 119         moltype = AA  length = 17
FEATURE                Location/Qualifiers
source                 1..17
                       mol_type = protein
                       organism = Homo sapiens
SEQUENCE: 119
THTANERRWR GEMRDLF                                                17

SEQ ID NO: 120         moltype = DNA  length = 51
FEATURE                Location/Qualifiers
source                 1..51
                       mol_type = genomic DNA
                       organism = Homo sapiens
SEQUENCE: 120
acacacactg ccaatgagcg gcggtggcgt ggtgaaatga gggatctctt t          51

SEQ ID NO: 121         moltype = AA  length = 17
FEATURE                Location/Qualifiers
source                 1..17
                       mol_type = protein
                       organism = Homo sapiens
SEQUENCE: 121
GRFSKVSSRA PMEGGEE                                                17

SEQ ID NO: 122         moltype = DNA  length = 51
FEATURE                Location/Qualifiers
source                 1..51
                       mol_type = genomic DNA
                       organism = Homo sapiens
SEQUENCE: 122
gggaggttca gcaaggtgtc tagtcgagct cccatggagg gtggggaaga a          51

SEQ ID NO: 123         moltype = AA  length = 17
FEATURE                Location/Qualifiers
source                 1..17
                       mol_type = protein
                       organism = Homo sapiens
SEQUENCE: 123
GKTEDLGCRY KLFSRVP                                                17

SEQ ID NO: 124         moltype = DNA  length = 51
FEATURE                Location/Qualifiers
source                 1..51
                       mol_type = genomic DNA
                       organism = Homo sapiens
SEQUENCE: 124
ggaaagacag aagaccttgg ttgcaggtac aagttattta gtcgtgtgcc a          51

SEQ ID NO: 125         moltype = AA  length = 12
FEATURE                Location/Qualifiers
source                 1..12
                       mol_type = protein
                       organism = Homo sapiens
SEQUENCE: 125
MNHHQQQQQQ KA                                                     12
```

```
SEQ ID NO: 126          moltype = DNA  length = 36
FEATURE                 Location/Qualifiers
source                  1..36
                        mol_type = genomic DNA
                        organism = Homo sapiens
SEQUENCE: 126
atgaaccacc accagcagca gcagcagcag aaagcg                          36

SEQ ID NO: 127          moltype = AA  length = 17
FEATURE                 Location/Qualifiers
source                  1..17
                        mol_type = protein
                        organism = Homo sapiens
SEQUENCE: 127
HGLVDEQQEV RTISALA                                               17

SEQ ID NO: 128          moltype = DNA  length = 51
FEATURE                 Location/Qualifiers
source                  1..51
                        mol_type = genomic DNA
                        organism = Homo sapiens
SEQUENCE: 128
catggtcttg tggatgagca gcaggaagtt cggaccatca gtgctttggc c           51

SEQ ID NO: 129          moltype = AA  length = 17
FEATURE                 Location/Qualifiers
source                  1..17
                        mol_type = protein
                        organism = Homo sapiens
SEQUENCE: 129
VCRHGDRCFR LHNKPTF                                               17

SEQ ID NO: 130          moltype = DNA  length = 51
FEATURE                 Location/Qualifiers
source                  1..51
                        mol_type = genomic DNA
                        organism = Homo sapiens
SEQUENCE: 130
gcatgtcgtc atggagacag gtgctttcgg ttgcacaata aaccgacgtt t           51

SEQ ID NO: 131          moltype = AA  length = 17
FEATURE                 Location/Qualifiers
source                  1..17
                        mol_type = protein
                        organism = Homo sapiens
SEQUENCE: 131
SCTTPQCKCL LAKCCVD                                               17

SEQ ID NO: 132          moltype = DNA  length = 51
FEATURE                 Location/Qualifiers
source                  1..51
                        mol_type = genomic DNA
                        organism = Homo sapiens
SEQUENCE: 132
agttgtacta caccgcaatg caaatgcctg cttgcaaaat gttgtgttga t           51

SEQ ID NO: 133          moltype = AA  length = 17
FEATURE                 Location/Qualifiers
source                  1..17
                        mol_type = protein
                        organism = Homo sapiens
SEQUENCE: 133
SILSKQVQHK PKTGRSL                                               17

SEQ ID NO: 134          moltype = DNA  length = 51
FEATURE                 Location/Qualifiers
source                  1..51
                        mol_type = genomic DNA
                        organism = Homo sapiens
SEQUENCE: 134
tccatattat ctaaacaggt tcaacataaa ccaaaaactg gtcgaagttt a           51

SEQ ID NO: 135          moltype = AA  length = 17
FEATURE                 Location/Qualifiers
source                  1..17
                        mol_type = protein
                        organism = Homo sapiens
SEQUENCE: 135
QRIGSGSFAT VYKGKWH                                               17
```

-continued

```
SEQ ID NO: 136         moltype = DNA  length = 51
FEATURE                Location/Qualifiers
source                 1..51
                       mol_type = genomic DNA
                       organism = Homo sapiens
SEQUENCE: 136
caaagaattg gatctggatc atttgcaaca gtctacaagg gaaagtggca t           51

SEQ ID NO: 137         moltype = AA  length = 17
FEATURE                Location/Qualifiers
source                 1..17
                       mol_type = protein
                       organism = Homo sapiens
SEQUENCE: 137
GDFGLATVES RWSGSHQ                                                 17

SEQ ID NO: 138         moltype = DNA  length = 51
FEATURE                Location/Qualifiers
source                 1..51
                       mol_type = genomic DNA
                       organism = Homo sapiens
SEQUENCE: 138
ggtgattttg gtctagctac agtggaatct cgatggagtg ggtcccatca g           51

SEQ ID NO: 139         moltype = AA  length = 17
FEATURE                Location/Qualifiers
source                 1..17
                       mol_type = protein
                       organism = Homo sapiens
SEQUENCE: 139
QANLRHLCCI CGNSFRA                                                 17

SEQ ID NO: 140         moltype = DNA  length = 51
FEATURE                Location/Qualifiers
source                 1..51
                       mol_type = genomic DNA
                       organism = Homo sapiens
SEQUENCE: 140
caagccaacc ttcgacatct ctgctgcatc tgtgggaatt cttttagagc t           51

SEQ ID NO: 141         moltype = AA  length = 17
FEATURE                Location/Qualifiers
source                 1..17
                       mol_type = protein
                       organism = Homo sapiens
SEQUENCE: 141
QANLRHLCHI CGNSFRA                                                 17

SEQ ID NO: 142         moltype = DNA  length = 51
FEATURE                Location/Qualifiers
source                 1..51
                       mol_type = genomic DNA
                       organism = Homo sapiens
SEQUENCE: 142
caagccaacc ttcgacatct ctgccacatc tgtgggaatt cttttagagc t           51

SEQ ID NO: 143         moltype = AA  length = 17
FEATURE                Location/Qualifiers
source                 1..17
                       mol_type = protein
                       organism = Homo sapiens
SEQUENCE: 143
DRCLKKVSKG VEQFEDI                                                 17

SEQ ID NO: 144         moltype = DNA  length = 51
FEATURE                Location/Qualifiers
source                 1..51
                       mol_type = genomic DNA
                       organism = Homo sapiens
SEQUENCE: 144
gatcgctgcc tcaagaaggt gtccaagggc gtggagcagt ttgaagatat t           51

SEQ ID NO: 145         moltype = AA  length = 17
FEATURE                Location/Qualifiers
source                 1..17
                       mol_type = protein
                       organism = Homo sapiens
SEQUENCE: 145
```

-continued

```
IKTWVASNKI KDKRQLI                                              17

SEQ ID NO: 146          moltype = DNA  length = 51
FEATURE                 Location/Qualifiers
source                  1..51
                        mol_type = genomic DNA
                        organism = Homo sapiens
SEQUENCE: 146
atcaagacat gggtagcgtc caacaagatc aaggacaaga ggcagcttat a          51

SEQ ID NO: 147          moltype = AA  length = 17
FEATURE                 Location/Qualifiers
source                  1..17
                        mol_type = protein
                        organism = Homo sapiens
SEQUENCE: 147
QKFDEALRKS WTTKVNW                                              17

SEQ ID NO: 148          moltype = DNA  length = 51
FEATURE                 Location/Qualifiers
source                  1..51
                        mol_type = genomic DNA
                        organism = Homo sapiens
SEQUENCE: 148
caaaaatttg atgaggcgct caggaaaagc tggactacta aagtgaactg g          51

SEQ ID NO: 149          moltype = AA  length = 17
FEATURE                 Location/Qualifiers
source                  1..17
                        mol_type = protein
                        organism = Homo sapiens
SEQUENCE: 149
WVKPIIIGCH AYGDQYR                                              17

SEQ ID NO: 150          moltype = DNA  length = 51
FEATURE                 Location/Qualifiers
source                  1..51
                        mol_type = genomic DNA
                        organism = Homo sapiens
SEQUENCE: 150
tgggtaaaac ctatcatcat aggttgtcat gcttatgggg atcaatacag a          51

SEQ ID NO: 151          moltype = AA  length = 17
FEATURE                 Location/Qualifiers
source                  1..17
                        mol_type = protein
                        organism = Homo sapiens
SEQUENCE: 151
WVKPIIIGGH AYGDQYR                                              17

SEQ ID NO: 152          moltype = DNA  length = 51
FEATURE                 Location/Qualifiers
source                  1..51
                        mol_type = genomic DNA
                        organism = Homo sapiens
SEQUENCE: 152
tgggtaaaac ctatcatcat aggtggtcat gcttatgggg atcaatacag a          51

SEQ ID NO: 153          moltype = AA  length = 17
FEATURE                 Location/Qualifiers
source                  1..17
                        mol_type = protein
                        organism = Homo sapiens
SEQUENCE: 153
WVKPIIIGHH AYGDQYR                                              17

SEQ ID NO: 154          moltype = DNA  length = 51
FEATURE                 Location/Qualifiers
source                  1..51
                        mol_type = genomic DNA
                        organism = Homo sapiens
SEQUENCE: 154
tgggtaaaac ctatcatcat aggtcatcat gcttatgggg atcaatacag a          51

SEQ ID NO: 155          moltype = AA  length = 17
FEATURE                 Location/Qualifiers
source                  1..17
                        mol_type = protein
                        organism = Homo sapiens
```

```
SEQUENCE: 155
YKLVVVGADG VGKSALT                                                17

SEQ ID NO: 156          moltype = DNA  length = 51
FEATURE                 Location/Qualifiers
source                  1..51
                        mol_type = genomic DNA
                        organism = Homo sapiens
SEQUENCE: 156
tataagctgg tggtggtggg cgccgacggt gtgggcaaga gtgcgctgac c          51

SEQ ID NO: 157          moltype = AA  length = 17
FEATURE                 Location/Qualifiers
source                  1..17
                        mol_type = protein
                        organism = Homo sapiens
SEQUENCE: 157
YKLVVVGARG VGKSALT                                                17

SEQ ID NO: 158          moltype = DNA  length = 51
FEATURE                 Location/Qualifiers
source                  1..51
                        mol_type = genomic DNA
                        organism = Homo sapiens
SEQUENCE: 158
tataagctgg tggtggtggg cgcccgcggt gtgggcaaga gtgcgctgac c          51

SEQ ID NO: 159          moltype = AA  length = 17
FEATURE                 Location/Qualifiers
source                  1..17
                        mol_type = protein
                        organism = Homo sapiens
SEQUENCE: 159
LDILDTAGKE EYSAMRD                                                17

SEQ ID NO: 160          moltype = DNA  length = 51
FEATURE                 Location/Qualifiers
source                  1..51
                        mol_type = genomic DNA
                        organism = Homo sapiens
SEQUENCE: 160
ttggacatcc tggataccgc cggaaaggag gagtacagcg ccatgcggga c          51

SEQ ID NO: 161          moltype = AA  length = 17
FEATURE                 Location/Qualifiers
source                  1..17
                        mol_type = protein
                        organism = Homo sapiens
SEQUENCE: 161
LDILDTAGLE EYSAMRD                                                17

SEQ ID NO: 162          moltype = DNA  length = 51
FEATURE                 Location/Qualifiers
source                  1..51
                        mol_type = genomic DNA
                        organism = Homo sapiens
SEQUENCE: 162
ttggacatcc tggataccgc cggcctggag gagtacagcg ccatgcggga c          51

SEQ ID NO: 163          moltype = AA  length = 17
FEATURE                 Location/Qualifiers
source                  1..17
                        mol_type = protein
                        organism = Homo sapiens
SEQUENCE: 163
LDILDTAGRE EYSAMRD                                                17

SEQ ID NO: 164          moltype = DNA  length = 51
FEATURE                 Location/Qualifiers
source                  1..51
                        mol_type = genomic DNA
                        organism = Homo sapiens
SEQUENCE: 164
ttggacatcc tggataccgc cggccgggag gagtacagcg ccatgcggga c          51

SEQ ID NO: 165          moltype = AA  length = 17
FEATURE                 Location/Qualifiers
source                  1..17
                        mol_type = protein
```

```
                        organism = Homo sapiens
SEQUENCE: 165
EGWLHKRGKY IKTWRPR                                                   17

SEQ ID NO: 166          moltype = DNA  length = 51
FEATURE                 Location/Qualifiers
source                  1..51
                        mol_type = genomic DNA
                        organism = Homo sapiens
SEQUENCE: 166
gagggttggc tgcacaaacg agggaagtac atcaagacct ggcggccacg c             51

SEQ ID NO: 167          moltype = AA  length = 17
FEATURE                 Location/Qualifiers
source                  1..17
                        mol_type = protein
                        organism = Homo sapiens
SEQUENCE: 167
IARELHQFAF DLLIKSH                                                   17

SEQ ID NO: 168          moltype = DNA  length = 51
FEATURE                 Location/Qualifiers
source                  1..51
                        mol_type = genomic DNA
                        organism = Homo sapiens
SEQUENCE: 168
attgcgagag agctgcatca gttcgctttt gacctgctaa tcaagtcaca c             51

SEQ ID NO: 169          moltype = AA  length = 17
FEATURE                 Location/Qualifiers
source                  1..17
                        mol_type = protein
                        organism = Homo sapiens
SEQUENCE: 169
IARELHQFGF DLLIKSH                                                   17

SEQ ID NO: 170          moltype = DNA  length = 51
FEATURE                 Location/Qualifiers
source                  1..51
                        mol_type = genomic DNA
                        organism = Homo sapiens
SEQUENCE: 170
attgcgagag agctgcatca gttcggtttt gacctgctaa tcaagtcaca c             51

SEQ ID NO: 171          moltype = AA  length = 17
FEATURE                 Location/Qualifiers
source                  1..17
                        mol_type = protein
                        organism = Homo sapiens
SEQUENCE: 171
QPDSFAALHS SLNELGE                                                   17

SEQ ID NO: 172          moltype = DNA  length = 51
FEATURE                 Location/Qualifiers
source                  1..51
                        mol_type = genomic DNA
                        organism = Homo sapiens
SEQUENCE: 172
cagcccgact cctttgcagc cttgcactct agcctcaatg aactgggaga g             51

SEQ ID NO: 173          moltype = AA  length = 17
FEATURE                 Location/Qualifiers
source                  1..17
                        mol_type = protein
                        organism = Homo sapiens
SEQUENCE: 173
QMAVIQYSLM GLMVFAM                                                   17

SEQ ID NO: 174          moltype = DNA  length = 51
FEATURE                 Location/Qualifiers
source                  1..51
                        mol_type = genomic DNA
                        organism = Homo sapiens
SEQUENCE: 174
cagatggctg tcattcagta ctccttgatg gggctcatgg tgtttgccat g             51

SEQ ID NO: 175          moltype = AA  length = 17
FEATURE                 Location/Qualifiers
source                  1..17
```

```
                        mol_type = protein
                        organism = Homo sapiens
SEQUENCE: 175
QMAVIQYSFM GLMVFAM                                                  17

SEQ ID NO: 176          moltype = DNA  length = 51
FEATURE                 Location/Qualifiers
source                  1..51
                        mol_type = genomic DNA
                        organism = Homo sapiens
SEQUENCE: 176
cagatggctg tcattcagta ctcctttatg gggctcatgg tgtttgccat g           51

SEQ ID NO: 177          moltype = AA  length = 68
FEATURE                 Location/Qualifiers
source                  1..68
                        mol_type = protein
                        organism = Homo sapiens
SEQUENCE: 177
QNLQNGGGSR SSATLPGRRR RRWLRRRRQP ISVAPAGPPR RPNQKPNPPG GARCVIMRPT  60
WPGTSAFT                                                            68

SEQ ID NO: 178          moltype = DNA  length = 204
FEATURE                 Location/Qualifiers
source                  1..204
                        mol_type = genomic DNA
                        organism = Homo sapiens
SEQUENCE: 178
cagaacctgc agaatggagg ggggagcagg tcttcagcca cactgccggg gcggcggcgg  60
cggcggtggc tgcggcggcg gcggcagcca atatcagtag ctcctgcggg gccccctcgc  120
cgaccaaacc aaaaaccaaa cccacctggc ggtgcgaggt gtgtgattat gagaccaacg  180
tggccaggaa cctccgcatt caca                                          204

SEQ ID NO: 179          moltype = AA  length = 33
FEATURE                 Location/Qualifiers
source                  1..33
                        mol_type = protein
                        organism = Homo sapiens
SEQUENCE: 179
QNLQNGGGGA GLQPHCRGGG GGGGCGGGGS QYQ                                33

SEQ ID NO: 180          moltype = DNA  length = 102
FEATURE                 Location/Qualifiers
source                  1..102
                        mol_type = genomic DNA
                        organism = Homo sapiens
SEQUENCE: 180
cagaacctgc agaatggagg ggggggagca ggtcttcagc cacactgccg ggcggcggc  60
ggcggcggtg gctgcggcgg cggcggcagc caatatcagt ag                      102

SEQ ID NO: 181          moltype = AA  length = 10
FEATURE                 Location/Qualifiers
source                  1..10
                        mol_type = protein
                        organism = Homo sapiens
SEQUENCE: 181
NQEKEAEKNY                                                          10

SEQ ID NO: 182          moltype = DNA  length = 33
FEATURE                 Location/Qualifiers
source                  1..33
                        mol_type = genomic DNA
                        organism = Homo sapiens
SEQUENCE: 182
aaccaagaga aagaggcaga aaaaaactat tga                                33

SEQ ID NO: 183          moltype = AA  length = 40
FEATURE                 Location/Qualifiers
source                  1..40
                        mol_type = protein
                        organism = Homo sapiens
SEQUENCE: 183
DAAVSPRGLQ HRQGRGNLGW WQSPLRKVRV PKRRMVYHPS                         40

SEQ ID NO: 184          moltype = DNA  length = 123
FEATURE                 Location/Qualifiers
source                  1..123
                        mol_type = genomic DNA
                        organism = Homo sapiens
```

```
SEQUENCE: 184
gatgctgctg tcagtcccag ggggctgcag cacaggcagg ggagagggaa tctggggtgg  60
tggcagtctc ccctgagaaa agtgagagtc cccaaaagga ggatggttta tcatcccagt  120
tga                                                                123

SEQ ID NO: 185         moltype = AA  length = 33
FEATURE                Location/Qualifiers
source                 1..33
                       mol_type = protein
                       organism = Homo sapiens
SEQUENCE: 185
FVVSVVKKNR TCPFRLFVRR MLQFTGNKVL DRP                               33

SEQ ID NO: 186         moltype = DNA  length = 102
FEATURE                Location/Qualifiers
source                 1..102
                       mol_type = genomic DNA
                       organism = Homo sapiens
SEQUENCE: 186
tttgtcgttt ctgttgtgaa aaaaaacagg acttgcccct ttcgtctatt tgtcagacga  60
atgttacaat ttactggcaa taaagttttg gatagacctt aa                     102

SEQ ID NO: 187         moltype = AA  length = 9
FEATURE                Location/Qualifiers
source                 1..9
                       mol_type = protein
                       organism = Homo sapiens
SEQUENCE: 187
RSRRSAIKR                                                          9

SEQ ID NO: 188         moltype = DNA  length = 32
FEATURE                Location/Qualifiers
source                 1..32
                       mol_type = genomic DNA
                       organism = Homo sapiens
SEQUENCE: 188
agaagcagaa gatcggctat aaaaagataa tg                                32

SEQ ID NO: 189         moltype = AA  length = 24
FEATURE                Location/Qualifiers
source                 1..24
                       mol_type = protein
                       organism = Homo sapiens
SEQUENCE: 189
SIIVQERERA ERRVRRGQVM EIVD                                         24

SEQ ID NO: 190         moltype = DNA  length = 75
FEATURE                Location/Qualifiers
source                 1..75
                       mol_type = genomic DNA
                       organism = Homo sapiens
SEQUENCE: 190
agtataattg tacaagagag agagagagca gagagaaggg tcagaagagg ccaagtgatg  60
gaaatagtgg attaa                                                   75

SEQ ID NO: 191         moltype = AA  length = 34
FEATURE                Location/Qualifiers
source                 1..34
                       mol_type = protein
                       organism = Homo sapiens
SEQUENCE: 191
NNLVTEKKHR NVQCHDAVEE NGQSSFITSP ILHS                              34

SEQ ID NO: 192         moltype = DNA  length = 107
FEATURE                Location/Qualifiers
source                 1..107
                       mol_type = genomic DNA
                       organism = Homo sapiens
SEQUENCE: 192
aataacttgg tcacagaaaa aaaacacaga aatgtgcaat gtcatgatgc agttgaggaa  60
aatggccaat catcctttat tacatcgcca atattacaca gctgaaa                107

SEQ ID NO: 193         moltype = AA  length = 48
FEATURE                Location/Qualifiers
source                 1..48
                       mol_type = protein
                       organism = Homo sapiens
SEQUENCE: 193
HPQRKRRGVP PSPPLALGPR MQLCTQLARF FPITPPVWHI LGPQRHTP               48
```

```
SEQ ID NO: 194          moltype = DNA  length = 149
FEATURE                 Location/Qualifiers
source                  1..149
                        mol_type = genomic DNA
                        organism = Homo sapiens
SEQUENCE: 194
cacccacaga ggaaaaggcg gggggtccct ccgagcccac ccctggctct cggccccagg  60
atgcaactgt gcacccagct tgccagattt ttccccatta cacccccagt gtggcatatc  120
cttggtcccc agaggcacac cccttgatc                                     149

SEQ ID NO: 195          moltype = AA  length = 31
FEATURE                 Location/Qualifiers
source                  1..31
                        mol_type = protein
                        organism = Homo sapiens
SEQUENCE: 195
ASRHHLWGAT AGTPAPPPVP TCSPRTLRCL P                                  31

SEQ ID NO: 196          moltype = DNA  length = 98
FEATURE                 Location/Qualifiers
source                  1..98
                        mol_type = genomic DNA
                        organism = Homo sapiens
SEQUENCE: 196
gccagccggc accatctgtg gggggcaaca gcgggcaccc ccgcaccacc ccccgtgccc  60
acctgttcac ccaggaccct gcgatgcctc ccctgacc                           98

SEQ ID NO: 197          moltype = AA  length = 13
FEATURE                 Location/Qualifiers
source                  1..13
                        mol_type = protein
                        organism = Homo sapiens
SEQUENCE: 197
GPGEAGGPSP QGG                                                      13

SEQ ID NO: 198          moltype = DNA  length = 44
FEATURE                 Location/Qualifiers
source                  1..44
                        mol_type = genomic DNA
                        organism = Homo sapiens
SEQUENCE: 198
gggcctgggg aggctggggg cccctcaccc caaggcgggt gagc                    44

SEQ ID NO: 199          moltype = AA  length = 19
FEATURE                 Location/Qualifiers
source                  1..19
                        mol_type = protein
                        organism = Homo sapiens
SEQUENCE: 199
GGGPSGSGEA PTSPSALRT                                                19

SEQ ID NO: 200          moltype = DNA  length = 62
FEATURE                 Location/Qualifiers
source                  1..62
                        mol_type = genomic DNA
                        organism = Homo sapiens
SEQUENCE: 200
ggcgggggc ccagcggctc aggggaggct cccacttctc cttcagccct gaggacatga   60
aa                                                                  62

SEQ ID NO: 201          moltype = AA  length = 23
FEATURE                 Location/Qualifiers
source                  1..23
                        mol_type = protein
                        organism = Homo sapiens
SEQUENCE: 201
GNPDVPPPVL FKADQSESSL SSG                                           23

SEQ ID NO: 202          moltype = DNA  length = 72
FEATURE                 Location/Qualifiers
source                  1..72
                        mol_type = genomic DNA
                        organism = Homo sapiens
SEQUENCE: 202
ggaaatccag atgtcccacc ccccgtcctc ttcaaggcag atcagagcga gagttctttg  60
tcaagtgggt ag                                                       72

SEQ ID NO: 203          moltype = AA  length = 10
```

-continued

```
FEATURE                 Location/Qualifiers
source                  1..10
                        mol_type = protein
                        organism = Homo sapiens
SEQUENCE: 203
AFCYCGEKVP                                                            10

SEQ ID NO: 204          moltype = DNA  length = 35
FEATURE                 Location/Qualifiers
source                  1..35
                        mol_type = genomic DNA
                        organism = Homo sapiens
SEQUENCE: 204
gctttttgtt actgtgggga aaaagttcct tagga                                35

SEQ ID NO: 205          moltype = AA  length = 16
FEATURE                 Location/Qualifiers
source                  1..16
                        mol_type = protein
                        organism = Homo sapiens
SEQUENCE: 205
TLHPDSGNGC YLRRQK                                                     16

SEQ ID NO: 206          moltype = DNA  length = 50
FEATURE                 Location/Qualifiers
source                  1..50
                        mol_type = genomic DNA
                        organism = Homo sapiens
SEQUENCE: 206
acgctgcacc cggactccgg caacggctgc tacttgcgcc gccagaagcg                50

SEQ ID NO: 207          moltype = AA  length = 16
FEATURE                 Location/Qualifiers
source                  1..16
                        mol_type = protein
                        organism = Homo sapiens
SEQUENCE: 207
LHPDSGNMYG CYLRRQ                                                     16

SEQ ID NO: 208          moltype = DNA  length = 53
FEATURE                 Location/Qualifiers
source                  1..53
                        mol_type = genomic DNA
                        organism = Homo sapiens
SEQUENCE: 208
acgctgcacc cggactccgg caacatgtac ggctgctact tgcgccgcca gaa            53

SEQ ID NO: 209          moltype = AA  length = 17
FEATURE                 Location/Qualifiers
source                  1..17
                        mol_type = protein
                        organism = Homo sapiens
SEQUENCE: 209
LHPDSGNMCC YLRRQKR                                                    17

SEQ ID NO: 210          moltype = DNA  length = 51
FEATURE                 Location/Qualifiers
source                  1..51
                        mol_type = genomic DNA
                        organism = Homo sapiens
SEQUENCE: 210
ctgcacccgg actccggcaa catgtgctgc tacttgcgcc gccagaagcg c              51

SEQ ID NO: 211          moltype = AA  length = 16
FEATURE                 Location/Qualifiers
source                  1..16
                        mol_type = protein
                        organism = Homo sapiens
SEQUENCE: 211
CGASACDVSL IAMDSA                                                     16

SEQ ID NO: 212          moltype = DNA  length = 48
FEATURE                 Location/Qualifiers
source                  1..48
                        mol_type = genomic DNA
                        organism = Homo sapiens
SEQUENCE: 212
tgcggggcct ctgcctgtga tgtctccctc attgctatgg acagtgct                  48
```

```
SEQ ID NO: 213         moltype = AA  length = 16
FEATURE                Location/Qualifiers
source                 1..16
                       mol_type = protein
                       organism = Homo sapiens
SEQUENCE: 213
TEYNQKLQVN QFSESK                                                    16

SEQ ID NO: 214         moltype = DNA  length = 48
FEATURE                Location/Qualifiers
source                 1..48
                       mol_type = genomic DNA
                       organism = Homo sapiens
SEQUENCE: 214
accgaataca accagaaatt acaagtgaat caatttagtg aatccaaa                 48

SEQ ID NO: 215         moltype = AA  length = 24
FEATURE                Location/Qualifiers
source                 1..24
                       mol_type = protein
                       organism = Homo sapiens
SEQUENCE: 215
TEISCCTLSS EENEYLPRPE WQLQ                                           24

SEQ ID NO: 216         moltype = DNA  length = 72
FEATURE                Location/Qualifiers
source                 1..72
                       mol_type = genomic DNA
                       organism = Homo sapiens
SEQUENCE: 216
acagaaattt catgttgcac cctgagcagt gaggagaatg aataccttcc aagaccagag  60
tggcagctcc ag                                                        72

SEQ ID NO: 217         moltype = AA  length = 16
FEATURE                Location/Qualifiers
source                 1..16
                       mol_type = protein
                       organism = Homo sapiens
SEQUENCE: 217
GLVSFGEHFC LPCALC                                                    16

SEQ ID NO: 218         moltype = DNA  length = 50
FEATURE                Location/Qualifiers
source                 1..50
                       mol_type = genomic DNA
                       organism = Homo sapiens
SEQUENCE: 218
gggctggtgt ccttcgggga gcacttttgt ctgccctgcg ccctctgcca               50

SEQ ID NO: 219         moltype = AA  length = 16
FEATURE                Location/Qualifiers
source                 1..16
                       mol_type = protein
                       organism = Homo sapiens
SEQUENCE: 219
NSKMALNSEA LSVVSE                                                    16

SEQ ID NO: 220         moltype = DNA  length = 48
FEATURE                Location/Qualifiers
source                 1..48
                       mol_type = genomic DNA
                       organism = Homo sapiens
SEQUENCE: 220
aacagcaaga tggctttgaa ctcagaagcc ttatcagttg tgagtgag                 48

SEQ ID NO: 221         moltype = AA  length = 14
FEATURE                Location/Qualifiers
source                 1..14
                       mol_type = protein
                       organism = Homo sapiens
SEQUENCE: 221
CEERGAAGSL ISCE                                                      14

SEQ ID NO: 222         moltype = DNA  length = 42
FEATURE                Location/Qualifiers
source                 1..42
                       mol_type = genomic DNA
                       organism = Homo sapiens
SEQUENCE: 222
```

```
tgtgaggagc gcggcgcggc aggaagcctt atcagttgtg ag                      42

SEQ ID NO: 223          moltype = AA  length = 69
FEATURE                 Location/Qualifiers
source                  1..69
                        mol_type = protein
                        organism = Homo sapiens
SEQUENCE: 223
LWFQSSELSP TGAPWPSRRP TWRGTTVSPR TATSSARTCC GTKWPSSQEA ALGLGSGLLR  60
FSCGTAAIR                                                           69

SEQ ID NO: 224          moltype = DNA  length = 207
FEATURE                 Location/Qualifiers
source                  1..207
                        mol_type = genomic DNA
                        organism = Homo sapiens
SEQUENCE: 224
ctgtggttcc agagcagtga gctgtccccg acgggagcgc catggcccag ccgccgcccg  60
acgtggaggg ggacgactgt ctccccgcgt accgccacct cttctgcccg gacctgctgc  120
gggacaaagt ggccttcatc acaggaggcg gctctgggat tgggttccgg attgctgaga  180
ttttcatgcg gcacggctgc catacgg                                       207

SEQ ID NO: 225          moltype = AA  length = 70
FEATURE                 Location/Qualifiers
source                  1..70
                        mol_type = protein
                        organism = Homo sapiens
SEQUENCE: 225
WGMELAASRR FSWDHHSAGG PPRVPSVRSG AAQVQPKDPL PLRTLAGCLA RTAHLRPGAE  60
SLPQPQLHCT                                                          70

SEQ ID NO: 226          moltype = DNA  length = 210
FEATURE                 Location/Qualifiers
source                  1..210
                        mol_type = genomic DNA
                        organism = Homo sapiens
SEQUENCE: 226
tgggggatgg agttggcagc gtctcggagg ttctcctggg accaccactc cgccgggggg  60
ccgcccagag tgccaagcgt ccgatccggc gccgcccaag tgcagcccaa ggacccgctc  120
ccgctccgca ccctggcagg ctgcctagcc aggactgcgc acctgcgccc tggggcggag  180
tccttacccc aaccccagct tcactgcaca                                    210

SEQ ID NO: 227          moltype = AA  length = 28
FEATURE                 Location/Qualifiers
source                  1..28
                        mol_type = protein
                        organism = Homo sapiens
SEQUENCE: 227
KEQILAVASL VSSQSIHPSW GQSPLSRI                                      28

SEQ ID NO: 228          moltype = DNA  length = 84
FEATURE                 Location/Qualifiers
source                  1..84
                        mol_type = genomic DNA
                        organism = Homo sapiens
SEQUENCE: 228
aaggaacaga ttttagctgt ggccagtctc gtttcctctc agtccatcca cccttcatgg  60
ggccagagcc ctctctccag aatc                                          84

SEQ ID NO: 229          moltype = AA  length = 14
FEATURE                 Location/Qualifiers
source                  1..14
                        mol_type = protein
                        organism = Homo sapiens
SEQUENCE: 229
LELELSEGVC FRLR                                                     14

SEQ ID NO: 230          moltype = DNA  length = 42
FEATURE                 Location/Qualifiers
source                  1..42
                        mol_type = genomic DNA
                        organism = Homo sapiens
SEQUENCE: 230
ctggagctgg agctgtcgga aggagtctgc ttcagattaa ga                      42

SEQ ID NO: 231          moltype = AA  length = 17
FEATURE                 Location/Qualifiers
source                  1..17
                        mol_type = protein
```

```
                        organism = Homo sapiens
SEQUENCE: 231
QQLRIFCAAM ASNEDFS                                                 17

SEQ ID NO: 232          moltype = DNA  length = 52
FEATURE                 Location/Qualifiers
source                  1..52
                        mol_type = genomic DNA
                        organism = Homo sapiens
SEQUENCE: 232
cagcagctaa ggatattttg tgcagccatg gcctccaacg aagatttctc ca          52

SEQ ID NO: 233          moltype = AA  length = 31
FEATURE                 Location/Qualifiers
source                  1..31
                        mol_type = protein
                        organism = Homo sapiens
SEQUENCE: 233
DGFSGSLFAV VTRRCYFLKW RTIFPQSLMW L                                 31

SEQ ID NO: 234          moltype = DNA  length = 93
FEATURE                 Location/Qualifiers
source                  1..93
                        mol_type = genomic DNA
                        organism = Homo sapiens
SEQUENCE: 234
gacgggttta gcggcagcct cttcgcagtt gtcaccagac gctgttactt cctaaaatgg  60
cggacaatct tcccacagag tttgatgtgg tta                               93

SEQ ID NO: 235          moltype = AA  length = 16
FEATURE                 Location/Qualifiers
source                  1..16
                        mol_type = protein
                        organism = Homo sapiens
SEQUENCE: 235
KMHFSLKEHP PPPCPP                                                  16

SEQ ID NO: 236          moltype = DNA  length = 48
FEATURE                 Location/Qualifiers
source                  1..48
                        mol_type = genomic DNA
                        organism = Homo sapiens
SEQUENCE: 236
aaaatgcact tctccctcaa ggagcaccca ccgcccccctt gcccgcct              48

SEQ ID NO: 237          moltype = AA  length = 31
FEATURE                 Location/Qualifiers
source                  1..31
                        mol_type = protein
                        organism = Homo sapiens
SEQUENCE: 237
DLRRVATYCA PLPSSWRPGT GTTIPPRMRS C                                 31

SEQ ID NO: 238          moltype = DNA  length = 93
FEATURE                 Location/Qualifiers
source                  1..93
                        mol_type = genomic DNA
                        organism = Homo sapiens
SEQUENCE: 238
gatctgcgcc gggtcgccac atactgcgct cctttaccct catcgtggag gcctgggact  60
gggacaacga taccaccccg aatgaggagc tgc                               93

SEQ ID NO: 239          moltype = AA  length = 48
FEATURE                 Location/Qualifiers
source                  1..48
                        mol_type = protein
                        organism = Homo sapiens
SEQUENCE: 239
LQERMELLAC GAERGAGGWG GGGGGGGGDR RGGGGSAPAL ADFAGGRG               48

SEQ ID NO: 240          moltype = DNA  length = 144
FEATURE                 Location/Qualifiers
source                  1..144
                        mol_type = genomic DNA
                        organism = Homo sapiens
SEQUENCE: 240
ttgcaggagc ggatggagtt gcttgcctgc ggagccgagc gcggggccgg cggctggggg  60
ggaggcggtg gcggcggcgg cggcgaccga agaggaggag gaggaagcgc gccagctctt  120
gcagactttg caggcggccg aggg                                         144
```

```
SEQ ID NO: 241          moltype = AA  length = 47
FEATURE                 Location/Qualifiers
source                  1..47
                        mol_type = protein
                        organism = Homo sapiens
SEQUENCE: 241
LTFLDFIQVT LRVMSGSQME NGSSYFFKPF SWGLGVGLSA WLCVMLT                47

SEQ ID NO: 242          moltype = DNA  length = 141
FEATURE                 Location/Qualifiers
source                  1..141
                        mol_type = genomic DNA
                        organism = Homo sapiens
SEQUENCE: 242
ctgacgtttt tagatttcat ccaggtaacg ttgagagtaa tgtcaggatc tcaaatggaa  60
aacggaagtt cctatttttt caagcccttt tcatggggtc tgggggtggg actctcggcc  120
tggctgtgtg taatgttaac t                                            141

SEQ ID NO: 243          moltype = AA  length = 51
FEATURE                 Location/Qualifiers
source                  1..51
                        mol_type = protein
                        organism = Homo sapiens
SEQUENCE: 243
FMIGELVGEL CCQLTFRLPF LESLCQAVVT QALRFNPSFQ EVCIYQDTDL M           51

SEQ ID NO: 244          moltype = DNA  length = 153
FEATURE                 Location/Qualifiers
source                  1..153
                        mol_type = genomic DNA
                        organism = Homo sapiens
SEQUENCE: 244
ttcatgattg gagaacttgt aggtgagttg tgttgccaac tcactttccg tttacctttc  60
ctcgagagtc tttgtcaagc tgtagttaca caggctttga ggtttaaccc atcttttcag  120
gaagtttgta tttatcaaga cactgatctc atg                              153

SEQ ID NO: 245          moltype = AA  length = 16
FEATURE                 Location/Qualifiers
source                  1..16
                        mol_type = protein
                        organism = Homo sapiens
SEQUENCE: 245
VAMMVPDRQV HYDFGL                                                  16

SEQ ID NO: 246          moltype = DNA  length = 48
FEATURE                 Location/Qualifiers
source                  1..48
                        mol_type = genomic DNA
                        organism = Homo sapiens
SEQUENCE: 246
gttgctatga tggttcctga tagacaggtt cattatgact ttggattg               48

SEQ ID NO: 247          moltype = AA  length = 24
FEATURE                 Location/Qualifiers
source                  1..24
                        mol_type = protein
                        organism = Homo sapiens
SEQUENCE: 247
WCPLDLRLGS TGCLTCRHHQ TSHE                                         24

SEQ ID NO: 248          moltype = DNA  length = 72
FEATURE                 Location/Qualifiers
source                  1..72
                        mol_type = genomic DNA
                        organism = Homo sapiens
SEQUENCE: 248
tggtgtccgc tggatcttag actcggttcc actggatgtc tcacatgcag acatcatcaa  60
acgtcacatg ag                                                      72

SEQ ID NO: 249          moltype = AA  length = 25
FEATURE                 Location/Qualifiers
source                  1..25
                        mol_type = protein
                        organism = Homo sapiens
SEQUENCE: 249
VVGRRHETAP QPLLVPDRAG GEGGA                                        25

SEQ ID NO: 250          moltype = DNA  length = 75
```

```
FEATURE                Location/Qualifiers
source                 1..75
                       mol_type = genomic DNA
                       organism = Homo sapiens
SEQUENCE: 250
gtcgtgggaa ggcgtcatga aacagctcct caacccctgc tggtgcccga ccgagctggt  60
ggtgaagggg gagca                                                   75

SEQ ID NO: 251         moltype = AA  length = 17
FEATURE                Location/Qualifiers
source                 1..17
                       mol_type = protein
                       organism = Homo sapiens
SEQUENCE: 251
DYWAQKEKIS IPRTHLC                                                 17

SEQ ID NO: 252         moltype = DNA  length = 51
FEATURE                Location/Qualifiers
source                 1..51
                       mol_type = genomic DNA
                       organism = Homo sapiens
SEQUENCE: 252
gactactggg ctcaaaagga gaagatcagc atccccagaa cacacctgtg t           51

SEQ ID NO: 253         moltype = AA  length = 18
FEATURE                Location/Qualifiers
source                 1..18
                       mol_type = protein
                       organism = Homo sapiens
SEQUENCE: 253
DYWAQKEKGS SSFLRPSC                                                18

SEQ ID NO: 254         moltype = DNA  length = 54
FEATURE                Location/Qualifiers
source                 1..54
                       mol_type = genomic DNA
                       organism = Homo sapiens
SEQUENCE: 254
gactactggg ctcaaaagga gaagggatca tcttcattcc tgcgaccatc ctgt        54

SEQ ID NO: 255         moltype = AA  length = 14
FEATURE                Location/Qualifiers
source                 1..14
                       mol_type = protein
                       organism = Homo sapiens
SEQUENCE: 255
LVLGVLSGHS GSRL                                                    14

SEQ ID NO: 256         moltype = DNA  length = 42
FEATURE                Location/Qualifiers
source                 1..42
                       mol_type = genomic DNA
                       organism = Homo sapiens
SEQUENCE: 256
cttgtacttg gtgtattgag cgggcacagt ggctcacgcc ta                     42

SEQ ID NO: 257         moltype = AA  length = 25
FEATURE                Location/Qualifiers
source                 1..25
                       mol_type = protein
                       organism = Homo sapiens
SEQUENCE: 257
PVPTATPGVR SVTSPQGLGL FLKFI                                        25

SEQ ID NO: 258         moltype = DNA  length = 75
FEATURE                Location/Qualifiers
source                 1..75
                       mol_type = genomic DNA
                       organism = Homo sapiens
SEQUENCE: 258
cctgtcccaa ctgctacacc tggggtaaga tcagtgacta gtccccaggg gctgggcctt  60
ttccttaagt ttatt                                                   75

SEQ ID NO: 259         moltype = AA  length = 28
FEATURE                Location/Qualifiers
source                 1..28
                       mol_type = protein
                       organism = Homo sapiens
SEQUENCE: 259
```

-continued

```
KENDVREVCD VYLQMQIFFH FKFRSYFH                                              28

SEQ ID NO: 260          moltype = DNA   length = 84
FEATURE                 Location/Qualifiers
source                  1..84
                        mol_type = genomic DNA
                        organism = Homo sapiens
SEQUENCE: 260
aaggaaaatg atgtccgtga ggtctgtgat gtgtatttac aaatgcagat cttcttccat         60
tttaagttca gaagttactt tcat                                                 84

SEQ ID NO: 261          moltype = AA   length = 90
FEATURE                 Location/Qualifiers
source                  1..90
                        mol_type = protein
                        organism = Homo sapiens
SEQUENCE: 261
VPFRELKNQR TAQGAPGIHH AASPVAANLC DPARHAQHTR IPCGAGQVRA GRGPEAGGGV         60
LQPQRPAPEK PGCPCRRGQP RLHTVKMWRA                                           90

SEQ ID NO: 262          moltype = DNA   length = 270
FEATURE                 Location/Qualifiers
source                  1..270
                        mol_type = genomic DNA
                        organism = Homo sapiens
SEQUENCE: 262
gtgcccttcc gggagctcaa gaaccagaga acagcacaag gggctcctgg gatccaccac         60
gcggcttccc ccgttgctgc caacctctgc gacccggcga gacacgcaca gcacacacgc        120
atcccctgcg gcgctggcca agtgcgtgct ggccgaggtc ccgaagcagg tggtggagta        180
ctacagccac agaggcctgc ccccgagaag cctgggtgtc cctgccggag aggccagccc        240
aggctgcaca ccgtgaagat gtggagggcg                                         270

SEQ ID NO: 263          moltype = AA   length = 22
FEATURE                 Location/Qualifiers
source                  1..22
                        mol_type = protein
                        organism = Homo sapiens
SEQUENCE: 263
FARKMLEKVH RQHLQLSHNS QE                                                   22

SEQ ID NO: 264          moltype = DNA   length = 66
FEATURE                 Location/Qualifiers
source                  1..66
                        mol_type = genomic DNA
                        organism = Homo sapiens
SEQUENCE: 264
tttgctagaa aaatgctgga gaaggtacac agacaacacc tacagctttc ccacaatagc         60
caggaa                                                                     66

SEQ ID NO: 265          moltype = AA   length = 11
FEATURE                 Location/Qualifiers
source                  1..11
                        mol_type = protein
                        organism = Homo sapiens
SEQUENCE: 265
KRSFAVTERI I                                                               11

SEQ ID NO: 266          moltype = DNA   length = 33
FEATURE                 Location/Qualifiers
source                  1..33
                        mol_type = genomic DNA
                        organism = Homo sapiens
SEQUENCE: 266
aagagaagtt ttgctgtcac ggagaggatc atc                                       33

SEQ ID NO: 267          moltype = AA   length = 17
FEATURE                 Location/Qualifiers
source                  1..17
                        mol_type = protein
                        organism = Homo sapiens
SEQUENCE: 267
MFLRKEQQVG PHSFSML                                                         17

SEQ ID NO: 268          moltype = DNA   length = 51
FEATURE                 Location/Qualifiers
source                  1..51
                        mol_type = genomic DNA
                        organism = Homo sapiens
SEQUENCE: 268
```

```
atgttcctta gaaaggagca gcaggtgggt ccccacagct tttctatgct t          51

SEQ ID NO: 269         moltype = AA  length = 14
FEATURE                Location/Qualifiers
source                 1..14
                       mol_type = protein
                       organism = Homo sapiens
SEQUENCE: 269
VLRFLDLKVR YLHS                                                   14

SEQ ID NO: 270         moltype = DNA  length = 42
FEATURE                Location/Qualifiers
source                 1..42
                       mol_type = genomic DNA
                       organism = Homo sapiens
SEQUENCE: 270
gtgctgcgct ttctggactt aaaggtgaga tacctgcact ct                    42

SEQ ID NO: 271         moltype = AA  length = 32
FEATURE                Location/Qualifiers
source                 1..32
                       mol_type = protein
                       organism = Homo sapiens
SEQUENCE: 271
GNTTLQQLGE ASQAPSGSLI PLRLPLLWEV RG                               32

SEQ ID NO: 272         moltype = DNA  length = 96
FEATURE                Location/Qualifiers
source                 1..96
                       mol_type = genomic DNA
                       organism = Homo sapiens
SEQUENCE: 272
ggcaacacca ccctccagca gctgggtgag gcctcccagg cgccctcagg ctccctcatc  60
cctctgaggc tgcctctgct ctgggaagtg aggggc                            96

SEQ ID NO: 273         moltype = AA  length = 25
FEATURE                Location/Qualifiers
source                 1..25
                       mol_type = protein
                       organism = Homo sapiens
SEQUENCE: 273
GLNLNTDRPG GYSYSIWWKN NAKNR                                       25

SEQ ID NO: 274         moltype = DNA  length = 75
FEATURE                Location/Qualifiers
source                 1..75
                       mol_type = genomic DNA
                       organism = Homo sapiens
SEQUENCE: 274
ggactgaact taaatactga tagaccaggt ggttacagct attcaatttg gtggaaaaac  60
aatgccaaga acaga                                                   75

SEQ ID NO: 275         moltype = AA  length = 27
FEATURE                Location/Qualifiers
source                 1..27
                       mol_type = protein
                       organism = Homo sapiens
SEQUENCE: 275
WKFEMSYTVG GPPPHVHARP RHWKTDR                                     27

SEQ ID NO: 276         moltype = DNA  length = 81
FEATURE                Location/Qualifiers
source                 1..81
                       mol_type = genomic DNA
                       organism = Homo sapiens
SEQUENCE: 276
tggaaattcg agatgagcta cacggtgggt ggcccgcctc cccatgttca tgctagaccc  60
aggcattgga aaactgatag a                                            81

SEQ ID NO: 277         moltype = AA  length = 22
FEATURE                Location/Qualifiers
source                 1..22
                       mol_type = protein
                       organism = Homo sapiens
SEQUENCE: 277
QWQHYHRSGE AAGTPLWRPT RN                                          22

SEQ ID NO: 278         moltype = DNA  length = 66
FEATURE                Location/Qualifiers
```

```
source                  1..66
                        mol_type = genomic DNA
                        organism = Homo sapiens
SEQUENCE: 278
cagtggcagc actaccaccg gtcaggtgag gccgcaggga ctcccctctg gagacccaca  60
agaaac                                                             66

SEQ ID NO: 279          moltype = AA  length = 29
FEATURE                 Location/Qualifiers
source                  1..29
                        mol_type = protein
                        organism = Homo sapiens
SEQUENCE: 279
KVLNEIDAVV TVPPSLSTSQ IPQGCCIIL                                    29

SEQ ID NO: 280          moltype = DNA  length = 87
FEATURE                 Location/Qualifiers
source                  1..87
                        mol_type = genomic DNA
                        organism = Homo sapiens
SEQUENCE: 280
aaggtcctca acgagatcga tgcggtagtt accgtccctc cctccctgtc tacctcccag  60
ataccgcagg gctgctgcat catattg                                      87

SEQ ID NO: 281          moltype = AA  length = 18
FEATURE                 Location/Qualifiers
source                  1..18
                        mol_type = protein
                        organism = Homo sapiens
SEQUENCE: 281
ANLKGTLQVR SGQAVSPR                                                18

SEQ ID NO: 282          moltype = DNA  length = 54
FEATURE                 Location/Qualifiers
source                  1..54
                        mol_type = genomic DNA
                        organism = Homo sapiens
SEQUENCE: 282
gccaatctga aaggcaccct gcaggtgagg agtgggcagg cagtgagtcc acgc        54

SEQ ID NO: 283          moltype = AA  length = 70
FEATURE                 Location/Qualifiers
source                  1..70
                        mol_type = protein
                        organism = Homo sapiens
SEQUENCE: 283
LQAAASGQGK QGVPCPWGCC AYAESPRALI SGDAPSQVER EVPGPCLNTH SLSHRSPQLP  60
GLPHPKQPSV                                                         70

SEQ ID NO: 284          moltype = DNA  length = 210
FEATURE                 Location/Qualifiers
source                  1..210
                        mol_type = genomic DNA
                        organism = Homo sapiens
SEQUENCE: 284
ctccaggcgg ctgcctcggg ccaaggcaag cagggcgtcc cttgtccctg ggttgctgt  60
gcctacgctg agagtccccg ggccctgatt tcgggagatg ctccatcaca ggtggagcgg  120
gaggtgccgg gcccctgcct caacacgcat tctctctccc acagatcccc acagctccca  180
ggccttccac accccaagca gccttctgtt                                   210

SEQ ID NO: 285          moltype = AA  length = 9
FEATURE                 Location/Qualifiers
source                  1..9
                        mol_type = protein
                        organism = Homo sapiens
SEQUENCE: 285
KIQNKNCPD                                                          9

SEQ ID NO: 286          moltype = DNA  length = 27
FEATURE                 Location/Qualifiers
source                  1..27
                        mol_type = genomic DNA
                        organism = Homo sapiens
SEQUENCE: 286
aaaattcaga ataaaaattg tccagac                                      27

SEQ ID NO: 287          moltype = AA  length = 37
FEATURE                 Location/Qualifiers
source                  1..37
```

-continued

```
                        mol_type = protein
                        organism = Homo sapiens
SEQUENCE: 287
GEVELSEGGE GQRHLAFPWA CSGPGWRGVC CAAVEPA                          37

SEQ ID NO: 288          moltype = DNA  length = 111
FEATURE                 Location/Qualifiers
source                  1..111
                        mol_type = genomic DNA
                        organism = Homo sapiens
SEQUENCE: 288
ggcgaggtgg agctctcaga gggcggtgag ggccagcggc accttgcatt tccctgggcc  60
tgctctgggc cgggctggag aggggtgtgc tgtgctgctg tggagcctgc t           111

SEQ ID NO: 289          moltype = AA  length = 9
FEATURE                 Location/Qualifiers
source                  1..9
                        mol_type = protein
                        organism = Homo sapiens
SEQUENCE: 289
IEMKKLLKS                                                         9

SEQ ID NO: 290          moltype = DNA  length = 27
FEATURE                 Location/Qualifiers
source                  1..27
                        mol_type = genomic DNA
                        organism = Homo sapiens
SEQUENCE: 290
attgaaatga aaaaactgtt aaaaagt                                     27

SEQ ID NO: 291          moltype = AA  length = 70
FEATURE                 Location/Qualifiers
source                  1..70
                        mol_type = protein
                        organism = Homo sapiens
SEQUENCE: 291
KMRAIQAEGG HGQACCGGAW GWAPGDGGPQ GMLTHTLPTL GFQSAWTWRR EDADRAWRTP  60
KACASRRWSI                                                        70

SEQ ID NO: 292          moltype = DNA  length = 210
FEATURE                 Location/Qualifiers
source                  1..210
                        mol_type = genomic DNA
                        organism = Homo sapiens
SEQUENCE: 292
aagatgcggg ccatccaggc cgagggtggg cacgggcagg cctgctgtgg aggggcctgg  60
ggatgggcac cgggggacgg gggcccccag gggatgctca cgcatactct gcccaccctg  120
ggcttccaga gcgcctggac atggagaaga gaagatgcag acagagcctg gaggactccg  180
aaagcctgcg catcaaggag gtggagcata                                  210

SEQ ID NO: 293          moltype = AA  length = 74
FEATURE                 Location/Qualifiers
source                  1..74
                        mol_type = protein
                        organism = Homo sapiens
SEQUENCE: 293
LLEPFRRGEP GPRGLLSGSS RGGEGPGRSI EAAPATPLPC CRKNPCRPQP SRFLPPRVLL  60
VIILPKLDCP KLGF                                                   74

SEQ ID NO: 294          moltype = DNA  length = 222
FEATURE                 Location/Qualifiers
source                  1..222
                        mol_type = genomic DNA
                        organism = Homo sapiens
SEQUENCE: 294
ctgctggagc ccttccgccg cggtgagccc gggccccgcg ggctgctctc gggaagttcc  60
cgcggagggg aggggcctgg ccgttcgatc gaggctgcac ccgccacacc tttgccctgt  120
tgccgcaaga acccttgtcg gccccagcct tccagatttt tgcctcctag ggtattgtta  180
gtgatcattc ttcccaaact ggattgtcca aaacttgggt tc                    222

SEQ ID NO: 295          moltype = AA  length = 65
FEATURE                 Location/Qualifiers
source                  1..65
                        mol_type = protein
                        organism = Homo sapiens
SEQUENCE: 295
PSGRRTKRLV TLRSGCAIQC WHPRAGPVPS ALPHTERPPR LVRGAADPRT VTLGRSPAVM  60
PRAPA                                                             65
```

```
SEQ ID NO: 296          moltype = DNA  length = 195
FEATURE                 Location/Qualifiers
source                  1..195
                        mol_type = genomic DNA
                        organism = Homo sapiens
SEQUENCE: 296
ccctcggggc ggagaaccaa acggttagtt accctgcgtt ctggctgcgc catacaatgc  60
tggcatcctc gtgccggccc agttccctca gcgcttcctc acacagagag gcccccaagg  120
cttgtcaggg gagcagcaga tcccaggaca gtgaccctgg gacggagccc tgcagtcatg  180
cctcgggccc ctgcg                                                   195

SEQ ID NO: 297          moltype = AA  length = 95
FEATURE                 Location/Qualifiers
source                  1..95
                        mol_type = protein
                        organism = Homo sapiens
SEQUENCE: 297
CHLFLQPQVG TPPPHTASAR APSGPPHPHE SCPAGRRPAR AAQTCARRQH GLPGCEEAGT  60
ARVPSLHLHL HQAALGAGRG RGWGEACAQV PPSRG                             95

SEQ ID NO: 298          moltype = DNA  length = 285
FEATURE                 Location/Qualifiers
source                  1..285
                        mol_type = genomic DNA
                        organism = Homo sapiens
SEQUENCE: 298
tgccacctct tcctgcagcc ccaggttggc accccccccc cccacactgc cagtgctcga  60
gcccccagtg gtccacccca ccctcatgaa agttgccctg cagggcgaag acctgcgaga  120
gctgcgcaga catgtgcacg ccgacagcac ggacttcctg gctgtgaaga ggctggtaca  180
gcgcgtgttc ccagcctgca cctgcacctg caccaggccg ccctcggagc aggaaggggc  240
cgtgggtggg gagaggcctg tgcccaagta cccccctcaa gaggc                  285

SEQ ID NO: 299          moltype = AA  length = 45
FEATURE                 Location/Qualifiers
source                  1..45
                        mol_type = protein
                        organism = Homo sapiens
SEQUENCE: 299
KELKLEQQVG GQGLRGVGQG VRGGFVTLTT HTPFPSQEAA ERESK                  45

SEQ ID NO: 300          moltype = DNA  length = 135
FEATURE                 Location/Qualifiers
source                  1..135
                        mol_type = genomic DNA
                        organism = Homo sapiens
SEQUENCE: 300
aaggagctca agctggagca gcaggtgggt gggcagggct tgagaggggt gggccaaggg  60
gtgcgtggcg gcttcgtgac cctcactacc catacccccgt tcccctccca ggaagctgca  120
gagcgggagt ctaaa                                                   135

SEQ ID NO: 301          moltype = AA  length = 175
FEATURE                 Location/Qualifiers
source                  1..175
                        mol_type = protein
                        organism = Homo sapiens
SEQUENCE: 301
GEISQEEVPP SRHLGVSWGA GVWAGLTLGA SAPPNSSFPS GAELQPVVCC IRSDTRQPRP  60
PDFPQHRGDP RLPQLSLGAE NQTVSYPAFW LRHTMLASSC RPSSLSASSH REAPKACQGS  120
SRSQDSDPGT EPCSHASGPC VTSTVSSPGL LPQRLLPLAL TGLPVEEDGF EHAGA       175

SEQ ID NO: 302          moltype = DNA  length = 525
FEATURE                 Location/Qualifiers
source                  1..525
                        mol_type = genomic DNA
                        organism = Homo sapiens
SEQUENCE: 302
ggagaaatca gccaggaaga ggtgcctccc tcccgccacc tgggcgtctc atggggtgct  60
ggggtgtggg cgggcctcac cctcggggcc tctgcacccc ctaactctag cttcccctca  120
ggtgctgagc tacagccagt tgtgtgctgc attaggagtg acacaagaca gccccgaccc  180
cccgactttc ctcagcacag gggagatcca cgccttcctc agctctccct cggggcggag  240
aaccaaacgg ttagttaccc tgcgttctgg ctgcgccata caatgctggc atcctcgtgc  300
cggcccagtt ccctcagcgc ttcctcacac agagaggccc ccaaggcttg tcaggggagc  360
agcagatccc aggacagtga ccctgggacg gagccctgca gtcatgcctc gggcccctgc  420
gtaacctcca ctgtctccag cccaggtctc cttcctcaga ggctattgcc tctcgctctg  480
actgggctcc ctgtggagga agatggtttc gagcacgcgg gagcc                  525

SEQ ID NO: 303          moltype = AA  length = 56
FEATURE                 Location/Qualifiers
source                  1..56
```

```
                        mol_type = protein
                        organism = Homo sapiens
SEQUENCE: 303
DCMLSEEGGQ ARRGGSLCSL AAHTIASAAR GRFLSRLSNF CAVVKASRGA PSCTWE      56

SEQ ID NO: 304          moltype = DNA  length = 168
FEATURE                 Location/Qualifiers
source                  1..168
                        mol_type = genomic DNA
                        organism = Homo sapiens
SEQUENCE: 304
gactgcatgc tcagcgagga aggtgggcag gcgcggcggg gtggatccct ctgctcctta  60
gctgcccaca ccattgcctc ggcagcccga ggtcgcttcc tctccaggct ctccaatttc  120
tgtgccgtag ttaaagcgag caggggcgcc ccttcctgca cctgggag               168

SEQ ID NO: 305          moltype = AA  length = 43
FEATURE                 Location/Qualifiers
source                  1..43
                        mol_type = protein
                        organism = Homo sapiens
SEQUENCE: 305
EAFQRAAGEG GPGRGGARRG ARVLQSPFCR AGAGEWLGHQ SLR                    43

SEQ ID NO: 306          moltype = DNA  length = 129
FEATURE                 Location/Qualifiers
source                  1..129
                        mol_type = genomic DNA
                        organism = Homo sapiens
SEQUENCE: 306
gaggccttcc agagggccgc tggtgagggc ggcccgggcc gcggtggggc acggcgcggt  60
gccagggtgt tgcagagccc cttttgcagg gcaggagctg gggagtggtt aggacatcag  120
tccctcagg                                                          129

SEQ ID NO: 307          moltype = AA  length = 35
FEATURE                 Location/Qualifiers
source                  1..35
                        mol_type = protein
                        organism = Homo sapiens
SEQUENCE: 307
PEPRRLSPGE PRGRPRKGWG IWGLCGARVG PKAWR                             35

SEQ ID NO: 308          moltype = DNA  length = 105
FEATURE                 Location/Qualifiers
source                  1..105
                        mol_type = genomic DNA
                        organism = Homo sapiens
SEQUENCE: 308
cctgagccca ggagactgag cccaggtgag cccaggggc gaccccggaa gggctggggg  60
atctggggtt tgtgtggagc gcgggtgggg cccaaggctt ggcgg                  105

SEQ ID NO: 309          moltype = AA  length = 61
FEATURE                 Location/Qualifiers
source                  1..61
                        mol_type = protein
                        organism = Homo sapiens
SEQUENCE: 309
VPFRELKNVS VLEGLRQGRL GGPCSCHCPR PSQARLTPVD VAGPFLCLGD PGLFPPVKSS  60
I                                                                  61

SEQ ID NO: 310          moltype = DNA  length = 183
FEATURE                 Location/Qualifiers
source                  1..183
                        mol_type = genomic DNA
                        organism = Homo sapiens
SEQUENCE: 310
gtgcccttcc gggagctcaa gaacgtgagt gtcctggagg ggctccgtca aggccggctt  60
gggggtccct gttcatgtca ctgcccaaga ccttcccagg ccaggctcac gccagtggat  120
gtggcaggtc ccttcttgtg tctgggggat cctgggctgt tccccccagt caagagcagt  180
atc                                                                183

SEQ ID NO: 311          moltype = AA  length = 98
FEATURE                 Location/Qualifiers
source                  1..98
                        mol_type = protein
                        organism = Homo sapiens
SEQUENCE: 311
FVSLTAIQMA SSATPWGRWP VATPTAACPR RRPSSLPTGG DSASKKPISR RAPWQPWACP  60
GRSVNSAAPR AWCPPATTPR TQSPSRDLRP RCLSSWSS                          98
```

```
SEQ ID NO: 312          moltype = DNA  length = 294
FEATURE                 Location/Qualifiers
source                  1..294
                        mol_type = genomic DNA
                        organism = Homo sapiens
SEQUENCE: 312
tttgtgagcc tgactgccat ccagatggca tcgtcggcca ctccctgggg gaggtggcct  60
gtggctacgc cgacggctgc ctgtcccagg aggaggccgt cctcgctgcc tactggaggg  120
gacagtgcat caaagaagcc catctcccgc cgggcgccat ggcagccgtg ggcttgtcct  180
gggaggagtg taaacagcgc tgccccccgg gcgtggtgcc cgcctgccac aactccaagg  240
acacagtcac catctcggga cctcaggccc cggtgtttga gttcgtggag cagc        294

SEQ ID NO: 313          moltype = AA  length = 109
FEATURE                 Location/Qualifiers
source                  1..109
                        mol_type = protein
                        organism = Homo sapiens
SEQUENCE: 313
PVAIKPGTGP PNNSSIHGGS KRSENSYCRD LRGQLRAICC SSYSHDRHTT EERGSRGRHV  60
WRIRRLHTSG LPCCCHSGPH PRRLPDILRL VTSTKTDHTN TTEGTLDYL              109

SEQ ID NO: 314          moltype = DNA  length = 327
FEATURE                 Location/Qualifiers
source                  1..327
                        mol_type = genomic DNA
                        organism = Homo sapiens
SEQUENCE: 314
ccagttgcca ttaaacctgg tacagggccg cccaataact ccagtataca cggtggctcc  60
aaacgttcag agaattccta ctgccgggat ctacggggcc agttacgtgc catttgctgc  120
tccagctaca gccacgatcg ccacactaca gaagaacgcg gcagccgcgg ccgccatgta  180
tggaggatac gcaggctaca tacctcaggc cttccctgct gctgccattc aggtccccat  240
ccccgacgtc taccagacat actgaggctg gtgaccagca cgaagacaga ccacacaaac  300
accactgaag gaacgcttga ctattta                                      327

SEQ ID NO: 315          moltype = AA  length = 40
FEATURE                 Location/Qualifiers
source                  1..40
                        mol_type = protein
                        organism = Homo sapiens
SEQUENCE: 315
KWNKNWTATL GALTIRGHKL LCHLPHLLSS VQQTCRSSSR                        40

SEQ ID NO: 316          moltype = DNA  length = 120
FEATURE                 Location/Qualifiers
source                  1..120
                        mol_type = genomic DNA
                        organism = Homo sapiens
SEQUENCE: 316
aagtggaaca agaactggac agccacactc ggggctctta caatcagggg tcataagctg  60
ctatgtcacc tacctcacct tctcagctct gtccagcaaa cctgcagaag tagttctaga  120

SEQ ID NO: 317          moltype = AA  length = 50
FEATURE                 Location/Qualifiers
source                  1..50
                        mol_type = protein
                        organism = Homo sapiens
SEQUENCE: 317
FKKFDGPCGE RGGGRTARAL WARGDSVLTP ALDPQTPVRA PSLTRAAAAV              50

SEQ ID NO: 318          moltype = DNA  length = 150
FEATURE                 Location/Qualifiers
source                  1..150
                        mol_type = genomic DNA
                        organism = Homo sapiens
SEQUENCE: 318
ttcaagaagt tcgacggccc ttgtggtgag cgcggcggcg ggcgcacggc tcgagctctg  60
tgggcgcgcg gcgacagcgt cctgactcct gccctcgacc cccagacccc tgtcagggcg  120
ccctccctga cccgagccgc agctgccgtg                                   150

SEQ ID NO: 319          moltype = AA  length = 52
FEATURE                 Location/Qualifiers
source                  1..52
                        mol_type = protein
                        organism = Homo sapiens
SEQUENCE: 319
ENASLVFTGS NSPIPACELS SHPAHGISPW IPSPGNEHFH GIKKQVKAIK VE          52

SEQ ID NO: 320          moltype = DNA  length = 156
FEATURE                 Location/Qualifiers
```

```
source                  1..156
                        mol_type = genomic DNA
                        organism = Homo sapiens
SEQUENCE: 320
gaaaatgcca gcctagtgtt tacaggatcc aacagcccca taccagcctg cgaactgagt  60
agtcacccag ctcatggtat cagtccttgg ataccctcac ctggaaatga acatttccat  120
ggcataaaga agcaagtaaa ggcaataaaa gtagaa                            156

SEQ ID NO: 321          moltype = AA  length = 55
FEATURE                 Location/Qualifiers
source                  1..55
                        mol_type = protein
                        organism = Homo sapiens
SEQUENCE: 321
RLTQRLVQGW TPMENRWCGR RAGGQPASSS TRWTTCRAAC LLTKWTAGRS QTSIG       55

SEQ ID NO: 322          moltype = DNA  length = 165
FEATURE                 Location/Qualifiers
source                  1..165
                        mol_type = genomic DNA
                        organism = Homo sapiens
SEQUENCE: 322
cggctgacgc aacggctggt ccagggctgg accccaatgg agaacaggtg gtgtggcagg  60
cgagcgggtg ggcagcccgc atcatccagc acgagatgga ccacctgcag ggctgcctgt  120
ttattgacaa aatggacagc aggacgttca caaacgtcta ttgga                  165

SEQ ID NO: 323          moltype = AA  length = 32
FEATURE                 Location/Qualifiers
source                  1..32
                        mol_type = protein
                        organism = Homo sapiens
SEQUENCE: 323
ENSGNASRWL HVPSSSDDWL GWKKSSAITS NS                                32

SEQ ID NO: 324          moltype = DNA  length = 96
FEATURE                 Location/Qualifiers
source                  1..96
                        mol_type = genomic DNA
                        organism = Homo sapiens
SEQUENCE: 324
gaaaattcag gcaacgcctc gcgttggctg catgtaccaa gtagttcaga cgattggctc  60
ggatggaaaa aatcttctgc aattacttcc aattcc                            96

SEQ ID NO: 325          moltype = AA  length = 59
FEATURE                 Location/Qualifiers
source                  1..59
                        mol_type = protein
                        organism = Homo sapiens
SEQUENCE: 325
GMECTLGQVG APSPRREEDG WRGGHSRFKA DVPAPQGPCW GGQPGSAPSS APPEQSLLD   59

SEQ ID NO: 326          moltype = DNA  length = 177
FEATURE                 Location/Qualifiers
source                  1..177
                        mol_type = genomic DNA
                        organism = Homo sapiens
SEQUENCE: 326
ggcatggagt gcaccctggg gcaggtgggt gccccgtccc ctcggaggga ggaggacggt  60
tggcgtgggg gccacagccg attcaaggct gatgtaccag caccgcaggg accctgctgg  120
ggtggccaac ctggctctgc cccctcctca gctcctcctg aacagtcatt attagat     177

SEQ ID NO: 327          moltype = AA  length = 110
FEATURE                 Location/Qualifiers
source                  1..110
                        mol_type = protein
                        organism = Homo sapiens
SEQUENCE: 327
KGSVERRSVS LGHPAEGWAW AERSLQPGMT TANTGCLSFH HRGCLLPVLP KLHCGLGGLP  60
LVRAKEIKRV QRAGESSLPV KGLLTVASAV IAVLWGRPSE VTGENEAQHD             110

SEQ ID NO: 328          moltype = DNA  length = 330
FEATURE                 Location/Qualifiers
source                  1..330
                        mol_type = genomic DNA
                        organism = Homo sapiens
SEQUENCE: 328
aaagggagtg tggagaggcg ctcggtgagc ctggggcatc ctgctgaggg ttgggcatgg  60
gcagagagga gcctccagcc aggcatgacc acagccaaca caggctgcct ctcattccac  120
cacagagggt gcctcctccc tgttttgccc aaattacact gtgggctagg tggactacct  180
```

```
cttgtcagag ctaaagaaat caagcgagtg cagagggcag gggagagttc gctgcctgtg  240
aagggccttc tcaccgtcgc ttcggctgtc atcgcagtcc tgtggggtag gccaagcgag  300
gtcacaggag aaaatgaggc tcagcatgat                                    330

SEQ ID NO: 329         moltype = AA  length = 75
FEATURE                Location/Qualifiers
source                 1..75
                       mol_type = protein
                       organism = Homo sapiens
SEQUENCE: 329
FGLTTLAGRS SHGTSGLRAA THTKSGDGGQ GAARQCEKLL ELARATRPWG RSTSASSRWT  60
HRGYMCPPRC AVACW                                                   75

SEQ ID NO: 330         moltype = DNA  length = 225
FEATURE                Location/Qualifiers
source                 1..225
                       mol_type = genomic DNA
                       organism = Homo sapiens
SEQUENCE: 330
tttggcctca ccacacttgc aggtagaagc tcccacggga cctcaggact gagggcagcc  60
acacacacca agtctgggga cggtggccag ggggctgcca ggcagtgtga gaagctcctg  120
gagctggccc gggctaccag accctggggg aggagtacgt cagcatcatc caggtggacc  180
catcgcggat acatgtgccc tcctcgctgc gccgtggcgt gctgg                   225

SEQ ID NO: 331         moltype = AA  length = 29
FEATURE                Location/Qualifiers
source                 1..29
                       mol_type = protein
                       organism = Homo sapiens
SEQUENCE: 331
IIDSDKIMAV CMGCLLTRHV QCQAMEMQQ                                    29

SEQ ID NO: 332         moltype = DNA  length = 87
FEATURE                Location/Qualifiers
source                 1..87
                       mol_type = genomic DNA
                       organism = Homo sapiens
SEQUENCE: 332
attattgaca gcgacaagat aatggcagtg tgcatggggt gcctgctcac acgtcatgtg  60
caatgccagg ccatggagat gcaacag                                      87

SEQ ID NO: 333         moltype = AA  length = 49
FEATURE                Location/Qualifiers
source                 1..49
                       mol_type = protein
                       organism = Homo sapiens
SEQUENCE: 333
DGHSYTSKVN CLLLQDGFHG CVSITGAAGR RNLSIFLFLM LCKLEFHAC               49

SEQ ID NO: 334         moltype = DNA  length = 147
FEATURE                Location/Qualifiers
source                 1..147
                       mol_type = genomic DNA
                       organism = Homo sapiens
SEQUENCE: 334
gatggccact cctacacatc caaggtgaat tgtttactcc ttcaagatgg gttccatggc  60
tgtgtgagca tcaccggggc agctggaaga agaaacctga gcatcttcct gttcttgatg  120
ctgtgcaaat tggagttcca tgcttgt                                       147

SEQ ID NO: 335         moltype = AA  length = 70
FEATURE                Location/Qualifiers
source                 1..70
                       mol_type = protein
                       organism = Homo sapiens
SEQUENCE: 335
LLNAEDYRCA IHSKEIYLLS PSPHQAMDKF SLCCINCNLC LHVFLLLLFF QNKDVWLISN  60
IILLWIYGGI                                                         70

SEQ ID NO: 336         moltype = DNA  length = 210
FEATURE                Location/Qualifiers
source                 1..210
                       mol_type = genomic DNA
                       organism = Homo sapiens
SEQUENCE: 336
ctactaaatg cagaagatta ccggtgtgcc attcattcaa aagagattta tcttctttcc  60
ccctcccccc accaggcaat ggacaagttt tctctctgct gcatcaactg caatctatgt  120
ttacatgtat tccttttact actatttttt caaaacaaag atgtatggct tatttcaaac  180
atcattttac tttggatata tggcggtatt                                    210
```

```
SEQ ID NO: 337          moltype = AA  length = 33
FEATURE                 Location/Qualifiers
source                  1..33
                        mol_type = protein
                        organism = Homo sapiens
SEQUENCE: 337
TGGKSTCSAP GPQSLPSTPF STYPQWVILI TEL                                33

SEQ ID NO: 338          moltype = DNA  length = 99
FEATURE                 Location/Qualifiers
source                  1..99
                        mol_type = genomic DNA
                        organism = Homo sapiens
SEQUENCE: 338
acagggggca aaagcacctg ctcggctcct ggccctcagt ctctcccctc cactccattc  60
tccacctacc cacagtgggt cattctgatc accgaactg                          99

SEQ ID NO: 339          moltype = AA  length = 28
FEATURE                 Location/Qualifiers
source                  1..28
                        mol_type = protein
                        organism = Homo sapiens
SEQUENCE: 339
VETLENANSF SSGIQPLLCS LIGLENPT                                      28

SEQ ID NO: 340          moltype = DNA  length = 84
FEATURE                 Location/Qualifiers
source                  1..84
                        mol_type = genomic DNA
                        organism = Homo sapiens
SEQUENCE: 340
gtggagaccc tggagaatgc caacagcttc tccagcggga tccagccact cctctgttcc  60
ctgattggcc tggagaatcc cacc                                          84

SEQ ID NO: 341          moltype = AA  length = 38
FEATURE                 Location/Qualifiers
source                  1..38
                        mol_type = protein
                        organism = Homo sapiens
SEQUENCE: 341
AGAGTISEGS VLHGQRLECD ARRFFGCGTT ILAEWEHH                           38

SEQ ID NO: 342          moltype = DNA  length = 114
FEATURE                 Location/Qualifiers
source                  1..114
                        mol_type = genomic DNA
                        organism = Homo sapiens
SEQUENCE: 342
gctggggctg gaacaatttc cgaaggtagt gttctccatg gtcagaggct ggagtgtgat  60
gccagacgtt tttttgggtg tgggactaca atactggcag agtgggagca ccat         114

SEQ ID NO: 343          moltype = AA  length = 17
FEATURE                 Location/Qualifiers
source                  1..17
                        mol_type = protein
                        organism = Homo sapiens
SEQUENCE: 343
GVPGDSTRRA VRRMNTF                                                  17

SEQ ID NO: 344          moltype = DNA  length = 51
FEATURE                 Location/Qualifiers
source                  1..51
                        mol_type = genomic DNA
                        organism = Homo sapiens
SEQUENCE: 344
ggagttccag gagattcaac caggagagca gtgaggagaa tgaatacctt c            51

SEQ ID NO: 345          moltype = AA  length = 20
FEATURE                 Location/Qualifiers
source                  1..20
                        mol_type = protein
                        organism = Homo sapiens
SEQUENCE: 345
HVVGYGHLDT SGSSSSSSWP                                               20

SEQ ID NO: 346          moltype = DNA  length = 60
FEATURE                 Location/Qualifiers
source                  1..60
                        mol_type = genomic DNA
```

```
                         organism = Homo sapiens
SEQUENCE: 346
cacgtggtgg gctatggcca ccttgatact tccgggtcat cctcctcctc ctcctggccc  60

SEQ ID NO: 347           moltype = AA  length = 64
FEATURE                  Location/Qualifiers
source                   1..64
                         mol_type = protein
                         organism = Homo sapiens
SEQUENCE: 347
WTPIPVLTRW PLPHPPPWRR ATSCRMARSS PSATSGSSVR RRCSSLPSWV WNLAASTRPR  60
STPS                                                               64

SEQ ID NO: 348           moltype = DNA  length = 196
FEATURE                  Location/Qualifiers
source                   1..196
                         mol_type = genomic DNA
                         organism = Homo sapiens
SEQUENCE: 348
tggacgccca tcccggtgct cacgagatgg ccactaccac atcctcctcc ctggagaaga  60
gctacaagct gccggatggc caggtcatca ccatcagcaa caagcggttc cagtgtccgg  120
aggcgctgtt ccagccttcc ttcctgggta tggaatcttg cggcatccac gagaccacgt  180
tcaactccat catgaa                                                  196

SEQ ID NO: 349           moltype = AA  length = 16
FEATURE                  Location/Qualifiers
source                   1..16
                         mol_type = protein
                         organism = Homo sapiens
SEQUENCE: 349
SLYHREKQLI AMDSAI                                                  16

SEQ ID NO: 350           moltype = DNA  length = 48
FEATURE                  Location/Qualifiers
source                   1..48
                         mol_type = genomic DNA
                         organism = Homo sapiens
SEQUENCE: 350
tccctctacc accgggagaa gcagctcatt gctatggaca gtgctatc               48

SEQ ID NO: 351           moltype = AA  length = 43
FEATURE                  Location/Qualifiers
source                   1..43
                         mol_type = protein
                         organism = Homo sapiens
SEQUENCE: 351
LHPQRETFTP RWSGANYWKL AFPVGAEGTF PAAATQRGVV RPA                    43

SEQ ID NO: 352           moltype = DNA  length = 131
FEATURE                  Location/Qualifiers
source                   1..131
                         mol_type = genomic DNA
                         organism = Homo sapiens
SEQUENCE: 352
cttcatcctc agagggaaac attcactccc cggtggtcgg gcgcgaatta ctggaaattg  60
gcttttcccg ttggggccga aggtaccttc cctgcggcgg cgactcagcg gggtgtcgtt  120
cggccggcgt g                                                       131

SEQ ID NO: 353           moltype = AA  length = 35
FEATURE                  Location/Qualifiers
source                   1..35
                         mol_type = protein
                         organism = Homo sapiens
SEQUENCE: 353
NSKMALNSLN SIDDAQLTRI APPRSHCCFW EVNAP                             35

SEQ ID NO: 354           moltype = DNA  length = 105
FEATURE                  Location/Qualifiers
source                   1..105
                         mol_type = genomic DNA
                         organism = Homo sapiens
SEQUENCE: 354
aacagcaaga tggctttgaa ctcattaaac tccattgatg atgcacagtt gacaagaatt  60
gcccctccaa gatctcattg ctgtttctgg gaagtaaacg ctcct                  105

SEQ ID NO: 355           moltype = AA  length = 50
FEATURE                  Location/Qualifiers
source                   1..50
                         mol_type = protein
```

-continued

```
                          organism = Homo sapiens
SEQUENCE: 355
MAGGVLRRLL CREPDRDGDK GASREETVVP LHIGDPVVLP GIGQCYSALF             50

SEQ ID NO: 356          moltype = DNA   length = 151
FEATURE                 Location/Qualifiers
source                  1..151
                        mol_type = genomic DNA
                        organism = Homo sapiens
SEQUENCE: 356
atggctggag gagtccttcg gcggctgttg tgtcgggagc ctgatcgcga tggggacaaa  60
ggcgcaagtc gagaggaaac tgttgtgcct cttcatattg gcgatcctgt tgtgctccct  120
ggcattgggc agtgttacag tgcactcttc t                                 151

SEQ ID NO: 357          moltype = AA   length = 39
FEATURE                 Location/Qualifiers
source                  1..39
                        mol_type = protein
                        organism = Homo sapiens
SEQUENCE: 357
DDRNTFDIVW WCPMSRLRLA LTVPPSTTTT CVTVPAWAA                         39

SEQ ID NO: 358          moltype = DNA   length = 120
FEATURE                 Location/Qualifiers
source                  1..120
                        mol_type = genomic DNA
                        organism = Homo sapiens
SEQUENCE: 358
gatgacagaa acactttcga catagtgtgg tggtgcccta tgagccgcct gaggttggct  60
ctgactgtac caccatccac tacaactaca tgtgtaacag ttcctgcatg ggcggcatga  120

SEQ ID NO: 359          moltype = AA   length = 17
FEATURE                 Location/Qualifiers
source                  1..17
                        mol_type = protein
                        organism = Homo sapiens
SEQUENCE: 359
VQPIARELYQ FTFDLLI                                                 17

SEQ ID NO: 360          moltype = DNA   length = 51
FEATURE                 Location/Qualifiers
source                  1..51
                        mol_type = genomic DNA
                        organism = Homo sapiens
SEQUENCE: 360
gtgcagccta ttgcgagaga gctgcatcag ttcacttttg acctgctaat c           51

SEQ ID NO: 361          moltype = AA   length = 17
FEATURE                 Location/Qualifiers
source                  1..17
                        mol_type = protein
                        organism = Homo sapiens
SEQUENCE: 361
QMAVIQYSCM GLMVFAM                                                 17

SEQ ID NO: 362          moltype = DNA   length = 51
FEATURE                 Location/Qualifiers
source                  1..51
                        mol_type = genomic DNA
                        organism = Homo sapiens
SEQUENCE: 362
cagatggctg tcattcagta ctcctgcatg gggctcatgg tgtttgccat g           51

SEQ ID NO: 363          moltype = AA   length = 17
FEATURE                 Location/Qualifiers
source                  1..17
                        mol_type = protein
                        organism = Homo sapiens
SEQUENCE: 363
PKSEVRAKCK FSILNAK                                                 17

SEQ ID NO: 364          moltype = DNA   length = 50
FEATURE                 Location/Qualifiers
source                  1..50
                        mol_type = genomic DNA
                        organism = Homo sapiens
SEQUENCE: 364
caaagagtga agttcgggca aaattcaaat gctccatcct gaatgccaag             50
```

```
SEQ ID NO: 365         moltype = AA  length = 17
FEATURE                Location/Qualifiers
source                 1..17
                       mol_type = protein
                       organism = Homo sapiens
SEQUENCE: 365
MMAEIISVHV PKILSGK                                                17

SEQ ID NO: 366         moltype = DNA  length = 51
FEATURE                Location/Qualifiers
source                 1..51
                       mol_type = genomic DNA
                       organism = Homo sapiens
SEQUENCE: 366
atgatggcag agatcatctc tgtgcacgtg cccaagatcc tttctgggaa a          51

SEQ ID NO: 367         moltype = AA  length = 17
FEATURE                Location/Qualifiers
source                 1..17
                       mol_type = protein
                       organism = Homo sapiens
SEQUENCE: 367
LHPDSGNMVE NGCYLRR                                                17

SEQ ID NO: 368         moltype = DNA  length = 51
FEATURE                Location/Qualifiers
source                 1..51
                       mol_type = genomic DNA
                       organism = Homo sapiens
SEQUENCE: 368
ctgcacccgg actccggcaa catggtcgag aacggctgct acttgcgccg c          51

SEQ ID NO: 369         moltype = AA  length = 17
FEATURE                Location/Qualifiers
source                 1..17
                       mol_type = protein
                       organism = Homo sapiens
SEQUENCE: 369
CYLRRQKRLK CEKQPGA                                                17

SEQ ID NO: 370         moltype = DNA  length = 51
FEATURE                Location/Qualifiers
source                 1..51
                       mol_type = genomic DNA
                       organism = Homo sapiens
SEQUENCE: 370
tgctacttgc gccgccagaa gcgcttgaag tgcgagaagc agccgggggc c          51

SEQ ID NO: 371         moltype = AA  length = 17
FEATURE                Location/Qualifiers
source                 1..17
                       mol_type = protein
                       organism = Homo sapiens
SEQUENCE: 371
MFENGCYLGR QKRFKCE                                                17

SEQ ID NO: 372         moltype = DNA  length = 51
FEATURE                Location/Qualifiers
source                 1..51
                       mol_type = genomic DNA
                       organism = Homo sapiens
SEQUENCE: 372
atgttcgaga acggctgcta cttgggccgc cagaagcgct tcaagtgcga g          51

SEQ ID NO: 373         moltype = AA  length = 16
FEATURE                Location/Qualifiers
source                 1..16
                       mol_type = protein
                       organism = Homo sapiens
SEQUENCE: 373
DSSGNLLERN SFEVRV                                                 16

SEQ ID NO: 374         moltype = DNA  length = 48
FEATURE                Location/Qualifiers
source                 1..48
                       mol_type = genomic DNA
                       organism = Homo sapiens
SEQUENCE: 374
gactccagtg gtaatctact ggaacggaac agctttgagg tgcgtgtt              48
```

```
SEQ ID NO: 375          moltype = AA  length = 61
FEATURE                 Location/Qualifiers
source                  1..61
                        mol_type = protein
                        organism = Homo sapiens
SEQUENCE: 375
VFFKRAAEGF FRMNKLKESS DTNPKPYCMA APMGLTENNR NRKKSYRETN LKAVSWPLNH  60
T                                                                  61

SEQ ID NO: 376          moltype = DNA  length = 183
FEATURE                 Location/Qualifiers
source                  1..183
                        mol_type = genomic DNA
                        organism = Homo sapiens
SEQUENCE: 376
gtcttcttca aaagagccgc tgaaggattt ttcagaatga acaaattaaa agaatcatca  60
gacactaacc ccaagccata ctgcatggca gcaccaatgg gactgacaga aaacaacaga  120
aataggaaga aatcctacag agaaacaaac ttgaaagctg tctcatggcc tttgaatcat  180
act                                                                183

SEQ ID NO: 377          moltype = AA  length = 15
FEATURE                 Location/Qualifiers
source                  1..15
                        mol_type = protein
                        organism = Homo sapiens
SEQUENCE: 377
LTFLDFIQVT LRVMS                                                   15

SEQ ID NO: 378          moltype = AA  length = 15
FEATURE                 Location/Qualifiers
source                  1..15
                        mol_type = protein
                        organism = Homo sapiens
SEQUENCE: 378
VTLRVMSGSQ MENGS                                                   15

SEQ ID NO: 379          moltype = AA  length = 24
FEATURE                 Location/Qualifiers
source                  1..24
                        mol_type = protein
                        organism = Homo sapiens
SEQUENCE: 379
YEAGMTLGEK FRVGNCKHLK MTRP                                         24

SEQ ID NO: 380          moltype = DNA  length = 72
FEATURE                 Location/Qualifiers
source                  1..72
                        mol_type = genomic DNA
                        organism = Homo sapiens
SEQUENCE: 380
tatgaagcag ggatgactct gggagaaaaa ttccgggttg gcaattgcaa gcatctcaaa  60
atgaccagac cc                                                      72

SEQ ID NO: 381          moltype = AA  length = 28
FEATURE                 Location/Qualifiers
source                  1..28
                        mol_type = protein
                        organism = Homo sapiens
SEQUENCE: 381
YEAGMTLGGK ILFFLFLLLP LSPFSLIF                                     28

SEQ ID NO: 382          moltype = DNA  length = 84
FEATURE                 Location/Qualifiers
source                  1..84
                        mol_type = genomic DNA
                        organism = Homo sapiens
SEQUENCE: 382
tatgaagcag ggatgactct gggaggtaag atacttttct ttctcttcct cctccttcct  60
ctctccccct tctccctcat tttc                                         84

SEQ ID NO: 383          moltype = AA  length = 16
FEATURE                 Location/Qualifiers
source                  1..16
                        mol_type = protein
                        organism = Homo sapiens
SEQUENCE: 383
GYLRMQGLMA QRLLLR                                                  16
```

```
SEQ ID NO: 384         moltype = DNA  length = 48
FEATURE                Location/Qualifiers
source                 1..48
                       mol_type = genomic DNA
                       organism = Homo sapiens
SEQUENCE: 384
gggtacctga ggatgcaggg actcatggct cagcgacttc ttctgagg              48

SEQ ID NO: 385         moltype = AA  length = 48
FEATURE                Location/Qualifiers
source                 1..48
                       mol_type = protein
                       organism = Homo sapiens
SEQUENCE: 385
DGHSYTSKVN CLLLQDGFHG CVSITGAAGR RNLSIFLFLM LCKLEFHA              48

SEQ ID NO: 386         moltype = DNA  length = 144
FEATURE                Location/Qualifiers
source                 1..144
                       mol_type = genomic DNA
                       organism = Homo sapiens
SEQUENCE: 386
gatggccact cctacacatc caaggtgaat tgtttactcc ttcaagatgg gttccatggc  60
tgtgtgagca tcaccggggc agctggaaga agaaacctga gcatcttcct gttcttgatg  120
ctgtgcaaat tggagttcca tgct                                         144

SEQ ID NO: 387         moltype = AA  length = 9
FEATURE                Location/Qualifiers
source                 1..9
                       mol_type = protein
                       organism = Homo sapiens
SEQUENCE: 387
STRRAVRRM                                                         9

SEQ ID NO: 388         moltype = AA  length = 9
FEATURE                Location/Qualifiers
source                 1..9
                       mol_type = protein
                       organism = Homo sapiens
SEQUENCE: 388
RAVRRMNTF                                                         9

SEQ ID NO: 389         moltype = AA  length = 9
FEATURE                Location/Qualifiers
source                 1..9
                       mol_type = protein
                       organism = Homo sapiens
SEQUENCE: 389
IPVLTRWPL                                                         9

SEQ ID NO: 390         moltype = AA  length = 9
FEATURE                Location/Qualifiers
source                 1..9
                       mol_type = protein
                       organism = Homo sapiens
SEQUENCE: 390
QLIAMDSAI                                                         9

SEQ ID NO: 391         moltype = AA  length = 9
FEATURE                Location/Qualifiers
source                 1..9
                       mol_type = protein
                       organism = Homo sapiens
SEQUENCE: 391
FPVGAEGTF                                                         9

SEQ ID NO: 392         moltype = AA  length = 9
FEATURE                Location/Qualifiers
source                 1..9
                       mol_type = protein
                       organism = Homo sapiens
SEQUENCE: 392
NSKMALNSL                                                         9

SEQ ID NO: 393         moltype = AA  length = 9
FEATURE                Location/Qualifiers
source                 1..9
                       mol_type = protein
                       organism = Homo sapiens
```

```
SEQUENCE: 393
GVLRRLLCR                                                   9

SEQ ID NO: 394          moltype = AA  length = 9
FEATURE                 Location/Qualifiers
source                  1..9
                        mol_type = protein
                        organism = Homo sapiens
SEQUENCE: 394
CPMSRLRLA                                                   9

SEQ ID NO: 395          moltype = AA  length = 9
FEATURE                 Location/Qualifiers
source                  1..9
                        mol_type = protein
                        organism = Homo sapiens
SEQUENCE: 395
YQFTFDLLI                                                   9

SEQ ID NO: 396          moltype = AA  length = 9
FEATURE                 Location/Qualifiers
source                  1..9
                        mol_type = protein
                        organism = Homo sapiens
SEQUENCE: 396
IQYSCMGLM                                                   9

SEQ ID NO: 397          moltype = AA  length = 9
FEATURE                 Location/Qualifiers
source                  1..9
                        mol_type = protein
                        organism = Homo sapiens
SEQUENCE: 397
RAKCKFSIL                                                   9

SEQ ID NO: 398          moltype = AA  length = 9
FEATURE                 Location/Qualifiers
source                  1..9
                        mol_type = protein
                        organism = Homo sapiens
SEQUENCE: 398
HVPKILSGK                                                   9

SEQ ID NO: 399          moltype = AA  length = 9
FEATURE                 Location/Qualifiers
source                  1..9
                        mol_type = protein
                        organism = Homo sapiens
SEQUENCE: 399
NMVENGCYL                                                   9

SEQ ID NO: 400          moltype = AA  length = 9
FEATURE                 Location/Qualifiers
source                  1..9
                        mol_type = protein
                        organism = Homo sapiens
SEQUENCE: 400
YLRRQKRLK                                                   9

SEQ ID NO: 401          moltype = AA  length = 9
FEATURE                 Location/Qualifiers
source                  1..9
                        mol_type = protein
                        organism = Homo sapiens
SEQUENCE: 401
CYLGRQKRF                                                   9

SEQ ID NO: 402          moltype = AA  length = 9
FEATURE                 Location/Qualifiers
source                  1..9
                        mol_type = protein
                        organism = Homo sapiens
SEQUENCE: 402
LLERNSFEV                                                   9

SEQ ID NO: 403          moltype = AA  length = 9
FEATURE                 Location/Qualifiers
source                  1..9
                        mol_type = protein
```

```
                        organism = Homo sapiens
SEQUENCE: 403
YCMAAPMGL                                                         9

SEQ ID NO: 404          moltype = AA  length = 9
FEATURE                 Location/Qualifiers
source                  1..9
                        mol_type = protein
                        organism = Homo sapiens
SEQUENCE: 404
FFKRAAEGF                                                         9

SEQ ID NO: 405          moltype = AA  length = 9
FEATURE                 Location/Qualifiers
source                  1..9
                        mol_type = protein
                        organism = Homo sapiens
SEQUENCE: 405
RVGNCKHLK                                                         9

SEQ ID NO: 406          moltype = AA  length = 9
FEATURE                 Location/Qualifiers
source                  1..9
                        mol_type = protein
                        organism = Homo sapiens
SEQUENCE: 406
FLFLLLPLS                                                         9

SEQ ID NO: 407          moltype = AA  length = 9
FEATURE                 Location/Qualifiers
source                  1..9
                        mol_type = protein
                        organism = Homo sapiens
SEQUENCE: 407
LMAQRLLLR                                                         9

SEQ ID NO: 408          moltype = AA  length = 9
FEATURE                 Location/Qualifiers
source                  1..9
                        mol_type = protein
                        organism = Homo sapiens
SEQUENCE: 408
IVWWCPMSR                                                         9

SEQ ID NO: 409          moltype = AA  length = 9
FEATURE                 Location/Qualifiers
source                  1..9
                        mol_type = protein
                        organism = Homo sapiens
SEQUENCE: 409
CTELKLSDY                                                         9

SEQ ID NO: 410          moltype = AA  length = 9
FEATURE                 Location/Qualifiers
source                  1..9
                        mol_type = protein
                        organism = Homo sapiens
SEQUENCE: 410
NLVPMVATV                                                         9

SEQ ID NO: 411          moltype = AA  length = 9
FEATURE                 Location/Qualifiers
source                  1..9
                        mol_type = protein
                        organism = Homo sapiens
SEQUENCE: 411
LIYRRRLMK                                                         9

SEQ ID NO: 412          moltype = AA  length = 9
FEATURE                 Location/Qualifiers
source                  1..9
                        mol_type = protein
                        organism = Homo sapiens
SEQUENCE: 412
LYSACFWWL                                                         9

SEQ ID NO: 413          moltype = AA  length = 9
FEATURE                 Location/Qualifiers
source                  1..9
```

```
                        mol_type = protein
                        organism = Homo sapiens
SEQUENCE: 413
NPKASLLSL                                                           9

SEQ ID NO: 414          moltype = AA  length = 9
FEATURE                 Location/Qualifiers
source                  1..9
                        mol_type = protein
                        organism = Homo sapiens
SEQUENCE: 414
ELRSRYWAI                                                           9

SEQ ID NO: 415          moltype = AA  length = 15
FEATURE                 Location/Qualifiers
source                  1..15
                        mol_type = protein
                        organism = Homo sapiens
SEQUENCE: 415
SQMENGSSYF FKPFS                                                    15

SEQ ID NO: 416          moltype = AA  length = 9
FEATURE                 Location/Qualifiers
source                  1..9
                        mol_type = protein
                        organism = Homo sapiens
SEQUENCE: 416
IVTDFSVIK                                                           9

SEQ ID NO: 417          moltype = AA  length = 15
FEATURE                 Location/Qualifiers
source                  1..15
                        mol_type = protein
                        organism = Homo sapiens
SEQUENCE: 417
YFFKPFSWGL GVGLS                                                    15

SEQ ID NO: 418          moltype = AA  length = 15
FEATURE                 Location/Qualifiers
source                  1..15
                        mol_type = protein
                        organism = Homo sapiens
SEQUENCE: 418
FMIGELVGEL CCQLT                                                    15

SEQ ID NO: 419          moltype = AA  length = 15
FEATURE                 Location/Qualifiers
source                  1..15
                        mol_type = protein
                        organism = Homo sapiens
SEQUENCE: 419
ELCCQLTFRL PFLES                                                    15

SEQ ID NO: 420          moltype = AA  length = 15
FEATURE                 Location/Qualifiers
source                  1..15
                        mol_type = protein
                        organism = Homo sapiens
SEQUENCE: 420
RLPFLESLCQ AVVTQ                                                    15

SEQ ID NO: 421          moltype = AA  length = 9
FEATURE                 Location/Qualifiers
source                  1..9
                        mol_type = protein
                        organism = Homo sapiens
SEQUENCE: 421
KLSRALRYY                                                           9

SEQ ID NO: 422          moltype = AA  length = 9
FEATURE                 Location/Qualifiers
source                  1..9
                        mol_type = protein
                        organism = Homo sapiens
SEQUENCE: 422
MVFELANSI                                                           9

SEQ ID NO: 423          moltype = AA  length = 9
FEATURE                 Location/Qualifiers
```

```
source                 1..9
                       mol_type = protein
                       organism = Homo sapiens
SEQUENCE: 423
ILFQNIDGK                                                   9

SEQ ID NO: 424         moltype = AA  length = 9
FEATURE                Location/Qualifiers
source                 1..9
                       mol_type = protein
                       organism = Homo sapiens
SEQUENCE: 424
KIVIARYGK                                                   9

SEQ ID NO: 425         moltype = AA  length = 9
FEATURE                Location/Qualifiers
source                 1..9
                       mol_type = protein
                       organism = Homo sapiens
SEQUENCE: 425
FLLELLSDS                                                   9

SEQ ID NO: 426         moltype = AA  length = 10
FEATURE                Location/Qualifiers
source                 1..10
                       mol_type = protein
                       organism = Homo sapiens
SEQUENCE: 426
VTFLKPCFLL                                                  10

SEQ ID NO: 427         moltype = AA  length = 8
FEATURE                Location/Qualifiers
source                 1..8
                       mol_type = protein
                       organism = Homo sapiens
SEQUENCE: 427
TDIVKQSV                                                    8

SEQ ID NO: 428         moltype = AA  length = 10
FEATURE                Location/Qualifiers
source                 1..10
                       mol_type = protein
                       organism = Homo sapiens
SEQUENCE: 428
SPAFPKPVRP                                                  10

SEQ ID NO: 429         moltype = AA  length = 12
FEATURE                Location/Qualifiers
source                 1..12
                       mol_type = protein
                       organism = Homo sapiens
SEQUENCE: 429
SYFSLTNIFN FV                                               12

SEQ ID NO: 430         moltype = AA  length = 12
FEATURE                Location/Qualifiers
source                 1..12
                       mol_type = protein
                       organism = Homo sapiens
SEQUENCE: 430
EFSPETCAFR LS                                               12

SEQ ID NO: 431         moltype = AA  length = 9
FEATURE                Location/Qualifiers
source                 1..9
                       mol_type = protein
                       organism = Homo sapiens
SEQUENCE: 431
FLSRALRAL                                                   9

SEQ ID NO: 432         moltype = AA  length = 8
FEATURE                Location/Qualifiers
source                 1..8
                       mol_type = protein
                       organism = Homo sapiens
SEQUENCE: 432
KKDLELIL                                                    8

SEQ ID NO: 433         moltype = AA  length = 8
```

-continued

```
FEATURE                Location/Qualifiers
source                 1..8
                       mol_type = protein
                       organism = Homo sapiens
SEQUENCE: 433
KLQKNCLL                                                          8

SEQ ID NO: 434         moltype = AA  length = 9
FEATURE                Location/Qualifiers
source                 1..9
                       mol_type = protein
                       organism = Homo sapiens
SEQUENCE: 434
SALSGNSWV                                                         9

SEQ ID NO: 435         moltype = AA  length = 7
FEATURE                Location/Qualifiers
source                 1..7
                       mol_type = protein
                       organism = Homo sapiens
SEQUENCE: 435
TVRAILL                                                           7

SEQ ID NO: 436         moltype = AA  length = 10
FEATURE                Location/Qualifiers
source                 1..10
                       mol_type = protein
                       organism = Homo sapiens
SEQUENCE: 436
GSLHFHEVLK                                                        10

SEQ ID NO: 437         moltype = AA  length = 75
FEATURE                Location/Qualifiers
source                 1..75
                       mol_type = protein
                       organism = Homo sapiens
SEQUENCE: 437
HYKLIQQPIS LFSITDRLHK TFSQLPSVHL CSITFQWGHP PIFCSTNDIC VTANFCISVT  60
FLKPCFLLHE ASASQ                                                  75

SEQ ID NO: 438         moltype = AA  length = 40
FEATURE                Location/Qualifiers
source                 1..40
                       mol_type = protein
                       organism = Homo sapiens
SEQUENCE: 438
WTDIVKQSVS TNCISIKKGS YTKLFSLVFL IFCWPLIIQL                        40

SEQ ID NO: 439         moltype = AA  length = 144
FEATURE                Location/Qualifiers
source                 1..144
                       mol_type = protein
                       organism = Homo sapiens
SEQUENCE: 439
RTALTHNQDF SIYRLCCKRG SLCHASQARS PAFPKPVRPL PAPITRITPQ LGGQSDSSQP  60
LLTTGRPQGW QDQALRHTQQ ASPASCATIT IPIHSAALGD HSGDPGPAWD TCPPLPLTTL  120
IPRAPPPYGD STARSWPSRC GPLG                                        144

SEQ ID NO: 440         moltype = AA  length = 36
FEATURE                Location/Qualifiers
source                 1..36
                       mol_type = protein
                       organism = Homo sapiens
SEQUENCE: 440
LRYGALCNVS RISYFSLTNI FNFVIKSLTA IFTVKF                            36

SEQ ID NO: 441         moltype = AA  length = 295
FEATURE                Location/Qualifiers
source                 1..295
                       mol_type = protein
                       organism = Homo sapiens
SEQUENCE: 441
RKERNIRKSE STLRLSPFPT PAPSGAPAAA QGKVVRVPGP AGGLVPRDAG ARLLPPAGGP  60
GGGAAAGEGR AGRGRFPSIT EPRPRDLPPR VATGRRAGGR RKGAGQGVRT RPLPASWPGG  120
RGPFRKGPRR LPLGSGPPAA GVQRLRCSHL SRGPRRRRGR VCGRACVSPP LPPRPPPVGL  180
SAENLSWLSS GLPRACSWRE FSPETCAFRL SGLDSKLSAR VERDLGALRA PGSRAAQGGG  240
RVRGSRSEWK TRPWRPPPAW PLTRAGGPLP KNPFLESCSE TAQRRRVFSF STPLS       295

SEQ ID NO: 442         moltype = AA  length = 67
```

```
FEATURE                 Location/Qualifiers
source                  1..67
                        mol_type = protein
                        organism = Homo sapiens
SEQUENCE: 442
YAYKDFLWCF PFSLVFLQEI QICCHVSCLC CICCSTRICL GCLLELFLSR ALRALHVLWN  60
GFQLHCQ                                                            67

SEQ ID NO: 443          moltype = AA  length = 82
FEATURE                 Location/Qualifiers
source                  1..82
                        mol_type = protein
                        organism = Homo sapiens
SEQUENCE: 443
SINKATITGK KDLELILHVS RKKPFLPRVN ITPTPISCCN LKMLKKFFLL YIIISIIDLT  60
NCLSCYLEHF YRFTFFTDVH YF                                           82

SEQ ID NO: 444          moltype = AA  length = 16
FEATURE                 Location/Qualifiers
source                  1..16
                        mol_type = protein
                        organism = Homo sapiens
SEQUENCE: 444
TMPAILKLQK NCLLSL                                                  16

SEQ ID NO: 445          moltype = AA  length = 84
FEATURE                 Location/Qualifiers
source                  1..84
                        mol_type = protein
                        organism = Homo sapiens
SEQUENCE: 445
PYYSALSGNS WVPSTLESDP FGYVFSPLAT RPALNDQESI LWPTLTSVVS CALSCPSLNL  60
PENWLTLITG GMKGGKKMKF TFRH                                         84

SEQ ID NO: 446          moltype = AA  length = 46
FEATURE                 Location/Qualifiers
source                  1..46
                        mol_type = protein
                        organism = Homo sapiens
SEQUENCE: 446
GLRNLGNTVR AILLSFLSKR NVKWCWGWGK PTSLGKACGR RALKLF                 46

SEQ ID NO: 447          moltype = AA  length = 22
FEATURE                 Location/Qualifiers
source                  1..22
                        mol_type = protein
                        organism = Homo sapiens
SEQUENCE: 447
MEAENAGSLH FHEVLKMGHV KF                                           22

SEQ ID NO: 448          moltype = DNA  length = 225
FEATURE                 Location/Qualifiers
source                  1..225
                        mol_type = genomic DNA
                        organism = Homo sapiens
SEQUENCE: 448
cactacaaat taattcaaca acccatatcc ctcttctcca tcactgatag gctccataag  60
acgttcagtc agctgccctc ggtccatctc tgctcaatca ccttccagtg gggacacccg  120
cccattttct gctcaacaaa tgatatctgt gtcacggcca acttctgcat ctcggtcaca  180
ttccttaaac cgtgcttcct cctacatgag gcatctgcct cacag                  225

SEQ ID NO: 449          moltype = DNA  length = 120
FEATURE                 Location/Qualifiers
source                  1..120
                        mol_type = genomic DNA
                        organism = Homo sapiens
SEQUENCE: 449
tggactgata tagttaagca gtctgtaagt acaaactgca tttctatcaa gaaaggtagc  60
tatacaaaac tgttttcctt agtctttctt attttctgtt ggccattaat tattcagttg  120

SEQ ID NO: 450          moltype = DNA  length = 432
FEATURE                 Location/Qualifiers
source                  1..432
                        mol_type = genomic DNA
                        organism = Homo sapiens
SEQUENCE: 450
aggaccgccc tgacacacaa tcaggacttc tctatctaca ggctctgttg caagaggggg  60
tccctctgcc acgcttccca ggccagatcc ccggctttcc cgaagccggt cagacctctt  120
cctgcccccca tcaccagaat caccccccaa ctggggggac aatctgactc gagtcaaccc  180
```

```
cttctcacta cgggaagacc tcaggggtgg caagatcaag ctcttagaca cacccagcaa  240
gccagtcctg cctcttgtgc caccatcacc attcccatcc actcagctgc ccttggtgac  300
cactccggag accctggtcc agcctgggac acctgcccgc cgctgccgct cactaccctc  360
atcccccgag ctcccccgcc gtatggagac agcactgcca ggtcctggcc ctcccgctgt  420
gggcccctcg gc                                                      432

SEQ ID NO: 451          moltype = DNA  length = 108
FEATURE                 Location/Qualifiers
source                  1..108
                        mol_type = genomic DNA
                        organism = Homo sapiens
SEQUENCE: 451
cttcgctatg gtgccttatg caatgtaagt agaataagtt atttcagtct aacaaatata  60
tttaattttg taattaaatc actaactgct atttttactg tgaaattt               108

SEQ ID NO: 452          moltype = DNA  length = 885
FEATURE                 Location/Qualifiers
source                  1..885
                        mol_type = genomic DNA
                        organism = Homo sapiens
SEQUENCE: 452
cgaaaagaga gaaacatccg aaaaagtgag tccacgctgc gcctgtcccc gttccccacc  60
cccgccccgt cgggggcgcc cgcggccgcg caggggaaag ttgtccgggt ccccgggccg  120
gcgggcgggc tggtccccg ggacgctggc gctcggctcc tgcccccggc gggcggcccg  180
gggggagggg cggcggcggg ggagggcgc gcgggccgcg gccggttccc tagcatcacg  240
gagcctcgac cccgcgacct cccgccccgg gtcgccaccg gccggcgggc gggaggccgg  300
cggaaaggcg ccgggcaggg cgtgcgcacc cgtcccttgc ccgcgagctg gcccgggggt  360
cgcggccctt tccggaaggg gccccggcgt ctgccgctgg gctccggccc gcccgctgcg  420
ggagtgcagc ggctgcgttg ctcccacctg agccgcgggc cgaggaggcg gaggggccga  480
gtgtgcggga gggcgtgtgt ctcgcctccc cttcctcccc ggcccccgcc tgtcggcctt  540
tctgctgaga acctaagctg gttgtcaagt ggtttgcctc gggcgtgttc ctggcgcgag  600
ttcagccccg agacctgtgc gtttcggctc tcgggtttgg attcgaaact ttccgctcgg  660
gttgagcgtg acttgggtgc gctgcgggcg ccggggtcgc gggctgcgca gggcggtggg  720
cgtgtgcgcg ggagccggtc ggagtggaaa acgcgcccgt ggcggccacc tccagcctgg  780
ccgctcaccc gagcaggggg gccgctgccc aagaaccctt tcctggagag ctgctccgag  840
accgcacagc gccgccgcgt cttctccttt tccactcctc tctcc                  885

SEQ ID NO: 453          moltype = DNA  length = 201
FEATURE                 Location/Qualifiers
source                  1..201
                        mol_type = genomic DNA
                        organism = Homo sapiens
SEQUENCE: 453
tatgcttaca aggactttct ctggtgtttt cctttttctt tagtttttct ccaagagatt  60
caaatctgct gccatgttag ctgtctttgc tgtatctgct gtagtacacg aatatgcctt  120
ggctgtttgc ttgagctttt tctatcccgt gctcttcgtg ctcttcatgt tctttggaat  180
ggctttcaac ttcattgtca a                                            201

SEQ ID NO: 454          moltype = DNA  length = 246
FEATURE                 Location/Qualifiers
source                  1..246
                        mol_type = genomic DNA
                        organism = Homo sapiens
SEQUENCE: 454
tccatcaaca aagccaccat aacaggtaag aaaagatctgg agcttattct tcatgtgtct  60
aggaagaaac catttctgcc aagagtcaat ataacaccaa caccaatttc atgctgcaat  120
ttgaaaatgt taaagaaatt ctttcttctc tacattatca tttctatcat tgatctcaca  180
aattgtctaa gctgttattt ggaacatttt taccgattta cgttttttac tgatgtacat  240
tatttt                                                             246

SEQ ID NO: 455          moltype = DNA  length = 48
FEATURE                 Location/Qualifiers
source                  1..48
                        mol_type = genomic DNA
                        organism = Homo sapiens
SEQUENCE: 455
accatgcctg ctattttaaa gttacagaag aattgtcttc tctcctta              48

SEQ ID NO: 456          moltype = DNA  length = 252
FEATURE                 Location/Qualifiers
source                  1..252
                        mol_type = genomic DNA
                        organism = Homo sapiens
SEQUENCE: 456
ccatactaca gcgcactgtc aggtaacagc tgggttccca gcaccctgga aagtgacccg  60
tttggctatg tttttagccc cttagcaaca cggccagctc tcaatgacca agagtccatc  120
ttgtggccga ccctgacttc tgtggtttcc tgtgctctat cctgcccatc tcttaactta  180
cctgagaatt ggctcactct catcacaggt ggaatgaaag ggggaaaaaa aatgaaattc  240
acattcagac ac                                                      252
```

```
SEQ ID NO: 457         moltype = DNA  length = 138
FEATURE                Location/Qualifiers
source                 1..138
                       mol_type = genomic DNA
                       organism = Homo sapiens
SEQUENCE: 457
ggccttcgaa acctgggaaa cacggtgaga gctattctcc tatctttcct ctctaaaagg  60
aatgtgaaat ggtgctgggg gtggggaaaa cccacgagct tggggaaggc atgtggaagg  120
agagctctga agctcttc                                                138

SEQ ID NO: 458         moltype = DNA  length = 66
FEATURE                Location/Qualifiers
source                 1..66
                       mol_type = genomic DNA
                       organism = Homo sapiens
SEQUENCE: 458
atggaagcgg agaacgcggg cagtttgcat tttcatgaag tgctcaaaat gggacatgtg  60
aaattc                                                             66

SEQ ID NO: 459         moltype = DNA  length = 81
FEATURE                Location/Qualifiers
misc_feature           1..81
                       note = Codon-optimized polynucleotide
source                 1..81
                       mol_type = other DNA
                       organism = synthetic construct
SEQUENCE: 459
tggaagttcg agatgagcta caccgtcggc ggacctccac ctcatgttca tgccagacct  60
cggcactgga aaaccgacag a                                            81

SEQ ID NO: 460         moltype = DNA  length = 84
FEATURE                Location/Qualifiers
misc_feature           1..84
                       note = Codon-optimized polynucleotide
source                 1..84
                       mol_type = other DNA
                       organism = synthetic construct
SEQUENCE: 460
tatgaggccg gcatgacact cggcggcaag atcctgttct tcctgttcct gctgctccct  60
ctgagcccct tcagcctgat cttc                                         84

SEQ ID NO: 461         moltype = DNA  length = 147
FEATURE                Location/Qualifiers
misc_feature           1..147
                       note = Codon-optimized polynucleotide
source                 1..147
                       mol_type = other DNA
                       organism = synthetic construct
SEQUENCE: 461
gatggccaca gctacaccag caaagtgaac tgcctcctgc tgcaggatgg cttccacggc  60
tgtgtgtcta ttactggcgc cgctggcaga cggaacctga gcatctttct gtttctgatg  120
ctgtgcaagc tcgagttcca cgcctgc                                      147

SEQ ID NO: 462         moltype = DNA  length = 99
FEATURE                Location/Qualifiers
misc_feature           1..99
                       note = Codon-optimized polynucleotide
source                 1..99
                       mol_type = other DNA
                       organism = synthetic construct
SEQUENCE: 462
acaggcggca agtccacatg ttctgcccct ggacctcaga gcctgcctag cacacccttc  60
agcacatacc ctcagtgggt catcctgatc accgaactc                          99

SEQ ID NO: 463         moltype = DNA  length = 42
FEATURE                Location/Qualifiers
misc_feature           1..42
                       note = Codon-optimized polynucleotide
source                 1..42
                       mol_type = other DNA
                       organism = synthetic construct
SEQUENCE: 463
gtgctgagat tcctggacct gaaagtgcgc tacctgcaca gc                     42

SEQ ID NO: 464         moltype = DNA  length = 54
FEATURE                Location/Qualifiers
misc_feature           1..54
                       note = Codon-optimized polynucleotide
```

```
source                  1..54
                        mol_type = other DNA
                        organism = synthetic construct
SEQUENCE: 464
gactattggg ctcaaaaaga gaagggcagc agcagcttcc tgcggcctag ctgt        54

SEQ ID NO: 465          moltype = DNA  length = 183
FEATURE                 Location/Qualifiers
misc_feature            1..183
                        note = Codon-optimized polynucleotide
source                  1..183
                        mol_type = other DNA
                        organism = synthetic construct
SEQUENCE: 465
gtccccttca gagagctgaa gaacgtttcc gtgctggaag gcctgagaca gggcagactt  60
ggcggccctt gtagctgtca ctgccccaga cctagtcagg ccagactgac acctgtggat  120
gtggccggac ctttcctgtg tctgggagat cctggcctgt ttccacctgt gaagtccagc  180
atc                                                                183

SEQ ID NO: 466          moltype = DNA  length = 177
FEATURE                 Location/Qualifiers
misc_feature            1..177
                        note = Codon-optimized polynucleotide
source                  1..177
                        mol_type = other DNA
                        organism = synthetic construct
SEQUENCE: 466
ggcatggaat gcaccctggg acaagtggga gccccatctc ctagaagaga agaggatggc  60
tggcgcggag gccactctag attcaaagct gatgtgcccg ctcctcaggg cccttgttgg  120
ggaggacaac ctggatctgc cccatcttct gccccacctg aacagtccct gctggat     177

SEQ ID NO: 467          moltype = DNA  length = 96
FEATURE                 Location/Qualifiers
misc_feature            1..96
                        note = Codon-optimized polynucleotide
source                  1..96
                        mol_type = other DNA
                        organism = synthetic construct
SEQUENCE: 467
ggcaacacaa ccctccagca actgggagaa gcctctcagg ctcctagcgg ctctctgatc  60
cctctcagac tgcctctcct gtgggaagtt cggggc                            96

SEQ ID NO: 468          moltype = DNA  length = 129
FEATURE                 Location/Qualifiers
misc_feature            1..129
                        note = Codon-optimized polynucleotide
source                  1..129
                        mol_type = other DNA
                        organism = synthetic construct
SEQUENCE: 468
gaggctttcc aaagagctgc tggcgaaggc ggacctggta gaggtggtgc tagaagaggt  60
gctagggtgc tgcagagccc attctgtaga gcaggcgcag gcgaatggct gggccatcag  120
agtctgaga                                                          129

SEQ ID NO: 469          moltype = DNA  length = 51
FEATURE                 Location/Qualifiers
misc_feature            1..51
                        note = Codon-optimized polynucleotide
source                  1..51
                        mol_type = other DNA
                        organism = synthetic construct
SEQUENCE: 469
gattattggg cccagaaaga aaagatcagc atccccagaa cacacctgtg c           51

SEQ ID NO: 470          moltype = DNA  length = 48
FEATURE                 Location/Qualifiers
misc_feature            1..48
                        note = Codon-optimized polynucleotide
source                  1..48
                        mol_type = other DNA
                        organism = synthetic construct
SEQUENCE: 470
gtggccatga tggtgcccga tagacaggtc cactacgact ttggactg               48

SEQ ID NO: 471          moltype = DNA  length = 270
FEATURE                 Location/Qualifiers
misc_feature            1..270
                        note = Codon-optimized polynucleotide
source                  1..270
```

```
                        mol_type = other DNA
                        organism = synthetic construct
SEQUENCE: 471
gtgcccttcc gggaactgaa gaaccagaga acagctcagg gcgctcctgg aatccaccat  60
gctgcttctc cagtggccgc caacctgtgt gatcctgcca gacatgccca gcacaccagg  120
attccttgtg gcgctggaca agtgcgcgct ggaagaggac ctgaagcagg cggaggtgtt  180
ctgcaacctc aaagacccgc tcctgagaag cctggctgcc cttgcagaag aggacagcct  240
agactgcaca ccgtgaaaat gtggcgagcc                                    270

SEQ ID NO: 472          moltype = DNA  length = 33
FEATURE                 Location/Qualifiers
misc_feature            1..33
                        note = Codon-optimized polynucleotide
source                  1..33
                        mol_type = other DNA
                        organism = synthetic construct
SEQUENCE: 472
aagagaagct ttgccgtgac cgagcggatc atc                                33

SEQ ID NO: 473          moltype = DNA  length = 150
FEATURE                 Location/Qualifiers
misc_feature            1..150
                        note = Codon-optimized polynucleotide
source                  1..150
                        mol_type = other DNA
                        organism = synthetic construct
SEQUENCE: 473
ttcaagaagt tcgacggccc ttgcggagaa agaggcggag gcagaacagc tagagccctt  60
tgggctagag gcgacagcgt tctgacacca gctctggacc ctcagacacc tgttagggcc  120
cctagcctga caagagctgc cgccgctgtg                                    150

SEQ ID NO: 474          moltype = DNA  length = 42
FEATURE                 Location/Qualifiers
misc_feature            1..42
                        note = Codon-optimized polynucleotide
source                  1..42
                        mol_type = other DNA
                        organism = synthetic construct
SEQUENCE: 474
ctggtgctgg gagtgctgtc tggacactct ggcagcagac tg                      42

SEQ ID NO: 475          moltype = DNA  length = 66
FEATURE                 Location/Qualifiers
misc_feature            1..66
                        note = Codon-optimized polynucleotide
source                  1..66
                        mol_type = other DNA
                        organism = synthetic construct
SEQUENCE: 475
cagtggcagc actatcacag atctggcgaa gccgccggaa cacccctttg gaggccaaca  60
agaaac                                                              66

SEQ ID NO: 476          moltype = DNA  length = 285
FEATURE                 Location/Qualifiers
misc_feature            1..285
                        note = Codon-optimized polynucleotide
source                  1..285
                        mol_type = other DNA
                        organism = synthetic construct
SEQUENCE: 476
tgccacttgt ttctgcagcc ccaagtgggc acacctcctc cacatacagc ctctgctaga  60
gcacctagcg gccctccaca tcctcacgaa tcttgtcctg ccggaagaag gcctgccaga  120
gccgctcaaa catgtgccag acgacagcac ggactgcctg gatgtgaaga ggctggaaca  180
gccagagtgc ctagcctgca cctccatctg catcaggctg ctcttggagc cggaagaggt  240
agaggatggg gcgaagcttg tgctcaggtg ccaccttcta gaggc                   285

SEQ ID NO: 477          moltype = DNA  length = 27
FEATURE                 Location/Qualifiers
misc_feature            1..27
                        note = Codon-optimized polynucleotide
source                  1..27
                        mol_type = other DNA
                        organism = synthetic construct
SEQUENCE: 477
aagatccaga acaagaactg ccccgac                                       27

SEQ ID NO: 478          moltype = DNA  length = 225
FEATURE                 Location/Qualifiers
misc_feature            1..225
```

```
                        note = Codon-optimized polynucleotide
source                  1..225
                        mol_type = other DNA
                        organism = synthetic construct
SEQUENCE: 478
cactacaagc tgatccagca gccaatcagc ctgttcagca tcaccgaccg gctgcacaag  60
acattcagcc agctgccaag cgtgcacctg tgctccatca ccttccagtg gggacaccct  120
cctatctttt gctccaccaa cgacatctgc gtgaccgcca acttctgtat cagcgtgacc  180
ttcctgaagc cttgctttct gctgcacgag gccagcgcct ctcag                    225

SEQ ID NO: 479          moltype = DNA  length = 432
FEATURE                 Location/Qualifiers
misc_feature            1..432
                        note = Codon-optimized polynucleotide
source                  1..432
                        mol_type = other DNA
                        organism = synthetic construct
SEQUENCE: 479
cgaaccgctc tgacacacaa ccaggacttc agcatctaca gactgtgttg caagcggggc  60
tccctgtgcc atgcaagcca agctagaagc cccgcctttc ctaaacctgt gcgacctctg  120
ccagctccaa tcaccagaat taccccctcag ctcggcggcc agagcgattc atctcaacct  180
ctgctgacca ccggcagacc tcaaggctgg caagaccaag ctctgagaca cacccagcag  240
gctagccctg cctcttgtgc caccatcaca atccccatcc actctgccgc tctgggcgat  300
cattctggcg atcctggacc agcctgggac acatgtcctc cactgccact cacaacactg  360
atccctaggg ctcctccacc ttacggcgat tctaccgcta gaagctggcc cagcagatgt  420
ggaccactcg ga                                                        432

SEQ ID NO: 480          moltype = DNA  length = 201
FEATURE                 Location/Qualifiers
misc_feature            1..201
                        note = Codon-optimized polynucleotide
source                  1..201
                        mol_type = other DNA
                        organism = synthetic construct
SEQUENCE: 480
tacgcctaca aggacttcct gtggtgcttc cccttctctc tggtgttcct gcaagagatc  60
cagatctgct gtcatgtgtc ctgcctgtgc tgcatctgct gtagcaccag aatctgcctg  120
ggctgtctgc tggaactgtt cctgagcaga gccctgagag cactgcacgt gctgtggaac  180
ggattccagc tgcactgcca g                                              201

SEQ ID NO: 481          moltype = DNA  length = 48
FEATURE                 Location/Qualifiers
misc_feature            1..48
                        note = Codon-optimized polynucleotide
source                  1..48
                        mol_type = other DNA
                        organism = synthetic construct
SEQUENCE: 481
acaatgcccg ccatcctgaa gctgcagaag aattgcctcc taagcctg                48

SEQ ID NO: 482          moltype = DNA  length = 72
FEATURE                 Location/Qualifiers
misc_feature            1..72
                        note = Codon-optimized polynucleotide
source                  1..72
                        mol_type = other DNA
                        organism = synthetic construct
SEQUENCE: 482
tacgaagccg ggatgaccct gggcgagaag ttcagagtgg gcaactgcaa gcacctgaag  60
atgacccggc ct                                                       72

SEQ ID NO: 483          moltype = DNA  length = 51
FEATURE                 Location/Qualifiers
misc_feature            1..51
                        note = Codon-optimized polynucleotide
source                  1..51
                        mol_type = other DNA
                        organism = synthetic construct
SEQUENCE: 483
ggcgtgccag gcgatagcac tcggagagcc gtcagacgga tgaacacctt t            51

SEQ ID NO: 484          moltype = DNA  length = 48
FEATURE                 Location/Qualifiers
misc_feature            1..48
                        note = Codon-optimized polynucleotide
source                  1..48
                        mol_type = other DNA
                        organism = synthetic construct
SEQUENCE: 484
```

```
tgtggcgcct ctgcctgtga cgtgtccctg atcgctatgg actccgcc              48

SEQ ID NO: 485         moltype = DNA  length = 48
FEATURE                Location/Qualifiers
misc_feature           1..48
                       note = Codon-optimized polynucleotide
source                 1..48
                       mol_type = other DNA
                       organism = synthetic construct
SEQUENCE: 485
agcctgtacc accgggaaaa gcagctcatt gccatggaca gcgccatc              48

SEQ ID NO: 486         moltype = DNA  length = 48
FEATURE                Location/Qualifiers
misc_feature           1..48
                       note = Codon-optimized polynucleotide
source                 1..48
                       mol_type = other DNA
                       organism = synthetic construct
SEQUENCE: 486
accgagtaca accagaaact gcaagtgaac cagttcagcg agagcaag              48

SEQ ID NO: 487         moltype = DNA  length = 72
FEATURE                Location/Qualifiers
misc_feature           1..72
                       note = Codon-optimized polynucleotide
source                 1..72
                       mol_type = other DNA
                       organism = synthetic construct
SEQUENCE: 487
accgagatca gctgctgcac cctgagcagc gaggaaaacg agtacctgcc tagacctgag  60
tggcagctgc ag                                                     72

SEQ ID NO: 488         moltype = DNA  length = 42
FEATURE                Location/Qualifiers
misc_feature           1..42
                       note = Codon-optimized polynucleotide
source                 1..42
                       mol_type = other DNA
                       organism = synthetic construct
SEQUENCE: 488
tgcgaagaga gaggcgccgc aggatctctg atctcctgcg aa                    42

SEQ ID NO: 489         moltype = DNA  length = 48
FEATURE                Location/Qualifiers
misc_feature           1..48
                       note = Codon-optimized polynucleotide
source                 1..48
                       mol_type = other DNA
                       organism = synthetic construct
SEQUENCE: 489
aacagcaaga tggccctgaa tagcgaggcc ctgtctgtgg tgtctgaa              48

SEQ ID NO: 490         moltype = DNA  length = 210
FEATURE                Location/Qualifiers
misc_feature           1..210
                       note = Codon-optimized polynucleotide
source                 1..210
                       mol_type = other DNA
                       organism = synthetic construct
SEQUENCE: 490
tggggcatgg aactggccgc cagcagaaga ttcagctggg atcatcatag cgcaggcggc  60
ccacctagag tgccatctgt tagaagcgga gctgcccagg tgcagcctaa agatcctctg  120
ccactgagaa cactggccgg ctgccttgct agaacagccc atcttagacc tggcgccgag  180
tctctgcctc agccacaact gcactgtacc                                  210

SEQ ID NO: 491         moltype = DNA  length = 60
FEATURE                Location/Qualifiers
misc_feature           1..60
                       note = Codon-optimized polynucleotide
source                 1..60
                       mol_type = other DNA
                       organism = synthetic construct
SEQUENCE: 491
catgtcgtcg gctacggcca cctggataca agcggaagca gctctagctc cagctggcct  60

SEQ ID NO: 492         moltype = DNA  length = 105
FEATURE                Location/Qualifiers
misc_feature           1..105
```

-continued

```
                         note = Codon-optimized polynucleotide
source                   1..105
                         mol_type = other DNA
                         organism = synthetic construct
SEQUENCE: 492
aactcaaaaa tggctctgaa cagcctgaac tccatcgacg acgcccagct gacaagaatc   60
gcccctccta gatctcactg ctgcttttgg gaagtgaacg cccca               105

SEQ ID NO: 493           moltype = DNA   length = 48
FEATURE                  Location/Qualifiers
misc_feature             1..48
                         note = Codon-optimized polynucleotide
source                   1..48
                         mol_type = other DNA
                         organism = synthetic construct
SEQUENCE: 493
aagatgcact ttagcctgaa agaacaccct ccaccacctt gtcctcca                48

SEQ ID NO: 494           moltype = DNA   length = 207
FEATURE                  Location/Qualifiers
misc_feature             1..207
                         note = Codon-optimized polynucleotide
source                   1..207
                         mol_type = other DNA
                         organism = synthetic construct
SEQUENCE: 494
ctgtggttcc agtccagcga gctgtctcct actggtgccc cttggccatc tagacgccct   60
acttggagag gcaccaccgt gtcaccaaga accgccacaa gcagcgccag aacctgttgt  120
ggcacaaagt ggccctccag ccaagaagcc gctctcggac ttggaagcgg actgctgagg  180
ttctcttgtg gaaccgccgc cattcgg                                     207

SEQ ID NO: 495           moltype = DNA   length = 51
FEATURE                  Location/Qualifiers
misc_feature             1..51
                         note = Codon-optimized polynucleotide
source                   1..51
                         mol_type = other DNA
                         organism = synthetic construct
SEQUENCE: 495
atcgctagag agctgcacca gttcgccttc gacctgctga tcaagagcca c             51

SEQ ID NO: 496           moltype = DNA   length = 51
FEATURE                  Location/Qualifiers
misc_feature             1..51
                         note = Codon-optimized polynucleotide
source                   1..51
                         mol_type = other DNA
                         organism = synthetic construct
SEQUENCE: 496
cagcctgatt cttttgccgc actgcacagc tccctgaacg agctgggaga g             51

SEQ ID NO: 497           moltype = DNA   length = 51
FEATURE                  Location/Qualifiers
misc_feature             1..51
                         note = Codon-optimized polynucleotide
source                   1..51
                         mol_type = other DNA
                         organism = synthetic construct
SEQUENCE: 497
ttcgtgcaag gcaaggattg gggcctcaaa aagtttatcc gcagagactt c             51

SEQ ID NO: 498           moltype = DNA   length = 51
FEATURE                  Location/Qualifiers
misc_feature             1..51
                         note = Codon-optimized polynucleotide
source                   1..51
                         mol_type = other DNA
                         organism = synthetic construct
SEQUENCE: 498
tttgtgcagg gcaaagactg gggcgtgaag aagttcatcc ggcgggactt c             51

SEQ ID NO: 499           moltype = DNA   length = 204
FEATURE                  Location/Qualifiers
misc_feature             1..204
                         note = Codon-optimized polynucleotide
source                   1..204
                         mol_type = other DNA
                         organism = synthetic construct
SEQUENCE: 499
```

```
cagaacctgc agaacggcgg aggctctaga agctctgcta cacttcctgg caggcggcgg  60
agaagatggc tgagaagaag gcggcagcct atctctgtgg ctcctgctgg acctcctaga  120
cggcccaacc agaagcctaa tcctcctggc ggagccagat gcgtgatcat gaggcctaca  180
tggcctggca ccagcgcctt cacc                                         204

SEQ ID NO: 500         moltype = DNA  length = 81
FEATURE                Location/Qualifiers
misc_feature           1..81
                       note = Codon-optimized polynucleotide
source                 1..81
                       mol_type = other DNA
                       organism = synthetic construct
SEQUENCE: 500
tggaagttcg agatgagcta caccgttggc ggccctccac cacatgttca cgccagacct  60
agacactgga aaaccgacag a                                            81

SEQ ID NO: 501         moltype = DNA  length = 84
FEATURE                Location/Qualifiers
misc_feature           1..84
                       note = Codon-optimized polynucleotide
source                 1..84
                       mol_type = other DNA
                       organism = synthetic construct
SEQUENCE: 501
tacgaggccg gcatgacact cggaggcaag atcctgttct tcctgttcct gctgctccct  60
ctgagcccct tcagcctgat cttt                                         84

SEQ ID NO: 502         moltype = AA  length = 15
FEATURE                Location/Qualifiers
source                 1..15
                       mol_type = protein
                       organism = Homo sapiens
SEQUENCE: 502
CQAVVTQALR FNPSF                                                   15

SEQ ID NO: 503         moltype = DNA  length = 99
FEATURE                Location/Qualifiers
misc_feature           1..99
                       note = Codon-optimized polynucleotide
source                 1..99
                       mol_type = other DNA
                       organism = synthetic construct
SEQUENCE: 503
acaggcggca agagcacatg ttctgcccct ggacctcagt ctctgcccag cacacccttc  60
agcacatacc ctcagtgggt catcctgatc accgagctg                         99

SEQ ID NO: 504         moltype = DNA  length = 42
FEATURE                Location/Qualifiers
misc_feature           1..42
                       note = Codon-optimized polynucleotide
source                 1..42
                       mol_type = other DNA
                       organism = synthetic construct
SEQUENCE: 504
gtgctgcggt tcctggatct caaagtgcgc tacctgcaca gc                     42

SEQ ID NO: 505         moltype = DNA  length = 54
FEATURE                Location/Qualifiers
misc_feature           1..54
                       note = Codon-optimized polynucleotide
source                 1..54
                       mol_type = other DNA
                       organism = synthetic construct
SEQUENCE: 505
gattattggg cccagaaaga aaagggcagc agcagcttcc tgcggcctag ctgt        54

SEQ ID NO: 506         moltype = DNA  length = 183
FEATURE                Location/Qualifiers
misc_feature           1..183
                       note = Codon-optimized polynucleotide
source                 1..183
                       mol_type = other DNA
                       organism = synthetic construct
SEQUENCE: 506
gtgcccttcc gggaactgaa gaacgtgtcc gttctggaag gcctgaggca gggcagactt  60
ggcggacctt gtagctgcca ctgtcctaga ccaagccagg ccagactgac ccctgtggat  120
gtggctggcc catttctgtg tctgggcgac cctggactgt tccctccagt gaagtctagc  180
atc                                                                183
```

```
SEQ ID NO: 507         moltype = DNA  length = 177
FEATURE                Location/Qualifiers
misc_feature           1..177
                       note = Codon-optimized polynucleotide
source                 1..177
                       mol_type = other DNA
                       organism = synthetic construct
SEQUENCE: 507
ggcatggaat gtacactggg ccaagtggga gccccatctc ctagaagaga agaggatggc  60
tggcgcggag gccactctag attcaaagct gatgtgcccg ctcctcaggg cccttgttgg  120
ggaggacaac ctggatctgc cccatcttct gccccacctg aacagagcct gctggat     177

SEQ ID NO: 508         moltype = DNA  length = 96
FEATURE                Location/Qualifiers
misc_feature           1..96
                       note = Codon-optimized polynucleotide
source                 1..96
                       mol_type = other DNA
                       organism = synthetic construct
SEQUENCE: 508
ggcaacacca cactgcaaca gctgggagaa gcctctcagg ccccaagcgg ttctctgatc  60
cctctcagac tgcccctcct gtgggaagtg cggggc                            96

SEQ ID NO: 509         moltype = DNA  length = 129
FEATURE                Location/Qualifiers
misc_feature           1..129
                       note = Codon-optimized polynucleotide
source                 1..129
                       mol_type = other DNA
                       organism = synthetic construct
SEQUENCE: 509
gaggctttcc agagagcagc tggcgaaggc ggacctggca gaggtggtgc tagaagaggt  60
gctagagtgc tgcagagccc attctgtaga gctggcgctg gcgaatggct gggccaccaa  120
tctcttaga                                                          129

SEQ ID NO: 510         moltype = DNA  length = 51
FEATURE                Location/Qualifiers
misc_feature           1..51
                       note = Codon-optimized polynucleotide
source                 1..51
                       mol_type = other DNA
                       organism = synthetic construct
SEQUENCE: 510
gactattggg ctcaaaaaga gaagatcagc atccccagaa cacacctgtg c           51

SEQ ID NO: 511         moltype = DNA  length = 48
FEATURE                Location/Qualifiers
misc_feature           1..48
                       note = Codon-optimized polynucleotide
source                 1..48
                       mol_type = other DNA
                       organism = synthetic construct
SEQUENCE: 511
gtggccatga tggtgcccga cagacaggtg cactacgact tcggcctg               48

SEQ ID NO: 512         moltype = DNA  length = 270
FEATURE                Location/Qualifiers
misc_feature           1..270
                       note = Codon-optimized polynucleotide
source                 1..270
                       mol_type = other DNA
                       organism = synthetic construct
SEQUENCE: 512
gtgcccttca gagagctgaa aaaccagaga acagcccagg gcgctcctgg aatccatcat  60
gctgcttctc cagtggccgc caatctgtgc gatcctgcca gacatgccca gcataccagg  120
attccttgtg gcgctggaca agtgcgcgct ggaagaggac ctgaagctgg tggcggagtt  180
ctgcagcctc aaagacctgc tcctgagaag cctggctgcc cctgtagaag aggacagcct  240
agactgcaca ccgtgaagat gtggcgggcc                                   270

SEQ ID NO: 513         moltype = DNA  length = 33
FEATURE                Location/Qualifiers
misc_feature           1..33
                       note = Codon-optimized polynucleotide
source                 1..33
                       mol_type = other DNA
                       organism = synthetic construct
SEQUENCE: 513
aagagaagct tcgccgtgac cgagcggatc atc                               33
```

```
SEQ ID NO: 514         moltype = DNA  length = 150
FEATURE                Location/Qualifiers
misc_feature           1..150
                       note = Codon-optimized polynucleotide
source                 1..150
                       mol_type = other DNA
                       organism = synthetic construct
SEQUENCE: 514
tttaagaagt ttgacggccc ctgcggcgag agaggcggag gaagaactgc aagagccctt  60
tgggccagag gcgactctgt tctgacacca gctctggacc ctcagacacc tgttagggcc  120
cctagcctga caagagctgc cgctgctgtt                                   150

SEQ ID NO: 515         moltype = DNA  length = 42
FEATURE                Location/Qualifiers
misc_feature           1..42
                       note = Codon-optimized polynucleotide
source                 1..42
                       mol_type = other DNA
                       organism = synthetic construct
SEQUENCE: 515
ctggtgctgg gcgtgctgtc tggccactct ggaagcagac tg                     42

SEQ ID NO: 516         moltype = DNA  length = 66
FEATURE                Location/Qualifiers
misc_feature           1..66
                       note = Codon-optimized polynucleotide
source                 1..66
                       mol_type = other DNA
                       organism = synthetic construct
SEQUENCE: 516
caatggcagc actaccacag atctggcgaa gccgctggaa ccccactttg gaggcctacc  60
agaaac                                                             66

SEQ ID NO: 517         moltype = DNA  length = 285
FEATURE                Location/Qualifiers
misc_feature           1..285
                       note = Codon-optimized polynucleotide
source                 1..285
                       mol_type = other DNA
                       organism = synthetic construct
SEQUENCE: 517
tgccacttgt ttctccagcc acaagtgggc acccctccac ctcatacagc ctctgctaga  60
gcacctagcg gcccacctca tcctcacgaa tcttgtcctg ccggaagaag gcctgccaga  120
gccgctcaaa catgtgccag acgacagcac ggactgcccg gatgtgaaga agccggaaca  180
gccagagtgc ctagcctgca ccttcatctg catcaggccg ctcttggagc cggaagaggt  240
agaggatggg gagaagcttg tgcccaggtg ccaccttcta gaggc                  285

SEQ ID NO: 518         moltype = AA  length = 15
FEATURE                Location/Qualifiers
source                 1..15
                       mol_type = protein
                       organism = Homo sapiens
SEQUENCE: 518
LRFNPSFQEV CIYQD                                                   15

SEQ ID NO: 519         moltype = DNA  length = 225
FEATURE                Location/Qualifiers
misc_feature           1..225
                       note = Codon-optimized polynucleotide
source                 1..225
                       mol_type = other DNA
                       organism = synthetic construct
SEQUENCE: 519
cactacaagc tgatccagca gccaatcagc ctgttctcca tcaccgaccg gctgcacaag  60
acattcagcc agctgccttc cgtgcatctg tgcagcatca ccttccagtg gggacaccct  120
cctatctttt gctccaccaa cgacatctgc gtgaccgcca acttctgtat cagcgtgacc  180
ttcctgaagc cttgctttct gctgcacgag gcctccgcca gccag                  225

SEQ ID NO: 520         moltype = DNA  length = 432
FEATURE                Location/Qualifiers
misc_feature           1..432
                       note = Codon-optimized polynucleotide
source                 1..432
                       mol_type = other DNA
                       organism = synthetic construct
SEQUENCE: 520
cggaccgctc tgacccacaa ccaggacttc agcatctacc ggctgtgctg caagaggggc  60
tctctgtgtc atgctagcca ggctagaagc cccgcctttc ctaagcctgt cagacctctg  120
cctgctccta tcaccagaat cacccctcag ctcggcggcc agtctgattc atctcagcca  180
```

```
ctgctgacca ccggcagacc tcaaggatgg caagaccagg ctctgagaca cacacagcag  240
gctagcccag cctcttgcgc caccatcaca ataccaatac attctgccgc tctgggcgat  300
cacagcggag atcctggacc tgcctgggat acttgtcctc ctctgcccct aactacactg  360
atccctaggg ctcctccacc ttacggcgat agcacagcca gatcctggcc tagcagatgt  420
ggccctctgg gc                                                      432

SEQ ID NO: 521         moltype = DNA  length = 201
FEATURE                Location/Qualifiers
misc_feature           1..201
                       note = Codon-optimized polynucleotide
source                 1..201
                       mol_type = other DNA
                       organism = synthetic construct
SEQUENCE: 521
tacgcctaca aggacttcct gtggtgcttc cccttctctc tggtgttcct gcaagaaatc  60
cagatctgct gtcacgtgtc ctgcctgtgc tgtatctgct gtagcacccg gatctgtctg  120
ggctgtctgc tggaactgtt cctgagcaga gccctgagag cactgcacgt gctgtggaac  180
ggattccagc tgcactgcca g                                           201

SEQ ID NO: 522         moltype = DNA  length = 48
FEATURE                Location/Qualifiers
misc_feature           1..48
                       note = Codon-optimized polynucleotide
source                 1..48
                       mol_type = other DNA
                       organism = synthetic construct
SEQUENCE: 522
accatgcctg ccattctgaa gctgcagaag aattgtcttc taagcctg              48

SEQ ID NO: 523         moltype = DNA  length = 72
FEATURE                Location/Qualifiers
misc_feature           1..72
                       note = Codon-optimized polynucleotide
source                 1..72
                       mol_type = other DNA
                       organism = synthetic construct
SEQUENCE: 523
tatgaggctg gaatgaccct gggcgagaag ttcagagtgg gcaactgcaa gcacctgaag  60
atgacccggc ct                                                     72

SEQ ID NO: 524         moltype = DNA  length = 51
FEATURE                Location/Qualifiers
misc_feature           1..51
                       note = Codon-optimized polynucleotide
source                 1..51
                       mol_type = other DNA
                       organism = synthetic construct
SEQUENCE: 524
ggagtgcctg gcgattctac tagaagggcc gtgcggcgga tgaacacctt t          51

SEQ ID NO: 525         moltype = DNA  length = 48
FEATURE                Location/Qualifiers
misc_feature           1..48
                       note = Codon-optimized polynucleotide
source                 1..48
                       mol_type = other DNA
                       organism = synthetic construct
SEQUENCE: 525
tgtggcgcat ctgcctgcga cgtgtccctg atcgctatgg atagcgcc              48

SEQ ID NO: 526         moltype = AA  length = 11
FEATURE                Location/Qualifiers
source                 1..11
                       mol_type = protein
                       organism = Homo sapiens
SEQUENCE: 526
EVCIYQDTDL M                                                      11

SEQ ID NO: 527         moltype = AA  length = 15
FEATURE                Location/Qualifiers
source                 1..15
                       mol_type = protein
                       organism = Homo sapiens
SEQUENCE: 527
WCPLDLRLGS TGCLT                                                  15

SEQ ID NO: 528         moltype = DNA  length = 72
FEATURE                Location/Qualifiers
misc_feature           1..72
```

```
                        note = Codon-optimized polynucleotide
source                  1..72
                        mol_type = other DNA
                        organism = synthetic construct
SEQUENCE: 528
accgagatca gctgctgcac cctgagcagc gaggaaaacg agtacctgcc tagacctgaa  60
tggcagctgc ag                                                      72

SEQ ID NO: 529          moltype = DNA  length = 42
FEATURE                 Location/Qualifiers
misc_feature            1..42
                        note = Codon-optimized polynucleotide
source                  1..42
                        mol_type = other DNA
                        organism = synthetic construct
SEQUENCE: 529
tgcgaggaaa gaggcgcagc cggatctctg atctcttgcg ag                     42

SEQ ID NO: 530          moltype = DNA  length = 48
FEATURE                 Location/Qualifiers
misc_feature            1..48
                        note = Codon-optimized polynucleotide
source                  1..48
                        mol_type = other DNA
                        organism = synthetic construct
SEQUENCE: 530
aacagcaaga tggccctgaa tagcgaggcc ctgtctgtgg tgtccgag               48

SEQ ID NO: 531          moltype = DNA  length = 210
FEATURE                 Location/Qualifiers
misc_feature            1..210
                        note = Codon-optimized polynucleotide
source                  1..210
                        mol_type = other DNA
                        organism = synthetic construct
SEQUENCE: 531
tggggaatgg aactggccgc tagcaggcgg tttagctggg atcatcattc tgccggcgga  60
cctccaagag tgccaagcgt tagaagcgga gcagcccagg tccagcctaa agatccactg  120
ccactgagaa cactggccgg ctgccttgcc agaacagctc atcttagacc tggcgccgaa  180
agcctgcctc aacctcagct gcattgcaca                                   210

SEQ ID NO: 532          moltype = DNA  length = 60
FEATURE                 Location/Qualifiers
misc_feature            1..60
                        note = Codon-optimized polynucleotide
source                  1..60
                        mol_type = other DNA
                        organism = synthetic construct
SEQUENCE: 532
cacgttgtcg gctatggcca cctggataca agcggctcct ctagcagtag ctcctggcct  60

SEQ ID NO: 533          moltype = DNA  length = 105
FEATURE                 Location/Qualifiers
misc_feature            1..105
                        note = Codon-optimized polynucleotide
source                  1..105
                        mol_type = other DNA
                        organism = synthetic construct
SEQUENCE: 533
aattctaaga tggctctcaa cagcctgaac tccatcgacg acgcccagct gacaagaatc  60
gcccctccaa gaagccactg ttgcttttgg gaagtgaacg cccct                  105

SEQ ID NO: 534          moltype = DNA  length = 48
FEATURE                 Location/Qualifiers
misc_feature            1..48
                        note = Codon-optimized polynucleotide
source                  1..48
                        mol_type = other DNA
                        organism = synthetic construct
SEQUENCE: 534
aagatgcact tctcactgaa agagcacccg ccaccgccgt gcccaccg               48

SEQ ID NO: 535          moltype = DNA  length = 207
FEATURE                 Location/Qualifiers
misc_feature            1..207
                        note = Codon-optimized polynucleotide
source                  1..207
                        mol_type = other DNA
                        organism = synthetic construct
```

```
SEQUENCE: 535
ctgtggttcc agtccagcga actgtctcct actggcgctc catggccaag cagaaggcct  60
acttggagag gcaccaccgt gtctccaaga accgctacaa gcagcgccag aacctgttgc  120
ggcacaaaat ggccctccag ccaagaagct gccctcggac ttggaagcgg actgctgaga  180
ttcagctgtg gcacagccgc catcaga                                    207

SEQ ID NO: 536         moltype = DNA  length = 51
FEATURE                Location/Qualifiers
misc_feature           1..51
                       note = Codon-optimized polynucleotide
source                 1..51
                       mol_type = other DNA
                       organism = synthetic construct
SEQUENCE: 536
atcgccagag aactgcacca gttcgccttc gacctgctga tcaagagcca c          51

SEQ ID NO: 537         moltype = DNA  length = 51
FEATURE                Location/Qualifiers
misc_feature           1..51
                       note = Codon-optimized polynucleotide
source                 1..51
                       mol_type = other DNA
                       organism = synthetic construct
SEQUENCE: 537
cagcctgaca gctttgctgc cctgcatagc tccctgaatg agctgggcga a          51

SEQ ID NO: 538         moltype = DNA  length = 51
FEATURE                Location/Qualifiers
misc_feature           1..51
                       note = Codon-optimized polynucleotide
source                 1..51
                       mol_type = other DNA
                       organism = synthetic construct
SEQUENCE: 538
tttgtgcagg gtaaagattg gggcctcaaa aagtttatca gacgggactt c          51

SEQ ID NO: 539         moltype = DNA  length = 51
FEATURE                Location/Qualifiers
misc_feature           1..51
                       note = Codon-optimized polynucleotide
source                 1..51
                       mol_type = other DNA
                       organism = synthetic construct
SEQUENCE: 539
ttcgtgcagg gcaaagactg gggcgtgaag aagttcatcc ggcgggactt t          51

SEQ ID NO: 540         moltype = DNA  length = 204
FEATURE                Location/Qualifiers
misc_feature           1..204
                       note = Codon-optimized polynucleotide
source                 1..204
                       mol_type = other DNA
                       organism = synthetic construct
SEQUENCE: 540
cagaacctgc agaacggcgg aggctctaga agctctgcta cacttcctgg caggcggcgg  60
agaagatggc tgagaagaag gcggcagcct atctctgtgg ctcctgctgg acctcctaga  120
cggcccaacc agaagcctaa tcctcctggc ggagccagat gcgtgatcat gaggcctaca  180
tggcctggca ccagcgcctt tacc                                       204

SEQ ID NO: 541         moltype = AA  length = 1479
FEATURE                Location/Qualifiers
REGION                 1..1479
                       note = Heterologous protein
source                 1..1479
                       mol_type = protein
                       organism = synthetic construct
SEQUENCE: 541
QNLQNGGGSR SSATLPGRRR RRWLRRRRQP ISVAPAGPPR RPNQKPNPPG GARCVIMRPT  60
WPGTSAFTKR SFAVTERIID YWAQKEKGSS SFLRPSCDYW AQKEKISIPR THLCLVLGVL  120
SGHSGSRLYE AGMTLGGKIL FFLFLLLPLS PFSLIFTEIS CCTLSSEENE YLPRPEWQLQ  180
VPFRELKNVS VLEGLRQGRL GGPCSCHCPR PSQARLTPVD VAGPFLCLGD PGLFPPVKSS  240
ITGGKSTCSA PGPQSLPSTP FSTYPQWVIL ITELGMECTL GQVGAPSPRR EEDGWRGGHS  300
RFKADVPAPQ GPCWGGQPGS APSSAPPEQS LLDWKFEMSY TVGGPPPHVH ARPRHWKTDR  360
DGHSYTSKVN CLLLQDGFHG CVSITGAAGR RNLSIFLFLM LCKLEFHACK IQNKNCPDFK  420
KFDGPCGERG GGRTARALWA RGDSVLTPAL DPQTPVRAPS LTRAAAAVHY KLIQQPISLF  480
SITDRLHKTF SQLPSVHLCS ITFQWGHPPI FCSTNDICVT ANFCISVTFL KPCFLLHEAS  540
ASQCHLFLQP QVGTPPPHTA SARAPSGPPH PHESCPAGRR PARAAQTCAR RQHGLPGCEE  600
AGTARVPSLH LHLHQAALGA GRGRGWGEAC AQVPPSRGVL RFLDLKVRYL HSQWQHYHRS  660
GEAAGTPLWR PTRNVPFREL KNQRTAQGAP GIHHAASPVA ANLCDPARHA QHTRIPCGAG  720
```

```
QVRAGRGPEA GGGVLQPQRP APEKPGCPCR RGQPRLHTVK MWRAVAMMVP DRQVHYDFGL  780
GVPGDSTRRA VRRMNTFYEA GMTLGEKFRV GNCKHLKMTR PNSKMALNSE ALSVVSECGA  840
SACDVSLIAM DSAFVQGKDW GVKKFIRRDF YAYKDFLWCF PFSLVFLQEI QICCHVSCLC  900
CICCSTRICL GCLLELFLSR ALRALHVLWN GFQLHCQTEY NQKLQVNQFS ESKSLYHREK  960
QLIAMDSAIC EERGAAGSLI SCETMPAILK LQKNCLLSLR TALTHNQDFS IYRLCCKRGS  1020
LCHASQARSP AFPKPVRPLP APITRITPQL GGQSDSSQPL LTTGRPQGWQ DQALRHTQQA  1080
SPASCATITI PIHSAALGDH SGDPGPAWDT CPPLPLTTLI PRAPPPYGDS TARSWPSRCG  1140
PLGGNTTLQQ LGEASQAPSG SLIPLRLPLL WEVRGQPDSF AALHSSLNEL GEIARELHQF  1200
AFDLLIKSHF VQGKDWGLKK FIRRDFWGME LAASRRFSWD HHSAGGPPRV PSVRSGAAQV  1260
QPKDPLPLRT LAGCLARTAH LRPGAESLPQ PQLHCTLWFQ SSELSPTGAP WPSRRPTWRG  1320
TTVSPRTATS SARTCCGTKW PSSQEAALGL GSGLLRFSCG TAAIRKMHFS LKEHPPPPCP  1380
PEAFQRAAGE GGPGRGGARR GARVLQSPFC RAGAGEWLGH QSLRHVVGYG HLDTSGSSSS  1440
SSWPNSKMAL NSLNSIDDAQ LTRIAPPRSH CCFWEVNAP                        1479

SEQ ID NO: 542          moltype = DNA  length = 4437
FEATURE                 Location/Qualifiers
misc_feature            1..4437
                        note = Heterologous polynucleotide
source                  1..4437
                        mol_type = other DNA
                        organism = synthetic construct
SEQUENCE: 542
cagaacctgc agaacggcgg aggctctaga agctctgcta cacttcctgg caggcggcgg  60
agaagatggc tgagaagaag gcggcagcct atctctgtgg ctcctgctgg acctcctaga  120
cggcccaacc agaagcctaa tcctcctggc ggagccagat gcgtgatcat gaggcctaca  180
tggcctggca ccagcgcctt caccaagaga agctttgccg tgaccgagcg gatcatcgac  240
tattgggctc aaaaagagaa gggcagcagc agcttcctgc ggcctagctg tgattattgg  300
gcccagaaag aaaagatcag catccccaga acacacctgt gcctggtgct gggagtgctg  360
tctggacact ctggcagcag actgtatgag gccggcatga cactcggcgg caagatcctg  420
ttcttcctgt tcctgctgct ccctctgagc cccttcagcc tgatcttcac cgagatcagc  480
tgctgcaccc tgagcagcga ggaaaacgag tacctgccta gacctgagtg gcagctgcag  540
gtccccttca gagagctgaa gaacgtttcc gtgctggaag gcctgagaca gggcagactt  600
ggcggccctt gtagctgtca ctgccccaga cctagtcagg ccagactgac acctgtggat  660
gtggccggac ctttcctgtg tctgggagat cctggcctgt ttccacctgt gaagtccagc  720
atcacaggcg gcaagtccac atgttctgcc cctggacctc agagcctgcc tagcacaccc  780
ttcagcacat accctcagtg ggtcatcctg atcaccgaac tcggcatgga atgcaccctg  840
ggacaagtgg gagccccatc tcctagaaga gaagaggatg gctggcgcgg aggccactct  900
agattcaaag ctgatgtgcc cgctcctcag ggcccttgtt ggggaggaca acctggatct  960
gccccatctt ctgccccacc tgaacagtcc ctgctggatt ggaagttcga gatgagctac  1020
accgtcggcg gacctccacc tcatgttcat gccagacctc ggcactggaa aaccgacaga  1080
gatggccaca gctacaccag caaagtgaac tgcctcctgc tgcaggatgg cttccacggc  1140
tgtgtgtcta ttactggcgc cgctggcaga cggaacctga gcatctttct gtttctgatg  1200
ctgtgcaagc tcgagttcca cgcctgcaag atccagaaca agaactgccc cgacttcaag  1260
aagttcgacg gcccttgcgg agaaagaggc ggaggcagaa cagctagagc cctttgggct  1320
agaggcgaca gcgttctgac accagctctg gaccctcaga cacctgttag ggcccctagc  1380
ctgacaagag ctgccgccgc tgtgcactac aagctgatcc agcagccaat cagcctgttc  1440
agcatcaccg accggctgca caagacattc agccagctgc caagcgtgca cctgtgctcc  1500
atcaccttcc agtggggaca ccctcctatc ttttgctcca ccaacgacat ctgcgtgacc  1560
gccaacttct gtatcagcgt gaccttcctg aagccttgct ttctgctgca cgaggccagc  1620
gcctctcagt gccacttgtt tctgcagccc caagtgggca cacctcctcc acatacagcc  1680
tctgctagag cacctagcgg ccctccacat cctcacgaat cttgtcctgc cggaagaagg  1740
cctgccagag ccgctcaaac atgtgccaga cgacagcacg gactgcctgg atgtgaagag  1800
gctggaacag ccagagtgcc tagcctgcac ctccatctgc atcaggctgc tcttggagcc  1860
ggaagaggta gaggatgggg cgaagcttgt gctcaggtgc caccttctag aggcgtgctg  1920
agattcctgg acctgaaagt gcgctacctg cacagccagt ggcagcacta tcacagatct  1980
ggcgaagccg ccggaacacc cctttggagg ccaacaagaa acgtgccctt ccgggaactg  2040
aagaaccaga gaacagctca gggcgctcct ggaatccacc atgctgcttc tccagtggcc  2100
gccaacctgt gtgatcctgc cagacatgcc cagcacacca ggattccttg tggcgctgga  2160
caagtgcgcg ctggaagagg acctgaagca ggcggaggtg ttctgcaacc tcaaagaccc  2220
gctcctgaga agcctggctg cccttgcaga agaggacagc ctagactgca caccgtgaaa  2280
atgtggcgag ccgtggccat gatggtgccc gatagacagg tccactacga ctttggactg  2340
ggcgtgccag gcgatagcac tcggagagcc gtcagacgga tgaacacctt ttacgaagcc  2400
gggatgaccc tgggcgagaa gttcagagtg ggcaactgca agcacctgaa gatgacccgg  2460
cctaacagca agatggccct gaatagcgag gccctgtctg tggtgtctga atgtggcgcc  2520
tctgcctgtg acgtgtccct gatcgctatg gactccgcct ttgtgcaggg caaagactgg  2580
ggcgtgaaga agttcatccg gcgggacttc tacgcctaca aggacttcct gtggtgcttc  2640
cccttctctc tggtgttcct gcaagagatc cagatctgct gtcatgtgtc ctgcctgtgc  2700
tgcatctgct gtagcaccag aatctgcctg ggctgtctgc tggaactgtt cctgagcaga  2760
gccctgagag cactgcacgt gctgtggaac ggattccagc tgcactgcca gaccgagtac  2820
aaccagaaac tgcaagtgaa ccagttcagc gagagcaaga gcctgtacca ccgggaaaag  2880
cagctcattg ccatggacag cgccatctgc gaagagagag gcgccgcagg atctctgatc  2940
tcctgcgaaa caatgcccgc catcctgaag ctgcagaaga attgcctcct aagcctgcga  3000
accgctctga cacacaacca ggacttcagc atctacagac tgtgttgcaa gcggggctcc  3060
ctgtgccatg caagccaagc tagaagcccc gcctttccta aacctgtgcg acctctgcca  3120
gctccaatca ccagaattac ccctcagctc ggcggccaga gcgattcatc tcaacctctg  3180
ctgaccaccg gcagacctca aggctggcaa gaccaagctc tgagacacac ccagcaggct  3240
agccctgcct cttgtgccac catcacaatc cccatccact ctgccgctct gggcgatcat  3300
tctggcgatc ctggaccagc ctgggacaca tgtcctccac tgccactcac aacactgatc  3360
cctagggctc ctccacctta cggcgattct accgctagaa gctggcccag cagatgtgga  3420
```

-continued

```
ccactcggag gcaacacaac cctccagcaa ctgggagaag cctctcaggc tcctagcggc  3480
tctctgatcc ctctcagact gcctctcctg tgggaagttc ggggccagcc tgattctttt  3540
gccgcactgc acagctccct gaacgagctg ggagagatcg ctagagagct gcaccagttc  3600
gccttcgacc tgctgatcaa gagccacttc gtgcaaggca aggattgggg cctcaaaaag  3660
tttatccgca gagacttctg ggcatggaa ctggccgcca gcagaagatt cagctgggat  3720
catcatagcg caggcggccc acctagagtg ccatctgtta gaagcggagc tgcccaggtg  3780
cagcctaaag atcctctgcc actgagaaca ctggccggct gccttgctag aacagcccat  3840
cttagacctg gcgccgagtc tctgcctcag ccacaactgc actgtaccct gtggttccag  3900
tccagcgagc tgtctcctac tggtgcccct tggccatcta gacgccctac ttggagaggc  3960
accaccgtgt caccaagaac cgccacaagc agcgccagaa cctgttgtgg cacaaagtgg  4020
ccctccagcc aagaagccgc tctcggactt ggaagcggac tgctgaggtt ctcttgtgga  4080
accgccgcca ttcggaagat gcactttagc ctgaaagaac accctccacc accttgtcct  4140
ccagaggctt tccaaagagc tgctggcgaa ggcggacctg gtagaggtgg tgctagaaga  4200
ggtgctaggg tgctgcagag cccattctgt agagcaggcg caggcgaatg gctgggccat  4260
cagagtctga gacatgtcgt cggctacggc cacctggata caagcggaag cagctctagc  4320
tccagctggc ctaactcaaa aatggctctg aacagcctga actccatcga cgacgcccag  4380
ctgacaagaa tcgcccctcc tagatctcac tgctgctttt gggaagtgaa cgcccca     4437
```

```
SEQ ID NO: 543          moltype = AA  length = 1479
FEATURE                 Location/Qualifiers
REGION                  1..1479
                        note = Hetereologous protein
source                  1..1479
                        mol_type = protein
                        organism = synthetic construct
SEQUENCE: 543
QNLQNGGGSR SSATLPGRRR RRWLRRRRQP ISVAPAGPPR RPNQKPNPPG GARCVIMRPT  60
WPGTSAFTGM ECTLGQVGAP SPRREEDGWR GGHSRFKADV PAPQGPCWGG QPGSAPSSAP  120
PEQSLLDDYW AQKEKISIPR THLCWKFEMS YTVGGPPPHV HARPRHWKTD RDYWAQKEKG  180
SSSFLRPSCV PFRELKNVSV LEGLRQGRLG GPCSCHCPRP SQARLTPVDV AGPFLCLGDP  240
GLFPPVKSSI TEISCCTLSS EENEYLPRPE WQLQYEAGMT LGGKILFFLF LLLPLSPFSL  300
IFLVLGVLSG HSGSRLKRSF AVTERIITGG KSTCSAPGPQ SLPSTPFSTY PQWVILITEL  360
DGHSYTSKVN CLLLQDGFHG CVSITGAAGR RNLSIFLFLM LCKLEFHACQ WQHYHRSGEA  420
AGTPLWRPTR NVAMMVPDRQ VHYDFGLKIQ NKNCPDVLRF LDLKVRYLHS VPFRELKNQR  480
TAQGAPGIHH AASPVAANLC DPARHAQHTR IPCGAGQVRA GRGPEAGGGV LQPQRPAPEK  540
PGCPCRRGQP RLHTVKMWRA CHLFLQPQVG TPPPHTASAR APSGPPHPHE SCPAGRRPAR  600
AAQTCARRQH GLPGCEEAGT ARVPSLHLHL HQAALGAGRG RGWGEACAQV PPSRGHYKLI  660
QQPISLFSIT DRLHKTFSQL PSVHLCSITF QWGHPPIFCS TNDICVTANF CISVTFLKPC  720
FLLHEASASQ FKKFDGPCGE RGGGRTARAL WARGDSVLTP ALDPQTPVRA PSLTRAAAAV  780
GVPGDSTRRA VRRMNTFCGA SACDVSLIAM DSACEERGAA GSLISCESLY HREKQLIAMD  840
SAIFVQGKDW GVKKFIRRDF TMPAILKLQK NCLLSLNSKM ALNSEALSVV SEYEAGMTLG  900
EKFRVGNCKH LKMTRPTEYN QKLQVNQFSE SKRTALTHNQ DFSIYRLCCK RGSLCHASQA  960
RSPAFPKPVR PLPAPITRIT PQLGGQSDSS QPLLTTGRPQ GWQDQALRHT QQASPASCAT  1020
ITIPIHSAAL GDHSGDPGPA WDTCPPLPLT TLIPRAPPPY GDSTARSWPS RCGPLGYAYK  1080
DFLWCFPFSL VFLQEIQICC HVSCLCCICC STRICLGCLL ELFLSRALRA LHVLWNGFQL  1140
HCQGNTTLQQ LGEASQAPSG SLIPLRLPLL WEVRGNSKMA LNSLNSIDDA QLTRIAPPRS  1200
HCCFWEVNAP FVQGKDWGLK KFIRRDFEAF QRAAGEGGPG RGGARRGARV LQSPFCRAGA  1260
GEWLGHQSLR WGMELAASRR FSWDHHSAGG PPRVPSVRSG AAQVQPKDPL PLRTLAGCLA  1320
RTAHLRPGAE SLPQPQLHCT IARELHQFAF DLLIKSHKMH FSLKEHPPPP CPPHVVGYGH  1380
LDTSGSSSSS SWPQPDSFAA LHSSLNELGE LWFQSSELSP TGAPWPSRRP TWRGTTVSPR  1440
TATSSARTCC GTKWPSSQEA ALGLGSGLLR FSCGTAAIR                        1479
```

```
SEQ ID NO: 544          moltype = DNA  length = 4437
FEATURE                 Location/Qualifiers
misc_feature            1..4437
                        note = Heterologous polynucleotide
source                  1..4437
                        mol_type = other DNA
                        organism = synthetic construct
SEQUENCE: 544
cagaacctgc agaacggcgg aggctctaga agctctgcta cacttcctgg caggcggcgg  60
agaagatggc tgagaagaag gcggcagcct atctctgtgg ctcctgctgg acctcctaga  120
cggcccaacc agaagcctaa tcctcctggc ggagccagat gcgtgatcat gaggcctaca  180
tggcctggca ccagcgcctt taccggcatg gaatgtacac tgggccaagt gggagcccca  240
tctcctagaa gagaagagga tggctggcgc ggaggccact ctagattcaa agctgatgtg  300
cccgctcctc agggcccttg ttggggagga caacctggat ctgccccatc ttctgcccca  360
cctgaacaga gcctgctgga tgactattgg gctcaaaaag agaagatcag catccccaga  420
acacacctgt gctggaagtt cgagatgagc tacaccgttg gcggccctcc accacatgtt  480
cacgccagac ctagacactg gaaaaccgac agagattatt gggcccagaa agaaaagggc  540
agcagcagct tcctgcggcc tagctgtgtg cccttccggg aactgaagaa cgtgtccgtt  600
ctggaaggcc tgaggcaggg cagacttggc ggaccttgta gctgccactg tcctagacca  660
agccaggcca gactgacccc tgtggatgtg gctggcccat ttctgtgtct gggcgaccct  720
ggactgttcc ctccagtgaa gtctagcatc accgagatca gctgctgcac cctgagcagc  780
gaggaaaacg agtacctgcc tagacctgaa tggcagctgc agtacgaggc cggcatgaca  840
ctcggaggca agatcctgtt cttcctgttc ctgctgctcc ctctgagccc cttcagcctg  900
atctttctgg tgctgggcgt gctgtctggc cactctggaa gcagactgaa gagaagcttc  960
gccgtgaccg agcggatcat cacaggcggc aagagcacat gttctgcccc tggacctcag  1020
tctctgccca gcacaccctt cagcacatac cctcagtggg tcatcctgat caccgagctg  1080
gatggccaca gctacaccag caaagtgaac tgcctcctgc tgcaggatgg cttccacggc  1140
```

-continued

```
tgtgtgtcta ttactggcgc cgctggcaga cggaacctga gcatctttct gtttctgatg  1200
ctgtgcaagc tcgagttcca cgcctgccaa tggcagcact accacagatc tggcgaagcc  1260
gctggaaccc cactttggag gcctaccaga aacgtggcca tgatggtgcc cgacagacag  1320
gtgcactacg acttcggcct gaagatccag aacaagaact gccccgacgt gctgcggttc  1380
ctggatctca aagtgcgcta cctgcacagc gtgcccttca gagagctgaa aaaccagaga  1440
acagcccagg gcgctcctgg aatccatcat gctgcttctc cagtggccgc caatctgtgc  1500
gatcctgcca gacatgccca gcataccagg attccttgtg gcgctggaca agtgcgcgct  1560
ggaagaggac ctgaagctgg tggcggagtt ctgcagcctc aaagacctgc tcctgagaag  1620
cctggctgcc cctgtagaag aggacagcct agactgcaca ccgtgaagat gtggcgggcc  1680
tgccacttgt ttctccagcc acaagtgggc accectccac ctcatacagc ctctgctaga  1740
gcacctagcg gcccacctca tcctcacgaa tcttgtcctg ccggaagaag gcctgccaga  1800
gccgctcaaa catgtgccag acgacagcac ggactgcccg gatgtgaaga agccggaaca  1860
gccagagtgc ctagcctgca ccttcatctg catcaggccg ctcttggagc cggaagaggt  1920
agaggatggg gagaagcttg tgcccaggtg ccaccttcta gaggccacta caagctgatc  1980
cagcagccaa tcagcctgtt ctccatcacc gaccggctgc acaagacatt cagccagctg  2040
ccttccgtgc atctgtgcag catcaccttc cagtggggac accctcctat cttttgctcc  2100
accaacgaca tctgcgtgac cgccaacttc tgtatcagcg tgaccttcct gaagccttgc  2160
tttctgctgc acgaggcctc cgccagccag tttaagaagt ttgacggccc ctgcggcgag  2220
agaggcggag gaagaactgc aagagccctt tgggccagag gcgactctgt tctgacacca  2280
gctctggacc ctcagacacc tgttagggcc cctagcctga caagagctgc cgctgctgtt  2340
ggagtgcctg gcgattctac tagaagggcc gtgcggcgga tgaacacctt ttgtggcgca  2400
tctgcctgcg acgtgtccct gatcgctatg gatagcgcct gcgaggaaag aggcgcagcc  2460
ggatctctga tctcttgcga gagcctgtac caccgggaaa agcagctcat tgccatggac  2520
agcgccatct tcgtgcaggg caaagactgg ggcgtgaaga agttcatccg gcgggacttt  2580
accatgcctg ccattctgaa gctgcagaag aattgtcttc taagcctgaa cagcaagatg  2640
gccctgaata gcgaggccct gtctgtggtg tccgagtatg aggctggaat gaccctgggc  2700
gagaagttca gagtgggcaa ctgcaagcac ctgaagatga cccggcctac cgagtacaac  2760
cagaaactgc aagtgaacca gttcagcgag agcaagcgga ccgctctgac ccacaaccag  2820
gacttcagca tctaccggct gtgctgcaag aggggctctc tgtgtcatgc tagccaggct  2880
agaagccccg cctttcctaa gcctgtcaga cctctgcctg ctcctatcac cagaatcacc  2940
cctcagctcg gcggccagtc tgattcatct cagccactgc tgaccaccgg cagacctcaa  3000
ggatggcaag accaggctct gagacacaca cagcaggcta gcccagcctc ttgcgccacc  3060
atcacaatac caatacattc tgccgctctg ggcgatcaca gcggagatcc tggacctgcc  3120
tgggatactt gtcctcctct gcccctaact acactgatcc ctagggctcc tccaccttac  3180
ggcgatagca cagccagatc ctggcctagc agatgtggcc ctctgggcta cgcctacaag  3240
gacttcctgt ggtgcttccc cttctctctg gtgttcctgc aagaaatcca gatctgctgt  3300
cacgtgtcct gcctgtgctg tatctgctgt agcacccgga tctgtctggg ctgtctgctg  3360
gaactgttcc tgagcagagc cctgagagca ctgcacgtgc tgtggaacgg attccagctg  3420
cactgccagg gcaacaccac actgcaacag ctgggagaag cctctcaggc cccaagcggt  3480
tctctgatcc ctctcagact gcccctcctg tgggaagtgc ggggcaattc taagatggct  3540
ctcaacagcc tgaactccat cgacgacgcc cagctgacaa gaatcgcccc tccaagaagc  3600
cactgttgct tttgggaagt gaacgcccct tttgtgcagg gtaaagattg ggggcctcaaa  3660
aagtttatca gacgggactt cgaggctttc cagagagcag ctggcgaagg cggacctggc  3720
agaggtggtg ctagaagagg tgctagagtg ctgcagagcc cattctgtag agctggcgct  3780
ggcgaatggc tgggccacca atctcttaga tggggaatgg aactggccgc tagcaggcgg  3840
tttagctggg atcatcattc tgccggcgga cctccaagag tgccaagcgt tagaagcgga  3900
gcagcccagg tccagcctaa agatccactg ccactgagaa cactggccgg ctgccttgcc  3960
agaacagctc atcttagacc tggcgccgaa agcctgcctc aacctcagct gcattgcaca  4020
atcgccagag aactgcacca gttcgccttc gacctgctga tcaagagcca caagatgcac  4080
ttctcactga aagagcaccc gccaccgccg tgcccaccgc acgttgtcgg ctatggccac  4140
ctggatacaa gcggctcctc tagcagtagc tcctggcctc agcctgacag ctttgctgcc  4200
ctgcatagct ccctgaatga gctgggcgaa ctgtggttcc agtccagcga actgtctcct  4260
actggcgctc catggccaag cagaaggcct acttggagag gcaccaccgt gtctccaaga  4320
accgctacaa gcagcgccag aacctgttgc ggcacaaaat ggccctccag ccaagaagct  4380
gccctcggac ttggaagcgg actgctgaga ttcagctgtg gcacagccgc catcaga     4437

SEQ ID NO: 545         moltype = DNA  length = 15
FEATURE                Location/Qualifiers
source                 1..15
                       mol_type = genomic DNA
                       organism = Homo sapiens
SEQUENCE: 545
cgcgacttcg ccgcc                                                   15

SEQ ID NO: 546         moltype = DNA  length = 84
FEATURE                Location/Qualifiers
misc_feature           1..84
                       note = T cell enhancer
source                 1..84
                       mol_type = other DNA
                       organism = synthetic construct
SEQUENCE: 546
atgggccaga aagagcagat ccacacactg cagaaaaaca gcgagcggat gagcaagcag  60
ctgaccagat cttctcaggc cgtg                                         84

SEQ ID NO: 547         moltype = DNA  length = 21
FEATURE                Location/Qualifiers
misc_feature           1..21
                       note = Tag seqeunce
```

```
source                  1..21
                        mol_type = other DNA
                        organism = synthetic construct
SEQUENCE: 547
agccatcacc atcaccacca t                                            21

SEQ ID NO: 548          moltype = AA  length = 12
FEATURE                 Location/Qualifiers
source                  1..12
                        mol_type = protein
                        organism = Homo sapiens
SEQUENCE: 548
IKSLTAIFTV KF                                                      12

SEQ ID NO: 549          moltype = AA  length = 28
FEATURE                 Location/Qualifiers
REGION                  1..28
                        note = T cell enhancer
source                  1..28
                        mol_type = protein
                        organism = synthetic construct
SEQUENCE: 549
MGQKEQIHTL QKNSERMSKQ LTRSSQAV                                     28

SEQ ID NO: 550          moltype = AA  length = 1507
FEATURE                 Location/Qualifiers
REGION                  1..1507
                        note = Heterologous polypeptide
source                  1..1507
                        mol_type = protein
                        organism = synthetic construct
SEQUENCE: 550
MGQKEQIHTL QKNSERMSKQ LTRSSQAVQN LQNGGGSRSS ATLPGRRRRR WLRRRRQPIS  60
VAPAGPPRRP NQKPNPPGGA RCVIMRPTWP GTSAFTKRSF AVTERIIDYW AQKEKGSSSF  120
LRPSCDYWAQ KEKISIPRTH LCLVLGVLSG HSGSRLYEAG MTLGGKILFF LFLLLPLSPF  180
SLIFTEISCC TLSSEENEYL PRPEWQLQVP FRELKNVSVL EGLRQGRLGG PCSCHCPRPS  240
QARLTPVDVA GPFLCLGDPG LFPPVKSSIT GGKSTCSAPG PQSLPSTPFS TYPQWVILIT  300
ELGMECTLGQ VGAPSPRREE DGWRGGHSRF KADVPAPQGP CWGGQPGSAP SSAPPEQSLL  360
DWKFEMSYTV GGPPPHVHAR PRHWKTDRDG HSYTSKVNCL LLQDGFHGCV SITGAAGRRN  420
LSIFLFLMLC KLEFHACKIQ NKNCPDFKKF DGPCGERGGG RTARALWARG DSVLTPALDP  480
QTPVRAPSLT RAAAAVHYKL IQQPISLFSI TDRLHKTFSQ LPSVHLCSIT FQWGHPPIFC  540
STNDICVTAN FCISVTFLKP CFLLHEASAS QCHLFLQPQV GTPPPHTASA RAPSGPPHPH  600
ESCPAGRRPA RAAQTCARRQ HGLPGCEEAG TARVPSLHLH LHQAALGAGR GRGWGEACAQ  660
VPPSRGVLRF LDLKVRYLHS QWQHYHRSGE AAGTPLWRPT RNVPFRELKN QRTAQGAPGI  720
HHAASPVAAN LCDPARHAQH TRIPCGAGQV RAGRGPEAGG GVLQPQRPAP EKPGCPCRRG  780
QPRLHTVKMW RAVAMMVPDR QVHYDFGLGV PGDSTRRAVR RMNTFYEAGM TLGEKFRVGN  840
CKHLKMTRPN SKMALNSEAL SVVSECGASA CDVSLIAMDS AFVQGKDWGV KKFIRRDFYA  900
YKDFLWCFPF SLVFLQEIQI CCHVSCLCCI CCSTRICLGC LLELFLSRAL RALHVLWNGF  960
QLHCQTEYNQ KLQVNQFSES KSLYHREKQL IAMDSAICEE RGAAGSLISC ETMPAILKLQ  1020
KNCLLSLRTA LTHNQDFSIY RLCCKRGSLC HASQARSPAF PKPVRPLPAP ITRITPQLGG  1080
QSDSSQPLLT TGRPQGWQDQ ALRHTQQASP ASCATITIPI HSAALGDHSG DPGPAWDTCP  1140
PLPLTTLIPR APPPYGDSTA RSWPSRCGPL GGNTTLQQLG EASQAPSGSL IPLRLPLLWE  1200
VRGQPDSFAA LHSSLNELGE IARELHQFAF DLLIKSHFVQ GKDWGLKKFI RRDFWGMELA  1260
ASRRFSWDHH SAGGPPRVPS VRSGAAQVQP KDPLPLRTLA GCLARTAHLR PGAESLPQPQ  1320
LHCTLWFQSS ELSPTGAPWP SRRPTWRGTT VSPRTATSSA RTCCGTKWPS SQEAALGLGS  1380
GLLRFSCGTA AIRKMHFSLK EHPPPPCPPE AFQRAAGEGG PGRGGARRGA RVLQSPFCRA  1440
GAGEWLGHQS LRHVVGYGHL DTSGSSSSSS WPNSKMALNS LNSIDDAQLT RIAPPRSHCC  1500
FWEVNAP                                                            1507

SEQ ID NO: 551          moltype = AA  length = 5703
FEATURE                 Location/Qualifiers
REGION                  1..5703
                        note = Heterologous polypeptide
source                  1..5703
                        mol_type = protein
                        organism = synthetic construct
SEQUENCE: 551
CCATTGCATA CGTTGTATCC ATATCATAAT ATGTACATTT ATATTGGCTC ATGTCCAACA  60
TTACCGCCAT GTTGACATTG ATTATTGACT AGTTATTAAT AGTAATCAAT TACGGGGTCA  120
TTAGTTCATA GCCCATATAT GGAGTTCCGC GTTACATAAC TTACGGTAAA TGGCCCGCCT  180
GGCTGACCGC CCAACGACCC CCGCCCATTG ACGTCAATAA TGACGTATGT TCCCATAGTA  240
ACGCCAATAG GGACTTTCCA TTGACGTCAA TGGGTGGAGT ATTTACGGTA AACTGCCCAC  300
TTGGCAGTAC ATCAAGTGTA TCATATGCCA AGTACGCCCC CTATTGACGT CAATGACGGT  360
AAATGGCCCG CCTGGCATTA TGCCCAGTAC ATGACCTTAT GGGACTTTCC TACTTGGCAG  420
TACATCTACG TATTAGTCAT CGCTATTACC ATGGTGATGC GGTTTTGGCA GTACATCAAT  480
GGGCGTGGAT AGCGGTTTGA CTCACGGGGA TTTCCAAGTC TCCACCCCAT TGACGTCAAT  540
GGGAGTTTGT TTTGGCACCA AAATCAACGG GACTTTCCAA AATGTCGTAA CAACTCCGCC  600
CCATTGACGC AAATGGGCGG TAGGCGTGTA CGGTGGGAGG TCTATATAAG CAGAGCTCTC  660
CCTATCAGTG ATAGAGATCT CCCTATCAGT GATAGAGATC GTCGACGAGC TCGTTTAGTG  720
```

-continued

```
AACCGTCAGA TCGCCTGGAG ACGCCATCCA CGCTGTTTTG ACCTCCATAG AAGACACCGG  780
GACCGATCCA GCCTCCGCGG CCGGGAACGG TGCATTGGAA CGCGGATTCC CCGTGCCAAG  840
AGTGAGATCT TCCGTTTATC TAGGTACCAG ATATCAGAAT TCGGATCCCG CGACTTCGCC  900
GCCATGGGCC AGAAAGAGCA GATCCACACA CTGCAGAAAA ACAGCGAGCG GATGAGCAAG  960
CAGCTGACCA GATCTTCTCA GGCCGTGCAG AACCTGCAGA ACGGCGGAGG CTCTAGAAGC  1020
TCTGCTACAC TTCCTGGCAG GCGGCGGAGA AGATGGCTGA GAAGAAGGCG GCAGCCTATC  1080
TCTGTGGCTC CTGCTGGACC TCCTAGACGG CCCAACCAGA AGCCTAATCC TCCTGGCGGA  1140
GCCAGATGCG TGATCATGAG GCCTACATGG CCTGGCACCA GCGCCTTCAC CAAGAGAAGC  1200
TTTGCCGTGA CCGAGCGGAT CATCGACTAT TGGGCTCAAA AAGAGAAGGG CAGCAGCAGC  1260
TTCCTGCGGC CTAGCTGTGA TTATTGGGCC CAGAAAGAAA AGATCAGCAT CCCCAGAACA  1320
CACCTGTGCC TGGTGCTGGG AGTGCTGTCT GGACACTCTG GCAGCAGACT GTATGAGGCC  1380
GGCATGACAC TCGGCGGCAA GATCCTGTTC TTCCTGTTCC TGCTGCTCCC TCTGAGCCCC  1440
TTCAGCCTGA TCTTCACCGA GATCAGCTGC TGCACCCTGA GCAGCGAGGA AAACGAGTAC  1500
CTGCCTAGAC CTGAGTGGCA GCTGCAGGTC CCCTTCAGAG AGCTGAAGAA CGTTTCCGTG  1560
CTGGAAGGCC TGAGACAGGG CAGACTTGGC GGCCCTTGTA GCTGTCACTG CCCCAGACCT  1620
AGTCAGGCCA GACTGACACC TGTGGATGTG GCCGGACCTT TCCTGTGTCT GGGAGATCCT  1680
GGCCTGTTTC CACCTGTGAA GTCCAGCATC ACAGGCGGCA AGTCCACATG TTCTGCCCCT  1740
GGACCTCAGA GCCTGCCTAG CACACCCTTC AGCACATACC CTCAGTGGGT CATCCTGATC  1800
ACCGAACTCG GCATGGAATG CACCCTGGGA CAAGTGGGAG CCCCATCTCC TAGAAGAGAA  1860
GAGGATGGCT GGCGCGGAGG CCACTCTAGA TTCAAAGCTG ATGTGCCCGC TCCTCAGGGC  1920
CCTTGTTGGG GAGGACAACC TGGATCTGCC CCATCTTCTG CCCCACCTGA ACAGTCCCTG  1980
CTGGATTGGA AGTTCGAGAT GAGCTACACC GTCGGCGGAC CTCCACCTCA TGTTCATGCC  2040
AGACCTCGGC ACTGGAAAAC CGACAGAGAT GGCCACAGCT ACACCAGCAA AGTGAACTGC  2100
CTCCTGCTGC AGGATGGCTT CCACGGCTGT GTGTCTATTA CTGGCGCCGC TGGCAGACGG  2160
AACCTGAGCA TCTTTCTGTT TCTGATGCTG TGCAAGCTCG AGTTCCACGC CTGCAAGATC  2220
CAGAACAAGA ACTGCCCCGA CTTCAAGAAG TTCGACGGCC CTTGCGGAGA AAGAGGCGGA  2280
GGCAGAACAG CTAGAGCCCT TTGGGCTAGA GGCGACAGCG TTCTGACACC AGCTCTGGAC  2340
CCTCAGACAC CTGTTAGGGC CCCTAGCCTG ACAAGAGCTG CCGCCGCTGT GCACTACAAG  2400
CTGATCCAGC AGCCAATCAG CCTGTTCAGC ATCACCGACC GGCTGCACAA GACATTCAGC  2460
CAGCTGCCAA GCGTGCACCT GTGCTCCATC ACCTTCCAGT GGGGACACCC TCCTATCTTT  2520
TGCTCCACCA ACGACATCTG CGTGACCGCC AACTTCTGTA TCAGCGTGAC CTTCCTGAAG  2580
CCTTGCTTTC TGCTGCACGA GGCCAGCGCC TCTCAGTGCC ACTTGTTTCT GCAGCCCCAA  2640
GTGGGCACAC CTCCTCCACA TACAGCCTCT GCTAGAGCAC CTAGCGGCCC TCCACATCCT  2700
CACGAATCTT GTCCTGCCGG AAGAAGGCCT GCCAGAGCCG CTCAAACATG TGCCAGACGA  2760
CAGCACGGAC TGCCTGGATG TGAAGAGGCT GGAACAGCCA GAGTGCCTAG CCTGCACCTC  2820
CATCTGCATC AGGCTGCTCT TGGAGCCGGA AGAGGTAGAG GATGGGGCGA AGCTTGTGCT  2880
CAGGTGCCAC CTTCTAGAGG CGTGCTGAGA TTCCTGGACC TGAAAGTGCG CTACCTGCAC  2940
AGCCAGTGGC AGCACTATCA CAGATCTGGC GAAGCCGCCG GAACACCCCT TTGGAGGCCA  3000
ACAAGAAACG TGCCCTTCCG GGAACTGAAG AACCAGAGAA CAGCTCAGGG CGCTCCTGGA  3060
ATCCACCATG CTGCTTCTCC AGTGGCCGCC AACCTGTGTG ATCCTGCCAG ACATGCCCAG  3120
CACACCAGGA TTCCTTGTGG CGCTGGACAA GTGCGCGCTG GAAGAGGACC TGAAGCAGGC  3180
GGAGGTGTTC TGCAACCTCA AAGACCCGCT CCTGAGAAGC CTGGCTGCCC TTGCAGAAGA  3240
GGACAGCCTA GACTGCACAC CGTGAAAATG TGGCGAGCCG TGGCCATGAT GGTGCCCGAT  3300
AGACAGGTCC ACTACGACTT TGGACTGGGC GTGCCAGGCG ATAGCACTCG GAGAGCCGTC  3360
AGACGGATGA ACACCTTTTA CGAAGCCGGG ATGACCCTGG GCGAGAAGTT CAGAGTGGGC  3420
AACTGCAAGC ACCTGAAGAT GACCCGGCCT AACAGCAAGA TGGCCCTGAA TAGCGAGGCC  3480
CTGTCTGTGG TGTCTGAATG TGGCGCCTCT GCCTGTGACG TGTCCCTGAT CGCTATGGAC  3540
TCCGCCTTTG TGCAGGGCAA AGACTGGGGC GTGAAGAAGT TCATCCGGCG GGACTTCTAC  3600
GCCTACAAGG ACTTCCTGTG GTGCTTCCCC TTCTCTCTGG TGTTCCTGCA AGAGATCCAG  3660
ATCTGCTGTC ATGTGTCCTG CCTGTGCTGC ATCTGCTGTA GCACCAGAAT CTGCCTGGGC  3720
TGTCTGCTGG AACTGTTCCT GAGCAGAGCC CTGAGAGCAC TGCACGTGCT GTGGAACGGA  3780
TTCCAGCTGC ACTGCCAGAC CGAGTACAAC CAGAAACTGC AAGTGAACCA GTTCAGCGAG  3840
AGCAAGAGCC TGTACCACCG GGAAAAGCAG CTCATTGCCA TGGACAGCGC CATCTGCGAA  3900
GAGAGAGGCG CCGCAGGATC TCTGATCTCC TGCGAAACAA TGCCCGCCAT CCTGAAGCTG  3960
CAGAAGAATT GCCTCCTAAG CCTGCGAACC GCTCTGACAC ACAACCAGGA CTTCAGCATC  4020
TACAGACTGT GTTGCAAGCG GGGCTCCCTG TGCCATGCAA GCCAAGCTAG AAGCCCCGCC  4080
TTTCCTAAAC CTGTGCGACC TCTGCCAGCT CCAATCACCA GAATTACCCC TCAGCTCGGC  4140
GGCCAGAGCG ATTCATCTCA ACCTCTGCTG ACCACCGGCA GACCTCAAGG CTGGCAAGAC  4200
CAAGCTCTGA GACACACCCA GCAGGCTAGC CCTGCCTCTT GTGCCACCAT CACAATCCCC  4260
ATCCACTCTG CCGCTCTGGG CGATCATTCT GGCGATCCTG GACCAGCCTG GGACACATGT  4320
CCTCCACTGC CACTCACAAC ACTGATCCCT AGGGCTCCTC CACCTTACGG CGATTCTACC  4380
GCTAGAAGCT GGCCCAGCAG ATGTGGACCA CTCGGAGGCA ACACAACCCT CCAGCAACTG  4440
GGAGAAGCCT CTCAGGCTCC TAGCGGCTCT CTGATCCCTC TCAGACTGCC TCTCCTGTGG  4500
GAAGTTCGGG GCCAGCCTGA TTCTTTTGCC GCACTGCACA GCTCCCTGAA CGAGCTGGGA  4560
GAGATCGCTA GAGAGCTGCA CCAGTTCGCC TTCGACCTGC TGATCAAGAG CCACTTCGTG  4620
CAAGGCAAGG ATTGGGGCCT CAAAAAGTTT ATCCGCAGAG ACTTCTGGGG CATGGAACTG  4680
GCCGCCAGCA GAAGATTCAG CTGGGATCAT CATAGCGCAG GCGGCCCACC TAGAGTGCCA  4740
TCTGTTAGAA GCGGAGCTGC CCAGGTGCAG CCTAAAGATC CTCTGCCACT GAGAACACTG  4800
GCCGGCTGCC TTGCTAGAAC AGCCCATCTT AGACCTGGCG CCGAGTCTCT GCCTCAGCCA  4860
CAACTGCACT GTACCCTGTG GTTCCAGTCC AGCGAGCTGT CTCCTACTGG TGCCCCTTGG  4920
CCATCTAGAC GCCCTACTTG GAGAGGCACC ACCGTGTCAC CAAGAACCGC CACAAGCAGC  4980
GCCAGAACCT GTTGTGGCAC AAAGTGGCCC TCCAGCCAAG AAGCCGCTCT CGGACTTGGA  5040
AGCGGACTGC TGAGGTTCTC TTGTGGAACC GCCGCCATTC GGAAGATGCA CTTTAGCCTG  5100
AAAGAACACC CTCCACCACC TTGTCCTCCA GAGGCTTTCC AAAGAGCTGC TGGCGAAGGC  5160
GGACCTGGTA GAGGTGGTGC TAGAAGAGGT GCTAGGGTGC TGCAGAGCCC ATTCTGTAGA  5220
GCAGGCGCAG GCGAATGGCT GGGCCATCAG AGTCTGAGAC ATGTCGTCGG CTACGGCCAC  5280
CTGGATACAA GCGGAAGCAG CTCTAGCTCC AGCTGGCCTA ACTCAAAAAT GGCTCTGAAC  5340
AGCCTGAACT CCATCGACGA CGCCCAGCTG ACAAGAATCG CCCCTCCTAG ATCTCACTGC  5400
TGCTTTTGGG AAGTGAACGC CCCAAGCCAT CACCATCACC ACCATTAGTA AAGGCGCGCC  5460
```

```
TAGCGGCCGC GATCTGCTGT GCCTTCTAGT TGCCAGCCAT CTGTTGTTTG CCCCTCCCCC  5520
GTGCCTTCCT TGACCCTGGA AGGTGCCACT CCCACTGTCC TTTCCTAATA AAATGAGGAA  5580
ATTGCATCGC ATTGTCTGAG TAGGTGTCAT TCTATTCTGG GGGGTGGGGT GGGGCAGGAC  5640
AGCAAGGGGG AGGATTGGGA AGACAATAGC AGGCATGCTG GGGATGCGGT GGGCTCTATG  5700
GCC                                                                5703

SEQ ID NO: 552          moltype = AA  length = 1507
FEATURE                 Location/Qualifiers
REGION                  1..1507
                        note = Heterologous polypeptide
source                  1..1507
                        mol_type = protein
                        organism = synthetic construct
SEQUENCE: 552
MGQKEQIHTL QKNSERMSKQ LTRSSQAVQN LQNGGGSRSS ATLPGRRRRR WLRRRRQPIS  60
VAPAGPPRRP NQKPNPPGGA RCVIMRPTWP GTSAFTGMEC TLGQVGAPSP RREEDGWRGG  120
HSRFKADVPA PQGPCWGGQP GSAPSSAPPE QSLLDDYWAQ KEKISIPRTH LCWKFEMSYT  180
VGGPPPHVHA RPRHWKTDRD YWAQKEKGSS SFLRPSCVPF RELKNVSVLE GLRQGRLGGP  240
CSCHCPRPSQ ARLTPVDVAG PFLCLGDPGL FPPVKSSITE ISCCTLSSEE NEYLPRPEWQ  300
LQYEAGMTLG GKILFFLFLL LPLSPFSLIF LVLGVLSGHS GSRLKRSFAV TERIITGGKS  360
TCSAPGPQSL PSTPFSTYPQ WVILITELDG HSYTSKVNCL LLQDGFHGCV SITGAAGRRN  420
LSIFLFLMLC KLEFHACQWQ HYHRSGEAAG TPLWRPTRNV AMMVPDRQVH YDFGLKIQNK  480
NCPDVLRFLD LKVRYLHSVP FRELKNQRTA QGAPGIHHAA SPVAANLCDP ARHAQHTRIP  540
CGAGQVRAGR GPEAGGGVLQ PQRPAPEKPG CPCRRGQPRL HTVKMWRACH LFLQPQVGTP  600
PPHTASARAP SGPPHPHESC PAGRRPARAA QTCARRQHGL PGCEEAGTAR VPSLHLHLHQ  660
AALGAGRGRG WGEACAQVPP SRGHYKLIQQ PISLFSITDR LHKTFSQLPS VHLCSITFQW  720
GHPPIFCSTN DICVTANFCI SVTFLKPCFL LHEASASQFK KFDGPCGERG GGRTARALWA  780
RGDSVLTPAL DPQTPVRAPS LTRAAAAVGV PGDSTRRAVR RMNTFCGASA CDVSLIAMDS  840
ACEERGAAGS LISCESLYHR EKQLIAMDSA IFVQGKDWGV KKFIRRDFTM PAILKLQKNC  900
LLSLNSKMAL NSEALSVVSE YEAGMTLGEK FRVGNCKHLK MTRPTEYNQK LQVNQFSESK  960
RTALTHNQDF SIYRLCCKRG SLCHASQARS PAFPKPVRPL PAPITRITPQ LGGQSDSSQP  1020
LLTTGRPQGW QDQALRHTQQ ASPASCATIT IPIHSAALGD HSGDPGPAWD TCPPLPLTTL  1080
IPRAPPPYGD STARSWPSRC GPLGYAYKDF LWCFPFSLVF LQEIQICCHV SCLCCICCST  1140
RICLGCLLEL FLSRALRALH VLWNGFQLHC QGNTTLQQLG EASQAPSGSL IPLRLPLLWE  1200
VRGNSKMALN SLNSIDDAQL TRIAPPRSHC CFWEVNAPFV QGKDWGLKKF IRRDFEAFQR  1260
AAGEGGPGRG GARRGARVLQ SPFCRAGAGE WLGHQSLRWG MELAASRRFS WDHHSAGGPP  1320
RVPSVRSGAA QVQPKDPLPL RTLAGCLART AHLRPGAESL PQPQLHCTIA RELHQFAFDL  1380
LIKSHKMHFS LKEHPPPPCP PHVVGYGHLD TSGSSSSSSW PQPDSFAALH SSLNELGELW  1440
FQSSELSPTG APWPSRRPTW RGTTVSPRTA TSSARTCCGT KWPSSQEAAL GLGSGLLRFS  1500
CGTAAIR                                                            1507

SEQ ID NO: 553          moltype = DNA  length = 4722
FEATURE                 Location/Qualifiers
misc_feature            1..4722
                        note = Heterologous polynucleotide
source                  1..4722
                        mol_type = other DNA
                        organism = synthetic construct
SEQUENCE: 553
gatcactaat tccaaaccca cccgcttttt atagtaagtt tttcacccat aaataataaa  60
tacaataatt aatttctcgt aaaagtagaa aatatattct aatttattgc acggtaagga  120
agtagaatca taaagaacag tgacggatcc cgcgacttcg ccgccatggg ccagaaagag  180
cagatccaca cactgcagaa aaacagcgag cggatgagca agcagctgac cagatcttct  240
caggccgtgc agaacctgca gaacggcgga ggctctagaa gctctgctac acttcctggc  300
aggcggcgga gaagatggct gagaagaagg cggcagccta tctctgtggc tcctgctgga  360
cctcctagac ggcccaacca gaagcctaat cctcctggcg gagccagatg cgtgatcatg  420
aggcctacat ggcctggcac cagcgccttt accggcatgg aatgtacact gggccaagtg  480
ggagccccat ctcctagaag agaagaggat ggctggcgcg gaggccactc tagattcaaa  540
gctgatgtgc ccgctcctca gggcccttgt tggggaggac aacctggatc tgccccatct  600
tctgccccac ctgaacagag cctgctggat gactattggg ctcaaaaaga gaagatcagc  660
atccccagaa cacacctgtg ctggaagttc gagatgagct acaccgttgg cggccctcca  720
ccacatgttc acgccagacc tagacactgg aaaaccgaca gagattattg ggcccagaaa  780
gaaaagggca gcagcagctt cctgcggcct agctgtgtgc ccttccggga actgaagaac  840
gtgtccgttc tggaaggcct gaggcagggc agacttggcg gaccttgtag ctgccactgt  900
cctagaccaa gccaggccag actgacccct gtggatgtgg ctggcccatt tctgtgtctg  960
ggcgaccctg gactgttccc tccagtgaag tctagcatca ccgagatcag ctgctgcacc  1020
ctgagcagcg aggaaaacga gtacctgcct agacctgaat ggcagctgca gtacgaggcc  1080
ggcatgacac tcggaggcaa gatcctgttc ttcctgttcc tgctgctccc tctgagcccc  1140
ttcagcctga tctttctggt gctgggcgtg ctgtctggcc actctggaag cagactgaag  1200
agaagcttcg ccgtgaccga gcggatcatc acaggcggca agagcacatg ttctgcccct  1260
ggacctcagt ctctgcccag cacacccttc agcacatacc ctcagtgggt catcctgatc  1320
accgagctgg atggccacag ctacaccagc aaagtgaact gcctcctgct gcaggatggc  1380
ttccacggct gtgtgtctat tactggcgcc gctggcagac ggaacctgag catctttctg  1440
tttctgatgc tgtgcaagct cgagttccac gcctgccaat ggcagcacta ccacagatct  1500
ggcgaagccg ctggaacccc actttggagg cctaccagaa acgtggccat gatggtgccc  1560
gacagacagg tgcactacga cttcggcctg aagatccaga acaagaactg ccccgacgtg  1620
ctgcggttcc tggatctcaa agtgcgctac ctgcacagcg tgcccttcag agagctgaaa  1680
aaccagagaa cagcccaggg cgctcctgga atccatcatg ctgcttctcc agtggccgcc  1740
aatctgtgcg atcctgccag acatgcccag cataccagga ttccttgtgg cgctggacaa  1800
```

```
gtgcgcgctg gaagaggacc tgaagctggt ggcggagttc tgcagcctca aagacctgct  1860
cctgagaagc ctggctgccc ctgtagaaga ggacagccta gactgcacac cgtgaagatg  1920
tggcgggcct gccacttgtt tctccagcca caagtgggca cccctccacc tcatacagcc  1980
tctgctagag cacctagcgg cccacctcat cctcacgaat cttgtcctgc cggaagaagg  2040
cctgccagag ccgctcaaac atgtgccaga cgacagcacg gactgcccgg atgtgaagaa  2100
gccggaacag ccagagtgcc tagcctgcac cttcatctgc atcaggccgc tcttggagcc  2160
ggaagaggta gaggatgggg agaagcttgt gcccaggtgc caccttctag aggccactac  2220
aagctgatcc agcagccaat cagcctgttc tccatcaccg accggctgca caagacattc  2280
agccagctgc cttccgtgca tctgtgcagc atcaccttcc agtggggaca ccctcctatc  2340
ttttgctcca ccaacgacat ctgcgtgacc gccaacttct gtatcagcgt gaccttcctg  2400
aagccttgct ttctgctgca cgaggcctcc gccagccagt ttaagaagtt tgacggcccc  2460
tgcggcgaga gaggcggagg aagaactgca agagcccttt gggccagagg cgactctgtt  2520
ctgacaccag ctctggaccc tcagacacct gttagggccc ctagcctgac aagagctgcc  2580
gctgctgttg gagtgcctgg cgattctact agaagggccg tgcggcggat gaacaccttt  2640
tgtggcgcat ctgcctgcga cgtgtccctg atcgctatgg atagcgcctg cgaggaaaga  2700
ggcgcagccg gatctctgat ctcttgcgag agcctgtacc accgggaaaa gcagctcatt  2760
gccatggaca gcgccatctt cgtgcagggc aaagactggg gcgtgaagaa gttcatccgg  2820
cgggacttta ccatgcctgc cattctgaag ctgcagaaga attgtcttct aagcctgaac  2880
agcaagatgg ccctgaatag cgaggccctg tctgtggtgt ccgagtatga ggctggaatg  2940
accctgggcg agaagttcag agtgggcaac tgcaagcacc tgaagatgac ccggcctacc  3000
gagtacaacc agaaactgca agtgaaccag ttcagcgaga gcaagcggac cgctctgacc  3060
cacaaccagg acttcagcat ctaccggctg tgctgcaaga ggggctctct gtgtcatgct  3120
agccaggcta gaagccccgc ctttcctaag cctgtcagac ctctgcctgc tcctatcacc  3180
agaatcaccc ctcagctcgg cggccagtct gattcatctc agccactgct gaccaccggc  3240
agacctcaag gatggcaaga ccaggctctg agacacacac agcaggctag cccagcctct  3300
tgcgccacca tcacaatacc aatacattct gccgctctgg gcgatcacag cggagatcct  3360
ggacctgcct gggatacttg tcctcctctg cccctaacta cactgatccc tagggctcct  3420
ccaccttacg gcgatagcac agccagatcc tggcctagca gatgtggccc tctgggctac  3480
gcctacaagg acttcctgtg gtgcttcccc ttctctctgg tgttcctgca agaaatccag  3540
atctgctgtc acgtgtcctg cctgtgctgt atctgctgta gcacccggat ctgtctgggc  3600
tgtctgctgg aactgttcct gagcagagcc ctgagagcac tgcacgtgct gtggaacgga  3660
ttccagctgc actgccaggg caacaccaca ctgcaacagc tgggagaagc ctctcaggcc  3720
ccaagcggtt ctctgatccc tctcagactg cccctcctgt gggaagtgcg gggcaattct  3780
aagatggctc tcaacagcct gaactccatc gacgacgccc agctgacaag aatcgcccct  3840
ccaagaagcc actgttgctt ttgggaagtg aacgcccctt ttgtgcaggg taaagattgg  3900
ggcctcaaaa agtttatcag acgggacttc gaggctttcc agagagcagc tggcgaaggc  3960
ggacctggca gaggtggtgc tagaagaggt gctagagtgc tgcagagccc attctgtaga  4020
gctggcgctg gcgaatggct gggccaccaa tctcttagat ggggaatgga actggccgct  4080
agcaggcggt ttagctggga tcatcattct gccggcggac ctccaagagt gccaagcgtt  4140
agaagcggag cagcccaggt ccagcctaaa gatccactgc cactgagaac actggccggc  4200
tgccttgcca gaacagctca tcttagacct ggcgccgaaa gcctgcctca acctcagctg  4260
cattgcacaa tcgccagaga actgcaccag ttcgccttcg acctgctgat caagagccac  4320
aagatgcact tctcactgaa agagcacccg ccaccgccgt gcccaccgca cgttgtcggc  4380
tatggccacc tggatacaag cggctcctct agcagtagct cctggcctca gcctgacagc  4440
tttgctgccc tgcatagctc cctgaatgag ctgggcgaac tgtggttcca gtccagcgaa  4500
ctgtctccta ctggcgctcc atggccaagc agaaggccta cttggagagg caccaccgtg  4560
tctccaagaa ccgctacaag cagcgccaga acctgttgcg gcacaaaatg gccctccagc  4620
caagaagctg ccctcggact tggaagcgga ctgctgagat tcagctgtgg cacagccgcc  4680
atcagaagcc atcaccatca ccaccattag taaaggcgcg cc                    4722

SEQ ID NO: 554          moltype = AA  length = 1507
FEATURE                 Location/Qualifiers
REGION                  1..1507
                        note = Heterologous polypeptide
source                  1..1507
                        mol_type = protein
                        organism = synthetic construct
SEQUENCE: 554
MGQKEQIHTL QKNSERMSKQ LTRSSQAVQN LQNGGGSRSS ATLPGRRRRR WLRRRRQPIS  60
VAPAGPPRRP NQKPNPPGGA RCVIMRPTWP GTSAFTKRSF AVTERIILVL GVLSGHSGSR  120
LYEAGMTLGG KILFFLFLLL PLSPFSLIFT EISCCTLSSE ENEYLPRPEW QLQVPFRELK  180
NVSVLEGLRQ GRLGGPCSCH CPRPSQARLT PVDVAGPFLC LGDPGLFPPV KSSITGGKST  240
CSAPGPQSLP STPFSTYPQW VILITELGME CTLGQVGAPS PRREEDGWRG GHSRFKADVP  300
APQGPCWGGQ PGSAPSSAPP EQSLLDDYWA QKEKGSSSFL RPSCDYWAQK EKISIPRTHL  360
CWKFEMSYTV GGPPPHVHAR PRHWKTDRGV PGDSTRRAVR RMNTFYEAGM TLGEKFRVGN  420
CKHLKMTRPN SKMALNSEAL SVVSECGASA CDVSLIAMDS AFVQGKDWGV KKFIRRDFYA  480
YKDFLWCFPF SLVFLQEIQI CCHVSCLCCI CCSTRICLGC LLELFLSRAL RALHVLWNGF  540
QLHCQTEYNQ KLQVNQFSES KSLYHREKQL IAMDSAICEE RGAAGSLISC ETMPAILKLQ  600
KNCLLSLRTA LTHNQDFSIY RLCCKRGSLC HASQARSPAF PKPVRPLPAP ITRITPQLGG  660
QSDSSQPLLT TGRPQGWQDQ ALRHTQQASP ASCATITIPI HSAALGDHSG DPGPAWDTCP  720
PLPLTTLIPR APPPYGDSTA RSWPSRCGPL GDGHSYTSKV NCLLLQDGFH GCVSITGAAG  780
RRNLSIFLFL MLCKLEFHAC KIQNKNCPDF KKFDGPCGER GGGRTARALW ARGDSVLTPA  840
LDPQTPVRAP SLTRAAAAVH YKLIQQPISL FSITDRLHKT FSQLPSVHLC SITFQWGHPP  900
IFCSTNDICV TANFCISVTF LKPCFLLHEA SASQCHLFLQ PQVGTPPPHT ASARAPSGPP  960
HPHESCPAGR RPARAAQTCA RRQHGLPGCE EAGTARVPSL HLHLHQAALG AGRGRGWGEA  1020
CAQVPPSRGV LRFLDLKVRY LHSQWQHYHR SGEAAGTPLW RPTRNVPFRE LKNQRTAQGA  1080
PGIHHAASPV AANLCDPARH AQHTRIPCGA GQVRAGRGPE AGGGVLQPQR PAPEKPGCPC  1140
RRGQPRLHTV KMWRAVAMMV PDRQVHYDFG LGNTTLQQLG EASQAPSGSL IPLRLPLLWE  1200
VRGQPDSFAA LHSSLNELGE IARELHQFAF DLLIKSHFVQ GKDWGLKKFI RRDFWGMELA  1260
```

-continued

```
ASRRFSWDHH SAGGPPRVPS VRSGAAQVQP KDPLPLRTLA GCLARTAHLR PGAESLPQPQ  1320
LHCTLWFQSS ELSPTGAPWP SRRPTWRGTT VSPRTATSSA RTCCGTKWPS SQEAALGLGS  1380
GLLRFSCGTA AIRKMHFSLK EHPPPPCPPE AFQRAAGEGG PGRGGARRGA RVLQSPFCRA  1440
GAGEWLGHQS LRHVVGYGHL DTSGSSSSSS WPNSKMALNS LNSIDDAQLT RIAPPRSHCC  1500
FWEVNAP                                                            1507

SEQ ID NO: 555          moltype = AA  length = 1507
FEATURE                 Location/Qualifiers
REGION                  1..1507
                        note = Heterologous polypeptide
source                  1..1507
                        mol_type = protein
                        organism = synthetic construct
SEQUENCE: 555
MGQKEQIHTL QKNSERMSKQ LTRSSQAVQN LQNGGGSRSS ATLPGRRRRR WLRRRRQPIS  60
VAPAGPPRRP NQKPNPPGGA RCVIMRPTWP GTSAFTKRSF AVTERIITEI SCCTLSSEEN  120
EYLPRPEWQL QYEAGMTLGG KILFFLFLLL PLSPFSLIFD YWAQKEKGSS SFLRPSCVPF  180
RELKNVSVLE GLRQGRLGGP CSCHCPRPSQ ARLTPVDVAG PFLCLGDPGL FPPVKSSITG  240
GKSTCSAPGP QSLPSTPFST YPQWVILITE LGMECTLGQV GAPSPRREED GWRGGHSRFK  300
ADVPAPQGPC WGGQPGSAPS SAPPEQSLLD DYWAQKEKIS IPRTHLCLVL GVLSGHSGSR  360
LWKFEMSYTV GGPPPHVHAR PRHWKTDRDG HSYTSKVNCL LLQDGFHGCV SITGAAGRRN  420
LSIFLFLMLC KLEFHACKIQ NKNCPDFKKF DGPCGERGGG RTARALWARG DSVLTPALDP  480
QTPVRAPSLT RAAAAVHYKL IQQPISLFSI TDRLHKTFSQ LPSVHLCSIT FQWGHPPIFC  540
STNDICVTAN FCISVTFLKP CFLLHEASAS QCHLFLQPQV GTPPPHTASA RAPSGPPHPH  600
ESCPAGRRPA RAAQTCARRQ HGLPGCEEAG TARVPSLHLH LHQAALGAGR GRGWGEACAQ  660
VPPSRGVLRF LDLKVRYLHS QWQHYHRSGE AAGTPLWRPT RNVPFRELKN QRTAQGAPGI  720
HHAASPVAAN LCDPARHAQH TRIPCGAGQV RAGRGPEAGG GVLQPQRPAP EKPGCPCRRG  780
QPRLHTVKMW RAVAMMVPDR QVHYDFGLGV PGDSTRRAVR RMNTFYEAGM TLGEKFRVGN  840
CKHLKMTRPN SKMALNSEAL SVVSECGASA CDVSLIAMDS AFVQGKDWGV KKFIRRDFYA  900
YKDFLWCFPF SLVFLQEIQI CCHVSCLCCI CCSTRICLGC LLELFLSRAL RALHVLWNGF  960
QLHCQTEYNQ KLQVNQFSES KSLYHREKQL IAMDSAICEE RGAAGSLISC ETMPAILKLQ  1020
KNCLLSLRTA LTHNQDFSIY RLCCKRGSLC HASQARSPAF PKPVRPLPAP ITRITPQLGG  1080
QSDSSQPLLT TGRPQGWQDQ ALRHTQQASP ASCATITIPI HSAALGDHSG DPGPAWDTCP  1140
PLPLTTLIPR APPPYGDSTA RSWPSRCGPL GGNTTLQQLG EASQAPSGSL IPLRLPLLWE  1200
VRGQPDSFAA LHSSLNELGE IARELHQFAF DLLIKSHFVQ GKDWGLKKFI RRDFWGMELA  1260
ASRRFSWDHH SAGGPPRVPS VRSGAAQVQP KDPLPLRTLA GCLARTAHLR PGAESLPQPQ  1320
LHCTLWFQSS ELSPTGAPWP SRRPTWRGTT VSPRTATSSA RTCCGTKWPS SQEAALGLGS  1380
GLLRFSCGTA AIRKMHFSLK EHPPPPCPPE AFQRAAGEGG PGRGGARRGA RVLQSPFCRA  1440
GAGEWLGHQS LRHVVGYGHL DTSGSSSSSS WPNSKMALNS LNSIDDAQLT RIAPPRSHCC  1500
FWEVNAP                                                            1507

SEQ ID NO: 556          moltype = AA  length = 1507
FEATURE                 Location/Qualifiers
REGION                  1..1507
                        note = Heterologous polypeptide
source                  1..1507
                        mol_type = protein
                        organism = synthetic construct
SEQUENCE: 556
MGQKEQIHTL QKNSERMSKQ LTRSSQAVQN LQNGGGSRSS ATLPGRRRRR WLRRRRQPIS  60
VAPAGPPRRP NQKPNPPGGA RCVIMRPTWP GTSAFTKRSF AVTERIIDYW AQKEKGSSSF  120
LRPSCVPFRE LKNVSVLEGL RQGRLGGPCS CHCPRPSQAR LTPVDVAGPF LCLGDPGLFP  180
PVKSSILVLG VLSGHSGSRL YEAGMTLGGK ILFFLFLLLP LSPFSLIFTE ISCCTLSSEE  240
NEYLPRPEWQ LQTGGKSTCS APGPQSLPST PFSTYPQWVI LITELGMECT LGQVGAPSPR  300
REEDGWRGGH SRFKADVPAP QGPCWGGQPG SAPSSAPPEQ SLLDDYWAQK EKISIPRTHL  360
CWKFEMSYTV GGPPPHVHAR PRHWKTDRDG HSYTSKVNCL LLQDGFHGCV SITGAAGRRN  420
LSIFLFLMLC KLEFHACKIQ NKNCPDFKKF DGPCGERGGG RTARALWARG DSVLTPALDP  480
QTPVRAPSLT RAAAAVHYKL IQQPISLFSI TDRLHKTFSQ LPSVHLCSIT FQWGHPPIFC  540
STNDICVTAN FCISVTFLKP CFLLHEASAS QCHLFLQPQV GTPPPHTASA RAPSGPPHPH  600
ESCPAGRRPA RAAQTCARRQ HGLPGCEEAG TARVPSLHLH LHQAALGAGR GRGWGEACAQ  660
VPPSRGVLRF LDLKVRYLHS QWQHYHRSGE AAGTPLWRPT RNVPFRELKN QRTAQGAPGI  720
HHAASPVAAN LCDPARHAQH TRIPCGAGQV RAGRGPEAGG GVLQPQRPAP EKPGCPCRRG  780
QPRLHTVKMW RAVAMMVPDR QVHYDFGLGV PGDSTRRAVR RMNTFYEAGM TLGEKFRVGN  840
CKHLKMTRPN SKMALNSEAL SVVSECGASA CDVSLIAMDS AFVQGKDWGV KKFIRRDFYA  900
YKDFLWCFPF SLVFLQEIQI CCHVSCLCCI CCSTRICLGC LLELFLSRAL RALHVLWNGF  960
QLHCQTEYNQ KLQVNQFSES KSLYHREKQL IAMDSAICEE RGAAGSLISC ETMPAILKLQ  1020
KNCLLSLRTA LTHNQDFSIY RLCCKRGSLC HASQARSPAF PKPVRPLPAP ITRITPQLGG  1080
QSDSSQPLLT TGRPQGWQDQ ALRHTQQASP ASCATITIPI HSAALGDHSG DPGPAWDTCP  1140
PLPLTTLIPR APPPYGDSTA RSWPSRCGPL GGNTTLQQLG EASQAPSGSL IPLRLPLLWE  1200
VRGQPDSFAA LHSSLNELGE IARELHQFAF DLLIKSHFVQ GKDWGLKKFI RRDFWGMELA  1260
ASRRFSWDHH SAGGPPRVPS VRSGAAQVQP KDPLPLRTLA GCLARTAHLR PGAESLPQPQ  1320
LHCTLWFQSS ELSPTGAPWP SRRPTWRGTT VSPRTATSSA RTCCGTKWPS SQEAALGLGS  1380
GLLRFSCGTA AIRKMHFSLK EHPPPPCPPE AFQRAAGEGG PGRGGARRGA RVLQSPFCRA  1440
GAGEWLGHQS LRHVVGYGHL DTSGSSSSSS WPNSKMALNS LNSIDDAQLT RIAPPRSHCC  1500
FWEVNAP                                                            1507

SEQ ID NO: 557          moltype = AA  length = 1507
FEATURE                 Location/Qualifiers
REGION                  1..1507
```

```
                         note = Heterologous polypeptide
source                   1..1507
                         mol_type = protein
                         organism = synthetic construct
SEQUENCE: 557
MGQKEQIHTL QKNSERMSKQ LTRSSQAVQN LQNGGGSRSS ATLPGRRRRR WLRRRRQPIS  60
VAPAGPPRRP NQKPNPPGGA RCVIMRPTWP GTSAFTGMEC TLGQVGAPSP RREEDGWRGG  120
HSRFKADVPA PQGPCWGGQP GSAPSSAPPE QSLLDDYWAQ KEKISIPRTH LCWKFEMSYT  180
VGGPPPHVHA RPRHWKTDRD YWAQKEKGSS SFLRPSCVPF RELKNVSVLE GLRQGRLGGP  240
CSCHCPRPSQ ARLTPVDVAG PFLCLGDPGL FPPVKSSITE ISCCTLSSEE NEYLPRPEWQ  300
LQYEAGMTLG GKILFFLFLL LPLSPFSLIF LVLGVLSGHS GSRLKRSFAV TERIITGGKS  360
TCSAPGPQSL PSTPFSTYPQ WVILITELDG HSYTSKVNCL LLQDGFHGCV SITGAAGRRN  420
LSIFLFLMLC KLEFHACCHL FLQPQVGTPP PHTASARAPS GPPHPHESCP AGRRPARAAQ  480
TCARRQHGLP GCEEAGTARV PSLHLHLHQA ALGAGRGRGW GEACAQVPPS RGHYKLIQQP  540
ISLFSITDRL HKTFSQLPSV HLCSITFQWG HPPIFCSTND ICVTANFCIS VTFLKPCFLL  600
HEASASQVAM MVPDRQVHYD FGLKIQNKNC PDVLRFLDLK VRYLHSVPFR ELKNQRTAQG  660
APGIHHAASP VAANLCDPAR HAQHTRIPCG AGQVRAGRGP EAGGGVLQPQ RPAPEKPGCP  720
CRRGQPRLHT VKMWRAQWQH YHRSGEAAGT PLWRPTRNFK KFDGPCGERG GGRTARALWA  780
RGDSVLTPAL DPQTPVRAPS LTRAAAAVGV PGDSTRRAVR RMNTFCGASA CDVSLIAMDS  840
ACEERGAAGS LISCESLYHR EKQLIAMDSA IFVQGKDWGV KKFIRRDFTM PAILKLQKNC  900
LLSLNSKMAL NSEALSVVSE YEAGMTLGEK FRVGNCKHLK MTRPTEYNQK LQVNQFSESK  960
RTALTHNQDF SIYRLCCKRG SLCHASQARS PAFPKPVRPL PAPITRITPQ LGGQSDSSQP  1020
LLTTGRPQGW QDQALRHTQQ ASPASCATIT IPIHSAALGD HSGDPGPAWD TCPPLPLTTL  1080
IPRAPPPYGD STARSWPSRC GPLGYAYKDF LWCFPFSLVF LQEIQICCHV SCLCCICCST  1140
RICLGCLLEL FLSRALRALH VLWNGFQLHC QGNTTLQQLG EASQAPSGSL IPLRLPLLWE  1200
VRGNSKMALN SLNSIDDAQL TRIAPPRSHC CFWEVNAPFV QGKDWGLKKF IRRDFEAFQR  1260
AAGEGGPGRG GARRGARVLQ SPFCRAGAGE WLGHQSLRWG MELAASRRFS WDHHSAGGPP  1320
RVPSVRSGAA QVQPKDPLPL RTLAGCLART AHLRPGAESL PQPQLHCTIA RELHQFAFDL  1380
LIKSHKMHFS LKEHPPPPCP PHVVGYGHLD TSGSSSSSSW PQPDSFAALH SSLNELGELW  1440
FQSSELSPTG APWPSRRPTW RGTTVSPRTA TSSARTCCGT KWPSSQEAAL GLGSGLLRFS  1500
CGTAAIR                                                           1507

SEQ ID NO: 558           moltype = AA  length = 1507
FEATURE                  Location/Qualifiers
REGION                   1..1507
                         note = Heterologous polypeptide
source                   1..1507
                         mol_type = protein
                         organism = synthetic construct
SEQUENCE: 558
MGQKEQIHTL QKNSERMSKQ LTRSSQAVDG HSYTSKVNCL LLQDGFHGCV SITGAAGRRN  60
LSIFLFLMLC KLEFHACQWQ HYHRSGEAAG TPLWRPTRNV AMMVPDRQVH YDFGLVLRFL  120
DLKVRYLHSK IQNKNCPDVP FRELKNQRTA QGAPGIHHAA SPVAANLCDP ARHAQHTRIP  180
CGAGQVRAGR GPEAGGGVLQ PQRPAPEKPG CPCRRGQPRL HTVKMWRACH LFLQPQVGTP  240
PPHTASARAP SGPPHPHESC PAGRRPARAA QTCARRQHGL PGCEEAGTAR VPSLHLHLHQ  300
AALGAGRGRG WGEACAQVPP SRGHYKLIQQ PISLFSITDR LHKTFSQLPS VHLCSITFQW  360
GHPPIFCSTN DICVTANFCI SVTFLKPCFL LHEASASQFK KFDGPCGERG GGRTARALWA  420
RGDSVLTPAL DPQTPVRAPS LTRAAAAVQN LQNGGGSRSS ATLPGRRRRR WLRRRRQPIS  480
VAPAGPPRRP NQKPNPPGGA RCVIMRPTWP GTSAFTGMEC TLGQVGAPSP RREEDGWRGG  540
HSRFKADVPA PQGPCWGGQP GSAPSSAPPE QSLLDDYWAQ KEKISIPRTH LCWKFEMSYT  600
VGGPPPHVHA RPRHWKTDRD YWAQKEKGSS SFLRPSCVPF RELKNVSVLE GLRQGRLGGP  660
CSCHCPRPSQ ARLTPVDVAG PFLCLGDPGL FPPVKSSITE ISCCTLSSEE NEYLPRPEWQ  720
LQYEAGMTLG GKILFFLFLL LPLSPFSLIF LVLGVLSGHS GSRLKRSFAV TERIITGGKS  780
TCSAPGPQSL PSTPFSTYPQ WVILITELGV PGDSTRRAVR RMNTFCGASA CDVSLIAMDS  840
ACEERGAAGS LISCESLYHR EKQLIAMDSA IFVQGKDWGV KKFIRRDFTM PAILKLQKNC  900
LLSLNSKMAL NSEALSVVSE YEAGMTLGEK FRVGNCKHLK MTRPTEYNQK LQVNQFSESK  960
RTALTHNQDF SIYRLCCKRG SLCHASQARS PAFPKPVRPL PAPITRITPQ LGGQSDSSQP  1020
LLTTGRPQGW QDQALRHTQQ ASPASCATIT IPIHSAALGD HSGDPGPAWD TCPPLPLTTL  1080
IPRAPPPYGD STARSWPSRC GPLGYAYKDF LWCFPFSLVF LQEIQICCHV SCLCCICCST  1140
RICLGCLLEL FLSRALRALH VLWNGFQLHC QGNTTLQQLG EASQAPSGSL IPLRLPLLWE  1200
VRGNSKMALN SLNSIDDAQL TRIAPPRSHC CFWEVNAPFV QGKDWGLKKF IRRDFEAFQR  1260
AAGEGGPGRG GARRGARVLQ SPFCRAGAGE WLGHQSLRWG MELAASRRFS WDHHSAGGPP  1320
RVPSVRSGAA QVQPKDPLPL RTLAGCLART AHLRPGAESL PQPQLHCTIA RELHQFAFDL  1380
LIKSHKMHFS LKEHPPPPCP PHVVGYGHLD TSGSSSSSSW PQPDSFAALH SSLNELGELW  1440
FQSSELSPTG APWPSRRPTW RGTTVSPRTA TSSARTCCGT KWPSSQEAAL GLGSGLLRFS  1500
CGTAAIR                                                           1507

SEQ ID NO: 559           moltype = AA  length = 1507
FEATURE                  Location/Qualifiers
REGION                   1..1507
                         note = Heterologous polypeptide
source                   1..1507
                         mol_type = protein
                         organism = synthetic construct
SEQUENCE: 559
MGQKEQIHTL QKNSERMSKQ LTRSSQAVGN TTLQQLGEAS QAPSGSLIPL RLPLLWEVRG  60
NSKMALNSLN SIDDAQLTRI APPRSHCCFW EVNAPFVQGK DWGLKKFIRR DFEAFQRAAG  120
EGGPGRGGAR RGARVLQSPF CRAGAGEWLG HQSLRWGMEL AASRRFSWDH HSAGGPPRVP  180
SVRSGAAQVQ PKDPLPLRTL AGCLARTAHL RPGAESLPQP QLHCTIAREL HQFAFDLLIK  240
```

-continued

```
SHKMHFSLKE HPPPPCPPHV VGYGHLDTSG SSSSSSWPQP DSFAALHSSL NELGELWFQS  300
SELSPTGAPW PSRRPTWRGT TVSPRTATSS ARTCCGTKWP SSQEAALGLG SGLLRFSCGT  360
AAIRDGHSYT SKVNCLLLQD GFHGCVSITG AAGRRNLSIF LFLMLCKLEF HACQWQHYHR  420
SGEAAGTPLW RPTRNVAMMV PDRQVHYDFG LKIQNKNCPD VLRFLDLKVR YLHSVPFREL  480
KNQRTAQGAP GIHHAASPVA ANLCDPARHA QHTRIPCGAG QVRAGRGPEA GGGVLQPQRP  540
APEKPGCPCR RGQPRLHTVK MWRACHLFLQ PQVGTPPPHT ASARAPSGPP HPHESCPAGR  600
RPARAAQTCA RRQHGLPGCE EAGTARVPSL HLHLHQAALG AGRGRGWGEA CAQVPPSRGH  660
YKLIQQPISL FSITDRLHKT FSQLPSVHLC SITFQWGHPP IFCSTNDICV TANFCISVTF  720
LKPCFLLHEA SASQFKKFDG PCGERGGGRT ARALWARGDS VLTPALDPQT PVRAPSLTRA  780
AAAVGVPGDS TRRAVRRMNT FCGASACDVS LIAMDSATEY NQKLQVNQFS ESKYEAGMTL  840
GEKFRVGNCK HLKMTRPTMP AILKLQKNCL LSLNSKMALN SEALSVVSEC EERGAAGSLI  900
SCESLYHREK QLIAMDSAIF VQGKDWGVKK FIRRDFRTAL THNQDFSIYR LCCKRGSLCH  960
ASQARSPAFP KPVRPLPAPI TRITPQLGGQ SDSSQPLLTT GRPQGWQDQA LRHTQQASPA  1020
SCATITIPIH SAALGDHSGD PGPAWDTCPP LPLTTLIPRA PPPYGDSTAR SWPSRCGPLG  1080
YAYKDFLWCF PFSLVFLQEI QICCHVSCLC CICCSTRICL GCLLELFLSR ALRALHVLWN  1140
GFQLHCQQNL QNGGGSRSSA TLPGRRRRRW LRRRRQPISV APAGPPRRPN QKPNPPGGAR  1200
CVIMRPTWPG TSAFTGMECT LGQVGAPSPR REEDGWRGGH SRFKADVPAP QGPCWGGQPG  1260
SAPSSAPPEQ SLLDDYWAQK EKISIPRTHL CWKFEMSYTV GGPPPHVHAR PRHWKTDRDY  1320
WAQKEKGSSS FLRPSCVPFR ELKNVSVLEG LRQGRLGGPC SCHCPRPSQA RLTPVDVAGP  1380
FLCLGDPGLF PPVKSSITEI SCCTLSSEEN EYLPRPEWQL QYEAGMTLGG KILFFLFLLL  1440
PLSPFSLIFL VLGVLSGHSG SRLKRSFAVT ERIITGGKST CSAPGPQSLP STPFSTYPQW  1500
VILITEL                                                            1507

SEQ ID NO: 560          moltype = AA  length = 15
FEATURE                 Location/Qualifiers
source                  1..15
                        mol_type = protein
                        organism = Homo sapiens
SEQUENCE: 560
WKFEMSYTVG GPPPH                                                   15

SEQ ID NO: 561          moltype = AA  length = 15
FEATURE                 Location/Qualifiers
source                  1..15
                        mol_type = protein
                        organism = Homo sapiens
SEQUENCE: 561
VGGPPPHVHA RPRHW                                                   15

SEQ ID NO: 562          moltype = AA  length = 14
FEATURE                 Location/Qualifiers
source                  1..14
                        mol_type = protein
                        organism = Homo sapiens
SEQUENCE: 562
PPHVHARPRH WKTD                                                    14

SEQ ID NO: 563          moltype = AA  length = 15
FEATURE                 Location/Qualifiers
source                  1..15
                        mol_type = protein
                        organism = Homo sapiens
SEQUENCE: 563
YEAGMTLGGK ILFFL                                                   15

SEQ ID NO: 564          moltype = AA  length = 15
FEATURE                 Location/Qualifiers
source                  1..15
                        mol_type = protein
                        organism = Homo sapiens
SEQUENCE: 564
GKILFFLFLL LPLSP                                                   15

SEQ ID NO: 565          moltype = AA  length = 16
FEATURE                 Location/Qualifiers
source                  1..16
                        mol_type = protein
                        organism = Homo sapiens
SEQUENCE: 565
FFLFLLLPLS PFSLIF                                                  16

SEQ ID NO: 566          moltype = AA  length = 15
FEATURE                 Location/Qualifiers
source                  1..15
                        mol_type = protein
                        organism = Homo sapiens
SEQUENCE: 566
DGHSYTSKVN CLLLQ                                                   15
```

```
SEQ ID NO: 567          moltype = AA  length = 15
FEATURE                 Location/Qualifiers
source                  1..15
                        mol_type = protein
                        organism = Homo sapiens
SEQUENCE: 567
VNCLLLQDGF HGCVS                                                    15

SEQ ID NO: 568          moltype = AA  length = 15
FEATURE                 Location/Qualifiers
source                  1..15
                        mol_type = protein
                        organism = Homo sapiens
SEQUENCE: 568
GFHGCVSITG AAGRR                                                    15

SEQ ID NO: 569          moltype = AA  length = 15
FEATURE                 Location/Qualifiers
source                  1..15
                        mol_type = protein
                        organism = Homo sapiens
SEQUENCE: 569
TGAAGRRNLS IFLFL                                                    15

SEQ ID NO: 570          moltype = AA  length = 15
FEATURE                 Location/Qualifiers
source                  1..15
                        mol_type = protein
                        organism = Homo sapiens
SEQUENCE: 570
LSIFLFLMLC KLEFH                                                    15

SEQ ID NO: 571          moltype = AA  length = 13
FEATURE                 Location/Qualifiers
source                  1..13
                        mol_type = protein
                        organism = Homo sapiens
SEQUENCE: 571
LFLMLCKLEF HAC                                                      13

SEQ ID NO: 572          moltype = AA  length = 15
FEATURE                 Location/Qualifiers
source                  1..15
                        mol_type = protein
                        organism = Homo sapiens
SEQUENCE: 572
TGGKSTCSAP GPQSL                                                    15

SEQ ID NO: 573          moltype = AA  length = 15
FEATURE                 Location/Qualifiers
source                  1..15
                        mol_type = protein
                        organism = Homo sapiens
SEQUENCE: 573
APGPQSLPST PFSTY                                                    15

SEQ ID NO: 574          moltype = AA  length = 15
FEATURE                 Location/Qualifiers
source                  1..15
                        mol_type = protein
                        organism = Homo sapiens
SEQUENCE: 574
STPFSTYPQW VILIT                                                    15

SEQ ID NO: 575          moltype = AA  length = 15
FEATURE                 Location/Qualifiers
source                  1..15
                        mol_type = protein
                        organism = Homo sapiens
SEQUENCE: 575
SRSSATLPGR RRRRW                                                    15

SEQ ID NO: 576          moltype = AA  length = 15
FEATURE                 Location/Qualifiers
source                  1..15
                        mol_type = protein
                        organism = Homo sapiens
SEQUENCE: 576
DYWAQKEKGS SSFLR                                                    15
```

```
SEQ ID NO: 577          moltype = AA  length = 14
FEATURE                 Location/Qualifiers
source                  1..14
                        mol_type = protein
                        organism = Homo sapiens
SEQUENCE: 577
QKEKGSSSFL RPSC                                                    14

SEQ ID NO: 578          moltype = AA  length = 15
FEATURE                 Location/Qualifiers
source                  1..15
                        mol_type = protein
                        organism = Homo sapiens
SEQUENCE: 578
VPFRELKNVS VLEGL                                                   15

SEQ ID NO: 579          moltype = AA  length = 15
FEATURE                 Location/Qualifiers
source                  1..15
                        mol_type = protein
                        organism = Homo sapiens
SEQUENCE: 579
VSVLEGLRQG RLGGP                                                   15

SEQ ID NO: 580          moltype = AA  length = 15
FEATURE                 Location/Qualifiers
source                  1..15
                        mol_type = protein
                        organism = Homo sapiens
SEQUENCE: 580
QGRLGGPCSC HCPRP                                                   15

SEQ ID NO: 581          moltype = AA  length = 15
FEATURE                 Location/Qualifiers
source                  1..15
                        mol_type = protein
                        organism = Homo sapiens
SEQUENCE: 581
SCHCPRPSQA RLTPV                                                   15

SEQ ID NO: 582          moltype = AA  length = 15
FEATURE                 Location/Qualifiers
source                  1..15
                        mol_type = protein
                        organism = Homo sapiens
SEQUENCE: 582
QARLTPVDVA GPFLC                                                   15

SEQ ID NO: 583          moltype = AA  length = 15
FEATURE                 Location/Qualifiers
source                  1..15
                        mol_type = protein
                        organism = Homo sapiens
SEQUENCE: 583
VAGPFLCLGD PGLFP                                                   15

SEQ ID NO: 584          moltype = AA  length = 13
FEATURE                 Location/Qualifiers
source                  1..13
                        mol_type = protein
                        organism = Homo sapiens
SEQUENCE: 584
GDPGLFPPVK SSI                                                     13

SEQ ID NO: 585          moltype = AA  length = 15
FEATURE                 Location/Qualifiers
source                  1..15
                        mol_type = protein
                        organism = Homo sapiens
SEQUENCE: 585
GMECTLGQVG APSPR                                                   15

SEQ ID NO: 586          moltype = AA  length = 15
FEATURE                 Location/Qualifiers
source                  1..15
                        mol_type = protein
                        organism = Homo sapiens
SEQUENCE: 586
```

```
VGAPSPRREE DGWRG                                                    15

SEQ ID NO: 587          moltype = AA  length = 15
FEATURE                 Location/Qualifiers
source                  1..15
                        mol_type = protein
                        organism = Homo sapiens
SEQUENCE: 587
EEDGWRGGHS RFKAD                                                    15

SEQ ID NO: 588          moltype = AA  length = 15
FEATURE                 Location/Qualifiers
source                  1..15
                        mol_type = protein
                        organism = Homo sapiens
SEQUENCE: 588
HSRFKADVPA PQGPC                                                    15

SEQ ID NO: 589          moltype = AA  length = 15
FEATURE                 Location/Qualifiers
source                  1..15
                        mol_type = protein
                        organism = Homo sapiens
SEQUENCE: 589
PAPQGPCWGG QPGSA                                                    15

SEQ ID NO: 590          moltype = AA  length = 15
FEATURE                 Location/Qualifiers
source                  1..15
                        mol_type = protein
                        organism = Homo sapiens
SEQUENCE: 590
GGQPGSAPSS APPEQ                                                    15

SEQ ID NO: 591          moltype = AA  length = 15
FEATURE                 Location/Qualifiers
source                  1..15
                        mol_type = protein
                        organism = Homo sapiens
SEQUENCE: 591
GSAPSSAPPE QSLLD                                                    15

SEQ ID NO: 592          moltype = AA  length = 15
FEATURE                 Location/Qualifiers
source                  1..15
                        mol_type = protein
                        organism = Homo sapiens
SEQUENCE: 592
GNTTLQQLGE ASQAP                                                    15

SEQ ID NO: 593          moltype = AA  length = 15
FEATURE                 Location/Qualifiers
source                  1..15
                        mol_type = protein
                        organism = Homo sapiens
SEQUENCE: 593
GEASQAPSGS LIPLR                                                    15

SEQ ID NO: 594          moltype = AA  length = 16
FEATURE                 Location/Qualifiers
source                  1..16
                        mol_type = protein
                        organism = Homo sapiens
SEQUENCE: 594
GSLIPLRLPL LWEVRG                                                   16

SEQ ID NO: 595          moltype = AA  length = 15
FEATURE                 Location/Qualifiers
source                  1..15
                        mol_type = protein
                        organism = Homo sapiens
SEQUENCE: 595
EAFQRAAGEG GPGRG                                                    15

SEQ ID NO: 596          moltype = AA  length = 15
FEATURE                 Location/Qualifiers
source                  1..15
                        mol_type = protein
                        organism = Homo sapiens
```

```
SEQUENCE: 596
EGGPGRGGAR RGARV                                                    15

SEQ ID NO: 597          moltype = AA  length = 15
FEATURE                 Location/Qualifiers
source                  1..15
                        mol_type = protein
                        organism = Homo sapiens
SEQUENCE: 597
ARRGARVLQS PFCRA                                                    15

SEQ ID NO: 598          moltype = AA  length = 15
FEATURE                 Location/Qualifiers
source                  1..15
                        mol_type = protein
                        organism = Homo sapiens
SEQUENCE: 598
QSPFCRAGAG EWLGH                                                    15

SEQ ID NO: 599          moltype = AA  length = 15
FEATURE                 Location/Qualifiers
source                  1..15
                        mol_type = protein
                        organism = Homo sapiens
SEQUENCE: 599
CRAGAGEWLG HQSLR                                                    15

SEQ ID NO: 600          moltype = AA  length = 15
FEATURE                 Location/Qualifiers
source                  1..15
                        mol_type = protein
                        organism = Homo sapiens
SEQUENCE: 600
DYWAQKEKIS IPRTH                                                    15

SEQ ID NO: 601          moltype = AA  length = 13
FEATURE                 Location/Qualifiers
source                  1..13
                        mol_type = protein
                        organism = Homo sapiens
SEQUENCE: 601
QKEKISIPRT HLC                                                      13

SEQ ID NO: 602          moltype = AA  length = 15
FEATURE                 Location/Qualifiers
source                  1..15
                        mol_type = protein
                        organism = Homo sapiens
SEQUENCE: 602
VAMMVPDRQV HYDFG                                                    15

SEQ ID NO: 603          moltype = AA  length = 13
FEATURE                 Location/Qualifiers
source                  1..13
                        mol_type = protein
                        organism = Homo sapiens
SEQUENCE: 603
VPDRQVHYDF GLR                                                      13

SEQ ID NO: 604          moltype = AA  length = 15
FEATURE                 Location/Qualifiers
source                  1..15
                        mol_type = protein
                        organism = Homo sapiens
SEQUENCE: 604
FKKFDGPCGE RGGGR                                                    15

SEQ ID NO: 605          moltype = AA  length = 15
FEATURE                 Location/Qualifiers
source                  1..15
                        mol_type = protein
                        organism = Homo sapiens
SEQUENCE: 605
GERGGGRTAR ALWAR                                                    15

SEQ ID NO: 606          moltype = AA  length = 15
FEATURE                 Location/Qualifiers
source                  1..15
                        mol_type = protein
```

```
                         organism = Homo sapiens
SEQUENCE: 606
ARALWARGDS VLTPA                                                   15

SEQ ID NO: 607           moltype = AA  length = 15
FEATURE                  Location/Qualifiers
source                   1..15
                         mol_type = protein
                         organism = Homo sapiens
SEQUENCE: 607
DSVLTPALDP QTPVR                                                   15

SEQ ID NO: 608           moltype = AA  length = 15
FEATURE                  Location/Qualifiers
source                   1..15
                         mol_type = protein
                         organism = Homo sapiens
SEQUENCE: 608
DPQTPVRAPS LTRAA                                                   15

SEQ ID NO: 609           moltype = AA  length = 14
FEATURE                  Location/Qualifiers
source                   1..14
                         mol_type = protein
                         organism = Homo sapiens
SEQUENCE: 609
PVRAPSLTRA AAAV                                                    14

SEQ ID NO: 610           moltype = AA  length = 15
FEATURE                  Location/Qualifiers
source                   1..15
                         mol_type = protein
                         organism = Homo sapiens
SEQUENCE: 610
GRRRRRWLRR RRQPI                                                   15

SEQ ID NO: 611           moltype = AA  length = 15
FEATURE                  Location/Qualifiers
source                   1..15
                         mol_type = protein
                         organism = Homo sapiens
SEQUENCE: 611
GVPGDSTRRA VRRMN                                                   15

SEQ ID NO: 612           moltype = AA  length = 13
FEATURE                  Location/Qualifiers
source                   1..13
                         mol_type = protein
                         organism = Homo sapiens
SEQUENCE: 612
DSTRRAVRRM NTF                                                     13

SEQ ID NO: 613           moltype = AA  length = 15
FEATURE                  Location/Qualifiers
source                   1..15
                         mol_type = protein
                         organism = Homo sapiens
SEQUENCE: 613
RRRRQPISVA PAGPP                                                   15

SEQ ID NO: 614           moltype = AA  length = 15
FEATURE                  Location/Qualifiers
source                   1..15
                         mol_type = protein
                         organism = Homo sapiens
SEQUENCE: 614
VAPAGPPRRP NQKPN                                                   15

SEQ ID NO: 615           moltype = AA  length = 15
FEATURE                  Location/Qualifiers
source                   1..15
                         mol_type = protein
                         organism = Homo sapiens
SEQUENCE: 615
TEISCCTLSS EENEY                                                   15

SEQ ID NO: 616           moltype = AA  length = 16
FEATURE                  Location/Qualifiers
source                   1..16
```

```
                        mol_type = protein
                        organism = Homo sapiens
SEQUENCE: 616
SSEENEYLPR PEWQLQ                                                 16

SEQ ID NO: 617          moltype = AA  length = 15
FEATURE                 Location/Qualifiers
source                  1..15
                        mol_type = protein
                        organism = Homo sapiens
SEQUENCE: 617
RPNQKPNPPG GARCV                                                  15

SEQ ID NO: 618          moltype = AA  length = 15
FEATURE                 Location/Qualifiers
source                  1..15
                        mol_type = protein
                        organism = Homo sapiens
SEQUENCE: 618
PGGARCVIMR PTWPG                                                  15

SEQ ID NO: 619          moltype = AA  length = 15
FEATURE                 Location/Qualifiers
source                  1..15
                        mol_type = protein
                        organism = Homo sapiens
SEQUENCE: 619
HVVGYGHLDT SGSSS                                                  15

SEQ ID NO: 620          moltype = AA  length = 16
FEATURE                 Location/Qualifiers
source                  1..16
                        mol_type = protein
                        organism = Homo sapiens
SEQUENCE: 620
YGHLDTSGSS SSSSWP                                                 16

SEQ ID NO: 621          moltype = AA  length = 12
FEATURE                 Location/Qualifiers
source                  1..12
                        mol_type = protein
                        organism = Homo sapiens
SEQUENCE: 621
MRPTWPGTSA FT                                                     12

SEQ ID NO: 622          moltype = DNA  length = 32363
FEATURE                 Location/Qualifiers
misc_feature            1..32363
                        note = GAd20
source                  1..32363
                        mol_type = other DNA
                        organism = synthetic construct
SEQUENCE: 622
catcatcaat aatatacctt attttggatt gaggccaata tgataatgag gtgggcgggg  60
cgaggcgggg cgggtgacgt aggacgcgcg agtagggttg ggaggtgtgg cggaagtgtg  120
gcatttgcaa gtgggaggag ctgacatgca atcttccgtc gcggaaaatg tgacgttttt  180
gatgagcgcc gcctacctcc ggaagtgcca attttcgcgc gcttttcacc ggatatcgta  240
gtaattttgg gcgggaccat gtaagatttg gccattttcg cgcgaaaagt gaaacgggga  300
agtgaaaact gaataatagg gcgttagtca tagcgcgtaa tatttaccga gggccgaggg  360
actttgaccg attacgtgga ggactcgccc aggtgttttt tacgtgaatt tccgcgttcc  420
gggtcaaagt ctccgttttt attgtcgccg tcatctgacg cggagggtat ttaaacccgc  480
tgcgctccta aagaggccac tcttgagtgc cagcgagaag agttttctcc tccgctccgt  540
ttcggcgatc gaaaaatgag acatttagcc tgcactccgg gtcttttgtc cggccgggcg  600
gcgtccgagc ttttggacgc tttgctcaat gaggttctga gcgatgattt tccgtctact  660
acccacttta gcccacctac tcttcacgaa ctgtacgatc tggatgtact ggtggatgtg  720
aacgatccca acgaggaggc ggtttctacg ttttttcccg agtctgcgct tttggctgcc  780
caggagggat ttgacctaca cactccgccg ctgcctattt tagagtctcc gctgccggag  840
cccagtggta taccttatat gcctgaactg cttcccgaag tggtagacct gacctgccac  900
gagccgggct ttccgcccag cgacgatgag ggtgagcctt ttgctttaga ctatgctgag  960
atacctgggc tcggttgcag gtcttgtgca tatcatcaga gggttaccgg agaccccgag  1020
gttaagtgtt cgctgtgcta tatgaggctg acctcttcct ttatctacag taagtttttt  1080
tgtgtaggtg ggctttttgg gtaggtgggt tttgtggcag gacaggtgta aatgttgctt  1140
gtgttttttg tacctgcagg tccggtgtcc gagccagacc cggagcccga ccgcgatccc  1200
gagccggatc ccgagcctcc tcgcaggcca aggaaattac cttccatttt gtgcaagcct  1260
aagacacctg tgaggaccag cgaggcggac agcactgact ctggcacttc tacctctcct  1320
cctgaaattc acccagtggt tcctctgggt atacatagac ctgttgctgt tagagtttgc  1380
gggcgacgcc ctgcagtaga gtgcattgag gacttgctta acgatcccga gggacctttg  1440
gacttgagca ttaaacgccc taggcaataa accccaccta agtaataaac cccacctaag  1500
taataaactt taccgccctt ggttattgag atgacgccca atgtttgctt ttgaatgact  1560
```

-continued

```
tcatgtgtat aataaaagtg agtgtggtca taggtctctt gtttgtctgg gcggggttta  1620
agggtatata agtttctcgg ggctaaactt ggttacactt gaccccaatg gaggcgtggg  1680
ggtgcttgga ggagtttgcg gacgtgcgcc gtttgctgga cgagagctct agcaatacct  1740
atagtatttg gaggtatctg tggggctcta ctcaggccaa gttggtcttc agaattaagc  1800
aggattacaa gtgcgatttt gaagagcttt ttagttcctg tggtgagctt ttgcaatcct  1860
tgaatctggg ccaccaggct atcttccagg aaaaggttct ctcgactttg gatttttcca  1920
ctcccgggcg caccgccgct tgtgtggctt ttgtgtcttt tgtgcaagat aaatggagcg  1980
gggagaccca cctgagtcac ggctacgtgc tggatttcat ggcgatggct ctttggaggg  2040
cttacaacaa atggaagatt cagaaggaac tgtacggttc cgccctacgt cgtccacttc  2100
tgcagcggca ggggctgatg tttcccgacc atcgccagca tcagaatctg gaagacgagc  2160
gagcggagaa gatcagcttg agagccggcc tggaccctcc tcaggaggaa tgaatctccc  2220
gcaggtggtt gagctgtttc ccgaactgag acgggtcctg actatcaggg aggatggtca  2280
gtttgtgaag aagctgaaga gggatcgggg tgagggagat gatgaggcgg ctagcaattt  2340
agcttttagt ctgataactc gccaccgacc ggaatgtatt acctatcagc agattaagga  2400
gagttgtgcc aacgagctgg atcttttggg tcagaagtat agcatagaac agcttaccac  2460
ttactggctt cagcccgggg atgattggga agaggcgatt agggtgtatg caaaggtggc  2520
cctgcggccc gattgcaagt ataagattac taagttggtt aatattagaa actgctgcta  2580
tatttctgga aacggggccg aagtggagat agatactgag gacagggtgg ctattaggtg  2640
ttgcatgata aacatgtggc ccgggatact ggggatggat ggggtgatat ttatgaatgt  2700
gaggttcacg ggccccaact ttaatggtac ggtgttcatg ggcaacacca acttgctcct  2760
gcatggtgcg agtttctatg ggtttaacaa cacctgtata gaggcctgga ccgatgtaaa  2820
ggttcgaggt tgttcctttt atagctgttg gaaggcggtg gtgtgtcgcc ctaaaagcag  2880
gggttctgtg aagaaatgct tgtttgaaag gtgcacccta ggtatccttt ctgagggcaa  2940
ctccagggtg cgccataatg tggcttcgaa ctgcggttgc ttcatgcaag tgaagggggt  3000
gagcgttatc aagcataact cggtctgtgg aaactgcgag gatcgcgcct ctcagatgct  3060
gacctgcttt gatggcaact gtcacctgtt gaagaccatt catataagca gtcaccccag  3120
aaaggcctgg cccgtgtttg agcataacat tctgacccgc tgttccttgc atctgggggt  3180
caggaggggt atgttcctgc cttaccagtg taactttagc cacactaaaa tcctgctgga  3240
acccgagtgc atgactaagg tcagcctgaa tggtgtgttt gatgtgagtc tgaagatttg  3300
gaaggtgctg aggtatgatg agaccaggac caggtgccga ccctgcgagt gcggcggcaa  3360
gcacatgaga aatcagcctg tgatgttgga tgtgaccgag gagcttaggc ctgaccatct  3420
ggtgctggcc tgcaccaggg ccgagtttgg gtctagcgat gaggataccg attgaggtgg  3480
gtaaggtggg cgtggctagc agggtgggcg tgtataaatt gggggtctaa ggggtctctc  3540
tgtttgtctt gcaacagccg ccgccatgag cgacaccggc aacagctttg atggaagcat  3600
ctttagtccc tatctgacag tgcgcatgcc tcactgggcc ggagtgcgtc agaatgtgat  3660
gggttccaac gtggatggac gtcccgttct gccttcaaat tcgtctacta tggcctacgc  3720
gaccgtggga ggaactccgc tggacgccgc gacctccgcc gccgcctccg ccgccgccgc  3780
gaccgcgcgc agcatggcta cggaccttta cagctctttg gtggcgagca gcgcggcctc  3840
tcgcgcgtct gctcgggatg agaaactgac tgctctgctg cttaaactgg aagacttgac  3900
ccgggagctg ggtcaactga cccagcaggt ttccagcttg cgtgagagca gccttgcctc  3960
cccctaatgg cccataatat aaataaaagc cagtctgttt ggattaagca agtgtatgtt  4020
ctttatttaa ctctccgcgc gcggtaagcc cgggaccagc ggtctcggtc gtttagggtg  4080
cggtggattt tttccaacac gtggtacagg tggctctgga tgtttagata catgggcatg  4140
agtccatccc tggggtggag gtagcaccac tgcagagctt cgtgctcggg ggtggtgttg  4200
tatatgatcc agtcgtagca ggagcgctgg gcgtggtgct gaaaaatgtc cttaagcaag  4260
aggcttatag ctagggggag gcccttggtg taagtgttta caaatctgct tagctgggag  4320
gggtgcatcc ggggggatat gatgtgcatc ttggactgga tttttaggtt ggctatgttc  4380
ccgcccagat cccttctggg attcatgttg tgcaggacca ccagcacggt atatccagtg  4440
cacttgggaa atttatcgtg gagcttagac gggaatgcat ggaagaactt ggagacgccc  4500
ttgtggcctc ccagattttc catacattcg tccatgatga tggcaatggg cccgtgggaa  4560
gctgcctgag caaaaacgtt tctggcatcg ctcacatcgt agttatgttc cagggtgagg  4620
tcatcatagg acatctttac gaatcggggg cgaagggtcc cggactgggg gatgatggta  4680
ccctcgggcc ccggggcgta gttcccctca cagatctgca tctcccaggc tttcatttca  4740
gagggaggga tcatatccac ctgcggggcg atgaaaaaga cagtttctgg cgcaggggag  4800
attaactggg atgagagcag gtttctgagc agctgtgact ttccacagcc ggtgggccca  4860
tatatcacgc ctatcaccgg ctgcagctgg tagttaagag agctgcagct gccgtcctcc  4920
cggagcaggg gggccacctc gttgagcata tccctgacgt ggatgttctc cctgaccagt  4980
tccgccagaa ggcgctcgcc gcccagcgaa agcagctctt gcaaggaagc aaaatttttc  5040
agcggtttca ggccatcggc cgtgggcatg tttttcagcg tctgggtcag cagctccagc  5100
ctgtcccaga gctcggtgat gtgctctacg gcatctcgat ccagcagatc tcctcgtttc  5160
gcgggttggg gcggctttcg ctgtagggca ccagccgatg ggcgtccagc ggggccagag  5220
tcatgtcctt ccatgggcgc agggtcctcg tcagggtggt ctgggtcacg gtgaaggggt  5280
gcgctccggg ttgggcactg gccagggtgc gcttgaggct ggttctgctg gtgctgaatc  5340
gctgccgctc ttcgccctgc gcgtcggcca ggtagcattt gaccatggtc tcgtagtcga  5400
gaccctcggc ggcgtgcccc ttggcgcgga gctttccctt ggaggtggcg ccgcacgagg  5460
ggcactgcag gctcttcagg gcgtagagct tgggagcgag aaacacggac tctggggagt  5520
aggcgtccgc gccgcaggcc gagcagaccg tctcgcattc caccagccaa gtgagttccg  5580
ggcggtcagg gtcaaaaacc aggttgcccc catgcttttt gatgcgtttc ttaccttggc  5640
tctccatgag gcggtgtccc ttctcggtga cgaagaggct gtccgtgtcc ccgtagaccg  5700
acttcagggg cctgtcttcc agcggagtgc ctctgtcctc ctcgtagaga aactctgacc  5760
actctgagac gaaggcccgc gtccaggcca ggacgaagga ggccacgtgg gaggggtagc  5820
ggtcgttgtc cactagcggg tccaccttct ccagggtgtg caggcacatg tccccctcct  5880
ccgcgtccag aaaagtgatt ggcttgtagg tgtaggacac gtgaccgggg gttcccaacg  5940
ggggggtata aaagggggtg ggtgcccttt catcttcact ctcttccgca tcgctgtctg  6000
cgagagccag ctgctggggt aagtattccc tctcgaaggc gggcatgacc tcagcgctca  6060
ggttgtcagt ttctaaaaat gaggaggatt tgatgttcac ctgtccggag gtgatacctt  6120
tgagggtacc tgggtccatc tggtcagaaa acactatttt tttgttatca agcttggtgg  6180
cgaatgaccc gtagagggcg ttggagagca gcttggcgat ggagcgcagg gtctggtttt  6240
tgtcgcggtc ggctcgctcc ttggccgcga tgttgagttg cacgtactcg cgggccacgc  6300
```

-continued

```
acttccactc ggggaacacg gtggtgcgct cgtctgggat caggcgcacc ctccagccgc  6360
ggttgtgcag ggtgaccatg tcgacgctgg tggcgacctc accgcgcaga cgctcgttgg  6420
tccagcagag gcggccgccc ttgcgcgagc agaagggggg tagggggtcc agctggtcct  6480
cgtttggggg gtccgcgtcg atggtaaaga ccccggggag caggcgcggg tcaaagtagt  6540
cgatcttgca agcttgcatg tccagagccc gctgccattc gcgggcggcg agcgcgcgct  6600
cgtaggggtt gaggggcggg ccccagggca tggggtgggt gagcgcggag gcgtacatgc  6660
cgcagatgtc atacacgtac aggggttccc tgaggatacc gaggtaggtg ggtagcagc  6720
gccccccgcg gatgctggcg cgcacgtagt catagagctc gtgggagggg gccagcatgt  6780
tgggcccgag gttggtgcgc tgggggcgct cggcgcggaa gacgatctgc ctgaagatgg  6840
cgtgggagtt ggaggagatg gtgggccgct ggaagacgtt gaagcttgct tcttgcaagc  6900
ccacggagtc cctgacgaag gaggcgtagg actcgcgcag cttgtgcacc agctcggcgg  6960
tgacctggac gtcgagcgca cagtagtcga gggtctcgcg gatgatgtca tacctatcct  7020
ccccccttctt tttccacagc tcgcggttga ggacgaactc ttcgcggtct ttccagtact  7080
cttggagggg aaacccgtcc gtgtccgaac ggtaagagcc tagcatgtag aactggttga  7140
cggcctggta ggggcagcag cccttctcca cgggcagcgc gtaggcctgc gccgccttgc  7200
ggagggaggt gtgggtgagg gcgaaagtgt ccctgaccat gactttgagg tattgatgtc  7260
tgaagtctgt gtcatcgcag ccgccctgtt cccacagggt gtagtccgtg cgctttttgg  7320
agcgcgggtt gggcagggag aaggtgaggt cattgaagag gatcttcccc gctcgaggca  7380
tgaagtttct ggtgatgcga aagggccctg ggaccgagga gcggttgttg atgacctggg  7440
cggccaggac gatctcgtca aagccgttta tgttgtgtcc cacgatgtag agctccagga  7500
agcggggctg gcccttgatg gaggggagct ttttaagttc ctcgtaggta agctcctcgg  7560
gcgattccag gccgtgctcc tccagggccc agtcttgcaa gtgagggttg gccgccagga  7620
aggatcgcca gaggtcgcgg gccatgaggg tctgcaggcg gtcgcggaag gttctgaact  7680
gccgccccac ggccattttt tcgggggtga tgcagtagaa ggtgaggggg tctttctccc  7740
aggggtccca tctgagctct cgggcgaggt cgcgcgcggc agcgaccaga gcctcgtcgc  7800
cccccagttt catgaccagc atgaagggca cgagttgctt gccaaaggct cccatccaag  7860
tgtaggtttc tacatcgtag gtgacaaaga ggcgctccgt gcgaggatga gagccgattg  7920
ggaagaactg gatctcccgc caccagttgg aggattggct gttgatgtgg tgaaagtaga  7980
agtcccgtct gcgggccgag cactcgtgct ggcttttgta aaagcgaccg cagtactggc  8040
agcgctgcac gggttgtata tcttgcacga ggtgaacctg gcgacctctg acgaggaagc  8100
gcagcgggaa tctaagtccc ccgcctgggg tcccgtgtgg ctggtggtct tttactttgg  8160
ttgtctggcc gccagcatct gtctcctgga gggcgatggt ggaacagacc accacgccgc  8220
gagagccgca ggtccagatc tcggcgctcg gcgggcggag tttgatgacg acatcgcgca  8280
cattggagct gtccatggtc tccagctccc gcggcggcag gtcagccggg agttcctgga  8340
ggttcacctc gcagagacgg gtcaaggcgc ggacagtgtt gagatggtat ctgatttcaa  8400
ggggcatgtt ggaggcggag tcgatggctt gcaggaggcc gcagccccgg ggggccacga  8460
tggttccccg cggggcgcga ggggaggcgg aagctggggg tgtgttcaga agcggtgacg  8520
cgggcgggcc cccggaggta ggggggggttc cggccccaca ggcatgggcg gcaggggcac  8580
gtcttcgccg cgcgcgggca ggggctggtg ctggctccga agagcgcttg cgtgcgcgac  8640
gacgcgacgg ttggtgtcct gtatctggcg cctctgagtg aagaccacgg gtcccgtgac  8700
cttgaacctg aaagagagtt cgacagaatc aatctcggca tcgttgacag cggcctggcg  8760
caggatctcc tgcacgtcgc ccgagttgtc ctggtaggcg atttctgcca tgaactgctc  8820
gatctcttcc tcctggagat ctcctcgtcc ggcgcgctcc acggtggccg ccaggtcgtt  8880
ggagatgcga cccatgagct gcgagaaggc gttgagtccg ccctcgttcc agacccggct  8940
gtagaccacg ccccccctcgg cgtcgcgggc gcgcatgacc acctgggcca ggttgagctc  9000
cacgtgtcgc gtgaagacgg cgtagttgcg caggcgctgg aaaaggtagt tcagggtggt  9060
ggcggtgtgc tcggcgacga agaagtacat gacccagcgc cgcaacgtgg attcattgat  9120
gtcccccaag gcctccaggc gctccatggc ctcgtagaag tccacggcga agttgaaaaa  9180
ctgggagttg cgagcggaca cggtcaactc ctcctccaga agacggatga gctcggcgac  9240
agtgtcgcgc acctcgcgct cgaaggccac ggggggcgct tcttcctctt ccacctcttc  9300
ttccatgatt gcttcttctt cttcctcagc cgggacggga gggggcggcg gcgggggagg  9360
ggcgcggcgg cggcggcggc gcaccgggag gcggtcgatg aagcgctcga tcatctcccc  9420
ccgcatgcgg cgcatggtct cggtgacggc gcggccgttc tcccgggggc gcagctcgaa  9480
gacgccgcct ctcatttcgc cgcggggcgg gcggccgtga ggtagcgaga cggcgctgac  9540
tatgcatctt aacaattgct gtgtaggtac gccgccaagg gacctgattg agtccagatc  9600
caccggatcc gaaaaccttt ggaggaaagc gtctatccag tcgcagtcgc aaggtaggct  9660
gagcaccgtg gcgggcgggg gcgggtcggg agagttcctg gcggagatgc tgctgatgat  9720
gtaattaaag taggcggtct tgagaaggcg gatggtggac aggagcacca tgtctttggg  9780
tccggcctgt tggatgcgga ggcggtcggc catgccccag gcctcgttct gacaccggcg  9840
caggtctttg tagtaatctt gcatgagtct ttccaccggc acttcttctc cttcctcttc  9900
ttcatctcgc cggtggtttc tcgcgccgcc catgcgcgtg accccaaagc ccctgagcgg  9960
ctgcagcagg gccaggtcgg cgaccacgcg ctcggccaag atggcctgct gtacctgagt  10020
gagggtcctc tcgaagtcat ccatgtccac gaagcggtgg taggcacccg tgttgatggt  10080
gtaggtgcag ttggccatga cggaccagtt gacggtctgg tgtcccggct gcgagagctc  10140
cgtgtaccgc aggcgcgaga aggcgcggga atcgaacacg tagtcgttgc aagtccgcac  10200
cagatactgg tagcccacca ggaagtgcgg cggaggttgg cgatagaggg gccagcgctg  10260
ggtggcgggg gcgccgggcg ccaggtcttc cagcatgagg cggtggtatc cgtagatgta  10320
cctggacatc caggtgatgc ctgcggcggt ggtggtggcg cgcgcgtagt cgcggacccg  10380
gttccagatg tttcgcaggg gcgagaagtg ttccatggtc ggcacgctct ggccggtgag  10440
gcgcgcgcag tcgttgacgc tctatacaca cacaaaaacg aaagcgttta cagggctttc  10500
gttctgtagc ctggaggaaa gtaaatgggt tgggttgcgg tgtgccccgg ttcgagacca  10560
agctgagctc agccggctga agccgcagct aacgtggtat tggcagtccc gtctcgaccc  10620
aggccctgta tcctccagga tacggtcgag agccctttttg ctttcttggc caagcgcccg  10680
tggcgcgatc tgggatagat ggtcgcgatg agaggacaaa agcggctcgc ttccgtagtc  10740
tggagaaaca atcgccaggg ttgcgttgcg gcgtaccccg gttcgagccc ctatggcggc  10800
ttggatcggc cggaaccgcg gctaacgtgg gctgtggcag ccccgtcctc aggaccccgc  10860
cagccgactt ctccagttac gggagcgagc cccttttgtt tttttatttt ttagatgcat  10920
cccgtgctgc ggcagatgcg cccctcgccc cggcccgatc agcagcagca acagcaggca  10980
tgcagacccc cctctcctct ccccgccccg gtcaccacgg ccgcggcggc cgtgtccggt  11040
```

-continued

```
gcggggggcg cgctggagtc agatgagcca ccgcggcggc gacctaggca gtatctggac  11100
ttggaagagg gcgagggact ggcgcggctg ggggcgagct ctccagagcg ccacccgcgg  11160
gtgcagttga aaagggacgc gcgtgaggcg tacctgccgc ggcaaaacct gtttcgcgac  11220
cgcgggggcg aggagcccga ggagatgcgg gactgcaggt tccaagcggg gcgcgagctg  11280
cgccgcggct tggacagaca gcgcctgctg cgcgaggagg actttgagcc cgacacgcag  11340
acgggcatca gccccgcgcg cgcgcacgtg gccgcggccg acctggtgac cgcctacgag  11400
cagacggtga accaggagcg caacttccaa aaaagcttca acaaccacgt gcgcacgctg  11460
gtggcgcgcg aggaggtgac cctgggtctc atgcatctgt gggacctggt ggaggcgatc  11520
gtgcagaacc ccagcagcaa gcccctgacc gcgcagctgt tcctggtggt gcagcacagc  11580
agggacaacg aggccttcag ggaggcgctg ctgaacatca ccgagccgga ggggcgctgg  11640
ctcctggacc tgataaacat cctgcagagc atagtggtgc aggagcgcag cctgagcctg  11700
gccgagaagg tggcggccat taactattct atgctgagcc tgggcaagtt ctacgctcgc  11760
aagatctaca agaccccccta cgtgcccata gacaaggagg tgaagataga cagcttctac  11820
atgcgcatgg cgctgaaggt gctaaccctg agcgacgacc tgggagtgta ccgcaacgag  11880
cgcatccaca aggccgtgag cgccagccgg cggcgcgagc tgagcgaccg cgaactgatg  11940
cacagtctgc agcgcgcgct gaccggcgcg ggcgagggcg acagggaggt cgagtcctac  12000
tttgacatgg gggccgacct gcactggcag ccgagccgcc gcgccctgga agcggcgggg  12060
gcgtacggcg gccccctggc ggccgatgac gaggaagagg aggactatga gctagaggag  12120
ggcgagtacc tggaggactg acctggctgg tggtgttttg gtatagatgc aagatccgaa  12180
cgtggcggac ccggcggtcc gggcggcgct gcagagccag ccgtccggca ttaactcctc  12240
tgacgactgg gccgcggcca tgggtcgcat catggccctg accgcgcgca accccgaggc  12300
cttcaggcag cagcctcagg ctaaccggct ggcggccatc ttggaagcgg tagtgcccgc  12360
gcgctccaac cccacccacg agaaggtgct ggccatagtc aacgcgctgg cggagagcag  12420
ggccatccgg gcagacgagg ccggactggt gtacgatgcg ctgctgcagc gggtggcgcg  12480
gtacaacagc ggcaacgtgc agaccaacct ggaccgcctg gtgacggacg tgcgcgaggc  12540
cgtggcgcag cgcgagcgct tgcatcagga cggcaacctg ggctcgctgg tggcgctaaa  12600
cgccttcctt agcacccagc cggccaacgt accgcggggg caggaggact acaccaactt  12660
cttgagcgcg ctgcggctga tggtgaccga ggtccctcag agcgaggtgt accagtcggg  12720
gcccgactac ttcttccaga ccagcagaca gggcttgcaa accgtgaacc tgagccaggc  12780
tttcaagaac ctgcgggggc tgtggggagt gaaggcgccc accggcgacc gggctacggt  12840
gtccagcctg ctaaccccca actcgcgcct gctgctgctg ctgatcgcgc ccttcacgga  12900
cagcgggagc gtctcgcggg agacctatct gggccacctg ctgacgctgt accgcgaggc  12960
catcgggcag gcgcaggtgg acgagcacac cttccaggag atcaccagcg tgagccacgc  13020
gctggggcag gaggacacgg gcagcctgca ggcgaccctg aactacctgc tgaccaacag  13080
gcggcagaag attcccacgc tgcacagcct gacccaggag gaggagcgca tcttgcgcta  13140
cgtgcagcag agcgtgagcc tgaacctgat gcgcgacggc gtgacgccca gcgtggcgct  13200
ggacatgacc gcgcgcaaca tggaaccggg catgtacgct tcccagcggc cgttcatcaa  13260
ccgcctgatg gactacttgc atcgggcggc ggccgtgaac cccgagtact tcaccaatgc  13320
cattctgaat ccccactgga tgccccctcc gggtttctac aacggggact tcgaggtgcc  13380
tgaggtcaac gatgggttcc tctgggatga catggatgac agtgtgttct cccccaaccc  13440
gctgcgcgcc gcgtctctgc gattgaagga gggctctgac agggaaggac caaggagtct  13500
ggcctcctcc ctggctctgg gggcggtggg cgccacgggc gcggcggcgc ggggcagcag  13560
ccccttcccc agcctggcgg actctctgaa tagcgggcgg gtgagcaggc cccgcttgct  13620
aggcgaggag gagtatctga acaactccct gctgcagccc gtgagggaca aaaacgctca  13680
gcggcagcag tttcccaaca atgggataga gagcctggtg gacaagatgt ccagatggaa  13740
gacgtatgcg caggagtaca aggagtggga ggaccgccag ccgcggcccc tgccgccccc  13800
tagacagcgc tggcagcggc gcgcgtccaa ccgccgctgg aggcaggggc ccgaggacga  13860
tgatgactct gcagatgaca gcagcgtgtt ggacctgggc gggagcggga acccctttttc  13920
gcacctgcgc ccacgcctgg gcaagatgtt ttaaaagaga aaaataaaaa ctcaccaagg  13980
ccatggcgac gagcgttggt tttttgttcc cttccttagt atgcggcgcg cggcgatgtt  14040
cgaggagggg cctcccccct cttacgagag cgcgatggga atttctcctg cggcgcccct  14100
gcagcctccc tacgtgcctc ctcggtacct gcaacctaca ggggggagaa atagcatctg  14160
ttactctgag ctgcagcccc tgtacgatac caccagactg tacctggtgg acaacaagtc  14220
cgcggacgtg gcctccctga actaccagaa cgaccacagc gattttttga ccacggtgat  14280
ccaaaacaac gacttcaccc caaccgaggc cagtacccag accataaacc tggacaacag  14340
gtcgaactgg ggcggcgacc tgaagactat cctgcacacc aatatgccca acgtgaacga  14400
gttcatgttc accaactctt ttaaggcgcg ggtgatggtg gcgcgcgagc agggggaggc  14460
gaagtacgag tgggtggact tcacgctgcc cgagggcaac tactcagaga ccatgactct  14520
cgacctgatg aacaatgcga tcgtggaaca ctatctgaaa gtgggcaggc agaacggggt  14580
gaaggagagc gatatcgggg tcaagtttga caccagaaac ttccgtctgg gctgggaccc  14640
tgtgaccggg ctggtcatgc cgggggtcta caccaacgag gcctttcatc ccgatatagt  14700
gctcctgccc ggctgtgggg tggacttcac ccagagccgg ctgagcaacc tgctgggcgt  14760
tcgcaagcgg caacctttcc aggagggttt caagatcacc tatgaggatc tggagggggg  14820
caacattccc gcgctccttg atctggacgc ctacgaggag agcttgaaac ccgaggagag  14880
cgctggcgac agcggcgaga gtggcgagga gcaagccggc ggcggcggca gcgcgtcggt  14940
agaaaacgaa agtactcccg cagtggcggc ggacgctgcg gaggtcgagc cggaggccat  15000
gcagcaggac gcagaggagg gcgcgcagga ggacatgaac aatggggaga tcaggggcga  15060
cactttcgcc acccggggcg aagaaaaaga ggcagaggcg gcggcggcga cggcggaagc  15120
cgaaaccgag gcagaggcag agcccgagac cgaagttatg gaagacatga atgatggaga  15180
acgtaggggt gacacgtttg ccacccgggg cgaagagaag gcggcggagg cagaagccgc  15240
ggctgaggag gcggctgcgg ctgcggccaa ggctgaggct gcggctgagg ctaaggtcga  15300
agccgatgtt gcggttgagg ctcaggctga ggaggaggcg gcggctgaag cagttaagga  15360
aaaggcccag gcagagcagg aagagaaaaa acctgtcatt caacctctaa aagaagatag  15420
caaaaagcgc agttacaacg tcattgaggg cagcaccttt acccaatacc gcagctggta  15480
cctggcttac aactacggcg acccggtcaa gggggtgcgc tcgtggaccc tgctctgcac  15540
gccggacgtc acctgcggct ccgagcagat gtactggtcg ctgccaaaca tgatgcaaga  15600
cccggtgacc ttccgttcca cgcggcaggt tagcaacttt ccggtggtgg gcgccgaact  15660
gctgccagta cactccaaga gtttttacaa cgagcaggcc gtctactccc agctgatccg  15720
ccaggccacc tctctgaccc acgtgttcaa tcgctttccc gagaaccaga ttttggcgcg  15780
```

-continued

```
cccgccggcc cccaccatca ccaccgtcag tgaaaacgtt cctgccctca cagatcacgg  15840
gacgctaccg ctgcgcaaca gcatctcagg agtccagcga gtgaccatta ctgacgccag  15900
acgccggacc tgcccctacg tttacaaggc cttgggcata gtctcgccgc gcgtcctctc  15960
cagtcgcact ttttaaaaca catccaccca cacgctccaa aatcatgtcc gtactcatct  16020
cgcccagcaa caacaccggc tggggctgc gcgcacccag caagatgttt ggaggggcaa  16080
ggaagcgctc cgaccagcac cccgtgcgcg tgcgcggcca ctaccgcgcg ccctggggtg  16140
cgcacaagcg cgggcgcaca gggcgcacca ctgtggatga tgtcattgac tccgtagtgg  16200
agcaggcgcg ccactacaca cccggcgcgc cgaccgcctc cgccgtgtcc accgtggacc  16260
aggcgatcga aagcgtggta caggggggcgc ggcactatgc caaccttaaa agtcgccgcc  16320
gccgcgtggc gcgccgccat cgccggagac ccgggctac tgccgccgcg cgccttacca  16380
aggctctgct caagcgcgcc aggcgaactg gccaccgggc cgccatgagg gccgcacggc  16440
gggctgccgc tgccgcgagc gccgtggccc cgcgggcacg aaggcgcgcg gccgctgccg  16500
ccgccgccgc catttccagc ttggcctcga cgcggcgcgg taacatatac tgggtgcgcg  16560
actcggtgag cggcacacgt gtgcccgtgc gctttcgccc cccacggaat tagcacaaga  16620
caacatacac actgagtctc ctgctgttgt gtatcccagc ggcgaccgtc agcagcggcg  16680
acatgtccaa gcgcaaaatt aaagaagaga tgctccaggt catcgcgccg gagatctatg  16740
ggcccccgaa gaaggaggag gaggattaca agccccgcaa gctaaagcgg gtcaaaaaga  16800
aaaagaaaga tgatgacgtt gacgaggcgg tggagtttgt ccgccgcatg gcgcccaggc  16860
gccctgtgca gtggaagggt cggcgcgtgc agcgagtcct gcgcccggc accgcggtgg  16920
tctttacgcc cggcgagcgt tccacgcgca ctttcaagcg ggtgtacgat gaggtgtacg  16980
gcgacgagga tctgttggag caggccaacc atcgatttgg ggagtttgca tatgggaaac  17040
ggcctcgcga gagtctaaaa gaggacctgc tggcgctacc gctggacgag ggcaatccca  17100
ccccgagtct gaagccggtg accctgcaac aggtgctgcc tttgagcgcg cccagcgagc  17160
agaagcgagg gttaaagcgc gagggcgggg acctggcacc caccgtgcag ttgatggtgc  17220
ccaagcggca gaagctggag gacgtgctgg agaaaatgaa agtagagccc gggatccagc  17280
ccgagatcaa ggtccgccct atcaagcagg tggcgcccgg cgtgggagtc cagaccgtgg  17340
acgttaggat tcccacggag gagatggaaa cccaaaccgc cactccctct tcggcagcaa  17400
gcgccaccac cggcgccgct tcggtagagg tgcagacgga cccctggcta cccgccgcca  17460
ctatcgccgt cgccgccgcc ccccgttcgc gcggacgcaa gagaaattat ccagcggcca  17520
gcgcgcttat gccccagtat gcgctgcatc catccatcgc gcccaccccc ggctaccgcg  17580
ggtactcgta ccgcccgcgc agatcagccg gcactcgcgg ccgccgccgc cgtgcgacca  17640
caaccagccg ccgccgtcgc cgccgccgcc agccagtgct gaccccgtg tctgtaagga  17700
aggtggctcg ctcggggagc acgctggtgg tgcccagagc gcgctaccac cccagcatcg  17760
tttaaagccg gtctctgtat ggttcttgca gatatggccc tcacttgtcg ccttcgcttc  17820
ccggtgccgg gataccgagg aagaactcac cgccgcaggg gcatggcggg cagcggtctc  17880
cgcggcggcc gtcgccatcg ccggcgcgca aagagcaggc gcatgcgcgg cggtgtgttg  17940
cccctgctgg tcccgctact cgccgcggcg atcggcgccg tgcccgggat cgcctccgtg  18000
gccctgcagg cgtcccagaa acattgactc ttgcaacctt gcaagcttgc atttttggag  18060
gaaaaaaataa aaaagtctag actctcacgc tcgcttggtc ctgtgactat tttgtagaaa  18120
aaagatggaa gacatcaact ttgcgtcgct ggccccgcgt cacggctcgc gcccgttcat  18180
gggagactgg acagatatcg gcaccagcaa tatgagcggt ggcgccttca gctggggcag  18240
tctgtggagc ggccttaaaa attttggttc caccattaag aactatggca acaaagcgtg  18300
gaacagcagc acgggtcaga tgctgagaga caagttgaaa gagcagaact tccaggagaa  18360
ggtggcgcag ggcctggcct ctggcatcag cggggtggtg gacatagcta accaggccgt  18420
gcagaaaaag ataaacagtc atctggaccc ccgccctcag gtggaggaaa cgcctccagc  18480
catggagacg gtgtctcccg agggcaaagg cgaaaagcgc ccgcggcccg acagggaaga  18540
gaccctggtg tcacacaccg aggagccgcc ctcttacgag gaggcagtca aggccggcct  18600
gcccaccact cgccccatag ctcccatggc caccggtgtg gtgggtcaca ggcaacacac  18660
ccccgcaaca ctagatctgc ccccgccgtc cgagccgact cgccagccaa aggcggtgac  18720
ggtgtccgct ccctccactt ccgccgccaa cagagtgcct ctgcgccgcg ctgcgagcgg  18780
cccccgggcc tcgcgagtca gcggcaactg gcagagcaca ctgaacagca tcgtgggcct  18840
gggagtgagg agtgtgaagc gccgccgttg ctactgaatg agcaagctag ctaacgtgtt  18900
gtatgtgtgt atgcgtccta tgtcgccgcc agaggagctg ttgagccgcc ggcgccgtct  18960
gcactccagc gaatttcaag atggcgaccc catcgatgat gcctcagtgg tcgtacatgc  19020
acatctcggg ccaggacgct tcggagtacc tgagccccgg gctggtgcag ttcgcccgcg  19080
ccacagacac ctacttcaac atgagtaaca agttcaggaa ccccactgtg gcgcccaccc  19140
acgatgtgac cacggaccgg tcgcagcgcc tgacgctgcg gttcatcccc gtggatcggg  19200
aggacaccgc ttactcttac aaggcgcggt tcacgctggc cgtgggcgac aaccgcgtgc  19260
tggacatggc ctccacttac tttgacatcc ggggggtgct ggacaggggc cccactttta  19320
agccctactc gggcactgcc tacaaccccc tggcccccaa gggcgccccc aattcttgtg  19380
agtgggaaca agaggaaaat caggtggtcg ctgcagatga tgaacttgaa gatgaagaag  19440
cgcaagcaca agaggaagcc cctgtgaaaa aaattcatgt atatgctcag gcgcctcttt  19500
ctggcgaaaa gatttccaag gatggtatcc aaataggtac tgaagtcgta ggagatacat  19560
ctaaggacac ttttgcagat aaaacattcc aacccgaacc tcagataggc gagtctcagt  19620
ggaacgaggc tgatgccaca gcagcaggag gtagagtttt gaaaaagact accctatga  19680
gaccttgcta tggatcctat gccaggccta ccaatgccaa cggggggtcaa ggaattatgg  19740
ttgccaatga acaaggagtg ttggagtcta aagtagaaat gcaatttttc tctaacacca  19800
caacccttaa tgcgcgggat ggaaccggca atcccgaacc aaaggtggtg ttgtacagcg  19860
aagatgtcca cttggaatct cccgatactc atctgtctta caagcccaaa aaggatgatg  19920
ttaatgccaa aatcatgttg ggtcagcaag ccatgcccaa cagacccaac ctcattggat  19980
ttagagataa tttcattggg cttatgtttt acaacagcac cggtaacatg ggagtgctgg  20040
cgggtcaggc ctctcagttg aatgctgtgg tggacttgca ggatagaaac acagaactgt  20100
catatcagct tctgcttgat tcaattgggg atagaaccag atacttctcc atgtggaacc  20160
aggcagtgga tagctatgat ccagatgtca gaattattga aaaccatggg actgaggatg  20220
aactgcccaa ctactgcttc cctttgggcg gcataggagt tactgatact tatcaaggga  20280
taaaaaatac caatggcaat ggtcagtgga ccaaagatga tcagttcgcg gaccgcaacg  20340
aaataggggt gggaaacaac ttcgccatgg agatcaacat ccaggccaac ctttggagaa  20400
acttcctcta tgcaaacgtg gggctctacc tgccagacaa gctcaagtac aaccccacca  20460
acgtggacat ctctgacaac cccaacacct atgactacat gaacaagcgg gtggtggccc  20520
```

```
ctggcctggt ggactgcttt gtcaatgtgg gagccaggtg gtccctggac tacatggaca  20580
acgtcaaccc cttcaaccac caccgcaatg cgggtctgcg ctaccgctcc atgatcctgg  20640
gcaacgggcg ctatgtgccc tttcacatcc aggtacccca gaagttcttt gccatcaaga  20700
acctcctgct cctgcccggc tcctacacct acgagtggaa cttcaggaag gatgtgaaca  20760
tggtcctaca gagctctctg ggcaatgacc ttagggtgga tggggccagc atcaagtttg  20820
acagcatcac cctctatgct acatttttcc ccatggccca caacaccgcc tccacgcttg  20880
aggccatgct gagaaacgac accaacgacc agtcctttaa tgactacctc tctggggcca  20940
acatgctcta cccaatccca gccaaggcca ccaacgtgcc catctccatc cctctcgca   21000
actgggccgc ctttagaggc tgggccttta cccgccttaa gaccaaggag acccccctccc 21060
tgggctcggg ttttgatccc tactttgttt actcgggatc catcccctac ctggatggca  21120
ccttctacct caaccacact ttcaagaaga tatccatcat gtatgactcc tccgtcagct  21180
ggccgggcaa cgaccgcttg ctcaccccca atgagttcga ggtcaagcgc gccgtggacg  21240
gcgagggcta caacgtggcc cagtgcaaca tgaccaagga ctggttcctg gtgcagatgc  21300
tggccaacta caacataggc taccagggct tttacatccc agagagctac aaggacagga  21360
tgtactcctt cttcagaaat ttccaaccca tgagccgaca ggtggtggac gagaccaatt  21420
acaaggacta tcaagccatt ggcatcaccc accagcacaa caactcgggt ttcgtgggct  21480
acctggcgcc caccatgcgc gagggtcagg cctaccccgc caacttcccc taccccttga  21540
taggcaagac cgcggtcgac agcgtcaccc agaaaaagtt cctctgcgac cgcaccctct  21600
ggcgcatccc cttctctagc aacttcatgt ccatgggtgc gctcacggac ctgggccaaa  21660
acctgcttta tgccaactct gcccatgcgc tggacatgac ttttgaggtg gaccccatgg  21720
acgagcccac ccttctctat attgtgtttg aagtgttcga cgtggtcaga gtgcaccagc  21780
cgcaccgcgg tgtcatcgag accgtgtacc tgcgtacgcc cttctcagcc ggcaacgcca  21840
ccacctaagg agacagcgcc gccgccgcct gcatgacggg ttccaccgag caagagctca  21900
gggccattgc cagagacctg ggatgcggac cctatttttt gggcacctat gacaaacgct  21960
tcccgggctt tatctcccga gacaagctcg cctgcgccat tgtcaacacg gccgcgcgcg  22020
agaccggggg cgtgcactgg ctggcctttg gctgggaccc gcgctccaaa acttgctacc  22080
tctttgaccc ctttggcttc tccgatcagc gcctcaggca gatttatgag tttgagtacg  22140
aggggctgct gcgccgcagc gcgctcgcct cctcgcccga ccgctgcatc acccttgaga  22200
agtccaccga aaccgtgcag gggcccccact cggccgcctg cggtctcttc tgttgcatgt 22260
ttttgcacgc ctttgtgcac tggcctcaga gtcccatgga ttgcaacccc accatgaact  22320
tgctaaaggg agtgcccaac gccatgctcc agagccccca ggtccagccc accctgcgcc  22380
gcaaccagga acagctttac cgcttcctgg agcgccactc cccctacttc cgcagccaca  22440
gcgcgcgcat ccggggggcc acctcttttt gccacttgca agaaaacatg caagacggaa  22500
aatgatgtac agcatgcttt taataaatgt aaagactgtg cactttaatt atacacgggc  22560
tctttctggt tatttattca acaccgccgt cgccatttag aaatcgaaag ggttctgccg  22620
tgcgtcgccg tgcgccacgg gcagagacac gttgcgatac tggaagcggc tcgcccactt  22680
gaactcgggc accaccatgc ggggcagtgg ttcctcgggg aagttctcgc tccacagggt  22740
gcgggtcagc tgcagcgcgc tcaggaggtc gggagccgag atcttgaagt cgcagttggg  22800
gccggaaccc tgcgcgcgcg agttgcggta cacggggttg cagcactgga acaccagcag  22860
ggccggatta ttcacgctgg ccagcaggct ctcgtcgctg atcatgtcgc tgtccagatc  22920
ctccgcgttg ctcagggcga atggggtcat cttgcagacc tgcctgccca ggaaaggcgg  22980
gagcccaggc ttgccgttgc agtcgcagcg caggggcatt agcaggtgcc cacggcccga  23040
ctgcgcctgc gggtacaacg cgcgcatgaa ggcttcgatc tgcctaaaag ccacctgggt  23100
cttggctccc tccgaaaaga acatcccaca ggacttgctg gagaactggt tcgcgggaca  23160
gctggcatcg tgcaggcagc agcgcgcgtc agtgttggca atctgcacca cgttgcgacc  23220
ccaccggttt ttcactatct tggccttgga agcctgctcc tttagcgcgc gctggccgtt  23280
ctcgctggtc acatccatct ctatcacctg ttccttgttg atcatgtttg tcccgtgcag  23340
acactttagg tcgccctccg tctgggtgca gcggtgctcc cacagcgcgc aaccggtggg  23400
ctcccaattc ttgtgggtca cccccgcgta ggcctgcagg taggcctgca ggaagcgccc  23460
catcatggtc ataaaggtct tctggctcgt aaaggtcagc tgcaggccgc gatgctcttc  23520
gttcagccag gtcttgcaga tggcggccag cgcctcggtc tgctcgggca gcatcttaaa  23580
atttgtcttc aggtcgttat ccacgtggta cttgtccatc atggcacgcg ccgcctccat  23640
gcccttctcc caggcggaca ccatgggcag gcttaggggg tttatcactt ccagcggcga  23700
ggacaccgta ctttcgattt cttcttcctc cccctcttcc cggcgcgcgc ccccgctgtt  23760
gcgcgctctt accgcctgca ccaaggggtc gtcttcaggc aagcgccgca ccgagcgctt  23820
gccgcccttg acctgcttga tcagtaccgg cgggttgctg aagcccacca tggtcagcgc  23880
cgcctgctct tcttcgtctt cgctgtctac cactatttct ggggaggggc ttctccgctc  23940
tgcggcaaag gcggcggatc gcttcttttt tttcttggga gccgccgcga tggagtccgc  24000
cacggcgacc gaggtcgagg gcgtggggct gggggtgcgc ggtaccaggg cctcgtcgcc  24060
ctcggactct tcctctgact ccaggcggcg gcggagtcgc ttctttgggg gcgcgcgcgt  24120
cagcggcggc ggagacgggg acggggacgg ggacgggacg ccctccacag gggtggtct   24180
tcgcgcagac ccgcggccgc gctcgggggt cttctcgcgc tggtcttggt cccgactggc  24240
cattgtatcc tcctcctcct aggcagagag acataaggag tctatcatgc aagtcgagaa  24300
ggaggagagc ttaaccaccc cctcagagac cgccgatgcg cccgccgtcg ccgtcgcccc  24360
cgctaccgcc gacgcgcccg ccacaccgag cgacaccccc acggaccccc ccgccgacgc  24420
accccctgttc gaggaagcgg ccgtggagca ggacccgggc tttgtctcgg cagaggagga 24480
tttgcaagag gaggagaata aggaggagaa gccctcagtg ccaaaagatc ataaagagca  24540
agacgagcac gacgcagacg cacaccaggg tgaagtcggg cgggggggacg gagggcatgg 24600
cggcgccgac tacctagacg aaggaaacga cgtgctcttg aagcacctgc atcgtcagtg  24660
cgccatcgtc tgcgacgctc tgcaggagcg cagcgaggtg cccctcagcg tggcggaggt  24720
cagccgcgcc tacgagctca gcctcttttc cccccgggtg cccccccgcc gccgcgaaaa  24780
cggcacatgc gagcccaacc cgcgcctcaa cttctacccc gcctttgtgg tgcccgaggt  24840
cctggccacc tatcacatct tctttcaaaa ttgcaagatc cccatctcgt gccgcgccaa  24900
ccgtagccgc gccgataaga tgctggccct gcgccagggc gaccacatac ctgatatcgc  24960
cgctttggaa gatgtgccaa agatcttcga gggtctgggg cgcaacgaga agcgggcagc  25020
aaactctctg caacaggaaa acagcgaaaa tgagagtcac actggagcgc tggtggagct  25080
ggagggcgac aacgcccgcc tggcggtgct caagcgcagc atcgaggtca cccactttgc  25140
ctaccccgcg ctcaacctgc cccccaaagt catgaacgcg gtcatggacg ggctgatcat  25200
gcgccgcggc cggcccctcg ctccagatgc aaacttgcat gaggagaccg aggacggtca  25260
```

```
gcccgtggtc agcgacgagc agctgacgcg ctggctggag agcgcggacc ccgccgaact  25320
ggaggagcgg cgcaagatga tgatggccgc ggtgctggtc accgtagagc tggagtgtct  25380
gcagcgcttc ttcggtgacc ccgagatgca gagaaaggtc gaggagaccc tacactacac  25440
cttccgccag ggctacgtgc gccaggcttg caagatctcc aacgtggagc tcagcaacct  25500
ggtgtcctac ctgggcatct tgcatgaaaa ccgccttggg cagagcgtgc tacactccac  25560
cctgcgcggg gaggcgcgcc gcgactacgt gcgcgactgc gtttacctct tcctctgcta  25620
cacctggcag acggccatgg gggtctggca gcagtgcctg gaggagcgca acctcaagga  25680
gctggagaag cttctgcagc gcgcgctcaa agacctctgg acgggcttca acgagcgctc  25740
ggtggccgcc gcgctagccg acctcatctt ccccgagcgc ctgctcaaaa ccctccagca  25800
ggggctgccc gacttcacca gccaaagcat gttgcaaaat tttaggaact ttatcctgga  25860
gcgttctggc atcctacccg ccacctgctg cgccctgccc agcgactttg tcccccctcgt  25920
gtaccgcgag tgcccccgc cgctgtgggg ccactgctac ctgttccaac tggccaacta  25980
cctgtcctac cacgcggacc tcatggagga ctccagcggc gaggggctca tggagtgcca  26040
ctgccgctgc aacctctgca cgccccaccg ctccctggtc tgcaacaccc aactgctcag  26100
cgagagtcag attatcggta ccttcgagct acagggtccg tcctcctcag acgagaagtc  26160
cgcggctccg gggctaaaac tcactccggg gctgtggact tccgcctacc tgcgcaaatt  26220
tgtacctgaa gactaccacg cccacgaaat caggttttac gaggaccaat cccgcccgcc  26280
caaggcggag ctgaccgcct gcgtcatcac ccagggcgag atcctaggcc aattgcaagc  26340
catccaaaaa gcccgccaag agtttttgct gaagaggggt cggggggtgt atctggaccc  26400
ccagtcgggt gaggagctca acccggttcc cccgctgcca ccgccgcggg accttgcttc  26460
ccaggataag catcgccatg gctcccagaa agaagcagca gcggccgccg ctgccgccgc  26520
cccacatgct ggaggaagag gaggaatact gggacagtca ggcagaggag gtttcggacg  26580
aggaggagcc ggagacggag atggaagagt gggaggagga cagcttagac gaggaggctt  26640
ccgaagccga agaggcaggc gcaacaccgt caccctcggc cgcagccccc tcgcaggcgc  26700
ccccgaagtc cgctcccagc atcagcagca acagcagcgc tataacctcc gctcctccac  26760
cgccgcgacc cacggccgac cgcagaccca accgtagatg ggacaccacc ggaaccgggg  26820
ccggtaagtc ctccgggaga ggcaagcaag cgcagcgcca aggctaccgc tcgtggcgcg  26880
ctcacaagaa cgccatagtc gcttgcttgc aagactgcgg ggggaacatc tccttcgccc  26940
gccgcttcct gctcttccac cacggtgtgg ccttcccccg taacgtcctg cattactacc  27000
gtcatctcta cagcccctac tgcggcggca gtgagccaga ggcggccagc ggcggcggcg  27060
cccgtttcgg tgcctaggaa gacccagggc aagacttcag ccaagaaact cgcggcgacc  27120
gcggcgaacg cggtcgcggg ggccctgcgc ctgacggtga acgaacccct gtcgacccgc  27180
gaactgagga accgaatctt ccccactctc tatgccatct tccagcagag cagagggcag  27240
gatcaggaac tgaaagtaaa aaacaggtct ctgcgctccc tcacccgcag ctgtctgtat  27300
cacaagagcg aagaccagct tcggcgcacg ctggaggacg ctgaggcact cttcagcaaa  27360
tactgcgcgc tcactcttaa ggactagctc cgcgcccttc tcgaatttag gcgggaacgc  27420
ctacgtcatc gcagcgccgc cgtcatgagc aaggacattc ccacgccata catgtggagc  27480
tatcagccgc agatgggact cgcggcgggc gcctcccaag actactccac ccgcatgaac  27540
tggctcagtg ccggcccaca catgatctca caggttaatg acatccgcac ccatcgaaac  27600
caaatattgg tgaagcaggc ggcaattacc accacgcccc gcaataatcc caaccccagg  27660
gagtggcccg cgtccctggt gtatcaggaa attcccggcc ccaccaccgt actacttccg  27720
cgtgattccc aggccgaagt ccaaatgact aactcagggg cacagctcgc gggcggctgt  27780
cgtcacaggg tgcggcctcc tcgccagggt ataactcacc tggagatccg aggcagaggt  27840
attcagctca acgacgagtc ggtgagctcc tcgctcggtc tcagacctga cgggaccttc  27900
cagatagccg gagccggccg atcttccttc acgccccgcc aggcgtacct gactctgcag  27960
agctcgtcct cggcgccgcg ctcgggcggc atcgggactc tccagttcgt gcaggagttt  28020
gtgccctcgg tctacttcaa ccccttctcg ggctctcccg gtcgctaccc ggaccagttt  28080
atcccgaact ttgacgccgc gagggactcg gtggacggct acgactgaat gtcgggtgga  28140
cccggtgcag agcaacttcg cctgaagcac cttgaccact gccgccgccc tcagtgcttt  28200
gcccgctgtc agaccggtga gttccagtac ttttccctgc ccgactcgca cccggacggc  28260
ccggcgcacg gggtgcgctt tttcatcccg agtcaggtcc gctctaccct aatcagggag  28320
ttcaccgccc gtcccctact ggcggagttg gaaaaggggc cttctatcct aaccattgcc  28380
tgcatttgct ctaaccctgg attacaccaa gatctttgct gtcatttgtg tgctgagtat  28440
aataaaggct gagatcagaa tctactcggg ctcctgtcgc catcctgtca acgccaccgt  28500
ccaagcccgg cccgatcagc ccgaggtgaa cctcacctgt ggtctgcacc ggcgcctgag  28560
gaaataccta gcttggtact acaacagcac tccctttgtg gtttacaaca gctttgacca  28620
ggacggggtc tcactgaggg ataacctctc gaacctgagc tactccatca ggaagaacaa  28680
caccctcgag ctacttcctc cttacctgcc cgggacttac cagtgtgtca ccggcccctg  28740
cacccacacc cacctgttga tcgtaaacga ctctcttccg agaacagacc tcaataactc  28800
ctctccgcag ttccccagaa caggaggtga gctcaggaaa ccccgggtaa agaagggtgg  28860
acaagagtta acacttgtgg ggtttctggt atatgtgacg ctggtggtgg ctcttttgat  28920
taaggctttt ccttccatgt ctgaactatc cctcttcttt tatgaacaac tcgactagtg  28980
ctaacgggac cctacccaac gaatcgggat tgaatatcgg taaccaggtt gcagtttcac  29040
ttttgattac cttcatagtc ctcttcctgc tagtgctgtc gcttctgtgc ctgcggatcg  29100
ggggctgctg catccacgtt tatatctggt gctggctgtt tagaaggttc ggagaccacc  29160
gcaggtagaa taatgctgct taccctcttt gtcctggcgc tggctgccag ctgccaagcc  29220
ttttccgagg ctgacttcat agagccccag tgcaatatca cttataaatc tgaacgtgcc  29280
atctgtacta ttctaatcaa atgtgttact caacacgata aggtgactgt taaatacaaa  29340
gatcaattaa aaaaagacgc actttacagc agctggcaac caggagatga tcaaaaatac  29400
aatgtaaccg tcttccaggg caaactctcc aaaacttaca attacaattt cccatttgag  29460
cagatgtgtg actttgtcat gtacatggaa aagcagtaca agctgtggcc tccaactccc  29520
cagggctgtg tggaaaatcc aggctctttc tgtatgatct ctctctgtgt aactgtgctg  29580
gcactaatac tcacgcttct gtatctcaga tttaaatcaa ggcaaagctt cattgatgaa  29640
aagaaaatgc cataatcgct caacgcttga ttgctaacac cgggtttttta tccgcagaat  29700
gattggaatc accctactaa tcacctccct ccttgcgatt gcccatgggt tggaacgaat  29760
cgaagtccct gtgggggcca atgttaccct ggtggggcct gtcggcaatg ctacattaat  29820
gtgggaaaaa tatactaaaa atcaatgggt ttcttactgc actaacaaaa acagccacaa  29880
gcccagagcc atctgcgatg ggcaaaatct aaccttgatt gatgttcaat tgctggatgc  29940
gggctactat tatgggcagc tgggtacaat gattaattac tggagacccc acagagatta  30000
```

```
catgcttcac gtagtaaagg gtcccattag cagcccaacc accacctcta ccacacccac  30060
taccaccact actcccacca ccagcactgc cgcccagcct cctcatagca gaacaaccac  30120
ttttatcaat tccaagtccc actcccccca cattgccggc gggccctccg cctcagactc  30180
cgagaccacc gagatctgct tctgcaaatg ctctgacgcc attgcccagg atttggaaga  30240
tcacgaggaa gatgagcatg actacgcaga tgcatgccag gcatcagagg cagaagcgct  30300
accggtggcc ctaaaacagt atgcagactc ccacaccacc cccaaccttc ctccaccttc  30360
ccagaagcca agtttcctgg gggaaaatga aactctgcct ctttccatac tagctctgac  30420
atctgttgct attttggccg ctctgctggt gcttctatgc tctatatgct acctgatctg  30480
ctgcagaaag aaaaaatctc acggccatgc tcaccagccc ctcatgcact tcccttaccc  30540
tccagagctg ggcgaccaca aactttaagt ctgcagtagc tatctgccca tcccttgtca  30600
gtcgacagcg atgagcccca ctaatctaac agcctctgga cttacaacat tgtctcttaa  30660
tgagaccacc gctcctcaag acctgtacga tggtgtctcc gcgctggtta accagtggga  30720
tcacctgggc atatggtggc tcctcatagg agcagtgacc ctgtgcctaa tcctggtctg  30780
gatcatctgc tgcatcaaaa gcagaagacc caggcggcgg cccatctaca ggcccttcgt  30840
catcacacct gaagataatg atgatgatga caccacctcc aggctgcaga gcctaaagca  30900
gctactcttc tcttttacag catggtaaat tgaatcatgc cccgcatttt catctacttg  30960
cttctccttc cactttttct gggctcctct acattggcca ctgtgtccca catcgaggta  31020
gactgcctca cgcccttcac agtctacctg cttttcggct ttgtcatctg cacctttgtc  31080
tgcagcgtta tcactgtagt gatctgcttc atacagtgca tcgactacat ctgtgtgcgg  31140
gtggcctact ttagacacca cccccagtat cgcaacaggg acatagcggc tctcctaaga  31200
cttgtttaaa tcatggccaa attacctgtg attggtcttc tgattatctg ctgcgtccta  31260
gccgcgattg ggactcaacc taataccacc accagcgctc ccagaaagag acatgtatcc  31320
tgcagcttca agcgtccctg gaatataccc caatgcttta ctgatgaacc tgaaatctct  31380
ttggcttggt acttcagcgt caccgccctt ctcatcttct gcagtacggt tattgctctt  31440
gccatctacc cttcccttaa cctgggctgg aatgctgtca actctatgga atatcccacc  31500
ttcccagaac cagacctgcc agacctggtt gttctaaacg cgtttcctcc tcctccagtt  31560
caaaatcagt ttcgccctcc gtcccctacg cccactgagg tcagctactt taatctaaca  31620
ggcggagatg actgaaaacc tagacctaga aatggacggt ctctgcagcg agcaacgcac  31680
actagagagg cgccggcaaa aagcagagct cgagcgtctt aaacaagagc tccaagacgc  31740
cgtggccata caccagtgca aaaaagggct cttctgtctg gtaaaacagg ccacgctcac  31800
ctatgaaaaa acaggtgaca cccaccgcct aggatacaag ctgcccacac agcgccaaaa  31860
gtttgccctt atgataggtg aacaacccat caccgtcacc cagcactccg tggagacaga  31920
aggctgcatt catgctccct gcaggggcgc tgactgcctc tacaccttga tcaaaaccct  31980
ctgcggtctc agagacctta tccctttcaa ttgatcataa ctgtaatcaa taaaaaatca  32040
cttacttgaa atctgatagc aagactctgt ccaatttttt cagcaacact tccttcccct  32100
cctcccaact ctggtactct aggcgcctcc tagctgcaaa cttcctccac agtctgaagg  32160
gaatgtcaga ttcctcctcc tgtccctccg cacccacgat cttcatgttg ttacagatga  32220
aacgcgcgag atcgtctgac gagaccttca accccgtgta cccctacgat accgagatcg  32280
ctccgacttc tgtccctttc cttacccctc cctttgtatc atccgcagga atgcaagaaa  32340
atccagctgg ggtgctgtcc ctg                                          32363
```

```
SEQ ID NO: 623          moltype = AA  length = 1507
FEATURE                 Location/Qualifiers
REGION                  1..1507
                        note = Heterologous polypeptide
source                  1..1507
                        mol_type = protein
                        organism = synthetic construct
SEQUENCE: 623
MGQKEQIHTL QKNSERMSKQ LTRSSQAVGV PGDSTRRAVR RMNTFYEAGM TLGEKFRVGN  60
CKHLKMTRPN SKMALNSEAL SVVSECGASA CDVSLIAMDS AFVQGKDWGV KKFIRRDFYA  120
YKDFLWCFPF SLVFLQEIQI CCHVSCLCCI CCSTRICLGC LLELFLSRAL RALHVLWNGF  180
QLHCQTEYNQ KLQVNQFSES KSLYHREKQL IAMDSAICEE RGAAGSLISC ETMPAILKLQ  240
KNCLLSLRTA LTHNQDFSIY RLCCKRGSLC HASQARSPAF PKPVRPLPAP ITRITPQLGG  300
QSDSSQPLLT TGRPQGWQDQ ALRHTQQASP ASCATITIPI HSAALGDHSG DPGPAWDTCP  360
PLPLTTLIPR APPPYGDSTA RSWPSRCGPL GGNTTLQQLG EASQAPSGSL IPLRLPLLWE  420
VRGQPDSFAA LHSSLNELGE IARELHQFAF DLLIKSHFVQ GKDWGLKKFI RRDFWGMELA  480
ASRRFSWDHH SAGGPPRVPS VRSGAAQVQP KDPLPLRTLA GCLARTAHLR PGAESLPQPQ  540
LHCTLWFQSS ELSPTGAPWP SRRPTWRGTT VSPRTATSSA RTCCGTKWPS SQEAALGLGS  600
GLLRFSCGTA AIRKMHFSLK EHPPPPCPPE AFQRAAGEGG PGRGGARRGA RVLQSPFCRA  660
GAGEWLGHQS LRHVVGYGHL DTSGSSSSSS WPNSKMALNS LNSIDDAQLT RIAPPRSHCC  720
FWEVNAPDGH SYTSKVNCLL LQDGFHGCVS ITGAAGRRNL SIFLFLMLCK LEFHACKIQN  780
KNCPDFKKFD GPCGERGGGR TARALWARGD SVLTPALDPQ TPVRAPSLTR AAAAVHYKLI  840
QQPISLFSIT DRLHKTFSQL PSVHLCSITF QWGHPPIFCS TNDICVTANF CISVTFLKPC  900
FLLHEASASQ CHLFLQPQVG TPPPHTASAR APSGPPHPHE SCPAGRRPAR AAQTCARRQH  960
GLPGCEEAGT ARVPSLHLHL HQAALGAGRG RGWGEACAQV PPSRGVLRFL DLKVRYLHSQ  1020
WQHYHRSGEA AGTPLWRPTR NVPFRELKNQ RTAQGAPGIH HAASPVAANL CDPARHAQHT  1080
RIPCGAGQVR AGRGPEAGGG VLQPQRPAPE KPGCPCRRGQ PRLHTVKMWR AVAMMVPDRQ  1140
VHYDFGLQNL QNGGGSRSSA TLPGRRRRRW LRRRRQPISV APAGPPRRPN QKPNPPGGAR  1200
CVIMRPTWPG TSAFTKRSFA VTERIILVLG VLSGHSGSRL YEAGMTLGGK ILFFLFLLLP  1260
LSPFSLIFTE ISCCTLSSEE NEYLPRPEWQ LQVPFRELKN VSVLEGLRQG RLGGPCSCHC  1320
PRPSQARLTP VDVAGPFLCL GDPGLFPPVK SSITGGKSTC SAPGPQSLPS TPFSTYPQWV  1380
ILITELGMEC TLGQVGAPSP RREEDGWRGG HSRFKADVPA PQGPCWGGQP GSAPSSAPPE  1440
QSLLDDYWAQ KEKGSSSFLR PSCDYWAQKE KISIPRTHLC WKFEMSYTVG GPPPHVHARP  1500
RHWKTDR                                                            1507

SEQ ID NO: 624          moltype = AA  length = 1507
FEATURE                 Location/Qualifiers
REGION                  1..1507
```

```
                         note = Heterologous polypeptide
source                   1..1507
                         mol_type = protein
                         organism = synthetic construct
SEQUENCE: 624
MGQKEQIHTL QKNSERMSKQ LTRSSQAVGN TTLQQLGEAS QAPSGSLIPL RLPLLWEVRG  60
QPDSFAALHS SLNELGEIAR ELHQFAFDLL IKSHFVQGKD WGLKKFIRRD FWGMELAASR  120
RFSWDHHSAG GPPRVPSVRS GAAQVQPKDP LPLRTLAGCL ARTAHLRPGA ESLPQPQLHC  180
TLWFQSSELS PTGAPWPSRR PTWRGTTVSP RTATSSARTC CGTKWPSSQE AALGLGSGLL  240
RFSCGTAAIR KMHFSLKEHP PPPCPPEAFQ RAAGEGGPGR GGARRGARVL QSPFCRAGAG  300
EWLGHQSLRH VVGYGHLDTS GSSSSSSWPN SKMALNSLNS IDDAQLTRIA PPRSHCCFWE  360
VNAPGVPGDS TRRAVRRMNT FYEAGMTLGE KFRVGNCKHL KMTRPNSKMA LNSEALSVVS  420
ECGASACDVS LIAMDSAFVQ GKDWGVKKFI RRDFYAYKDF LWCFPFSLVF LQEIQICCHV  480
SCLCCICCST RICLGCLLEL FLSRALRALH VLWNGFQLHC QTEYNQKLQV NQFSESKSLY  540
HREKQLIAMD SAICEERGAA GSLISCETMP AILKLQKNCL LSLRTALTHN QDFSIYRLCC  600
KRGSLCHASQ ARSPAFPKPV RPLPAPITRI TPQLGGQSDS SQPLLTTGRP QGWQDQALRH  660
TQQASPASCA TITIPIHSAA LGDHSGDPGP AWDTCPPLPL TTLIPRAPPP YGDSTARSWP  720
SRCGPLGDGH SYTSKVNCLL LQDGFHGCVS ITGAAGRRNL SIFLFLMLCK LEFHACKIQN  780
KNCPDFKKFD GPCGERGGGR TARALWARGD SVLTPALDPQ TPVRAPSLTR AAAAVHYKLI  840
QQPISLFSIT DRLHKTFSQL PSVHLCSITF QWGHPPIFCS TNDICVTANF CISVTFLKPC  900
FLLHEASASQ CHLFLQPQVG TPPPHTASAR APSGPPHPHE SCPAGRRPAR AAQTCARRQH  960
GLPGCEEAGT ARVPSLHLHL HQAALGAGRG RGWGEACAQV PPSRGVLRFL DLKVRYLHSQ  1020
WQHYHRSGEA AGTPLWRPTR NVPFRELKNQ RTAQGAPGIH HAASPVAANL CDPARHAQHT  1080
RIPCGAGQVR AGRGPEAGGG VLQPQRPAPE KPGCPCRRGQ PRLHTVKMWR AVAMMVPDRQ  1140
VHYDFGLQNL QNGGGSRSSA TLPGRRRRRW LRRRRQPISV APAGPPRRPN QKPNPPGGAR  1200
CVIMRPTWPG TSAFTKRSFA VTERIITEIS CCTLSSEENE YLPRPEWQLQ YEAGMTLGGK  1260
ILFFLFLLLP LSPFSLIFDY WAQKEKGSSS FLRPSCVPFR ELKNVSVLEG LRQGRLGGPC  1320
SCHCPRPSQA RLTPVDVAGP FLCLGDPGLF PPVKSSITGG KSTCSAPGPQ SLPSTPFSTY  1380
PQWVILITEL GMECTLGQVG APSPRREEDG WRGGHSRFKA DVPAPQGPCW GGQPGSAPSS  1440
APPEQSLLDD YWAQKEKISI PRTHLCLVLG VLSGHSGSRL WKFEMSYTVG GPPPHVHARP  1500
RHWKTDR                                                            1507

SEQ ID NO: 625           moltype = AA  length = 1507
FEATURE                  Location/Qualifiers
REGION                   1..1507
                         note = Heterologous polypeptide
source                   1..1507
                         mol_type = protein
                         organism = synthetic construct
SEQUENCE: 625
MGQKEQIHTL QKNSERMSKQ LTRSSQAVGN TTLQQLGEAS QAPSGSLIPL RLPLLWEVRG  60
NSKMALNSLN SIDDAQLTRI APPRSHCCFW EVNAPFVQGK DWGLKKFIRR DFEAFQRAAG  120
EGGPGRGGAR RGARVLQSPF CRAGAGEWLG HQSLRWGMEL AASRRFSWDH HSAGGPPRVP  180
SVRSGAAQVQ PKDPLPLRTL AGCLARTAHL RPGAESLPQP QLHCTIAREL HQFAFDLLIK  240
SHKMHFSLKE HPPPPCPPHV VGYGHLDTSG SSSSSSWPQP DSFAALHSSL NELGELWFQS  300
SELSPTGAPW PSRRPTWRGT TVSPRTATSS ARTCCGTKWP SSQEAALGLG SGLLRFSCGT  360
AAIRQNLQNG GGSRSSATLP GRRRRRWLRR RRQPISVAPA GPPRRPNQKP NPPGGARCVI  420
MRPTWPGTSA FTGMECTLGQ VGAPSPRREE DGWRGGHSRF KADVPAPQGP CWGGQPGSAP  480
SSAPPEQSLL DDYWAQKEKI SIPRTHLCWK FEMSYTVGGP PPHVHARPRH WKTDRDYWAQ  540
KEKGSSSFLR PSCVPFRELK NVSVLEGLRQ GRLGGPCSCH CPRPSQARLT PVDVAGPFLC  600
LGDPGLFPPV KSSITEISCC TLSSEENEYL PRPEWQLQYE AGMTLGGKIL FFLFLLLPLS  660
PFSLIFLVLG VLSGHSGSRL KRSFAVTERI ITGGKSTCSA PGPQSLPSTP FSTYPQWVIL  720
ITELDGHSYT SKVNCLLLQD GFHGCVSITG AAGRRNLSIF LFLMLCKLEF HACQWQHYHR  780
SGEAAGTPLW RPTRNVAMMV PDRQVHYDFG LVLRFLDLKV RYLHSKIQNK NCPDVPFREL  840
KNQRTAQGAP GIHHAASPVA ANLCDPARHA QHTRIPCGAG QVRAGRGPEA GGGVLQPQRP  900
APEKPGCPCR RGQPRLHTVK MWRACHLFLQ PQVGTPPPHT ASARAPSGPP HPHESCPAGR  960
RPARAAQTCA RRQHGLPGCE EAGTARVPSL HLHLHQAALG AGRGRGWGEA CAQVPPSRGH  1020
YKLIQQPISL FSITDRLHKT FSQLPSVHLC SITFQWGHPP IFCSTNDICV TANFCISVTF  1080
LKPCFLLHEA SASQFKKFDG PCGERGGGRT ARALWARGDS VLTPALDPQT PVRAPSLTRA  1140
AAAVGVPGDS TRRAVRRMNT FCGASACDVS LIAMDSACEE RGAAGSLISC ESLYHREKQL  1200
IAMDSAIFVQ GKDWGVKKFI RRDFTMPAIL KLQKNCLLSL NSKMALNSEA LSVVSEYEAG  1260
MTLGEKFRVG NCKHLKMTRP TEYNQKLQVN QFSESKRTAL THNQDFSIYR LCCKRGSLCH  1320
ASQARSPAFP KPVRPLPAPI TRITPQLGGQ SDSSQPLLTT GRPQGWQDQA LRHTQQASPA  1380
SCATITIPIH SAALGDHSGD PGPAWDTCPP LPLTTLIPRA PPPYGDSTAR SWPSRCGPLG  1440
YAYKDFLWCF PFSLVFLQEI QICCHVSCLC CICCSTRICL GCLLELFLSR ALRALHVLWN  1500
GFQLHCQ                                                            1507

SEQ ID NO: 626           moltype = AA  length = 1507
FEATURE                  Location/Qualifiers
REGION                   1..1507
                         note = Heterologous polypeptide
source                   1..1507
                         mol_type = protein
                         organism = synthetic construct
SEQUENCE: 626
MGQKEQIHTL QKNSERMSKQ LTRSSQAVDG HSYTSKVNCL LLQDGFHGCV SITGAAGRRN  60
LSIFLFLMLC KLEFHACVPF RELKNQRTAQ GAPGIHHAAS PVAANLCDPA RHAQHTRIPC  120
GAGQVRAGRG PEAGGGVLQP QRPAPEKPGC PCRRGQPRLH TVKMWRAQWQ HYHRSGEAAG  180
TPLWRPTRNK IQNKNCPDVA MMVPDRQVHY DFGLVLRFLD LKVRYLHSCH LFLQPQVGTP  240
```

```
PPHTASARAP SGPPHPHESC PAGRRPARAA QTCARRQHGL PGCEEAGTAR VPSLHLHLHQ  300
AALGAGRGRG WGEACAQVPP SRGHYKLIQQ PISLFSITDR LHKTFSQLPS VHLCSITFQW  360
GHPPIFCSTN DICVTANFCI SVTFLKPCFL LHEASASQFK KFDGPCGERG GGRTARALWA  420
RGDSVLTPAL DPQTPVRAPS LTRAAAAVQN LQNGGGSRSS ATLPGRRRRR WLRRRRQPIS  480
VAPAGPPRRP NQKPNPPGGA RCVIMRPTWP GTSAFTGMEC TLGQVGAPSP RREEDGWRGG  540
HSRFKADVPA PQGPCWGGQP GSAPSSAPPE QSLLDDYWAQ KEKISIPRTH LCWKFEMSYT  600
VGGPPPHVHA RPRHWKTDRD YWAQKEKGSS SFLRPSCVPF RELKNVSVLE GLRQGRLGGP  660
CSCHCPRPSQ ARLTPVDVAG PFLCLGDPGL FPPVKSSITE ISCCTLSSEE NEYLPRPEWQ  720
LQYEAGMTLG GKILFFLFLL LPLSPFSLIF LVLGVLSGHS GSRLKRSFAV TERIITGGKS  780
TCSAPGPQSL PSTPFSTYPQ WVILITELGN TTLQQLGEAS QAPSGSLIPL RLPLLWEVRG  840
NSKMALNSLN SIDDAQLTRI APPRSHCCFW EVNAPFVQGK DWGLKKFIRR DFEAFQRAAG  900
EGGPGRGGAR RGARVLQSPF CRAGAGEWLG HQSLRWGMEL AASRRFSWDH HSAGGPPRVP  960
SVRSGAAQVQ PKDPLPLRTL AGCLARTAHL RPGAESLPQP QLHCTIAREL HQFAFDLLIK  1020
SHKMHFSLKE HPPPPCPPHV VGYGHLDTSG SSSSSSWPQP DSFAALHSSL NELGELWFQS  1080
SELSPTGAPW PSRRPTWRGT TVSPRTATSS ARTCCGTKWP SSQEAALGLG SGLLRFSCGT  1140
AAIRGVPGDS TRRAVRRMNT FCGASACDVS LIAMDSACEE RGAAGSLISC ESLYHREKQL  1200
IAMDSAIFVQ GKDWGVKKFI RRDFYEAGMT LGEKFRVGNC KHLKMTRPTM PAILKLQKNC  1260
LLSLNSKMAL NSEALSVVSE TEYNQKLQVN QFSESKRTAL THNQDFSIYR LCCKRGSLCH  1320
ASQARSPAFP KPVRPLPAPI TRITPQLGGQ SDSSQPLLTT GRPQGWQDQA LRHTQQASPA  1380
SCATITIPIH SAALGDHSGD PGPAWDTCPP LPLTTLIPRA PPPYGDSTAR SWPSRCGPLG  1440
YAYKDFLWCF PFSLVFLQEI QICCHVSCLC CICCSTRICL GCLLELFLSR ALRALHVLWN  1500
GFQLHCQ                                                            1507

SEQ ID NO: 627          moltype = AA  length = 7
FEATURE                 Location/Qualifiers
REGION                  1..7
                        note = protein tag
source                  1..7
                        mol_type = protein
                        organism = synthetic construct
SEQUENCE: 627
SHHHHHH                                                            7

SEQ ID NO: 628          moltype = DNA  length = 845
FEATURE                 Location/Qualifiers
misc_feature            1..845
                        note = Promoter
source                  1..845
                        mol_type = other DNA
                        organism = synthetic construct
SEQUENCE: 628
ccattgcata cgttgtatcc atatcataat atgtacattt atattggctc atgtccaaca  60
ttaccgccat gttgacattg attattgact agttattaat agtaatcaat tacggggtca  120
ttagttcata gcccatatat ggagttccgc gttacataac ttacggtaaa tggcccgcct  180
ggctgaccgc ccaacgaccc ccgcccattg acgtcaataa tgacgtatgt tcccatagta  240
acgccaatag ggactttcca ttgacgtcaa tgggtggagt atttacggta aactgcccac  300
ttggcagtac atcaagtgta tcatatgcca agtacgcccc ctattgacgt caatgacggt  360
aaatggcccg cctggcatta tgcccagtac atgaccttat gggactttcc tacttggcag  420
tacatctacg tattagtcat cgctattacc atggtgatgc ggttttggca gtacatcaat  480
gggcgtggat agcggtttga ctcacgggga tttccaagtc tccaccccat tgacgtcaat  540
gggagtttgt tttggcacca aaatcaacgg gactttccaa aatgtcgtaa caactccgcc  600
ccattgacgc aaatgggcgg taggcgtgta cggtgggagg tctatataag cagagctctc  660
cctatcagtg atagagatct ccctatcagt gatagagatc gtcgacgagc tcgtttagtg  720
aaccgtcaga tcgcctggag acgccatcca cgctgttttg acctccatag aagacaccgg  780
gaccgatcca gcctccgcgg ccgggaacgg tgcattggaa cgcggattcc ccgtgccaag  840
agtga                                                              845

SEQ ID NO: 629          moltype = DNA  length = 227
FEATURE                 Location/Qualifiers
misc_feature            1..227
                        note = polyA site
source                  1..227
                        mol_type = other DNA
                        organism = synthetic construct
SEQUENCE: 629
ctgtgccttc tagttgccag ccatctgttg tttgcccctc ccccgtgcct tccttgaccc  60
tggaaggtgc cactcccact gtcctttcct aataaaatga ggaaattgca tcgcattgtc  120
tgagtaggtg tcattctatt ctggggggtg gggtggggca ggacagcaag ggggaggatt  180
gggaagacaa tagcaggcat gctggggatg cggtgggctc tatggcc                227

SEQ ID NO: 630          moltype = DNA  length = 149
FEATURE                 Location/Qualifiers
misc_feature            1..149
                        note = Promoter
source                  1..149
                        mol_type = other DNA
                        organism = synthetic construct
SEQUENCE: 630
gatcactaat tccaaaccca cccgcttttt atagtaagtt tttcacccat aaataataaa  60
```

```
tacaataatt aatttctcgt aaaagtagaa aatatattct aatttattgc acggtaagga  120
agtagaatca taaagaacag tgacggatc                                    149

SEQ ID NO: 631          moltype = AA  length = 15
FEATURE                 Location/Qualifiers
source                  1..15
                        mol_type = protein
                        organism = Homo sapiens
SEQUENCE: 631
VPFRELKNQR TAQGA                                                   15

SEQ ID NO: 632          moltype = AA  length = 15
FEATURE                 Location/Qualifiers
source                  1..15
                        mol_type = protein
                        organism = Homo sapiens
SEQUENCE: 632
QRTAQGAPGI HHAAS                                                   15

SEQ ID NO: 633          moltype = AA  length = 15
FEATURE                 Location/Qualifiers
source                  1..15
                        mol_type = protein
                        organism = Homo sapiens
SEQUENCE: 633
GIHHAASPVA ANLCD                                                   15

SEQ ID NO: 634          moltype = AA  length = 15
FEATURE                 Location/Qualifiers
source                  1..15
                        mol_type = protein
                        organism = Homo sapiens
SEQUENCE: 634
VAANLCDPAR HAQHT                                                   15

SEQ ID NO: 635          moltype = AA  length = 15
FEATURE                 Location/Qualifiers
source                  1..15
                        mol_type = protein
                        organism = Homo sapiens
SEQUENCE: 635
ARHAQHTRIP CGAGQ                                                   15

SEQ ID NO: 636          moltype = AA  length = 15
FEATURE                 Location/Qualifiers
source                  1..15
                        mol_type = protein
                        organism = Homo sapiens
SEQUENCE: 636
IPCGAGQVRA GRGPE                                                   15

SEQ ID NO: 637          moltype = AA  length = 15
FEATURE                 Location/Qualifiers
source                  1..15
                        mol_type = protein
                        organism = Homo sapiens
SEQUENCE: 637
RAGRGPEAGG GVLQP                                                   15

SEQ ID NO: 638          moltype = AA  length = 15
FEATURE                 Location/Qualifiers
source                  1..15
                        mol_type = protein
                        organism = Homo sapiens
SEQUENCE: 638
GGGVLQPQRP APEKP                                                   15

SEQ ID NO: 639          moltype = AA  length = 15
FEATURE                 Location/Qualifiers
source                  1..15
                        mol_type = protein
                        organism = Homo sapiens
SEQUENCE: 639
RPAPEKPGCP CRRGQ                                                   15

SEQ ID NO: 640          moltype = AA  length = 15
FEATURE                 Location/Qualifiers
source                  1..15
                        mol_type = protein
```

```
                        organism = Homo sapiens
SEQUENCE: 640
CPCRRGQPRL HTVKM                                                    15

SEQ ID NO: 641          moltype = AA  length = 14
FEATURE                 Location/Qualifiers
source                  1..14
                        mol_type = protein
                        organism = Homo sapiens
SEQUENCE: 641
RGQPRLHTVK MWRA                                                     14

SEQ ID NO: 642          moltype = AA  length = 15
FEATURE                 Location/Qualifiers
source                  1..15
                        mol_type = protein
                        organism = Homo sapiens
SEQUENCE: 642
CHLFLQPQVG TPPPH                                                    15

SEQ ID NO: 643          moltype = AA  length = 15
FEATURE                 Location/Qualifiers
source                  1..15
                        mol_type = protein
                        organism = Homo sapiens
SEQUENCE: 643
VGTPPPHTAS ARAPS                                                    15

SEQ ID NO: 644          moltype = AA  length = 15
FEATURE                 Location/Qualifiers
source                  1..15
                        mol_type = protein
                        organism = Homo sapiens
SEQUENCE: 644
ASARAPSGPP HPHES                                                    15

SEQ ID NO: 645          moltype = AA  length = 15
FEATURE                 Location/Qualifiers
source                  1..15
                        mol_type = protein
                        organism = Homo sapiens
SEQUENCE: 645
PPHPHESCPA GRRPA                                                    15

SEQ ID NO: 646          moltype = AA  length = 15
FEATURE                 Location/Qualifiers
source                  1..15
                        mol_type = protein
                        organism = Homo sapiens
SEQUENCE: 646
PAGRRPARAA QTCAR                                                    15

SEQ ID NO: 647          moltype = AA  length = 15
FEATURE                 Location/Qualifiers
source                  1..15
                        mol_type = protein
                        organism = Homo sapiens
SEQUENCE: 647
AAQTCARRQH GLPGC                                                    15

SEQ ID NO: 648          moltype = AA  length = 15
FEATURE                 Location/Qualifiers
source                  1..15
                        mol_type = protein
                        organism = Homo sapiens
SEQUENCE: 648
QHGLPGCEEA GTARV                                                    15

SEQ ID NO: 649          moltype = AA  length = 15
FEATURE                 Location/Qualifiers
source                  1..15
                        mol_type = protein
                        organism = Homo sapiens
SEQUENCE: 649
EAGTARVPSL HLHLH                                                    15

SEQ ID NO: 650          moltype = AA  length = 15
FEATURE                 Location/Qualifiers
source                  1..15
```

```
                        mol_type = protein
                        organism = Homo sapiens
SEQUENCE: 650
SLHLHLHQAA LGAGR                                                15

SEQ ID NO: 651          moltype = AA  length = 15
FEATURE                 Location/Qualifiers
source                  1..15
                        mol_type = protein
                        organism = Homo sapiens
SEQUENCE: 651
AALGAGRGRG WGEAC                                                15

SEQ ID NO: 652          moltype = AA  length = 15
FEATURE                 Location/Qualifiers
source                  1..15
                        mol_type = protein
                        organism = Homo sapiens
SEQUENCE: 652
RGWGEACAQV PPSRG                                                15

SEQ ID NO: 653          moltype = AA  length = 15
FEATURE                 Location/Qualifiers
source                  1..15
                        mol_type = protein
                        organism = Homo sapiens
SEQUENCE: 653
HYKLIQQPIS LFSIT                                                15

SEQ ID NO: 654          moltype = AA  length = 15
FEATURE                 Location/Qualifiers
source                  1..15
                        mol_type = protein
                        organism = Homo sapiens
SEQUENCE: 654
ISLFSITDRL HKTFS                                                15

SEQ ID NO: 655          moltype = AA  length = 15
FEATURE                 Location/Qualifiers
source                  1..15
                        mol_type = protein
                        organism = Homo sapiens
SEQUENCE: 655
RLHKTFSQLP SVHLC                                                15

SEQ ID NO: 656          moltype = AA  length = 15
FEATURE                 Location/Qualifiers
source                  1..15
                        mol_type = protein
                        organism = Homo sapiens
SEQUENCE: 656
LPSVHLCSIT FQWGH                                                15

SEQ ID NO: 657          moltype = AA  length = 15
FEATURE                 Location/Qualifiers
source                  1..15
                        mol_type = protein
                        organism = Homo sapiens
SEQUENCE: 657
ITFQWGHPPI FCSTN                                                15

SEQ ID NO: 658          moltype = AA  length = 15
FEATURE                 Location/Qualifiers
source                  1..15
                        mol_type = protein
                        organism = Homo sapiens
SEQUENCE: 658
PIFCSTNDIC VTANF                                                15

SEQ ID NO: 659          moltype = AA  length = 15
FEATURE                 Location/Qualifiers
source                  1..15
                        mol_type = protein
                        organism = Homo sapiens
SEQUENCE: 659
ICVTANFCIS VTFLK                                                15

SEQ ID NO: 660          moltype = AA  length = 15
FEATURE                 Location/Qualifiers
```

```
source                  1..15
                        mol_type = protein
                        organism = Homo sapiens
SEQUENCE: 660
ISVTFLKPCF LLHEA                                                      15

SEQ ID NO: 661          moltype = AA  length = 11
FEATURE                 Location/Qualifiers
source                  1..11
                        mol_type = protein
                        organism = Homo sapiens
SEQUENCE: 661
CFLLHEASAS Q                                                          11

SEQ ID NO: 662          moltype = AA  length = 15
FEATURE                 Location/Qualifiers
source                  1..15
                        mol_type = protein
                        organism = Homo sapiens
SEQUENCE: 662
RTALTHNQDF SIYRL                                                      15

SEQ ID NO: 663          moltype = AA  length = 15
FEATURE                 Location/Qualifiers
source                  1..15
                        mol_type = protein
                        organism = Homo sapiens
SEQUENCE: 663
DFSIYRLCCK RGSLC                                                      15

SEQ ID NO: 664          moltype = AA  length = 15
FEATURE                 Location/Qualifiers
source                  1..15
                        mol_type = protein
                        organism = Homo sapiens
SEQUENCE: 664
CKRGSLCHAS QARSP                                                      15

SEQ ID NO: 665          moltype = AA  length = 15
FEATURE                 Location/Qualifiers
source                  1..15
                        mol_type = protein
                        organism = Homo sapiens
SEQUENCE: 665
ASQARSPAFP KPVRP                                                      15

SEQ ID NO: 666          moltype = AA  length = 15
FEATURE                 Location/Qualifiers
source                  1..15
                        mol_type = protein
                        organism = Homo sapiens
SEQUENCE: 666
FPKPVRPLPA PITRI                                                      15

SEQ ID NO: 667          moltype = AA  length = 15
FEATURE                 Location/Qualifiers
source                  1..15
                        mol_type = protein
                        organism = Homo sapiens
SEQUENCE: 667
PAPITRITPQ LGGQS                                                      15

SEQ ID NO: 668          moltype = AA  length = 15
FEATURE                 Location/Qualifiers
source                  1..15
                        mol_type = protein
                        organism = Homo sapiens
SEQUENCE: 668
PQLGGQSDSS QPLLT                                                      15

SEQ ID NO: 669          moltype = AA  length = 15
FEATURE                 Location/Qualifiers
source                  1..15
                        mol_type = protein
                        organism = Homo sapiens
SEQUENCE: 669
SSQPLLTTGR PQGWQ                                                      15

SEQ ID NO: 670          moltype = AA  length = 15
```

```
FEATURE                Location/Qualifiers
source                 1..15
                       mol_type = protein
                       organism = Homo sapiens
SEQUENCE: 670
GRPQGWQDQA LRHTQ                                                    15

SEQ ID NO: 671         moltype = AA  length = 15
FEATURE                Location/Qualifiers
source                 1..15
                       mol_type = protein
                       organism = Homo sapiens
SEQUENCE: 671
QALRHTQQAS PASCA                                                    15

SEQ ID NO: 672         moltype = AA  length = 15
FEATURE                Location/Qualifiers
source                 1..15
                       mol_type = protein
                       organism = Homo sapiens
SEQUENCE: 672
ASPASCATIT IPIHS                                                    15

SEQ ID NO: 673         moltype = AA  length = 15
FEATURE                Location/Qualifiers
source                 1..15
                       mol_type = protein
                       organism = Homo sapiens
SEQUENCE: 673
ITIPIHSAAL GDHSG                                                    15

SEQ ID NO: 674         moltype = AA  length = 15
FEATURE                Location/Qualifiers
source                 1..15
                       mol_type = protein
                       organism = Homo sapiens
SEQUENCE: 674
ALGDHSGDPG PAWDT                                                    15

SEQ ID NO: 675         moltype = AA  length = 15
FEATURE                Location/Qualifiers
source                 1..15
                       mol_type = protein
                       organism = Homo sapiens
SEQUENCE: 675
PGPAWDTCPP LPLTT                                                    15

SEQ ID NO: 676         moltype = AA  length = 15
FEATURE                Location/Qualifiers
source                 1..15
                       mol_type = protein
                       organism = Homo sapiens
SEQUENCE: 676
PPLPLTTLIP RAPPP                                                    15

SEQ ID NO: 677         moltype = AA  length = 15
FEATURE                Location/Qualifiers
source                 1..15
                       mol_type = protein
                       organism = Homo sapiens
SEQUENCE: 677
IPRAPPPYGD STARS                                                    15

SEQ ID NO: 678         moltype = AA  length = 16
FEATURE                Location/Qualifiers
source                 1..16
                       mol_type = protein
                       organism = Homo sapiens
SEQUENCE: 678
GDSTARSWPS RCGPLG                                                   16

SEQ ID NO: 679         moltype = AA  length = 15
FEATURE                Location/Qualifiers
source                 1..15
                       mol_type = protein
                       organism = Homo sapiens
SEQUENCE: 679
YAYKDFLWCF PFSLV                                                    15
```

```
SEQ ID NO: 680          moltype = AA  length = 15
FEATURE                 Location/Qualifiers
source                  1..15
                        mol_type = protein
                        organism = Homo sapiens
SEQUENCE: 680
CFPFSLVFLQ EIQIC                                                   15

SEQ ID NO: 681          moltype = AA  length = 15
FEATURE                 Location/Qualifiers
source                  1..15
                        mol_type = protein
                        organism = Homo sapiens
SEQUENCE: 681
LQEIQICCHV SCLCC                                                   15

SEQ ID NO: 682          moltype = AA  length = 15
FEATURE                 Location/Qualifiers
source                  1..15
                        mol_type = protein
                        organism = Homo sapiens
SEQUENCE: 682
HVSCLCCICC STRIC                                                   15

SEQ ID NO: 683          moltype = AA  length = 15
FEATURE                 Location/Qualifiers
source                  1..15
                        mol_type = protein
                        organism = Homo sapiens
SEQUENCE: 683
CCSTRICLGC LLELF                                                   15

SEQ ID NO: 684          moltype = AA  length = 15
FEATURE                 Location/Qualifiers
source                  1..15
                        mol_type = protein
                        organism = Homo sapiens
SEQUENCE: 684
GCLLELFLSR ALRAL                                                   15

SEQ ID NO: 685          moltype = AA  length = 15
FEATURE                 Location/Qualifiers
source                  1..15
                        mol_type = protein
                        organism = Homo sapiens
SEQUENCE: 685
SRALRALHVL WNGFQ                                                   15

SEQ ID NO: 686          moltype = AA  length = 11
FEATURE                 Location/Qualifiers
source                  1..11
                        mol_type = protein
                        organism = Homo sapiens
SEQUENCE: 686
VLWNGFQLHC Q                                                       11

SEQ ID NO: 687          moltype = AA  length = 15
FEATURE                 Location/Qualifiers
source                  1..15
                        mol_type = protein
                        organism = Homo sapiens
SEQUENCE: 687
YEAGMTLGEK FRVGN                                                   15

SEQ ID NO: 688          moltype = AA  length = 16
FEATURE                 Location/Qualifiers
source                  1..16
                        mol_type = protein
                        organism = Homo sapiens
SEQUENCE: 688
EKFRVGNCKH LKMTRP                                                  16

SEQ ID NO: 689          moltype = AA  length = 15
FEATURE                 Location/Qualifiers
source                  1..15
                        mol_type = protein
                        organism = Homo sapiens
SEQUENCE: 689
WGMELAASRR FSWDH                                                   15
```

```
SEQ ID NO: 690          moltype = AA  length = 15
FEATURE                 Location/Qualifiers
source                  1..15
                        mol_type = protein
                        organism = Homo sapiens
SEQUENCE: 690
RRFSWDHHSA GGPPR                                                 15

SEQ ID NO: 691          moltype = AA  length = 15
FEATURE                 Location/Qualifiers
source                  1..15
                        mol_type = protein
                        organism = Homo sapiens
SEQUENCE: 691
SAGGPPRVPS VRSGA                                                 15

SEQ ID NO: 692          moltype = AA  length = 15
FEATURE                 Location/Qualifiers
source                  1..15
                        mol_type = protein
                        organism = Homo sapiens
SEQUENCE: 692
PSVRSGAAQV QPKDP                                                 15

SEQ ID NO: 693          moltype = AA  length = 15
FEATURE                 Location/Qualifiers
source                  1..15
                        mol_type = protein
                        organism = Homo sapiens
SEQUENCE: 693
QVQPKDPLPL RTLAG                                                 15

SEQ ID NO: 694          moltype = AA  length = 15
FEATURE                 Location/Qualifiers
source                  1..15
                        mol_type = protein
                        organism = Homo sapiens
SEQUENCE: 694
PLRTLAGCLA RTAHL                                                 15

SEQ ID NO: 695          moltype = AA  length = 15
FEATURE                 Location/Qualifiers
source                  1..15
                        mol_type = protein
                        organism = Homo sapiens
SEQUENCE: 695
LARTAHLRPG AESLP                                                 15

SEQ ID NO: 696          moltype = AA  length = 14
FEATURE                 Location/Qualifiers
source                  1..14
                        mol_type = protein
                        organism = Homo sapiens
SEQUENCE: 696
PGAESLPQPQ LHCT                                                  14

SEQ ID NO: 697          moltype = AA  length = 15
FEATURE                 Location/Qualifiers
source                  1..15
                        mol_type = protein
                        organism = Homo sapiens
SEQUENCE: 697
NSKMALNSLN SIDDA                                                 15

SEQ ID NO: 698          moltype = AA  length = 15
FEATURE                 Location/Qualifiers
source                  1..15
                        mol_type = protein
                        organism = Homo sapiens
SEQUENCE: 698
LNSIDDAQLT RIAPP                                                 15

SEQ ID NO: 699          moltype = AA  length = 15
FEATURE                 Location/Qualifiers
source                  1..15
                        mol_type = protein
                        organism = Homo sapiens
SEQUENCE: 699
```

-continued

```
LTRIAPPRSH CCFWE                                                    15

SEQ ID NO: 700          moltype = AA  length = 15
FEATURE                 Location/Qualifiers
source                  1..15
                        mol_type = protein
                        organism = Homo sapiens
SEQUENCE: 700
APPRSHCCFW EVNAP                                                    15

SEQ ID NO: 701          moltype = AA  length = 15
FEATURE                 Location/Qualifiers
source                  1..15
                        mol_type = protein
                        organism = Homo sapiens
SEQUENCE: 701
LWFQSSELSP TGAPW                                                    15

SEQ ID NO: 702          moltype = AA  length = 15
FEATURE                 Location/Qualifiers
source                  1..15
                        mol_type = protein
                        organism = Homo sapiens
SEQUENCE: 702
SPTGAPWPSR RPTWR                                                    15

SEQ ID NO: 703          moltype = AA  length = 15
FEATURE                 Location/Qualifiers
source                  1..15
                        mol_type = protein
                        organism = Homo sapiens
SEQUENCE: 703
SRRPTWRGTT VSPRT                                                    15

SEQ ID NO: 704          moltype = AA  length = 15
FEATURE                 Location/Qualifiers
source                  1..15
                        mol_type = protein
                        organism = Homo sapiens
SEQUENCE: 704
TTVSPRTATS SARTC                                                    15

SEQ ID NO: 705          moltype = AA  length = 15
FEATURE                 Location/Qualifiers
source                  1..15
                        mol_type = protein
                        organism = Homo sapiens
SEQUENCE: 705
TSSARTCCGT KWPSS                                                    15

SEQ ID NO: 706          moltype = AA  length = 15
FEATURE                 Location/Qualifiers
source                  1..15
                        mol_type = protein
                        organism = Homo sapiens
SEQUENCE: 706
GTKWPSSQEA ALGLG                                                    15

SEQ ID NO: 707          moltype = AA  length = 15
FEATURE                 Location/Qualifiers
source                  1..15
                        mol_type = protein
                        organism = Homo sapiens
SEQUENCE: 707
EAALGLGSGL LRFSC                                                    15

SEQ ID NO: 708          moltype = AA  length = 13
FEATURE                 Location/Qualifiers
source                  1..13
                        mol_type = protein
                        organism = Homo sapiens
SEQUENCE: 708
GLLRFSCGTA AIR                                                      13

SEQ ID NO: 709          moltype = AA  length = 15
FEATURE                 Location/Qualifiers
source                  1..15
                        mol_type = protein
                        organism = Homo sapiens
```

```
SEQUENCE: 709
QNLQNGGGSR SSATL                                              15

SEQ ID NO: 710          moltype = AA  length = 15
FEATURE                 Location/Qualifiers
source                  1..15
                        mol_type = protein
                        organism = Homo sapiens
SEQUENCE: 710
QWQHYHRSGE AAGTP                                              15

SEQ ID NO: 711          moltype = AA  length = 14
FEATURE                 Location/Qualifiers
source                  1..14
                        mol_type = protein
                        organism = Homo sapiens
SEQUENCE: 711
GEAAGTPLWR PTRN                                               14

SEQ ID NO: 712          moltype = AA  length = 16
FEATURE                 Location/Qualifiers
source                  1..16
                        mol_type = protein
                        organism = Homo sapiens
SEQUENCE: 712
TEYNQKLQVN QFSESK                                             16

SEQ ID NO: 713          moltype = DNA  length = 32767
FEATURE                 Location/Qualifiers
misc_feature            1..32767
                        note = recombinant GAd20
source                  1..32767
                        mol_type = other DNA
                        organism = synthetic construct
SEQUENCE: 713
catcatcaat aatatacctt attttggatt gaggccaata tgataatgag gtgggcgggg  60
cgaggcgggg cgggtgacgt aggacgcgcg agtagggttg ggaggtgtgg cggaagtgtg  120
gcatttgcaa gtgggaggag ctgacatgca atcttccgtc gcggaaaatg tgacgttttt  180
gatgagcgcc gcctacctcc ggaagtgcca attttcgcgc gcttttcacc ggatatcgta  240
gtaattttgg gcgggaccat gtaagatttg gccattttcg cgcgaaaagt gaaacgggga  300
agtgaaaact gaataatagg gcgttagtca tagcgcgtaa tatttaccga gggccgaggg  360
actttgaccg attacgtgga ggactcgccc aggtgttttt tacgtgaatt tccgcgttcc  420
gggtcaaagt ctccgttttt attgtcgccg tcatctgacg ggccgccatt gcatacgttg  480
tatccatatc ataatatgta catttatatt ggctcatgtc caacattacc gccatgttga  540
cattgattat tgactagtta ttaatagtaa tcaattacgg ggtcattagt tcatagccca  600
tatatggagt tccgcgttac ataacttacg gtaaatggcc cgcctggctg accgcccaac  660
gacccccgcc cattgacgtc aataatgacg tatgttccca tagtaacgcc aatagggact  720
ttccattgac gtcaatgggt ggagtattta cggtaaactg cccacttggc agtacatcaa  780
gtgtatcata tgccaagtac gccccctatt gacgtcaatg acggtaaatg gcccgcctgg  840
cattatgccc agtacatgac cttatgggac tttcctactt ggcagtacat ctacgtatta  900
gtcatcgcta ttaccatggt gatgcggttt tggcagtaca tcaatgggcg tggatagcgg  960
tttgactcac ggggatttcc aagtctccac cccattgacg tcaatgggag tttgttttgg  1020
caccaaaatc aacgggactt tccaaaatgt cgtaacaact ccgccccatt gacgcaaatg  1080
ggcggtaggc gtgtacggtg ggaggtctat ataagcagag ctctccctat cagtgataga  1140
gatctcccta tcagtgatag agatcgtcga cgagctcgtt tagtgaaccg tcagatcgcc  1200
tggagacgcc atccacgctg ttttgacctc catagaagac accgggaccg atccagcctc  1260
cgcggccggg aacggtgcat tggaacgcgg attccccgtg ccaagagtga gatcttccgt  1320
ttatctaggt accagatatc agaattcgga tcccgcgact tcgccgccat gggccagaaa  1380
gagcagatcc acacactgca gaaaaacagc gagcggatga gcaagcagct gaccagatct  1440
tctcaggccg tgcagaacct gcagaacggc ggaggctcta gaagctctgc tacacttcct  1500
ggcaggcggc ggagaagatg gctgagaaga aggcggcagc ctatctctgt ggctcctgct  1560
ggacctccta gacggcccaa ccagaagcct aatcctcctg gcggagccag atgcgtgatc  1620
atgaggccta catggcctgg caccagcgcc ttcaccaaga gaagctttgc cgtgaccgag  1680
cggatcatcg actattgggc tcaaaaagag aagggcagca gcagcttcct gcggcctagc  1740
tgtgattatt gggcccagaa agaaaagatc agcatcccca gaacacacct gtgcctggtg  1800
ctgggagtgc tgtctggaca ctctggcagc agactgtatg aggccggcat gacactcggc  1860
ggcaagatcc tgttcttcct gttcctgctg ctccctctga gccccttcag cctgatcttc  1920
accgagatca gctgctgcac cctgagcagc gaggaaaacg agtacctgcc tagacctgag  1980
tggcagctgc aggtcccctt cagagagctg aagaacgttt ccgtgctgga aggcctgaga  2040
cagggcagac ttggcggccc ttgtagctgt cactgcccca gacctagtca ggccagactg  2100
acacctgtgg atgtggccgg acctttcctg tgtctgggag atcctggcct gtttccacct  2160
gtgaagtcca gcatcacagg cggcaagtcc acatgttctg cccctggacc tcagagcctg  2220
cctagcacac ccttcagcac ataccctcag tgggtcatcc tgatcaccga actcggcatg  2280
gaatgcaccc tgggacaagt gggagcccca tctcctagaa gagaagagga tggctggcgc  2340
ggaggccact ctagattcaa agctgatgtg cccgctcctc agggcccttg ttggggagga  2400
caacctggat ctgccccatc ttctgcccca cctgaacagt ccctgctgga ttggaagttc  2460
gagatgagct acaccgtcgg cggacctcca cctcatgttc atgccagacc tcggcactgg  2520
aaaaccgaca gagatggcca cagctacacc agcaaagtga actgcctcct gctgcaggat  2580
ggcttccacg gctgtgtgtc tattactggc gccgctggca gacggaacct gagcatcttt  2640
```

-continued

```
ctgtttctga tgctgtgcaa gctcgagttc cacgcctgca agatccagaa caagaactgc  2700
cccgacttca agaagttcga cggcccttgc ggagaaagag gcggaggcag aacagctaga  2760
gccctttggg ctagaggcga cagcgttctg acaccagctc tggaccctca gacacctgtt  2820
agggccccta gcctgacaag agctgccgcc gctgtgcact acaagctgat ccagcagcca  2880
atcagcctgt tcagcatcac cgaccggctg cacaagacat tcagccagct gccaagcgtg  2940
cacctgtgct ccatcacctt ccagtgggga caccctccta tcttttgctc caccaacgac  3000
atctgcgtga ccgccaactt ctgtatcagc gtgaccttcc tgaagccttg ctttctgctg  3060
cacgaggcca gcgcctctca gtgccacttg tttctgcagc cccaagtggg cacacctcct  3120
ccacatacag cctctgctag agcacctagc ggccctccac atcctcacga atcttgtcct  3180
gccggaagaa ggcctgccag agccgctcaa acatgtgcca gacgacagca cggactgcct  3240
ggatgtgaag aggctggaac agccagagtg cctagcctgc acctccatct gcatcaggct  3300
gctcttggag ccggaagagg tagaggatgg ggcgaagctt gtgctcaggt gccaccttct  3360
agaggcgtgc tgagattcct ggacctgaaa gtgcgctacc tgcacagcca gtggcagcac  3420
tatcacagat ctggcgaagc cgccggaaca cccctttgga ggccaacaag aaacgtgccc  3480
ttccgggaac tgaagaacca gagaacagct cagggcgctc ctggaatcca ccatgctgct  3540
tctccagtgg ccgccaacct gtgtgatcct gccagacatg cccagcacac caggattcct  3600
tgtggcgctg gacaagtgcg cgctggaaga ggacctgaag caggcggagg tgttctgcaa  3660
cctcaaagac ccgctcctga gaagcctggc tgcccttgca gaagaggaca gcctagactg  3720
cacaccgtga aaatgtggcg agccgtggcc atgatggtgc ccgatagaca ggtccactac  3780
gactttggac tgggcgtgcc aggcgatagc actcggagag ccgtcagacg gatgaacacc  3840
ttttacgaag ccgggatgac cctgggcgag aagttcagag tgggcaactg caagcacctg  3900
aagatgaccc ggcctaacag caagatggcc ctgaatagcg aggccctgtc tgtggtgtct  3960
gaatgtggcg cctctgcctg tgacgtgtcc ctgatcgcta tggactccgc ctttgtgcag  4020
ggcaaagact ggggcgtgaa gaagttcatc cggcgggact tctacgccta caaggacttc  4080
ctgtggtgct tccccttctc tctggtgttc ctgcaagaga tccagatctg ctgtcatgtg  4140
tcctgcctgt gctgcatctg ctgtagcacc agaatctgcc tgggctgtct gctggaactg  4200
ttcctgagca gagccctgag agcactgcac gtgctgtgga acggattcca gctgcactgc  4260
cagaccgagt acaaccagaa actgcaagtg aaccagttca gcgagagcaa gagcctgtac  4320
caccgggaaa agcagctcat tgccatggac agcgccatct gcgaagagag aggcgccgca  4380
ggatctctga tctcctgcga aacaatgccc gccatcctga agctgcagaa gaattgcctc  4440
ctaagcctgc gaaccgctct gacacacaac caggacttca gcatctacag actgtgttgc  4500
aagcggggct ccctgtgcca tgcaagccaa gctagaagcc ccgcctttcc taaacctgtg  4560
cgacctctgc cagctccaat caccagaatt accccctcagc tcggcggcca gagcgattca  4620
tctcaacctc tgctgaccac cggcagacct caaggctggc aagaccaagc tctgagacac  4680
acccagcagg ctagccctgc ctcttgtgcc accatcacaa tccccatcca ctctgccgct  4740
ctgggcgatc attctggcga tcctggacca gcctgggaca catgtcctcc actgccactc  4800
acaacactga tccctagggc tcctccacct tacggcgatt ctaccgctag aagctggccc  4860
agcagatgtg gaccactcgg aggcaacaca accctccagc aactgggaga agcctctcag  4920
gctcctagcg gctctctgat ccctctcaga ctgcctctcc tgtgggaagt tcggggccag  4980
cctgattctt ttgccgcact gcacagctcc ctgaacgagc tgggagagat cgctagagag  5040
ctgcaccagt tcgccttcga cctgctgatc aagagccact tcgtgcaagg caaggattgg  5100
ggcctcaaaa agtttatccg cagagacttc tggggcatgg aactggccgc cagcagaaga  5160
ttcagctggg atcatcatag cgcaggcggc ccacctagag tgccatctgt tagaagcgga  5220
gctgcccagg tgcagcctaa agatcctctg ccactgagaa cactggccgg ctgccttgct  5280
agaacagccc atcttagacc tggcgccgag tctctgcctc agccacaact gcactgtacc  5340
ctgtggttcc agtccagcga gctgtctcct actggtgccc cttggccatc tagacgccct  5400
acttggagag gcaccaccgt gtcaccaaga accgccacaa gcagcgccag aacctgttgt  5460
ggcacaaagt ggccctccag ccaagaagcc gctctcggac ttggaagcgg actgctgagg  5520
ttctcttgtg gaaccgccgc cattcggaag atgcacttta gcctgaaaga acaccctcca  5580
ccaccttgtc ctccagaggc tttccaaaga gctgctggcg aaggcggacc tggtagaggt  5640
ggtgctagaa gaggtgctag ggtgctgcag agcccattct gtagagcagg cgcaggcgaa  5700
tggctgggcc atcagagtct gagacatgtc gtcggctacg gccacctgga tacaagcgga  5760
agcagctcta gctccagctg gcctaactca aaaatggctc tgaacagcct gaactccatc  5820
gacgacgccc agctgacaag aatcgcccct cctagatctc actgctgctt ttgggaagtg  5880
aacgccccaa gccatcacca tcaccaccat tagtaaaggc gcgcctagcg gccgcgatct  5940
gctgtgcctt ctagttgcca gccatctgtt gtttgcccct cccccgtgcc ttccttgacc  6000
ctggaaggtg ccactcccac tgtcctttcc taataaaatg aggaaattgc atcgcattgt  6060
ctgagtaggt gtcattctat tctggggggt ggggtggggc aggacagcaa gggggaggat  6120
tgggaagaca atagcaggca tgctggggat gcggtgggct ctatggccgg gccgcgatcg  6180
cgcttaggcc tgaccatctg gtgctggcct gcaccagggc cgagtttggg tctagcgatg  6240
aggataccga ttgaggtggg taaggtgggc gtggctagca gggtgggcgt gtataaattg  6300
ggggtctaag ggtctctct gtttgtcttg caacagccgc cgccatgagc gacaccggca  6360
acagctttga tggaagcatc tttagtccct atctgacagt gcgcatgcct cactgggccg  6420
gagtgcgtca gaatgtgatg ggttccaacg tggatggacg tcccgttctg ccttcaaatt  6480
cgtctactat ggcctacgcg accgtgggag gaactccgct ggacgccgcg acctccgccg  6540
ccgcctccgc cgccgccgcg accgcgcgca gcatggctac ggacctttac agctctttgg  6600
tggcgagcag cgcggcctct cgcgcgtctg ctcgggatga gaaactgact gctctgctgc  6660
ttaaactgga agacttgacc cgggagctgg gtcaactgac ccagcaggtt tccagcttgc  6720
gtgagagcag ccttgcctcc ccctaatggc ccataatata aataaaagcc agtctgtttg  6780
gattaagcaa gtgtatgttc tttatttaac tctccgcgcg cggtaagccc gggaccagcg  6840
gtctcggtcg tttagggtgc ggtggatttt ttccaacacg tggtacaggt ggctctggat  6900
gtttagatac atgggcatga gtccatccct ggggtggagg tagcaccact gcagagcttc  6960
gtgctcgggg gtggtgttgt atatgatcca gtcgtagcag gagcgctggg cgtggtgctg  7020
aaaaatgtcc ttaagcaaga ggcttatagc tagggggagg cccttggtgt aagtgtttac  7080
aaatctgctt agctgggagg ggtgcatccg gggggatatg atgtgcatct tggactggat  7140
ttttaggttg gctatgttcc cgcccagatc ccttctggga ttcatgttgt gcaggaccac  7200
cagcacggta tatccagtgc acttgggaaa tttatcgtgg agcttagacg ggaatgcatg  7260
gaagaacttg gagacgccct tgtggcctcc cagattttcc atacattcgt ccatgatgat  7320
ggcaatgggc ccgtgggaag ctgcctgagc aaaaacgttt ctggcatcgc tcacatcgta  7380
```

```
gttatgttcc agggtgaggt catcatagga catctttacg aatcgggggc gaagggtccc  7440
ggactggggg atgatggtac cctcgggccc cggggcgtag ttcccctcac agatctgcat  7500
ctcccaggct ttcatttcag agggagggat catatccacc tgcggggcga tgaaaaagac  7560
agtttctggc gcaggggaga ttaactggga tgagagcagg tttctgagca gctgtgactt  7620
tccacagccg gtgggcccat atatcacgcc tatcaccggc tgcagctggt agttaagaga  7680
gctgcagctg ccgtcctccc ggagcagggg ggccacctcg ttgagcatat ccctgacgtg  7740
gatgttctcc ctgaccagtt ccgccagaag gcgctcgccg cccagcgaaa gcagctcttg  7800
caaggaagca aaatttttca gcggtttcag gccatcggcc gtgggcatgt tttcagcgt  7860
ctgggtcagc agctccagcc tgtcccagag ctcggtgatg tgctctacgg catctcgatc  7920
cagcagatct cctcgtttcg cgggttgggg cggctttcgc tgtagggcac cagccgatgg  7980
gcgtccagcg gggccagagt catgtccttc catgggcgca gggtcctcgt cagggtggtc  8040
tgggtcacgg tgaaggggtg cgctccgggt tgggcactgg ccagggtgcg cttgaggctg  8100
gttctgctgg tgctgaatcg ctgccgctct tcgccctgcg cgtcggccag gtagcatttg  8160
accatggtct cgtagtcgag accctcggcg gcgtgcccct tggcgcggag ctttcccttg  8220
gaggtggcgc cgcacgaggg gcactgcagg ctcttcaggg cgtagagctt gggagcgaga  8280
aacacggact ctggggagta ggcgtccgcg ccgcaggccg agcagaccgt ctcgcattcc  8340
accagccaag tgagttccgg gcggtcaggg tcaaaaacca ggttgccccc atgctttttg  8400
atgcgtttct taccttggct ctccatgagg cggtgtccct tctcggtgac gaagaggctg  8460
tccgtgtccc cgtagaccga cttcaggggc ctgtcttcca gcggagtgcc tctgtcctcc  8520
tcgtagagaa actctgacca ctctgagacg aaggcccgcg tccaggccag gacgaaggag  8580
gccacgtggg aggggtagcg gtcgttgtcc actagcgggt ccaccttctc cagggtgtgc  8640
aggcacatgt ccccctcctc cgcgtccaga aaagtgattg gcttgtaggt gtaggacacg  8700
tgaccggggg ttcccaacgg gggggtataa aagggggtgg gtgccctttc atcttcactc  8760
tcttccgcat cgctgtctgc gagagccagc tgctggggta agtattccct ctcgaaggcg  8820
ggcatgacct cagcgctcag gttgtcagtt tctaaaaatg aggaggattt gatgttcacc  8880
tgtccggagg tgataccttt gagggtacct gggtccatct ggtcagaaaa cactattttt  8940
ttgttatcaa gcttggtggc gaatgacccg tagagggcgt tggagagcag cttggcgatg  9000
gagcgcaggg tctggttttt gtcgcggtcg gctcgctcct tggccgcgat gttgagttgc  9060
acgtactcgc gggccacgca cttccactcg gggaacacgg tggtgcgctc gtctgggatc  9120
aggcgcaccc tccagccgcg gttgtgcagg gtgaccatgt cgacgctggt ggcgacctca  9180
ccgcgcagac gctcgttggt ccagcagagg cggccgccct tgcgcgagca gaagggggggt  9240
agggggtcca gctggtcctc gtttgggggg tccgcgtcga tggtaaagac cccggggagc  9300
aggcgcgggt caaagtagtc gatcttgcaa gcttgcatgt ccagagcccg ctgccattcg  9360
cgggcggcga gcgcgcgctc gtaggggttg aggggcgggc cccagggcat ggggtgggtg  9420
agcgcggagg cgtacatgcc gcagatgtca tacacgtaca ggggttccct gaggataccg  9480
aggtaggtgg ggtagcagcg ccccccgcgg atgctggcgc gcacgtagtc atagagctcg  9540
tgggaggggg ccagcatgtt gggcccgagg ttggtgcgct gggggcgctc ggcgcggaag  9600
acgatctgcc tgaagatggc gtgggagttg gaggagatgg tgggccgctg gaagacgttg  9660
aagcttgctt cttgcaagcc cacggagtcc ctgacgaagg aggcgtagga ctcgcgcagc  9720
ttgtgcacca gctcggcggt gacctggacg tcgagcgcac agtagtcgag ggtctcgcgg  9780
atgatgtcat acctatcctc cccccttcttt ttccacagct cgcggttgag gacgaactct  9840
tcgcggtctt tccagtactc ttggagggga aacccgtccg tgtccgaacg gtaagagcct  9900
agcatgtaga actggttgac ggcctggtag gggcagcagc ccttctccac gggcagcgcg  9960
taggcctgcg ccgccttgcg gagggaggtg tgggtgaggg cgaaagtgtc cctgaccatg  10020
actttgaggt attgatgtct gaagtctgtg tcatcgcagc cgccctgttc ccacagggtg  10080
tagtccgtgc gctttttgga gcgcgggttg ggcaggggaga aggtgaggtc attgaagagg  10140
atcttccccg ctcgaggcat gaagtttctg gtgatgcgaa agggccctgg gaccgaggag  10200
cggttgttga tgacctgggc ggccaggacg atctcgtcaa agccgtttat gttgtgtccc  10260
acgatgtaga gctccaggaa gcggggctgg cccttgatgg aggggagctt tttaagttcc  10320
tcgtaggtaa gctcctcggg cgattccagg ccgtgctcct ccagggccca gtcttgcaag  10380
tgagggttgg ccgccaggaa ggatcgccag aggtcgcggg ccatgagggt ctgcaggcgg  10440
tcgcggaagg ttctgaactg ccgccccacg gccatttttt cgggggtgat gcagtagaag  10500
gtgagggggt ctttctccca ggggtcccat ctgagctctc gggcgaggtc gcgcgcggca  10560
gcgaccagag cctcgtcgcc ccccagtttc atgaccagca tgaagggcac gagttgcttg  10620
ccaaaggctc ccatccaagt gtaggtttct acatcgtagg tgacaaagag gcgctccgtg  10680
cgaggatgag agccgattgg gaagaactgg atctcccgcc accagttgga ggattggctg  10740
ttgatgtggt gaaagtagaa gtcccgtctg cgggccgagc actcgtgctg gcttttgtaa  10800
aagcgaccgc agtactggca gcgctgcacg ggttgtatat cttgcacgag gtgaacctgg  10860
cgacctctga cgaggaagcg cagcgggaat ctaagtcccc cgcctggggt cccgtgtggc  10920
tggtggtctt ttactttggt tgtctggccg ccagcatctg tctcctggag ggcgatggtg  10980
gaacagacca ccacgccgcg agagccgcag gtccagatct cggcgctcgg cgggcggagt  11040
ttgatgacga catcgcgcac attggagctg tccatggtct ccagctcccg cggcggcagg  11100
tcagccggga gttccctgga ggttcacctc gcagagacgg gtcaaggcgc ggacagtgtt  11160
gagatggtat ctgatttcaa ggggcatgtt ggaggcggag tcgatggctt gcaggaggcc  11220
gcagccccgg ggggccacga tggttccccg cggggcgcga ggggaggcgg aagctggggg  11280
tgtgttcaga agcggtgacg cgggcgggcc cccggaggta ggggggggttc cggccccaca  11340
ggcatgggcg gcaggggcac gtcttcgccg cgcgcgggca ggggctggtg ctggctccga  11400
agagcgcttg cgtgcgcgac gacgcgacgg ttggtgttcc tgtatctggc gcctctgagt  11460
gaagaccacg ggtcccgtga ccttgaacct gaaagagagt tcgacagaat caatctcggc  11520
atcgttgaca gcggcctggc gcaggatctc ctgcacgtcg cccgagttgt cctggtaggc  11580
gatttctgcc atgaactgct cgatctcttc ctcctggaga tctcctcgtc cggcgcgctc  11640
cacggtggcc gccaggtcgt tggagatgcg acccatgagc tgcgagaagg cgttgagtcc  11700
gccctcgttc cagacccggc tgtagaccac gcccccctcg gcgtcgcggg cgcgcatgac  11760
cacctgggcc aggttgagct ccacgtgtcg cgtgaagacg gcgtagttgc gcaggcgctg  11820
gaaaaggtag ttcagggtgg tggcggtgtg ctcggcgacg aagaagtaca tgacccagcg  11880
ccgcaacgtg gattcattga tgtcccccaa ggcctccagg cgctccatgg cctcgtagaa  11940
gtccacggcg aagttgaaaa actgggagtt gcgagcggac acggtcaact cctcctccag  12000
aagaacggat gagctcggcg acagtgtcgc gcacctcgcg ctcgaaggcc acggggggcg  12060
cttcttcctc ttccacctct tcttccatga ttgcttcttc ttcttcctca gccgggacgg  12120
```

-continued

```
gagggggcgg cggcggggga ggggcgcggc ggcggcggcg gcgcaccggg aggcggtcga  12180
tgaagcgctc gatcatctcc ccccgcatgc ggcgcatggt ctcggtgacg gcgcggccgt  12240
tctcccgggg gcgcagctcg aagacgccgc ctctcatttc gccgcggggc gggcggccgt  12300
gaggtagcga gacggcgctg actatgcatc ttaacaattg ctgtgtaggt acgccgccaa  12360
gggacctgat tgagtccaga tccaccggat ccgaaaacct ttggaggaaa gcgtctatcc  12420
agtcgcagtc gcaaggtagg ctgagcaccg tggcgggcgg gggcgggtcg ggagagttcc  12480
tggcggagat gctgctgatg atgtaattaa agtaggcggt cttgagaagg cggatggtgg  12540
acaggagcac catgtctttg ggtccggcct gttggatgcg gaggcggtcg gccatgcccc  12600
aggcctcgtt ctgacaccgg cgcaggtctt tgtagtaatc ttgcatgagt ctttccaccg  12660
gcacttcttc tccttcctct tcttcatctc gccggtggtt tctcgcgccg cccatgcgcg  12720
tgaccccaaa gcccctgagc ggctgcagca gggccaggtc ggcgaccacg cgctcggcca  12780
agatggcctg ctgtacctga gtgagggtcc tctcgaagtc atccatgtcc acgaagcggt  12840
ggtaggcacc cgtgttgatg gtgtaggtgc agttggccat gacggaccag ttgacggtct  12900
ggtgtcccgg ctgcgagagc tccgtgtacc gcaggcgcga gaaggcgcgg gaatcgaaca  12960
cgtagtcgtt gcaagtccgc accagatact ggtagcccac caggaagtgc ggcggaggtt  13020
ggcgatagag gggccagcgc tgggtggcgg gggcgccggg cgccaggtct tccagcatga  13080
ggcggtggta tccgtagatg tacctggaca tccaggtgat gcctgcggcg gtggtggtgg  13140
cgcgcgcgta gtcgcggacc cggttccaga tgtttcgcag ggcgagaaag tgttccatgg  13200
tcggcacgct ctggccggtg aggcgcgcgc agtcgttgac gctctataca cacacaaaaa  13260
cgaaagcgtt tacagggctt tcgttctgta gcctggagga aagtaaatgg gttgggttgc  13320
ggtgtgcccc ggttcgagac caagctgagc tcagccggct gaagccgcag ctaacgtggt  13380
attggcagtc ccgtctcgac ccaggccctg tatcctccag gatacggtcg agagcccttt  13440
tgctttcttg gccaagcgcc cgtggcgcga tctgggatag atggtcgcga tgagaggaca  13500
aaagcggctc gcttccgtag tctggagaaa caatcgccag ggttgcgttg cggcgtaccc  13560
cggttcgagc ccctatggcg gcttggatcg gccggaaccg cggctaacgt gggctgtggc  13620
agccccgtcc tcaggacccc gccagccgac ttctccagtt acgggagcga gcccctttttg  13680
tttttttatt ttttagatgc atcccgtgct gcggcagatg cgccccctcgc cccggcccga  13740
tcagcagcag caacagcagg catgcagacc cccctctcct ctccccgccc cggtcaccac  13800
ggccgcggcg gccgtgtccg gtgcgggggg cgcgctggag tcagatgagc caccgcggcg  13860
gcgacctagg cagtatctgg acttggaaga gggcgaggga ctggcgcggc tgggggcgag  13920
ctctccagag cgccacccgc gggtgcagtt gaaaagggac gcgcgtgagg cgtacctgcc  13980
gcggcaaaac ctgtttcgcg accgcggggg cgaggagccc gaggagatgc gggactgcag  14040
gttccaagcg gggcgcgagc tgcgccgcgg cttggacaga cagcgcctgc tgcgcgagga  14100
ggactttgag cccgacacgc agacgggcat cagccccgcg cgcgcgcacg tggccgcggc  14160
cgacctggtg accgcctacg agcagacggt gaaccaggag cgcaacttcc aaaaaagctt  14220
caacaaccac gtgcgcacgc tggtggcgcg cgaggaggtg accctgggtc tcatgcatct  14280
gtgggacctg gtggaggcga tcgtgcagaa ccccagcagc aagcccctga ccgcgcagct  14340
gttcctggtg gtgcagcaca gcagggacaa cgaggccttc agggaggcgc tgctgaacat  14400
caccgagccg gaggggcgct ggctcctgga cctgataaac atcctgcaga gcatagtggt  14460
gcaggagcgc agcctgagcc tggccgagaa ggtggcggcc attaactatt ctatgctgag  14520
cctgggcaag ttctacgctc gcaagatcta caagaccccc tacgtgccca tagacaagga  14580
ggtgaagata gacagcttct acatgcgcat ggcgctgaag gtgctaaccc tgagcgacga  14640
cctgggagtg taccgcaacg agcgcatcca caaggccgtg agcgccagcc ggcggcgcga  14700
gctgagcgac cgcgaactga tgcacagtct gcagcgcgcg ctgaccggcg cgggcgaggg  14760
cgacagggag gtcgagtcct actttgacat gggggcgac ctgcactggc agccgagccg  14820
ccgcgccctg gaagcggcgg gggcgtacgg cggcccctg gcggccgatg acgaggaaga  14880
ggaggactat gagctagagg agggcgagta cctggaggac tgacctggct ggtggtgttt  14940
tggtatagat gcaagatccg aacgtggcgg acccggcggt ccgggcggcg ctgcagagcc  15000
agccgtccgg cattaactcc tctgacgact gggccgcggc catgggtcgc atcatggccc  15060
tgaccgcgcg caaccccgag gccttcaggc agcagcctca ggctaaccgg ctggcggcca  15120
tcttggaagc ggtagtgccc gcgcgctcca accccaccca cgagaaggtg ctggccatag  15180
tcaacgcgct ggcggagagc aggccatcc gggcagacga ggccggactg gtgtacgatg  15240
cgctgctgca gcgggtggcg cggtacaaca gcggcaacgt gcagaccaac ctggaccgcc  15300
tggtgacgga cgtgcgcgag gccgtggcgc agcgcgagcg cttgcatcag gacggcaacc  15360
tgggctcgct ggtggcgcta aacgccttcc ttagcaccca gccggccaac gtaccgcggg  15420
ggcaggagga ctacaccaac ttcttgagcg cgctgcggct gatggtgacc gaggtccctc  15480
agagcgaggt gtaccagtcg ggcccgact acttcttcca gaccagcaga cagggcttgc  15540
aaaccgtgaa cctgagccag gctttcaaga acctgcgggg gctgtgggga gtgaaggcgc  15600
ccaccggcga ccgggctacg gtgtccagcc tgctaacccc caactcgcgc ctgctgctgc  15660
tgctgatcgc gcccttcacg gacagcggga gcgtctcgcg ggagacctat ctgggccacc  15720
tgctgacgct gtaccgcgag gccatcgggc aggcgcaggt ggacgagcac accttccagg  15780
agatcaccag cgtgagccac gcgctggggc aggaggacac gggcagcctg caggcgaccc  15840
tgaactacct gctgaccaac aggcggcaga agattcccac gctgcacagc ctgacccagg  15900
aggaggagcg catcttgcgc tacgtgcagc agagcgtgag cctgaacctg atgcgcgacg  15960
gcgtgacgcc cagcgtggcg ctggacatga ccgcgcgcaa catggaaccg ggcatgtacg  16020
cttcccagcg gccgttcatc aaccgcctga tggactactt gcatcgggcg gcggccgtga  16080
accccgagta cttcaccaat gccattctga atccccactg gatgccccct ccgggtttct  16140
acaacgggga cttcgaggtg cctgaggtca acgatgggtt cctctgggat gacatggatg  16200
acagtgtgtt ctcccccaac ccgctgcgcg ccgcgtctct gcgattgaag gagggctctg  16260
acagggaagg accaaggagt ctggcctcct ccctggctct gggggcggtg ggcgccacgg  16320
gcgcggcggc gcggggcagc agccccttcc ccagcctggc ggactctctg aatagcgggc  16380
gggtgagcag gccccgcttg ctaggcgagg aggagtatct gaacaactcc ctgctgcagc  16440
ccgtgaggga caaaaacgct cagcggcagc agtttcccaa caatgggata gagagcctgg  16500
tggacaagat gtccagatgg aagacgtatg cgcaggagta caaggagtgg gaggaccgcc  16560
agccgcggcc cctgccgccc cctagacagc gctggcagcg gcgcgcgtcc aaccgccgct  16620
ggaggcaggg gcccgaggac gatgatgact ctgcagatga cagcagcgtg ttggacctgg  16680
gcgggagcgg gaacccccttt tcgcacctgc gcccacgcct gggcaagatg ttttaaaaga  16740
gaaaaataaa aactcaccaa ggccatggcg acgagcgttg gtttttttgtt cccttcctta  16800
gtatgcggcg cgcggcgatg ttcgaggagg ggcctccccc ctcttacgag agcgcgatgg  16860
```

-continued

```
gaatttctcc tgcggcgccc ctgcagcctc cctacgtgcc tcctcggtac ctgcaaccta  16920
caggggggag aaatagcatc tgttactctg agctgcagcc cctgtacgat accaccagac  16980
tgtacctggt ggacaacaag tccgcggacg tggcctccct gaactaccag aacgaccaca  17040
gcgatttttt gaccacggtg atccaaaaca acgacttcac cccaaccgag gccagtaccc  17100
agaccataaa cctggacaac aggtcgaact ggggcggcga cctgaagact atcctgcaca  17160
ccaatatgcc caacgtgaac gagttcatgt tcaccaactc ttttaaggcg cgggtgatgg  17220
tggcgcgcga gcagggggag gcgaagtacg agtgggtgga cttcacgctg cccgagggca  17280
actactcaga gaccatgact ctcgacctga tgaacaatgc gatcgtggaa cactatctga  17340
aagtgggcag gcagaacggg gtgaaggaga gcgatatcgg ggtcaagttt gacaccagaa  17400
acttccgtct gggctgggac cctgtgaccg ggctggtcat gccgggggtc tacaccaacg  17460
aggcctttca tcccgatata gtgctcctgc ccggctgtgg ggtggacttc acccagagcc  17520
ggctgagcaa cctgctgggc gttcgcaagc ggcaaccttt ccaggagggt ttcaagatca  17580
cctatgagga tctggagggg ggcaacattc ccgcgctcct tgatctggac gcctacgagg  17640
agagcttgaa acccgaggag agcgctggcg acagcggcga gagtggcgag gagcaagccg  17700
gcggcggcgg cagcgcgtcg gtagaaaacg aaagtactcc cgcagtggcg gcggacgctg  17760
cggaggtcga gccggaggcc atgcagcagg acgcagagga gggcgcgcag gaggacatga  17820
acaatgggga gatcagggggc gacactttcg ccacccgggg cgaagaaaaa gaggcagagg  17880
cggcggcggc gacggcggaa gccgaaaccg aggcagaggc agagcccgag accgaagtta  17940
tggaagacat gaatgatgga gaacgtaggg gtgacacgtt tgccacccgg ggcgaagaga  18000
aggcggcgga ggcagaagcc gcggctgagg aggcggctgc ggctgcggcc aaggctgagg  18060
ctgcggctga ggctaaggtc gaagccgatg ttgcggttga ggctcaggct gaggaggagg  18120
cggcggctga agcagttaag gaaaaggccc aggcagagca ggaagagaaa aaacctgtca  18180
ttcaacctct aaaagaagat agcaaaaagc gcagttacaa cgtcattgag ggcagcacct  18240
ttacccaata ccgcagctgg tacctggctt acaactacgg cgacccggtc aaggggggtgc  18300
gctcgtggac cctgctctgc acgccggacg tcacctgcgg ctccgagcag atgtactggt  18360
cgctgccaaa catgatgcaa gacccggtga ccttccgttc cacgcggcag gttagcaact  18420
ttccggtggt gggcgccgaa ctgctgccag tacactccaa gagtttttac aacgagcagg  18480
ccgtctactc ccagctgatc cgccaggcca cctctctgac ccacgtgttc aatcgctttc  18540
ccgagaacca gattttggcg cgcccgccgg cccccaccat caccaccgtc agtgaaaacg  18600
ttcctgccct cacagatcac gggacgctac cgctgcgcaa cagcatctca ggagtccagc  18660
gagtgaccat tactgacgcc agacgccgga cctgccccta cgtttacaag gccttgggca  18720
tagtctcgcc gcgcgtcctc tccagtcgca ctttttaaaa cacatccacc cacacgctcc  18780
aaaatcatgt ccgtactcat ctcgcccagc aacaacaccg gctgggggct gcgcgcaccc  18840
agcaagatgt ttggaggggc aaggaagcgc tccgaccagc accccgtgcg cgtgcgcggc  18900
cactaccgcg cgccctgggg tgcgcacaag cgcgggcgca cagggcgcac cactgtggat  18960
gatgtcattg actccgtagt ggagcaggcg cgccactaca cacccggcgc gccgaccgcc  19020
tccgccgtgt ccaccgtgga ccaggcgatc gaaagcgtgg tacagggggc gcggcactat  19080
gccaacctta aaagtcgccg ccgccgcgtg gcgcgccgcc atcgccggag accccgggct  19140
actgccgccg cgcgccttac caaggctctg ctcaagcgcg ccaggcgaac tggccaccgg  19200
gccgccatga gggccgcacg gcgggctgcc gctgccgcga gcgccgtggc cccgcgggca  19260
cgaaggcgcg cggccgctgc cgccgccgcc gccatttcca gcttggcctc gacgcggcgc  19320
ggtaacatat actgggtgcg cgactcggtg agcggcacac gtgtgcccgt gcgctttcgc  19380
cccccacgga attagcacaa gacaacatac acactgagtc tcctgctgtt gtgtatccca  19440
gcggcgaccg tcagcagcgg cgacatgtcc aagcgcaaaa ttaaagaaga gatgctccag  19500
gtcatcgcgc cggagatcta tgggccccccg aagaaggagg aggaggatta caagccccgc  19560
aagctaaagc gggtcaaaaa gaaaaagaaa gatgatgacg ttgacgaggc ggtggagttt  19620
gtccgccgca tggcgcccag gcgccctgtg cagtggaagg gtcggcgcgt gcagcgagtc  19680
ctgcgccccg gcaccgcggt ggtctttacg cccggcgagc gttccacgcg cactttcaag  19740
cgggtgtacg atgaggtgta cggcgacgag gatctgttgg agcaggccaa ccatcgattt  19800
ggggagtttg catatgggaa acggcctcgc gagagtctaa aagaggacct gctggcgcta  19860
ccgctggacg agggcaatcc caccccgagt ctgaagccgg tgaccctgca acaggtgctg  19920
cctttgagcg cgcccagcga gcagaagcga gggttaaagc gcgagggcgg ggacctggca  19980
cccaccgtgc agttgatggt gcccaagcgg cagaagctgg aggacgtgct ggagaaaatg  20040
aaagtagagc ccgggatcca gcccgagatc aaggtccgcc ctatcaagca ggtggcgccc  20100
ggcgtgggag tccagaccgt ggacgttagg attcccacgg aggagatgga aacccaaacc  20160
gccactccct cttcggcagc aagcgccacc accggcgccg cttcggtaga ggtgcagacg  20220
gacccctggc tacccgccgc cactatcgcc gtcgccgccg ccccccgttc gcgcggacgc  20280
aagagaaatt atccagcggc cagcgcgctt atgccccagt atgcgctgca tccatccatc  20340
gcgcccaccc ccggctaccg cgggtactcg taccgcccgc gcagatcagc cggcactcgc  20400
ggccgccgcc gccgtgcgac cacaaccagc cgccgccgtc gccgccgccg ccagccagtg  20460
ctgacccccg tgtctgtaag gaaggtggct cgctcgggga gcacgctggt ggtgcccaga  20520
gcgcgctacc accccagcat cgtttaaagc cggtctctgt atggttcttg cagatatggc  20580
cctcacttgt cgccttcgct tcccggtgcc gggataccga ggaagaactc accgccgcag  20640
gggcatggcg ggcagcggtc tccgcggcgg ccgtcgccat cgccggcgcg caaagagcag  20700
gcgcatgcgc ggcggtgtgt tgcccctgct ggtcccgcta ctcgccgcgg cgatcggcgc  20760
cgtgcccggg atcgcctccg tggccctgca ggcgtcccag aaacattgac tcttgcaacc  20820
ttgcaagctt gcatttttgg aggaaaaaat aaaaaagtct agactctcac gctcgcttgg  20880
tcctgtgact attttgtaga aaaaagatgg aagacatcaa ctttgcgtcg ctggccccgc  20940
gtcacggctc gcgcccgttc atgggagact ggacagatat cggcaccagc aatatgagcg  21000
gtggcgcctt cagctggggc agtctgtgga gcggccttaa aaattttggt tccaccatta  21060
agaactatgg caacaaagcg tggaacagca gcacgggtca gatgctgaga gacaagttga  21120
aagagcagaa cttccaggag aaggtggcgc agggcctggc ctctggcatc agcggggtgg  21180
tggacatagc taaccaggcc gtgcagaaaa agataaacag tcatctggac ccccgccctc  21240
aggtggagga aacgcctcca gccatggaga cggtgtctcc cgagggcaaa ggcgaaaagc  21300
gcccgcggcc cgacagggaa gagaccctgg tgtcacacac cgaggagccg ccctcttacg  21360
aggaggcagt caaggccggc ctgcccacca ctcgccccat agctcccatg gccaccggtg  21420
tggtgggtca caggcaacac acccccgcaa cactagatct gcccccgccg tccgagccga  21480
ctcgccagcc aaaggcggtg acggtgtccg ctccctccac ttccgccgcc aacagagtgc  21540
ctctgcgccg cgctgcgagc ggcccccggg cctcgcgagt cagcggcaac tggcagagca  21600
```

-continued

```
cactgaacag catcgtgggc ctgggagtga ggagtgtgaa gcgccgccgt tgctactgaa  21660
tgagcaagct agctaacgtg ttgtatgtgt gtatgcgtcc tatgtcgccg ccagaggagc  21720
tgttgagccg ccggcgccgt ctgcactcca gcgaatttca agatggcgac cccatcgatg  21780
atgcctcagt ggtcgtacat gcacatctcg ggccaggacg cttcggagta cctgagcccc  21840
gggctggtgc agttcgcccg cgccacagac acctacttca acatgagtaa caagttcagg  21900
aaccccactg tggcgcccac ccacgatgtg accacggacc ggtcgcagcg cctgacgctg  21960
cggttcatcc ccgtggatcg ggaggacacc gcttactctt acaaggcgcg gttcacgctg  22020
gccgtgggcg acaaccgcgt gctggacatg gcctccactt actttgacat ccggggggtg  22080
ctggacaggg gccccacttt taagccctac tcgggcactg cctacaaccc cctggccccc  22140
aagggcgccc ccaattcttg tgagtgggaa caagaggaaa atcaggtggt cgctgcagat  22200
gatgaacttg aagatgaaga agcgcaagca caagaggaag cccctgtgaa aaaaattcat  22260
gtatatgctc aggcgcctct ttctggcgaa aagatttcca aggatggtat ccaaataggt  22320
actgaagtcg taggagatac atctaaggac acttttgcag ataaaacatt ccaacccgaa  22380
cctcagatag gcgagtctca gtggaacgag gctgatgcca cagcagcagg aggtagagtt  22440
ttgaaaaaga ctacccctat gagaccttgc tatggatcct atgccaggcc taccaatgcc  22500
aacgggggtc aaggaattat ggttgccaat gaacaaggag tgttggagtc taaagtagaa  22560
atgcaatttt tctctaacac cacaaccctt aatgcgcggg atggaaccgg caatcccgaa  22620
ccaaaggtgg tgttgtacag cgaagatgtc cacttggaat ctcccgatac tcatctgtct  22680
tacaagccca aaaaggatga tgttaatgcc aaaatcatgt tgggtcagca agccatgccc  22740
aacagaccca acctcattgg atttagagat aatttcattg ggcttatgtt ttacaacagc  22800
accggtaaca tgggagtgct ggcgggtcag gcctctcagt tgaatgctgt ggtggacttg  22860
caggatagaa acacagaact gtcatatcag cttctgcttg attcaattgg ggatagaacc  22920
agatacttct ccatgtggaa ccaggcagtg gatagctatg atccagatgt cagaattatt  22980
gaaaaccatg ggactgagga tgaactgccc aactactgct tcccctttgg cggcatagga  23040
gttactgata cttatcaagg gataaaaaat accaatggca atggtcagtg gaccaaagat  23100
gatcagttcg cggaccgcaa cgaaataggg gtgggaaaca acttcgccat ggagatcaac  23160
atccaggcca acctttggag aaacttcctc tatgcaaacg tggggctcta cctgccagac  23220
aagctcaagt acaaccccac caacgtggac atctctgaca accccaacac ctatgactac  23280
atgaacaagc gggtggtggc ccctggcctg gtggactgct ttgtcaatgt gggagccagg  23340
tggtccctgg actacatgga caacgtcaac cccttcaacc accaccgcaa tgcgggtctg  23400
cgctaccgct ccatgatcct gggcaacggg cgctatgtgc cctttcacat ccaggtaccc  23460
cagaagttct ttgccatcaa gaacctcctg ctcctgcccg gctcctacac ctacgagtgg  23520
aacttcagga aggatgtgaa catggtccta cagagctctc tgggcaatga ccttagggtg  23580
gatggggcca gcatcaagtt tgacagcatc accctctatg ctacattttt ccccatggcc  23640
cacaacaccg cctccacgct tgaggccatg ctgagaaacg acaccaacga ccagtccttt  23700
aatgactacc tctctggggc caacatgctc tacccaatcc cagccaaggc caccaacgtg  23760
cccatctcca tcccctctcg caactgggcc gcctttagag gctgggcctt tacccgcctt  23820
aagaccaagg agacccccto cctgggctcg ggttttgatc cctactttgt ttactcggga  23880
tccatcccct acctggatgg caccttctac ctcaaccaca ctttcaagaa gatatccatc  23940
atgtatgact cctccgtcag ctggccggac aacgaccgct tgctcacccc caatgagttc  24000
gaggtcaagc gcgccgtgga cggcgagggc tacaacgtgg cccagtgcaa catgaccaag  24060
gactggttcc tggtgcagat gctggccaac tacaacatag gctaccaggg cttttacatc  24120
ccagagagct acaaggacag gatgtactcc ttcttcagaa atttccaacc catgagccga  24180
caggtggtgg acgagaccaa ttacaaggac tatcaagcca ttggcatcac ccaccagcac  24240
aacaactcgg gtttcgtggg ctacctggcg cccaccatgc gcgagggtca ggcctacccc  24300
gccaacttcc cctacccctt gataggcaag accgcggtcg acagcgtcac ccagaaaaag  24360
ttcctctgcg accgcaccct ctggcgcatc cccttctcta gcaacttcat gtccatgggt  24420
gcgctcacgg acctgggcca aaacctgctt tatgccaact ctgcccatgc gctggacatg  24480
acttttgagg tggaccccat ggacgagccc acccttctct atattgtgtt tgaagtgttc  24540
gacgtggtca gagtgcacca gccgcaccgc ggtgtcatcg agaccgtgta cctgcgtacg  24600
cccttctcag ccggcaacgc caccacctaa ggagacagcg ccgccgccgc ctgcatgacg  24660
ggttccaccg agcaagagct cagggccatt gccagagacc tgggatgcgg accctatttt  24720
ttgggcacct atgacaaacg cttcccgggc tttatctccc gagacaagct cgcctgcgcc  24780
attgtcaaca cggccgcgcg cgagaccggg ggcgtgcact ggctggcctt tggctgggac  24840
ccgcgctcca aaacttgcta cctctttgac ccctttggct tctccgatca gcgcctcagg  24900
cagatttatg agtttgagta cgaggggctg ctgcgccgca gcgcgctcgc ctcctcgccc  24960
gaccgctgca tcacccttga gaagtccacc gaaaccgtgc agggggccca ctcggccgcc  25020
tgcggtctct tctgttgcat gtttttgcac gcctttgtgc actggcctca gagtcccatg  25080
gattgcaacc ccaccatgaa cttgctaaag ggagtgccca acgccatgct ccagagcccc  25140
caggtccagc ccaccctgcg ccgcaaccag gaacagcttt accgcttcct ggagcgccac  25200
tccccctact tccgcagcca cagcgcgcgc atccgggggg ccacctcttt ttgccacttg  25260
caagaaaaca tgcaagacgg aaaatgatgt acagcatgct tttaataaat gtaaagactg  25320
tgcactttaa ttatacacgg gctctttctg gttatttatt caacaccgcc gtcgccattt  25380
agaaatcgaa agggttctgc cgtgcgtcgc cgtgcgccac gggcagagac acgttgcgat  25440
actggaagcg gctcgcccac ttgaactcgg gcaccaccat gcggggcagt ggttcctcgg  25500
ggaagttctc gctccacagg gtgcgggtca gctgcagcgc gctcaggagg tcgggagccg  25560
agatcttgaa gtcgcagttg gggccggaac cctgcgcgcg cgagttgcgg tacacggggt  25620
tgcagcactg gaacaccagc agggccggat tattcacgct ggccagcagg ctctcgtcgc  25680
tgatcatgtc gctgtccaga tcctccgcgt tgctcagggc gaatggggtc atcttgcaga  25740
cctgcctgcc caggaaaggc gggagcccag gcttgccgtt gcagtcgcag cgcaggggca  25800
ttagcaggtg cccacggccc gactgcgcct gcgggtacaa cgcgcgcatg aaggcttcga  25860
tctgcctaaa agccacctgg gtcttggctc cctccgaaaa gaacatccca caggacttgc  25920
tggagaactg gttcgcggga cagctggcat cgtgcaggca gcagcgcgcg tcagtgttgg  25980
caatctgcac cacgttgcga ccccaccggt ttttcactat cttggccttg gaagcctgct  26040
cctttagcgc gcgctggccg ttctcgctgg tcacatccat ctctatcacc tgttccttgt  26100
tgatcatgtt tgtcccgtgc agacacttta ggtcgccctc cgtctgggtg cagcggtgct  26160
cccacagcgc gcaaccggtg ggctcccaat tcttgtgggt cacccccgcg taggcctgca  26220
ggtaggcctg caggaagcgc cccatcatgg tcataaaggt cttctggctc gtaaaggtca  26280
gctgcaggcc gcgatgctct tcgttcagcc aggtcttgca gatggcggcc agcgcctcgg  26340
```

-continued

```
tctgctcggg cagcatctta aaatttgtct tcaggtcgtt atccacgtgg tacttgtcca  26400
tcatggcacg cgccgcctcc atgcccttct cccaggcgga caccatgggc aggcttaggg  26460
ggtttatcac ttccagcggc gaggacaccg tactttcgat ttcttcttcc tccccctctt  26520
cccggcgcgc gcccccgctg ttgcgcgctc ttaccgcctg caccaagggg tcgtcttcag  26580
gcaagcgccg caccgagcgc ttgccgccct tgacctgctt gatcagtacc ggcgggttgc  26640
tgaagcccac catggtcagc gccgcctgct cttcttcgtc ttcgctgtct accactattt  26700
ctggggaggg gcttctccgc tctgcggcaa aggcggcgga tcgcttcttt tttttcttgg  26760
gagccgccgc gatggagtcc gccacggcga ccgaggtcga gggcgtgggg ctgggggtgc  26820
gcggtaccag ggcctcgtcg ccctcggact cttcctctga ctccaggcgg cggcggagtc  26880
gcttctttgg gggcgcgcgc gtcagcggcg gcggagacgg ggacggggac ggggacggga  26940
cgccctccac agggggtggt cttcgcgcag acccgcggcc gcgctcgggg gtcttctcgc  27000
gctggtcttg gtcccgactg gccattgtat cctcctcctc ctaggcagag agacataagg  27060
agtctatcat gcaagtcgag aaggaggaga gcttaaccac cccctcagag accgccgatg  27120
cgcccgccgt cgccgtcgcc cccgctaccg ccgacgcgcc cgccacaccg agcgacaccc  27180
ccacggaccc ccccgccgac gcacccctgt tcgaggaagc ggccgtggag caggacccgg  27240
gctttgtctc ggcagaggag gatttgcaag aggaggagaa taaggaggag aagccctcag  27300
tgccaaaaga tcataaagag caagacgagc acgacgcaga cgcacaccag ggtgaagtcg  27360
ggcgggggga cggagggcat ggcggcgccg actacctaga cgaaggaaac gacgtgctct  27420
tgaagcacct gcatcgtcag tgcgccatcg tctgcgacgc tctgcaggag cgcagcgagg  27480
tgcccctcag cgtggcggag gtcagccgcg cctacgagct cagcctcttt tccccccggg  27540
tgcccccccg ccgccgcgaa aacggcacat gcgagcccaa cccgcgcctc aacttctacc  27600
ccgcctttgt ggtgcccgag gtcctggcca cctatcacat cttctttcaa aattgcaaga  27660
tccccatctc gtgccgcgcc aaccgtagcc gcgccgataa gatgctggcc ctgcgccagg  27720
gcgaccacat acctgatatc gccgctttgg aagatgtgcc aaagatcttc gagggtctgg  27780
ggcgcaacga gaagcgggca gcaaactctc tgcaacagga aaacagcgaa aatgagagtc  27840
acactggagc gctggtggag ctggagggcg acaacgcccg cctggcggtg ctcaagcgca  27900
gcatcgaggt cacccacttt gcctaccccg cgctcaacct gccccccaaa gtcatgaacg  27960
cggtcatgga cgggctgatc atgcgccgcg gccggcccct cgctccagat gcaaacttgc  28020
atgaggagac cgaggacggt cagcccgtgg tcagcgacga gcagctgacg cgctggctgg  28080
agagcgcgga ccccgccgaa ctggaggagc ggcgcaagat gatgatggcc gcggtgctgg  28140
tcaccgtaga gctggagtgt ctgcagcgct tcttcggtga ccccgagatg cagagaaagg  28200
tcgaggagac cctacactac accttccgcc agggctacgt gcgccaggct tgcaagatct  28260
ccaacgtgga gctcagcaac ctggtgtcct acctgggcat cttgcatgaa aaccgccttg  28320
ggcagagcgt gctacactcc accctgcgcg gggaggcgcg ccgcgactac gtgcgcgact  28380
gcgtttacct cttcctctgc tacacctggc agacggccat gggggtctgg cagcagtgcc  28440
tggaggagcg caacctcaag gagctggaga agcttctgca gcgcgcgctc aaagacctct  28500
ggacgggctt caacgagcgc tcggtggccg ccgcgctagc cgacctcatc ttccccgagc  28560
gcctgctcaa aaccctccag caggggctgc ccgacttcac cagccaaagc atgttgcaaa  28620
attttaggaa ctttatcctg gagcgttctg gcatcctacc cgccacctgc tgcgccctgc  28680
ccagcgactt tgtccccctc gtgtaccgcg agtgcccccc gccgctgtgg ggccactgct  28740
acctgttcca actggccaac tacctgtcct accacgcgga cctcatggag gactccagcg  28800
gcgaggggct catggagtgc cactgccgct gcaacctctg cacgccccac cgctccctgg  28860
tctgcaacac ccaactgctc agcgagagtc agattatcgg taccttcgag ctacagggtc  28920
cgtcctcctc agacgagaag tccgcggctc cggggctaaa actcactccg gggctgtgga  28980
cttccgccta cctgcgcaaa tttgtacctg aagactacca cgcccacgaa atcaggtttt  29040
acgaggacca atcccgcccg cccaaggcgg agctgaccgc ctgcgtcatc acccagggcg  29100
agatcctagg ccaattgcaa gccatccaaa aagcccgcca agagtttttg ctgaagaggg  29160
gtcggggggt gtatctggac ccccagtcgg gtgaggagct caacccggtt cccccgctgc  29220
caccgccgcg ggaccttgct tcccaggata agcatcgcca tggctcccag aaagaagcag  29280
cagcggccgc cgctgccgcc gccccacatg ctggaggaag aggaggaata ctgggacagt  29340
caggcagagg aggtttcgga cgaggaggag ccggagacgg agatggaaga gtgggaggag  29400
gacagcttag acgaggaggc ttccgaagcc gaagaggcag gcgcaacacc gtcaccctcg  29460
gccgcagccc cctcgcaggc gcccccgaag tccgctccca gcatcagcag caacagcagc  29520
gctataacct ccgctcctcc accgccgcga cccacggccg accgcagacc caaccgtaga  29580
tgggacacca ccggaaccgg ggccggtaag tcctccggga gaggcaagca agcgcagcgc  29640
caaggctacc gctcgtggcg cgctcacaag aacgccatag tcgcttgctt gcaagactgc  29700
ggggggaaca tctccttcgc ccgccgcttc ctgctcttcc accacggtgt ggccttcccc  29760
cgtaacgtcc tgcattacta ccgtcatctc tacagcccct actgcggcgg cagtgagcca  29820
gaggcggcca gcggcggcgg cgcccgtttc ggtgcctagg aagacccagg gcaagacttc  29880
agccaagaaa ctcgcggcga ccgcggcgaa cgcggtcgcg ggggccctgc gcctgacggt  29940
gaacgaaccc ctgtcgaccc gcgaactgag gaaccgaatc ttccccactc tctatgccat  30000
cttccagcag agcagagggc aggatcagga actgaaagta aaaaacaggt ctctgcgctc  30060
cctcacccgc agctgtctgt atcacaagag cgaagaccag cttcggcgca cgctggagga  30120
cgctgaggca ctcttcagca aatactgcgc gctcactctt aaggactagc tccgcgccct  30180
tctcgaattt aggcgggaac gcctacgtca tcgcagcgcc gccgtcatga gcaaggacat  30240
tcccacgcca tacatgtgga gctatcagcc gcagatggga ctcgcggcgg gcgcctccca  30300
agactactcc acccgcatga actggctcag tgccggccca cacatgatct cacaggttaa  30360
tgacatccgc acccatcgaa accaaatatt ggtgaagcag gcggcaatta ccaccacgcc  30420
ccgcaataat cccaacccca gggagtggcc cgcgtccctg gtgtatcagg aaattcccgg  30480
ccccaccacc gtactacttc cgcgtgattc ccaggccgaa gtccaaatga ctaactcagg  30540
ggcacagctc gcgggcggct gtcgtcacag ggtgcggcct cctcgccagg gtataactca  30600
cctggagatc cgaggcagag gtattcagct caacgacgag tcggtgagct cctcgctcgg  30660
tctcagacct gacgggacct tccagatagc cggagccggc cgatcttcct tcacgccccg  30720
ccaggcgtac ctgactctgc agagctcgtc ctcggcgccg cgctcgggcg gcatcgggac  30780
tctccagttc gtgcaggagt ttgtgccctc ggtctacttc aaccccttct cgggctctcc  30840
cggtcgctac ccggaccagt ttatcccgaa ctttgacgcc gcgagggact cggtggacgg  30900
ctacgactga atgtcgggtg gacccggtgc agagcaactt cgcctgaagc accttgacca  30960
ctgccgccgc cctcagtgct ttgcccgctg tcagaccggt gagttccagt acttttccct  31020
gcccgactcg cacccggacg gcccggcgca cggggtgcgc tttttcatcc cgagtcaggt  31080
```

```
ccgctctacc ctaatcaggg agttcaccgc ccgtccccta ctggcggagt tggaaaaggg  31140
gccttctatc ctaaccattg cctgcatttg ctctaaccct ggattacacc aagatctttg  31200
ctgtcatttg tgtgctgagt ataataaagg ctgagatcag aatctactcg gaccttatcc  31260
ctttcaattg atcataactg taatcaataa aaaatcactt acttgaaatc tgatagcaag  31320
actctgtcca attttttcag caacacttcc ttcccctcct cccaactctg gtactctagg  31380
cgcctcctag ctgcaaactt cctccacagt ctgaagggaa tgtcagattc ctcctcctgt  31440
ccctccgcac ccacgatctt catgttgtta cagatgaaac gcgcgagatc gtctgacgag  31500
accttcaacc ccgtgtaccc ctacgatacc gagatcgctc cgacttctgt ccctttcctt  31560
acccctccct ttgtatcatc cgcaggaatg caagaaaatc cagctggggt gctgtccctg  31620
cacctgtcag agccccttac cacccacaat ggggccctga ctctaaaaat ggggggcggc  31680
ctgaccctgg acaaggaagg gaatctcact tcccaaaaca tcaccagtgt cgatcccccct  31740
ctcaaaaaaa gcaagaacaa catcagcctt cagaccgccg cacccctcgc cgtcagctcc  31800
ggggccctaa cccttttgc cactcccccc ctagcggtca gtggcgacaa ccttactgtg  31860
cagtctcagg cccctcttac tttggaagac tcaaaactaa ctctggccac caaaggaccc  31920
ctaactgtgt ccgaaggcaa acttgtccta gaaacagagc ctcccctgca tgcaagtgac  31980
agcagtagcc tgggccttag cgtcacggcc ccacttagca ttaacaatga cagcctagga  32040
ctagacatgc aagcgcccat cagctctcga gatggaaaac tggctctaac agtggcggcc  32100
cccctaactg tggccgaggg tatcaatgct ttggcagtag ccacaggtaa tggtattgga  32160
ctaaatgaaa ccaacacaca cctgcaggca aaactggtcg cgcccctagg ctttgatacc  32220
aacggcaaca ttaagctaag cgtcgcagga ggcatgaggc taaacaataa cacactgata  32280
ctagatgtaa actacccatt tgaggctcaa ggccaactga gcctaagagt gggctcgggc  32340
ccactatatg tagattctag tagtcataac ctaaccatta gatgccttag gggattgtat  32400
gtaacatctt ctaacaacca aaacggtcta gaggccaaca ttaaactaac aaaaggcctt  32460
gtgtatgacg gaaatgccat agcagttaat gttggcaaag ggctggaata cagccctact  32520
ggcacaacag aaaaacctat acagactaaa ataggtctag gcatggagta tgacactgag  32580
ggagccatga tgacaaaact aggctctgga ctaagctttg acaattcagg agccattgtg  32640
gtgggaaaca aaaatgatga caggcttact ttgtggacca caccggaccc atcgcccaac  32700
tgtcagattt actctgaaaa agatgctaaa ctaaccttgg tactgactaa atgtggcagt  32760
caggttg                                                            32767
```

```
SEQ ID NO: 714          moltype = AA  length = 16
FEATURE                 Location/Qualifiers
source                  1..16
                        mol_type = protein
                        organism = Homo sapiens
SEQUENCE: 714
GSTGCLTCRH HQTSHE                                                  16

SEQ ID NO: 715          moltype = AA  length = 15
FEATURE                 Location/Qualifiers
source                  1..15
                        mol_type = protein
                        organism = Homo sapiens
SEQUENCE: 715
VVGRRHETAP QPLLV                                                   15

SEQ ID NO: 716          moltype = AA  length = 15
FEATURE                 Location/Qualifiers
source                  1..15
                        mol_type = protein
                        organism = Homo sapiens
SEQUENCE: 716
APQPLLVPDR AGGEG                                                   15

SEQ ID NO: 717          moltype = AA  length = 9
FEATURE                 Location/Qualifiers
source                  1..9
                        mol_type = protein
                        organism = Homo sapiens
SEQUENCE: 717
DRAGGEGGA                                                          9

SEQ ID NO: 718          moltype = AA  length = 15
FEATURE                 Location/Qualifiers
source                  1..15
                        mol_type = protein
                        organism = Homo sapiens
SEQUENCE: 718
PVPTATPGVR SVTSP                                                   15

SEQ ID NO: 719          moltype = AA  length = 15
FEATURE                 Location/Qualifiers
source                  1..15
                        mol_type = protein
                        organism = Homo sapiens
SEQUENCE: 719
VRSVTSPQGL GLFLK                                                   15

SEQ ID NO: 720          moltype = AA  length = 9
```

```
FEATURE                Location/Qualifiers
source                 1..9
                       mol_type = protein
                       organism = Homo sapiens
SEQUENCE: 720
GLGLFLKFI                                                  9

SEQ ID NO: 721         moltype = AA  length = 15
FEATURE                Location/Qualifiers
source                 1..15
                       mol_type = protein
                       organism = Homo sapiens
SEQUENCE: 721
KENDVREVCD VYLQM                                           15

SEQ ID NO: 722         moltype = AA  length = 15
FEATURE                Location/Qualifiers
source                 1..15
                       mol_type = protein
                       organism = Homo sapiens
SEQUENCE: 722
CDVYLQMQIF FHFKF                                           15

SEQ ID NO: 723         moltype = AA  length = 12
FEATURE                Location/Qualifiers
source                 1..12
                       mol_type = protein
                       organism = Homo sapiens
SEQUENCE: 723
IFFHFKFRSY FH                                              12

SEQ ID NO: 724         moltype = AA  length = 15
FEATURE                Location/Qualifiers
source                 1..15
                       mol_type = protein
                       organism = Homo sapiens
SEQUENCE: 724
FARKMLEKVH RQHLQ                                           15

SEQ ID NO: 725         moltype = AA  length = 14
FEATURE                Location/Qualifiers
source                 1..14
                       mol_type = protein
                       organism = Homo sapiens
SEQUENCE: 725
VHRQHLQLSH NSQE                                            14

SEQ ID NO: 726         moltype = AA  length = 15
FEATURE                Location/Qualifiers
source                 1..15
                       mol_type = protein
                       organism = Homo sapiens
SEQUENCE: 726
MFLRKEQQVG PHSFS                                           15

SEQ ID NO: 727         moltype = AA  length = 9
FEATURE                Location/Qualifiers
source                 1..9
                       mol_type = protein
                       organism = Homo sapiens
SEQUENCE: 727
VGPHSFSML                                                  9

SEQ ID NO: 728         moltype = AA  length = 15
FEATURE                Location/Qualifiers
source                 1..15
                       mol_type = protein
                       organism = Homo sapiens
SEQUENCE: 728
GLNLNTDRPG GYSYS                                           15

SEQ ID NO: 729         moltype = AA  length = 15
FEATURE                Location/Qualifiers
source                 1..15
                       mol_type = protein
                       organism = Homo sapiens
SEQUENCE: 729
PGGYSYSIWW KNNAK                                           15
```

SEQ ID NO: 730 moltype = AA length = 9
FEATURE Location/Qualifiers
source 1..9
mol_type = protein
organism = Homo sapiens
SEQUENCE: 730
WWKNNAKNR 9

SEQ ID NO: 731 moltype = AA length = 15
FEATURE Location/Qualifiers
source 1..15
mol_type = protein
organism = Homo sapiens
SEQUENCE: 731
KVLNEIDAVV TVPPS 15

SEQ ID NO: 732 moltype = AA length = 15
FEATURE Location/Qualifiers
source 1..15
mol_type = protein
organism = Homo sapiens
SEQUENCE: 732
VVTVPPSLST SQIPQ 15

SEQ ID NO: 733 moltype = AA length = 13
FEATURE Location/Qualifiers
source 1..13
mol_type = protein
organism = Homo sapiens
SEQUENCE: 733
STSQIPQGCC IIL 13

SEQ ID NO: 734 moltype = AA length = 15
FEATURE Location/Qualifiers
source 1..15
mol_type = protein
organism = Homo sapiens
SEQUENCE: 734
ANLKGTLQVR SGQAV 15

SEQ ID NO: 735 moltype = AA length = 10
FEATURE Location/Qualifiers
source 1..10
mol_type = protein
organism = Homo sapiens
SEQUENCE: 735
VRSGQAVSPR 10

SEQ ID NO: 736 moltype = AA length = 15
FEATURE Location/Qualifiers
source 1..15
mol_type = protein
organism = Homo sapiens
SEQUENCE: 736
LQAAASGQGK QGVPC 15

SEQ ID NO: 737 moltype = AA length = 15
FEATURE Location/Qualifiers
source 1..15
mol_type = protein
organism = Homo sapiens
SEQUENCE: 737
GKQGVPCPWG CCAYA 15

SEQ ID NO: 738 moltype = AA length = 15
FEATURE Location/Qualifiers
source 1..15
mol_type = protein
organism = Homo sapiens
SEQUENCE: 738
WGCCAYAESP RALIS 15

SEQ ID NO: 739 moltype = AA length = 15
FEATURE Location/Qualifiers
source 1..15
mol_type = protein
organism = Homo sapiens
SEQUENCE: 739
SPRALISGDA PSQVE 15

```
SEQ ID NO: 740          moltype = AA  length = 15
FEATURE                 Location/Qualifiers
source                  1..15
                        mol_type = protein
                        organism = Homo sapiens
SEQUENCE: 740
DAPSQVEREV PGPCL                                                             15

SEQ ID NO: 741          moltype = AA  length = 15
FEATURE                 Location/Qualifiers
source                  1..15
                        mol_type = protein
                        organism = Homo sapiens
SEQUENCE: 741
EVPGPCLNTH SLSHR                                                             15

SEQ ID NO: 742          moltype = AA  length = 15
FEATURE                 Location/Qualifiers
source                  1..15
                        mol_type = protein
                        organism = Homo sapiens
SEQUENCE: 742
THSLSHRSPQ LPGLP                                                             15

SEQ ID NO: 743          moltype = AA  length = 14
FEATURE                 Location/Qualifiers
source                  1..14
                        mol_type = protein
                        organism = Homo sapiens
SEQUENCE: 743
PQLPGLPHPK QPSV                                                              14

SEQ ID NO: 744          moltype = AA  length = 15
FEATURE                 Location/Qualifiers
source                  1..15
                        mol_type = protein
                        organism = Homo sapiens
SEQUENCE: 744
GEVELSEGGE GQRHL                                                             15

SEQ ID NO: 745          moltype = AA  length = 15
FEATURE                 Location/Qualifiers
source                  1..15
                        mol_type = protein
                        organism = Homo sapiens
SEQUENCE: 745
GEGQRHLAFP WACSG                                                             15

SEQ ID NO: 746          moltype = AA  length = 15
FEATURE                 Location/Qualifiers
source                  1..15
                        mol_type = protein
                        organism = Homo sapiens
SEQUENCE: 746
FPWACSGPGW RGVCC                                                             15

SEQ ID NO: 747          moltype = AA  length = 15
FEATURE                 Location/Qualifiers
source                  1..15
                        mol_type = protein
                        organism = Homo sapiens
SEQUENCE: 747
KMRAIQAEGG HGQAC                                                             15

SEQ ID NO: 748          moltype = AA  length = 15
FEATURE                 Location/Qualifiers
source                  1..15
                        mol_type = protein
                        organism = Homo sapiens
SEQUENCE: 748
GGHGQACCGG AWGWA                                                             15

SEQ ID NO: 749          moltype = AA  length = 15
FEATURE                 Location/Qualifiers
source                  1..15
                        mol_type = protein
                        organism = Homo sapiens
SEQUENCE: 749
```

-continued

```
GGAWGWAPGD GGPQG                                                  15

SEQ ID NO: 750          moltype = AA  length = 15
FEATURE                 Location/Qualifiers
source                  1..15
                        mol_type = protein
                        organism = Homo sapiens
SEQUENCE: 750
GDGGPQGMLT HTLPT                                                  15

SEQ ID NO: 751          moltype = AA  length = 15
FEATURE                 Location/Qualifiers
source                  1..15
                        mol_type = protein
                        organism = Homo sapiens
SEQUENCE: 751
LTHTLPTLGF QSAWT                                                  15

SEQ ID NO: 752          moltype = AA  length = 15
FEATURE                 Location/Qualifiers
source                  1..15
                        mol_type = protein
                        organism = Homo sapiens
SEQUENCE: 752
GFQSAWTWRR EDADR                                                  15

SEQ ID NO: 753          moltype = AA  length = 15
FEATURE                 Location/Qualifiers
source                  1..15
                        mol_type = protein
                        organism = Homo sapiens
SEQUENCE: 753
RREDADRAWR TPKAC                                                  15

SEQ ID NO: 754          moltype = AA  length = 14
FEATURE                 Location/Qualifiers
source                  1..14
                        mol_type = protein
                        organism = Homo sapiens
SEQUENCE: 754
WRTPKACASR RWSI                                                   14

SEQ ID NO: 755          moltype = AA  length = 15
FEATURE                 Location/Qualifiers
source                  1..15
                        mol_type = protein
                        organism = Homo sapiens
SEQUENCE: 755
LLEPFRRGEP GPRGL                                                  15

SEQ ID NO: 756          moltype = AA  length = 15
FEATURE                 Location/Qualifiers
source                  1..15
                        mol_type = protein
                        organism = Homo sapiens
SEQUENCE: 756
EPGPRGLLSG SSRGG                                                  15

SEQ ID NO: 757          moltype = AA  length = 15
FEATURE                 Location/Qualifiers
source                  1..15
                        mol_type = protein
                        organism = Homo sapiens
SEQUENCE: 757
SGSSRGGEGP GRSIE                                                  15

SEQ ID NO: 758          moltype = AA  length = 15
FEATURE                 Location/Qualifiers
source                  1..15
                        mol_type = protein
                        organism = Homo sapiens
SEQUENCE: 758
GPGRSIEAAP ATPLP                                                  15

SEQ ID NO: 759          moltype = AA  length = 15
FEATURE                 Location/Qualifiers
source                  1..15
                        mol_type = protein
                        organism = Homo sapiens
```

```
SEQUENCE: 759
APATPLPCCR KNPCR                                                     15

SEQ ID NO: 760         moltype = AA  length = 15
FEATURE                Location/Qualifiers
source                 1..15
                       mol_type = protein
                       organism = Homo sapiens
SEQUENCE: 760
CRKNPCRPQP SRFLP                                                     15

SEQ ID NO: 761         moltype = AA  length = 15
FEATURE                Location/Qualifiers
source                 1..15
                       mol_type = protein
                       organism = Homo sapiens
SEQUENCE: 761
QPSRFLPPRV LLVII                                                     15

SEQ ID NO: 762         moltype = AA  length = 15
FEATURE                Location/Qualifiers
source                 1..15
                       mol_type = protein
                       organism = Homo sapiens
SEQUENCE: 762
RVLLVIILPK LDCPK                                                     15

SEQ ID NO: 763         moltype = AA  length = 10
FEATURE                Location/Qualifiers
source                 1..10
                       mol_type = protein
                       organism = Homo sapiens
SEQUENCE: 763
PKLDCPKLGF                                                           10

SEQ ID NO: 764         moltype = AA  length = 15
FEATURE                Location/Qualifiers
source                 1..15
                       mol_type = protein
                       organism = Homo sapiens
SEQUENCE: 764
PSGRRTKRLV TLRSG                                                     15

SEQ ID NO: 765         moltype = AA  length = 15
FEATURE                Location/Qualifiers
source                 1..15
                       mol_type = protein
                       organism = Homo sapiens
SEQUENCE: 765
LVTLRSGCAI QCWHP                                                     15

SEQ ID NO: 766         moltype = AA  length = 15
FEATURE                Location/Qualifiers
source                 1..15
                       mol_type = protein
                       organism = Homo sapiens
SEQUENCE: 766
AIQCWHPRAG PVPSA                                                     15

SEQ ID NO: 767         moltype = AA  length = 15
FEATURE                Location/Qualifiers
source                 1..15
                       mol_type = protein
                       organism = Homo sapiens
SEQUENCE: 767
AGPVPSALPH TERPP                                                     15

SEQ ID NO: 768         moltype = AA  length = 15
FEATURE                Location/Qualifiers
source                 1..15
                       mol_type = protein
                       organism = Homo sapiens
SEQUENCE: 768
PHTERPPRLV RGAAD                                                     15

SEQ ID NO: 769         moltype = AA  length = 15
FEATURE                Location/Qualifiers
source                 1..15
                       mol_type = protein
```

```
                        organism = Homo sapiens
SEQUENCE: 769
LVRGAADPRT VTLGR                                                  15

SEQ ID NO: 770          moltype = AA  length = 15
FEATURE                 Location/Qualifiers
source                  1..15
                        mol_type = protein
                        organism = Homo sapiens
SEQUENCE: 770
RTVTLGRSPA VMPRA                                                  15

SEQ ID NO: 771          moltype = AA  length = 9
FEATURE                 Location/Qualifiers
source                  1..9
                        mol_type = protein
                        organism = Homo sapiens
SEQUENCE: 771
PAVMPRAPA                                                         9

SEQ ID NO: 772          moltype = AA  length = 15
FEATURE                 Location/Qualifiers
source                  1..15
                        mol_type = protein
                        organism = Homo sapiens
SEQUENCE: 772
DCMLSEEGGQ ARRGG                                                  15

SEQ ID NO: 773          moltype = AA  length = 15
FEATURE                 Location/Qualifiers
source                  1..15
                        mol_type = protein
                        organism = Homo sapiens
SEQUENCE: 773
GQARRGGSLC SLAAH                                                  15

SEQ ID NO: 774          moltype = AA  length = 15
FEATURE                 Location/Qualifiers
source                  1..15
                        mol_type = protein
                        organism = Homo sapiens
SEQUENCE: 774
LCSLAAHTIA SAARG                                                  15

SEQ ID NO: 775          moltype = AA  length = 15
FEATURE                 Location/Qualifiers
source                  1..15
                        mol_type = protein
                        organism = Homo sapiens
SEQUENCE: 775
IASAARGRFL SRLSN                                                  15

SEQ ID NO: 776          moltype = AA  length = 15
FEATURE                 Location/Qualifiers
source                  1..15
                        mol_type = protein
                        organism = Homo sapiens
SEQUENCE: 776
FLSRLSNFCA VVKAS                                                  15

SEQ ID NO: 777          moltype = AA  length = 16
FEATURE                 Location/Qualifiers
source                  1..16
                        mol_type = protein
                        organism = Homo sapiens
SEQUENCE: 777
CAVVKASRGA PSCTWE                                                 16

SEQ ID NO: 778          moltype = AA  length = 15
FEATURE                 Location/Qualifiers
source                  1..15
                        mol_type = protein
                        organism = Homo sapiens
SEQUENCE: 778
PEPRRLSPGE PRGRP                                                  15

SEQ ID NO: 779          moltype = AA  length = 15
FEATURE                 Location/Qualifiers
source                  1..15
```

```
                        mol_type = protein
                        organism = Homo sapiens
SEQUENCE: 779
GEPRGRPRKG WGIWG                                                    15

SEQ ID NO: 780          moltype = AA  length = 15
FEATURE                 Location/Qualifiers
source                  1..15
                        mol_type = protein
                        organism = Homo sapiens
SEQUENCE: 780
KGWGIWGLCG ARVGP                                                    15

SEQ ID NO: 781          moltype = AA  length = 11
FEATURE                 Location/Qualifiers
source                  1..11
                        mol_type = protein
                        organism = Homo sapiens
SEQUENCE: 781
CGARVGPKAW R                                                        11

SEQ ID NO: 782          moltype = AA  length = 15
FEATURE                 Location/Qualifiers
source                  1..15
                        mol_type = protein
                        organism = Homo sapiens
SEQUENCE: 782
FVSLTAIQMA SSATP                                                    15

SEQ ID NO: 783          moltype = AA  length = 15
FEATURE                 Location/Qualifiers
source                  1..15
                        mol_type = protein
                        organism = Homo sapiens
SEQUENCE: 783
MASSATPWGR WPVAT                                                    15

SEQ ID NO: 784          moltype = AA  length = 15
FEATURE                 Location/Qualifiers
source                  1..15
                        mol_type = protein
                        organism = Homo sapiens
SEQUENCE: 784
GRWPVATPTA ACPRR                                                    15

SEQ ID NO: 785          moltype = AA  length = 15
FEATURE                 Location/Qualifiers
source                  1..15
                        mol_type = protein
                        organism = Homo sapiens
SEQUENCE: 785
TAACPRRRPS SLPTG                                                    15

SEQ ID NO: 786          moltype = AA  length = 15
FEATURE                 Location/Qualifiers
source                  1..15
                        mol_type = protein
                        organism = Homo sapiens
SEQUENCE: 786
PSSLPTGGDS ASKKP                                                    15

SEQ ID NO: 787          moltype = AA  length = 15
FEATURE                 Location/Qualifiers
source                  1..15
                        mol_type = protein
                        organism = Homo sapiens
SEQUENCE: 787
DSASKKPISR RAPWQ                                                    15

SEQ ID NO: 788          moltype = AA  length = 15
FEATURE                 Location/Qualifiers
source                  1..15
                        mol_type = protein
                        organism = Homo sapiens
SEQUENCE: 788
SRRAPWQPWA CPGRS                                                    15

SEQ ID NO: 789          moltype = AA  length = 15
FEATURE                 Location/Qualifiers
```

```
source                  1..15
                        mol_type = protein
                        organism = Homo sapiens
SEQUENCE: 789
WACPGRSVNS AAPRA                                                  15

SEQ ID NO: 790          moltype = AA  length = 15
FEATURE                 Location/Qualifiers
source                  1..15
                        mol_type = protein
                        organism = Homo sapiens
SEQUENCE: 790
NSAAPRAWCP PATTP                                                  15

SEQ ID NO: 791          moltype = AA  length = 15
FEATURE                 Location/Qualifiers
source                  1..15
                        mol_type = protein
                        organism = Homo sapiens
SEQUENCE: 791
CPPATTPRTQ SPSRD                                                  15

SEQ ID NO: 792          moltype = AA  length = 15
FEATURE                 Location/Qualifiers
source                  1..15
                        mol_type = protein
                        organism = Homo sapiens
SEQUENCE: 792
TQSPSRDLRP RCLSS                                                  15

SEQ ID NO: 793          moltype = AA  length = 10
FEATURE                 Location/Qualifiers
source                  1..10
                        mol_type = protein
                        organism = Homo sapiens
SEQUENCE: 793
RPRCLSSWSS                                                        10

SEQ ID NO: 794          moltype = AA  length = 15
FEATURE                 Location/Qualifiers
source                  1..15
                        mol_type = protein
                        organism = Homo sapiens
SEQUENCE: 794
PVAIKPGTGP PNNSS                                                  15

SEQ ID NO: 795          moltype = AA  length = 15
FEATURE                 Location/Qualifiers
source                  1..15
                        mol_type = protein
                        organism = Homo sapiens
SEQUENCE: 795
GPPNNSSIHG GSKRS                                                  15

SEQ ID NO: 796          moltype = AA  length = 15
FEATURE                 Location/Qualifiers
source                  1..15
                        mol_type = protein
                        organism = Homo sapiens
SEQUENCE: 796
HGGSKRSENS YCRDL                                                  15

SEQ ID NO: 797          moltype = AA  length = 15
FEATURE                 Location/Qualifiers
source                  1..15
                        mol_type = protein
                        organism = Homo sapiens
SEQUENCE: 797
NSYCRDLRGQ LRAIC                                                  15

SEQ ID NO: 798          moltype = AA  length = 15
FEATURE                 Location/Qualifiers
source                  1..15
                        mol_type = protein
                        organism = Homo sapiens
SEQUENCE: 798
GQLRAICCSS YSHDR                                                  15

SEQ ID NO: 799          moltype = AA  length = 15
```

```
FEATURE                Location/Qualifiers
source                 1..15
                       mol_type = protein
                       organism = Homo sapiens
SEQUENCE: 799
SSYSHDRHTT EERGS                                                    15

SEQ ID NO: 800         moltype = AA  length = 15
FEATURE                Location/Qualifiers
source                 1..15
                       mol_type = protein
                       organism = Homo sapiens
SEQUENCE: 800
TTEERGSRGR HVWRI                                                    15

SEQ ID NO: 801         moltype = AA  length = 15
FEATURE                Location/Qualifiers
source                 1..15
                       mol_type = protein
                       organism = Homo sapiens
SEQUENCE: 801
GRHVWRIRRL HTSGL                                                    15

SEQ ID NO: 802         moltype = AA  length = 15
FEATURE                Location/Qualifiers
source                 1..15
                       mol_type = protein
                       organism = Homo sapiens
SEQUENCE: 802
RLHTSGLPCC CHSGP                                                    15

SEQ ID NO: 803         moltype = AA  length = 15
FEATURE                Location/Qualifiers
source                 1..15
                       mol_type = protein
                       organism = Homo sapiens
SEQUENCE: 803
CCCHSGPHPR RLPDI                                                    15

SEQ ID NO: 804         moltype = AA  length = 15
FEATURE                Location/Qualifiers
source                 1..15
                       mol_type = protein
                       organism = Homo sapiens
SEQUENCE: 804
PRRLPDILRL VTSTK                                                    15

SEQ ID NO: 805         moltype = AA  length = 15
FEATURE                Location/Qualifiers
source                 1..15
                       mol_type = protein
                       organism = Homo sapiens
SEQUENCE: 805
RLVTSTKTDH TNTTE                                                    15

SEQ ID NO: 806         moltype = AA  length = 13
FEATURE                Location/Qualifiers
source                 1..13
                       mol_type = protein
                       organism = Homo sapiens
SEQUENCE: 806
DHTNTTEGTL DYL                                                      13

SEQ ID NO: 807         moltype = AA  length = 15
FEATURE                Location/Qualifiers
source                 1..15
                       mol_type = protein
                       organism = Homo sapiens
SEQUENCE: 807
KWNKNWTATL GALTI                                                    15

SEQ ID NO: 808         moltype = AA  length = 15
FEATURE                Location/Qualifiers
source                 1..15
                       mol_type = protein
                       organism = Homo sapiens
SEQUENCE: 808
TLGALTIRGH KLLCH                                                    15
```

```
SEQ ID NO: 809          moltype = AA  length = 15
FEATURE                 Location/Qualifiers
source                  1..15
                        mol_type = protein
                        organism = Homo sapiens
SEQUENCE: 809
GHKLLCHLPH LLSSV                                                   15

SEQ ID NO: 810          moltype = AA  length = 16
FEATURE                 Location/Qualifiers
source                  1..16
                        mol_type = protein
                        organism = Homo sapiens
SEQUENCE: 810
PHLLSSVQQT CRSSSR                                                  16

SEQ ID NO: 811          moltype = AA  length = 15
FEATURE                 Location/Qualifiers
source                  1..15
                        mol_type = protein
                        organism = Homo sapiens
SEQUENCE: 811
ENASLVFTGS NSPIP                                                   15

SEQ ID NO: 812          moltype = AA  length = 15
FEATURE                 Location/Qualifiers
source                  1..15
                        mol_type = protein
                        organism = Homo sapiens
SEQUENCE: 812
GSNSPIPACE LSSHP                                                   15

SEQ ID NO: 813          moltype = AA  length = 15
FEATURE                 Location/Qualifiers
source                  1..15
                        mol_type = protein
                        organism = Homo sapiens
SEQUENCE: 813
CELSSHPAHG ISPWI                                                   15

SEQ ID NO: 814          moltype = AA  length = 15
FEATURE                 Location/Qualifiers
source                  1..15
                        mol_type = protein
                        organism = Homo sapiens
SEQUENCE: 814
HGISPWIPSP GNEHF                                                   15

SEQ ID NO: 815          moltype = AA  length = 15
FEATURE                 Location/Qualifiers
source                  1..15
                        mol_type = protein
                        organism = Homo sapiens
SEQUENCE: 815
SPGNEHFHGI KKQVK                                                   15

SEQ ID NO: 816          moltype = AA  length = 12
FEATURE                 Location/Qualifiers
source                  1..12
                        mol_type = protein
                        organism = Homo sapiens
SEQUENCE: 816
GIKKQVKAIK VE                                                      12

SEQ ID NO: 817          moltype = AA  length = 15
FEATURE                 Location/Qualifiers
source                  1..15
                        mol_type = protein
                        organism = Homo sapiens
SEQUENCE: 817
RLTQRLVQGW TPMEN                                                   15

SEQ ID NO: 818          moltype = AA  length = 15
FEATURE                 Location/Qualifiers
source                  1..15
                        mol_type = protein
                        organism = Homo sapiens
SEQUENCE: 818
GWTPMENRWC GRRAG                                                   15
```

```
SEQ ID NO: 819          moltype = AA  length = 15
FEATURE                 Location/Qualifiers
source                  1..15
                        mol_type = protein
                        organism = Homo sapiens
SEQUENCE: 819
WCGRRAGGQP ASSST                                                    15

SEQ ID NO: 820          moltype = AA  length = 15
FEATURE                 Location/Qualifiers
source                  1..15
                        mol_type = protein
                        organism = Homo sapiens
SEQUENCE: 820
QPASSSTRWT TCRAA                                                    15

SEQ ID NO: 821          moltype = AA  length = 15
FEATURE                 Location/Qualifiers
source                  1..15
                        mol_type = protein
                        organism = Homo sapiens
SEQUENCE: 821
WTTCRAACLL TKWTA                                                    15

SEQ ID NO: 822          moltype = AA  length = 15
FEATURE                 Location/Qualifiers
source                  1..15
                        mol_type = protein
                        organism = Homo sapiens
SEQUENCE: 822
LLTKWTAGRS QTSIG                                                    15

SEQ ID NO: 823          moltype = AA  length = 15
FEATURE                 Location/Qualifiers
source                  1..15
                        mol_type = protein
                        organism = Homo sapiens
SEQUENCE: 823
ENSGNASRWL HVPSS                                                    15

SEQ ID NO: 824          moltype = AA  length = 15
FEATURE                 Location/Qualifiers
source                  1..15
                        mol_type = protein
                        organism = Homo sapiens
SEQUENCE: 824
WLHVPSSSDD WLGWK                                                    15

SEQ ID NO: 825          moltype = AA  length = 16
FEATURE                 Location/Qualifiers
source                  1..16
                        mol_type = protein
                        organism = Homo sapiens
SEQUENCE: 825
DDWLGWKKSS AITSNS                                                   16

SEQ ID NO: 826          moltype = AA  length = 15
FEATURE                 Location/Qualifiers
source                  1..15
                        mol_type = protein
                        organism = Homo sapiens
SEQUENCE: 826
KGSVERRSVS LGHPA                                                    15

SEQ ID NO: 827          moltype = AA  length = 15
FEATURE                 Location/Qualifiers
source                  1..15
                        mol_type = protein
                        organism = Homo sapiens
SEQUENCE: 827
VSLGHPAEGW AWAER                                                    15

SEQ ID NO: 828          moltype = AA  length = 15
FEATURE                 Location/Qualifiers
source                  1..15
                        mol_type = protein
                        organism = Homo sapiens
SEQUENCE: 828
```

```
GWAWAERSLQ PGMTT                                                    15

SEQ ID NO: 829          moltype = AA  length = 15
FEATURE                 Location/Qualifiers
source                  1..15
                        mol_type = protein
                        organism = Homo sapiens
SEQUENCE: 829
LQPGMTTANT GCLSF                                                    15

SEQ ID NO: 830          moltype = AA  length = 15
FEATURE                 Location/Qualifiers
source                  1..15
                        mol_type = protein
                        organism = Homo sapiens
SEQUENCE: 830
NTGCLSFHHR GCLLP                                                    15

SEQ ID NO: 831          moltype = AA  length = 15
FEATURE                 Location/Qualifiers
source                  1..15
                        mol_type = protein
                        organism = Homo sapiens
SEQUENCE: 831
HRGCLLPVLP KLHCG                                                    15

SEQ ID NO: 832          moltype = AA  length = 15
FEATURE                 Location/Qualifiers
source                  1..15
                        mol_type = protein
                        organism = Homo sapiens
SEQUENCE: 832
LPKLHCGLGG LPLVR                                                    15

SEQ ID NO: 833          moltype = AA  length = 15
FEATURE                 Location/Qualifiers
source                  1..15
                        mol_type = protein
                        organism = Homo sapiens
SEQUENCE: 833
GGLPLVRAKE IKRVQ                                                    15

SEQ ID NO: 834          moltype = AA  length = 15
FEATURE                 Location/Qualifiers
source                  1..15
                        mol_type = protein
                        organism = Homo sapiens
SEQUENCE: 834
KEIKRVQRAG ESSLP                                                    15

SEQ ID NO: 835          moltype = AA  length = 15
FEATURE                 Location/Qualifiers
source                  1..15
                        mol_type = protein
                        organism = Homo sapiens
SEQUENCE: 835
AGESSLPVKG LLTVA                                                    15

SEQ ID NO: 836          moltype = AA  length = 15
FEATURE                 Location/Qualifiers
source                  1..15
                        mol_type = protein
                        organism = Homo sapiens
SEQUENCE: 836
KGLLTVASAV IAVLW                                                    15

SEQ ID NO: 837          moltype = AA  length = 15
FEATURE                 Location/Qualifiers
source                  1..15
                        mol_type = protein
                        organism = Homo sapiens
SEQUENCE: 837
AVIAVLWGRP SEVTG                                                    15

SEQ ID NO: 838          moltype = AA  length = 14
FEATURE                 Location/Qualifiers
source                  1..14
                        mol_type = protein
                        organism = Homo sapiens
```

SEQUENCE: 838
RPSEVTGENE AQHD 14

SEQ ID NO: 839 moltype = AA length = 15
FEATURE Location/Qualifiers
source 1..15
mol_type = protein
organism = Homo sapiens
SEQUENCE: 839
FGLTTLAGRS SHGTS 15

SEQ ID NO: 840 moltype = AA length = 15
FEATURE Location/Qualifiers
source 1..15
mol_type = protein
organism = Homo sapiens
SEQUENCE: 840
RSSHGTSGLR AATHT 15

SEQ ID NO: 841 moltype = AA length = 15
FEATURE Location/Qualifiers
source 1..15
mol_type = protein
organism = Homo sapiens
SEQUENCE: 841
LRAATHTKSG DGGQG 15

SEQ ID NO: 842 moltype = AA length = 15
FEATURE Location/Qualifiers
source 1..15
mol_type = protein
organism = Homo sapiens
SEQUENCE: 842
SGDGGQGAAR QCEKL 15

SEQ ID NO: 843 moltype = AA length = 15
FEATURE Location/Qualifiers
source 1..15
mol_type = protein
organism = Homo sapiens
SEQUENCE: 843
ARQCEKLLEL ARATR 15

SEQ ID NO: 844 moltype = AA length = 15
FEATURE Location/Qualifiers
source 1..15
mol_type = protein
organism = Homo sapiens
SEQUENCE: 844
ELARATRPWG RSTSA 15

SEQ ID NO: 845 moltype = AA length = 15
FEATURE Location/Qualifiers
source 1..15
mol_type = protein
organism = Homo sapiens
SEQUENCE: 845
WGRSTSASSR WTHRG 15

SEQ ID NO: 846 moltype = AA length = 15
FEATURE Location/Qualifiers
source 1..15
mol_type = protein
organism = Homo sapiens
SEQUENCE: 846
SRWTHRGYMC PPRCA 15

SEQ ID NO: 847 moltype = AA length = 11
FEATURE Location/Qualifiers
source 1..11
mol_type = protein
organism = Homo sapiens
SEQUENCE: 847
MCPPRCAVAC W 11

SEQ ID NO: 848 moltype = AA length = 15
FEATURE Location/Qualifiers
source 1..15
mol_type = protein

```
                        organism = Homo sapiens
SEQUENCE: 848
IIDSDKIMAV CMGCL                                                        15

SEQ ID NO: 849          moltype = AA  length = 15
FEATURE                 Location/Qualifiers
source                  1..15
                        mol_type = protein
                        organism = Homo sapiens
SEQUENCE: 849
DKIMAVCMGC LLTRH                                                        15

SEQ ID NO: 850          moltype = AA  length = 15
FEATURE                 Location/Qualifiers
source                  1..15
                        mol_type = protein
                        organism = Homo sapiens
SEQUENCE: 850
AVCMGCLLTR HVQCQ                                                        15

SEQ ID NO: 851          moltype = AA  length = 15
FEATURE                 Location/Qualifiers
source                  1..15
                        mol_type = protein
                        organism = Homo sapiens
SEQUENCE: 851
GCLLTRHVQC QAMEM                                                        15

SEQ ID NO: 852          moltype = AA  length = 13
FEATURE                 Location/Qualifiers
source                  1..13
                        mol_type = protein
                        organism = Homo sapiens
SEQUENCE: 852
TRHVQCQAME MQQ                                                          13

SEQ ID NO: 853          moltype = AA  length = 16
FEATURE                 Location/Qualifiers
source                  1..16
                        mol_type = protein
                        organism = Homo sapiens
SEQUENCE: 853
LSIFLFLMLC KLEFHA                                                       16

SEQ ID NO: 854          moltype = AA  length = 15
FEATURE                 Location/Qualifiers
source                  1..15
                        mol_type = protein
                        organism = Homo sapiens
SEQUENCE: 854
LLNAEDYRCA IHSKE                                                        15

SEQ ID NO: 855          moltype = AA  length = 15
FEATURE                 Location/Qualifiers
source                  1..15
                        mol_type = protein
                        organism = Homo sapiens
SEQUENCE: 855
CAIHSKEIYL LSPSP                                                        15

SEQ ID NO: 856          moltype = AA  length = 15
FEATURE                 Location/Qualifiers
source                  1..15
                        mol_type = protein
                        organism = Homo sapiens
SEQUENCE: 856
YLLSPSPHQA MDKFS                                                        15

SEQ ID NO: 857          moltype = AA  length = 15
FEATURE                 Location/Qualifiers
source                  1..15
                        mol_type = protein
                        organism = Homo sapiens
SEQUENCE: 857
QAMDKFSLCC INCNL                                                        15

SEQ ID NO: 858          moltype = AA  length = 15
FEATURE                 Location/Qualifiers
source                  1..15
```

```
                        mol_type = protein
                        organism = Homo sapiens
SEQUENCE: 858
CCINCNLCLH VFLLL                                                  15

SEQ ID NO: 859          moltype = AA  length = 15
FEATURE                 Location/Qualifiers
source                  1..15
                        mol_type = protein
                        organism = Homo sapiens
SEQUENCE: 859
LHVFLLLLFF QNKDV                                                  15

SEQ ID NO: 860          moltype = AA  length = 15
FEATURE                 Location/Qualifiers
source                  1..15
                        mol_type = protein
                        organism = Homo sapiens
SEQUENCE: 860
FFQNKDVWLI SNIIL                                                  15

SEQ ID NO: 861          moltype = AA  length = 14
FEATURE                 Location/Qualifiers
source                  1..14
                        mol_type = protein
                        organism = Homo sapiens
SEQUENCE: 861
LISNIILLWI YGGI                                                   14

SEQ ID NO: 862          moltype = AA  length = 15
FEATURE                 Location/Qualifiers
source                  1..15
                        mol_type = protein
                        organism = Homo sapiens
SEQUENCE: 862
VETLENANSF SSGIQ                                                  15

SEQ ID NO: 863          moltype = AA  length = 15
FEATURE                 Location/Qualifiers
source                  1..15
                        mol_type = protein
                        organism = Homo sapiens
SEQUENCE: 863
SFSSGIQPLL CSLIG                                                  15

SEQ ID NO: 864          moltype = AA  length = 12
FEATURE                 Location/Qualifiers
source                  1..12
                        mol_type = protein
                        organism = Homo sapiens
SEQUENCE: 864
LLCSLIGLEN PT                                                     12

SEQ ID NO: 865          moltype = AA  length = 15
FEATURE                 Location/Qualifiers
source                  1..15
                        mol_type = protein
                        organism = Homo sapiens
SEQUENCE: 865
AGAGTISEGS VLHGQ                                                  15

SEQ ID NO: 866          moltype = AA  length = 15
FEATURE                 Location/Qualifiers
source                  1..15
                        mol_type = protein
                        organism = Homo sapiens
SEQUENCE: 866
GSVLHGQRLE CDARR                                                  15

SEQ ID NO: 867          moltype = AA  length = 15
FEATURE                 Location/Qualifiers
source                  1..15
                        mol_type = protein
                        organism = Homo sapiens
SEQUENCE: 867
LECDARRFFG CGTTI                                                  15

SEQ ID NO: 868          moltype = AA  length = 14
FEATURE                 Location/Qualifiers
```

```
source                  1..14
                        mol_type = protein
                        organism = Homo sapiens
SEQUENCE: 868
FGCGTTILAE WEHH                                                   14

SEQ ID NO: 869          moltype = AA  length = 15
FEATURE                 Location/Qualifiers
source                  1..15
                        mol_type = protein
                        organism = Homo sapiens
SEQUENCE: 869
KEQILAVASL VSSQS                                                  15

SEQ ID NO: 870          moltype = AA  length = 15
FEATURE                 Location/Qualifiers
source                  1..15
                        mol_type = protein
                        organism = Homo sapiens
SEQUENCE: 870
SLVSSQSIHP SWGQS                                                  15

SEQ ID NO: 871          moltype = AA  length = 12
FEATURE                 Location/Qualifiers
source                  1..12
                        mol_type = protein
                        organism = Homo sapiens
SEQUENCE: 871
HPSWGQSPLS RI                                                     12

SEQ ID NO: 872          moltype = AA  length = 15
FEATURE                 Location/Qualifiers
source                  1..15
                        mol_type = protein
                        organism = Homo sapiens
SEQUENCE: 872
QQLRIFCAAM ASNED                                                  15

SEQ ID NO: 873          moltype = AA  length = 9
FEATURE                 Location/Qualifiers
source                  1..9
                        mol_type = protein
                        organism = Homo sapiens
SEQUENCE: 873
AMASNEDFS                                                         9

SEQ ID NO: 874          moltype = AA  length = 15
FEATURE                 Location/Qualifiers
source                  1..15
                        mol_type = protein
                        organism = Homo sapiens
SEQUENCE: 874
DGFSGSLFAV VTRRC                                                  15

SEQ ID NO: 875          moltype = AA  length = 15
FEATURE                 Location/Qualifiers
source                  1..15
                        mol_type = protein
                        organism = Homo sapiens
SEQUENCE: 875
AVVTRRCYFL KWRTI                                                  15

SEQ ID NO: 876          moltype = AA  length = 15
FEATURE                 Location/Qualifiers
source                  1..15
                        mol_type = protein
                        organism = Homo sapiens
SEQUENCE: 876
FLKWRTIFPQ SLMWL                                                  15

SEQ ID NO: 877          moltype = AA  length = 15
FEATURE                 Location/Qualifiers
source                  1..15
                        mol_type = protein
                        organism = Homo sapiens
SEQUENCE: 877
DLRRVATYCA PLPSS                                                  15

SEQ ID NO: 878          moltype = AA  length = 15
```

```
FEATURE                 Location/Qualifiers
source                  1..15
                        mol_type = protein
                        organism = Homo sapiens
SEQUENCE: 878
CAPLPSSWRP GTGTT                                                    15

SEQ ID NO: 879          moltype = AA  length = 15
FEATURE                 Location/Qualifiers
source                  1..15
                        mol_type = protein
                        organism = Homo sapiens
SEQUENCE: 879
RPGTGTTIPP RMRSC                                                    15

SEQ ID NO: 880          moltype = AA  length = 15
FEATURE                 Location/Qualifiers
source                  1..15
                        mol_type = protein
                        organism = Homo sapiens
SEQUENCE: 880
LQERMELLAC GAERG                                                    15

SEQ ID NO: 881          moltype = AA  length = 15
FEATURE                 Location/Qualifiers
source                  1..15
                        mol_type = protein
                        organism = Homo sapiens
SEQUENCE: 881
ACGAERGAGG WGGGG                                                    15

SEQ ID NO: 882          moltype = AA  length = 15
FEATURE                 Location/Qualifiers
source                  1..15
                        mol_type = protein
                        organism = Homo sapiens
SEQUENCE: 882
GGWGGGGGGG GGDRR                                                    15

SEQ ID NO: 883          moltype = AA  length = 15
FEATURE                 Location/Qualifiers
source                  1..15
                        mol_type = protein
                        organism = Homo sapiens
SEQUENCE: 883
GGGGDRRGGG GSAPA                                                    15

SEQ ID NO: 884          moltype = AA  length = 16
FEATURE                 Location/Qualifiers
source                  1..16
                        mol_type = protein
                        organism = Homo sapiens
SEQUENCE: 884
GGGSAPALAD FAGGRG                                                   16

SEQ ID NO: 885          moltype = AA  length = 15
FEATURE                 Location/Qualifiers
source                  1..15
                        mol_type = protein
                        organism = Homo sapiens
SEQUENCE: 885
WTDIVKQSVS TNCIS                                                    15

SEQ ID NO: 886          moltype = AA  length = 15
FEATURE                 Location/Qualifiers
source                  1..15
                        mol_type = protein
                        organism = Homo sapiens
SEQUENCE: 886
VSTNCISIKK GSYTK                                                    15

SEQ ID NO: 887          moltype = AA  length = 15
FEATURE                 Location/Qualifiers
source                  1..15
                        mol_type = protein
                        organism = Homo sapiens
SEQUENCE: 887
KKGSYTKLFS LVFLI                                                    15
```

```
SEQ ID NO: 888          moltype = AA  length = 16
FEATURE                 Location/Qualifiers
source                  1..16
                        mol_type = protein
                        organism = Homo sapiens
SEQUENCE: 888
FSLVFLIFCW PLIIQL                                                   16

SEQ ID NO: 889          moltype = AA  length = 15
FEATURE                 Location/Qualifiers
source                  1..15
                        mol_type = protein
                        organism = Homo sapiens
SEQUENCE: 889
LRYGALCNVS RISYF                                                    15

SEQ ID NO: 890          moltype = AA  length = 15
FEATURE                 Location/Qualifiers
source                  1..15
                        mol_type = protein
                        organism = Homo sapiens
SEQUENCE: 890
VSRISYFSLT NIFNF                                                    15

SEQ ID NO: 891          moltype = AA  length = 15
FEATURE                 Location/Qualifiers
source                  1..15
                        mol_type = protein
                        organism = Homo sapiens
SEQUENCE: 891
LTNIFNFVIK SLTAI                                                    15

SEQ ID NO: 892          moltype = AA  length = 15
FEATURE                 Location/Qualifiers
source                  1..15
                        mol_type = protein
                        organism = Homo sapiens
SEQUENCE: 892
RKERNIRKSE STLRL                                                    15

SEQ ID NO: 893          moltype = AA  length = 15
FEATURE                 Location/Qualifiers
source                  1..15
                        mol_type = protein
                        organism = Homo sapiens
SEQUENCE: 893
SESTLRLSPF PTPAP                                                    15

SEQ ID NO: 894          moltype = AA  length = 15
FEATURE                 Location/Qualifiers
source                  1..15
                        mol_type = protein
                        organism = Homo sapiens
SEQUENCE: 894
PFPTPAPSGA PAAAQ                                                    15

SEQ ID NO: 895          moltype = AA  length = 15
FEATURE                 Location/Qualifiers
source                  1..15
                        mol_type = protein
                        organism = Homo sapiens
SEQUENCE: 895
GAPAAAQGKV VRVPG                                                    15

SEQ ID NO: 896          moltype = AA  length = 15
FEATURE                 Location/Qualifiers
source                  1..15
                        mol_type = protein
                        organism = Homo sapiens
SEQUENCE: 896
KVVRVPGPAG GLVPR                                                    15

SEQ ID NO: 897          moltype = AA  length = 15
FEATURE                 Location/Qualifiers
source                  1..15
                        mol_type = protein
                        organism = Homo sapiens
SEQUENCE: 897
AGGLVPRDAG ARLLP                                                    15
```

```
SEQ ID NO: 898          moltype = AA  length = 15
FEATURE                 Location/Qualifiers
source                  1..15
                        mol_type = protein
                        organism = Homo sapiens
SEQUENCE: 898
AGARLLPPAG GPGGG                                                    15

SEQ ID NO: 899          moltype = AA  length = 15
FEATURE                 Location/Qualifiers
source                  1..15
                        mol_type = protein
                        organism = Homo sapiens
SEQUENCE: 899
AGGPGGGAAA GEGRA                                                    15

SEQ ID NO: 900          moltype = AA  length = 15
FEATURE                 Location/Qualifiers
source                  1..15
                        mol_type = protein
                        organism = Homo sapiens
SEQUENCE: 900
AAGEGRAGRG RFPSI                                                    15

SEQ ID NO: 901          moltype = AA  length = 15
FEATURE                 Location/Qualifiers
source                  1..15
                        mol_type = protein
                        organism = Homo sapiens
SEQUENCE: 901
RGRFPSITEP RPRDL                                                    15

SEQ ID NO: 902          moltype = AA  length = 15
FEATURE                 Location/Qualifiers
source                  1..15
                        mol_type = protein
                        organism = Homo sapiens
SEQUENCE: 902
EPRPRDLPPR VATGR                                                    15

SEQ ID NO: 903          moltype = AA  length = 15
FEATURE                 Location/Qualifiers
source                  1..15
                        mol_type = protein
                        organism = Homo sapiens
SEQUENCE: 903
PRVATGRRAG GRRKG                                                    15

SEQ ID NO: 904          moltype = AA  length = 15
FEATURE                 Location/Qualifiers
source                  1..15
                        mol_type = protein
                        organism = Homo sapiens
SEQUENCE: 904
AGGRRKGAGQ GVRTR                                                    15

SEQ ID NO: 905          moltype = AA  length = 15
FEATURE                 Location/Qualifiers
source                  1..15
                        mol_type = protein
                        organism = Homo sapiens
SEQUENCE: 905
GQGVRTRPLP ASWPG                                                    15

SEQ ID NO: 906          moltype = AA  length = 15
FEATURE                 Location/Qualifiers
source                  1..15
                        mol_type = protein
                        organism = Homo sapiens
SEQUENCE: 906
LPASWPGGRG PFRKG                                                    15

SEQ ID NO: 907          moltype = AA  length = 15
FEATURE                 Location/Qualifiers
source                  1..15
                        mol_type = protein
                        organism = Homo sapiens
SEQUENCE: 907
```

RGPFRKGPRR LPLGS 15

SEQ ID NO: 908 moltype = AA length = 15
FEATURE Location/Qualifiers
source 1..15
mol_type = protein
organism = Homo sapiens
SEQUENCE: 908
RRLPLGSGPP AAGVQ 15

SEQ ID NO: 909 moltype = AA length = 15
FEATURE Location/Qualifiers
source 1..15
mol_type = protein
organism = Homo sapiens
SEQUENCE: 909
PPAAGVQRLR CSHLS 15

SEQ ID NO: 910 moltype = AA length = 15
FEATURE Location/Qualifiers
source 1..15
mol_type = protein
organism = Homo sapiens
SEQUENCE: 910
LRCSHLSRGP RRRRG 15

SEQ ID NO: 911 moltype = AA length = 15
FEATURE Location/Qualifiers
source 1..15
mol_type = protein
organism = Homo sapiens
SEQUENCE: 911
GPRRRRGRVC GRACV 15

SEQ ID NO: 912 moltype = AA length = 15
FEATURE Location/Qualifiers
source 1..15
mol_type = protein
organism = Homo sapiens
SEQUENCE: 912
VCGRACVSPP LPPRP 15

SEQ ID NO: 913 moltype = AA length = 15
FEATURE Location/Qualifiers
source 1..15
mol_type = protein
organism = Homo sapiens
SEQUENCE: 913
PPLPPRPPPV GLSAE 15

SEQ ID NO: 914 moltype = AA length = 15
FEATURE Location/Qualifiers
source 1..15
mol_type = protein
organism = Homo sapiens
SEQUENCE: 914
PVGLSAENLS WLSSG 15

SEQ ID NO: 915 moltype = AA length = 15
FEATURE Location/Qualifiers
source 1..15
mol_type = protein
organism = Homo sapiens
SEQUENCE: 915
LSWLSSGLPR ACSWR 15

SEQ ID NO: 916 moltype = AA length = 15
FEATURE Location/Qualifiers
source 1..15
mol_type = protein
organism = Homo sapiens
SEQUENCE: 916
PRACSWREFS PETCA 15

SEQ ID NO: 917 moltype = AA length = 15
FEATURE Location/Qualifiers
source 1..15
mol_type = protein
organism = Homo sapiens

SEQUENCE: 917
FSPETCAFRL SGLDS 15

SEQ ID NO: 918 moltype = AA length = 15
FEATURE Location/Qualifiers
source 1..15
mol_type = protein
organism = Homo sapiens
SEQUENCE: 918
RLSGLDSKLS ARVER 15

SEQ ID NO: 919 moltype = AA length = 15
FEATURE Location/Qualifiers
source 1..15
mol_type = protein
organism = Homo sapiens
SEQUENCE: 919
LSARVERDLG ALRAP 15

SEQ ID NO: 920 moltype = AA length = 15
FEATURE Location/Qualifiers
source 1..15
mol_type = protein
organism = Homo sapiens
SEQUENCE: 920
LGALRAPGSR AAQGG 15

SEQ ID NO: 921 moltype = AA length = 15
FEATURE Location/Qualifiers
source 1..15
mol_type = protein
organism = Homo sapiens
SEQUENCE: 921
SRAAQGGGRV RGSRS 15

SEQ ID NO: 922 moltype = AA length = 15
FEATURE Location/Qualifiers
source 1..15
mol_type = protein
organism = Homo sapiens
SEQUENCE: 922
RVRGSRSEWK TRPWR 15

SEQ ID NO: 923 moltype = AA length = 15
FEATURE Location/Qualifiers
source 1..15
mol_type = protein
organism = Homo sapiens
SEQUENCE: 923
WKTRPWRPPP AWPLT 15

SEQ ID NO: 924 moltype = AA length = 15
FEATURE Location/Qualifiers
source 1..15
mol_type = protein
organism = Homo sapiens
SEQUENCE: 924
PPAWPLTRAG GPLPK 15

SEQ ID NO: 925 moltype = AA length = 15
FEATURE Location/Qualifiers
source 1..15
mol_type = protein
organism = Homo sapiens
SEQUENCE: 925
AGGPLPKNPF LESCS 15

SEQ ID NO: 926 moltype = AA length = 15
FEATURE Location/Qualifiers
source 1..15
mol_type = protein
organism = Homo sapiens
SEQUENCE: 926
PFLESCSETA QRRRV 15

SEQ ID NO: 927 moltype = AA length = 15
FEATURE Location/Qualifiers
source 1..15
mol_type = protein -continued

```
                        organism = Homo sapiens
SEQUENCE: 927
TAQRRRVFSF STPLS                                                        15

SEQ ID NO: 928          moltype = AA  length = 15
FEATURE                 Location/Qualifiers
source                  1..15
                        mol_type = protein
                        organism = Homo sapiens
SEQUENCE: 928
SINKATITGK KDLEL                                                        15

SEQ ID NO: 929          moltype = AA  length = 15
FEATURE                 Location/Qualifiers
source                  1..15
                        mol_type = protein
                        organism = Homo sapiens
SEQUENCE: 929
GKKDLELILH VSRKK                                                        15

SEQ ID NO: 930          moltype = AA  length = 15
FEATURE                 Location/Qualifiers
source                  1..15
                        mol_type = protein
                        organism = Homo sapiens
SEQUENCE: 930
LHVSRKKPFL PRVNI                                                        15

SEQ ID NO: 931          moltype = AA  length = 15
FEATURE                 Location/Qualifiers
source                  1..15
                        mol_type = protein
                        organism = Homo sapiens
SEQUENCE: 931
FLPRVNITPT PISCC                                                        15

SEQ ID NO: 932          moltype = AA  length = 15
FEATURE                 Location/Qualifiers
source                  1..15
                        mol_type = protein
                        organism = Homo sapiens
SEQUENCE: 932
PTPISCCNLK MLKKF                                                        15

SEQ ID NO: 933          moltype = AA  length = 15
FEATURE                 Location/Qualifiers
source                  1..15
                        mol_type = protein
                        organism = Homo sapiens
SEQUENCE: 933
LKMLKKFFLL YIIIS                                                        15

SEQ ID NO: 934          moltype = AA  length = 15
FEATURE                 Location/Qualifiers
source                  1..15
                        mol_type = protein
                        organism = Homo sapiens
SEQUENCE: 934
LLYIIISIID LTNCL                                                        15

SEQ ID NO: 935          moltype = AA  length = 15
FEATURE                 Location/Qualifiers
source                  1..15
                        mol_type = protein
                        organism = Homo sapiens
SEQUENCE: 935
IDLTNCLSCY LEHFY                                                        15

SEQ ID NO: 936          moltype = AA  length = 15
FEATURE                 Location/Qualifiers
source                  1..15
                        mol_type = protein
                        organism = Homo sapiens
SEQUENCE: 936
CYLEHFYRFT FFTDV                                                        15

SEQ ID NO: 937          moltype = AA  length = 10
FEATURE                 Location/Qualifiers
source                  1..10
```

```
                        mol_type = protein
                        organism = Homo sapiens
SEQUENCE: 937
FTFFTDVHYF                                                          10

SEQ ID NO: 938          moltype = AA  length = 15
FEATURE                 Location/Qualifiers
source                  1..15
                        mol_type = protein
                        organism = Homo sapiens
SEQUENCE: 938
PYYSALSGNS WVPST                                                    15

SEQ ID NO: 939          moltype = AA  length = 15
FEATURE                 Location/Qualifiers
source                  1..15
                        mol_type = protein
                        organism = Homo sapiens
SEQUENCE: 939
NSWVPSTLES DPFGY                                                    15

SEQ ID NO: 940          moltype = AA  length = 15
FEATURE                 Location/Qualifiers
source                  1..15
                        mol_type = protein
                        organism = Homo sapiens
SEQUENCE: 940
ESDPFGYVFS PLATR                                                    15

SEQ ID NO: 941          moltype = AA  length = 15
FEATURE                 Location/Qualifiers
source                  1..15
                        mol_type = protein
                        organism = Homo sapiens
SEQUENCE: 941
FSPLATRPAL NDQES                                                    15

SEQ ID NO: 942          moltype = AA  length = 15
FEATURE                 Location/Qualifiers
source                  1..15
                        mol_type = protein
                        organism = Homo sapiens
SEQUENCE: 942
ALNDQESILW PTLTS                                                    15

SEQ ID NO: 943          moltype = AA  length = 15
FEATURE                 Location/Qualifiers
source                  1..15
                        mol_type = protein
                        organism = Homo sapiens
SEQUENCE: 943
LWPTLTSVVS CALSC                                                    15

SEQ ID NO: 944          moltype = AA  length = 15
FEATURE                 Location/Qualifiers
source                  1..15
                        mol_type = protein
                        organism = Homo sapiens
SEQUENCE: 944
VSCALSCPSL NLPEN                                                    15

SEQ ID NO: 945          moltype = AA  length = 15
FEATURE                 Location/Qualifiers
source                  1..15
                        mol_type = protein
                        organism = Homo sapiens
SEQUENCE: 945
SLNLPENWLT LITGG                                                    15

SEQ ID NO: 946          moltype = AA  length = 15
FEATURE                 Location/Qualifiers
source                  1..15
                        mol_type = protein
                        organism = Homo sapiens
SEQUENCE: 946
LTLITGGMKG GKKMK                                                    15

SEQ ID NO: 947          moltype = AA  length = 12
FEATURE                 Location/Qualifiers
```

```
source                 1..12
                       mol_type = protein
                       organism = Homo sapiens
SEQUENCE: 947
KGGKKMKFTF RH                                                      12

SEQ ID NO: 948         moltype = AA  length = 15
FEATURE                Location/Qualifiers
source                 1..15
                       mol_type = protein
                       organism = Homo sapiens
SEQUENCE: 948
GLRNLGNTVR AILLS                                                   15

SEQ ID NO: 949         moltype = AA  length = 15
FEATURE                Location/Qualifiers
source                 1..15
                       mol_type = protein
                       organism = Homo sapiens
SEQUENCE: 949
VRAILLSFLS KRNVK                                                   15

SEQ ID NO: 950         moltype = AA  length = 15
FEATURE                Location/Qualifiers
source                 1..15
                       mol_type = protein
                       organism = Homo sapiens
SEQUENCE: 950
LSKRNVKWCW GWGKP                                                   15

SEQ ID NO: 951         moltype = AA  length = 15
FEATURE                Location/Qualifiers
source                 1..15
                       mol_type = protein
                       organism = Homo sapiens
SEQUENCE: 951
CWGWGKPTSL GKACG                                                   15

SEQ ID NO: 952         moltype = AA  length = 14
FEATURE                Location/Qualifiers
source                 1..14
                       mol_type = protein
                       organism = Homo sapiens
SEQUENCE: 952
SLGKACGRRA LKLF                                                    14

SEQ ID NO: 953         moltype = AA  length = 15
FEATURE                Location/Qualifiers
source                 1..15
                       mol_type = protein
                       organism = Homo sapiens
SEQUENCE: 953
MEAENAGSLH FHEVL                                                   15

SEQ ID NO: 954         moltype = AA  length = 14
FEATURE                Location/Qualifiers
source                 1..14
                       mol_type = protein
                       organism = Homo sapiens
SEQUENCE: 954
LHFHEVLKMG HVKF                                                    14

SEQ ID NO: 955         moltype = AA  length = 15
FEATURE                Location/Qualifiers
source                 1..15
                       mol_type = protein
                       organism = Homo sapiens
SEQUENCE: 955
WTPIPVLTRW PLPHP                                                   15

SEQ ID NO: 956         moltype = AA  length = 15
FEATURE                Location/Qualifiers
source                 1..15
                       mol_type = protein
                       organism = Homo sapiens
SEQUENCE: 956
RWPLPHPPPW RRATS                                                   15

SEQ ID NO: 957         moltype = AA  length = 15
```

-continued

```
FEATURE                 Location/Qualifiers
source                  1..15
                        mol_type = protein
                        organism = Homo sapiens
SEQUENCE: 957
PWRRATSCRM ARSSP                                                15

SEQ ID NO: 958          moltype = AA  length = 15
FEATURE                 Location/Qualifiers
source                  1..15
                        mol_type = protein
                        organism = Homo sapiens
SEQUENCE: 958
RMARSSPSAT SGSSV                                                15

SEQ ID NO: 959          moltype = AA  length = 15
FEATURE                 Location/Qualifiers
source                  1..15
                        mol_type = protein
                        organism = Homo sapiens
SEQUENCE: 959
ATSGSSVRRR CSSLP                                                15

SEQ ID NO: 960          moltype = AA  length = 15
FEATURE                 Location/Qualifiers
source                  1..15
                        mol_type = protein
                        organism = Homo sapiens
SEQUENCE: 960
RRCSSLPSWV WNLAA                                                15

SEQ ID NO: 961          moltype = AA  length = 16
FEATURE                 Location/Qualifiers
source                  1..16
                        mol_type = protein
                        organism = Homo sapiens
SEQUENCE: 961
WVWNLAASTR PRSTPS                                               16

SEQ ID NO: 962          moltype = AA  length = 15
FEATURE                 Location/Qualifiers
source                  1..15
                        mol_type = protein
                        organism = Homo sapiens
SEQUENCE: 962
LHPQRETFTP RWSGA                                                15

SEQ ID NO: 963          moltype = AA  length = 15
FEATURE                 Location/Qualifiers
source                  1..15
                        mol_type = protein
                        organism = Homo sapiens
SEQUENCE: 963
TPRWSGANYW KLAFP                                                15

SEQ ID NO: 964          moltype = AA  length = 15
FEATURE                 Location/Qualifiers
source                  1..15
                        mol_type = protein
                        organism = Homo sapiens
SEQUENCE: 964
YWKLAFPVGA EGTFP                                                15

SEQ ID NO: 965          moltype = AA  length = 15
FEATURE                 Location/Qualifiers
source                  1..15
                        mol_type = protein
                        organism = Homo sapiens
SEQUENCE: 965
GAEGTFPAAA TQRGV                                                15

SEQ ID NO: 966          moltype = AA  length = 11
FEATURE                 Location/Qualifiers
source                  1..11
                        mol_type = protein
                        organism = Homo sapiens
SEQUENCE: 966
AATQRGVVRP A                                                    11
```

```
SEQ ID NO: 967          moltype = AA  length = 15
FEATURE                 Location/Qualifiers
source                  1..15
                        mol_type = protein
                        organism = Homo sapiens
SEQUENCE: 967
MAGGVLRRLL CREPD                                                    15

SEQ ID NO: 968          moltype = AA  length = 15
FEATURE                 Location/Qualifiers
source                  1..15
                        mol_type = protein
                        organism = Homo sapiens
SEQUENCE: 968
LLCREPDRDG DKGAS                                                    15

SEQ ID NO: 969          moltype = AA  length = 15
FEATURE                 Location/Qualifiers
source                  1..15
                        mol_type = protein
                        organism = Homo sapiens
SEQUENCE: 969
DGDKGASREE TVVPL                                                    15

SEQ ID NO: 970          moltype = AA  length = 15
FEATURE                 Location/Qualifiers
source                  1..15
                        mol_type = protein
                        organism = Homo sapiens
SEQUENCE: 970
EETVVPLHIG DPVVL                                                    15

SEQ ID NO: 971          moltype = AA  length = 15
FEATURE                 Location/Qualifiers
source                  1..15
                        mol_type = protein
                        organism = Homo sapiens
SEQUENCE: 971
IGDPVVLPGI GQCYS                                                    15

SEQ ID NO: 972          moltype = AA  length = 10
FEATURE                 Location/Qualifiers
source                  1..10
                        mol_type = protein
                        organism = Homo sapiens
SEQUENCE: 972
GIGQCYSALF                                                          10

SEQ ID NO: 973          moltype = AA  length = 15
FEATURE                 Location/Qualifiers
source                  1..15
                        mol_type = protein
                        organism = Homo sapiens
SEQUENCE: 973
VFFKRAAEGF FRMNK                                                    15

SEQ ID NO: 974          moltype = AA  length = 15
FEATURE                 Location/Qualifiers
source                  1..15
                        mol_type = protein
                        organism = Homo sapiens
SEQUENCE: 974
GFFRMNKLKE SSDTN                                                    15

SEQ ID NO: 975          moltype = AA  length = 15
FEATURE                 Location/Qualifiers
source                  1..15
                        mol_type = protein
                        organism = Homo sapiens
SEQUENCE: 975
KESSDTNPKP YCMAA                                                    15

SEQ ID NO: 976          moltype = AA  length = 15
FEATURE                 Location/Qualifiers
source                  1..15
                        mol_type = protein
                        organism = Homo sapiens
SEQUENCE: 976
KPYCMAAPMG LTENN                                                    15
```

```
SEQ ID NO: 977          moltype = AA  length = 15
FEATURE                 Location/Qualifiers
source                  1..15
                        mol_type = protein
                        organism = Homo sapiens
SEQUENCE: 977
MGLTENNRNR KKSYR                                                   15

SEQ ID NO: 978          moltype = AA  length = 15
FEATURE                 Location/Qualifiers
source                  1..15
                        mol_type = protein
                        organism = Homo sapiens
SEQUENCE: 978
NRKKSYRETN LKAVS                                                   15

SEQ ID NO: 979          moltype = AA  length = 13
FEATURE                 Location/Qualifiers
source                  1..13
                        mol_type = protein
                        organism = Homo sapiens
SEQUENCE: 979
TNLKAVSWPL NHT                                                     13

SEQ ID NO: 980          moltype = AA  length = 13
FEATURE                 Location/Qualifiers
source                  1..13
                        mol_type = protein
                        organism = Homo sapiens
SEQUENCE: 980
GWRGVCCAAV EPA                                                     13
```